(12) United States Patent
Smith et al.

(10) Patent No.: US 6,967,196 B1
(45) Date of Patent: Nov. 22, 2005

(54) SULFONAMIDE COMPOUNDS AND USES THEREOF

(75) Inventors: David W. Smith, Madison, CT (US); Benito Munoz, San Diego, CA (US); Kumar Srinivasan, Chicago, IL (US); Carl P. Bergstrom, Madison, CT (US); Prasad V. Chaturvedula, Cheshire, CT (US); Milind S. Deshpande, Madison, CT (US); Daniel J. Keavy, Killingworth, CT (US); Wai Yu Lau, Meriden, CT (US); Michael F. Parker, Higganum, CT (US); Charles P. Sloan, Wallingford, CT (US); Owen B. Wallace, Zionsville, IN (US); Henry Hui Wang, Milford, CT (US)

(73) Assignees: Bristol-Myers Squibb Company, Princeton, NJ (US); Merck & Co. Inc., Rahway, NJ (US)

( * ) Notice: Subject to any disclaimer, the term of this patent is extended or adjusted under 35 U.S.C. 154(b) by 0 days.

(21) Appl. No.: 09/890,927

(22) PCT Filed: Feb. 22, 2000

(86) PCT No.: PCT/US00/04560

§ 371 (c)(1),
(2), (4) Date: Feb. 19, 2002

(87) PCT Pub. No.: WO00/50391

PCT Pub. Date: Aug. 31, 2000

Related U.S. Application Data

(60) Provisional application No. 60/130,995, filed on Apr. 23, 1999, provisional application No. 60/130,994, filed on Apr. 23, 1999, provisional application No. 60/122,748, filed on Feb. 26, 1999, provisional application No. 60/121,906, filed on Feb. 26, 1999, and provisional application No. 60/122,746, filed on Feb. 26, 1999.

(51) Int. Cl.$^7$ ...................... A61K 31/407; A61K 31/40; A61K 31/54; A61K 31/4965; A61K 31/47

(52) U.S. Cl. ................. 514/210.1; 514/425; 514/227.5; 514/255.01; 514/307; 514/315; 514/217.12; 514/278; 514/412; 514/428; 514/357; 514/331; 514/408; 514/602; 514/365; 514/381; 514/406; 514/359; 548/565; 548/229; 548/470; 548/546; 548/566; 548/340.1; 548/252; 548/375.1; 548/255; 540/362; 540/609; 546/16; 546/229; 546/334; 546/220

(58) Field of Search ................. 548/565, 229, 548/470, 546; 540/362, 609; 546/16, 229, 334, 220; 544/398, 58.1; 514/425, 227.5, 255.01, 307, 315, 217.12, 278, 412, 210.1, 428, 357

(56) References Cited

U.S. PATENT DOCUMENTS 5,624,937 A * 4/1997 Reel et al.
5,981,168 A * 11/1999 Reiner et al.

FOREIGN PATENT DOCUMENTS

WO    WO 98 02166 A   *   1/1998
WO    WO 98 22104 A   *   5/1998

OTHER PUBLICATIONS

Negishi et al., Journal of Organic Chemistry (1965), 30(1), 43–8.*
Linfield et al., Journal of Medicinal Chemistry (1983), 26(12), 1741–6.*
FDA mulls drug to slow late-stage Alzheimer's [online], [retrieved on Sep. 24, 2003]. Retrieved from the Internet<URL:http://www.cnn.com/2003/HEALTH/conditions/09/24/alzheimers.drug.ap/index.html>.*
*These references are not being furnished because they are US patents or were cited on the international search report.*

* cited by examiner

Primary Examiner—Joseph K. McKane
Assistant Examiner—Rebecca Anderson
(74) Attorney, Agent, or Firm—Hoffmann & Baron, LLP

(57) ABSTRACT

In accordance with the present invention, there is provided a novel class of sulfonamide compounds. Compounds of the invention contain a core sulfonamide group. Variable moieties connected to the sulfur atom and nitrogen atom of the sulfonamide group include substituted or unsubstituted hydrocarbyl moieties, substituted or unsubstituted heterocycle moieties, polycyclic moieties, halogen, alkoxy, ether, ester, amide, sulfonyl, sulfonamidyl, sulfide, carbamate, and the like. Invention compounds are capable of a wide variety of uses. For example sulfonamide compounds can act to modulate production of amyloid β protein and are useful in the prevention or treatment of a variety of diseases. Pharmaceutical compositions containing invention compounds are also provided. Such compositions have wide utility for the prevention or treatment of a variety of diseases.

4 Claims, No Drawings

SULFONAMIDE COMPOUNDS AND USES THEREOF

This application is a 371 of PCT/US00//04560 filed in English on 22 Feb. 2000 which claims the benefit of provisional application, 60/121,906, 60/122,746, 60/122,748 filed Feb. 26, 1999, and 60/130,994, 60/130,995, both filed Apr. 23, 1999.

FIELD OF INVENTION

The present invention relates to novel compounds which contain a sulfonamide moiety, and pharmaceutical compositions containing invention compounds. In addition, the present invention relates to therapeutic methods for the treatment and prevention of various disease conditions, especially Alzheimer's disease and other diseases relating to the deposition of amyloid.

BACKGROUND OF THE INVENTION

Alzheimer's disease (AD) is a progressive, neurodegenerative disease characterized by memory loss, language deterioration, impaired visuospatial skills, poor judgment, and indifferent attitude. It is the most common form of dementia, affecting nearly 50% of the elderly population over 85 years of age. There is currently no effective treatment to prevent the disease.

One of the major histopathological hallmarks of Alzheimer's disease is senile plaques which are found only in the brain, and especially in regions associated with memory, reasoning and cognition. The major constituent of senile plaques is amyloid β protein, an insoluble 40–42 amino acid polypeptide. Amyloid β protein is normally found in the plasma and cerebrospinal fluid of healthy individuals although its function is unknown. In the disease state increased production and/or reduced removal of amyloid β protein results in increases in protein levels in plasma and cerebrospinal fluid and accumulation of the protein in the brain.

Amyloid β protein is derived from amyloid precursor protein (APP) by proteolytic cleavage. Processing of APP to amyloid β protein and other APP cleavage fragments is governed by a group of enzymes termed secretases. One type of secretase, γ-secretase, is responsible for the protein cleavage that gives rise to amyloid β protein. Although the existence of a protein having the activity of γ-secretase has been suggested, neither the gene encoding the protein, nor the protein itself has been completely isolated and characterized.

Thus, there is a continuing need in the art for compounds that can specifically inhibit proteolytic cleavage of APP, thereby inhibiting amyloid β protein production. The present invention meets this and related needs by providing a family of novel compounds and related methods of use.

BRIEF DESCRIPTION OF THE INVENTION

In accordance with the present invention, we have discovered a class of sulfonamide compounds that inhibit amyloid β protein production. Compounds of the invention contain a core sulfonamide group. Variable moieties are connected to the sulfur atom and nitrogen atom of the sulfonamide group and include substituted or unsubstituted hydrocarbyl moieties, substituted or unsubstituted heterocyclic moieties, polycyclic moieties, halogen, alkoxy, ether, ester, amide, sulfonyl, sulfonamidyl, sulfide, and carbamate. Invention compounds are capable of a wide variety of uses. For example, invention sulfonamide compounds can act to modulate amyloid β protein and are useful in the prevention and/or treatment of a variety of diseases. Without wishing to be bound by any theory, invention compounds are believed to act by blocking the proteolytic processing pathways that result in the formation of amyloid β proteins. Invention compounds are believed to act by inhibiting proteolytic cleavage of amyloid precursor protein (APP), the large precursor protein from which amyloid β protein is derived. Therapeutic indications for compounds with this inhibitory activity include disorders of the central nervous system in which amyloid β protein accumulates in the cerebral extracellular perivascular space, such as Alzheimer's disease. Pharmaceutical compositions containing invention compounds also have wide utility.

DETAILED DESCRIPTION OF THE INVENTION

In accordance with the present invention, there are provided compounds having the structure:

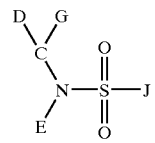

and pharmaceutically acceptable salts thereof, wherein:

D is hydrogen, substituted or unsubstituted hydrocarbyl, substituted or unsubstituted heterocycle optionally having one or more double bonds, halogen, alkoxyl, ester, amide, or D and G, taken together, form a substituted or unsubstituted cyclic moiety; and E, is hydrogen, substituted or unsubstituted hydrocarbyl, substituted or unsubstituted heterocycle optionally having one or more double bonds, alkoxyl, amide, sulfonyl, sulfonamidyl, sulfide or alkoxyl; or E and J, taken together, form a substituted or unsubstituted cyclic moiety; and G, when not part of a cyclic moiety including D, is substituted or unsubstituted hydrocarbyl, substituted or unsubstituted heterocycle optionally having one or more double bonds, amine, amide, ester, ether or carbamate; and J, when not part of a cyclic moiety including E, is substituted or unsubstituted hydrocarbyl, heterocycle optionally having one or more double bonds.

As employed herein, "hydrocarbyl" refers to straight chain, branched chain and cyclic (ie., ring-containing) monovalent and bivalent radicals derived from saturated or unsaturated moieties containing only carbon and hydrogen atoms. Straight and branched chain radicals have in the range of about 1 up to 12 carbon atoms and cyclic hydrocarbyl radicals have in the range of about 3 up to about 20 carbon atoms. The term "substituted hydrocarbyl" refers to hydrocarbyl moieties further bearing substituents as set forth below.

Exemplary straight or branched chain hydrocarbyl moieties include alkyl moieties, alkenyl moieties, polyalkenyl (e.g., dialkenyl moieties, and trialkenyl moieties), alkynyl moieties, alkadiynal moieties, alkatriynal moieties, alkenyne moieties, alkadienyne moieties, alkenediyne moieties, and the like.

Exemplary cyclic hydrocarbyl moieties include cycloalkyl moieties, cycloalkenyl moieties, cycloalkadienyl moieties, cycloalkatrienyl moieties, cycloalkynyl moieties, cycloalkadiynyl moieties, aromatic moieties, spiro hydrocarbon moieties wherein two rings are joined by a single atom which is the only common member of the two rings (e.g., spiro[3.4]octanyl, and the like), bicyclic hydrocarbon moieties wherein two rings are joined and have at least two atoms in common (e.g., bicyclo [3.2.1]octane, bicyclo [2.2.1]hept-2-ene, and the like), ring assemblies wherein two or more cyclic systems (i.e., single rings or fused systems) are directly joined to each other by single or double bonds, and the number of such ring junctions is one less than the number of cyclic systems involved (e.g., biphenylyl, biphenylylene, radicals of p-terphenyl, cyclohexylbenzyl, and the like), polycyclic moieties, and the like;

"alkyl" refers to straight or branched chain alkyl radicals having in the range of about 1 up to 12 carbon atoms; "substituted alkyl" refers to alkyl radicals further bearing one or more substituents such as cycloalkyl, cycloalkenyl, aryl, heterocycle optionally having one or more double bonds, halogen, alkoxy, cyano, cyanomethyl, nitro, amino, amide, amidine, hydroxy, carboxyl, carbamate, ether, ester, sulfonyl, sulfonamide, mercapto, and the like; "lower alkyl" refers to alkyl radicals having in the range of about 1 up to 6 carbon atoms; "substituted lower alkyl" refers to lower alkyl radicals further bearing one or more substituents as set forth above;

"alkenyl" refers to straight or branched chain hydrocarbyl radicals having at least one carbon—carbon double bond, and having in the range of about 2 up to 12 carbon atoms, and "substituted alkenyl" refers to alkenyl radicals further bearing one or more substituents as set forth above; "lower alkenyl" refers to alkenyl radicals having in the range of about 2 up to 6 carbon atoms; "substituted lower alkenyl" refers to lower alkenyl radicals further bearing one or more substituents as set forth above;

"alkynyl" refers to straight or branched chain hydrocarbyl radicals having at least one carbon—carbon triple bond, and having in the range of about 2 up to 12 carbon atoms, and "substituted alkynyl" refers to alkynyl radicals further bearing one or more substituents as set forth above;

"cycloalkyl" refers to ring-containing radicals containing in the range of about 3 up to 20 carbon atoms, and "substituted cycloalkyl" refers to cycloalkyl radicals further bearing one or more substituents as set forth above;

"cycloalkenyl" refers to ring-containing radicals having at least one carbon—carbon double bond in the ring, and having in the range of about 3 up to 20 carbon atoms, and "substituted cycloalkenyl" refers to cyclic alkenyl radicals further bearing one or more substituents as set forth above;

"cycloalkynyl" refers to ring-containing radicals having at least one carbon—carbon triple bond in the ring, and having in the range of about 7 up to 20 carbon atoms, and "substituted cycloalkynyl" refers to cyclic alkynyl radicals further bearing one or more substituents as set forth above;

"aromatic" refers to hydrocarbyl radicals having one or more polyunsaturated carbon rings having aromatic character, and having in the range of about 6 up to about 14 carbon atoms, and "substituted aromatic" refers to aromatic radicals further bearing one or more substituents as set forth above;

"aryl" refers to mononuclear aromatic radicals having 6 carbon atoms and fused ring aromatic radicals having up to about 14 carbon atoms, i.e. polynuclear aromatic radicals, and "substituted aryl" refers to aryl radicals further bearing one or more substituents as set forth above;

"alkylene" refers to divalent alkyl moieties wherein said moiety serves to link two structures together; "substituted alkylene" refers to alkylene moieties further bearing one or more substituents as set forth above;

"alkenylene", refers to divalent alkenyl moieties wherein said moiety serves to link two structures together, "substituted alkenylene" refers to alkenylene moieties further bearing one or more substituents as set forth above;

"arylene" refers to divalent aryl moieties wherein said moiety serves to link two structures together; "substituted arylene" refers to arylene moieties further bearing one or more substituents as set forth above;

"heterocycle" refers to ring-containing monovalent and bivalent radicals having one or more heteroatoms (e.g., N, O, S) as part of the ring structure, and having in the range of 3 up to 20 atoms in the rings. Heterocyclic moieties may be saturated or unsaturated containing one or more double bonds, and may contain more than one ring. Heterocyclic moieties include, for example, monocyclic moieties such as piperazinyl, morpholinyl, thiomorpholinyl, imidazolyl, pyrimidinyl, isothiazolyl, isoxazolyl, pyrazinyl, pyrimidinyl, pyrazolyl, pyrrolyl, furanyl, pyranyl, thienyl, isoimidazolyl, triazolyl, dithiolyl, oxadithiolyl, isoxazolyl, oxazolyl, thiazolyl, isothiazolyl, pyronyl, dioxinyl, pyridinyl, pyridazinyl, triazinyl, oxazinyl, isoxazinyl, and the like, bicyclic heterocyclic moieties such as azabicycloalkanyl moieties, oxabicycloalkyl moieties, and the like, spiro compounds containing heteroatoms, and ring assemblies containing heteroatoms. The term "substituted heterocycle" refers to heterocycles further bearing one or more substituents as set forth above. Exemplary radicals include radicals of polycyclic, bicyclic and spiro heterocycles such as

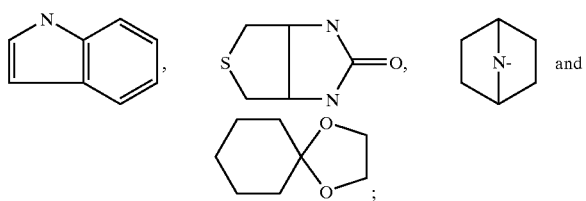

"halogen" refers to fluoride, chloride, bromide or iodide radicals;

"cyclic moiety" refers to substituted and unsubstituted cyclic hydrocarbyl moieties, as described above, and substituted and unsubstituted heterocycles, as described above;

"alkoxy" refers to radicals of the general formula —O—R, where R is substituted or unsubstituted hydrocarbyl; exemplary alkoxy radicals include methoxy, ethoxy, propoxy, isopropoxy, butoxy, isobutoxy, t-butoxy, and the like;

"ether" refers to radicals of the general formula —R'—O—R'', where R' and R'' are independently substituted or unsubstituted hydrocarbyl, or substituted or unsubstituted heterocycle optionally having one or more double bonds;

"ester" refers to radicals of the general formulae —C(O)O—R and —O—C(O)R, where R is substituted or unsubstituted hydrocarbyl, substituted or unsubstituted heterocycle optionally having one or more double bonds; it is understood that the carbon atom of the ester group may be linked directly to the moiety of which ester is a substituent, or may be linked via a linker, such as substituted or unsubstituted alkylene, alkenylene, arylene, and the like;

"amine" refers to radicals of the general formula —NRR', R and R' are independently hydrogen, substituted or unsubstituted hydrocarbyl, substituted or unsubstituted heterocycle optionally having one or more double bonds, alkoxy, ether, ester, amide. Thus, the radical may be a primary amine of the general formula, —NH$_2$, a secondary amine of the general formula —NHR, or a tertiary amine of the general formula —NRR'. It is understood that R and R' may cooperate to form a cyclic moiety having a nitrogen atom as a member of a ring, and that the nitrogen atom of the amine group may be linked directly to the moiety of which amine is a substituent, or may be linked via a linker, such as substituted or unsubstituted alkylene, alkenylene, arylene, and the like;

"amide" refers to radicals of the general formula —C(O) NRR', wherein R and R' are independently hydrogen, substituted or unsubstituted hydrocarbyl, substituted or unsubstituted heterocycle optionally having one or more double bonds; it is understood that R and R' may cooperate to form a cyclic moiety having a nitrogen atom as a member of a ring; and that the carbon atom of the amide group may be linked directly to the moiety of which amide is a substituent, or may be linked via a linker, such as substituted or unsubstituted alkylene, alkenylene, arylene, and the like;

"sulfide" refers to radicals of the general formula —SR, wherein R is substituted or unsubstituted hydrocarbyl, substituted or unsubstituted heterocycle optionally having one or more double bonds, ester, amine, amide, and the like;

"sulfonyl" refers to moieties containing a sulfonyl radical (—$SO_2$—);

"sulfonamidyl" refers to moieties containing a sulfonamide radical (—$SO_2$.NRR'), wherein R and R' are independently substituted or unsubstituted hydrocarbyl, substituted or unsubstituted heterocycle optionally having one or more double bonds; it is understood that R and R' may cooperate to form a cyclic moiety having a nitrogen atom as a member of a ring; and that the sulfur atom of the sulfonamide radical may be linked directly to the moiety of which amide is a substituent, or may be linked via a linker, such as substituted or unsubstituted alkylene, alkenylene, arylene, ether, ester, and the like;

"carbamate" refers to moieties containing a radical having the general formula —O—C(O)—NRR' wherein R and R' are independently substituted or unsubstituted hydrocarbyl, substituted or unsubstituted heterocycle optionally having one or more double bonds; it is understood that R and R' may cooperate to form a cyclic moiety having a nitrogen atom as a member of a ring; and that the oxygen atom of the carbamate group may be linked directly to the moiety of which carbamate is a substituent, or may be linked via a linker, such as substituted or unsubstituted alkylene, substituted or unsubstituted alkenylene, ether, ester, and the like;

In accordance with the present invention, D is hydrogen, substituted or unsubstituted hydrocarbyl, substituted or unsubstituted heterocycle optionally having one or more double bonds, halogen, alkoxyl, ester or amide, or D and E, taken together, form a substituted or unsubstituted cyclic moiety. In accordance with one embodiment of the invention, D is substituted or unsubstituted hydrocarbyl. Moieties contemplated for use in this embodiment of the invention include those wherein D is hydrogen or substituted or unsubstituted lower alkyl, with hydrogen and unsubstituted lower alkyl preferred, and hydrogen and unsubstituted methyl especially preferred.

Further in accordance with the present invention, E is selected from substituted or unsubstituted hydrocarbyl, heterocycle optionally having one or more double bonds, alkoxyl, amide, sulfonyl, sulfonamidyl or sulfide. Presently preferred compounds of the invention are those wherein E is substituted or unsubstituted alky, substituted or unsubstituted alkenyl, substituted or unsubstituted alkynyl, substituted or unsubstituted cycloalkyl, substituted or unsubstituted heterocycle optionally having one or more double bonds, substituted or unsubstituted polycyclic moiety, substituted or unsubstituted aryl, and the like. Especially preferred moieties include substituted or unsubstituted aryl; when E is substituted aryl, a mono substituted or di-substituted aryl is preferred, and preferred substituents are halogen, ester, alkyl, sulfur-linked alkyl, $NO_2$, $SO_2$, and the like, with halogen especially preferred.

In accordance with the present invention, G is substituted or unsubstituted hydrocarbyl, substituted or unsubstituted heterocycle optionally having one or more double bonds, amine, amide, ester, ether or carbamate. Thus, G can be substituted or unsubstituted alkyl, substituted or unsubstituted alkenyl, substituted or unsubstituted alkynyl, substituted or substituted cycloalkyl, substituted or unsubstituted aryl, substituted or unsubstituted cyclic moiety, ester, amide, carboxylate, and the like.

In one embodiment of the invention, G is substituted or unsubstituted alkyl, with substituted lower alkyl presently preferred. Presently preferred substituents are halogen and heterocycle optionally containing one or more double bonds such as imidazolyl, morpholinyl, pyrazolyl, pyrrolyl, 1,2,3-triazolyl, 1,2,4-triazolyl, tetrazolyl, and 5-methyltetrazolyl, and the like. In another embodiment of the invention, G is substituted or unsubstituted alkenyl, with substituted lower alkenyl preferred. A presently preferred substituent of lower alkenyl is halogen. In yet another embodiment of the invention, G is unsubstituted alkynyl, with lower unsubstituted alkynyl presently preferred. In still another embodiment of the invention, G is unsubstituted cycloalkyl.

In accordance with another embodiment of the invention, G is a substituted or unsubstituted cyclic moiety. Presently preferred cyclic moieties include substituted or unsubstituted naphthalenyl; when substituted, preferred substituents are ether moieties, especially 1-piperidinyl propoxyl.

In accordance with still another embodiment of the invention, G is an ester, represented by the formula —C(O)—OR. In presently preferred embodiments of the invention, R is substituted or unsubstituted lower alkyl or substituted aryl.

In accordance with another embodiment of the invention, G is carboxylate.

In accordance with a further embodiment of the invention, G is substituted or unsubstituted aryl. When G is substituted aryl, presently preferred substituents are substituted or unsubstituted alkyl, substituted or unsubstituted alkenyl, substituted or unsubstituted alkynyl, halogen, amide, ester, hydroxy, sulfonamide, sulfonyl, ether, and radicals of the general formula —O—$(CH_2)_n$—S-aryl, wherein n is 1 to 6.

In accordance with the present invention, J is a moiety attached to the sulfur atom of a sulfonamide group. J is substituted or unsubstituted hydrocarbyl, heterocycle optionally having one or more double bonds, or J and E, taken together, form a substituted or unsubstituted cyclic moiety. Thus J can be substituted or unsubstituted alkyl, substituted or unsubstituted alkenyl, substituted or unsubstituted aryl, substituted or unsubstituted heterocycle optionally having one or more double bonds, or J and E, taken together can form a substituted or unsubstituted polycyclic moiety or substituted or unsubstituted ring assembly.

In accordance with a particular embodiment of the invention, J is substituted or unsubstituted alkyl, with substituted or unsubstituted lower alkyl presently preferred. Substituents of alkyl presently preferred in this embodiment are substituted and unsubstituted aryl. In accordance with another embodiment of invention, J is substituted or unsubstituted alkenyl with substituted lower alkenyl preferred, and aryl a preferred substituent.

In accordance with still another embodiment of the invention, J is a substituted or unsubstituted polycyclic moiety. Thus J can be pentalene, indene, naphthalene, azulene, and the like. Moieties contemplated for use in this embodiment of the present invention include substituted or unsubstituted naphthalene; preferred substituents are secondary and tertiary amines.

In accordance with yet another embodiment of the invention, J is substituted or unsubstituted heterocycle optionally containing one or more double bonds. Moieties contemplated for use in this embodiment of the invention include those where J is isothiazolyl, thiazolyl, thiazinyl, thiazepinyl, and the like, with substituted thiazolyl preferred.

In still another embodiment of the invention, J is substituted or unsubstituted aryl. When J is substituted, preferred substituent moieties include alkyl, O-alkyl, —S-alkyl, —S-aryl, halogen, nitro and trifluoromethyl.

In yet another embodiment of the invention, J cooperates with E to form a substituted or unsubstituted polycyclic moiety. Thus, J can be a fused moiety such as substituted or unsubstituted bicyclic, or a substituted or unsubstituted ring assembly. Moieties contemplated for use in this embodiment include substituted and unsubstituted naphthalenyl and substituted and unsubstituted biphenylyl.

Those of skill in the art will recognize that multiple isomers exist for a single chemical formula; each of the possible isomeric forms of the various empirical formulae set forth herein are contemplated by the invention.

Those of skill in the art recognize that invention compounds may contain one or more chiral centers, and thus can exist as racemic mixtures as well as in individual enantiomeric forms. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions. Those of skill in the art will further recognize that invention compounds may exist in polymorphic forms wherein a compound is capable of crystallizing in different forms. Suitable methods for identifying and separating polymorphisms are known in the art.

In accordance with another embodiment of the present invention, there are provided pharmaceutical compositions comprising sulfonamide compounds as described above, in combination with pharmaceutically acceptable carriers. Optionally, invention compounds can be converted into non-toxic acid addition salts, depending on the substituents thereon. Thus, the above-described compounds (optionally in combination with pharmaceutically acceptable carriers) can be used in the manufacture of medicaments useful for the treatment of a variety of indications.

"Pharmaceutically acceptable salt" refers to a salt of the compound used for treatment which possesses the desired pharmacological activity and which is physiologically suitable. The salt can be formed with organic acids such as acetate, adipate, alginate, aspartate, benzoate, benzenesulfonate, butyrate, citrate, camphorate, camphorsulfonate, cyclopentanepropionate, digluconate, dodecylsulfate, ethanesulfonate, fumarate, glucoheptanoate, glycerophosphate, heptanoate, hexanoate, 2-hydroxyethanesulfonate, lactate, malate, maleate, methanesulfonate, 2-naphthalenesulfonate, nicotinate, oxalate, tartrate, toluenesulfonate, undecanoate, and the like. The salt can also be formed with inorganic acids such as sulfate, bisulfate, chlorate, perchlorate, hemisulfate, hydrochloride, hydrobromide, hydroiodide, and the like. In addition, the salt can be formed with a base salt, including ammonium salts, alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like.

Sulfonamide compounds as described above can be readily prepared using synthetic chemistry techniques known to those of skill in the art. See the Examples section herein for detailed description of numerous exemplary synthetic protocols.

In accordance with the present invention, a method of modulating the level of Amyloid Precursor Protein (APP) is provided. The method includes contacting APP with at least one sulfonamide compound according to the invention. As employed herein, the phrase "modulating the level of refers to altered levels of protein so that the level is different as a result of employing the invention method when compared to the level without employing the invention method. Modulating the level of APP includes the suppression or augmentation of the level of any one of a number of APP proteins such as a full-length APP, APP proteins having deletions, additions or substitutions of amino acids, APP proteins that are fragments of full-length APP protein, soluble APP (s-APP), insoluble APP, and the like. Exemplary APP proteins include $APP_{770}$, $APP_{751}$, $APP_{695wt}$, $APP_{670/671}$, $APP_{670/671/717}$, sAPP, α-sAPP, β-sAPP, and the like.

A variety of APP proteins are found in neural and non-neural tissues. $APP_{770}$ and $APP_{751}$ are wild-type APPs of 770 and 751 amino acid residues, respectively, that are found in non-neural tissues. $APP_{695wt}$ is an APP of 695 residues that is expressed in neurons. $APP_{670/671}$, is human APP, 695 residues in length, that has mutations at codons 670 and 671 (Swedish double mutation). $APP_{670/671/717}$ is a similar to $APP_{670/671}$ with an additional mutation at codon 717 (Phe for Val). sAPP is soluble APP, α-sAPP is α-secretase-cleaved soluable APP and β-sAPP is β-secretase-cleaved APP.

In accordance with another embodiment of the invention, there are provided methods of treating a wide variety of disease conditions, said method comprising administering to a patient in need thereof a therapeutically effective amount of at least one of the sulfonamide compounds described above.

APP is believed to be involved in numerous disease states. Therefore, modulating the level of APP also provides a variety of therapeutic applications, such as the treatment of amyloid angiopathy, cerebral amyloid angiopathy, systemic amyloidosis, Alzheimer's disease, hereditary cerebral hemorrhage with amyloidosis of the Dutch type, inclusion body myositis, Down's syndrome, and the like.

As used herein, "treating" refers to inhibiting or arresting the development of a disease, disorder or condition and/or causing the reduction, remission, or regression of the symptoms of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition.

As used herein, "administering" refers to means for providing sulfonamide compounds and/or salts thereof, optionally employing pharmaceutically acceptable carriers, as described herein, to a patient, using any suitable method of delivery, e.g., oral, sublingual intravenous, subcutaneous, transcutaneous, intramuscular, intracutaneous, intrathecal, epidural, intraoccular, intracranial, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

"Contacting" as employed herein may include administering in solution or in solid phase.

For purposes of oral administration, tablets, capsules, troches, aqueous or oily suspensions, dispersible powders or granules, emulsions, hard or soft capsules, or syrups, elixirs and lozenges containing various excipients such as calcium carbonate, lactose, calcium phosphate, sodium phosphate, and the like may be employed along with various granulating and disintegrating agents such as corn starch, potato starch, alginic acid, and the like, together with binding agents such as gum tragacanth, corn starch, gelatin, acacia, and the like. Lubricating agents such as magnesium striethylaminerate, striethylamineric acid, talc, and the like may also be added. Preparations intended for oral use may be prepared according to any methods known to the art for the manufacture of pharmaceutical preparations and such preparations may contain one or more agents selected from the group consisting of a sweetening agent such as sucrose, lactose, saccharin, and the like, flavoring agents such as peppermint, oil of wintergreen, and the like, coloring agents and preserving agents in order to provide pharmaceutically palatable preparations. Preparations for oral use may also contain suitable carriers include emulsions, solutions, suspensions, syrups, and the like, optionally containing additives such as wetting agents, emulsifying and suspending agents, sweetening, flavoring and perfuming agents, and the like. Tablets may be uncoated or they may be coated by known techniques to delay disintegration and absorption in the gastrointestinal tract and thereby provide a sustained action over a longer period of time.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. For parenteral administration, solutions for the practice of the invention may comprise sterile aqueous saline solutions, or the corresponding water soluble pharmaceutically acceptable metal salts, as previously described. For parenteral administration, solutions of the compounds used in the practice of the invention may also comprise non-aqueous solutions, suspensions, emulsions, and the like. Examples of non-aqueous solvents or vehicles are propylene glycol, polyethylene glycol, vegetable oils, such as olive oil and corn oil, gelatin, and injectable organic esters such as ethyl oleate, and the like. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Aqueous solutions may also be suitable for intravenous, intramuscular, intrathecal, subcutaneous, and intraperitoneal injection. The sterile aqueous media employed are all readily obtainable by standard techniques well known to those skilled in the art. They may be sterilized, for example, by filtration through a bacteria-retaining filter, by incorporating sterilizing agents into the compositions, by irradiating the compositions, by heating the compositions, and the like. They can also be manufactured in the form of sterile water, or some other sterile medium capable of injection immediately before use.

Compounds contemplated for use in the practice of the present invention may also be administered in the form of suppositories for rectal or vaginal administration. These compositions may be prepared by mixing the drug with a suitable non-irritating excipient, such as cocoa butter, synthetic glyceride esters of polyethylene glycols, and the like, such materials being solid at ambient temperatures but liquify and/or dissolve in internal cavities to release the drug.

The preferred therapeutic compositions for inocula and dosage will vary with the clinical indication. Some variation in dosage will necessarily occur depending upon the condition of the patient being treated, and the physician will, in any event, determine the appropriate dose for the individual patient. The effective amount of compound per unit dose depends, among other things, on the body weight, physiology, and chosen inoculation regimen. A unit dose of compound refers to the weight of compound without the weight of carrier (when carrier is used).

The route of delivery compounds and compositions used for the practice of the invention is determined by the disease and the site where treatment is required. Since the pharmacokinetics and pharmacodynamics of the compounds and compositions described herein will vary somewhat, the most preferred method for achieving a therapeutic concentration in a tissue is to gradually escalate the dosage and monitor the clinical effects. The initial dose, for such an escalating dosage regimen of therapy, will depend upon the route of administration.

In accordance with invention methods, the medicinal preparation can be introduced parenterally, by dermal application, and the like, in any medicinal form or composition. It is used as a solitary agent of medication or in combination with other medicinal preparations. Single and multiple therapeutic dosage regimens may prove useful in therapeutic protocols.

As employed herein, the phrase "a therapeutically effective amount", when used in reference to invention methods employing sulfonamide compounds and pharmaceutically acceptable salts thereof, refers to a dose of compound sufficient to provide circulating concentrations high enough to impart a beneficial effect on the recipient thereof. The specific therapeutically effective dose level for any particular patient will depend upon a variety of factors including the disorder being treated, the severity of the disorder, the activity of the specific compound used, the route of administration, the rate of clearance of the specific compound, the duration of treatment, the drugs used in combination or coincident with the specific compound, the age, body weight, sex, diet and general health of the patient, and like factors well known in the medical arts and sciences. Dosage levels typically fall in the range of about 0.001 up to 100 ing/kg/day; with levels in the range of about 0.05 up to 10 mg/kg/day being preferred.

In still another embodiment of the invention, there are provided methods for preventing disease conditions in a subject at risk thereof, said method comprising administering to said subject a therapeutically effective amount of at least one of the sulfonamide compounds described above.

As used herein, the phrase "preventing disease conditions" refers to preventing a disease, disorder or condition from occurring in a subject who may be at risk for the disease, but has not yet presented any symptoms thereof. Those of skill in the art will understand that a variety of methods may be used to determine a subject at risk for a disease, and that whether a subject is at risk for a disease will depend on a variety of factors known to those of skill in the art, including genetic make-up of the subject, age, body weight, sex, diet, general physical and mental health, occupation, exposure to environmental conditions, marital status, and the like, of the subject.

"Subject in need thereof" is intended to mean a mammal, e.g., humans, domestic animals and livestock, having or at risk of having one or more diseases associated with a modified level of APP.

Those of skill in the art can readily identify a variety of assays that can be used to assess the activity of sulfonamide compounds of the invention. For example, one can use in vitro cell-based assays to assess amyloid β protein production in cells that are exposed to invention compounds compared to cells exposed to control conditions. For such assays, transfected cells that stably express various forms of APP and from which amyloid β protein is secreted are used. Methods to measure amyloid β protein, such as immunoprecipitation, enzyme-linked immunosorbant assay (ELISA) and radioimmunoassay, and the like are known in the art. Immunoprecipitation methodology can be used to detect radiolabeled amyloid β protein derived from transfected cells having $^{35}$S-methionine-labeled APP (Haass et al., (1992) Nature, 32:322–325 and Shoji et al. (1992) Science, 258:126–129). ELISA can be used to detect unlabeled amyloid β protein (Seubert et al. (1992) Nature, 359:325–327).

The invention will now be described in greater detail by reference to the following non-limiting examples.

EXAMPLE 1

(S)-5-[[dimethyl(1,1-dimethylethyl)silyl]oxy]-1-pentanol

To a stirred solution of (4S)-pentane-1,4-diol [CAS 24347-57-7] (21.0 g, 0.202 mol) and t-butyldimethylsilyl chloride (30.5 g, 0.202 mol) in CH$_2$Cl$_2$ (400 mL) was added triethylamine (43.0 mL, 0.305 mol) followed by 4-(dimethylamino)pyridine (2.50 g, 20.2 mmol) at 0° C. The mixture was stirred for 3 h at 0° C. and was diluted with diethyl ether (300 mL). The white precipitate was filtered and washed with diethyl ether. The filtrate was concentrated under reduced pressure. The pale yellow oil was distilled (100° C.–103° C. at 0.7 mm) to afford the title compound (41 g, 92%) as a colorless oil.

$^1$H NMR (CDCl$_3$) δ 3.81 (m, 1H), 3.65 (m, 2H), 1.48–1.63 (m, 4H), 1.19 (d, 3H), 0.91 (s, 9H), 0.07 (s, 6H).

EXAMPLE 2

4-Chloro-2-nitro-1-[[(tetrahydro-2H-pyran-2-yl)oxy]methyl]benzene

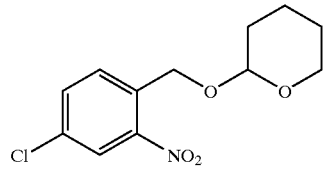

A magnetically stirred solution of 4-chloro-2-nitrobenzyl alcohol (25.0 g, 133 mmol) and 3,4-dihydro-2H-pyran (118.2 mL, 16.8 g, 200 mol) in anhydrous dichloromethane (250 mL) was treated at 25° C. with pyridinium (toluenesulfonate (PPTS, 50 mg). The solution was stirred for 12 h, washed with 1 N NaOH (250 mL), brine (250 mL), dried (K$_2$CO$_3$), filtered, and concentrated in vacuo. Silica gel chromatography (4:1 hexane:ethyl acetate) of the concentrate gave 22.5 g (62%) of the title compound as an oil.

EXAMPLE 3

5-Chloro-2-[[(tetrahydro-2H-pyran-2-yl)oxy]methyl]benzenamine

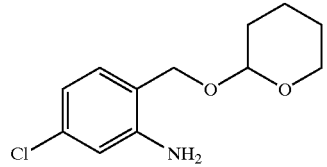

A Parr bottle containing 4-chloro-2-nitro-1-[[(tetrahydro-2H-pyran-2-yl)oxy]methyl]benzene (22.6 g, 82.8 mmol) and ethanol (150 mL) was treated with Raney nickel (50% slurry in water, 2.0 g), charged with hydrogen (60 psi) and rocked until hydrogen uptake ceased (3 h). The resultant suspension was filtered through celite, and the celite cake thoroughly washed with fresh ethanol (5×150 mL). The combined organic extracts were concentrated in vacuo to give an orange oil that crystallized on standing. Recrystallization (ethyl acetate/hexane) gave the title compound as a white solid (19.64 g, 98%). $^1$H NMR (CDCl$_3$) δ7.00 (d, J=8 Hz, 1H), 6.65–6.60 (m, 2H), 4.72 (A of ABq, J=12 Hz, 1H), 4.79–4.77 (m, 1H), 4.45 (B of ABq, J=12 Hz, 1H), 4.27 (bs, 2H), 3.94–3.85 (m, 1H), 3.58–3.50 (m, I), 1.88–1.65 (m, 2H), 1.58–1.46 (m, 4H).

EXAMPLE 4

4-Chloro-N-[5-chloro-2-hydroxymethyl)phenyl]
benzenesulfonamide

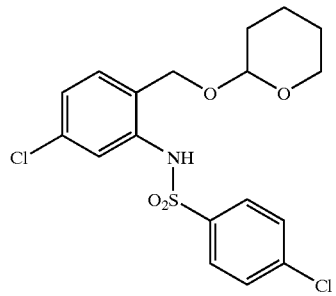

To a magnetically stirred solution of 5-chloro-2-[[(tetrahydro-2H-pyran-2-yl)oxy)methyl]benzenamine (4.38 g, 18.1 Immunol) in anhydrous pyridine (100 mL) at 25° C. was added 4-chlorobenzenesulfonyl chloride (3.82 g, 18.1 mmol). The solution was stirred for 24 h and concentrated in vacuo. The residue was dissolved in dichloromethane (150 mL), washed with brine (3×150 mL) and concentrated in vacuo. Silica gel chromatography (6:1 hexane:ethyl acetate) of the concentrate afforded the title compound (5.27 g, 76%) as a crystalline solid. $^1$H NMR (CDCl$_3$) δ8.70 (bs, 1H), 7.71 (d, J=8.5 Hz, 2H), 7.58 (s, 1H), 7.39 (d, J=8.5 Hz, 2H), 7.05–6.99 (m, 2H), 4.52–4.48 (m, 1H), 4.31 (A of ABq, J=12 Hz, 1H), 4.24 (B of ABq, J=12 Hz, 1H), 4.13–4.05 (m, 1H), 3.63–3.55 (m, 1H), 1.88–1.71 (m, 2H), 1.62–1.45 (m, 4H).

EXAMPLE 5

4-Chloro-N-[5-chloro-2-[[O-(2-tetrahydropyranyl)
methyl]phenyl]]-N-[[4-[dimethyl(1,1-dimethylethyl)
silyl]oxy]-1(R)-methylbutyl]benzenesulfonamide

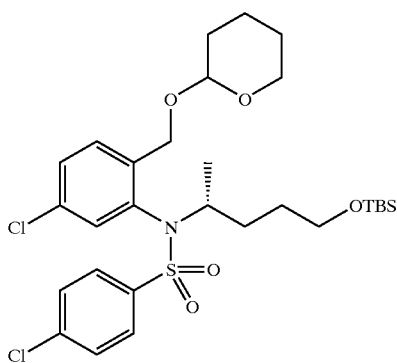

To a solution of 4-chloro-N-[5-chloro-2-[O-(2-tetrahydropyranyl)methyl]phenyl]benzenesulfonamide (2.70 g, 6.40 mmol), triphenylphosphine (3.40 g, 12.8 mmol) and (S)-5-[[dimethyl(1,1-dimethylethyl)silyl]oxy]-2-pentanol (2.40 g, 12.8 mmol) in THF (25 mL) was added diisopropylazodicarboxylate (2.40 mL, 12.8 mmol) dropwise at 0° C. under nitrogen atmosphere. The resulting mixture was allowed to warm to 22° C. with stirring. Stirring was continued for a period of 18 h and diethyl ether (100 mL) was added. The white solid was filtered, washed with ether (50 mL), and the combined ether solution was concentrated under reduced pressure. Silica gel chromatography (3:17 ethyl acetate:hexanes) of the concentrate afforded the tide compound (4.00 g, 100%) as a colorless oil. MS (ESI) m/e 615 (M–H).

EXAMPLE 6

4-Chloro-N-[5-chloro-2-[[O-(2-tetrahydropyranyl)
methyl]phenyl]]-N-(4-hydroxy-1-methylbutyl)
benzenesulfonamide

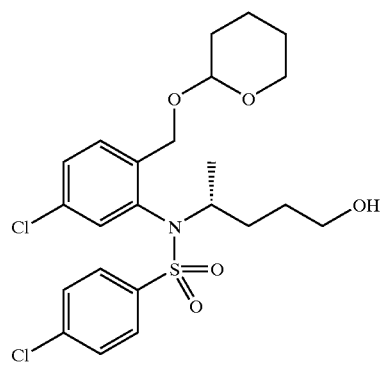

To a solution of 4-chloro-N-[5-chloro-2-[[O-(2-tetrahydropyranyl)methyl]phenyl]]-N-[[4-[dimethyl(1,1-dimethylethyl)silyl]oxy]-1-methylbutyl]benzene sulfonamide (3.80 g, 6.40 mmol) in THF (10 mL) was added 1M tetrabutylammonium fluoride (10 mL, 10 mmol) at 0° C. The resulting solution was allowed to stir at 0° C. for 2 h and concentrated under reduced pressure. Silica gel chromatography (1:1 ethyl acetate:hexane) of the concentrate afforded the title compound (3.20 g, 100%) as a colorless oil. MS (ESI) m/e 500 (M–H).

EXAMPLE 7

4-Chloro-N-[5-chloro-2-[[O-(2-tetrahydropyranyl)
methyl]phenyl]]-N-(4-bromo-1-methylbutyl)
benzenesulfonamide

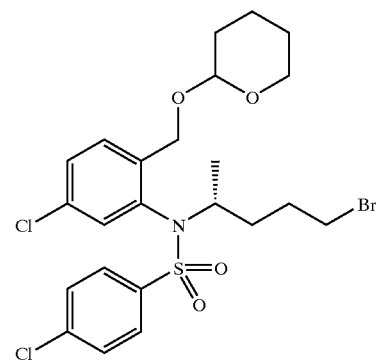

To a solution of 4-chloro-N-[5-chloro-2-[[O-(2-tetrahydropyranyl)methyl]phenyl]]-N-(4-hydroxy-1'-methylbutyl)benzenesulfonamide (3.20 g, 6.40 mmol) and triphenylphosphine (2.1 o g, 8.03 mmol) in methylene chloride (30 mL) was added carbon tetrabromide (2.60 mL, 8.03 mmol) dropwise at 0° C. The resulting solution was allowed to stir and warm to 22° C. for 12 h. A saturated solution of ammonium chloride (25 mL) was added. The reaction was extracted with methylene chloride (2×100 mL). The organic phase was dried over Na$_2$SO$_4$, filtered, and concentrated under reduced pressure. Silica gel chromatography (3:17 ethyl acetate:hexanes) of the concentrate afforded the title compound (2.10 g, 56%) as a colorless oil. MS (ESI) m/e 564 (M+H).

EXAMPLE 8

4-Chloro-N-[5-chloro-2-(acetoxymethyl)phenyl]-N-[(R)-1-methyl-4-[(1,1-dimethylethyl)dimethylsilyl)oxy)butyl]benzenesulfonamide

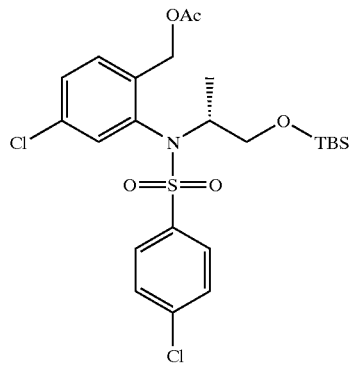

To a solution of 4-chloro-N-[5-chloro-2-(acetoxyoxymethyl)phenyl]benzenesulfonamide (13.7 g, 36.6 mmol), triphenylphosphine (21.1 g, 80.6 mmol) and 5S-[[(1,1-dimethylethyl)dimethylsilyl]oxy-2-pentanol (16.0 g, 73.3 mmol) in THF (130 mL) was added diisopropylazodicarboxylate (15.9 mL, 80.6 mmol) dropwise at 0° C. under nitrogen. The resulting mixture was allowed to warm to 22° C. with stirring. Stirring was continued for a period of 12 h followed by the addition of 150 ml of H₂O. The mixture was extracted with ether (3×100 mL). The combined organic extracts were washed with 1M NaHCO₃ and sat. brine. The organic phase was dried over Na₂SO₄, filtered, and concentrated under reduced pressure. Silica gel chromatography (1:5 ethyl acetate:hexanes) of the concentrate afforded 16.6 g of 4-chloro-N-[5-chloro-2-(acetoxymethyl)phenyl]-N-[(R)-1-methyl-4-[(1,1-dimethylethyl)dimethylsilyl]oxy)butyl]benzenesulfonamide as a yellow oil in 79% yield.

EXAMPLE 9

4-Chloro-N-[5-chloro-2-(acetoxymethyl)phenyl]-N-[(R)-1-methyl-4-hydroxybutyl]benzenesulfonamide

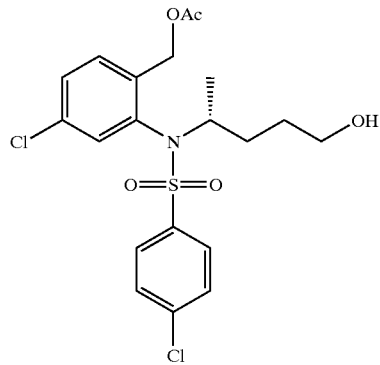

To a solution of 4 chloro-N-[5-chloro-2-(acetoxymethyl)phenyl-N-[(R)-1-methyl-4-[(1,1-dimethylethyl) dimethylsilyl]oxy)butyl]benzenesulfonamide (15.9 g, 27.8 mmol) in acetonitrile (45 mL) was added 48% aqueous HF (16 mL) dropwise at 0° C. The resulting solution was stirred for lb at 0° C. followed by addition of 50 mL of 1M NaHCO₃. The product was extracted with ether (2×50 mL), dried over Na₂SO₄, filtered, and concentrated under reduced pressure. Silica gel chromatography (ethyl acetate) of the concentrate afforded 10.4 g of 4-chloro-N-[5-chloro-2-(acetoxymethyl)phenyl]-N-[(R)-1-methyl-4-hydroxybutyl] benzenesulfonamide as a colorless oil in 81% yield.

EXAMPLE 10

4-Chloro-N-[5-chloro-2-(acetoxymethyl)phenyl]-N-[(R)-1-methyl-4-bromobutyl]benzenesulfonamide

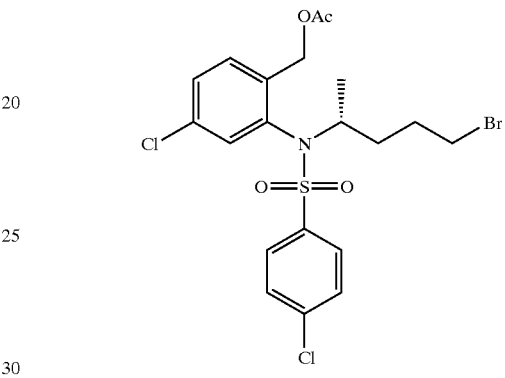

To a solution of 4-chloro-N-[5-chloro-2-(acetoxymethyl)phenyl]-N-[(R)-1-methyl-4-hydroxybutyl]benzenesulfonamide (500 mg, 1.09 mmol) in acetonitrile (2 mL) was added triphenylphosphine (571 mg, 2.18 mmol) and carbon tetrabromide (720 mg, 2.18 mmol) at 0° C. The resulting mixture was allowed to stir at 22° C. for 12 h followed by the addition of 25 mL of sat. ammonium chloride. The product was extracted with ether (2×25 mL), dried over Na₂SO₄, filtered, and concentrated under reduced pressure. Silica gel chromatography (1:4 ethyl acetate:hexanes) of the concentrate afforded 479 mg of 4-chloro-N-[5-chloro-2-(acetoxymethyl)phenyl]-N-[(R)-1-methyl-4-bromobutyl]benzenesulfonamide as a colorless oil in 84% yield.

EXAMPLE 11

(4R)-4-[5-chloro-2-(acetoxymethyl)phenyl][4-chlorophenyl)sulfonyl]-amino]pentylsulfonic Acid

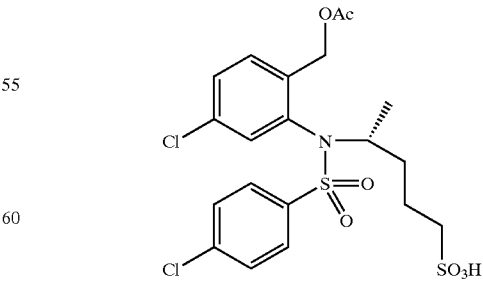

To a solution of 4-chloro-N-[5-chloro-2-(acetoxymethyl)phenyl]-N-[(R)-1-methyl-4-bromobutyl]benznesulfonamide (1.00 g, 1.91 mmol) in methanol/water (1:1, 4 mL) was added Na$_2$SO$_3$ (0.723 g, 5.74 mmol). The mixture was heated to reflux for 12 hours and then evaporated under reduced pressure. 2M HCl (25 mL) was added to the resulting oil. This mixture was extracted with CH$_2$Cl$_2$ (2×50 mL), dried over Na$_2$SO$_4$, and filtered. Solvent was concentrated under reduced pressure to afford (4R)-4-[5-chloro-2-(acetoxymethyl)phenyl][4-chlorophenyl)sulfonyl]-amine]pentylsulfonic acid (821 mg) as colorless oil in 88% yield. MS (ESI), 526 (M+1).

EXAMPLE 12

(4R)-4-[5-chloro-2-(hydroxymethyl)phenyl](4-chlorophenyl)sulfonyl]-amino]pentylsulfonyl Chloride

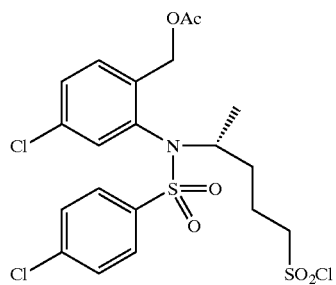

To a solution of (4R)-4-[5-chloro-2-(acetoxymethyl)phenyl][4-chlorophenyl)sulfonyl]-amino]pentylsulfonic acid (560 mg, 1.07 mmol) in benzene (5 mL) was added phosphorus pentachloride (445 mg, 2.14 mmol) at 22° C. The mixture was heated to reflux for 2 hours. This mixture was concentrated under reduced pressure and rediluted with CH$_2$Cl$_2$ (100 mL). This solution was washed with water (100 mL), dried over Na$_2$SO$_4$ and filtered. The organic solution was concentrated to afford 442 mg of (4R)-4-[5-chloro-2-(acetoxymethyl)phenyl](4-chlorophenyl)sulfonyl]-amino]pentylsulfonyl chloride as a pale yellow oil in 76% yield.

EXAMPLE 13

4-Chloro-N-[5-chloro-2-chlorophenyl]-N-[(R)-1-methyl-4-[(1,1-dimethylethyl)dimethylsilyl]oxy)butyl]benzenesulfonamide

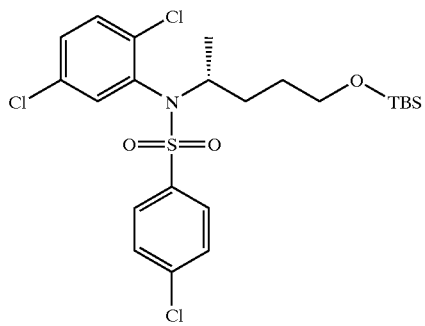

To a solution of 4-chloro-N-[5-chloro-2-chlorophenyl]benzenesulfonamide (1.00 g, 2.97 mmol), triphenylphosphine (1.64 g, 6.24 mmol) and 5S-[[(1,1-dimethylethyl)dimethylsilyl]oxy]-2-pentanol (1.30 g, 5.94 mmol) in THF (12 mL) was added diisopropylazodicarboxylate (1.23 mL, 6.24 mol) dropwise at 0° C. under nitrogen. The resulting mixture was allowed to warm to 22 DC with stirring. Stirring was continued for a period of 12 h followed by the addition of 25 mL of H$_2$O. The mixture was extracted with ether (3×25 mL). The combined organic extracts were washed with 1M NaHCO$_3$ and sat. brine. The organic phase was dried over Na$_2$SO$_4$, filtered, and concentrated under reduced pressure. Silica gel chromatography (1:5 ethyl acetate:hexanes) of the concentrate afforded 830 mg of 4-chloro-N-[5-chloro-2-chlorophenyl]-N-[(R)-1-methyl-4-[(1,1-dimethylethyl)-dimethylsilyl]oxy)butyl]benzenesulfonamide as a yellow oil in 52% yield.

EXAMPLE 14

4-Chloro-N-[5-chloro-2-chlorophenyl]-N-[(R)-1-methyl-4-hydroxybutyl]benzenesulfonamide

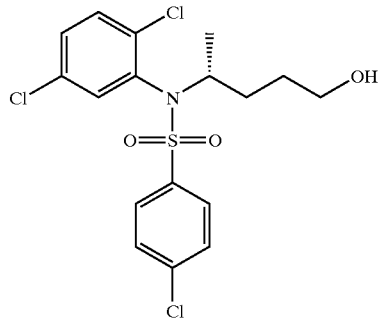

To a solution of 4-chloro-N-[5-chloro-2-chlorophenyl]-N-[(R)-1-methyl-4-[(1,1-dimethylethyl)dimethylsilyl]oxy)butyl]benzenesulfonamide (650 mg, 1.21 mmol) in acetonitrile (4 mL) was added 48% aqueous HF (2 mL) dropwise at 0° C. The resulting solution was stirred for 1 h at 0° C. followed by addition of 10 ml of 1M NaHCO$_3$. The product was extracted with ether (2×25 mL), dried over Na$_2$SO$_4$, filtered, and concentrated under reduced pressure. Silica gel chromatography (ethyl acetate) of the concentrate afforded 430 mg of 4-chloro-N-[5-chloro-2-chlorophenyl]-N-[(R)-1-methyl 4-hydroxybutyl]benzenesulfonamide as a yellow oil in 84% yield.

EXAMPLE 15

4-Chloro-N-2,5-dichlorophenyl)-N-(3-(carboxy)-1(R)methylpropyl)benzenesulfonamide

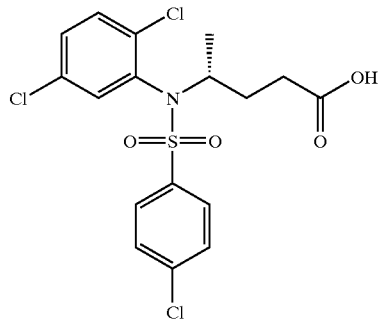

4-chloro-N-[5-chloro-2-chlorophenyl]-N-[(R)$_7$-methyl-4-hydroxybutyl]benzenesulfonamide (1.57 g, 0.0037 moles) was dissolved in acetonitrile (25 mL) and water (2 mL). RuCl$_3$ (50 mg), and NaIO$_4$ (1.19 g, 0.0056 moles, 1.5 eq) were added and the mixture was stirred at room temperature for 18 hours. The mixture was filtered, concentrated, dissolved in CH$_2$Cl$_2$, washed with 1N HCl, dried over Na$_2$SO$_4$ and evaporated. Chromatography over silica gel using 50–100% ethyl acetate/Hexane gave pure product (1.00 g, 62%) as a beige solid.

EXAMPLE 16

4-Chloro-N-[2,5-dichlorophenyl]-N-[(R)-1-methyl-4-bromobutyl]benzenesulfonamide

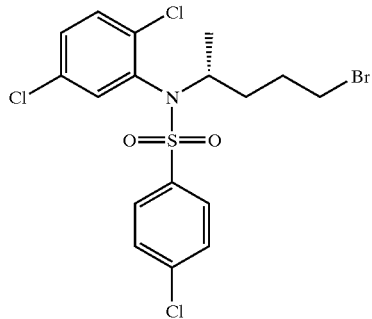

To a solution of 4-chloro-N-[2,5-dichlorophenyl]-N-[R]-1-methyl-4-hydroxybutyl]benzene-sulfonamide (3.90 g, 9.20 mmol) in CH$_2$Cl$_2$ (20 mL) was added triphenylphosphine (4.87 g, 18.4 mmol) and carbon tetrabromide (6.09 g, 18.4 mmol) at 0° C. The resulting mixture was allowed to stir at 22° C. overnight. To the reaction was added sat. ammonium chloride (200 mL). The product was extracted with CH$_2$Cl$_2$ (2×200 mL), dried over Na$_2$SO$_4$, filtered, and concentrated under reduced pressure. Silica gel chromatography (1:4 ethyl acetate:hexanes) of the concentrate afforded 3.13 g of 4-chloro-N-[2,5-dichlorophenyl]-N-[(R)-1-methyl-4-bromobutyl]benzenesulfonamide as a colorless oil in 70% yield. MS (ESI) 486 (M+H).

EXAMPLE 17

(4R)-4-[2,5-dichlorophenyl][4-chlorophenyl)sulfonyl]-amine]pentylsulfonic Acid

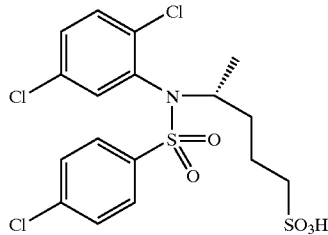

To a solution of 4-chloro-N-[5-chloro-2-chlorophenyl]-N-[(R)-1-methyl-4-bromobutyl]benzne-sulfonamide (2.85 g, 5.88 mmol) in methanol/water (1:1, 12 mL) was added Na$_2$SO$_3$ (7.40 g, 58.8 mmol). The mixture was heated to reflux for 12 hours and then evaporated under reduced pressure. 2M HCl was added to the resulting oil. This mixture was extracted with CH$_2$Cl$_2$ (2×50 mL), dried over Na$_2$SO$_4$, and filtered. Solvent was concentrated under reduced pressure to afford (4R)-4-[2,5 dichlorophenyl][4-chlorophenyl)sulfonyl]-amine]pentylsulfonic acid (2.34 g) as colorless oil in 82% yield. MS (ESI) 486 (M+1).

EXAMPLE 18

(4R)-4-[2,5-dichlorophenyl][4-chlorophenyl)sulfonyl]-amino]pentylsulfonyl Chloride

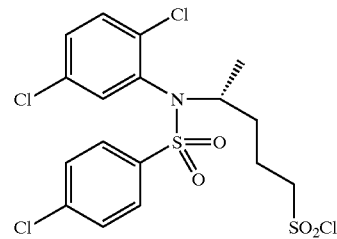

To a solution of (4R)-4-[2,5-dichlorophenyl][4-chlorophenyl)sulfonyl]amino]pentylsulfonic acid (2.34 g, 4.80 mmol) in benzene (10 mL) was added phosphorus pentachloride (1.48 g, 7.21 mmol) at 22° C. The mixture was heated to reflux for 2 hours. This mixture was concentrated under reduced pressure and redulited with CH$_2$Cl$_2$ (120 mL). This solution was washed with water (100 mL), dried over Na$_2$SO$_4$ and filtered. The organic solution was concentrated to afford 2.21 g of (4R)-4-[2, 5-dichlorophenyl][4-chlorophenyl)sulfonyl]-amino]pentylsulfonyl chloride as pale yellow oil in 91% yield. LC/MS 504.

EXAMPLE 19

4-Chloro-N-[2,5-dichlorophenyl]-N-[(R)-1-methyl-4-azidobutyl]benzenesulfonamide

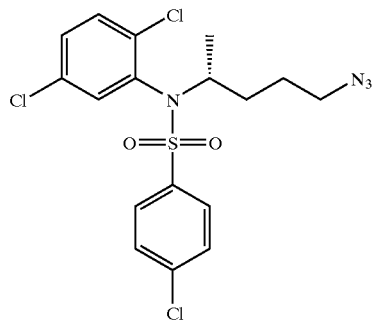

To a solution of 4-chloro-N-[2,5-dichlorophenyl]-N-[R]-1-methyl-4-bromobutyl]benzene-sulfonamide (1.06 g, 2.50 mmol) in DMF (2.5 mL) was added diphenylphosphoryl azide (1.08 mL, 5.00 mmol) and 1,8-diazabicyclo[5.4.0]undec-7-ene (0.935 mL, 6.25 mmol) at 0° C. The resulting mixture was allowed to stir at 100° C. overnight. To the reaction was added sat. ammonium chloride (200 mL). The product was extracted with CH$_2$Cl$_2$ (2×100 mL), dried over Na$_2$SO$_4$, filtered, and concentrated under reduced pressure. Silica gel chromatography (1:4 ethyl acetate:hexanes) of the concentrate afforded 977 mg of 4-chloro-N-[2,5-dichlorophenyl]-N-[(R)-1-methyl-4-azidobutyl]-benzenesulfonamide as a colorless oil in 87% yield. MS (ESI) 447 (M+H).

EXAMPLE 20

4-Chloro-N-[2,5-dichlorophenyl]-N-[(R)-1-methyl-4-aminobutyl]benzenesulfonamide

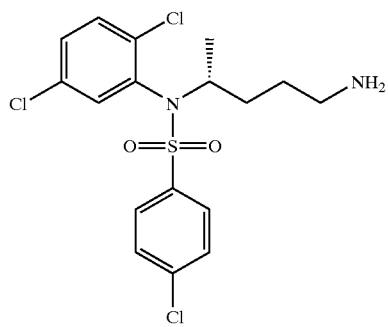

To a solution of 4-chloro-N-[2,5-dichlorophenyl]-N-[R]-1-methyl-4-azidobutyl]benzene-sulfonamide (1.20 g, 2.68 mmol) in THF (5 mL) was added a THF solution of lithium aluminum hydride (1.0 M, 2.68 mL) at −20° C. The resulting mixture was allowed to stir at −20° C. overnight. To the reaction was added 0.5M NaOH (6 mL). This mixture was filtered through celite, dried over $Na_2SO_4$, filtered, and concentrated under reduced pressure. Silica gel chromatography (1:9 methanol/$CHCl_3$) of the concentrate afforded 972 mg of 4-chloro-N-[2,5-dichlorophenyl)-N-[(R)-1-methyl-4-aminobutyl]benzenesulfonamide as a colorless oil in 86% yield. MS (ESI) 421 (M+H).

EXAMPLE 21

(S-[3-[(1,1-dimethylethyl)dimethylsilyl]oxy]-2-propanol

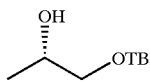

To a solution of (S)-1,2-propanediol (20.0 g, 0.263 mol), triethylamine (31.9 g, 0.315 mol), 4-dimethylaminopyridine (1.28 g, 10.5 mmol) in $CH_2Cl_2$ (200 mL) was added tert-butyldimethylsiloxy chloride (47.3 g, 0.315 mol) at 22° C. The mixture was allowed to stir for 18 h. The mixture was diluted with $CH_2Cl_2$, washed with water and sat. aqueous $NH_4Cl$. The organic solution was dried over $Na_2SO_4$, filtered and concentrated under reduced pressure. Silica gel chromatography (5% ethyl acetate/hexanes) of the concentrate gave 45.0 g of the title compound as a clear oil in 90% yield.

EXAMPLE 22

4-Chloro-N-(2,5-dichlorophenyl)-N-[(R)-1-methyl-4-[(1,1-dimethylethyl)dimethylsilyl]ethyl]benezenesulfonamide

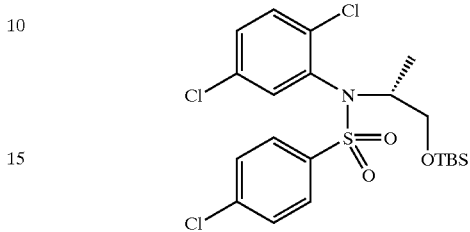

To a solution of 4-chloro-N-[2,5-dichlorophenyl]benzenesulfonamide (5.74 g, 17.1 mmol), triphenylphosphine (6.70 g, 25.7 mmol), (S)-[3-[(1,1-dimethylethyl)dimethylsilyl]oxy]-2-propanol (4.90 g, 25.7 mmol) in THF (50 mL) was added diisopropylazodicarboxylate (5.19 g, 25.7 mmol) dropwise at 0° C. under nitrogen atmosphere. The resulting mixture was allowed to warm to 22° C. Stirring was continued for a period of 18 h followed by the addition of water. The mixture was extracted with diethyl ether. The combined organic extracts were washed with $NaHCO_3$, sat. brine and dried over $Na_2SO_4$. Silica gel chromatography (1:10 ethyl acetate:hexanes) of the concentrate produced the title compound in 90% yield.

EXAMPLE 23

4-Chloro-N-(2,5-dichlorophenyl)-N-[(R)-1-methyl-(2-hydroxyethyl]benzenesulfonamide

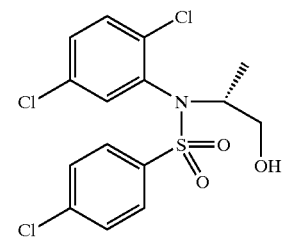

To a solution of 4-chloro-N-(2,5-dichlorophenyl)-N—(R)-1-methyl-[[4-(1,1-dimethylethyl) dimethylsilyl]oxy]ethyl]benzenesulfonamide (07.80 g, 15.3 mmol) in $CH_3CN$ was added HF (5.5 mL) at 0° C. The resulting mixture was allowed to stir at 0° C. for 2 h and concentrated under reduced pressure. Silica gel chromatography (1:1 ethyl acetate:hexanes) of the concentrate afforded the title compound (5.70 g, 95%/o) as a colorless oil.

EXAMPLE 24

4-Chloro-N-(2,5-dichlorophenyl)-N-[(R)-1-methyl (2-iodoethyl)]benzene Sulfonamide

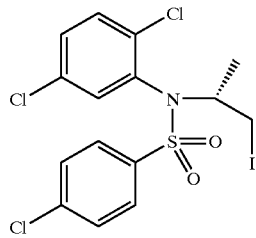

To a solution of 4 chloro-N-2,5-dichlorophenyl)-N-[(R)-1-methyl(2-hydroxyethyl)benzene-sulfonamide (0.660 g, 1.67 mmol), triphenylphosphine (0.530 g, 2.00 mmol) and imidazole (0.136 g, 2.00 mmol) in diethyl ether/$CH_3CN$(2:1, 3.0 mL) was added iodine (0.430 g, 1.67 mol) at 0° C. under nitrogen and stirred for 12 hr. This mixture was concentrated under reduced pressure and diluted with $CH_2Cl_2$. This solution was washed with water (50 ml), dried over $Na_2SO_4$ and filtered. The organic solution was concentrated to afford the title compound as a light yellow oil in 96% yield.

EXAMPLE 25

(S)-4-triphenylmethyloxy-2-butanol

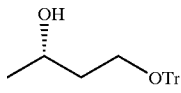

To a solution of (S)+}1,3-butanediol (10.0 g, 0.110 mol), was added triphenylmethylchloride (33.0 g, 0.330 mol), 4-dimethylaminopyridine (1.40 g, 11.5 mmol) in $CH_2Cl$/pyridine (1:1, 500 mL).

Stirring was continued over 48 h. The solvent was removed, the mixture was diluted with ether, washed with brine and dried over $Na_2SO_4$. The organic solution was filtered and concentrated. Silica gel chromatography with (5% ethyl acetate/hexanes) produced a clear oil (24 g) in 70% yield.

EXAMPLE 26

4-Chloro-N-(2,5-dichlorophenyl]-N-[1(R)-methyl-(3-triphenylmethyloxy)-propyl]benezenesulfonamide

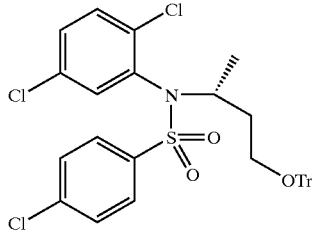

To a solution of 4-chloro-N-(2,5-dichlorophenyl) benzenesulfonamide (7.00 g, 20.8 mmol), triphenylphosphine (7.00 g, 27.0 mmol), (S)-4-triphenylmethyloxy-2-butanol (8.60 g, 27.0 mmol) in THF (30 mL) was added diisopropylazodicarboxylate (5.48 g, 27.0 mmol) dropwise at 0° C. under nitrogen atmosphere. The resulting mixture was allowed to warm to 22° C. with stirring. After 18 h the mixture was washed with water, brine, dried over $Na_2SO_4$ and filtered. Silica gel chromatography (1:10 ethyl acetate/hexanes) of the concentrate produced the title compound in 90% yield.

EXAMPLE 27

4-Chloro-N-(2,5-dichlorophenyl)-N-[1(R)-methyl-(3-hydroxy)-propyl]benzenesulfonamide

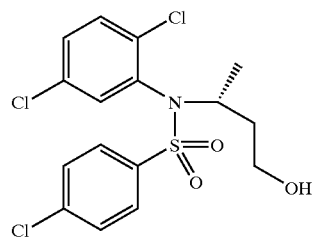

To a solution of 4-chloro-N-(2,5-dichlorophenyl)-N-[1(R)-methyl-(3-triphenylmethyloxy)-propyl) benzenesulfonamide (2.00 g, 3.00 mmol) in $CH_3CN$ (20 mL) was added Amberlyst 15 ion-exchange resin (6.0 g). The resulting mixture was allowed to stir at 22° C. for 12 h and filtered. Silica gel chromatography (1:1 ethyl acetate:hexanes) of the concentrate afforded the title compound as a colorless oil in quantitative yield.

EXAMPLE 28

4-Chloro-N-(2,5-dichlorophenyl)-N-[1(R)methyl-(3-iodo)-propyl]benzene Sulfonamide

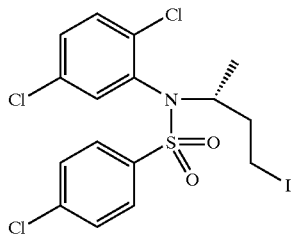

To a solution of 4-chloro-N-(2,5-dichlorophenyl)-N-[1(R)-methyl-(3-hydroxy)-propyl]benzene-sulfonamide (1.40 g, 3.40 mmol), triphenylphosphine (0.900 g, 3.40 mmol) and imidazole (0.230 g, 3.40 mmol) in diethyl ether/$CH_3CN$ (2:1, 7.0 mL) was added iodine (0.860 g, 3.40 mmol) at 0° C. under nitrogen and stirred for 12 h. The solvent was removed, the residue was taken into $CH_2Cl_2$, washed with water, dried over $Na_2SO_4$ and filtered. The organic solution was concentrated to afford the title compound as a light yellow oil in 96% yield.

EXAMPLE 29

4-Chloro-N-(2,5-dichlorophenyl)-N-[(R)-1-methyl-3-azidopropyl]]benzenesulfonamide

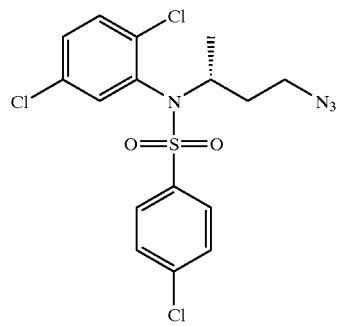

To a solution of 4-chloro-N-(2,5-dichlorophenyl)-N-[(R)-1-methyl-3-bromopropylbenzene-sulfonamide (1.188 g, 2.295 mmol) in THF/H₂O (20/4, 24 mL) was added sodium azide (1.49 g, 22.9 mmol) at 22° C. The resulting mixture was allowed to stir at 22° C. for 4 days. The mixture was extracted with ether (3×60 mL). The combined organic extracts were washed with sat. NaHCO₃, dried over MgSO₄, filtered, and concentrated under reduced pressure. Silica gel chromatography (1:9 ethyl acetate:hexanes) of the concentrate afforded 0.941 g of 4-chloro-N-(2,5-dichlorophenyl)-N-[(R)-1-methyl-3-azidopropyl]]benzenesulfonamide as a colorless oil in 94% yield.

EXAMPLE 30

4-Chloro-N-(2,5-dichlorophenyl)-N-[(R)-1-methyl-3-aminopropyl]benzenesulfonamide

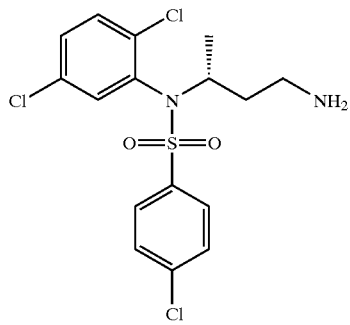

To a solution of 4-chloro-N-(2,5-dichlorophenyl)-N-[(R)-1-methyl-3-azidopropyl]benzenesulfonamide (0.941 g, 2.16 mmol) in THF (21 mL) was added lithium aluminum hydride (4.33 mL, 1 M in THF) at 0° C. under nitrogen atmosphere. The resulting mixture was allowed to stir at 0° C. for 1 h and subsequently treated by successive dropwise addition of 0.165 mL of water, 0.165 mL of 15% sodium hydroxide solution, and 0.493 mL of water. The mixture was filtered and concentrated under reduced pressure. Silica gel chromatography (3:10 ethyl acetate:hexanes) of the concentrate afforded 0.748 g of 4-chloro-N-2,5-dichlorophenyl)-N-[(R)-1-methyl-3-aminopropyl]benzenesulfonamide as a light brown oil in 85% yield.

EXAMPLE 31

(3S)-(1,1-dimethylethyl)dimethylsiloxy Butanal

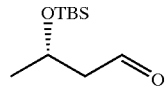

A solution of methyl (S)-3-tert-butyldimethylsiloxy butyrate (35.0 g 151 mmol) in hexane (400 mL) was cooled to −78° C. DIBAL-H (195 mL, 195 mmol, 1M in hexanes) was added dropwise. Stirring was continued for 1 h after which time water (75 mL) was cautiously added dropwise, after addition was complete stirring was continued at 22° C. for 18 h. The reaction was diluted with diethyl ether and then decanted several times. The solvents were removed to afford (3S)-(1,1-dimethylethyl)dimethylsiloxy butanal as a clear oil in quantitative yield. ¹H NMR (CDCl₃) δ9.85 (s br, 1H), 4.40–4.51 (m, 1H), 2.42–2.65 (m, 2H), 1.29 (d, 3H, J=6.0 Hz), 0.96 (s, 9H), 0.14 (d, 6H, J=3 Hz).

EXAMPLE 32

(Trans)1,1-dimethylethyl-(5S)-(1,1-dimethylethyl)dimethylsiloxy-hex-2-enoate,

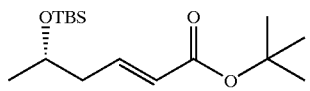

To a solution of (3S)-(1,1-dimethylethyl)dimethylsiloxy butanal (24.0 g 121 mmol), in dichloromethane (400 mL) at 0° C. was added tert-butoxy carbonylmethylene triphenylphosphorane (50.0 g, 133 mmol). Stirring was continued for 2 h after which time the reaction was concentrated and the resulting oil was purified by silica gel chromatography (5% ethyl acetate/Hexane) to afford (trans)1,1-dimethylethyl-(5S)-(1,1-dimethylethyl)dimethylsiloxy-hex-2-enoate as a clear oil in 93% yield. ¹H NMR (CDCl₃) δ6.79–6.90 (m, 1H) 5.75 (m 1H, J=15.6 Hz), 3.85–3.87 (m, 1H), 226–2.32 (m, 2H), 1.47 (s, 9H), 1.15 (d, 3H, J=6.0 Hz), 0.90 (s, 9H), 0.06 (s, 6H).

EXAMPLE 33

1,1-dimethylethyl-butyl-(5S)-(1,1-dimethylethyl)dimethylsiloxy-hexanoate,

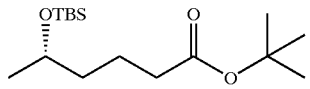

A suspension of (trans)tert-butyl-(5S)-tert-butyldimethylsiloxy-hex-2-enoate (33.5 g, 111 mmol), 10% Pd/C (5 g), in ethanol (250 mL), was hydrogenated at 45 psi for 1 h. The catalyst was filtered off and the filtrate was concentrated to afford 1,1-dimethylethyl-butyl-(5S)-(1,1-dimethylethyl)dimethylsiloxy-hexanoate as a white wax in quantitative yield. ¹H NMR (CDCl₁) 83.72–3.84 (m, 1H), 2.20 (t, 2H, J=7.0 Hz), 1.60–1.74 (m, 2H), 1.35–1.70 (m, 4H), 1.44 (s, 9H), 1.35 (d, 3H, J=6.0 Hz), 0.88 (s, 9H), 0.10 (s, 6H).

EXAMPLE 34

1,1-Dimethylethyl (5S)-5-hydroxyhexanoate

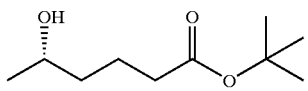

A solution of 1,1-dimethylethyl-(5S)-(1,1-dimethylethyl) dimethylsiloxy-hexanoate (19.0 g, 63.0 mmol) in THF (250 mL) was treated with tetrabutylammonium fluoride (94 mL, 94 mmol, 1M in THF) at 0° C. The reaction mixture was allowed to warm to 22° C., and stirring was continued for 18 h. The reaction mixture was diluted with diethyl ether, washed with water, and dried over MgSO$_4$. Silica gel chromatography (20% ethyl acetate/hexane) of the concentrate produced 1 μl-dimethylethyl (5S)-5-hydroxyhexanoate in 89% yield. $^1$H NMR (CDCl$_3$) δ3.74–3.86 (m, 1H), 2.32 (t, 2H, J=6.6 Hz), 1.60–1.74 (m, 2H), 1.57 (s, 1H, OH), 1.44–1.48 (m, 2H), 1.45 (s, 9H), 1.20 (d, 3H, J=6.0 Hz).

EXAMPLE 35

1,1-dimethylethyl(5R)-5-[(2,5-dichlorophenyl)-[(4-chlorophenyl)sulfonyl]-amino]hexanoate

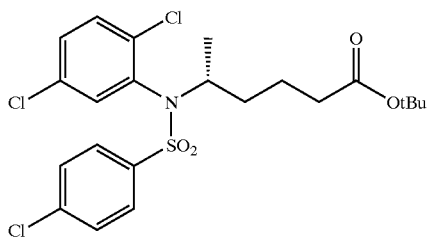

To a solution 2,5-dichloro-N[[(4-chlorophenyl)]amino]phenyl)sulfonamide (2.42 g, 7.20 mmol), triphenyl phosphine (3.70 g, 14.4 mmol) and 1,1-dimethylethyl(5S)-5-hydroxyhexanoate (2.70 g, 14.4 mmol) in THF (100 mL) was added diisopropylazodicarboxylate (2.51 g, 14.4 mmol) dropwise at 0° C. under nitrogen. The reaction mixture was allowed to warm to 22° C. with stirring for a period of 18 h. The reaction mixture was diluted with ethyl acetate then washed with water, brine and dried over MgSO$_4$. Silica gel chromatography (20% ethyl acetate/hexane) of the concentrate produced 1,1-dimethylethyl(5R)-5-[(2,5-dichlorophenyl)[(4-chlorophenyl)sulfonyl]-amino]hexanoate in 60% yield.

EXAMPLE 36

(5R)-5-[(2,5-dichlorophenyl][(4-chlorophenyl)sulfonyl]-amino]hexanoic Acid

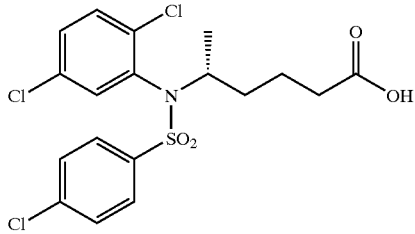

1,1-dimethylethyl(5R)-5-[(2,5-dichlorophenyl)-[(4-chlorophenyl)sulfonyl]-amino]hexanoate (700 g, 1.40 mmol) was treated with a 50% solution of trifluoroacetic acid in dichloromethane (20 mL). After 3 h the reaction was diluted with dichloromethane then washed with water, brine and dried over MgSO$_4$. Concentration under reduced pressure afforded (5R)-5-[(2,5-dichlorophenyl][(4-chlorophenyl)sulfonyl]-amino]hexanoic acid in quantitative yield. MS (ESI), (M–H$^-$) 450. IR-2975,1706,1466, 1348.

EXAMPLE 37

4-Chloro-N(2,5-dichlorophenyl)-N-[5-(1R)-methyl-5-oxo-(4-thiomorpholinyl)pentyl]benzenesulfonamide

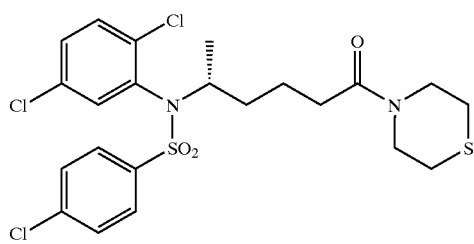

To a solution of (5R)-5-[(2,5-dichlorophenyl][(4-chlorophenyl)sulfonyl]-amino]hexanoic acid (2.00 g, 4.40 mmol), N,N-diisopropylethylamine (1.62 mL, 8.80 mmol) and 1-hydroxybenzotriazole (645 mg, 4.80 mmol), in dichloromethane (100 mL) was added 1-[3-(dimethylamino)propyl]-3-ethylcarbodiimide hydrochloride (920 mg, 4.80 mmol). After 18 h the solvent is removed and the residue is taken into ethyl acetate and successively washed with aqueous HCl, water, brine and then concentrated to afford the title compound as a white solid (1.43 g) in 61% yield. MS (ESI), (MHz) 537.2. IR-2910,1643,1581,1466,1348.

EXAMPLE 38

4-Chloro-N(2,5-dichlorophenyl)-N-[5-(1R)-methyl-
5-oxo-(1,1-dioxido-4-thiomorpholinyl)pentyl]
benzenesulfonamide

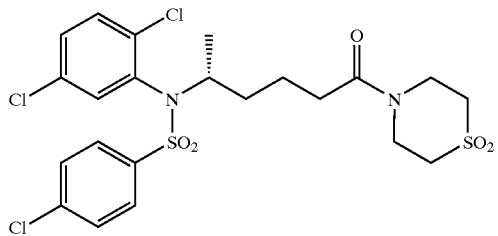

A solution of 4-chloro-N(2,5-dichlorophenyl)-N-[5-(1R)-methyl-5-oxo-(4-thiomorpholinyl)-pentyl]benzenesulfonamide (1.10 g, 2.10 mmol) in dichloromethane (100 mL) was treated with 3-chloroperoxybenzoic acid (1.10 g, 5.10 mmol) at 0° C. After stirring for 1 h the ice bath was removed and stirring was continued for 18 h. The reaction mixture was diluted with dichloromethane, and washed with 1N NaOH, H$_2$O, brine, and dried over MgSO$_4$. Concentration produced the title compound (1.01 g) in 91% yield. MS (ESI), (M+H)$^{30}$ 569.2. IR-3441,2935,1653,1467,1428,1318.

EXAMPLE 39

4-Chloro-N-[5-chloro-2-fluorophenyl]-N-[(R)-1-
methyl-4-[(1,1-dimethylethyl)dimethylsilyl]oxy)
butyl]benzenesulfonamide

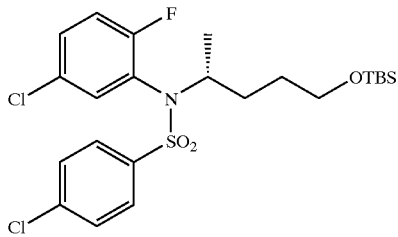

To a solution of 4-chloro-N-[5-chloro-2-fluorophenyl] benzenesulfonamide (500 mg, 1.56 mmol), triphenylphosphine (859 mg, 3.28 mmol) and 5S-[[(1,1-dimethylethyl)dimethylsilyl]oxy]-2-pentanol (682 mg, 3.12 mmol) in THF (7 mL) was added diisopropylazodicarboxylate (0.645 mL, 3.28 mol) dropwise at 0° C. under nitrogen. The resulting mixture was allowed to warm to 22° C. with stirring. Stirring was continued for a period of 12 h followed by the addition of 15 mL of H$_2$O. The mixture was extracted with ether (3×15 mL). The combined organic extracts were washed with NaHCO$_3$ and sat. brine. The organic phase was dried over Na$_2$SO$_4$, filtered, and concentrated under reduced pressure. Silica gel chromatography (1:5 ethyl acetate:hexanes) of the concentrate afforded 495 mg of 4-chloro-N-[5-chloro-2-fluorophenyl]-N-[(R)-1-methyl-4-[(1,1-dimethylethyl)-dimethylsilyl]oxy)butyl]benzenesulfonamide as a yellow oil in 61% yield.

EXAMPLE 40

4-Chloro-N-[5-chloro-2-fluorophenyl]-N-[(R)-1-
methyl-4-hydroxybutyl]benzenesulfonamide

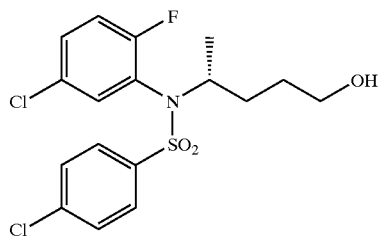

To a solution of 4-chloro-N-[5-chloro-2-fluorophenyl]-N-[(R)-1-methyl-4-[(1,1-dimethylethyl)-dimethylsilyl]oxy)butyl]benzenesulfonamide (495 mg, 0.951 mmol) in acetonitrile (4 mL) was added 48% aqueous HF (2 n-LL) dropwise at 0° C. The resulting solution was stirred for 1 h at 0° C. followed by addition of 10 mL of 1M NaHCO$_3$. The product was extracted with ether (2×25 mL), dried over Na$_2$SO$_4$, filtered, and concentrated under reduced pressure. Silica gel chromatography (ethyl acetate) of the concentrate afforded 336 mg of 4-chloro-N-[S-chloro-2-fluorophenyl]-N-[(R)-1-methyl-4-hydroxybutyl]benzenesulfonamide as a yellow oil in 87% yield.

EXAMPLE 41

4-Chloro-N-[5-chloro-2-fluorophenyl]-N-[(R)-1-
methyl-4-bromobutyl]benzenesulfonamide

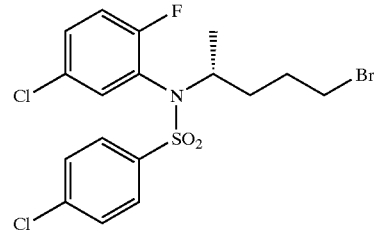

To a solution of 4-chloro-N-[5-chloro-2-fluorophenyl]-N-[(R)-1-methyl-4-hydroxybutyl]-benzenesulfonamide (336 mg, 0.827 mmol) in acetonitrile (4 mL) was added triphenylphosphine (433 mg, 1.65 mmol) and carbon tetrabromide (548 mg, 1.65 mmol) at 0° C. The resulting mixture was allowed to stir at 22° C. for 12 h followed by the addition of 25 mL of sat. ammonium chloride. The product was extracted with ether (2×25 mL), dried over Na$_2$SO$_4$, filtered, and concentrated under reduced pressure. Silica gel chromatography (1:4 ethyl acetate:hexanes) of the concentrate afforded 349 mg of 4-chloro-N-[5-chloro-2-fluorophenyl]-N-[(R)-1-methyl-4-bromobutyl] benzenesulfonamide as a yellow oil in 88% yield.

EXAMPLE 42

(4R)-4-[N-[5-chloro-2-fluorophenyl][(4-chlorophenyl)sulfonyl]amino]pentylsulfonic Acid

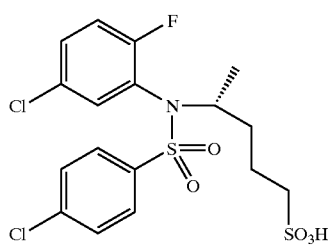

(4R)-4-[5-chloro-2-fluorophenyl][(4-chlorophenyl)sulfonyl]amino]pentylsulfonic acid was prepared analogous to (4R)-4-[2,5 dichlorophenyl][4-chlorophenyl)sulfonyl]-amine]pentylsulfonic acid by reacting 4-chloro-N-[5-chloro-2-fluorophenyl]-N-[(R)-1-methyl-4-bromobutyl] benzenesulfonamide with Na$_2$SO$_3$. Yield=86%; MS (ESI) 470 (M+1).

EXAMPLE 43

(4R)-4-[N-[5-chloro-2-fluorophenyl][(4-chlorophenyl)sulfonyl]amino]pentylsulfonyl Chloride

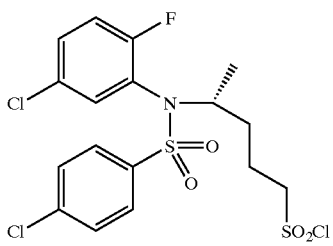

(4R)-4-[N-[5-chloro-2-fluorophenyl][(4-chlorophenyl)sulfonyl]amino]pentylsulfonyl chloride was prepared analogous to (4R)-4-[N-[2,5-dichlororophenyl][(4-chlorophenyl)sulfonyl]amino]pentyl-sulfonyl chloride by reacting (4R)-4-[N-[5-chloro-2-fluorophenyl][(4-chlorophenyl)sulfonyl]amino]-pentylsulfonic acid with phosphorus pentachloride: Yield=81%; MS (ESI) 489 (+1).

EXAMPLE 44

4-Chloro-N-(5-chloro-2-fluorophenyl)-4-azidobutyl]benzenesulfonamide

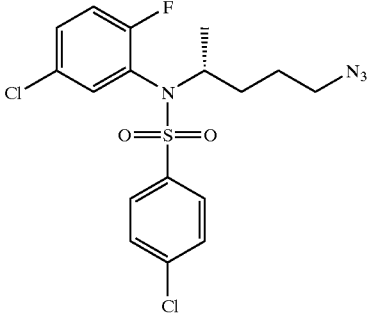

To a solution of 4-chloro-N-(5-chloro-2-fluorophenyl)-N-[(R)-1-methyl-4-bromobutyl]-benzenesulfonamide (0.343 g, 0.730 mmol) in THF/H$_2$O (8/2 mL) was added sodium azide (0.237 g, 7.30 mmol) at 22° C. The resulting mixture was allowed to stir at 22° C. for 10 days. The mixture was extracted with ether (3×20 mL). The combined organic extracts were washed with sat. NaHCO$_3$, dried over MgSO$_4$, filtered, and concentrated under reduced pressure. Silica gel chromatography (1:9 ethyl acetate:hexanes) of the concentrate afforded 0.227 g of 4-chloro-N-(5-chloro-2-fluorophenyl)-N-[(R)-1-methyl-4-azidobutyl] benzenesulfonamide as a colorless oil in 72% yield.

EXAMPLE 45

4-Chloro-N-(5-chloro-2-fluorophenyl)-N-[(R)-1-methyl-4-aminobutyl]benzenesulfonamide

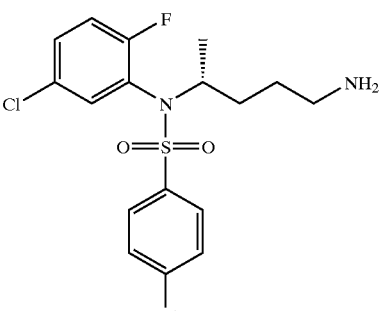

To a solution of 4-chloro-N-(5-chloro-2-fluorophenyl)-N-[(R)-1-methyl]4-azidobutyl]-benzenesulfonamide (0.325 g, 7.77 mmol) in THF (7 mL) was added lithium aluminum hydride (1.55 mL, 1 M in THF) at 0° C. under nitrogen atmosphere. The resulting mixture was allowed to stir at 0° C. for 1 h and subsequently treated by successive dropwise addition of 0.060 mL of water, 0.060 ml of 15% sodium hydroxide solution, and 0.180 mL of water. The mixture was filtered and concentrated under reduced pressure. Silica gel chromatography (3:10 ethyl acetate:hexanes) of the concentrate afforded 0.207 g of the title compound as a light brown oil in 91% yield.

EXAMPLE 46

4-Chloro-N-(5-chloro-2-fluorophenyl)-N-[(R)-1-methyl-3-azidopropyl]benzenesulfonamide

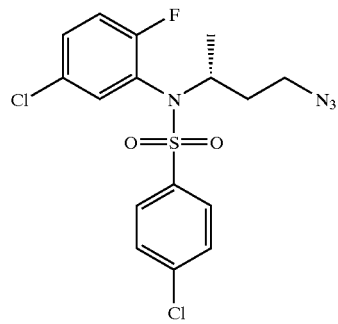

To a solution of 4-chloro-N-(5-chloro-2-fluorophenyl)-N-[(R)-1-methyl-3-bromopropyl]benzenesulfonamide (1.64 g, 3.27 mmol) in THF/H₂O (20/4, 24 mL) was added sodium azide (2.13 g, 32.7 mmol) at 22° C. The resulting mixture was allowed to stir at 22° C. for 4 days. The mixture was extracted with ether (3×60 mL). The combined organic extracts were washed with sat. NaHCO₃, dried over MgSO₄, filtered, and concentrated under reduced pressure. Silica gel chromatography (1:9 ethyl acetate:hexanes) of the concentrate afforded 1.38 g of 4-chloro-N-(5-chloro-2-fluorophenyl)-N-[(R)-1-methyl-3-azidopropyl]benzenesulfonamide as a colorless oil in 95% yield.

EXAMPLE 47

4-Chloro-N-(5-chloro-2-fluorophenyl)-N-[(R)-1-methyl-3-aminopropyl]benzenesulfonamide

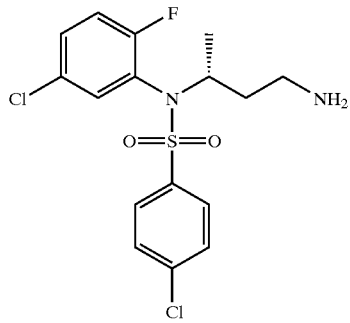

To a solution of 4-chloro-N-(5-chloro-2-fluorophenyl)-N-[(R)-1-methyl-3-azidopropyl]-benzenesulfonamide (1.34 g, 3.27 mmol) in THF (32 mL) was added lithium aluminum hydride (6.53 mL, 1 M in THF) at 0° C. under nitrogen atmosphere. The resulting mixture was allowed to stir at 0° C. for 1 h and subsequently treated by successive dropwise addition of 0.248 mL of water, 0.248 mL of 15% sodium hydroxide solution, and 0.744 mL of water. The mixture was filtered and concentrated under reduced pressure. Silica gel chromatography (3:10 ethyl acetate:hexanes) of the concentrate afforded 1.12 g of 4-chloro-N-(5-chloro-2-fluorophenyl)-N-[(R)-1-methyl-3-aminopropyl]benzenesulfonamide as a light brown oil in 85% yield.

EXAMPLE 48

4-Chloro-N-[5-fluoro-2-flurophenyl]-N-[(R)-1-methyl-4-[((1,1-dimethylethyl)dimethylsilyl]oxy)butyl]benzenesulfonamide

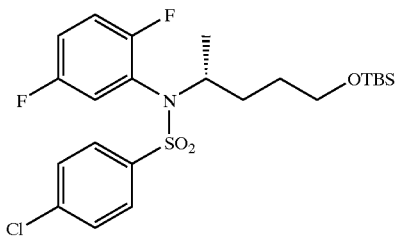

To a solution of 4-chloro-N-[5-fluoro-2-fluorophenyl]benzenesulfonamide (500 mg, 1.65 mmol), triphenylphosphine (909 mg, 3.47 mmol) and 5S-[[(1,1-dimethylethyl)dimethylsilyl]oxy]-2-pentanol (719 mg, 3.30 mmol) in THF (7 mL) was added diisopropylazodicarboxylate (0.682 mL, 3.47 mol) dropwise at 0° C. under nitrogen. The resulting mixture was allowed to warm to 22° C. with stirring. Stirring was continued for a period of 12 h followed by the addition of 15 mL of H₂O. The mixture was extracted with ether (3×15 mL). The combined organic extracts were washed with NaHCO₃ and sat. brine. The organic phase was dried over Na₂SO₄, filtered, and concentrated under reduced pressure. Silica gel chromatography (1:5 ethyl acetate:hexanes) of the concentrate afforded 466 mg of 4-chloro-N-[5-fluoro-2-flurophenyl]-N-[(R)-1-methyl-4-[(1,1-dimethylethyl)-dimethylsilyl]oxy)butyl]benzene-sulfonamide as a yellow oil in 56% yield.

EXAMPLE 49

4-Chloro-N-[5-fluoro-2-flurophenyl]-N-[(R)-1-methyl-4-hydroxybutyl]benzenesulfonamide

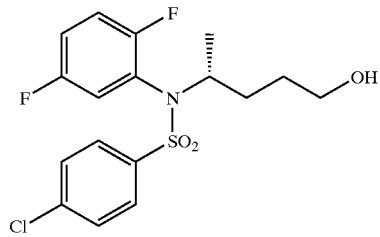

To a solution of 4-chloro-N-[5-fluoro-2-flurophenyl]-N-[(R)-1-methyl-4-[(1,1-dimethylethyl)-dimethylsilyl]oxy)butyl]benzenesulfonamide (466 mg, 0.924 mmol) in acetonitrile (4 mL) was added 48% aqueous HF (2 mL) dropwise at 0° C. The resulting solution was stirred for 1 h at 0° C. followed by addition of 10 ml of 1M NaHCO₃. The product was extracted with ether (2×25 mL), dried over Na₂SO₄, filtered, and concentrated under reduced pressure. Silica gel chromatography (ethyl acetate) of the concentrate afforded 317 mg of 4-chloro-N-[5-fluoro-2-flurophenyl]-N-[(R)-1-methyl-4-hydroxybutyl]benzenesulfonamide as a yellow oil in 88% yield.

EXAMPLE 50

4-Chloro-N-[5-fluoro-2-flurophenyl]-N-[(R)-1-methyl-4-bromobutyl]benzenesulfonamide

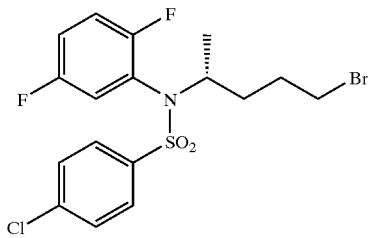

To a solution of 4-chloro-N-[5-fluoro-2-flurophenyl]-N-[(R)-1-methyl-4-hydroxybutyl]-benzenesulfonamide (317 mg, 0.813 mmol) in acetonitrile (4 mL) was added triphenylphosphine (425 mg, 1.62 mmol) and carbon tetrabromide (537 mg, 1.62 mmol) at 0° C. The resulting mixture was allowed to stir at 22° C. for 12 h followed by the addition of 25 mL of sat. ammonium chloride. The product was extracted with ether (2×25 mL), dried over $Na_2SO_4$, filtered, and concentrated under reduced pressure. Silica gel chromatography (1:4 ethyl acetate:hexanes) of the concentrate afforded 323 mg of 4-chloro-N-[5-fluoro-2-flurophenyl]-N-[(R)-1-methyl-4-bromobutyl]benzenesulfonamide as a yellow oil in 86% yield.

EXAMPLE 51

(4R)-4-[N-[2,5-difluorophenyl][(4-chlorophenyl)sulfonyl]amino]pentylsulfonic Acid

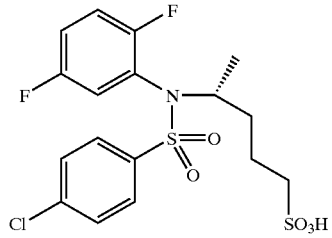

(4R)-4-[N-[2,5-difluorophenyl][(4-chlorophenyl)sulfonyl]amino]pentylsulfonic acid was prepared analogous to (4R)-4-[2,5-dichlorophenyl][4-chlorophenyl)sulfonyl]-amine]pentylsulfonic acid by reacting 4-chloro-N-[2,5-difluorophenyl]-N-[(R)-1-methyl-4-bromobutyl]benznesulfonamide with $Na_2SO_3$. Yield=84%; MS (ESI) 453 (M+1).

EXAMPLE 52

(4R)-4-[N-[2,5-difluorophenyl][(4-chlorophenyl)sulfonyl]amino]pentylsulfonyl chloride

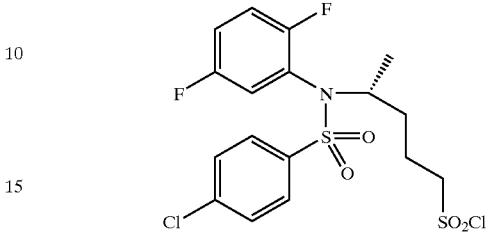

(4R)-4-[N-[2,5-difluorophenyl][(4-chlorophenyl)sulfonyl]amino]pentylsulfonyl chloride was prepared analogous to (4R)-4-[2,5-dichlorophenyl][4-chlorophenyl)sulfonyl]-amino]pentylsulfonyl chloride by reacting (4R)-4-[N-[2,5-difluorophenyl][(4-chlorophenyl)sulfonyl]amino]pentylsulfonic acid with phosphorus pentachloride. Yield=88%; MS (ESI) 434 (M+1).

EXAMPLE 53

4-Chloro-N-(2,5-difluorophenyl)-N-[(R)-1-methyl-4-azidobutyl]benzenesulfonamide

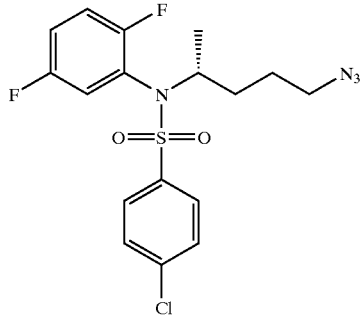

To a solution of 4-chloro-N-(2,5-difluorophenyl)-N-[(R)-1-methyl-4-bromobutyl]-benzenesulfonamide (0.505 g, 1.12 mmol) in $THF/H_2O$ (8/2, 10 mL) was added sodium azide (0.363 g, 5.58 mmol) at 22° C. The resulting mixture was allowed to stir at 22° C. for 10 days. The mixture was extracted with ether (3×20 mL). The combined organic extracts were washed with sat. $NaHCO_3$, dried over $MgSO_4$, filtered, and concentrated under reduced pressure. Silica gel chromatography (1:9 ethyl acetate:hexanes) of the concentrate afforded 0.455 g of 4-chloro-N-(2,5-difluorophenyl)-N-[(R)-1-methyl-4-azidobutyl]benzenesulfonamide as a colorless oil in 98% yield.

EXAMPLE 54

4-Chloro-N-(2,5-difluorophenyl)-N-[(R)-1-methyl-4-aminobutyl]benzenesulfonamide

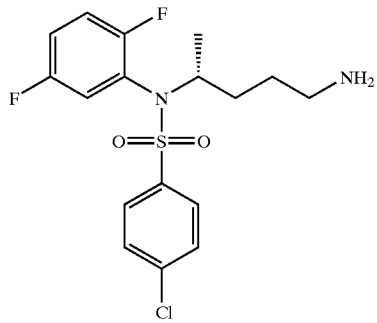

To a solution of 4-chloro-N-(2,5-difluorophenyl)-N-[(R)-1-methyl-4-azidobutyl]benzene-sulfonamide (0.394 g, 0.949 mmol) in THF (10 mL) was added lithium aluminum hydride (1.90 mL, 1 M in THF) at 0° C. under nitrogen atmosphere. The resulting mixture was allowed to stir at 0° C. for 1 h and subsequently treated by successive dropwise addition of 0.072 mL of water, 0.072 mL of 15% sodium hydroxide solution, and 0.216 mL of water. The mixture was filtered and concentrated under reduced pressure. Silica gel chromatography (3:10 ethyl acetate:hexanes) of the concentrate afforded 0.329 g of 4-chloro-N-(2,5-difluorophenyl)-N-[(R)-1-methyl-4-aminobutyl]benzenesulfonamide as a light brown oil in 89% yield.

EXAMPLE 55

4-Chloro-N-(2,5-difluorophenyl)-N-[(R)-1-methyl-3-azidopropyl]benzenesulfonamide

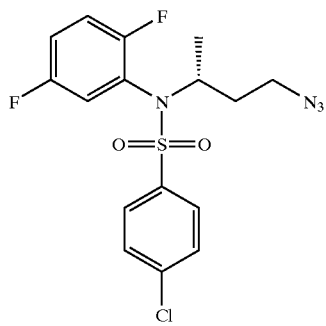

To a solution of 4-chloro-N-(2,5-difluorophenyl)-N-[(R)-1-methyl-3-bromopropyl]-benzenesulfonamide (1.74 g, 3.58 mmol) in THF/H$_2$O (20/4, 24 mL) was added sodium azide (2.33 g, 35.8 mmol) at 22° C. The resulting mixture was allowed to stir at 22° C. for 4 days. The mixture was extracted with ether (3×60 mL). The combined organic extracts were washed with sat. NaHCO$_3$, dried over MgSO$_4$, filtered, and concentrated under reduced pressure. Silica gel chromatography (1:9 ethyl acetate:hexanes) of the concentrate afforded 1.53 g of 4-chloro-N-(2,5-difluorophenyl)-N-[(R)-1-methyl-3-azidopropyl]benzenesulfonamide as a colorless oil in 95% yield.

EXAMPLE 56

4-Chloro-N-(2,5-difluorophenyl)-N-[(R)-1-methyl-3-aminopropyl]benzenesulfonamide

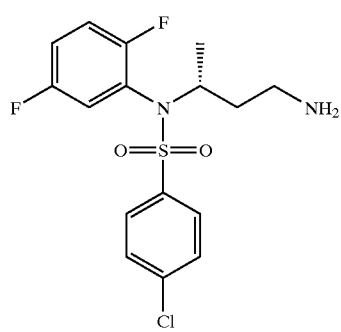

To a solution of 4-chloro-N-(2,5-difluorophenyl)-N-[(R)-1-methyl-3-azidopropyl]benzenesulfonamide (0.144 g, 3.59 mmol) in THF (35 mL) was added lithium aluminum hydride (7.16 mL, 1 M in THF) at 0° C. under nitrogen atmosphere. The resulting mixture was allowed to stir at 0° C. for 1 h w and subsequently treated by successive dropwise addition of 0.272 mL of water, 0.272 mL of 15% sodium hydroxide solution, and 0.816 mL of water. The mixture was concentrated under reduced pressure. Silica gel chromatography (3:10 ethyl acetate:hexanes) of the concentrate afforded 1.12 g of 4-chloro-N-(2,5-difluorophenyl)-N-[(R)-1-methyl-3-aminopropyl]benzenesulfonamide as a light brown oil in 97% yield.

EXAMPLE 57

4-Chloro-N(2,5-dichlorophenyl)-N-(5-(1.1-dioxido-4-thiomorpholinyl)-1(R)-methylpentyl)benzenesulfonamide

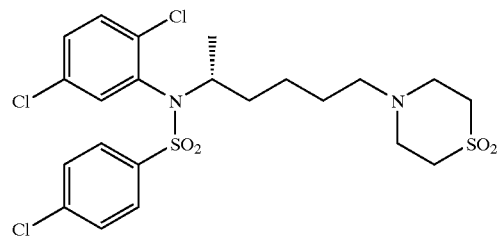

A solution of 4-chloro-N(2,5-dichlorophenyl)-N-[5-(1R)-methyl-5-oxo-(1.1-dioxido-4-thiomorpholinyl)pentyl]benzenesulfonamide (700 mg, 1.20 mmol) in THF (45 mL) was treated with a solution of borane-methyl sulfide complex (2M in THF, 1.8 mL, 3.6 mmol) dropwise at room temperature. After stirring for 18 h the reaction was cooled to 0° C. and quenched with methanol (50 mL), followed by treatment with HCl gas. The solvents were removed and the material was then purified by flash chromatography (silica gel, 15% ethyl acetate/hexane) to afford the title compound (300 mg) as a white solid in 50% yield. MS (ESI), (M+H)+ 553.0. IR-3430,2933,1467,1348,1326.

EXAMPLE 58

N-cyclopropylmethyl-3-(1H)-imidazolylpropylamine

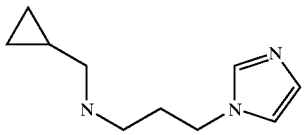

1-(3-aminopropyl)imidazole (Aldrich, 10.0 g, 0.0799 moles) was dissolved in $CH_2Cl_2$ (100 mL) along with pyridine (7.57 g, 0.0959 moles, 1.2 eq.). Cyclopropanecarbonyl chloride (Aldrich, 8.76 g, 0.0839 moles, 1.05 eq.) was added dropwise and the mixture was stirred for 18 hours. The solvent was removed and the crude mixture was chromatographed over silica gel using 5–10% methanol in $CH_2Cl_2$ with 0.5% $NH_4OH$, give the amide (14.3 g, 93%). The purified amide intermediate (14.3 g, 0.074 moles) was dissolved in THF (300 mL). Lithium aluminum hydride (0.148 moles, 148 mL of 1M soln. in THF, 2.0 eq.) was added and the mixture was refluxed for 3 days. The mixture was carefully quenched with 1N NaOH (10 mL) and refluxed for three hours. The hot solution was filtered over celite, and the solvent was removed to give pure N-cyclopropylmethyl-3-(1H)-imidazolylpropylamine (7.57 g, 57%) as a viscous yellow oil. NMR ($CDCl_3$); 0.09 (m, 2H); 0.46 (m, 2H); 0.90 (m, 1H); 1.89 (quintet, J=6.9 Hz, 2H); 2.43 (d, J=6.9 Hz, 2H); 2.61 (t, J=6.8 Hz, 2H); 4.05 (t, J=6.9 Hz, 2H); 6.92 (s, 1H); 7.05 (s, 1H); 7.48 (s, 1H).

EXAMPLE 59

4-Chloro-N-(2,5-dichlorophenyl)-N-[3-[(N'-cyclopropylmethyl)-N'(3-(1H)-imidazolylpropyl)]-[(R)-methylpropylcarboxamido]benzenesulfonamide

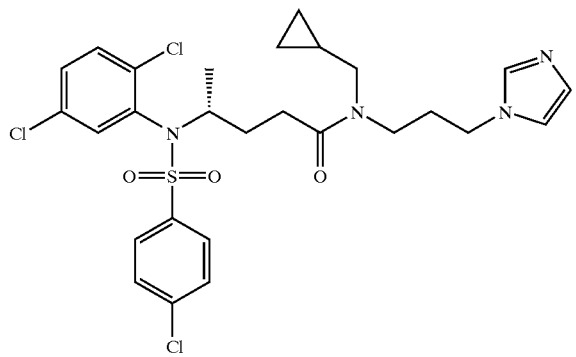

4-chloro-N-(2,5-dichlorophenyl)-N-(3-(carboxy)-1(R)-methylpropyl)benzenesulfonamide (405 mg, 0.928 mmoles) was dissolved in THF (10 mL) and $CH_2Cl_2$ (15 mL). N-Cyclopropylmethyl-3-(1H)-imidazolylpropylamine (166 mg, 0.928 mmoles) was added along with 1-(3-(dimethylamino)propyl)-3-ethylcarbodiimide hydrochloride (230 mg, 0.0012 moles, 1.3 eq.) and Hunig's base (I drop). The mixture was stirred at room temperature for 18 hours and the solvents were removed. The residue was dissolved in $CH_2Cl_2$, washed with sat. $NaHCO_3$, and brine. The organic layer was dried over $Na_2SO_4$ and evaporated. Chromatography over silica gel using 2–10% methanol in $CH_2Cl_2$ with 0.5% $NH_4OH$ gave 4-chloro-N-(2,5-dichlorophenyl)-N-[3-[(N'-cyclopropylmethyl)-N'(3-(1H)-imidazolylpropyl)]-1(R)-methylpropylcarboxamido]benzenesulfonamide (370 mg, 67%). Yellow viscous oil: IR (neat, $CH_2Cl_2$) 1637, 1467, 1348, 1166, 1095, 622 $cm^{-1}$; MS (ESI+), 599 $(M+H)^+$.

EXAMPLE 60

4-Chloro-N-(2,5-dichlorophenyl)-N-[4-(N'-cyclopropylmethyl)-N'(3-(1H)-imidazolylpropylamino)-1(R)-methylbutyl]benzenesulfonamide

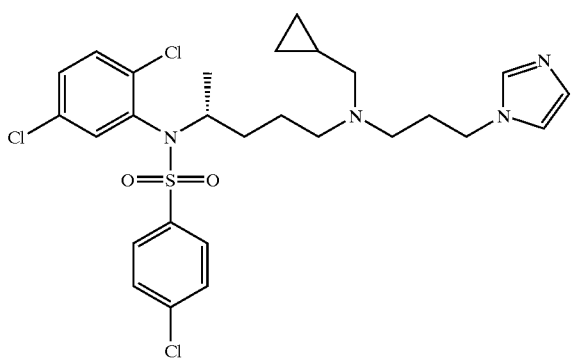

4-chloro-N-(2,5-dichlorophenyl)-N-(4-(N-cyclopropylmethyl-N-3-(1H)-imidazolylpropyl)-1(R)-methylbutylcarboxamide)benzenesulfonamide (1.00 g, 1.67 mmoles) was dissolved in THF (50 mL). Borane dimethyl sulfide (2.51 moles, 1.25 mL of a 2.0M solution in toluene, 1.5 eq.) was added and the mixture was refluxed for 6 hours, then allowed to stir at room temperature for 18 hours. The mixture was slowly quenched with methanol (5 mL), and 1N HCl (5 mL). The solvent was removed, the residue was dissolved in $CH_2Cl_2$ and washed with 1N NaOH, then brine. Prep HPLC (Reverse phase, methanol/$H_2O$/0.1% trifluoroacetic acid) gave a small amount of pure product (75.2 mg, 8%). Yield=8%; Colorless viscous oil: IR (neat, $CH_2Cl_2$) 1467, 1350, 1167, 1094, 753, 622 $cm^{-1}$; MS (ESI+), 583 $(M+H)^+$.

EXAMPLE 61

2-(Methylsulfonylmethyl)piperidine1)2-methylsulfonylmethyl)pyridine

Picolyl chloride hydrochloride (15.9 g, 0.0967 moles) was dissolved in DMF (70 mL) and methanesulfinic acid sodium salt (10.9 g, 0.106 moles, 1.1 eq.) was added along with triethylamine (10.7 g, 0.106 moles, 1.1 eq.). The mixture was refluxed for 1 hour. The DMF was removed, the residue dissolved in $CH_2Cl_2$, washed with sat. $Na_2CO_3$, and brine. The organic layer was dried over $Na_2SO_4$ and evaporated to give crude product. Purification was performed over silica gel using 20–100% ethyl acetate/hexane to give a yellow oil which solidified on standing (4.50 g, 27%).

EXAMPLE 62

(2) 2-(Methylsulfonylmethyl)piperidine 2-(Methylsulfonylmethyl)pyridine (4.40 g, 0.0257 moles) and $PtO_2$ (0.50 g) were suspended in ethanol (80 mL) with 1N HCl (15 mL). The mixture was hydrogenated at 50 psi for 18 hours. The catalyst was filtered and the solvent removed. The residue was dissolved in $CH_2Cl_2$ and washed with sat. $Na_2CO_3$. The aqueous layer was extracted with $CH_2Cl_2$ (3×25 mL). The organic layers were combined and dried over $Na_2SO_4$ and evaporated to give a yellow oil (4.11 g, 90%) which solidified on standing. Further purification was unnecessary. LCMS (178, M+H).

EXAMPLE 63

4-(Methylsulfonylmethyl)piperidine

To a stirred solution of 4-(hydroxymethyl)piperidine (6.00 g, 52.0 mmol) in 100 mL of $CH_2Cl_2$ was added di-tert-butyl dicarbonate (12.52 g, 57.0 mmol) at 0° C. and stirred for 1 h. The reaction mixture was warmed to room temperature over a period of 1 h. The solvents were removed and the solid was diluted with 250 mL of ethyl acetate, washed with 1M NaOH (200 mL), brine (200 mL), and and dried over $Na_2SO_4$. The solvent was evaporated to afford an oil.

The resulting oil was dissolved in toluene (300 mL) and triphenylphosphine (14 g, 55 mmol), iodine (14 g, 55 mmol), and imidazole (4.3 g, 63 mmol) were added. The reaction mixture was stirred at room temperature for 1 h and the solvent was removed. The crude product was passed through silica gel using 10% ethyl acetate in hexanes as the eluent to yield an oil after concentration of the desired fractions.

The resulting oil was dissolved in THF (100 mL) and sodium thiomethoxide (1.20 g, 16.0 mmol) was added at room temperature. The reaction mixture was stirred for 12 h and then diluted with ethyl acetate (100 mL), washed with water (200 mL), and dried over $Na_2SO_4$. The solvents were removed to afford an oil.

The resulting oil was dissolved in $CH_2Cl_2$ and 3-chloroperoxybenzoic acid (5.90 g, 34.0 mmol) at room temperature and allowed to stir overnight. The reaction mixture was washed with 1N NaOH (50 mL), and dried over $Na_2SO_4$. The crude sulfone was purified using silica gel chromatography (ethyl acetate) to yield the title compound as an oil in 41% overall yield.

EXAMPLE 64

3-(Methylsulfonylmethyl)piperidine

To a stirred solution of 3-(hydroxymethyl)piperidine (4.43 g, 35.0 mmol) and pyridine (14.2 mL) in 100 mL of $CH_2Cl_2$ was added benzoyl chloride (4.06 mL, 35.0 mmol) at 0° C. and stirred for 18 h. This mixture was washed with 2M HCl (50 mL), dried over $Na_2SO_4$ and the solvent was evaporated to afford an oil.

The resulting oil was dissolved in $CH_2Cl_2$ (70 mL), triethylamine (17.6 mL), and methanesulfonyl chloride (5.74 mL, 70.0 mmol). The reaction mixture was stirred at room temperature for 12 h. This mixture was washed with water (50 mL), dried over $Na_2SO_4$ and the solvent was evaporated to afford an oil.

The resulting oil was dissolved in THF (70 mL) and sodium thiomethoxide (4.48 g, 64.2 mmol) was added at room temperature. The reaction mixture was stirred for 12 h and then diluted with ethyl acetate (100 mL), washed with water (200 mL), and dried over $Na_2SO_4$. The solvents were removed to afford an oil.

The resulting oil was dissolved in $CH_2Cl_2$ (100 mL) and 80% 3-chloroperoxybenzoic acid (20.1 g, 70.0 mmol) was added at room temperature and allowed to stir overnight. The reaction mixture was washed with 1N NaOH (50 mL), and dried over $Na_2SO_4$. The crude sulfone was purified using silica gel chromatography (ethyl acetate) to yield an 4.69 g of an oil.

The resulting oil was suspended in 50 mL of 6N HCl and heated to 110° C. for 18 h. To the resulting solution was added 35 mL of 10N NaOH and the mixture was extracted with ether (10×100 mL). After evaporation of the solvent, the title compound was isolated as an oil in 30% overall yield.

EXAMPLE 65

4-(Sulfonylmethyl)piperidine

To a stirred solution of 4-(hydroxy)piperidine (3.89 g, 35.0 mmol) and pyridine (14.2 mL) in 100 mL of $CH_2Cl_2$ was added benzoyl chloride (4.06 mL, 35.0 mmol) at 0° C. and stirred for 18 h. This mixture was washed with 2M HCl (50 mL), dried over $Na_2SO_4$ and the solvent was evaporated to afford an oil.

The resulting oil was dissolved in $CH_2Cl_2$ (70 mL), triethylamine (17.6 mL), and methanesulfonyl chloride (5.74 ml, 70.0 mmol). The reaction mixture was stirred at room temperature for 12 h. This mixture was washed with water (50 mL), dried over $Na_2SO_4$ and the solvent was evaporated to afford an oil.

The resulting oil was dissolved in THF (70 mL) and sodium thiomethoxide (4.48 g, 64.2 mmol) was added at room temperature. The reaction mixture was stirred for 12 h and then diluted with ethyl acetate (100 mL), washed with water (200 mL), and dried over $Na_2SO_4$. The solvents were removed to afford an oil.

The resulting oil was dissolved in $CH_2Cl_2$ (100 mL) and 80% 3-chloroperoxybezoic acid (20.1 g, 70.0 mmol) was added at room temperature and allowed to stir overnight. The reaction mixture was washed with 1N NaOH (50 mL), and dried over $Na_2SO_4$. The crude sulfone was purified using silica gel chromatography (ethyl acetate) to yield 5.18 g of an oil.

The resulting oil was suspended in 50 mL of 6N HCl and heated to 110° C. for 18 h. To the resulting solution was added 35 mL of 10N NaOH and the mixture was extracted with ether (10×100 mL). After evaporation of the solvent, the title compound was isolated as an oil in 36% overall yield.

EXAMPLE 66

3-(Sulfonylmethyl)piperidine

To a stirred solution of 3-(hydroxy)piperidine hydrochloride (5.29 g, 35.0 mmol) and pyridine (14.2 mL) in 100 mL of $CH_2Cl_2$ was added benzoyl chloride (4.06 mL, 35.0 mmol) at 0° C. and stirred for 18 h. This mixture was washed with 2M HCl (50 mL), dried over $Na_2SO_4$ and the solvent was evaporated to afford an oil.

The resulting oil was dissolved in $CH_2Cl_2$ (70 mL), triethylamine (17.6 mL), and methanesulfonyl chloride (5.74 mL, 70.0 mmol). The reaction mixture was stirred at room temperature for 12 h. This mixture was washed with water (50 mL), dried over $Na_2SO_4$ and the solvent was evaporated to afford an oil.

The resulting oil was dissolved in THF (70 mL) and sodium thiomethoxide (4.48 g, 64.2 mmol) was added at room temperature. The reaction mixture was stirred for 12 h and then diluted with ethyl acetate (100 mL), washed with water (200 mL), and dried over $Na_2SO_4$. The solvents were removed to afford an oil.

The resulting oil was dissolved in $CH_2Cl_2$ (100 mL) and 80% 3-chloroperoxybezoic acid (20.1 g, 70.0 mmol) was added at room temperature and allowed to stir overnight. The reaction mixture was washed with 1N NaOH (50 mL), and dried over $Na_2SO_4$. The crude sulfone was purified using silica gel chromatography (ethyl acetate) to yield 5.20 g of an oil.

The resulting oil was suspended in 50 mL of 6N HCl and heated to 110° C. for 18 h. To the resulting solution was added 35 mL of 10N NaOH and the mixture was extracted with ether (10×100 mL). After evaporation of the solvent, the title compound was isolated as an oil in 38% overall yield.

EXAMPLE 67

(S)-3-(sulfonylmethyl)pyrrolidine

To a stirred solution of (R)-3-pyrrolidinol hydrochloride (4.76 g, 35.0 mmol) and pyridine (14.2 mL) in 100 mL of $CH_2Cl_2$ was added benzoyl chloride (4.06 mL, 35.0 mmol) at 0° C. and stirred for 18 h. This mixture was washed with 2M HCl (50 mL), dried over $Na_2SO_4$ and the solvent was evaporated to afford an oil.

The resulting oil was dissolved in $CH_2Cl_2$ (70 mL), triethylamine (17.6 mL), and methanesulfonyl chloride (5.74 mL, 70.0 mmol). The reaction mixture was stirred at room temperature for 12 h. This mixture was washed with water (50 mL), dried over $Na_2SO_4$ and the solvent was evaporated to afford an oil.

The resulting oil was dissolved in THF (70 mL) and sodium thiomethoxide (4.48 g, 64.2 mmol) was added at room temperature. The reaction mixture was stirred for 12 h and then diluted with ethyl acetate (100 mL), washed with water (200 mL), and dried over $Na_2SO_4$. The solvents were removed to afford an oil.

The resulting oil was dissolved in $CH_2Cl_2$ (100 mL) and 80% 3-chloroperoxybenzoic acid (20.1 g, 70.0 mmol) at room temperature and allowed to stir overnight. The reaction mixture was washed with 1N NaOH (50 mL), and dried over $Na_2SO_4$. The crude sulfone was purified using silica gel chromatography (ethyl acetate) to yield 5.49 g of an oil.

The resulting oil was suspended in 50 mL of EN HCl and heated to 110° C. for 18 h. To the resulting solution was added 35 mL of 10N NaOH and the mixture was extracted with ether (10×100 mL). After evaporation of the solvent, the title compound was isolated as an oil in 39% overall yield.

EXAMPLE 68

(R)-2-methylsulfonyl)methyl)pyrrolidine

N-Benzoyl-(R)-2-(methylthio)methyl)pyrrolidine was prepared by the method of Dieter and Tokles (J.A.C.S., 1987, 109, 2040–2046).

N-Benzoyl-(R)-(2-(methylthio)methyl)pyrrolidine (2.70 g, 0.0115 moles) was dissolved in $CH_2Cl_2$ (50 mL), cooled to 0° C., then meta-chloroperbenzoic acid (3.97 g, 0.0287 moles, 2.5 eq.) was added over 10 min. The mixture was stirred at room temperature for 2 hours, diluted with $CH_2Cl_2$, and washed with brine. The organic layer was dried over $Na_2SO_4$ and evaporated to give crude product. Purification was performed over silica gel using 20–100% ethyl acetate/hexane to give N-benzoyl-(R)-(2-(methylsulfonyl) methyl)pyrrolidine as a yellow solid (1.70 g, 0.00637 moles, 55%). LCMS (268, (M+H)).

N-Benzoyl-(R)(2-(methylsulfonyl)methyl)pyrrolidine (1.70 g, 0.00637 moles) was dissolved in 2N HCl (20 mL) and refluxed for 48 hours. The mixture was cooled and neutralized with sat. $K_2CO_3$. The aqueous layer was extracted using 50% ethyl acetate/t-BuOH, dried over $MgSO_4$, dried over $Na_2SO_4$ and evaporated to give (R)(2-(methylsulfonyl)methyl)pyrrolidine as a yellow oil (600 mg, 0.00368 moles, 58%) which was used without further purification. LCMS (186, (M+23)).

The preparation of ester intermediates can be carried out according to the general procedure described herein for coupling of N-aryl-N-haloalkyl sulfonamides with amines, using commercially available methyl thiazolidine-2-carboxylate (Lancaster, CAS# 50703-06-5). Methyl (R)-thiazolidine-4-carboxylate (CAS#65983-36-0) was prepared from the acid following literature procedures.

EXAMPLE 69

4-Chloro-N-(2,5-dichlorophenyl)-N-(3-(2-((methylsulfonyl)methyl)-1-piperidinyl)-1(R)-methylpropyl)benzenesulfonamide

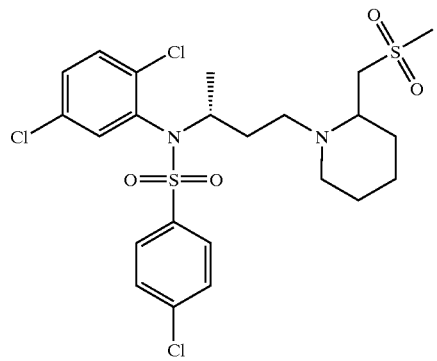

To a solution of 4-chloro-N-[2,5-dichlorophenyl]-N-1(R)-1-methyl-3-bromopropyl]benzenesulfonamide (0.375 mg, 0.795 mmol) in $CH_3CN$ (20 mL), was added 2-(methylsulfonyl-methyl)piperidine (0.282 g, 1.59 mmol), $K_2CO_3$ (500 mg), and Hunigs base (2 drops). The mixture was refluxed for 2 days. The solvent was removed and the crude mixture was dissolved in $CH_2Cl_2$ and washed with brine. The $CH_2Cl_2$ layer was dried over $Na_2SO_4$ and evaporated to give crude product. Purification was performed over silica gel using 10% methanol in $CH_2Cl_2$ with 0.5% $NH_4OH$ to afford 4-chloro-N-(2,5-dichlorophenyl)-N-(3-(2-(methylsulfonyl)methyl)-1-piperidinyl)-1(R)-methylpropyl)-benzenesulfonamide as a yellow glassy olid in 80% yield. IR (KBr) 1468, 1349, 1296, 1167, 1138, 1095, $cm^{-1}$; MS (ESI+), 567 (M+H)$^+$.

EXAMPLE 70

4-Chloro-N-(2,5-dichlorophenyl)-N-[3-[[3-(methylthio)methyl]-1-piperidinyl]-1(R)-methylpropyl]benzenesulfonamide

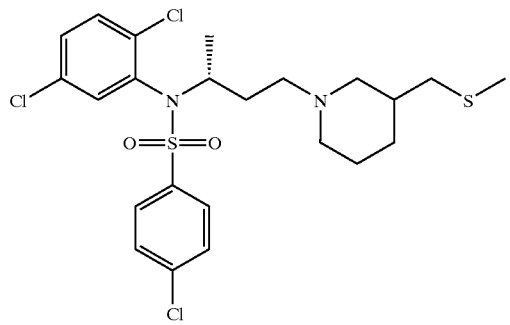

4-chloro-N-(2,5-dichlorophenyl)-N-[3-[[3-(methylthio)methyl]-1-piperidinyl]-1(R)-methylpropyl]benzenesulfonamide was prepared analogous to 4-chloro-N-2,5-dichlorophenyl)-N-(3-(2-(methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 3-(methylthiomethyl)piperidine. Yield=86%; MS (ESI+), 535 (M+H)$^+$.

EXAMPLE 71

4-Chloro-N-(2,5-dichlorophenyl)-N-[3-[(3-(methylsulfonyl)methyl]-1-piperidinyl-1(R)-methylpropyl]benzenesulfonamide

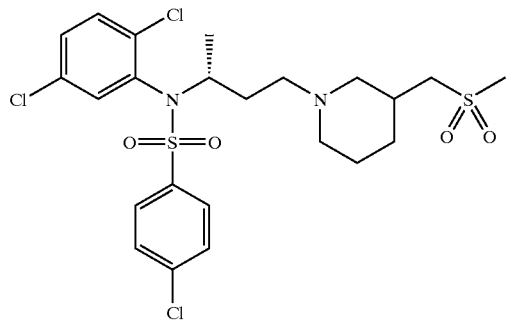

4-chloro-N-(2,5-dichlorophenyl)-N-[3-[[3{methylsulfonyl)methyl]-1-piperidinyl]-1(R)-methylpropyl]benzenesulfonamide was prepared analogous to 4-chloro-N-(2,5-dichlorophenyl)-N-3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 3-(methylsulfonylmethyl)piperidine. Yield=81%; MS (ESI+), 567 (M+H)$^+$.

EXAMPLE 72

4-Chloro-N-(2,5-dichlorophenyl)-N-[3-[(4-methylthio)-1-piperidinyl]-1(R)-methylpropyl] benzenesulfonamide

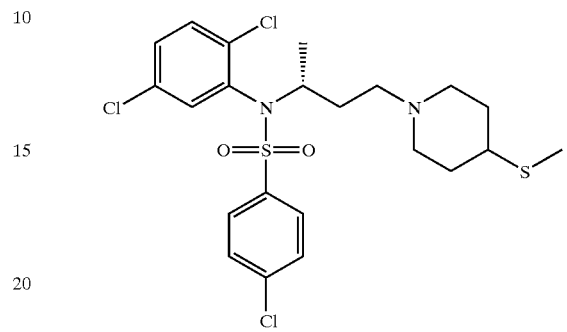

4-chloro-N-(2,5-dichlorophenyl)-N-[3-[(4-methylthio)-1-piperidinyl]-1(R)-methylpropyl]-benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 4-(methylthio)-piperidine. Yield=88%; MS (ESI+), 521 (M+H)$^+$.

EXAMPLE 73

4-Chloro-N-(2,5-dichlorophenyl)-N-[3-[(4-methylsulfonyl)-1-piperidinyl]-1(R)-methylpropyl] benzenesulfonamide

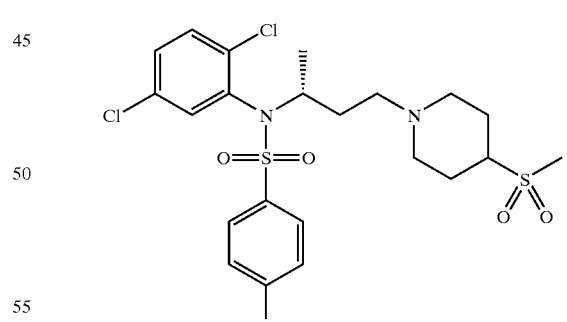

4-chloro-N-(2,5-dichlorophenyl)-N-[3-[(4-methylsulfonyl)-1-piperidinyl]-1(R)-methylpropyl]-benzenesulfonamide was prepared analogous to 4-chloro-N-(2,5-dichlorophenyl)-N-(3-(2-(methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 4-(methylsulfonyl)-piperidine. Yield=9%; MS (ESI+), 553 (M+H)$^+$.

EXAMPLE 74

4-Chloro-N-(2,5-dichlorophenyl)-N-[3-[(3-methylthio)-1-piperidinyl]-1(R)-methylpropyl]benzenesulfonamide

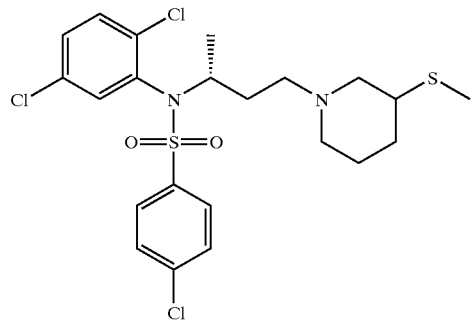

4-chloro-N-2,5-dichlorophenyl)-N-[3-[(3-methylthio)-1-piperidinyl]-1(R)-methylpropyl]-15 benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 3-(methylthio)-piperidine. Yield=85%; MS (ESI+), 521 (M+H)$^+$.

EXAMPLE 75

4-Chloro-N-(2,5-dichlorophenyl)-N-[3-[(3-methylsulfonyl)-1-piperidinyl]-1(R)-methylpropyl]benzenesulfonamide

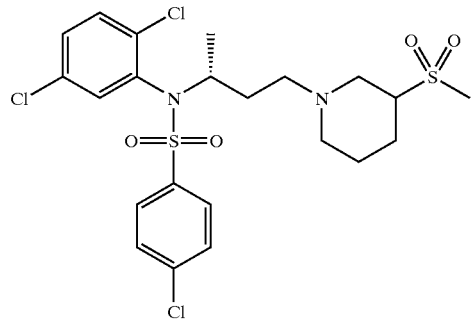

4-chloro-N-(2,5-dichlorophenyl)-N-[3-[(3-methylsulfonyl)-1-piperidinyl]-1(R)-methylpropyl]-benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 3-(methylsulfonyl)-piperidine. Yield=90%; MS (ESI+), 553 (M+H)$^+$.

EXAMPLE 76

4-Chloro-N-(2,5-dichlorophenyl)-N-[3-[(3-methylthio)-1-pyrrolidinyl]-1(R)-methylpropyl]benzenesulfonamide

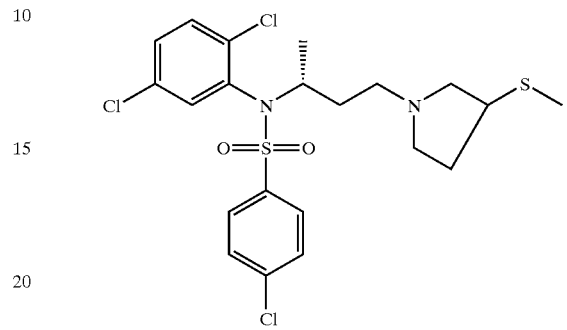

4-chloro-N-2,5-dichlorophenyl)-N-[3-[(3-methylthio)-1-pyrrolidinyl]-2 (R)-methylpropyl]benzenesulfonamide was prepared analogous to 4-chloro-N-(2,5-dichlorophenyl)-N-(3-(2-((methyl-sulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 3-(methylthio)pyrrolidine. Yield= 83%; MS (ESI+), 507 (M+H)$^+$.

EXAMPLE 77

4-Chloro-N-2,5-dichlorophenyl)-N-[3-[(3-methylsulfonyl)-1-pyrrolidinyl]-1(R)-methylpropyl]benzenesulfonamide

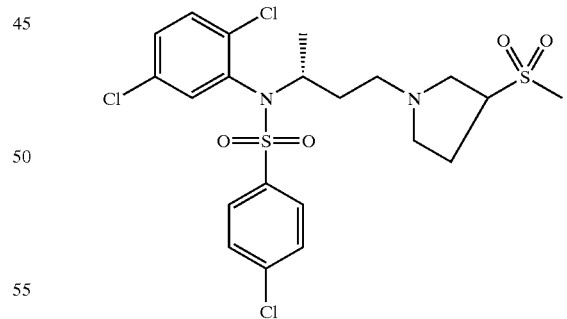

4-chloro-N-(2,5-dichlorophenyl)-N-[3-[(3-methylsulfonyl)-1-pyrrolidinyl]-1(R)-methylpropyl]-benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 3-(methylsulfonyl)-pyrrolidine. Yield=86%; MS (ESI+), 539 (M+H)$^+$.

EXAMPLE 78

4-Chloro-N-(2,5-dichlorophenyl)-N-(4-(2-((methylsulfonyl)methyl)-1-piperidinyl)-1(R)-methylbutyl)benzenesulfonamide

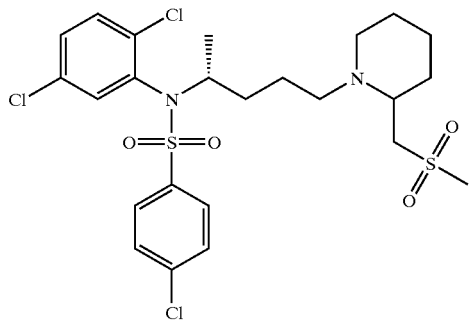

4-chloro-N-(2,5-dichlorophenyl)-N-[4-[[2-(methylsulfonyl)methyl-1-piperidinyl]-1(R)-methylbutyl] benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-4-bromobutyl]benzenesulfonamide with 2-(methylsulfonylmethyl)piperidine. Yield=28%; yellow foam: IR (neat, $CH_2Cl_2$) 1467, 1296, 1166, 1138, 1095, 622, $cm^{-1}$; MS (ESI+), 581 $(M+H)^+$.

EXAMPLE 79

4-Chloro-N-(2,5-dichlorophenyl)-N-[4-[[4-methylsulfonyl)methyl]-1-piperidinyl]-1(R)-methylbutyl]benzenesulfonamide

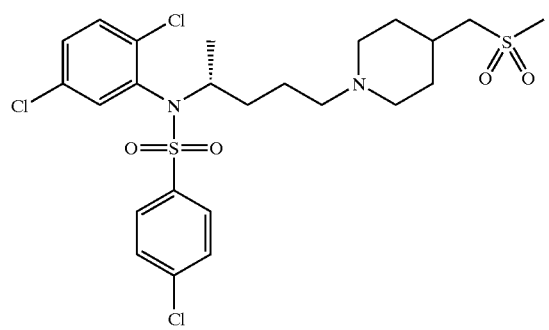

4-chloro-N-2,5-dichlorophenyl)-N-[4-[[4-methylsulfonyl)methyl]-1-piperidinyl]-1(R)-methylbutyl] benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-4-bromobutyl]benzenesulfonamide with 4-(methylsulfonylmethyl)piperidine. Yield=60%; MS (ESI+), 581 $(M+H)^+$.

EXAMPLE 80

4-Chloro-N-(2,5-dichlorophenyl)-N-[4-[3-[(methylthio)methyl]-1-piperidinyl]-1(R)-methylbutyl]benzenesulfonamide

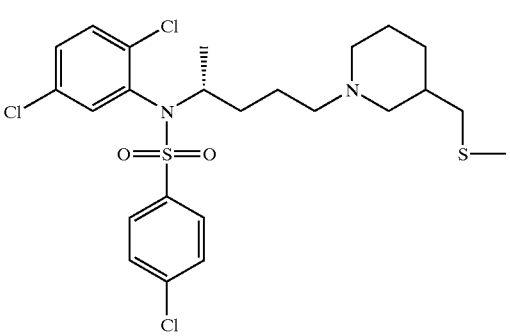

4-chloro-N-(2,5-dichlorophenyl)-N-[4-[[3-(methylthio)methyl]-1-piperidinyl]-1(R)-methylbutyl]benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-4-bromobutyl]benzenesulfonamide with 3-(methylthiomethyl)piperidine. Yield=91%; MS (ESI+), 549 $(M+H)^+$.

EXAMPLE 81

4-Chloro-N-2,5-dichlorophenyl)-N-[3-[(methylsulfonyl)methyl]-1-piperidinyl]-1(R)-methylbutyl]benzenesulfonamide

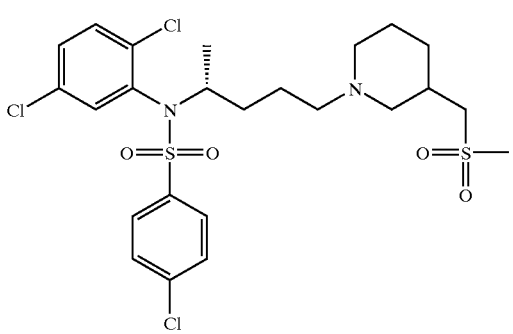

4-chloro-N-(2,5-dichlorophenyl)-N-[4-[[3-(methylsulfonyl)methyl]-1-piperidinyl]-1(R)-methylbutyl] benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-4-bromobutyl]benzenesulfonamide with 3-(methylsulfonylmethyl)piperidine. Yield=77%; MS (ESI+), 581 $(M+H)^+$.

EXAMPLE 82

4-Chloro-N-(2,5-dichlorophenyl)-N-[4-[(4-methylthio)-1-piperidinyl]-1(R)-methylbutyl]benzenesulfonamide

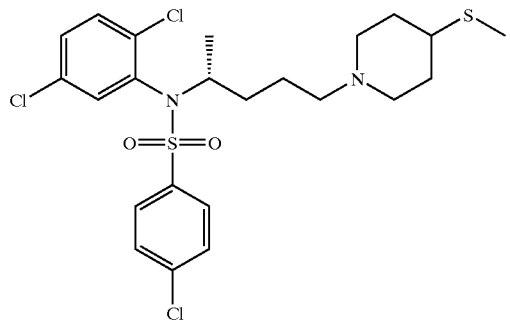

4-chloro-N-(2,5-dichlorophenyl)-N-[4-[(4-methylthio)-1-piperidinyl]-1(R)-methylbutyl]benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-4-bromobutyl]benzenesulfonamide with 4-(methylthio)-piperidine. Yield= 88%; MS (ESI+), 535 (M+H)$^+$.

EXAMPLE 83

4-Chloro-N-(2,5-dichlorophenyl)-N-[4-[(4-methylsulfonyl)-1-piperidinyl]-1(R)-methylbutyl]benzenesulfonamide

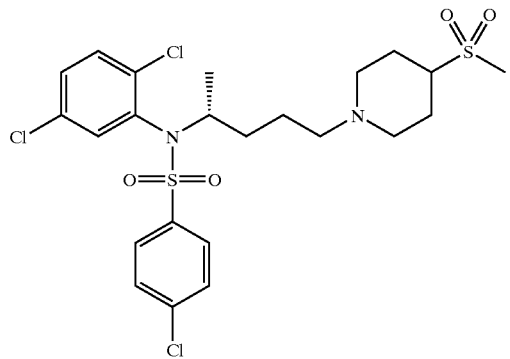

4-chloro-N-(2,5-dichlorophenyl)-N-[4[(4-methylsulfonyl)-1-piperidinyl]-1(R)-methylbutyl]-benzenesulfonamide was prepared analogous to 4-chloro-N-(2,5-dichlorophenyl])—N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl]4-bromobutyl]benzenesulfonamide with 4-(methylsulfonyl)-piperidine. Yield=92%; MS (ESI+), 567 (M+H)$^+$.

EXAMPLE 84

4-Chloro-N-(2,5-dichlorophenyl)-N-[4-[(3-methylthio)-1-piperidinyl-1(R)-methylbutyl]benzenesulfonamide

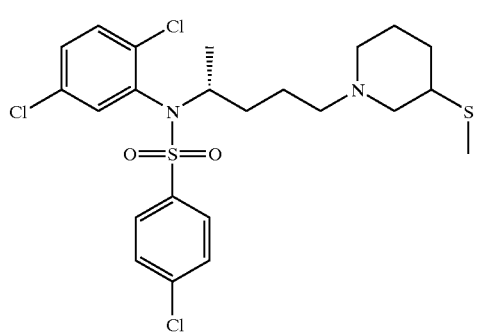

4-chloro-N-(2,5-dichlorophenyl)-N-[4-[(3-methylthio)-1-piperidinyl]-1(R)-methylbutyl]-benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-4-bromobutyl]benzenesulfonamide with 3-(methylthio)piperidine. Yield= 89%; MS (ESI+), 535 (M+H)$^+$.

EXAMPLE 85

4-Chloro-(2,5-dichlorophenyl)-N-[4-[(3-methylsulfonyl)-1-piperidinyl]-1(R)-methylbutyl]benzenesulfonamide 4-chloro-N-(2,5-dichlorophenyl)-N-[4-[(3-methylsulfonyl)-1-piperidinyl]-1(R)-methylbutyl]-benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-4-bromobutyl]benzenesulfonamide with 3-(methylsulfonyl)-piperidine. Yield=93%; MS (ESI+), 567 (M+H)$^+$.

EXAMPLE 86

4-Chloro-N-(2,5-dichlorophenyl)-N-[4-[(3-methylthio)-1-pyrrolidinyl]-1(R)-methylbutyl]benzenesulfonamide

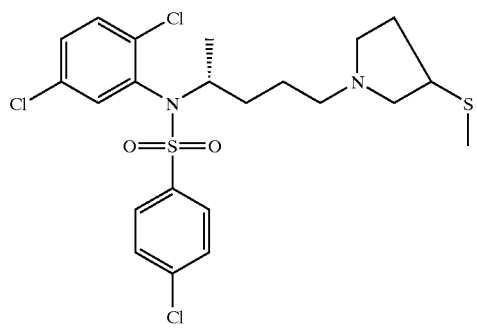

4-chloro-N-(2,5-dichlorophenyl)-N-[4[(3-methylthio)-1-pyrrolidinyl]-1(R)-methylbutyl]benzenesulfonamide was prepared analogous to 4-chloro-N-(2,5-dichlorophenyl)-N-(3-(2-((methylsulfonyl)methyl)-1-piperidinyl-1(R)-methylpropyl)benzenesulfonamide by reacting 4-chloro-N-[2,5-dichlorophenyl]-N-[(R)-1-methyl-4-bromobutyl]benzenesulfonamide with 3-(methylthio)-pyrrolidine. Yield=86%; MS (ESI+), 521 (M+H)$^+$.

EXAMPLE 87

4-Chloro-N-(2,5-dichlorophenyl)-N-[4-[(3-methylsulfonyl)-1-pyrrolidinyl]-1(R) methylbutyl]benzenesulfonamide

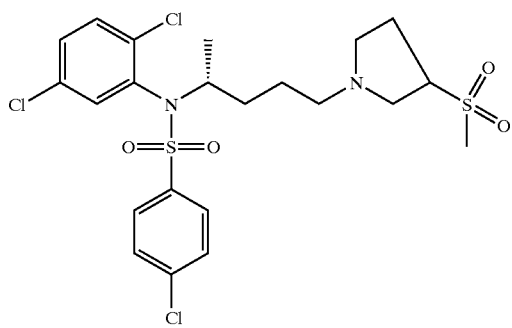

4-chloro-N{2,5-dichlorophenyl)-N-[4-[(3-methylsulfonyl)-1-pyrrolidinyl]-1(R)-methylbutyl]-benzenesulfonamide was prepared analogous to 4-chloro-N-(2,5-dichlorophenyl)-N-3-(2-((methylsulfonyl)methyl)-1-piperidinyl)-1(R)-methylpropyl)benzenesulfonamide by reacting 4-chloro-N-[2,5-dichlorophenyl-N-[(R)-1-methyl-4-bromobutyl]benzenesulfonamide with 3-(methylsulfonyl)-pyrrolidine. Yield=88%; MS (ESI+), 553 (M+H)$^+$.

EXAMPLE 88

4-Chloro-N-(2,5-dichlorophenyl)-N-(4-(2-(((R)methylsulfonyl)methyl)-1-pyrrolidinyl)-1(R)-methylbutyl)benzenesulfonamide

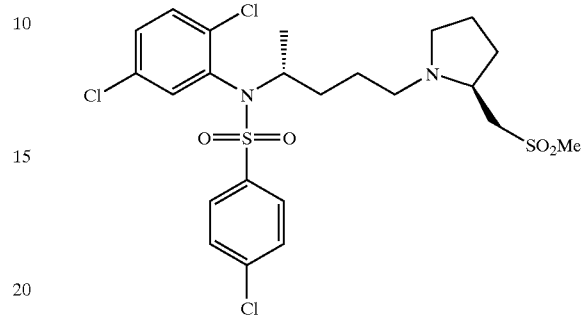

4-chloro-N-(2,5-dichlorophenyl)-N-(4-(2-(((R)-methylsulfonyl)methyl)-1-pyrrolidinyl)-1(R)-methylbutyl)benzenesulfonamide was prepared analogous to 4-chloro-N-(2,5-dichlorophenyl)-N-(3-(2-((methylsulfonyl)methyl)-1-piperidinyl)-1(R)methylpropyl)benzenesulfonamide by reacting 4-chloro-N-[2,5-dichlorophenyl]-N-[(R)-1-methyl-4-bromobutyl]benzenesulfonamide with (R)-2-(methylsulfonyl])methyl)pyrrolidine. Yield=10%; yellow oil: IR (neat, CH$_2$Cl$_2$) 1349, 1301, 1166, 1130, 1094, 622, cm$^{-1}$; MS (ESI+), 569 (M+H)$^+$.

EXAMPLE 89

4-Chloro-N-(2,5-dichlorophenyl)-N-(4-(2-(((S)-methylsulfonyl)methyl)-1-pyrrolidinyl)-1(R)-methylbutyl)benzenesulfonamide

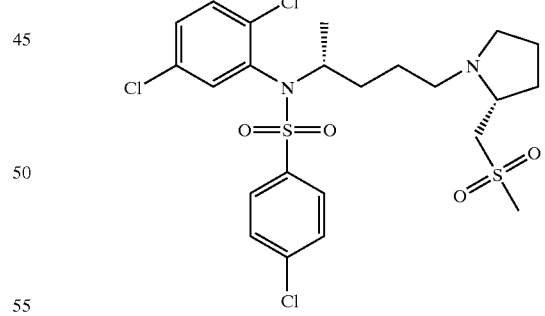

4-chloro-N-(2,5-dichlorophenyl)-N-(4-(2-(((S)-methylsulfonyl)methyl)—pyrrolidinyl)-1(R)-methylbutyl)benzenesulfonamide was prepared analogous to 4-chloro-N-2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R) 1-methyl-4-bromobutyl]benzenesulfonamide with (S)-(2-(methylsulfonyl)methyl)pyrrolidine. Yield=43%; yellow oil: IR (neat, CH$_2$Cl$_2$) 1467, 1350, 1302, 1167, 1094, 622, cm$^{-1}$; MS (ESI+), 569 (M+H)$^+$.

EXAMPLE 90

4-Chloro-N-2,5-dichlorophenyl)-N-[5-[3-[(methylsulfonyl)methyl]-1-piperidinyl]-1(R)-methylpentyl]benzenesulfonamide

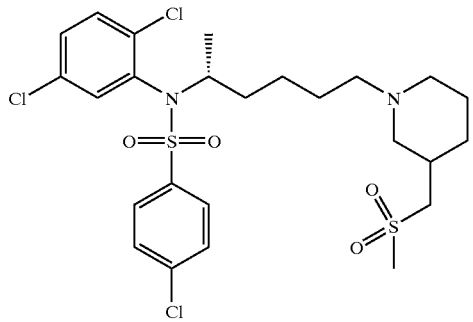

4-chloro-N-(2,5-dichlorophenyl)-N-[5-[[3-(methylsulfonyl)methyl]-1-piperidinyl]]-1(R)-methylpentyl]benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-5-bromopentyl]benzenesulfonamide with 3-(methylsulfonylmethyl)piperidine. Yield=74%; MS (ESI+), 595 (M+H)+.

EXAMPLE 91

4-Chloro-N-(2,5-dichlorophenyl)-N-[5-[(4-methylsulfonyl)-1-piperidinyl-1(R)-methylpentyl]benzenesulfonamide

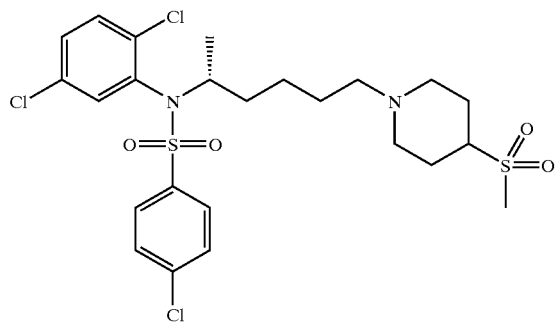

4-chloro-N-(2,5-dichlorophenyl)-N-[5-[(4-methylsulfonyl)-1-piperidinyl]-1(R)-methylpentyl]-benzenesulfonamide was prepared analogous to 4-chloro-N-(2,5-dichlorophenyl)-N-(3-(2-((methylsulfonyl)methyl 1-piperidinyl)-1(R)-methylpropyl)benzenesulfonamide by reacting 4-chloro-N-[2,5-dichlorophenyl]-N-[(R)-1-methyl-5-bromopentyl]benzenesulfonamide with 4-methylsulfonyl)-piperidine. Yield=79%; MS (ESI+), 581 (M+H)+.

EXAMPLE 92

4-Chloro-N-(2,5-dichlorophenyl)-N-[5-[(3-methylsulfonyl)-1-piperidinyl]-1(R)-methylpentyl]benzenesulfonamide

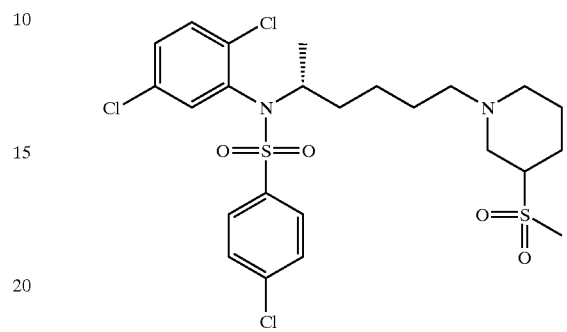

4-chloro-N-(2,5-dichlorophenyl)-N-[5-[(3-methylthsulfonyl)-1-piperidinyl]-1(R)-methylpentyl]benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-5-bromopentyl]benzenesulfonamide with 3-(methylsulfonyl)-piperidine. Yield=82%; MS (ESI+), 581 (M+H)+.

EXAMPLE 93

4-Chloro-N-(2,5-dichlorophenyl)-N-[5-[(3-methylsulfonyl)-1-pyrrolidinyl]-1(R)-methylpentyl]benzenesulfonamide

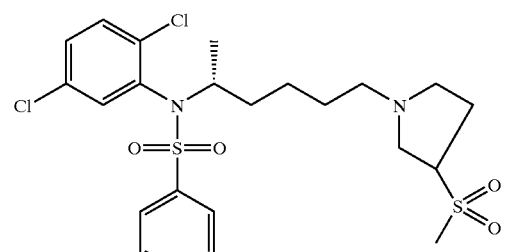

4-chloro-N-(2,5-dichlorophenyl)-N-[5-[(3-methylthsulfonyl)-1-pyrrolidinyl]-1(R)-methylpentyl]benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-5-bromopentyl]benzenesulfonamide with 3-(methylsulfonyl)-pyrrolidine. Yield=72%; MS (ESI+), 567 (M+H)+.

EXAMPLE 94

4-Chloro-N-(2,5-dichlorophenyl)-N-(5-(4-((methylsulfonyl)methyl)-1-piperidinyl)-1(R)-methylpentyl)benzenesulfonamide

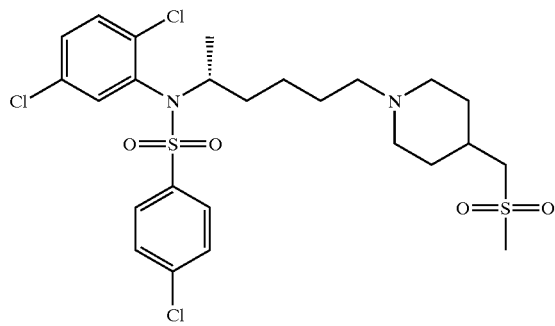

4-chloro-N-(2,5-dichlorophenyl)-N-[5-[[4-(methylsulfonyl)methyl]-1-piperidinyl]-1(R)-methylpentyl] benzenesulfonamide was prepared analogous to 4-chloro-N-(2,5-dichlorophenyl)-N-(3-(2-((methylsulfonyl)methyl)-1-piperidinyl)-1(R)methylpropyl)benzenesulfonamide by reacting 4-chloro-N-[2,5-dichlorophenyl]-N-[(R) 1-methyl-5-bromopentyl]benzenesulfonamide with 4-(methylsulfonylmethyl)piperidine. Yield=68%; yellow oil: IR (neat, CH$_2$Cl$_2$) 1467, 1301, 1166, 1136, 1093, 622 cm$^{-1}$; MS (ESI+), 595 (M+H)$^+$.

EXAMPLE 95

4-Chloro-N-(2,5-dichlorophenyl)-N-(5-(2-(methylsulfonyl)methyl)-1-piperidinyl)-1(R)-methylpentyl)benzenesulfonamide

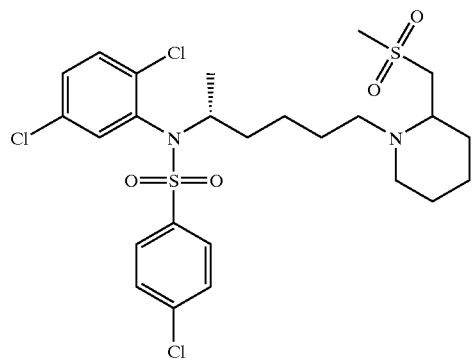

4-chloro-N-(2,5-dichlorophenyl)-N-[5-[[2-(methylsulfonyl)methyl]-1-piperidinyl-1(R)-methylpentyl] benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-5-bromopentyl]benzenesulfonamide with 2-(methylsulfonylmethyl)piperidine. Yield=73%; yellow oil: IR (neat, CH$_2$Cl$_2$) 1467, 1297, 1166, 1139, 1094, 623, cm$^{-1}$; MS (ESI+), 595 (M+H)$^+$.

EXAMPLE 96

4-Chloro-N-(2,5-dichlorophenyl)-N-(3-(2-carboxymethyl-3-thiazolidinyl)-1(R)-methylpropyl)benzenesulfonamide

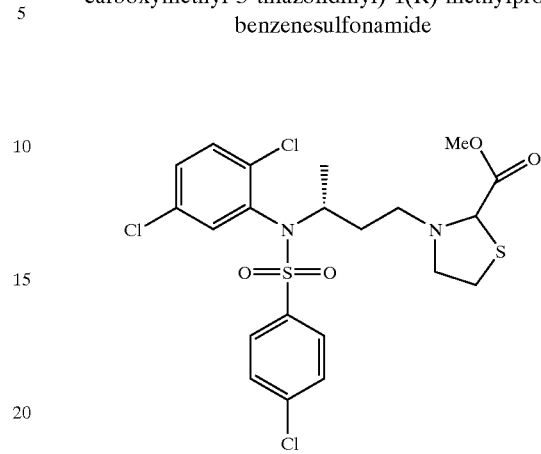

4-chloro-N-2,5-dichlorophenyl)-N-3-(2-carboxymethyl-3-thiazolidinyl)-1(R)-methylpropyl)-benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 2-carboxymethyl-3-thiazolidine. Yield=6%; White powder: IR (KBr) 1747, 1467, 1352, 1166, 1094, 622 cm$^{-1}$; MS (ESI+), 537 (M+H)$^+$.

EXAMPLE 97

4-Chloro-N-(2,5-dichlorophenyl)-N-(3-(2-carboxymethyl-3-thiazolidinyl)-1(R)-methylpropyl)benzenesulfonamide

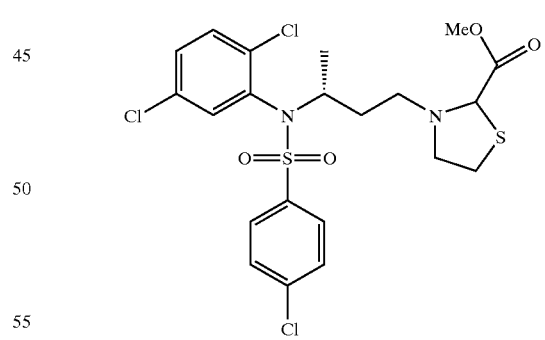

4-chloro-N-(2,5-dichlorophenyl)-N-(3-(2-carboxymethyl-3-thiazolidinyl)-1(R)-methylpropyl)-benzenesulfonamide was prepared analogous to 4-chloro-N-(2,5-dichlorophenyl)-N-(3-(2-((methylsulfonyl)methyl-piperidinyl)-1(R)methylpropyl)benzenesulfonamide by reacting 4-chloro-N-[2,5-dichlorophenyl]-N-[(R)-1-methyl-3-bromopropyl]benzenesulfonamide with 2-carboxymethyl-3-thiazolidine. Yield=7%; White powder: IR (KBr) 1747, 1467, 1352, 1167, 1094, 622 cm$^{-1}$; MS (ESI+), 537 (M+H)$^+$.

EXAMPLE 98

4-Chloro-N-(2,5-dichlorophenyl)-N-(4-(2-carboxymethyl-3-thiazolidinyl)-1(R)-methylbutyl)benzenesulfonamide

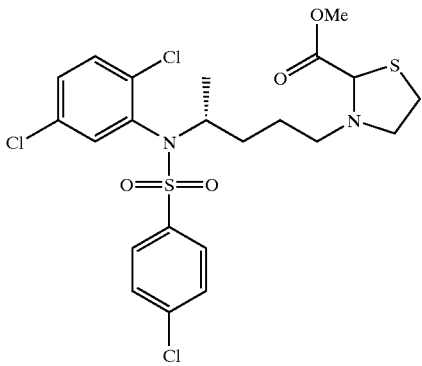

4-chloro-N'-(2,5-dichlorophenyl)-N-(4-(2-carboxymethyl-3-thiazolidinyl)-1(R)-methylbutyl)-benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-4-bromobutyl]benzenesulfonamide with 2-carboxymethyl-3-thiazolidine. Yield=25%; MS (ESI+), 551 (M+H)$^+$.

EXAMPLE 99

4-Chloro-N-(2,5-dichlorophenyl)-N-(5-(2-carboxymethyl-3-thiazolidinyl)-1(R)-methylpentyl)benzenesulfonamide

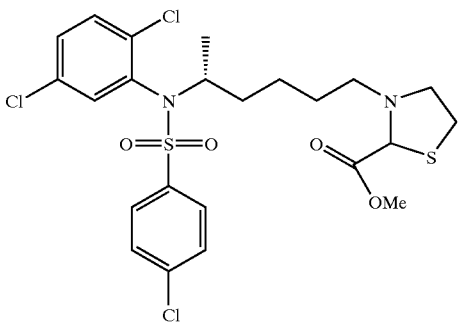

4-chloro-N-(2,5-dichlorophenyl)-N-(5-(2-carboxymethyl-3-thiazolidinyl)-1(R)-methylpentyl)-benzenesulfonamide was prepared analogous to 4-chloro-N-(2,5-dichlorophenyl)-N-(3-(2-((methylsulfonyl)methyl)-1-piperidinyl)-1(R)methylpropyl)benzenesulfonamide by reacting 4-chloro-N-[2,5-dichlorophenyl]-N-[(R)-1-methyl-5-bromopentyl]benzenesulfonamide with 2-carboxymethyl-3-thiazolidine. Yield=39%; Colorless oil: IR (neat, CH$_2$Cl$_2$) 1748, 1467, 1352, 1167, 1095, 623 cm$^{-1}$; MS (ESI+), 565 (M+H)$^+$.

EXAMPLE 100

4-Chloro-N-(2,5-dichlorophenyl)-N-(3-(5-carboxymethyl-3-thiazolidinyl)-1(R)-methylpropyl)benzenesulfonamide-

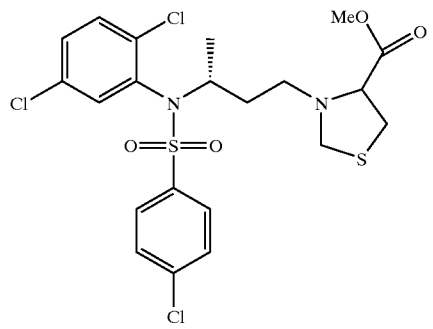

4-chloro-N-(2,5-dichlorophenyl)-N-(3-(5-carboxymethyl-3-thiazolidinyl)-1(R)-methylpropyl)-benzenesulfonamide was prepared analogous to 4-chloro-N-(2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 5-carboxymethyl-3-thiazolidine. Yield=31%; Colorless oil: IR (neat, CH$_2$Cl$_2$) 1742, 1467, 1352, 1167, 1094, 622 cm$^{-1}$; MS (ESI+), 539 (M+H)$^+$.

EXAMPLE 101

4-Chloro-N-(2,5-dichlorophenyl)-N-(3-(5-carboxymethyl-3-thiazolidinyl)-1(R)-methylpropyl)benzenesulfonamide

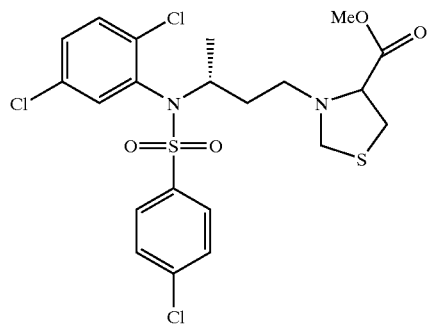

4-chloro-N-(2,5-dichlorophenyl)-N-(3-(5-carboxymethyl-3-thiazolidinyl)-1(R)-methylpropyl)-benzenesulfonamide was prepared analogous to 4-chloro-N-2,5-dichlorophenyl)-N-(3-(2-((methylsulfonyl)methyl)-1-piperidinyl)-1(R)-methylpropyl)benzenesulfonamide by reacting 4-chloro-N-[2,5-dichlorophenyl]-N-[(R)-1-methyl-3-bromopropyl]benzenesulfonamide with 5-carboxymethyl-3-thiazolidine. Yield=21%; Colorless oil: IR (neat, CH$_2$Cl$_2$) 1738, 1467, 1351, 1167, 1095, 622 cm$^{-1}$; MS (ESI+), 539 (M+H)$^+$.

EXAMPLE 102

4-Chloro-N-(2,5-dichlorophenyl)-N-(3-(2-carboxy-3-thiazolidinyl)-1(R)-methylpropyl)benzenesulfonamide

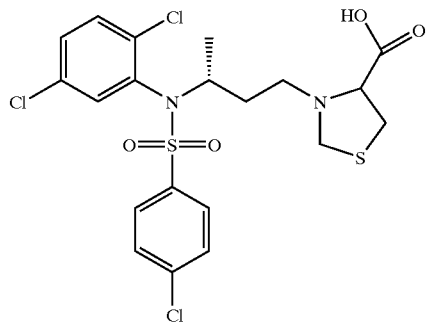

To a stirring solution of 4-chloro-N-(2,5-dichlorophenyl)-N-(3-(2-carboxymethyl-3-thiazolidinyl)-1(R)-methylpropyl)benzenesulfonamide (109 mg, 0.203 mmol) in methanol (20 mL) was added 50% aqueous KOH (1.0 mL) and the mixture was stirred at room temperature for 18 hours. The solvent was removed and the crude mixture was dissolved in $CH_2Cl_2$ and washed with 1N HCl. The $CH_2Cl_2$ layer was dried over $Na_2SO_4$ and evaporated to give crude product. Purification was performed over silica gel using 5–10% methanol in $CH_2Cl_2$ with 0.5% $NH_4OH$ to afford 4-chloro-N-(2,5-dichlorophenyl)-N-(3-(2-carboxy-3-thiazolidinyl)-1(R)-methylpropyl)benzenesulfonamide as a beige foam in 66% yield. IR (KBr) 1467, 1351, 1167, 1094, 753, 622 $cm^{-1}$; MS (ESI+), 523 $(M+H)^+$.

EXAMPLE 103

4-Chloro-N-(2,5-dichlorophenyl-N-(4-(2-carboxy-3-thiazolidinyl)-1(R)-methylbutyl)benzenesulfonamide

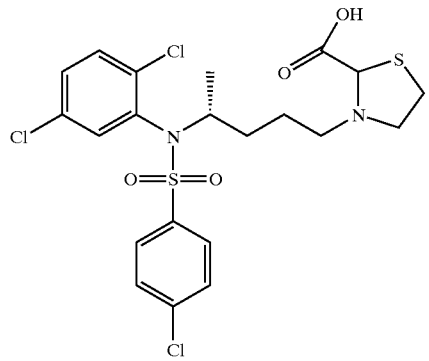

4-chloro-N-(2,5-dichlorophenyl)-N-(4-(2-carboxy-3-thiazolidinyl)-1(R)-methylbutyl)benzenesulfonamide was prepared analogous to 4-chloro-N-(2,5-dichlorophenyl)-N-(3-(2-carboxy-3-thiazolidinyl)-1(R)-methylpropyl)benzenesulfonamide by reacting 4-chloro-N-(2,5-dichlorophenyl)-N-(4-(2-carboxymethyl-3-thiazolidinyl)-1(R)-methylbutyl)benzenesulfonamide with 50% aqueous KOH. Yield=77%; White foam: IR (KBr) 1467, 1351, 1167, 1093, 753, 622 $cm^{-1}$; MS (ESI+), 537 $(M+H)^+$.

EXAMPLE, 104

4-Chloro-N-(2,5-dichlorophenyl)-N-(5-(2-carboy-3-thiazolidinyl)-1(R)-methylpentyl)benzenesulfonamide

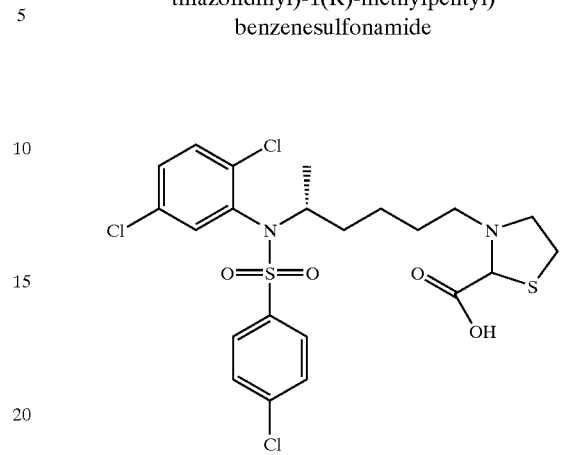

4-chloro-N-(2,5-dichlorophenyl)-N-(5-(2-carboxy-3-thiazolidinyl)-1(R)-methylpentyl)benzenesulfonamide was prepared analogous to 4-chloro-N-(2,5-dichlorophenyl)-N-(3-(2-carboxy-3-thiazolidinyl)-1(R)-methylpropyl)benzenesulfonamide by reacting 4-chloro-N-(2,5-dichlorophenyl)-N-(5-(2-carboxymethyl-3-thiazolidinyl)-1(R)-methylpentyl)benzenesulfonamide with 50% aqueous KOH. Yield=67%; White foam: IR (neat, $CH_2Cl_2$) 1467, 1350, 1167, 1093, 753, 622 $cm^{-1}$; MS (ESI+), 553 $(M+H)^+$.

EXAMPLE 105

4-Chloro-N-(2,5-dichlorophenyl)-N-(3-(5-carboxy-3-thiazolidinyl)-1(R)-methylpropyl)benzenesulfonamide

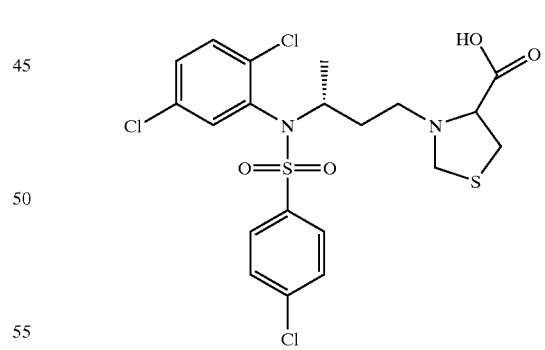

4-chloro-N-(2,5-dichlorophenyl)-N-(3-(5-carboxy-3-thiazolidinyl)-1(R)-methylpropyl)benzenesulfonamide was prepared analogous to 4-chloro-N-2,5-dichlorophenyl)-N-(3-(2-carboxy-3-thiazolidinyl)-1(R)-methylpropyl)benzenesulfonamide by reacting 4-chloro-N-(2,5-dichlorophenyl)-N-(3-(5-carboxymethyl-3-thiazolidinyl)-1(R)-methylpropyl)benzenesulfonamide with 50% aqueous KOH. Yield=70%; White foam: IR (KBr) 1467, 1350, 1167, 1094, 753, 622 $cm^{-1}$; MS (ESI+), 525 $(M+H)^+$.

EXAMPLE 106

4-Chloro-N-5-(2,5-dichlorophenyl)-N-(4-(5-carboxy-3-thiazolidinyl)-1(R)-methylbutyl)benzenesulfonamide

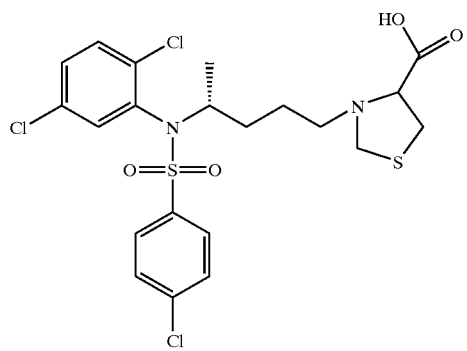

4-chloro-N-(2,5-dichlorophenyl)-N-(4-(5-carboxy-3-thiazolidinyl)-1(R)-methylbutyl)benzenesulfonamide was prepared analogous to 4-chloro-N-(2,5-dichlorophenyl)-N-(3-(2-carboxy-3-thiazolidinyl)-1(R)-methylpropyl)benzenesulfonamide by reacting 4-chloro-N-(2,5-dichlorophenyl)-N-(4-(5-carboxymethyl-3-thiazolidinyl)-1(R)-methylbutyl)benzenesulfonamide with 50% aqueous KOH. Yield=45%; White powder: IR (KBr) 1467, 1350, 1167, 1094, 754, 622 cm$^{-1}$; MS (ESI+), 537 (M+H)$^+$.

EXAMPLE 107

4-Chloro-N-(2,5-dichlorophenyl)-N-(5-(5-carboxy-3-thiazolidinyl)-[(R)-methylpentyl)benzenesulfonamide

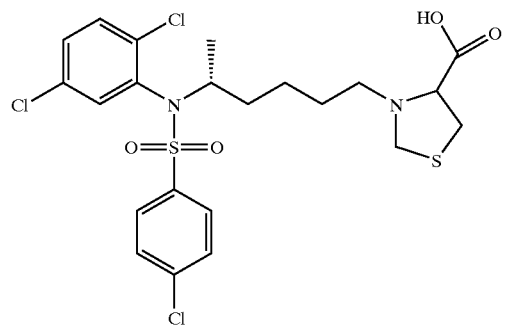

4-chloro-N-(2,5-dichlorophenyl)-N-(5-(5-carboxy-3-thiazolidinyl)-1(R)-methylpentyl)benzenesulfonamide was prepared analogous to 4-chloro-N-(2,5-dichlorophenyl)-N-(3-(2-carboxy-3-thiazolidinyl)-1(R)-methylpropyl)benzenesulfonamide by reacting 4-chloro-N-(2,5-dichlorophenyl)-N-(5-(5-carboxymethyl-3-thiazolidinyl)-1(R)-methylpentyl)benzenesulfonamide with 50% aqueous KOH, Yield=34%; White powder: IR (KBr) 1467, 1350, 1167, 1094, 754, 623 cm$^{-1}$; MS (ESI+), 551 (M+H)$^+$.

EXAMPLE 108

4-Chloro-N-(2,5-dichlorophenyl)-N-[5-[N-(2,5-dichlorophenyl)-N-[(4-chlorophenyl)sulfonyl]amino]-1(R)-methylpentyl]benzenesulfonamide

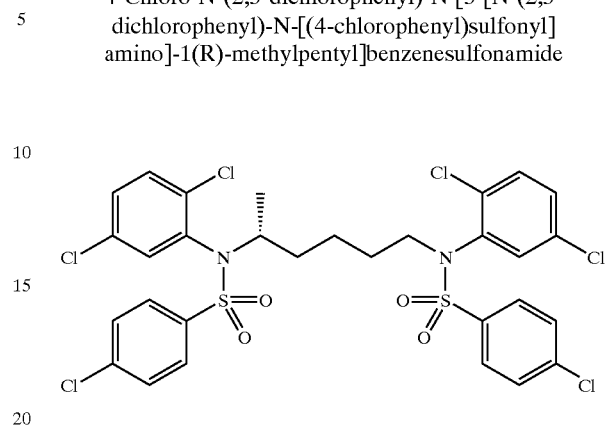

4-chloro-N-(2,5-dichlorophenyl)-N-[5-[N-(2,5-dichlorophenyl)-N-[(4-chlorophenyl)-sulfonyl]amino]-1(R)-methylpentyl]benzenesulfonamide was prepared analogous to 4-chloro-N-(2,5-dichlorophenyl)-N-[4-[[4-(methylsulfonyl)methyl]-1-piperidinyl]-1(R)-methylbutyl]benzenesulfonamide by reacting 4-chloro-N-(2,5-dichlorophenyl)-N-[4-bromo-1(R)-methylbutyl]benzenesulfonamide with 4-chloro-N-(2,5-dichlorophenyl)benzenesulfonamide. Yield=20%; MS (ESI+), 771 (M+NH$_3$)$^+$.

EXAMPLE 109

4-Chloro-N-(5-chloro-2-fluorophenyl)-N-[4-[(methylsulfonyl)amino]-1(R)-methylbutyl]benzenesulfonamide

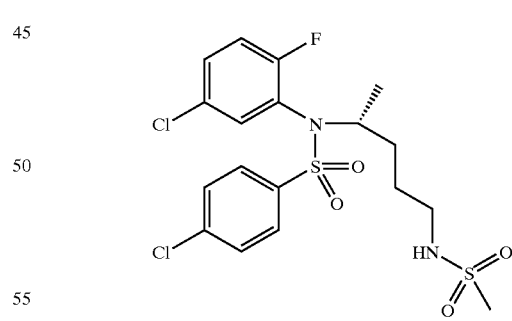

4-chloro-N-(5-chloro-2-fluorophenyl)-N-[4-[(methylsulfonyl)amino]-1(R)-methylbutyl]-benzenesulfonamide was prepared analogous to 4-chloro-N-(2,5-dichlorophenyl)-N-[4-[[4 (methylsulfonyl)methyl]-1-piperidinyl]-1(R)-methylbutyl]benzenesulfonamide by reacting 4-chloro-N-(5-chloro-2-fluorophenyl)-N-[4-bromo-1(R)-methylbutyl]benzenesulfonamide with methanesulfonamide. Yield=89%; MS (ESI+), 483 (M+H)$^+$.

EXAMPLE 110

4-Chloro-N-(5-chloro-2-fluorophenyl)-N-4-[(methylsulfonyl)methylamino]-1(R)-methylbutyl]benzenesulfonamide

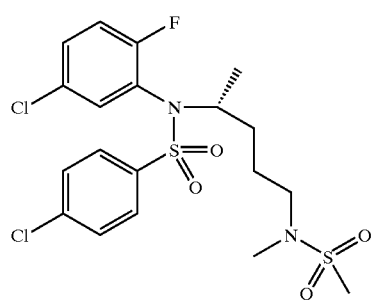

4-chloro-N-(5-chloro-2-fluorophenyl)-N-[4-[(methylsulfonyl)methylamino]-1(R)methylbutyl]-benzenesulfonamide was prepared analogous to 4-chloro-N-(2,5-dichlorophenyl)-N-[4-[[4-(methylsulfonyl)methyl]-1-piperidinyl]-1(R)-methylbutyl]benzenesulfonamide by reacting 4-chloro-N-(5-chloro-2-fluorophenyl)-N-[4-bromo-1(R)-methylbutyl]benzenesulfonamide with N-methyl-methanesulfonamide. Yield=81%; MS (ESI+), 497 (M+H)$^+$.

EXAMPLE 111

4-Chloro-N-(5-chloro-2-fluorophenyl)-N-[4-(4-morpholinyl)-1(R)-methylbutyl]benzenesulfonamide

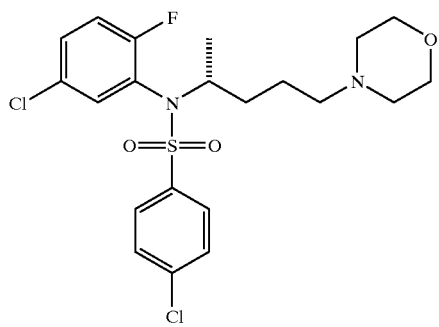

4-chloro-N-(5-chloro-2-fluorophenyl)-N-[4-(morpholinyl)-1(R)-methylbutyl]benzenesulfonamide was prepared analogous to 4-chloro-N-(2,5-dichlorophenyl)-N-[4-[[4-(methylsulfonyl)methyl]-1-piperidinyl]-1(R)-methylbutyl]benzenesulfonamide by reacting 4-chloro-N-(5-chloro-2-fluorophenyl)-N-[4-bromo-1(R)-methylbutyl]benzenesulfonamide with morpholine. Yield=87%; MS (ESI+), 475 (M+H)$^+$.

EXAMPLE 112

4-Chloro-N-(2,5-dichlorophenyl)-N-[4-nitro-1(R)-methylbutyl]benzenesulfonamide

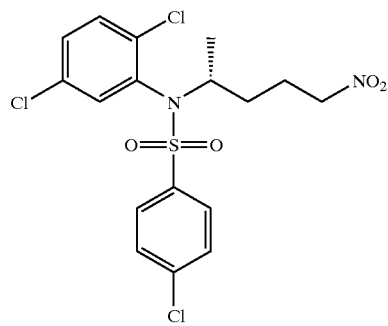

To a solution of 4-chloro-n-(2,5-dichlorophenyl)-n-[(r)-1-methyl-4-bromobutyl]benzenesulfonamide (0.216 g, 0.444 mmol) in ether (4 mL) was added AgNO$_2$ (0.410 g, 2.67 mmol) at 22° C. The resulting mixture was allowed to stir at 22° C. for 4 days and the mixture was filtered and concentrated under reduced pressure. Silica get chromatography (1:9 ethyl acetate:hexanes) of the concentrate afforded 0.129 g of 4-chloro-N-(2,5-dichlorophenyl)-N-[(R)-1-methyl-4-nitrobutyl]-benzenesulfonamide as a light brown oil in 64% yield. MS (ESI) 451.1 (M+h).

EXAMPLE 113

4-Chloro-N-(2,5-difluorophenyl-N-[4-nitro-1(R)-methylbutyl]benzenesulfonamide

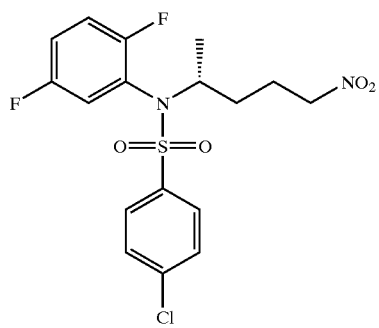

To a solution of 4-chloro-N-(2,5-difluorophenyl)-N-[(R)-1-methyl-4-bromobutyl]benzenesulfonamide (0.194 g, 0.427 mmol) in ether (4 mL) was added AgNO$_2$ (0.395 g, 2.56 mmol) at 22° C. The resulting mixture was allowed to stir at 22° C. for 4 days. The mixture was filtered and concentrated under reduced pressure. Silica gel chromatography (1:9 ethyl acetate:hexanes) of the concentrate afforded 0.0913 g of 4-chloro-N-(2,5-difluorophenyl)-N-[(R)-1-methyl-4-nitrobutyl]]-benzenesulfonamide as a light brown oil in 50% yield. MS (ESI) 419.1 (M+H).

EXAMPLE 114

4-Chloro-N-(5-chloro-2-fluorophenyl)-N-[4-nitro-1(R)-methylbutyl]benzenesulfon-amide

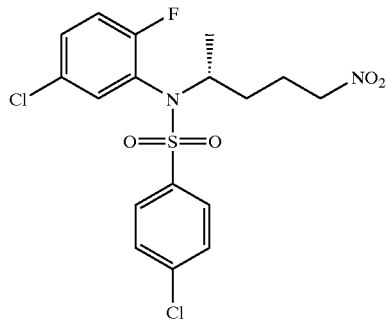

To a solution of 4-chloro-N-(5-chloro-2-fluorophenyl)-N-[(R)-1-methyl-4-bromobutyl]-benzenesulfonamide (0.150 g, 0.320 mmol) in ether (4 mL) was added $AgNO_2$ (0.296 g, 1.92 mmol) at 22° C. The resulting mixture was allowed to stir at 22° C. for 4 days. The mixture was filtered and concentrated under reduced pressure. Silica gel chromatography (1:9 ethyl acetate:hexanes) of the concentrate afforded 0.0746 g of 4-chloro-N-(5-chloro-2-fluorophenyl)-N-[(R)-1-methyl-4-nitrobutyl]benzenesulfonamide as a light brown oil in 53% yield. MS (ESI) 435.1 (M+H).

EXAMPLE 115

4-Chloro-N-[2,5-dichlorophenyl]-N-[(R)-1-methyl(acetylamino)butyl]benzenesulfonamide

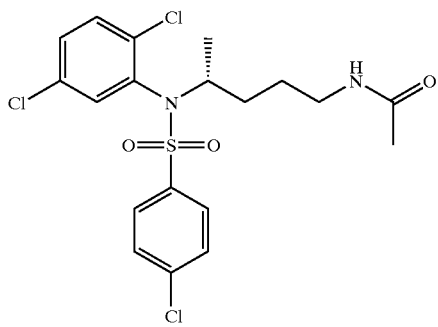

To a solution of 4-chloro-N-[2,5-dichlorophenyl]-N-[R]-1-methyl-4-aminobutyl]benzenesulfonamide (35.0 mg, 0.083 mmol) in $CH_2Cl_2$ (2 mL) was added acetic anhydride (0.024 mL, 0.249 mmol) and pyridine (0.027 mL, 0.332 mmol) at 0° C. The resulting mixture was allowed to stir at 22° C. overnight. To the reaction was added sat. sodium bicarbonate (20 mL). The product was extracted with $CH_2Cl_2$ (2×20 mL), dried over $Na_2SO_4$, filtered, and concentrated under reduced pressure. Silica gel chromatography (1:4 ethyl acetate:hexanes) of the concentrate afforded 37.8 mg of 4-chloro-N-[2,5-dichlorophenyl]-N-[(R)-1-methyl-4-acetylamino)butyl]benzenesulfonamide as a colorless oil in 98% yield. MS (ESI) 463 (M+H).

EXAMPLE 116

4-Chloro-N-(2,5-dichlorophenyl)-N-[4-[[[(S)hydroxy]phenylmethyl]carbonyl]amino]-1(R)-methylbutyl]benzenesulfonamide

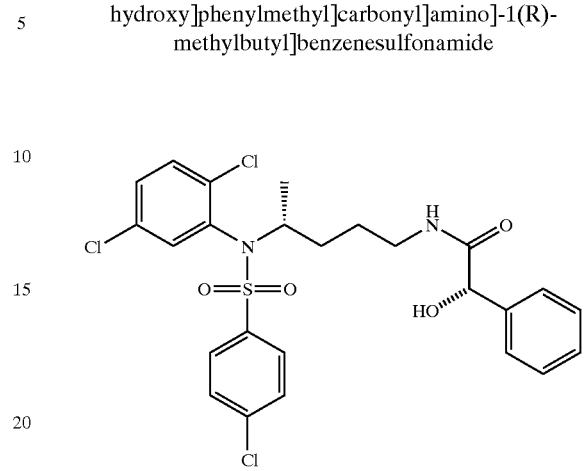

4-chloro-N-(2,5-dichlorophenyl)-N-[4-[[[(S)hydroxy]phenylmethyl]carbonyl]amino]-1(R)-methylbutyl]benzenesulfonamide was prepared analogous to 4-chloro-N-[2,5-dichlorophenyl]-N-[(R)-1-methyl-4-(acetylamino)butyl]benzenesulfonamide by reacting 4-chloro-N-[2,5-dichlorophenyl]-N-[R]-1-methyl-4-aminobutyl]benzenesulfonamide with (S)—O-acetyl-mandelic chloride. Yield=64%; MS (ESI+), 555 $(M+H)^+$.

EXAMPLE 117

4-Chloro-N-(2,5-dichlorophenyl)-N-[4-[[[(R)hydroxy]phenylmethyl]carbonyl]amino]-1(R)methylbutyl]benzenesulfonamide

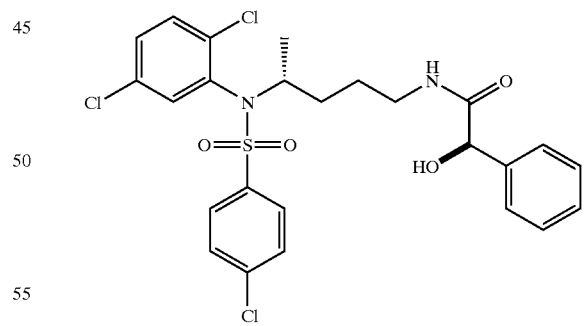

4-chloro-N-(2,5-dichlorophenyl)-N-[4-[[[(R)hydroxy]phenylmethyl]carbonyl]amino]-1(R)-methylbutyl]benzenesulfonamide was prepared analogous to 4-chloro-N-[2,5-dichlorophenyl]-N-[(R)-1-methyl-4-(acetylamino)butyl]benzenesulfonamide by reacting 4-chloro-N-[2,5-dichlorophenyl]-N-[R]-1-methyl-4-aminobutyl]benzenesulfonamide with (O-acetyl-mandelic chloride. Yield=57%; MS (ESI+), 555 $(M+H)^+$.

EXAMPLE 118

4-Chloro-N-(2,5-dichlorophenyl)-N-[4-[[(1,1-dimethylethyl)carbonyl]amino]-1-methylbutyl]benzenesulfonamide

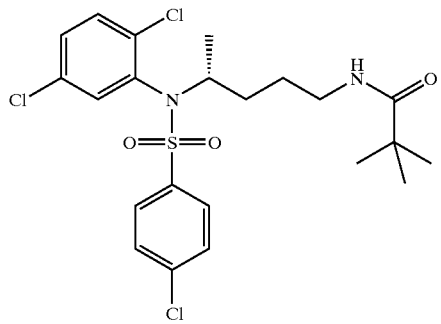

4-chloro-N-(2,5-dichlorophenyl)-N-[4-[[(1,1-dimethylethyl)carbonyl]amino]-1-methylbutyl]benzenesulfonamide was prepared analogous to 4-chloro-N-[2,5-dichlorophenyl]-N-[(R)-1-methyl-4-(acetylamino)butyl]benzenesulfonamide by reacting 4-chloro-N-[2,5-dichlorophenyl]-N-[R]-1-methyl-4-aminobutyl]benzenesulfonamide with pivaloyl chloride. Yield=86%; MS (ESI+), 505 (M+H)$^+$.

EXAMPLE 119

4-Chloro-N-(2,5-dichlorophenyl)-N-[4-[[(phenyl)carbonyl]amino]-1-methylbutyl]benzenesulfonamide

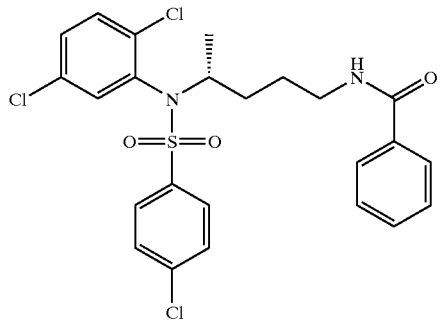

4-chloro-N-2,5-dichlorophenyl)-N-(4-[[(phenyl)carbonyl]amino]-1(R)-methylbutyl]benzenesulfonamide was prepared analogous to 4-chloro-N-[2,5-dichlorophenyl]-N-[(R)-1-methyl-4-(acetylamino)butyl]benzenesulfonamide by reacting 4-chloro-N-[2,5-dichlorophenyl]-N-[R]-1-methyl-4-aminobutyl]benzenesulfonamide with benzoyl chloride. Yield=84%; MS (ESI+), 525 (M+H)$^+$.

EXAMPLE 120

4-Chloro-N-(2,5-dichlorophenyl)-N-[4-[[(methoxy)carbonyl]amino]-1-methylbutyl]benzenesulfonamide

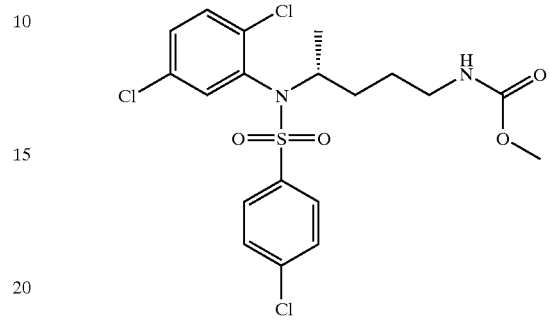

4-chloro-N-2,5-dichlorophenyl)-N-[4-[[(methoxy)carbonyl]amino]-1(R)-methylbutyl]benzenesulfonamide was prepared analogous to 4-chloro-N-[2,5-dichlorophenyl]-N-[(R)-1-methyl-4-(acetylamino)butyl]benzenesulfonamide by reacting 4-chloro-N-[2,5-dichlorophenyl]-N-[R]-1-methyl-4-aminobutyl]benzenesulfonamide with methyl chloroformate. Yield=96%; MS (ESI+), 479 (M+H)$^+$.

EXAMPLE 121

4-Chloro-N-(2,5-dichlorophenyl)-N-[4-[[(1,1-dimethylethoxy)carbonyl]amino]-1-methylbutyl]benzenesulfonamide

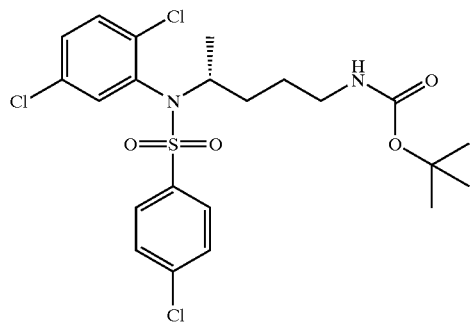

4-chloro-N-(2,5-dichlorophenyl)-N-[4-[[(1,1-dimethylethoxy)phenylmethyl]carbonyl]amino]-1(R)-methylbutyl]benzenesulfonamide was prepared analogous to 4-chloro-N-[2,5-dichlorophenyl]-N-[(R)-1-methyl-4-(acetylamino)butyl]benzenesulfonamide by reacting 4-chloro-N-[2,5-dichlorophenyl]-N-[R]-1-methyl-4-aminobutyl]benzenesulfonamide with di-tert-butyl dicarbonate. Yield=91%; MS (ESI+), 521 (M+H)$^+$.

EXAMPLE 122

4-Chloro-N-(2,5-dichlorophenyl)-N-[4-[[(phenoxy)carbonyl]amino]-1-methylbutyl]benzenesulfonamide

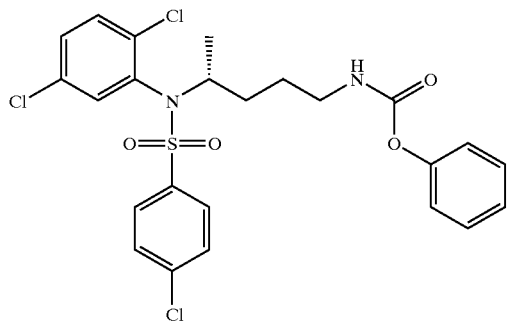

4-chloro-N-(2,5-dichlorophenyl)-N-[4-[[(phenoxy)carbonyl]amino]-1(R)-methylbutyl]benzenesulfonamide was prepared analogous to 4-chloro-N-[2,5-dichlorophenyl]-N-[(R)-1-methyl (acetylamino)butyl] benzenesulfonamide by reacting 4-chloro-N-[2,5-dichlorophenyl]-N-[R]-]-methyl-4-aminobutyl] benzenesulfonamide with phenyl chloroformate. Yield= 82%; MS (ESI+), 541 (M+H)+.

EXAMPLE 123

4-Chloro-N-(2,5-dichlorophenyl)-N-[4-[[(benzoxy)carbonyl]amino]-1-methylbutyl]benzenesulfonamide

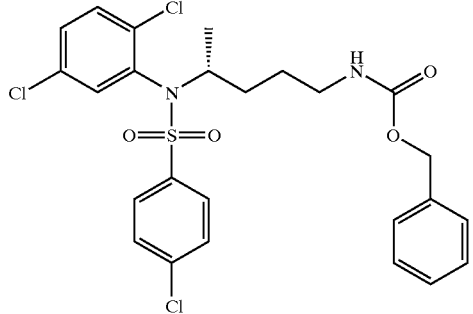

4-chloro-N-(2,5-dichlorophenyl)-N-[4-[[(benzyloxy)carbonyl]amino]-1(R)-methylbutyl]-benzenesulfonamide was prepared analogous to 4-chloro-N-[2,5-dichlorophenyl]-N-[(R)-1-methyl-4-(acetylamino)butyl] benzenesulfonamide by reacting 4-chloro-N-[2,5-dichlorophenyl]-N-[R]-1-methyl-4-aminobutyl] benzenesulfonamide with benzyl chloroformate. Yield= 81%; MS (ESI+), 555 (M+H)+.

EXAMPLE 124

4-Chloro-N-(2,5-dichlorophenyl)-N-[4-(2-isopropoxy-3,4-dioxo-1-cyclobutenyl)amine-1(R)-methylbutyl]benzenesulfonamide

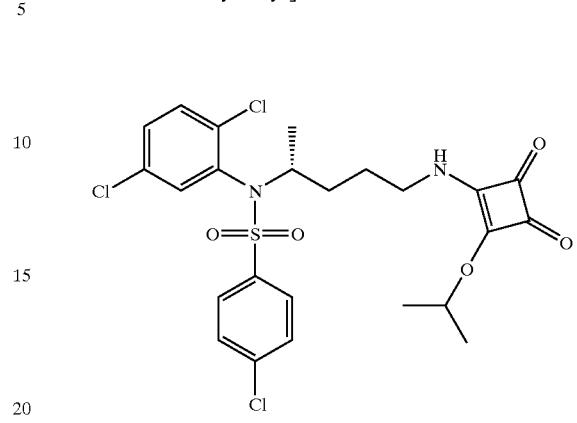

To a solution of 4-chloro-N-(2,5-dichlorophenyl)-N-[(R)-1-methyl-4-aminobutyl]benzenesulfonamide (0.207 g, 0.463 mmol) in THF (3 mL) was added 3,4-diisopropoxy-3-cyclobutene-1,2-dione (0.0963 g, 0.486 mmol) dissolved in THF (2 mL) at 22° C. under nitrogen atmosphere. The resulting mixture was allowed to stir at 22° C. for 12 h. The mixture was concentrated under reduced pressure. Silica gel chromatography (3:7 ethyl acetate:hexanes) of the concentrate afforded 0.135 g of 4-chloro-N-(2,5-dichlorophenyl])-N-[4-(2-isopropoxy-3,4-dioxo-1-cyclobutenyl)amine-1(R)-methylbutyl]benzenesulfonamide as a white solid in 50% yield. MS (ESI) 559.2 (M+H).

EXAMPLE 125

4-Chloro-N-(5-chloro-2-fluorophenyl)-N-[4-(2-isopropoxy-3,4-dioxo-1-cyclobutenyl)amine-1(R)-methylbutyl]benzenesulfonamide

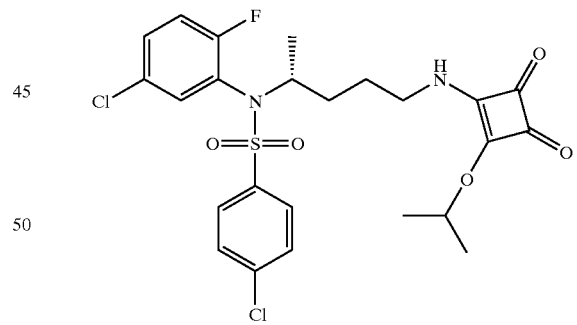

To a solution of 4-chloro-N-(5-chloro-2-fluorophenyl)-N-[(R)-1-methyl-4-aminobutyl]-benzenesulfonamide (0.185 g, 0.455 mmol) in THF (4 mL) was added 3,4-diisopropoxy-3-cyclobutene-1,2-dione (0.0948 g, 0.478 mmol) dissolved in THF (2 mL) at 22° C. under nitrogen atmosphere. The resulting mixture was allowed to stir at 22° C. for 12 h. The mixture was concentrated under reduced pressure. Silica gel chromatography (3:7 ethyl acetate:hexanes) of the concentrate afforded 0.182 g of 4-chloro-N-(5-chloro-2-fluorophenyl)-N-[4-(2-isopropoxy-3,4-dioxo-1-cyclobutenyl)amine-1(R)-methylbutyl]benzenesulfonamide as a white solid in 74% yield. MS (ESI) 543.2 (M+H).

EXAMPLE 126

4-Chloro-N-(2,5-difluorophenyl)-N-[4-(2-isopropoxy-3,4-dioxo-1-cyclobutenyl)amine-1(R)-methylbutyl]benzenesulfonamide

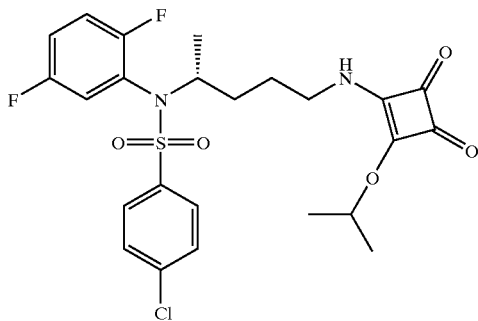

To a solution of 4-chloro-N-(2,5-difluorophenyl)-N-[(R)-1-methyl-4-aminobutyl]benzenesulfonamide (0.243 g, 0.635 mmol) in THF (7 mL) was added 3,4-diisopropoxy-3-cyclobutene-1,2-dione (0.138 g, 0.698 mmol) dissolved in THF (3 mL) at 22° C. under nitrogen atmosphere. The resulting mixture was allowed to stir at 22° C. for 12 h. The mixture was concentrated under reduced pressure. Silica gel chromatography (3:7 ethyl acetate:hexanes) of the concentrate afforded 0.135 g of 4-chloro-N-(2,5-difluorophenyl)-N-4-(2-isopropoxy-3,4-dioxo-1 cyclobutenyl)amine-1(R)-methylbutyl]benzenesulfonamide as a white solid in 47% yield. MS (ESI) 527.2 (M+H).

EXAMPLE 127

4-Chloro-N-(2,5-dichlorophenyl)-N-[4-(2-isopropoxy-3,4-dioxo-1-cyclobutenyl)amine-1(R)-methylpropyl]benzenesulfonamide

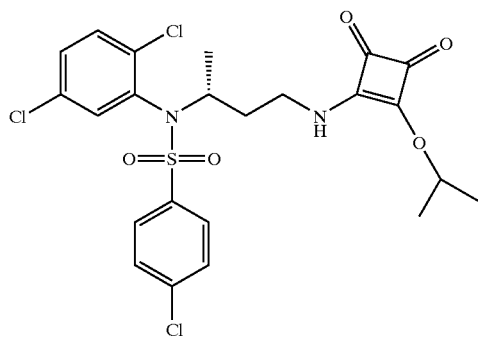

To a solution of 4-chloro-N-(2,5-dichlorophenyl)-N-[(R)-1-methyl-3-aminopropyl]benzenesulfonamide (0.328 g, 0.805 mmol) in THF (6 mL) was added 3,4-diisopropoxy-3-cyclobutene-1,2-dione (0.176 g, 0.885 mmol) dissolved in THF (2 mL) at 22° C. under nitrogen atmosphere. The resulting mixture was allowed to stir at 22° C. for 12 h. The mixture was concentrated under reduced pressure. Silica gel chromatography (3:7 ethyl acetate:hexanes) of the concentrate afforded 0.185 g of 4-chloro-N-2,5-dichlorophenyl)-N-[3-(2-isopropoxy-3,4-dioxo-1-cyclobutenyl)amine-1(R)-methylpropyl]benzene-sulfonamide as a white solid in 80% yield. MS (ESI) 545 (M+H).

EXAMPLE 128

4-Chloro-N-(5-chloro-2-fluorophenyl)-N-[4-(2-isopropoxy-3,4-dioxo-1-cyclobutenyl)amine-1(R)-methylpropyl]benzenesulfonamide

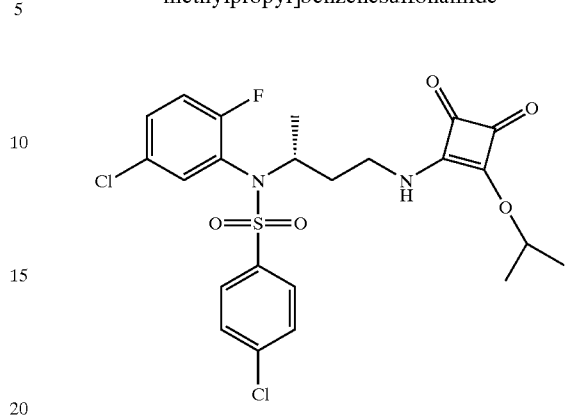

To a solution of 4-chloro-N-(5-chloro-2-fluorophenyl)-N-[(R)-1-methyl-3-aminopropyl]-benzenesulfonamide (0.389 g, 0.995 mmol) in THF (7 mL) was added 3,4-diisopropoxy-3-cyclobutene-1,2-dione (0.217 g, 1.09 mmol) dissolved in THF (3 mL) at 22° C. under nitrogen atmosphere. The resulting mixture was allowed to stir at 22° C. for 12 h. The mixture was concentrated under reduced pressure. Silica gel chromatography (3:7 ethyl acetate:hexanes) of the concentrate afforded 0.243 g of 4-chloro-N-(5-chloro-2-fluorophenyl)-N-[3-(2-isopropoxy-3,4-dioxo-1-cyclobutenyl)amine-1(R)-methylpropyl]benzenesulfonamide as a white solid in 46% yield. MS (ESI) 529.1 (M+H).

EXAMPLE 129

4-Chloro-N-2,5-difluorophenyl)-N-[4-(2-isopropoxy-3,4-dioxo-1-cyclobutenyl)amine-1(R)-methylpropyl]benzenesulfonamide

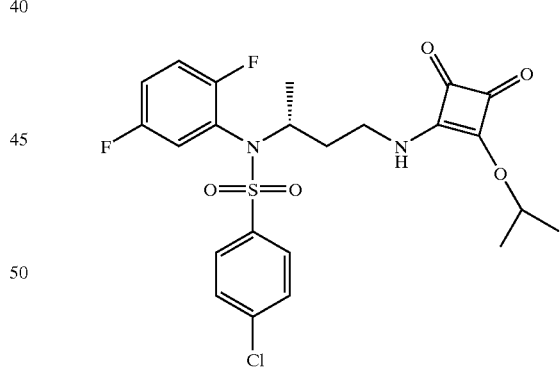

To a solution of 4-chloro-N-(2,5-difluorophenyl)-N-[(R)-1-methyl-3-aminopropyl]benzenesulfonamide (0.401 g, 1.07 mmol) in THF (6 mL) was added 3,4-diisopropoxy-3-cyclobutene-1,2-dione (0.233 g, 1.18 mmol) dissolved in THF (4 mL) at 22° C. under nitrogen atmosphere. The resulting mixture was allowed to stir at 22° C. for 12 h. The mixture was concentrated under reduced pressure. Silica gel chromatography (3:7 ethyl acetate:hexanes) of the concentrate afforded 0.392 g of 4-chloro-N-2,5-difluorophenyl)-N-[3-(2-isopropoxy-3,4-dioxo-1-cyclobutenyl)amine-1(R)-methylpropyl]-benzenesulfonamide as a white solid in 71% yield. MS (ESI) 513.1 (M+H).

EXAMPLE 130

4-Chloro-N-(2,5-dichlorophenyl)-N-[3-[2-[4-chloro-N-(2,5-dichlorophenyl)-N-[(3-amino)-1(R)-methylpropyl]benzenesulfonamide]-3,4-dioxo-1-cyclobutenyl]amine-1(R)-methylpropyl]benzenesulfonamide

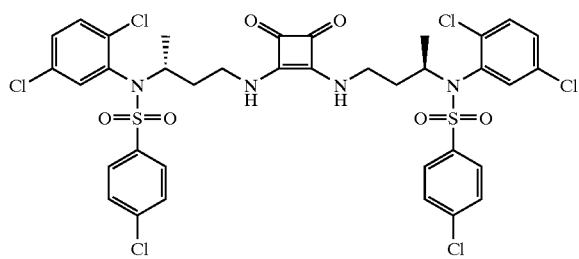

To a solution of 4-chloro-N-(2,5-dichlorophenyl)-N-[(R)-1-methyl-4-aminobutyl]benzenesulfonamide (0.125 g, 0.367 mmol) in methanol (3.0 mL) was added 4-chloro-N-(2,5-dichlorophenyl)-N-[4-(2-isopropoxy-3,4-dioxo-1-cyclobutenyl)amine-1(R)-methylpropyl]benzenesulfonamide (0.167 g, 0.306 mmol) at 22° C. The resulting mixture was heated to reflux for 12 hours. The desired compound precipitated while the mixture cooled to 22° C. The mixture was filtered, washed with ethyl acetate (4 mL×2), and dried under reduced pressure to afford 0.140 g of 4-chloro-N-(2,5-dichlorophenyl)-N-[3-[2-[4-chloro-N-(2,5-dichlorophenyl)-N-[(3-amino)-1(R)-methylpropyl]benzenesulfonamide]-3,4-dioxo-1-cyclobutenyl]amine-1(R)-methylpropyl]benzenesulfonamide as a white solid in 52% yield. MS (ESI) 893.1 (M+H).

EXAMPLE 131

4-Chloro-N-(5-chloro-2-fluorophenyl)-N-[3-[2-[4-chloro-N-(5-chloro-2-fluorophenyl)-N-[(3-amino)-1(R)-methylpropyl]benzenesulfonamide]-3,4-dioxo-1-cyclobutenyl]amine-1(R)-methylpropyl]benzenesulfonamide

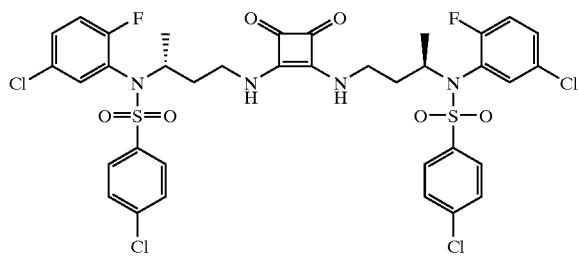

To a solution of 4-chloro-N-(5-fluoro-2-chlorophenyl)-N-[(R)-1-methyl-4-aminobutyl]-benzenesulfonamide (0.189 g, 0.483 mmol) in methanol (4.0 mL) was added 4-chloro-N-(5-fluoro-2-chlorophenyl)-N-[4-(2-isopropoxy-3,4-dioxo-1-cyclobutenyl)-amine-1(R)-methylpropyl]benzenesulfonamide (0.214 g, 0.403 mmol) at 22° C. The resulting mixture was heated to reflux for 12 hours. The desired compound precipitated while the mixture cooled to 22° C. The mixture was filtered, washed with ethyl acetate (4 mL×2), and dried under reduced pressure to afford 0.174 g of 4-chloro-N-(5-chloro-2-fluorophenyl)-N-[3-[2-[4-chloro-N-(5-chloro-2-fluorophenyl)-N-[(3-amino)-1(R)-methylpropyl]benzenesulfonamide]-3,4-dioxo-1-cyclobutenyl]amine-1 (R)-methylpropyl]benzenesulfonamide as a white solid in 50% yield. MS (ESI) 861.1 (M+H).

EXAMPLE 132

4-Chloro-N-(2,5-difluorophenyl)-N-[3-[2-[4-chloro-N-(2,5-difluorophenyl)-N-[(3-amino)-1(R)-methylpropyl]benzenesulfonamide]-3,4-dioxo-1-cyclobutenyl]amine-1(R)-methylpropyl]benzenesulfonamide

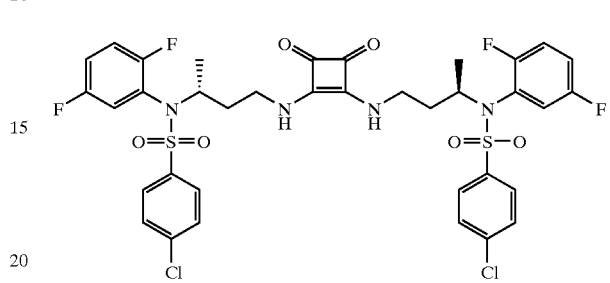

To a solution of 4-chloro-N-(2,5-difluorophenyl)-N-[(R)-1-methyl-4-aminobutyl]-benzenesulfonamide (0.140 g, 0.374 mmol) in methanol (3.0 mL) was added 4-chloro-N-(2,5-difluorophenyl)-N-[4-(2-isopropoxy-3,4-dioxo-1-cyclobutenyl)amine-1(R)-methylpropyl]benzenesulfonamide (0.159 g, 0.311 mmol) at 22° C. The resulting mixture was heated at reflux to 12 hours. The desired compound precipitated while the mixture cooled to 22° C. The mixture was filtered, washed with ethyl acetate (3 mL×2), and dried under reduced pressure to afford 0.124 g of 4-chloro-N-(2,5-difluorophenyl)-N-[3-[2-[4-chloro-N-(2,5-difluorophenyl)-N-[(3-amino)-1(R)-methylpropyl]benzenesulfonamide]-3,4-dioxo-1-cyclobutenyl]amine-1 (R)-methylpropyl]benzenesulfonamide as a white solid in 48% yield. MS (ESI) 5' 827.2 (M+H).

EXAMPLE 133

4-Chloro-N-[5-chloro-2-(hydroxymethyl)phenyl]-N-[4-(ethylthio)]-1-(R)-methylbutyl]benzenesulfonamide

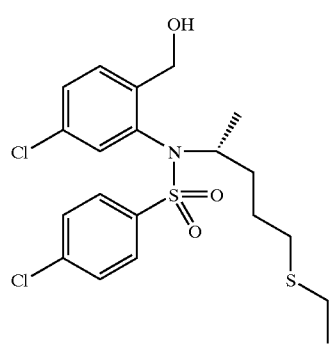

To a solution of 4-chloro-N-[5-chloro-2-(acetoxymethyl)phenyl]-N-[(R)-1-methyl-4-bromobutyl-benzenesulfonamide (0.650 g, 1.24 mmol) in tetrahydrofuran (2 mL) was added sodium thioethoxide (0.115 g, 1.36 mmol) under nitrogen at 0° C. The mixture was stirred overnight at 22° C. The mixture was quenched with 2M NaOH (3 mL), extracted with ethyl ether (2×20 mL), dried over Na$_2$SO$_4$, and filtered. The organic solvent was concentrated under reduced pressure. Silica gel chromatography (1:9 ethyl acetate:hexanes) afforded 0.500 g of 4-chloro-N-[5-chloro-2-(hydroxymethyl)phenyl]-N-[4-(ethylthio)]-1-(R)-methylbutyl]benzenesulfonamide as a yellow oil in 87% yield. MS (ESI+), 462 (M+H)+.

EXAMPLE 134

4-Chloro-N-[5-chloro-2-(hydroxymethyl)phenyl]-N-[1(R)-methyl-(4-methylthio)butyl]benzenesulfonamide

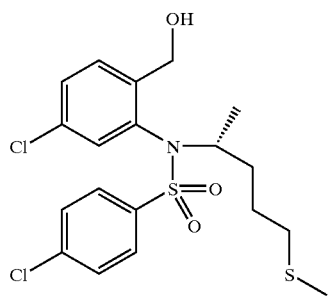

4-chloro-N-[5-chloro-2-(hydroxymethyl)phenyl]-N-[4-(methylthio)]-1R)-methylbutyl]-benzenesulfonamide was prepared analogous to 4-chloro-N-[5-chloro-2-(hydroxymethyl)phenyl]-N-[4-(ethylthio)]-1-(R)-methylbutyl]benzenesulfonamide by reacting 4-chloro-N-[5-chloro-2-(acetoxymethyl)phenyl]-N-[(R)-1-methyl-4-bromobutyl-benzenesulfonamide with sodium thiomethoxide. Yield=77%; MS (ESI+), 448 (M+H)+.

EXAMPLE 135

4-Chloro-N-[5-chloro-2-(hydroxymethyl)phenyl]-N-[1(R)-(methyl-(4-[(1-methylethyl)thio]butyl]benzenesulfonamide

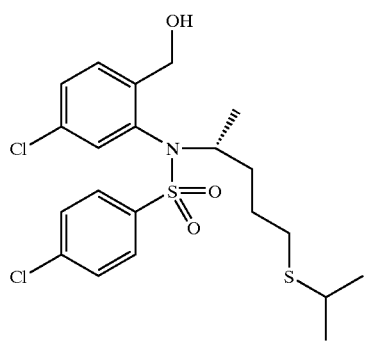

4-chloro-N-[5-chloro-2-(hydroxymethyl)phenyl]-N-[(1-methylethyl)thio]-1-(R)-methylbutyl]-benzenesulfonamide was prepared analogous to 4-chloro-N-[5-chloro-2-(hydroxymethyl)phenyl]-N-[4-(ethylthio)]-1-(R)-methylbutyl]benzenesulfonamide by reacting 4-chloro-N-[5-chloro-2-(acetoxymethyl)phenyl]-N-[(R)-1-methyl-4-bromobutyl-benzenesulfonamide with sodium thio-isopropoxide. Yield=84%; MS (ESI+), 476 (M+H)+.

EXAMPLE 136

4-Chloro-N-[5-chloro-2-hydroxymethyl)phenyl]-N-[1(R)-methyl-(4-[(1,1-dimethylethyl)thio]butyl]benzenesulfonamide

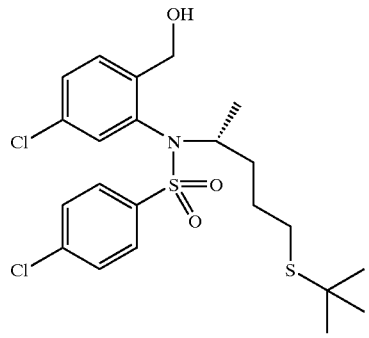

4-chloro-N-[5-chloro-2-(hydroxymethyl)phenyl]-N-[1(R)-methyl-(4-[(1,1-dimethylethyl)thio]butyl]benzenesulfonamide was prepared analogous to 4-chloro-N-[5-chloro-2-(hydroxymethyl)phenyl]-N-[4-(ethylthio)]-1-(R)-methylbutyl]benzenesulfonamide by reacting 4-chloro-N-[5-chloro-2-(acetoxymethyl)phenyl]-N-[(R)-1-methyl-4-bromobutyl-benzenesulfonamide with sodium thio-tert-butoxide. Yield=84%; MS (ESI+), 490 (M+H)+.

EXAMPLE 137

4-Chloro-N-[5-chloro-2-(hydroxymethyl)phenyl]-N-[1(R)-methyl-(4-phenylthio)butyl]benzenesulfonamide

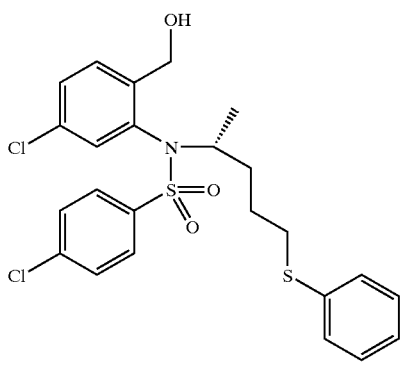

4-chloro-N-[5-chloro-2-(hydroxymethyl)phenyl]-N-[4-(phenylthio)]-1-(R)-methylbutyl]benzenesulfonamide was prepared analogous to 4-chloro-N-[5-chloro-2-(hydroxymethyl)phenyl]-N-[4-(ethylthio)]-1-(R) methylbutyl]benzenesulfonamide by reacting 4-chloro-N-[5-chloro-2-(acetoxymethyl)phenyl]-N-[(R)-1-methyl-4-bromobutyl-benzenesulfonamide with sodium thiophenoxide. Yield=79/o; MS (ESI+), 510 (M+H)+.

EXAMPLE 138

4-Ethylthio-N-[5-chloro-2-(hydroxymethyl)phenyl]-N-[1(R)-methyl-(4-ethylthio)butyl]benzenesulfonamide

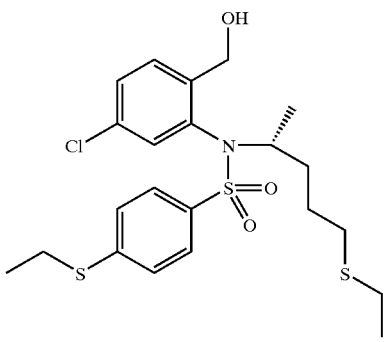

To a solution of 4-chloro-N-[5-chloro-2-(acetoxymethyl)phenyl}-N-[(R)-1-methyl-4-bromobutyl]benzenesulfonamide (1.00 g, 1.91 mmol) in DMF (4 mL) was added sodium thioethoxide (0.535 g, 7.63 mmol) under nitrogen at 0° C. The mixture was stirred overnight at 22° C. The mixture was quenched with $H_2O$ (3 mL), extracted with ethyl ether (2×20 mL), dried over $Na_2SO_4$, and filtered. The organic solvent was concentrated under reduced pressure. Silica gel chromatography (1:9 ethyl acetate:hexanes) afforded 0.123 g of 4-ethylthio-N-[5-chloro-2-(hydroxymethyl)phenyl]-N-[4-(ethylthio)]-1-(R)-methylbutyl]benzenesulfonamide as a yellow oil in 14% yield. MS (ESI+), 488 (M+H)+.

EXAMPLE 139

4-Chloro-N-[5-chloro-2-(hydroxymethyl)phenyl]-N-[4-[ethyl)sulfonyl]-1-(R)-methylbutyl]benzenesulfonamide

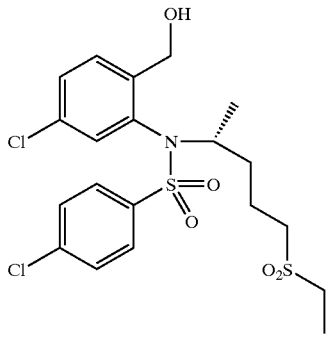

4-Chloro-N-[5-chloro-2-(hydroxymethyl)phenyl]-N-[4-(ethyl)sulfinyl]-1-(R)-methylbutyl]benzenesulfonamide

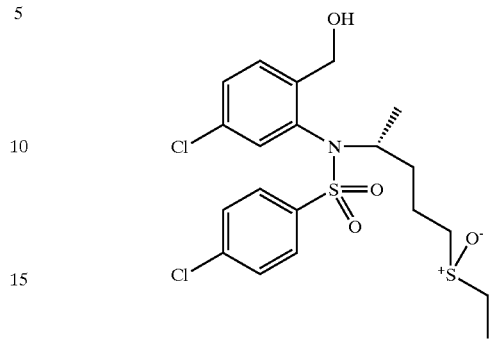

To a solution of 4-chloro-N-[5-chloro-2-(hydroxymethyl phenyl]-N-[4-(ethylthio)]-1-(R)-methylbutyl]benzenesulfonamide (0.088 g, 0.190 mmol) in $CH_2Cl_2$ (2 mL) was added 80% 3-chloroperoxybezoic acid (0.062 g, 0.285 mmol) at 0° C. Stirring was continued for 2 h at 22° C. The mixture was quenched with $H_2O$ (10 mL), extracted with $CH_2Cl_2$ (2×20 mL), dried over $Na_2SO_4$, and filtered. Solvent was concentrated under reduced pressure to afford a yellow oil. Silica gel chromatography (2% methanol:$CH_2Cl_2$, 5% methanol:$CH_2Cl_2$) gave 48.7 mg of 4-chloro-N-[5-chloro-2-(hydroxymethyl)phenyl]-N-[4-[(ethyl)sulfonyl]-1-(R)-methylbutyl]benzenesulfonamide in 52% yield and 39.8 mg of 4-chloro N-[5-chloro-2-(hydroxymethyl)phenyl]-N-[4-[ethyl)sulfinyl]-1-(R)-methylbutyl]benzenesulfonamide in 44% yield; MS (ESI) 494 (M+1); MS (ESI) 478 (M+1).

EXAMPLE 140

4-Chloro-N-[5-chloro-2-(hydroxymethyl)phenyl]-N-[1(R)-methyl-(4-methylsulfinyl)butyl]benzenesulfonamide

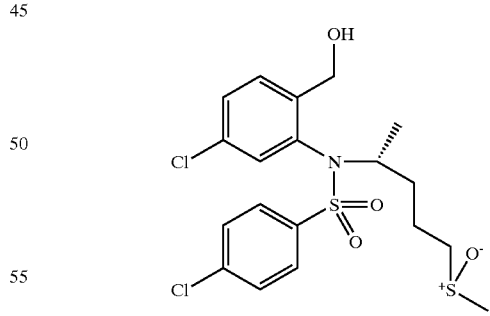

4-chloro-N-[5-chloro-2-(hydroxymethyl)phenyl]-N-[1(R)-methyl-(4-methylsulfinyl)butyl]-benzenesulfonamide was prepared analogous to 4-chloro-N-[5-chloro-2-(hydroxymethyl)phenyl]-N-[4-(ethyl)sulfinyl]-1-(R)-methylbutyl]benzenesulfonamide by reacting 4-chloro-N-[5-chloro-2-(hydroxymethyl)phenyl]-N-[4-methylthio)]-1-(R)-methylbutyl]benzenesulfonamide with 3-chloroperoxybezoic acid. Yield=61%; MS (ESI+), 464 (M+H)+.

EXAMPLE 141

4-Chloro-N-[5-chloro-2-(hydroxymethyl)phenyl]-N-[1(R)-methyl-(4-methylsulfonyl)butyl]benzenesulfonamide

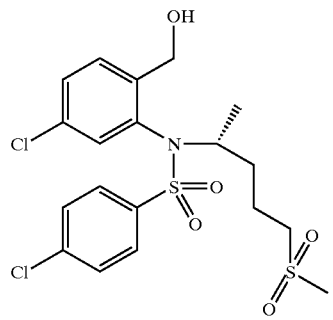

4-chloro-N-[5-chloro-2-(hydroxymethyl)phenyl-N-[1(R)-methyl-(4-methylsulfonyl)butyl]-benzenesulfonamide was prepared analogous to 4-chloro-N-[5-chloro-2-(hydroxymethyl)phenyl]-N-[4-[ethyl)sulfonyl]-1-(R)-methylbutyl]benzenesulfonamide by reacting 4-chloro-N-[5-chloro-2-(hydroxymethyl)phenyl]-N-[-(methylthio)]-1-(R)-methylbutyl]benzenesulfonamide with 3-chloroperoxybezoic acid. Yield=71%; MS (ESI+), 480 (M+H)+.

EXAMPLE 142

4-Chloro-N-[5-chloro-2-(hydroxymethyl)phenyl]-N-[1(R)-methyl-(4-[(1-methylethyl)sulfinyl]butyl]benzenesulfonamide

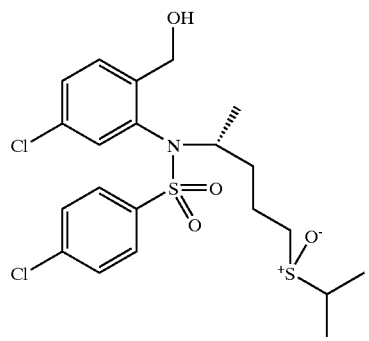

4 chloro-N-[5-chloro-2-(hydroxymethyl)phenyl]-N-[(1-methylethyl)sulfinyl]-1-(R)-methylbutyl]benzenesulfonamide was prepared analogous to 4-chloro-N-[5-chloro-2-(hydroxymethyl)phenyl]-N-[4-(ethyl)sulfinyl]-1-(R)methylbutyl]benzenesulfonamide by reacting 4-chloro-N-[5-chloro-2-(hydroxymethyl)phenyl]-N-[(1-methylethyl)thio]-1-(R)-methylbutyl]benzenesulfonamide with 3-chloroperoxybezoic acid. Yield=43%; MS (ESI+), 492 (M+H)+.

EXAMPLE 143

4-Chloro-N-[5-chloro-2-(hydroxymethyl)phenyl]-N-[1(R)-methyl-(4[(1-methylethyl)sulfonyl]butyl]benzenesulfonamide

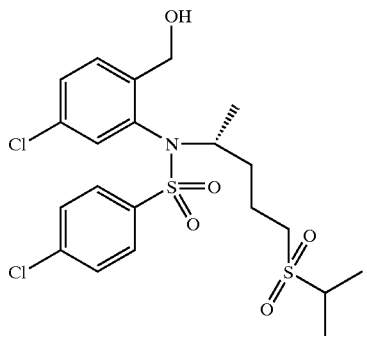

4-chloro-N-[5-chloro-2-(hydroxymethyl)phenyl]-N-[(1-methylethyl)sulfinyl]-1-(R)-methylbutyl]benzenesulfonamide was prepared analogous to 4-chloro-N-[5-chloro-2-(hydroxymethyl)phenyl]-N-[4-(ethyl)sulfonyl]-1-(R)-methylbutyl]benzenesulfonamide by reacting 4-chloro-N-[S-chloro-2-(hydroxymethyl)phenyl]-N-[(1-methylethyl)thio]-1-(R)-methylbutyl]benzenesulfonamide with 3-chloroperoxybezoic acid. Yield=46%; MS (ESI+), 508 (M+H)+.

EXAMPLE 144

4-Chloro-N-[5-chloro-2-(hydroxymethyl)phenyl]-N-[1(R)-methyl-(4-[(1,1-dimethylethyl)sulfinyl]butyl]benzenesulfonamide

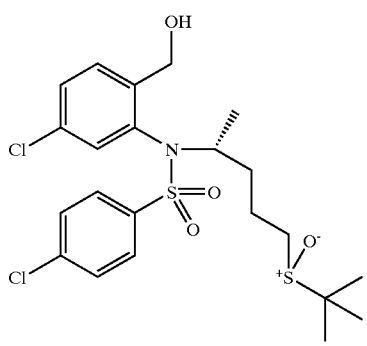

4-chloro-N-[5-chloro-2-(hydroxymethyl)phenyl]-N-[1(R)-methyl-(4-[(1,1-dimethylethyl)sulfinyl]butyl]benzenesulfonamide was prepared analogous to 4-chloro-N-[5-chloro-2-(hydroxymethyl)phenyl]-N-(4-(ethyl)sulfinyl]-1-(R)-methylbutyl]benzenesulfonamide by reacting 4-chloro-N-[5-chloro-2-(hydroxymethyl)phenyl]-N-[1(R)methyl-(4-[(1,1-dimethylethyl)thio]butyl]-benzenesulfonamide with 3-chloroperoxybezoic acid. Yield=50%; MS (ESI+), 506 (M+H)+.

EXAMPLE 145

4-Chloro-N-(5-chloro-2-hydroxymethyl)phenyl]-N-
[1(R)-methyl-(4-[(1,1-dimethylethyl)sulfonyl]butyl]
benzenesulfonamide

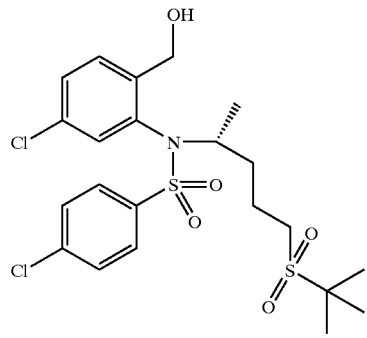

4-chloro-N-[5-chloro-2-(hydroxymethyl)phenyl]-N-[1
(R)-methyl-4-[(1,1-dimethylethyl)sulfonyl]butyl]
benzenesulfonamide was prepared analogous to 4-chloro-
N-[S-chloro-2-(hydroxymethyl)phenyl]-N-[4-(ethyl)
sulfonyl]-1-(R)-methylbutyl]benzenesulfonamide by
reacting 4-chloro-N-[5-chloro-2-(hydroxymethyl)phenyl]-
N-[1(R)-methyl-(4-[(1,1-dimethylethyl)thio]butyl]-
benzenesulfonamide with 3-chloroperoxybezoic acid.
Yield=41%; MS (ESI) 522 (M+1).

EXAMPLE 146

4-Ethylsulfonyl-N-[5-chloro-2-(hydroxymethyl)
phenyl]-N-[1(R)-methyl-(4-ethylsulfonyl)butyl]
benzenesulfonamide

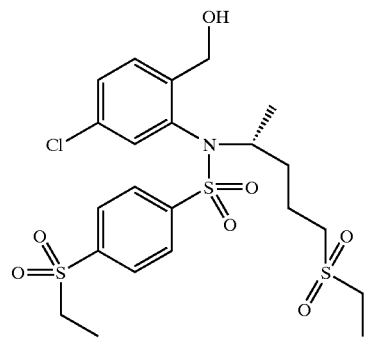

To a solution of 4-ethylthio-N-[5-chloro-2-
hydroxymethyl)phenyl]-N-[1(R)-methyl-(4-ethylthio)butyl]
benzenesulfonamide (0.123 g, 0.267 mmol) in CH$_2$Cl$_2$ (3
mL) was added 80% 3-chloroperoxybezoic acid (0.231 g,
1.07 mmol) at 0° C. Stirring was continued for 2 h at 22° C.
The mixture was quenched with H$_2$O (10 mL), extracted
with CH$_2$Cl$_2$ (2×20 mL), dried over Na$_2$SO$_4$, and filtered.
Solvent was concentrated under reduced pressure to afford a
yellow oil. Silica gel chromatography (2%
methanol:CH$_2$Cl$_2$, 5% methanol:CH$_2$Cl$_2$) gave 99.3 mg of
4-ethylsulfonyl-N-[5-chloro-2-(hydroxymethyl)phenyl]-N-
[1(R)-methyl-(4-ethylsulfonyl)butyl]benzenesulfonamide in
71% yield. MS (ESI+), 569 (M+NH3)–.

EXAMPLE 147

4-Chloro-N-[2,5-dichlorophenyl]-N-[4-(ethylthio)]-1
(R)-methylbutyl]benzenesulfonamide

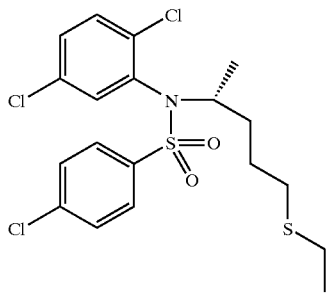

To a solution of NaH (0.025 g, 1.03 mmol) in tetrahy-
drofuran (2 mL) was added ethanethiol (0.096 g, 1.54
mmol), followed by 4-chloro-N-[2,5-dichlorophenyl]-N-
[(R)-1-methyl-4-bromobutyl]benzenesulfonamide (0.500 g
1.03 mmol) under nitrogen at 0° C. The reaction was stirred
overnight at 22° C. The mixture was quenched with H$_2$° (3
mL), extracted with ethyl ether (2×10 mL), dried over
Na$_2$SO$_4$, and filtered. The organic solvent was concentrated
under reduced pressure. Silica gel chromatography (1:9,
ethyl acetate:hexanes) afforded 0.460 g of 4-chloro-N-[2,5-
dichlorophenyl}-N-[4-(ethylthio)]-1-(R)-methylbutyl]
benzenesulfonamide as a yellow oil in 59% yield. LC/MS
466.

EXAMPLE 148

4-Chloro-N-[2,5-dichlorophenyl]-N-[1(R)-methyl-
(4-methylthio)butyl]benzenesulfonamide

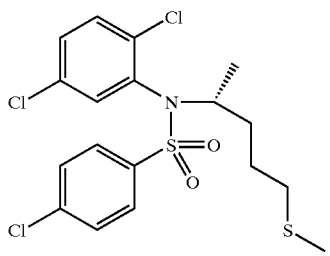

4-chloro-N-[2,5-dichlorophenyl]-N-[1(R)-methyl-(4-
methylthio)butyl]benzenesulfonamide prepared analogous
to 4-chloro-1N-[2,5-dichlorophenyl]-N-[1(R)-methyl-(4-
ethylthio)butyl]-benzenesulfonamide by reacting 4-chloro-
N-[2,5-dichlorophenyl]-N-1(R)-methyl-4-bromobutyl]-
benzenesulfonamide with sodium thiomethoxide. Yield=
100%; MS (ESI+), 452 (M+H)+.

EXAMPLE 149

4-Chloro-N-[2,5-dichlorophenyl]-N-[1(R)-methyl-(4-[(1-methylethyl)thio[butyl]benzenesulfonamide

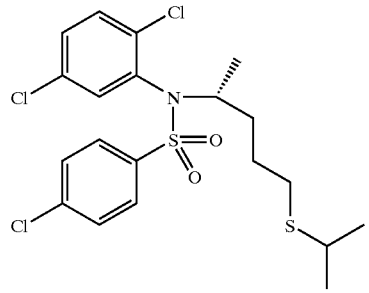

4-chloro-N-[2,5-dichlorophenyl]-N-[1(R)methyl-(4-[(1-methylethyl)thio]butyl]benzenesulfonamide was prepared analogous to 4-chloro-N-[2,5-dichlorophenyl]-N-[1(R)-methyl-(4 ethylthio)butyl]benzenesulfonamide by reacting 1 chloro-N-[2,5-dichlorophenyl]-N-[(R)-1-methyl-4-bromobutyl]benzenesulfonamide with sodium thio-isopropoxide. Yield=100%; MS (ESI+), 478 (M−H)+.

EXAMPLE 150

4-Chloro-N-[2,5-dichlorophenyl]-N-[1(R)-methyl-(4-[(2-methylpropyl)thio)sulfonyl]butyl]benzenesulfonamide

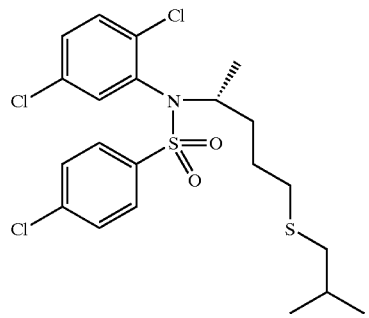

4-chloro-N-[2,5-dichlorophenyl]-N-[1(R)methyl-(4[(2-methylpropyl)thio)sulfonyl]butyl]benzenesulfonamide was prepared analogous to 4-chloro-N-[2,5-dichlorophenyl]-N-[1(R)-methyl(4-ethylthio)butyl]benzenesulfonamide by reacting 4-chloro-N-[2,5-dichlorophenyl]-N-[(R)-1-methyl-4-bromobutyl]benzenesulfonamide with sodium thio-isobutoxide. Yield=100%; MS (ESI+), 494 (M+H)+.

EXAMPLE 151

4-Chloro-N-[5-chloro-2-fluorophenyl]-N-[1(R)-methyl-(4-methylthio)butyl]benzenesulfonamide

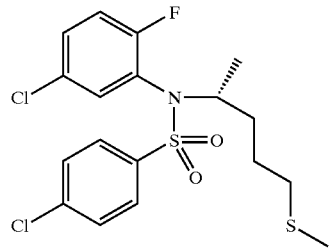

4-chloro-N-[5-chloro-2-fluorophenyl]-N-[4-(methylthio)]-1-(R)-methylbutyl]benzenesulfonamide was prepared analogous to 4-chloro-N-[2,5-dichlorophenyl]-N-[4-(ethylthio)]-1-(R)-methylbutyl]benzenesulfonamide by reacting 4-chloro-N-[5-chloro-2-fluorophenyl]-N-[(R)-1-methyl-4-bromobutyl]benzenesulfonamide with sodium thiomethoxide. Yield=98%; MS (ESI+), 436 (M+H)+.

EXAMPLE 152

4-Chloro-N-[5-chloro-2-fluorophenyl]-N-[1(R)-methyl-(4-ethylthio)butyl]benzenesulfonamide

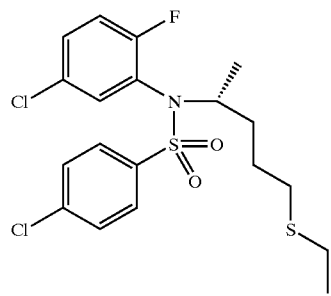

4-chloro-N-[5-chloro-2-fluorophenyl]-N-[4-(ethylthio)]-1-(R)-methylbutyl]benzenesulfonamide was prepared analogous to 4-chloro-N-[2,5-dichlorophenyl]-N-[4-(ethylthio)]-1-(R)-methylbutyl]benzenesulfonamide by reacting 4-chloro-N-[5-chloro-2-fluorophenyl]-N-[(R)-1-methyl-4-bromobutyl)benzenesulfonamide with sodium thioethoxide. Yield=92%; MS (ESI+), 450 (M+H)+.

EXAMPLE 153

4-Chloro-N-[2,5-difluorophenyl]-N-[1(R)-methyl-(4-methylthio)butyl]benzenesulfonamide

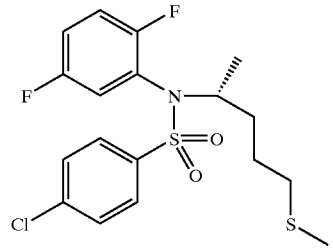

4-chloro-N-[2,5-difluorophenyl]-N-[1 (R)methyl-(4-methylthio)butyl]benzenesulfonamide was prepared analogous to 4-chloro-N-[2,5-dichlorophenyl]-N-[4-[ethyl)thio]-1-(R)methylbutyl]-benzenesulfonamide by reacting 4-chloro-N-[2,5-difluorophenyl]-N-[(R)-1-methyl-4-bromobutyl]-benzenesulfonamide with sodium thiomethoxide. Yield=97%; MS (ESI+), 420 (M+H)+.

EXAMPLE 154

4-Chloro-N-[2,5-difluorophenyl]-N-[1(R)-methyl(4-ethylthio)butyl]benzenesulfonamide

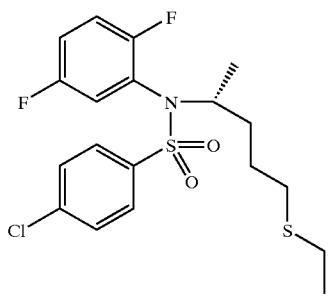

4-chloro-N-[2,5-difluorophenyl]-N-[1(R)-methyl-(4-ethylthio)butyl]benzenesulfonamide was prepared analogous to 4-chloro-N-[2,5-dichlorophenyl]-N-[4-(ethyl)thio]-1-(R)-methylbutyl]-benzenesulfonamide by reacting 4-chloro-N-[2,5-difluorophenyl]-N-[1(R)-methyl-(4-bromo)butyl]-benzenesulfonamide with sodium thioethoxide. Yield=96%; MS (ESI+), 434 (M+H)+.

EXAMPLE 155

4-Chloro-N-[2,5-difluorophenyl]-N-[1(R)-methyl-(4-[(1-methylethyl)thio]butyl]benzenesulfonamide

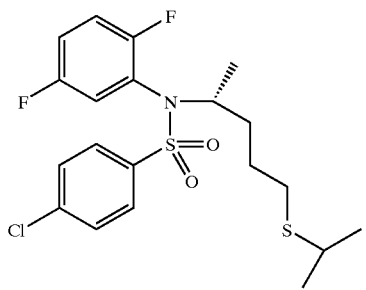

4-chloro-N-[2,5-difluorophenyl]-N-[1(R)methyl-(4[(1-methylethyl)thio]butyl]benzenesulfonamide was prepared analogous to 4-chloro-N-[2,5-dichlorophenyl]-N-[4-(ethyl)thio]-1-(R)-methylbutyl]benzenesulfonamide by reacting 4-chloro-N-[2,5-difluorophenyl]-N-[(R)-1-methyl-4-bromobutyl]benzenesulfonamide with sodium thio-isopropoxide. Yield=89%; MS (ESI+), 448 (M+H)+.

EXAMPLE 156

4-Chloro-N-[2,5-dichlorophenyl]-N-[4-(ethyl)sulfinyl]-1-(R)-methylbutyl]benzenesulfonamide

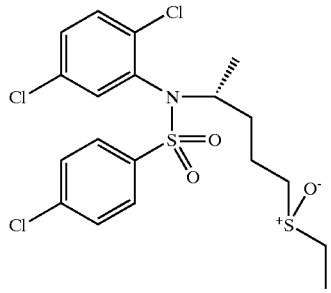

4-Chloro-N-[2,5-dichlorophenyl]-N-[4-(ethyl)sulfonyl]-1-(R)methylbutyl]benzenesulfonamide

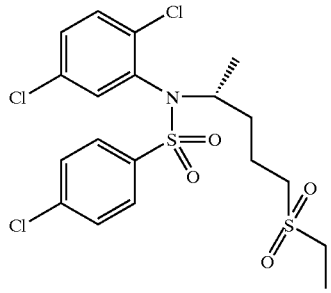

To a solution of 4-chloro-N-[2,5-dichlorophenyl]-N-[4-(ethylthio)]-1-(R)-methylbutyl]benzenesulfonamide (0.460 g, 0.600 mmol) in CH$_2$Cl$_2$ (6 mL) was added 80% 3-chloroperoxybezoic acid (0.166 g, 0.957 mmol) at 0° C. Stirring was continued for 2 h at 22° C. The mixture was quenched with 1120 (10 mL) extracted with CH$_2$Cl$_2$ (2×10 mL), dried over Na$_2$SO$_4$, and filtered. Solvent was concentrated under reduced pressure to afford a yellow oil. Silica gel chromatography (2% methanol:CH$_2$Cl$_2$, 5% methanol:CH$_2$Cl$_2$) gave 0.170 g of 4-chloro-N-[2,5-dichlorophenyl]-N-[4-[(ethyl)sulfonyl]-(R)-methylbutyl]benzenesulfonamide in 56% yield and 0.130 g of 4-chloro-N-[2,5-dichlorophenyl]-N-[4-[ethyl)sulfoxyl]-1-(R)-methylbutyl]benzene sulfonamide in 44% yield. MS (ESI) 498 (M+1); MS (ESI) 482 (M+1).

EXAMPLE 157

4-Chloro-N-[2,5-dichlorophenyl]-N-[1(R)-methyl-(4-methylsulfinyl)butyl]benzenesulfonamide

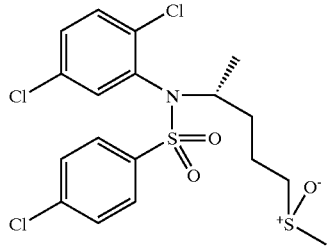

4-chloro-N-[2,5-dichlorophenyl]-N-[1(R)methyl(4-methylsulfinyl)butyl]benzenesulfonamide was prepared analogous to 4-chloro-N-[2,5-dichlorophenyl]-N-[4-(ethyl)sulfinyl]-1-(R)-methylbutyl]benzenesulfonamide by reacting 4-chloro-N-[2,5-dichlorophenyl]-N-[4-(methylthio)]-1-(R)-methylbutyl]benzenesulfonamide with 3-chloroperoxybezoic acid. Yield=47%; MS (ESI+), 466 (M—H)+.

EXAMPLE 158

4-Chloro-N-[2,5-dichlorophenyl]-N-[1(R)-methyl-(4-methylsulfonyl)butyl]benzenesulfonamide

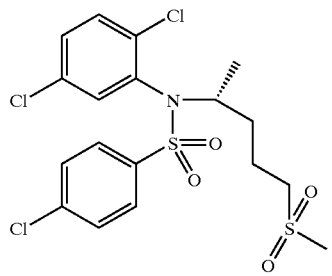

4-chloro-N-[2,5-dichlorophenyl]-N-[I (R)-methyl-(4-methylsulfonyl)butyl]benzenesulfonamide was prepared analogous to 4-chloro-N-[2,5-dichlorophenyl]-N-[4[ethyl)sulfonyl]-1-(R)-methylbutyl]benzenesulfonamide by reacting 4-chloro-N-[2,5-dichlorophenyl)-N-[4-(methylthio)]-1-(R)-methylbutyl]benzenesulfonamide with 3-chloroperoxybezoic acid. Yield=42%; MS (ESI+), 482 (M–H)+.

EXAMPLE 159

4-Chloro-N-[2,5-dichlorophenyl]-N-[1(R)-methyl-(4-[(1-methylethyl)sulfinyl]butyl]benzenesulfonamide

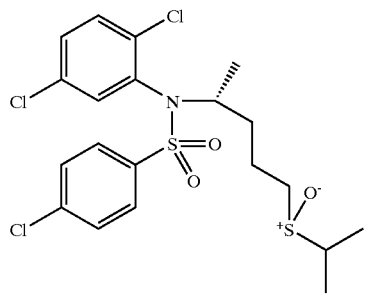

4-chloro-N'-[2,5-dichlorophenyl]-N-[1(R)-methyl-(4-[(1-methylethyl)sulfinyl]butyl]benzenesulfonamide was prepared analogous to 4-chloro-N-[2,5-dichlorophenyl]-N-[4-[ethyl)sulfinyl]-1-(R)-methylbutyl]benzenesulfonamide by reacting 4-chloro-N-[2,5-dichlorophenyl]-N-[I (R)-methyl-(4-[(1-methylethyl)thio]butyl]benzenesulfonamide with 3-chloroperoxybezoic acid. Yield=54%; MS (ESI+), 496 (M+H)+.

EXAMPLE 160

4-Chloro-N-[2,5-dichlorophenyl]-N-[1(R)-methyl-(4-[(1-methylethyl)sulfonyl]butyl]benzenesulfonamide

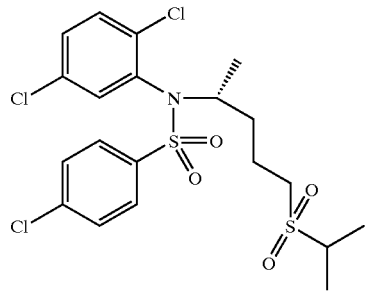

4-chloro-N-[2,5-dichlorophenyl]-N-[1(R)-methyl-(4-[(1-methylethyl)sulfonyl]butyl]benzenesulfonamide was prepared analogous to 4-chloro-N-[2,5-dichlorophenyl]-N-[4-[ethyl)sulfonyl]-1-(Re methylbutyl]benzenesulfonamide by reacting 4-chloro-N-[2,5-dichlorophenyl]-N'-[1(R)-methyl-(4-[(]-methylethyl)thio]butyl]benzenesulfonamide with 3-chloroperoxybezoic acid. Yield=38%; MS (ESI+), 512 (M+H)+.

EXAMPLE 161

4-Chloro-N-[2,5-dichlorophenyl]-N-[1(R)-methyl-(4-[(2-methylpropyl)sulfinyl]butyl]benzenesulfonamide

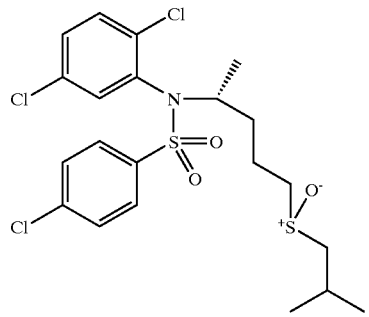

4-chloro-N-[2,5-dichlorophenyl]-N-[1(R)-methyl-(4-[(2-methylpropyl)sulfinyl]butyl]benzenesulfonamide was prepared analogous to 4-chloro-N-[2,5-dichlorophenyl]-N-[4-[ethyl)sulfinyl]-1-(R)-methylbutyl]benzenesulfonamide by reacting 4-chloro-N-[2,5-dichlorophenyl]-N-[1(R)-methyl-(4-[(2-methylpropyl)thio]butyl]benzenesulfonamide with 3-chloroperoxybezoic acid. Yield=29%; MS (ESI+), 508 (M–H)+.

EXAMPLE 162

4-Chloro-N-[2,5-dichlorophenyl]-N-[1(R)-methyl-(4-[(2-methylpropyl)sulfonyl]butyl]benzenesulfonamide

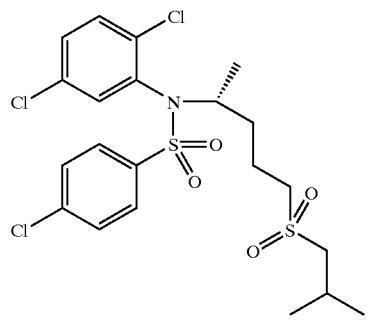

This compound was prepared analogous to 4-chloro-N-[2,5-dichlorophenyl]-N-[4 (ethyl)sulfonyl]-1-(R)-methylbutyl]benzenesulfonamide by reacting 4-chloro-N-[2,5-dichlorophenyl]-N-[1(R)-methyl-(4-[(2-methylpropyl]thio]butyl]benzenesulfonamide with 3-chloroperoxybezoic acid. Yield=35%; MS (ESI+), 526 (M+H)+.

EXAMPLE 163

4-Chloro-N-[5-chloro-2-fluorophenyl]-N-[1(R)-methyl-(4-methylsulfinyl)butyl]benzenesulfonamide

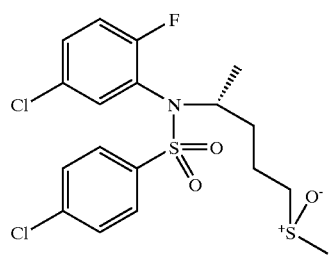

4-chloro-N-[5-chloro-2-fluorophenyl]-N-[1 (R)-methyl-(4-methylsulfinyl)butyl]benzenesulfonamide was prepared analogous to 4-chloro-N-[2,5-dichlorophenyl]-N-[4-(ethyl)sulfinyl]-1-(R)-methylbutyl]benzenesulfonamide by reacting 4-chloro-N-[5-chloro-2-fluorophenyl]-N-[4-(methylthio)]-1-(R)-methylbutyl]benzenesulfonamide with 3-chloroperoxybezoic acid. Yield=61%; MS (ESI+), 452 (M+H)+.

EXAMPLE 164

4-Chloro-N-[5-chloro-2-fluorophenyl]-N-[1(R)-methyl-(4-methylsulfonyl)butyl]benzenesulfonamide

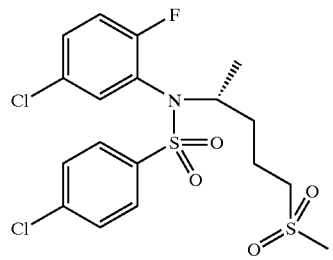

4-chloro-N-[5-chloro-2-fluorophenyl]-N-[1(R)-methyl-(4-methylsulfonyl)butyl]benzenesulfonamide was prepared analogous to 4-chloro-N-2,5-dichlorophenyl]-N-[4-(ethyl)sulfonyl]-1-(R)-methyl butyl]benzenesulfonamide by reacting 4-chloro-N-[5-chloro-2-fluorophenyl]-N-[4-(methylthio)]-1-(R)-methylbutyl]benzenesulfonamide with 3-chloroperoxybezoic acid. Yield=37%; MS (ESI+), 466 (M−H)+.

EXAMPLE 165

4-Chloro-N-[5-chloro-2-fluorophenyl]-N-[1(R)-methyl-(4-ethylsulfinyl)butyl]benzenesulfonamide

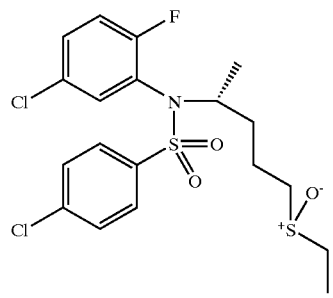

4-chloro-N-[5-chloro-2-fluorophenyl]-N-[1(R)-methyl-(4-ethylsulfinyl)butyl]benzenesulfonamide was prepared analogous to 4-chloro-N-[2,5-dichlorophenyl]-N-[4-ethyl)sulfinyl]1-]-(R)-methylbutyl]benzenesulfonamide by reacting 4-chloro-N-[5-chloro-2-flurophenyl]-N-[4-(ethylthio)]-1-(R)-methylbutyl]benzenesulfonamide with 3-chloroperoxybezoic acid. Yield=48%; MS (ESI+), 466 (M+H)+.

EXAMPLE 166

4-Chloro-N-[5-chloro-2-fluorophenyl]-N-[1(R)-methyl-(4-ethylsulfonyl)butyl]benzenesulfonamide

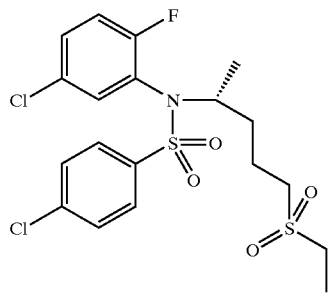

4-chloro-N-[5-chloro-2-fluorophenyl]-N-[1(R)methyl-(4-ethylsulfonyl)butyl]benzenesulfonamide was prepared analogous to 4-chloro-N-[2,5-dichlorophenyl]-N-[4-(ethyl)sulfonyl]-1-(R)-methylbutyl]benzenesulfonamide by reacting 4-chloro-N-[5-chloro-2-fluorophenyl]-N-[4-(ethylthio)]-1-(R)-methylbutyl]benzenesulfonamide with 3-chloroperoxybezoic acid. Yield=44%; MS (ESI+), 482 (M+H)+.

EXAMPLE 167

4-Chloro-N-[2,5-difluorophenyl]-N-[1(R)-methyl-(4-methylsulfinyl)butyl]benzenesulfonamide

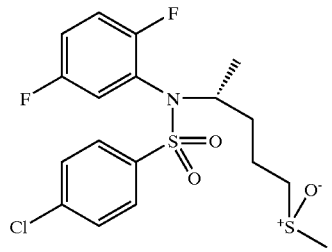

4-chloro-N-[2,5-difluorophenyl]-N-[1(R)methyl-(4-methylsulfinyl)butyl]benzenesulfonamide was prepared analogous to 4-chloro-N-[2,5-dichlorophenyl]-N-[4-(ethyl)sulfinyl]-1-(R)-methylbutyl]benzenesulfonamide by reacting 4-chloro-N-[2,5-difluorophenyl]-N-[4-(methylthio)]-1-(R)-methylbutyl]benzenesulfonamide with 3-chloroperoxybezoic acid. Yield=35%; MS (ESI+), 436 (M+H)+.

EXAMPLE 168

4-Chloro-N-[2,5-difluorophenyl]-N-[1(R)-methyl-(4-methylsulfonyl)butyl]benzenesulfonamide

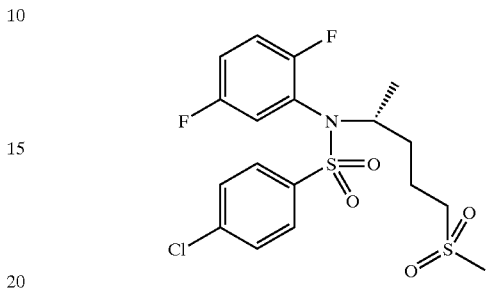

4-chloro-N-[2,5-difluorophenyl]-N-[1(R)-methyl-(4-methylsulfonyl)butyl]benzenesulfonamide was prepared analogous to 4-chloro-N-[2,5-dichlorophenyl]-N-[4-(ethyl)sulfonyl]-1-(R)-methylbutyl]benzenesulfonamide by reacting 4-chloro-N-[2,5-difluorophenyl]-N-[4-(methylthio)]-1-(R)-methylbutyl]benzenesulfonamide with 3-chloroperoxybezoic acid. Yield=30%; MS (ESI+), 452 (M+H)+.

EXAMPLE 169

4-Chloro-N-[2,5-difluorophenyl]-N-[1(R)-methyl-(4-ethylsulfinyl)butyl]benzenesulfonamide

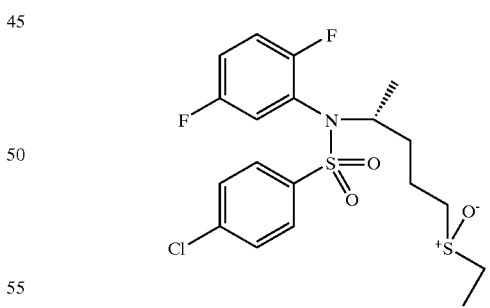

4-chloro-N-[2,5-difluorophenyl]-N-[1(R)methyl-(4-ethylsulfinyl)butyl]benzenesulfonamide was prepared analogous to 4-chloro-N-[2,5-dichlorophenyl]-N-[4-(ethyl)sulfinyl]-1-(R)-methylbutyl]benzenesulfonamide by reacting 4-chloro-N-[2,5-difluorophenyl]-N-[4-(ethylthio)]-1-(R)-methylbutyl]benzenesulfonamide with 3-chloroperoxybezoic acid. Yield=40%; MS (ESI+), 450 (M+H)+.

EXAMPLE 170

4-Chloro-N-[2,5-difluorophenyl]-N-[1(R)-methyl-(4-ethylsulfonyl)butyl]benzenesulfonamide

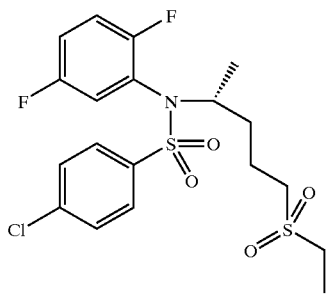

4-chloro-N-[2,5-difluorophenyl]-N-[1(R)-methyl-(4-ethylsulfonyl)butyl]benzenesulfonamide was prepared analogous to 4-chloro-N-[2,5-dichlorophenyl]-N-[4-(ethyl)sulfonyl]-1-(R)-methylbutyl]benzenesulfonamide by reacting 4-chloro-N-12,5-diflurophenyl]-N-[4-(ethylthio)]-1-(R)-methylbutyl]benzenesulfonamide with 3-chloroperoxybezoic acid. Yield=57%; MS (ESI+), 466 (M+H)+.

EXAMPLE 171

4-Chloro-N-[2,5-difluorophenyl]-N-[1(R)-methyl-(4-[(1-methylethyl)sulfinyl]butyl]benzenesulfonamide

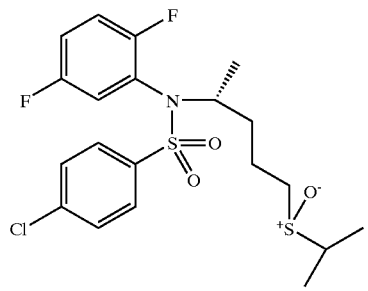

4-chloro-N-[2,5-difluorophenyl]-N-[1 (R)-methyl-(4-[(1-methylethyl)sulfinyl]butyl]benzenesulfonamide was prepared analogous to 4-chloro-N-[2,5-dichlorophenyl]-N-[1 (ethyl)sulfinyl]-1-(R)-methylbutyl]benzenesulfonamide by reacting 4-chloro-N-[2,5-diflurophenyl]-N-[1(R)-methyl-(4 [(1-methylethyl)thio]butyl]benzenesulfonamide with 3-chloroperoxybezoic acid. Yield=32%; MS (ESI+), 464 (M+H)+.

EXAMPLE 172

4-Chloro-N-[2,5-dichlorophenyl]-N-[1(R)methyl-(3-ethylthio)propyl]benzenesulfonamide

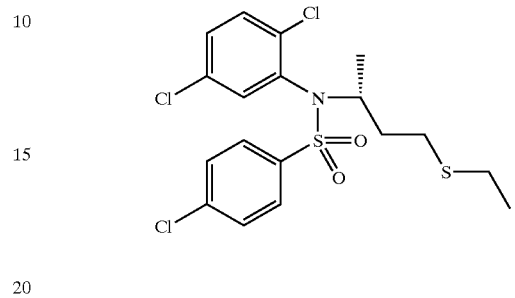

To a solution of 4-chloro-N-(2,5-dichlorophenyl)-N-[1 (R)-methyl-(3-iodo)propyl]benzenesulfonamide (0.500 g, 0.960 mmol) in THF (2 mL) was added sodium thioethoxide (0.080 g, 0.960 mmol) at 22° C. The reaction was allowed to stir for 12 h at 22° C. The solvent was removed, the residue was taken into $CH_2Cl_2$ (50 mL) and washed with water (50 mL). The organic solution was dried over $Na_2SO_4$, filtered and concentrated to afford (0.330 g) of 4-chloro-N-[2,5-dichlorophenyl]-N-[1(R)-methyl-(3-ethylthio)propyl]benzenesulfonamide as a colorless oil in 77% yield. MS (ESI+), (M+H)+.

EXAMPLE 173

4-Chloro-N-[2,5-dichlorophenyl]-N-[1(R)-methyl-(3-ethylsulfonyl)propyl]benzenesulfonamide

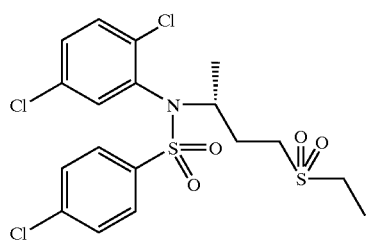

To a solution of 4-chloro-N-[2,5-dichlorophenyl]-N-[(R)-1-methyl-(3-ethylthio)propyl]benzenesulfonamide (0.330 g, 0.730 mmol) was added 3-chloroperoxybenzoic acid, (0.250 g, 0.960 mmol) in THF (50 mL) at 22° C. After 2 h the mixture was washed with water (50 mL) and extracted with ether (50 mL). The organic solution was dried over $Na_2SO_4$, filtered and concentrated under reduced pressure. Silica gel chromatography (5% $CH_2Cl_2$/methanol) of the concentrate gave 0.198 g of 4-chloro-N-[2,5-dichlorophenyl]-N-[1(R)-methyl-(3-ethylsulfonyl)propyl}benzenesulfonamide in 56% yield. MS ESI (483).

EXAMPLE 174

4-Chloro-N-[2,5-dichlorophenyl]-N-[1(R)-methyl-(5-ethylthio)pentyl]benzenesulfonamide

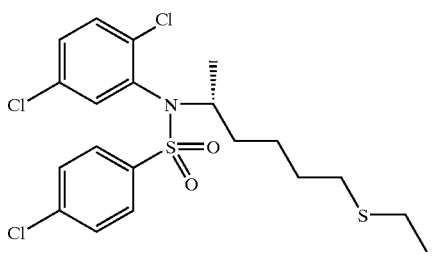

To a solution of 4-chloro-N-(2,5-dichlorophenyl)-N-[1(R)-methyl-(5-iodo)pentyl]benzenesulfonamide (0.500 g, 0.938 mmol) in THF (8 mL) was added sodium thioethoxide (0.078 g, 9.38 mmol) at 22° C. After 12 h the solvent was removed, the residue was taken into $CH_2Cl_2$ (50 mL) and washed with water. The organic solution was dried over $Na_2SO_4$, filtered and concentrated to afford (0.300 g) of 4-chloro-N-[2,5-dichlorophenyl]-N-[1(R)-methyl(5-ethylthio)pentyl]benzenesulfonamide as a colorless oil in 67% yield.

EXAMPLE 175

4-Chloro-N-[2,5-dichlorophenyl]-N-[1(R)-methyl-(5-ethylsulfonyl) pentyl]benzenesulfonamide

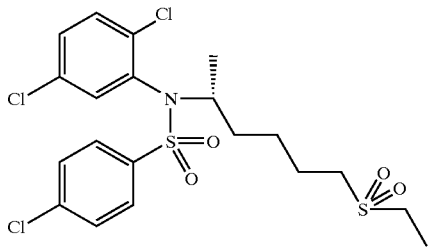

To a solution of 4-chloro-N-[2,5-dichlorophenyl]-N-[1(R)-methyl-(5-ethylthio)pentyl]benzenesulfonamide (0.300 g, 0.650 mmol) was added 3-chloroperoxybenzoic acid, (0.170 g, 0.970 mmol) in $CH_2Cl_2$ (1.5 mL). Stirring was continued for 2 h at 22° C. The product was washed with water (50 mL) and extracted with $CH_2Cl_2$ (50 mL). The organic solution was dried over $Na_2SO_4$, filtered and concentrated under reduced pressure. Silica gel chromatography (5% $CH_2Cl_2$/methanol) of the concentrate gave 0.062 g of 4-chloro-N-[2,5-dichlorophenyl]-N-[1 (R)-methyl-(5-ethylsulfonyl) pentyl]benzenesulfonamide in 19% yield. MS ESI (511).

EXAMPLE 176

Methyl(5R)-5-[(2,5-dichlorophenyl)[(4-chlorophenyl)sulfonyl]amino]-3-thiohexanoate

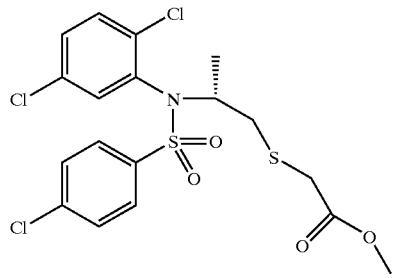

To a solution of 4-chloro-N-(2,5-dichlorophenyl)-N-[(R)-1-methyl(2-iodoethyl)]benzenesulfonamide (0.840 g, 1.66 mmol) and methyl thioglycolate (1.05 g, 9.90 mmol) in diethyl ether was added triethylamine (1.33 g, 13.2 mmol) at 22° C. This mixture was heated to reflux for 12 h. The product was washed with aqueous $NaHCO_3$ extracted with diethyl ether, dried over $Na_2SO_4$ and filtered. Concentration in vacuo, followed by silica gel chromatography (15% ethyl acetate/hexanes) of the concentrate produced the title compound (800 mg, 98% yield).

EXAMPLE 177

Methyl(5R)-5-[(2,5-dichlorophenyl)[(4-chlorophenyl)sulfonyl]amino]-3-thiohexanoic Acid

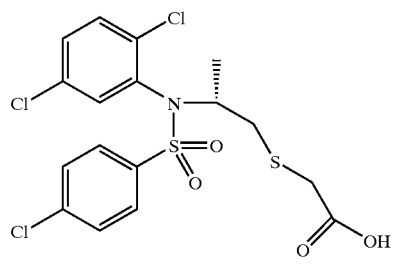

To a solution of methyl (5R)-5-[(2,5-dichlorophenyl)[(4-chlorophenyl)sulfonyl]amino]-3-thiohexanoate (0.050 g, 1.00 mmol) in methanol (1 mL) was added 1 mL of 0.5M sodium hydroxide at 22° C. The mixture was stirred for 1 h. The methanol was evaporated. The residue was diluted with ether and washed with water. The collected aqueous layer was acidified with 1N hydrochloride, and extracted with ether (2×50 mL). The organic layer was dried over $Na_2SO_4$, filtered and concentrated under reduced pressure to afford methyl (5R)-5-[(2,5-dichlorophenyl)[(4-chlorophenyl)sulfonyl]amino]-3-thiohexanoate (33.3 mg, 70% yield). MS ESI (467).

EXAMPLE 178

Methyl(5R)-5-[(2,5-dichlorophenyl)[(4-chlorophenyl)sulfonyl]amino]-3-thiohexanoate,3 Oxide

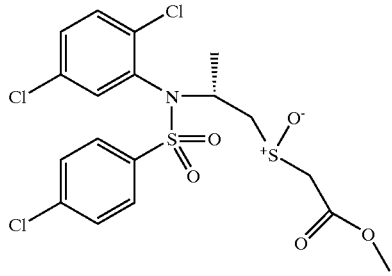

To a solution of methyl(5R)-5-[(2,5-dichlorophenyl)[(4-chlorophenyl)sulfonyl]amino]-3-thiohexanoate (0.790 g, 1.70 mmol) in $CH_2Cl_2$ (2 mL) was added 3-chloroperoxybenzoic acid (0.350 g, 2.00 mmol) at 22° C. The mixture was allowed to stirred for 2 h. The mixture was diluted with $CH_2Cl_2$, washed with water, dried over $Na_2SO_4$ and filtered. Silica gel chromatography (10% $CH_2Cl_2$/methanol) afforded methyl(5R)-5-[(2,5-dichlorophenyl)[(4-chlorophenyl)sulfonyl]amino]-3-thiohexanoate,3 oxide (0.380 g, 46% yield). MS ESI (497).

EXAMPLE 179

Methyl(6R)-6-[(2,5-dichlorophenyl)[(4-chlorophenyl)sulfonyl]amino]-3-thioheptanoate

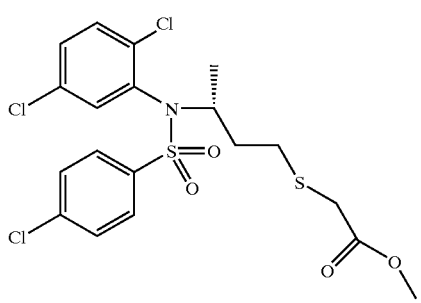

To a solution of 4-chloro-N-(2,5-dichlorophenyl)-N-[1(R) methyl-(3-iodo)-propyl]benzenesulfonamide (0.850 g, 1.64 mmol) and methyl thioglycolate (0.174 g, 1.60 mmol) in diethyl ether was added triethylamine (1.94 g, 1.92 mmol) at 22° C. This mixture was heated to reflux for 12 h. The product was washed with aqueous $NaHCO_3$, extracted with diethyl ether, dried over $Na_2SO_4$ and filtered. Concentration under reduced pressure, followed by silica gel chromatography (15% ethyl acetate/hexane) of the concentrate produced methyl(6R)-6-[(2,5-dichlorophenyl)[(4-chlorophenyl)sulfonyl]amino]-3-thioheptanoate (0.650 g, 80% yield). MS ESI (495).

EXAMPLE 180

(6R)-6-[(2,5-dichlorophenyl)[(4-chlorophenyl)sulfonyl]amino]-3-thioheptanoic Acid

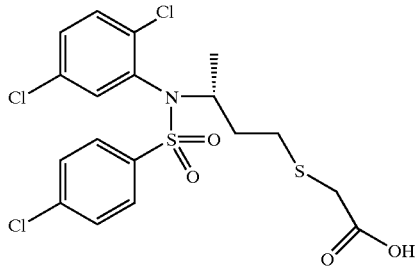

To a solution of methyl(6R)-6-[(2,5,dichlorophenyl)[(4-chlorophenyl)sulfonyl]amino)-3-thioheptanoate (0.100 g, 0.200 mmol) 2 mL of methanol was added 1M sodium hydroxide (1 mL) at 22° C. The mixture was stirred for 1 h and the methanol was evaporated. The residue was diluted with ether and washed with water. The collected aqueous layer was acidified with 1N hydrochloride, and extracted with ether (3×25 mL). The organic layer was dried over $Na_2SO_4$, filtered and concentrated under reduced pressure to afford (6R)-6-[(2,5-dichlorophenyl)[(4-chlorophenyl) sulfonyl]amino]-3-thioheptanoic acid (0.090 g, 90%/o yield). MS ESI (481).

EXAMPLE 181

Methyl(6R)-6[(2,5,dichlorophenyl)[(4-chlorophenyl)sulfonyl]amino]-3-thioheptanoate, 3-Oxide

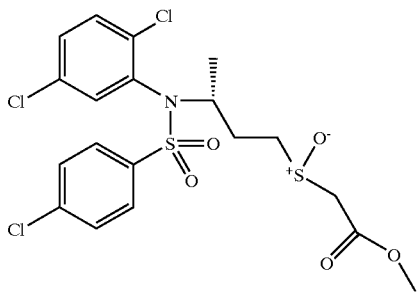

Methyl(6R)-6-[(2,5,dichlorophenyl)[(4-chlorophenyl)sulfonyl]amino]-3-thioheptanoate, 3,3 Dioxide

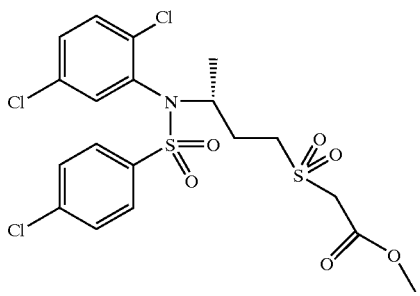

To a solution of methyl(6R)-6-[(2,5-dichlorophenyl)[(4-chlorophenyl)sulfonyl]amino]-3-thioheptanoate (0.650 g, 1.30 mmol) in CH₂Cl, (5 mL) was added 3-chloroperoxybenzoic acid (0.452 g, 2.60 mmol) at 22° C. The mixture was allowed to stir for 2 h. The solution was washed with water, A" extracted with CH₂Cl₂, dried over Na₂SO₄ and filtered. Silica gel chromatography (10% CH₂Cl₂/ methanol) of the concentrate afforded (0.380 g) of methyl (6R)-6[(2,5-dichlorophenyl)[(4-chlorophenyl)sulfonyl] amino-3-thioheptanoate, 3-oxide in 46% yield and (0.340 g) of methyl(6R)-6-[(2,5-dichlorophenyl) [(4-chlorophenyl) sulfonyl]amino]-3-thio heptanoate, 3,3 dioxide in 50% yield. MS ESI (511). MS ESI (527).

EXAMPLE 182

(6R)-6-[(2,5-dichlorophenyl)[(4-chlorophenyl) sulfonyl]amino-3-thioheptanoic Acid, 3-Oxide

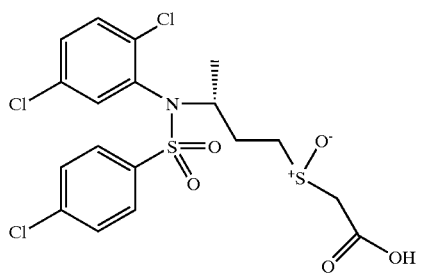

To a solution of methyl(6R)-6-[(2,5,dichlorophenyl)[(4-chlorophenyl)sulfonyl]amino]-3-thioheptanoate, 3-oxide (0.150 g, 0.290 mmol) in 4 mL of methanol was added 1M sodium hydroxide (2 mL) at 22° C. The mixture was stirred for 1 h and the methanol was evaporated. The residue was diluted with ether and washed with water. The collected aqueous layer was acidified with 1N hydrochloride, and extracted with ether (3×50 mL). The organic layer was dried over Na₂SO₄, filtered and concentrated under reduced pressure to afford (6R)-6-[(2,5-dichlorophenyl)[(4-chlorophenyl)sulfonyl]amino]-3-thioheptanoic acid, 3-oxide (0.130 g, 85% yield). MS ESI (497).

EXAMPLE 183

(6R)-6-[(2,5-dichlorophenyl)[(4-chlorophenyl) sulfonyl]amino]-3-thioheptanoic Acid, 3,3 Dioxide

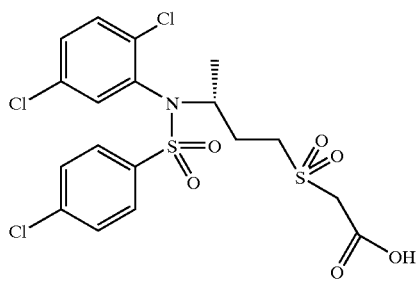

To a solution of methyl(6R)-6-[(2,5,dichlorophenyl)[(4-chlorophenyl)sulfonyl]amino]-3-thioheptanoate, 3,3 dioxide (0.150 g, 2.90 mmol) in 4 mL of methanol was added 1M sodium hydroxide (2 mL) at 22° C. The mixture was stirred for 1 h and the methanol was evaporated. The residue was diluted with ether and washed with water. The collected aqueous layer was acidified with 1N hydrochloride, and extracted with ether (3×50 mL). The organic layer was dried over Na₂SO₄, filtered and concentrated under reduced pressure to afford (6R)-6-[(2,5-dichlorophenyl)[(4-chlorophenyl)sulfonyl)amino]-3-thioheptanoic acid, 3,3 dioxide (0.140 g, 90% yield). MS ESI (513).

EXAMPLE 184

4-Chloro-N-[5-chloro-2-(hydroxymethyl)phenyl]-N-[4-[(methylamino)sulfonyl]-1(R)-methylbutyl] benzenesulfonamide

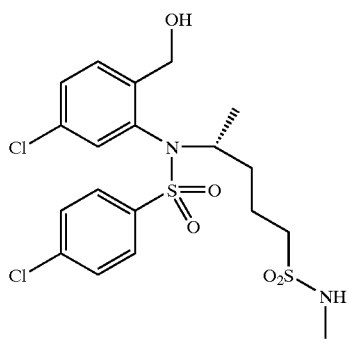

To a solution of (4R)-4-[5-chloro-2-(acetoxymethyl) phenyl][4-chlorophenyl)sulfonyl]-amino]pentylsulfonyl chloride (150 mg, 0.276 mmol) in CH₂Cl₂ (2 ml) was added a 2M THF solution of methylamine (1.38 mL, 2.76 mmol). The mixture was stirred at 22° C. overnight. 1N HCl (1 mL) was added to the mixture, followed by extraction with CH₂Cl₂. The organic layer was dried over Na₂SO₄, filtered, and concentrated under reduced pressure to afford a colorless oil. This oil was purified by prep HPLC to afford 4-chloro-N-[5-chloro-2-(hydroxymethyl)phenyl]-N-[4-[(methylamino)sulfonyl]-1(R)-methylbutyl] benzenesulfonamide in 64% yield. MS (ESI) 495 (M+1).

EXAMPLE 185

4-Chloro-N-[5-chloro-2-(hydroxymethyl)phenyl]-N-[4-(aminosulfonyl)-1(R)-methylbutyl]-benzenesulfonamide

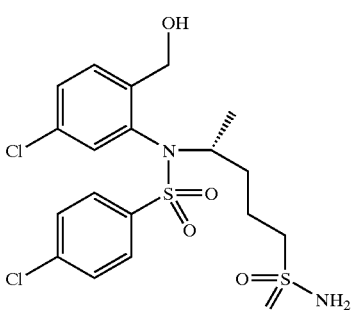

4-chloro-N-[5-chloro-2-(hydroxymethyl)phenyl]-N-[4-(aminosulfonyl)-1(R)-methylbutyl]-benzenesulfonamide was prepared analogous to 4-chloro-N-[5-chloro-2-(hydroxymethyl)phenyl]-N-[4-[(methylamino)sulfonyl]-1 (R)-methylbutyl]benzenesulfonamide by reacting (4R)-4-[5-chloro-2-(acetoxymethyl)phenyl][4-chlorophenyl) sulfonyl]-amino]pentylsulfonyl chloride with ammonia.

Yield=60%; MS (ESI+), 481 (M+H)⁺.

EXAMPLE 186

4-Chloro-N-[5-chloro-2-(hydroxymethyl)phenyl]-N-[4-[(dimethylamino)sulfonyl]-1(R)-methylbutyl]benzenesulfonamide

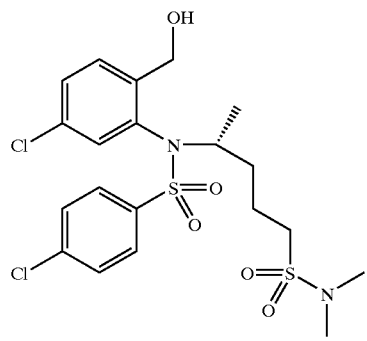

4-chloro-N-[5-chloro-2-(hydroxymethyl)phenyl]-N-[4-(dimethylaminoaminosulfonyl)-1(R)-methylbutyl]-benzenesulfonamide was prepared analogous to 4-chloro-N-[5-chloro-2-(hydroxymethyl)phenyl]-N-[4-[(methylamino)sulfonyl]-1(R)-methylbutyl]benzenesulfonamide by reacting (4R)-4-[5-chloro-2-(acetoxymethyl)phenyl][4-chlorophenyl)sulfonyl]-amino]pentylsulfonyl chloride with dimethylamine. Yield=73%; MS (ESI+), 509 (M+H)$^+$.

EXAMPLE 187

4-Chloro-N-[5-chloro-2-(hydroxymethyl)phenyl]-N-[4[N-cyclopropylmethyl)-N-[3-(1H-imidazol-1-yl)propyl]aminosulfonyl]-1(R)-methylbutyl]benzenesulfonamide

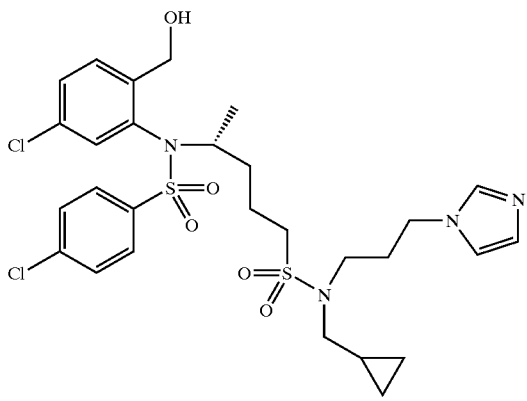

4-chloro-N-[5-chloro-2-(hydroxymethyl)phenyl]-N-[4-[N-(cyclopropylmethyl)-N-[3-(1H-imidazol-1-yl)propyl]aminosulfonyl]-1(R)-methylbutyl]benzenesulfonamide was prepared analogous to 4-chloro-N-[5-chloro-2-(hydroxymethyl)phenyl]-N-[4-[(methylamino)sulfonyl]-1(R)methylbutyl]benzenesulfonamide by reacting (4R)-4-[5-chloro-2-(acetoxymethyl)phenyl][4-chlorophenyl)sulfonyl]-amino]pentylsulfonyl chloride with N-(cyclopropylmethyl)-N-[3-(1H-imidazol-1-yl)propyl]amine.

Yield=49%; MS (ESI+), 643 (M+H)+.

EXAMPLE 188

4-Chloro-N-[2,5-dichlorophenyl]-N-[4-[(methylamino)sulfonyl]-1(R)-methylbutyl]benzenesulfonamide

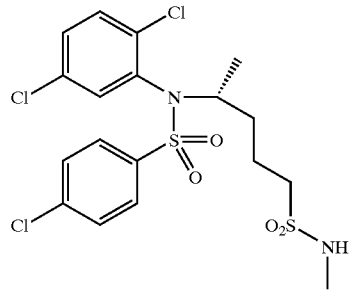

To a solution of (4R)-4-[2,5-dichlorophenyl][4-chlorophenyl)sulfonyl]-amino]pentylsulfonyl chloride (212 mg, 1.69 mmol) in CH$_2$Cl$_2$ (2 ml) was added methylamine (52.0 mg, 6.76 mmol). The mixture was stirred at 22° C. overnight. 1N HCl (1 mL) was added to the mixture, followed by extraction with CH$_2$Cl$_2$. The organic layer was dried over Na$_2$SO$_4$, filtered, and concentrated under reduced pressure to afford a colorless oil. This oil was purified by prep HPLC to afford 4-chloro-N-[2,5-dichlorophenyl]-N-[4-[(methylamino)sulfonyl]-1(R)-methylbutyl] benzenesulfonamide in 84% yield. MS (ESI) 499 (M+1).

EXAMPLE 189

4-Chloro-N-[2,5-dichlorophenyl]-N-[4-[(amino)sulfonyl]-1(R)-methylbutyl]benzenesulfonamide

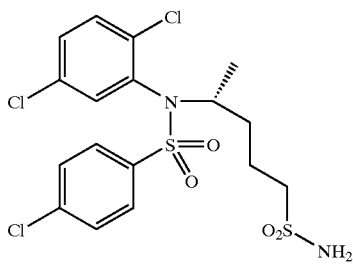

4-chloro-N-[2,5-dichlorophenyl]-N-[4-(aminosulfonyl)-1(R)-methylbutyl]-benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl][4-chlorophenyl)sulfonyl]amino]pentylsulfonyl chloride with ammonia. Yield=41%; MS (ESI+), 485 (M+H)+.

EXAMPLE 190

4-Chloro-N-[2,5-dichlorophenyl]-N-[4-[(ethylamino)sulfonyl]-1(R)-methylbutyl]benzenesulfonamide

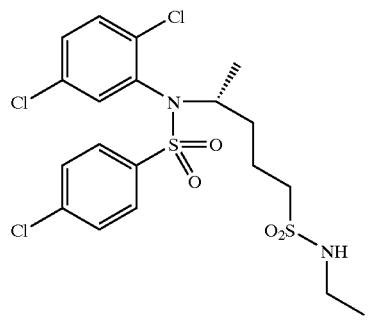

4-chloro-N-[2,5-dichlorophenyl]-N-[4-ethylaminosulfonyl)-1(R)-methylbutyl]benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with ethylamine. Yield=37%; MS (ESI+), 513 (M+H)+.

EXAMPLE 191

4-Chloro-N-[2,5-dichlorophenyl]-N-[4-[(2-methylpropylamino)sulfonyl]-1(R)-methylbutyl]benzenesulfonamide

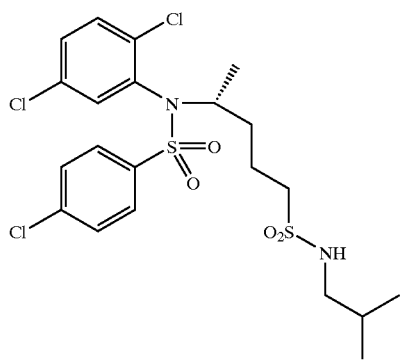

4-chloro-N-[2,5-dichlorophenyl]-N-[4-[(2-methylpropyl amino)sulfonyl]-1(R)-methylbutyl]benzenesulfonamide was prepared analogous to 4-chloro-N-[2,5-dichlorophenyl]-N-[4 [(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with iso-butylamine. Yield=66%; MS (ESI+), 541 (M+H)+.

EXAMPLE 192

4-Chloro-N-[2,5-dichlorophenyl]-N-[4-[(dimethylamino)sulfonyl]-1(R)-methylbutyl]benzenesulfonamide

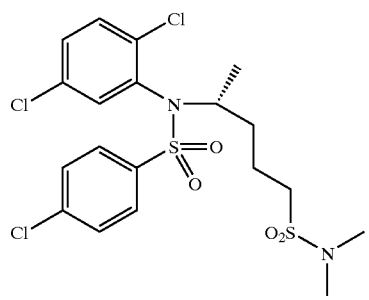

4-chloro-N-[2,5-dichlorophenyl]-N-[4-(dimethylaminosulfonyl)-1(R)-methylbutyl]-benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with dimethylamine. Yield=65%; MS (ESI+), 513 (M+H)+.

EXAMPLE 193

4-Chloro-N-[2,5-dichlorophenyl]-N-[4-[(diethylamino)sulfonyl]-1(R)-methylbutyl]benzenesulfonamide

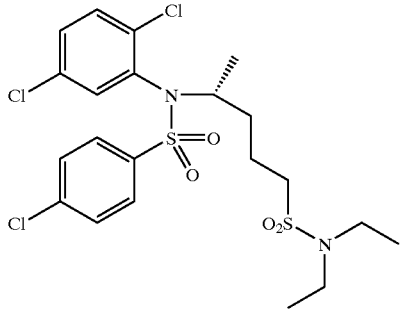

4-chloro-N-[2,5-dichlorophenyl]-N-[4-(diethylaminosulfonyl)-1(R)-methylbutyl]-benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with diethylamine. Yield=59%; MS (ESI+), 541 (M+H)+.

EXAMPLE 194

4-Chloro-N-[2,5-dichlorophenyl]-N-[[4-[[N-1-methylethyl)methylamino]sulfonyl]-1(R)-methylbutyl]benzenesulfonamide

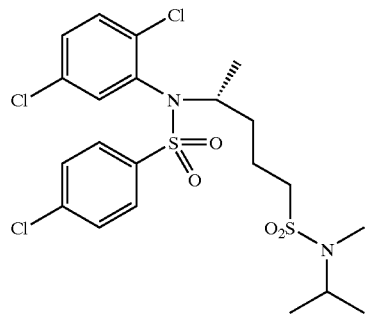

4-chloro-N-[2,5-dichlorophenyl]-N-[4-[[N-(1-methylethyl)methylamino]sulfonyl]-1(R)-methylbutyl]benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl](4-chlorophenyl)sulfonyl]-amino]pentylsulfonyl chloride with N-(1-methylethyl)-methylamine. Yield=37%; MS (ESI+), 541 (M+H)+.

EXAMPLE 195

4-Chloro-N-[2,5-dichlorophenyl]-N-[4-[[(N-cyclopentyl)methylamino]sulfonyl]-1(R)-methylbutyl)benzenesulfonamide

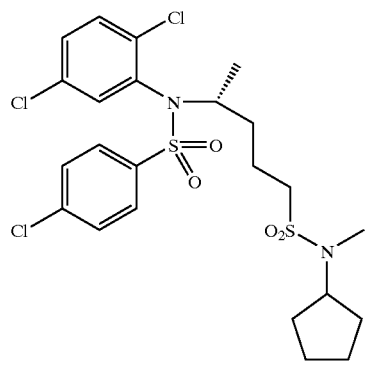

4-chloro-N-[2,5-dichlorophenyl]-N-[4-[[N-(cyclopentyl)methylamino]sulfonyl]-1(R)-methylbutyl]benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with N-(cyclopentyl)-methylamine. Yield=15%; MS (ESI+), 567 (M+H)+.

EXAMPLE 196

4-Chloro-N-[2,5-dichlorophenyl]-N-[4-[(1-azetidinyl)sulfonyl]-1(R)-methylbutyl]benzenesulfonamide

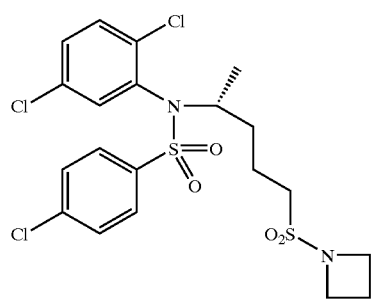

4-chloro-N-[2,5-dichlorophenyl]-N-[4-[(1-azetidinyl)sulfonyl]-1(R)-methylbutyl]benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with azetidine. Yield=24%; MS (ESI+), 526 (M+H)+.

EXAMPLE 197

4-Chloro-N-[2,5-dichlorophenyl]-N-[4-[(1-pyrrolidinyl)sulfonyl]-1(R)-methylbutyl]benzenesulfonamide

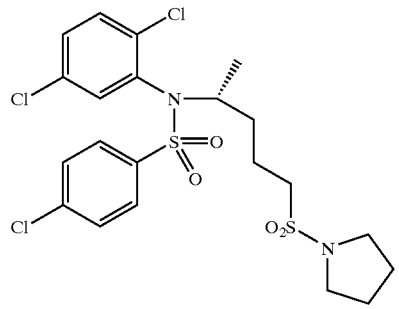

4-chloro-N-(2,5-dichlorophenyl]-N-[4-[(1-pyrrolidinyl)sulfonyl]-1(R)-methylbutyl]benzenesulfonamide was prepared analogous to 4-chloro-N-[2,5-dichlorophenyl]-N-[4-[(methylamino)sulfonyl)-1(R)-methylbutyl]benzenesulfonamide by reacting (4R)-4-[2,5-dichlorophenyl][4-chlorophenyl)sulfonyl]-amino]pentylsulfonyl chloride with pyrrolidine. Yield=61%; MS (ESI+), 539 (M+H)+.

EXAMPLE 198

4-Chloro-N-[2,5-dichlorophenyl]-N-[4-[(4-morpholinyl)sulfonyl]-1(R)-methylbutyl]benzenesulfonamide

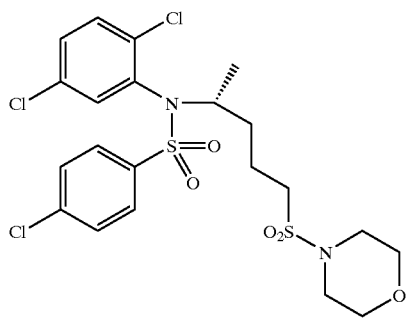

4-chloro-N-[2,5-dichlorophenyl]-N-[4-[(1-morpholinyl)sulfonyl]-1(R)-methylbutyl]benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with morpholine. Yield=37%; MS (ESI+), 555 (M+H)+.

EXAMPLE 199

4-Chloro-N-[2,5-dichlorophenyl]-N-[4-[(4-thiomorpholinyl)sulfonyl]-1(R)-methylbutyl]benzenesulfonamide

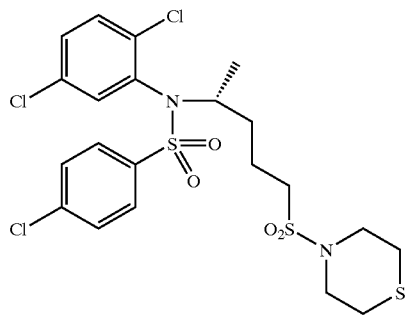

4-chloro-N-[2,5-dichlorophenyl]-N-[4[(4-thiomorpholinyl)sulfonyl]-1(R)-methylbutyl]benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with thiomorpholine. Yield=64%; MS (ESI+), 571 (M+H)+.

EXAMPLE 200

4-Chloro-N-[2,5-dichlorophenyl]-N-[4-[[(tetrahydro-1,1-dioxido-3-thienyl)amino]sulfonyl]-1(R)-methylbutyl]benzenesulfonamide

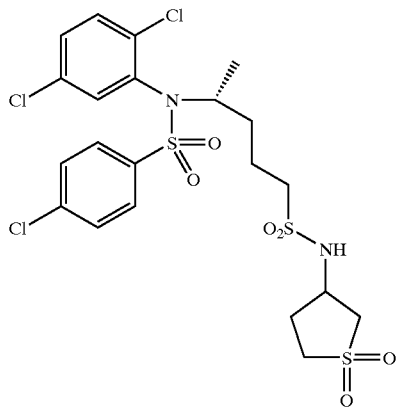

4-chloro-N-[2,5-dichlorophenyl]-N-[4-[[(tetrahydro-], 1-dioxido-3-thienyl)amino]sulfonyl]-1(R)-methylbutyl]benzenesulfonamide was prepared analogous to 4-chloro-N-[2,5-dichlorophenyl]-N-[4[(methylamino)sulfonyl]-1(R)-methylbutyl]benzenesulfonamide by reacting (4R)-4-[2,5-dichlorophenyl][4-chlorophenyl)sulfonyl]-amino]pentylsulfonyl chloride with tetrahydro-1,1-dioxido-3-thienylamine. Yield=23%; MS (ESI+), 603 (M+H)+.

EXAMPLE 201

4-Chloro-N-(5-chloro-2-fluorophenyl)-N-[4-[(methylamino)sulfonyl]-1(R)-methylbutyl]benzenesulfonamide

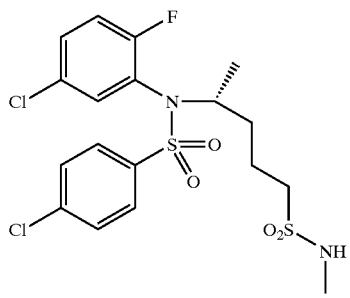

4-chloro-N-[S-chloro-2-fluorophenyl]-N-[4-(methylaminosulfonyl)-1(R)-methylbutyl]benzenesulfonamide was prepared analogous to 4-chloro-N-[2,5-dichlorophenyl]-N-[4-[(methylamino)sulfonyl]-1(R)methylbutyl]benzenesulfonamide by reacting (4R)-4-[5-chloro-2-fluorophenyl][4-chlorophenyl)sulfonyl]-amino]pentylsulfonyl chloride with methylamine. Yield=81%; MS (ESI+), 483 (M+H)+.

EXAMPLE 202

4-Chloro-N-(5-chloro-2-fluorophenyl)-N-[4-[(dimethylamino)sulfonyl]-1(R)-methylbutyl]benzenesulfonamide

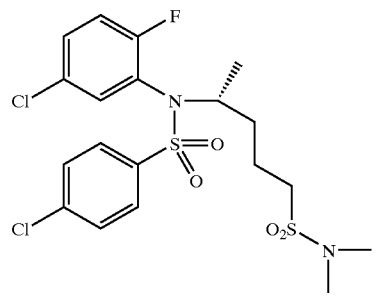

4-chloro-N-[5-chloro-2-fluorophenyl]-N-[4-(dimethylaminosulfonyl)-1(R)-methylbutyl]-benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[5-chloro-2-fluorophenyl][4-chlorophenyl)sulfonyl]-amino]pentylsulfonyl chloride with dimethylamine. Yield=85%; MS (ESI+), 497 (M+H)+.

EXAMPLE 203

4-Chloro-N-(5-chloro-2-fluorophenyl)-N-[4-[(1-pyrrolidinyl)sulfonyl]-1(R)-methylbutyl]benzenesulfonamide

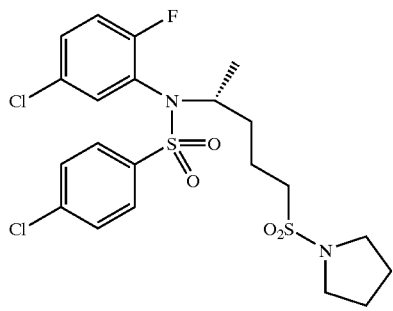

4-chloro-N-(5-chloro-2-fluorophenyl)-N-[4-[(1-pyrrolidinyl)sulfonyl]-1(R)-methylbutyl]-benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[5-chloro-2-fluorophenyl][4-chlorophenyl)sulfonyl]-amino]pentylsulfonyl chloride with pyrrolidine. Yield=86%; MS (ESI+), 523 (M+H)+.

EXAMPLE 204

4-Chloro-N-[2,5-difluorophenyl]-N-[4-[(methylamino)sulfonyl]-1(R)-methylbutyl]benzenesulfonamide

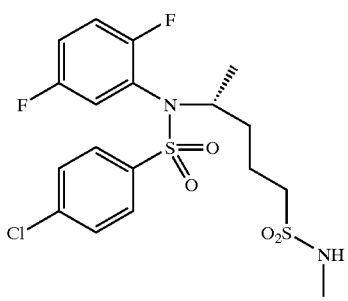

4-chloro-N-[2,5-difluorophenyl]-N-[4-(methylaminosulfonyl)-1(R)-methylbutyl]-benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-difluorophenyl][4-chlorophenyl)sulfonyl]-amino]pentylsulfonyl chloride with methylamine. Yield=86%; MS (ESI+), 467 (M–H)+.

EXAMPLE 205

4-Chloro-N-[2,5-difluorophenyl]-N-[4-[(dimethylamino)sulfonyl]-1(R)-methylbutyl]benzenesulfonamide

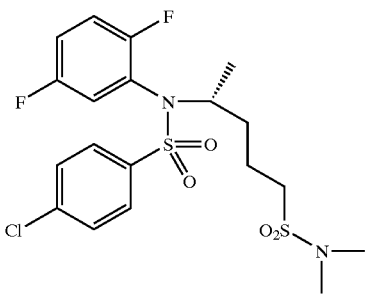

4-chloro-N-[2,5-difluorophenyl]-N-[4-(dimethylaminosulfonyl)-1(R)-methylbutyl]-benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-difluorophenyl][4-chlorophenyl)sulfonyl]-amino]pentylsulfonyl chloride with dimethylamine. Yield=90%; MS (ESI+), 481 (M+H)+.

EXAMPLE 206

4-Chloro-N-[2,5-difluorophenyl]-N-[4-[(1-azetidinyl)sulfonyl]-1(R)-methylbutyl]benzenesulfonamide

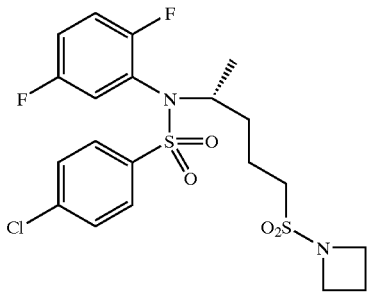

4-chloro-N-[2,5-difluorophenyl]-N-[4-[(1-azetidinyl)sulfonyl]-1(R)-methylbutyl]benzenesulfonamide was prepared analogous to 4-chloro-N-[2,5-dichlorophenyl]-N-[4-[(methylamino)sulfonyl]-1(R)-methylbutyl]benzenesulfonamide by reacting (4R)-4-[2,5-difluorophenyl][chlorophenyl)sulfonyl]-amino]pentylsulfonyl chloride with azetidine. Yield=50%; MS (ESI+), 493 (M+H)+.

EXAMPLE 207

The general reaction scheme outlined in Scheme 207 is described in detail in the text following the scheme.

SCHEME 207

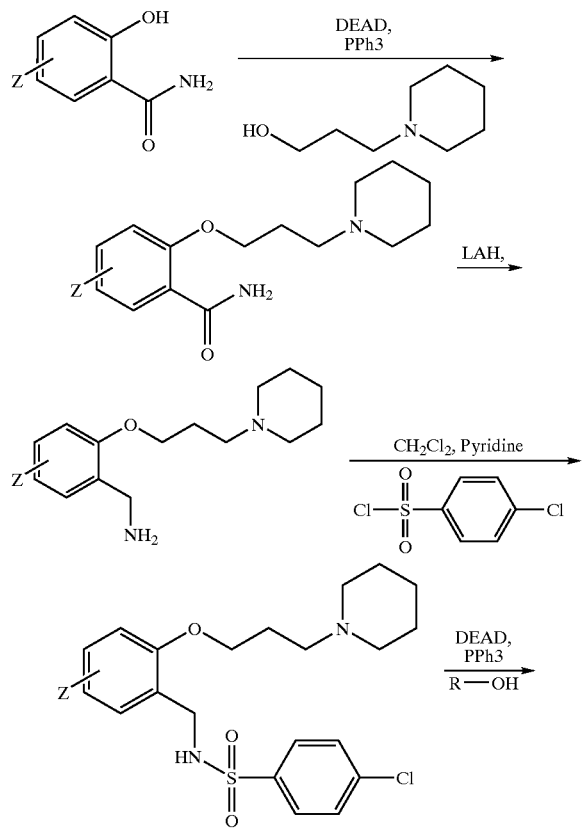

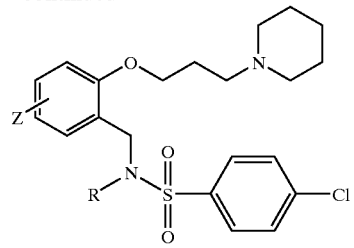

To a stirred solution of salicylamide (1.5 g, 11 mmol) in benzene (15 mL) at room temperature (room temperature) was added N-(3-hydroxypropyl)piperidine (1.43 g, 10 mmol), triphenylphosphine (Triphenylphosphine) (2.62 g, 10 mmol) followed by diethylazodicarboxylate (DEAD), (1.74 g, 10.0 mmol) in benzene (5 mL) over a period of 15 min. The reaction mixture was then left stirred at room temperature for 40 h, concentrated under reduced pressure. The residue was re-dissolved in methylene chloride (DCM; 100 mL). The DCM solution was washed with 1.0 N NaOH (2×75 mL), water (2×75 mL) and extracted with 1.0 N HCl (3×40 mL). The HCl solution was basified with solid NaOH to pH 14 to yield a turbid solution that was extracted with DCM (2×50 mL). The combined DCM solution was washed with water (2×50 mL), dried with anhydrous MgSO$_4$, filtered and concentrated under reduced pressure to yield 2.05 g of pale yellow oil (y: 78%). $^1$H NMR (300 MHz, CDCl$_3$) δ (ppm): 8.20 (dd, 1H), 7.9 (br, 1H), 7.44 (m, 1H), 7.05 (t, 1H), 7.99 (d, 1H) 6.6 (b, 1H), 4.15, (t, 2H), 2.65–2.27 (m, 6H), 2.05 (p, 2H), 1.67–1.54 (m, 2H), 1.45–138 (m, 2H).

To a stirred solution of the above amide (1.5 g, 4.6 mmol) in anhydrous THF (40 mL) at room temperature was added solid lithium aluminum hydride (lithium aluminum hydride) (473 mg, 11.8 mmol). The reaction mixture was heated at refluxing conditions for 6 h, cooled to room temperature then quenched with 1.0 N NaOH (0.5 mL). The precipitate was filtered through celite and the celite pad was washed with ethyl acetate (30 mL). The filtrate was diluted with ethyl acetate (100 mL) and washed with water (2×75 mL), dried with anhydrous MgSO$_4$, filtered and concentrated to give 1.1 g of product as colorless oil (y: 96%). $^1$H NMR (300 MHz, CDCl$_3$) δ (ppm): 7.26–7.20 (m 2H), 6.90–6.86 (m, 2H), 4.02 (t, 2H), 3.84 (s, 3H), 2.59–2.43 (m, 6H), 2.06 (d, 2H), 1.68–1.56 (m, 4H), 1.48–1.46 (m, 2H).

To a cooled (0° C., ice bath) solution of the diamine (500 mg, 2.0 mmol) in of DCM (20 mL) was added dry pyridine (164 μL, 2.0 mmol), followed by 4-chlorobenzenesulfonylchloride (422 mg, 2.0 mmol). The reaction mixture was allowed to stir at 0° C. for 2 h then concentrated under reduced pressure. Recrystallization (ethyl acetate/hexanes) of the crude mixture afforded the desired product as HCl salt. (840 mg of pale yellow solid, y: 99%). $^1$H NMR (CDCl$_3$) δ (ppm): (7.64–7.59 (m, 2H), 7.34–7.26, (m, 2H), 7.20, (t, 1H), 7.28–7.24, (m, 1H), 6.86 (m, 1H), 6.61 (d, 1H), 4.10 (t, 2H), 4.04 (d, 2H), 3.54 (d, 2H), 3.43 (t, 2H), 2.76–2.72 (m, 2H), 2.52–2.43 (m, 2H), 2.20–2.00 (m, 2H), 1.87–1.72 (m 4H).

General Procedure for the Mitsunobu Alkylation of Sulfonamide with Alcohols

To a solution of the sulfonamide (AA) (1.0 mmol) in anhydrous THF (10 mL) at room temperature was added Triphenylphosphine (1.5 mmol) followed by the appropriate alcohol (1.5 mmol) and DEAD (1.5 mmol) in that order. The clear reaction mixture was stirred at RT for 24 h then concentrated under reduced pressure. The crude product was purified by silica gel chromatography (multiple elution, 200 mL of ethyl acetate, 300–500 mL of 0.5% triethylamine, 0.5% methanol in ethyl acetate). The desired product was isolated as a colorless oil (45–65% yield). The free base was dissolved in DCM to which an excess of a 1.0 M solution of HCl in ether was added. The resulting solution was concentrated under reduced pressure to give a colorless solid. The HCl salt was purified by passing through a short column of silica (10% methanol in DCM) to afford the desired product in good yield.

The compounds of Examples 208–222 were prepared according to the scheme described in the previous example.

EXAMPLE 208

4-Chloro-N-(cyclopentylmethyl)-N-{2-[3-(1-piperidinyl)propoxy]benzyl}benzenesulfonamide Hydrochloride

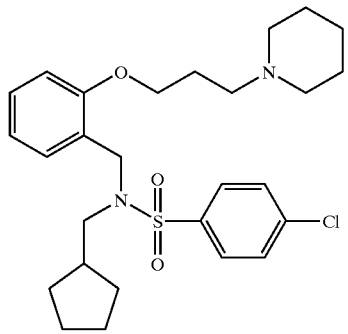

$R_f$ =0.34 (5% methanol, 1% triethylamine in DCM), $^1$H NMR (300 MHz, CD$_3$OD) δ (ppm): 7.82–7.80 (m, 2H), 7.65–7.62 (m, 2H), 7.35 (t, 1H), 7.22–7.17 (m, 1H), 6.95–6.90 (m, 2H), 4.31 (s, 2H), 4.14 (t, 2H), 3.67–3.45 (m, 4H), 3.03 (t, 2H), 2.36 (d, 2H), 2.44–2.35 (m 2H), 2.03–1.84 (m, 5H), 1.66–1.62 (m, 2H), 1.38–1.24 (m, 6H), 0.97–0.96 (m, 2H).

EXAMPLE 209

4-Chloro-N-(1-methylbutyl-N-{2-[3-(1-piperidinyl)propoxy]benzyl}benzenesulfonamide Hydrochloride

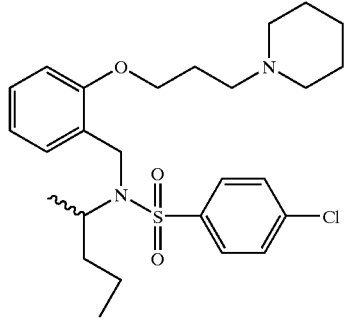

$R_f$=0.34 (5% methanol, 1% triethylamine in DCM), $^1$H NMR (300 MHz, CD$_3$OD) δ (ppm): 7.84–7.82 (m, 2H), 7.62–7.60 (m, 2H), 7.35–7.26 (m, 2H), 6.97–6.89 (m, 2H), 4.90 (d, 1H), 4.32 (d, 1H), 4.13 (t, 2H), 3.84 (m, 1H), 3.59–3.40 (m, 4H), 3.03–2.96 (m, 2H), 2.36–2.27 (m, 2H), 1.97–1.48 (m, 6H), 1.15–0.97 (m, 4H), 0.83 (d, 3H), 0.63 (t, 3H). $^{13}$C NMR (75 MHz, CD$_3$OD) δ (ppm) 159.3, 141.0, 138.0, 132.1, 130.6, 130.5, 129.9, 126.6, 121.8, 112.3, 66.0, 56.1, 55.4, 54.5, 44.2, 38.6, 25.3, 24.3, 22.8, 20.8, 18.2, 14.0. ESI calculated for C$_{26}$H$_{37}$ClN$_2$O$_3$S [MH+] 493; Observed; 493.

EXAMPLE 210

N-allyl-4-chloro-N-{2-[3-(1-piperidinyl)propoxy]benzyl}benzenesulfonamide Hydrochloride

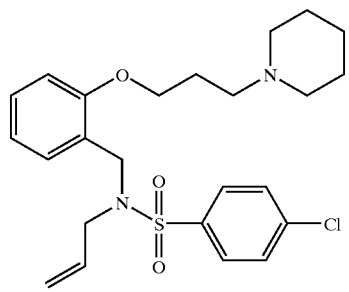

$R_f$=0.28 (1% triethylamine/5% methanol/DCM) $^1$H NMR (300 MHz, CD$_3$OD) δ (ppm); 7.64 (m, 2H), 7.40 (m, 2H), 7.09 (in, 1H), 6.95 (m, 1H), 6.71 (dt, 2H), 5.14 (m, 1H), 4.65 (d, 2H), 4.22 (s, 2H), 3.90 (t, 2H), 3.46–3.16 (m, 6H), 2.80 (m, 2H), 2.06 (m, 2H), 1.78–1.29 (m, 6H).

EXAMPLE 211

4-Chloro-N-(2-methyl-2-propenyl)-N-{2-[3-(1-piperidinyl)propoxy]benzyl)benzenesulfonamide Hydrochoride

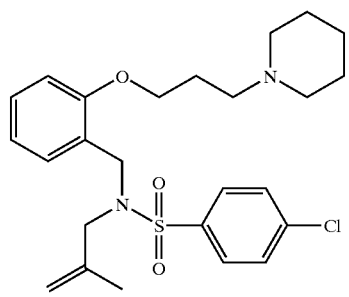

$R_f$ 0.26 (1% triethylamine/5% methanol/DCM) $^1$H NMR (300 MHz, CD$_3$OD) δ (ppm): 7.62 (m, 2H), 7.41 (m, 2H), 7.08 (m, 1H), 6.91 (dd, 1H), 6.67 (dt, 2H), 4.39 (s, 2H), 4.19 (s, 2H), 3.89 (t, 2H), 3.46–3.27 (m, 6H), 2.82 (m, 2H), 2.09 (m, 2H), 1.81–1.11 (m, 9H).

EXAMPLE 212

4-Chloro-N-(4-nitrobenzyl)-N-{2-[3-(1-piperidinyl)propoxy]benzyl}benzenesulfonamide Hydrochloride

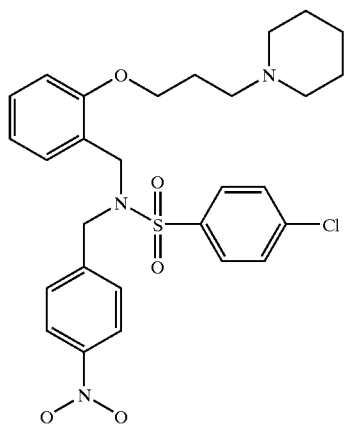

$R_f$ =0.24 (19:1; DCM:methanol). $^1$H NMR (CD$_3$OD) δ (ppm): 7.86–7.81 (m, 4H), 7.60 (m, 2H), 7.10–6.99 (m, 4H), 6.66 (t, 1H), 6.48 (d, 1H), 4.33 (s, 2H), 4.19 (s, 2H), 3.82 (t, 2H), 3.56–3.45 (mg 4H), 2.98–2.96 (m, 2H), 2.24–2.14 (m, 2H), 1.72–1.36 (m, 6H).

EXAMPLE 213

4-Chloro-{2-[3-(1-piperidinyl)propoxy]benzyl}-N-(3-pyridinylmethyl)benzenesulfonamide hydrochloride

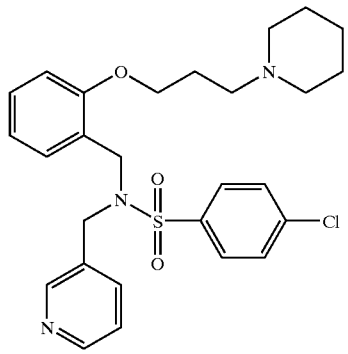

$R_f$=0.20 (4% methanol, 1% triethylamine in DCM), $^1$H NMR (300 MHz, CD$_3$OD) δ (ppm): 8.25–8.15 (m, 2H), 7.96–7.93 (m, 2H), 7.71–7.68 (m, 2H), 7.43 (d, 1H), 7.17–7.11 (m, 3H), 6.81–6.79, (m, 1H), 6.60–6.57 (m, 1H). $^{13}$C NMR (75 MHz, CD$_3$OD) δ (ppm): 158.5, 148.9, 147.6, 140.7, 138.3, 138.1, 133.0, 131.6, 131.0, 130.3, 123.6, 121.8, 111.8, 65.5, 56.1, 54.6, 51.7, 50.3, 25.3, 24.4, 22.9.

EXAMPLE 214

4-Chloro-N-[(1R)-1-methylbutyl]-N-{2-[3-(1-piperidinyl)propoxy]benzyl}benzenesulfonamide hydrochloride

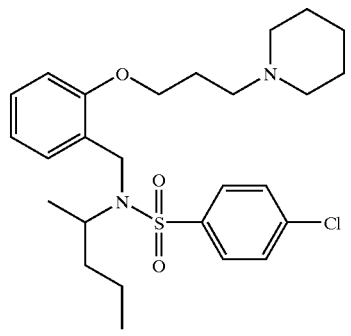

$R_f$ 0.28 (4% methanol, 1% triethylamine in DCM), $^1$H NMR (300 MHz, CD$_3$OD) δ (ppm): 7.84–7.82 (m, 2H), 7.62–7.60 (m, 2H), 7.35–7.26 (m, 2H), 6.97–6.89 (m, 2H), 4.90 (d, 1H), 4.32 (d, 1H), 4.13 (t, 2H), 3.84 (m, 1H), 3.59–3.40 (m, 4H), 3.03–2.96 (m, 2H), 2.36–2.27 (m, 2H), 1.97–1.48 (m, 6H), 1.15–0.97 (m, 4H), 0.83 (d, 3H), 0.63 (t, 3H). $^{13}$C NMR (75 MHz, CD$_3$OD) δ (ppm): 159.3, 141.0, 138.0, 132.1, 130.6, 130.5, 129.9, 126.6, 121.8, 112.3, 66.0, 56.1, 55.4, 54.5, 44.2, 38.6, 25.3, 24.3, 22.8, 20.8, 18.2, 14.0. ESI calculated for C$_{26}$H$_{37}$ClN$_2$O$_3$S [MH+] 493; Observed: 493.

EXAMPLE 215

4-Chloro-N-[(1S)-1-methylbutyl]-N-[2-[3-(1-piperidinyl)propoxy]benzyl}benzenesulfonamide Hydrochloride

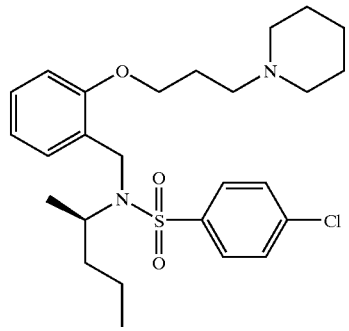

$R_f$=0.28 (4% methanol, 1% triethylamine in DCM), $^1$H NMR (300 MHz, CD$_3$OD) δ (ppm): 7.84–7.82 (m, 2H), 7.62–7.60 (m, 2H), 7.35–7.26 (m, 2H), 6.97–6.89 (m, 2H), 4.90 (d, 1H), 4.32 (d, 1H), 4.13 (t, 2H), 3.84 (m, 1H), 3.59–3.40 (m, 4H), 3.03–2.96 (m, 2H), 2.36–2.27 (m, 2H), 1.97–1.48 (m, 6H), 1.15–0.97 (m, 4H), 0.83 (d, 3H), 0.63 (t, 3H). $^{13}$C NMR (75 MHz, CD$_3$OD) δ (ppm):159.3, 141.0, 138.0, 132.1, 130.6, 130.5, 129.9, 126.6, 121.8, 112.3, 66.0, 56.1, 55.4, 54.5, 44.2, 38.6, 25.3, 24.3, 22.8, 20.8, 18.2, 14.0. ESI calculated for C$_{26}$H$_{37}$ClN$_2$O$_3$S [MH+] 493; Observed: 493.

EXAMPLE 216

4-Chloro-N-(cyclopropylmethyl)-N-{2-[3-(1-piperidinyl)propoxy]benzyl}benzenesulfonamide hydrochloride

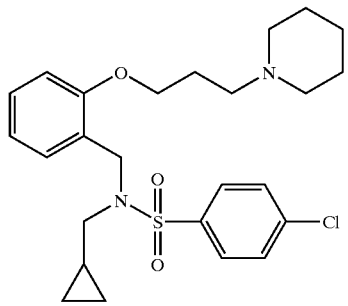

$R_f$=0.25 (5% methanol, 1% triethylamine in DCM) $^1$H NMR (300 MHz, CD$_3$OD) δ (ppm): 7.84 (d, 2H), 7.62 (d, 2H), 7.30 (dt, 1H), 7.21 (dd, 2H), 6.98 (d, 1H), 6.94 (t, 2H), 4.42 (s, 2H), 4.13 (t, 2H), 3.63 (d, 2H), 3.51–4.46 (m, 2H), 3.02 (t, 2H), 2.88 (d, 2H), 2.34–2.28 (m, 2H), 1.94–1.79 (m, 5H), 1.69–1.49 (m, 1H), 0.61–0.54 (m, 1H), 0.24–0.21 (m, 2H), (–)0.12-(–)0.14 (m, 2H). $^{13}$C NMR (75 MHz, CD$_3$OD) δ 158.6, 140, 139.4, 132.2, 130.9, 130.6, 130.0, 125.1, 121.8, 112.4, 66.0, 56.1, 54.4, 53.8, 50.0, 25.3, 24.3, 22.8, 11.28, 4.7. ESI calculated for C$_{25}$H$_{33}$ClN$_2$O$_3$S [MH+] 477; Observed: 477.

EXAMPLE 217

4-Chloro-N-(5-hexynyl-N-{2-[3-(1-piperidinyl)propoxy]benzyl}benzenesulfonamide Hydrochloride

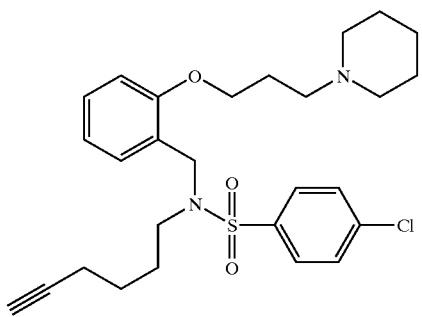

$R_f$=0.19 (1% triethylamine/5% methanol/ethyl acetate) $^1$H NMR (300 MHz, CD$_3$OD) δ (ppm): 7.86–7.83 (m, 2H), 7.66–7.31 (m, 2H), 7.36–7.31 (m, 2H), 7.22–7.19 (m, 1H), 7.10–7.09 (m, 1H), 7.00–6.92 (m, 2H), 4.41 (s, 2H), 4.15 (t, 2H), 3.33 (m, 2H), 2.99 (m, 2H), 2.34–2.24 5 (m, 2H), 2.17 (t, 1H), 1.93–1.68 (m, 8H), 1.22–1.15 (m, 4H). $^{13}$C NMR (75 MHz, CD$_3$OD) δ (ppm): 159.1, 140.6, 139.2, 133.0, 131.6, 131.1, 130.5, 125.03, 122.2, 112.8, 85.1, 70.3, 66.3, 56.5, 54.9, 50.9, 29.4, 26.9, 25.7, 24.7, 23.2, 18.9. ESI calculated for C$_{27}$H$_{35}$N$_2$O$_3$ClS [MH+] 503: Observed: 503.

EXAMPLE 218

4-Chloro-N-(4-methylpentyl)-N-{2-[3-(1-piperidinyl)propoxy]benzyl}benzenesulfonamide Hydrochloride

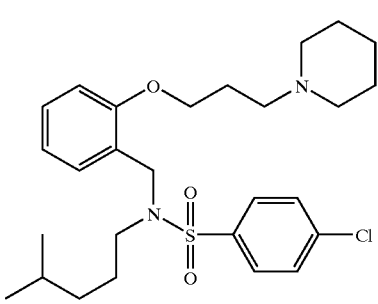

$R_f$ =0.33 (1% triethylamine/5% methanol/ethyl acetate) $^1$H NMR (300 MHz, CD$_3$OD) δ (ppm): 7.86–7.83 (m, 2H), 7.66–7.63 (m, 2H), 7.36–7.31 (m, 2H), 7.18 (m, 2H), 7.94 (dt, 2H), 4.36 (s, 2H), 4.14 (t, 2H), 3.67–3.51 (m, 4H), 3.07–2.90 (m, 4H), 2.30 (m, 2H), 2.00–1.50 (m, 6H), 0.84 (m, 2H), 0.68 (d, 6H). $^{13}$C NMR (75 MHz, CD$_3$OD) δ (ppm): 157.8, 139.3, 138.1, 131.8, 130.3, 129.9, 129.3, 123.9, 120.9, 111.5, 55.4, 53.8, 49.7, 48.6, 35.9, 27.8, 26.9, 24.6, 23.5, 22.0.

EXAMPLE 219

4-Chloro-N-(cyclobutylmethyl)-N-{2-[3-(1-piperidinyl)propoxy]benzyl}benzenesulfonamide Hydrochloride

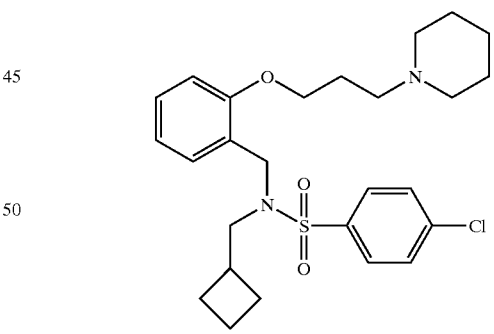

$R_f$ 038 (1% triethylamine/5% methanol/ethyl acetate) $^1$H NMR (300 MHz, CD$_3$OD) δ (ppm): 7.67 (d, 2H), 7.47 (d, 2H), 7.18–7.01 (m, 2H), 6.82–6.72 (m, 2H), 4.13 (s, 2H), 3.95 (t, 2H), 3.47 (m, 2H), 3.33 (m, 2H), 2.83 (m, 4H), 2.11 (m, 2H), 1.93–1.07 (m, 13H). $^{13}$C NMR (75 MHz, CD$_3$OD) δ 158.6, 140.2, 138.7, 132.5, 131.1, 130.7, 130.3, 125.2, 121.8, 112.4, 66.0, 56.2, 55.01, 54.7, 51.0, 36.1, 27.1, 25.5, 24.4, 22.9, 18.6. ESI calculated for C$_{26}$H$_{35}$ClN$_2$O$_3$S [MH+] 491; Observed: 591.

EXAMPLE 220

4-Chloro-N-{2-[3-(1-piperidinyl)propoxy]benzyl}-
N-(4-pyridinylmethyl)benzenesulfonamide
Dihydrochloride

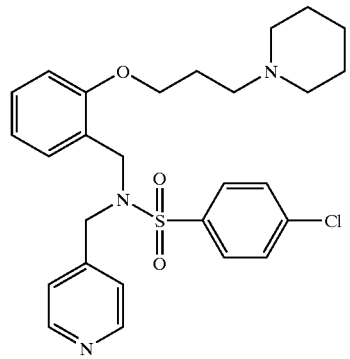

$R_f$=0.23 (5% methanol/DCM) $^1$H NMR (300 MHz, CD$_3$OD) δ (ppm): 7.86–7.82 (br, 2H), 7.22–7.18 (br, 2H), 6.97–6.89 br, 4H), 6.38–6.32 (br, 2H), 6.0–5.83 br, 2H), 4.55 (br, 4H), 3.81–3.65 (m, 4H), 3.35–3.25 (m, 2H), 2.97–2.85 (m, 4H), 2.35–2.2.8 (m, 2H), 1.64–1.61 (br, 2H), 1.22–1.06 (m, 5H), $^{13}$C NMR (75 MHz, CD$_3$OD) δ (ppm): 161.7, 158.5, 142.02, 140.9, 137.5, 132.0, 126.9, 123.4, 121.9, 112.1, 66.2, 56.2, 54.9, 54.8, 52.6, 52.0, 25.5, 24.4, 22.9.

EXAMPLE 221

N-benzyl-4-chloro-N-{2-[3-(1-piperidinyl)propoxy]
benzyl}benzenesulfonamide Hydrochloride

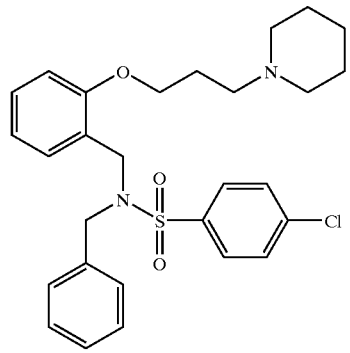

$R_f$=0.24 (1% triethylamine/5% methanol/ethyl acetate)
$^1$H NMR (300 MHz, CD$_3$OD) δ (ppm): 7.64 (d, 2H), 7.40 (d, 2H), 7.05–6.86 (m, 5H), 6.70 (m, 2H), 6.58 (t, 1H), 6.47 (d, 1H), 4.19 (s, 2H), 3.98 (s, 2H), 3.68 (t, 2H), 3.38 (m, 2H), 3.18 (m, 2H), 2.75 (t, 2H), 1.99 (m, 2H), 1.89–1.14 (m, 6H). $^{13}$C NMR (75 MHz, CD$_3$OD) δ (ppm): 159.6, 141.4, 140.3, 139.5, 133.8, 132.3, 131.9, 131.4, 130.4, 130.2, 129.4, 125.2, 122.8, 113.3, 66.9, 57.5, 55.9, 53.7, 51.5, 26.5, 25.6, 24.0.

EXAMPLE 222

4-Chloro-N-(2,3,4,5,6-pentafluorobenzyl)-N-{2-[3-
(1-piperidinyl)propoxy]benzyl}benzenesulfonamide
Hydrochloride

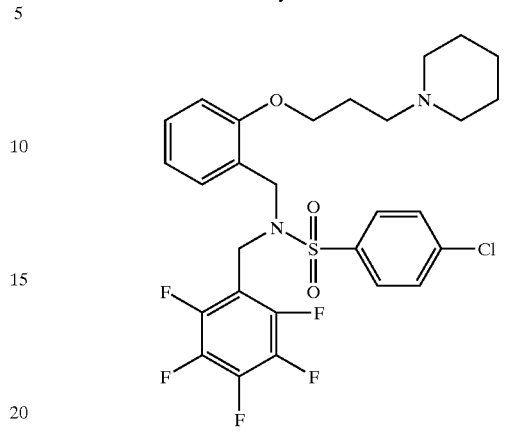

$R_f$=0.29 (1% triethylamine/5% methanol/ethyl acetate)
$^1$H NMR (300 MHz, CD$_3$OD) δ (ppm): 7.91–7.87 (m, 2H), 7.01–7.67 (m, 2H), 7.14 (m, 2H), 6.76 (m, 2H), 4.36 (d, 4H), 3.99 (d, 2H), 3.61–3.47 (m, 4H), 3.03 (m, 2H), 2.28 (m, 2H), 1.93–1.54 (m, 6H). $^{13}$C NMR (75 MHz, CD$_3$OD) δ (ppm): 157.9, 140.5 137.6 133.3, 130.9 130.6, 130.0, 127.5, 121.2 111.2 65.5, 55.8, 54.2, 51.1, 41.5, 24.9, 24.1 22.5. EST calculated for C$_{28}$H$_{28}$ClF$_5$N$_2$O$_3$S [MH+] 603; Observed: 603.

EXAMPLE 223

The general reaction scheme outlined in Scheme 223 is described in detail in the text following the scheme.

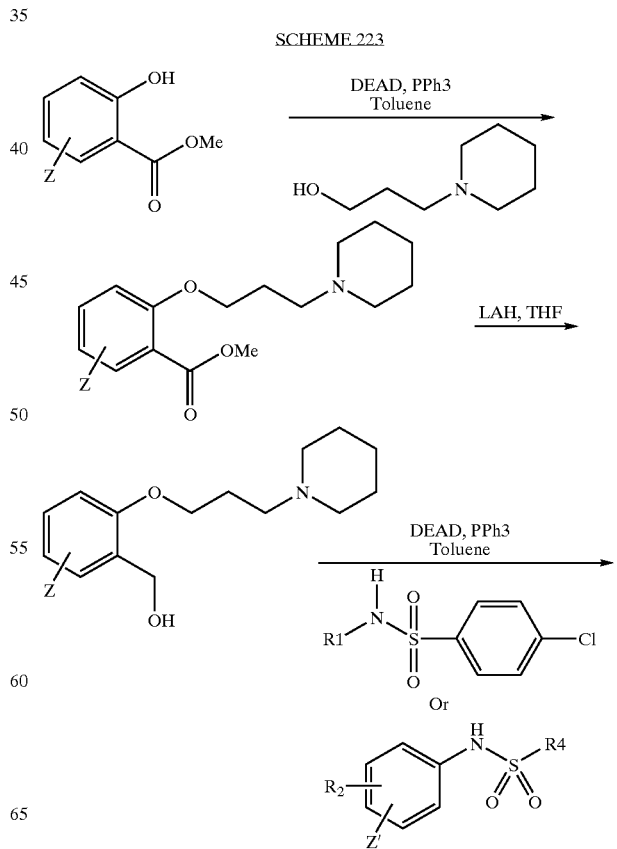

SCHEME 223

123

-continued

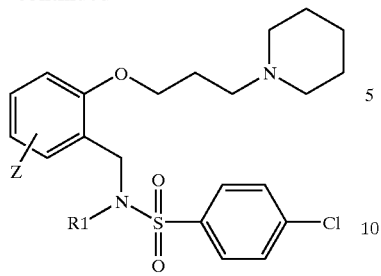

2-(3'-Piperidinylpropyloxy)-methyl Benzoate

To a solution of methylsalicylate (15.0 g, 98.8 mmol) in dry benzene (300 mL) was added Triphenylphosphine (25.8 g, 98.8 mmol) followed by N-(3-hydroxypropyl)piperidine (14.12 g, 98.8 mmol). The clear reaction mixture was cooled to 0° C. in an ice bath and DEAD (16.5 mL, 108.7 mmol) was added in drops over a period of 15 min. The reaction mixture was slowly warmed to room temperature and left stirred at room temperature for 15 h. The reaction mixture was filtered to remove the precipitated triphenylphosphineoxide and the filtrate was extracted with 1.0 M HCl (2×100 mL), the combined HCl solution was basified to pH 9 by the addition of solid NaHCO$_3$. The basic solution was extracted with ethyl acetate (3×100 mL). The combined ethyl acetate extracts were washed with saturated brine (2×75 mL), dried with MgSO$_4$, filtered and concentrated under reduced pressure to give 20.97 g of pale yellow oil (y: 77%) $^1$H NMR (CDCl$_3$) δ (ppm): 7.70 (dd, 1.8 Hz H), 7.42 (dt, 1.5 Hz, 1H), 6.99–6.94 (m, 2H), 4.08 (t, 2H), 3.88 (s, 3H), 2.58–2.45 9m, 6H), 2.04 (p, 2H), 1.65–1.60 (in, 4H), 1.47–1.45 (m, 2H).

2-(3'-Piperidinylpropyloxy)-benzylalcohol

To a suspension of lithium aluminum hydride (5.48 g, 144 mmol) in anhydrous THF (500 mL) was added a solution of the methyl ester (20 g, 72.1 mmol) in THF (200 mL) over a period of 30 min. The reaction mixture was refluxed for 6 h, cooled to 0° C. and quenched with water (5.48 mL) followed by 15% NaOH solution (5.48 mL) and finally with water (16.5 mL). The crystalline precipitate was filtered through the celite. The filtrate was concentrated to yield 18.9 g of crude product which was purified by chromatography on SiO$_2$ (2% methanol in CHCl$_3$) to yield 17.98 g of product as white crystalline solid (y: 91%). $^1$H NMR (CDCl$_3$) δ (ppm): 7.27–7.22 (m, 2H), 6.96–6.89 (m, 2H), 4.63 (s, 2H), 4.07 (t, J=2H), 2.55–2.40 (in, 6H), 2.00 (p, 2H), 1.66–1.58 (m, 4H), 1.46–1.43 (m, 2H).

The following compounds were similarly prepared.

3-Chloro 6-(3'-piperidinylpropyloxy)-benzylalcohol

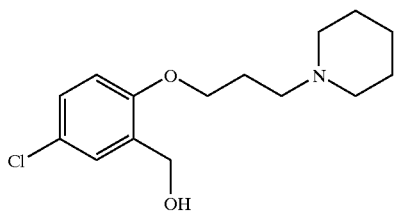

2-(3'-Piperidinylpropyloxy)-phenethylalcohol

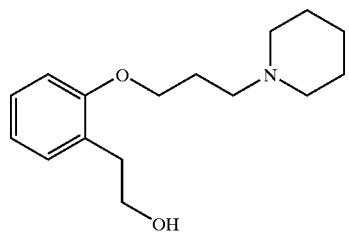

$^1$H NMR (300 MHz, CDCl$_3$) δ (ppm): 7.23–7.12 (m, 2H), 6.90–6.83 (m, 2H), 4.05 (t, 214), 3.83 (t, 2H), 2.91 (t, 3H), 2.51–2.47 (m, 6H), 1.99 (p, 2H), 1.72–1.58 (m, 4H), 1.48–1.40 (m, 2H).

3-(3'-Piperidinylpropyloxy)-benzylalcohol

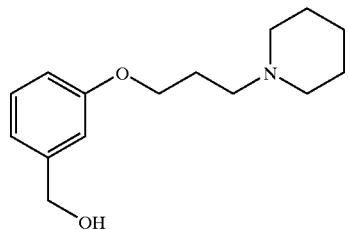

2-(3-N,N'-dimethylaminopropyloxy)benzylalcohol

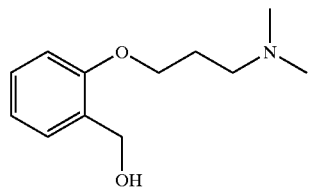

2-(3'-Piperidinylpropyloxy-β-naphthylalcohol

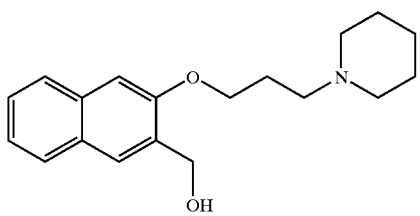

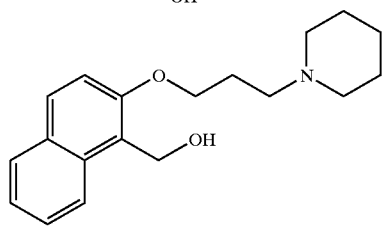

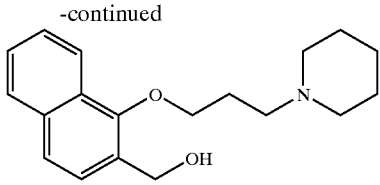

3-(3'-Piperidinylpropyloxy)-2-hydroxymethylpyridine

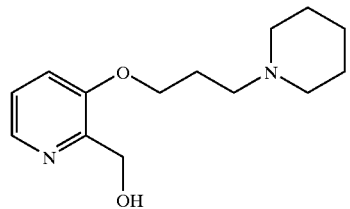

¹H NMR (300 MHz, CDCl₃) δ (ppm): 8.14 (dd, 1H), 7.20–7.12 (m, 2H), 4.72 (s, 2H), 4.05 (t, 3H), 2.51–2.40 (m, 6H), 2.00 (p, 2H), 1.64–1.57 (m, 4H), 1.46–1.44 (m, 2H).

2(3-Bromopropyloxy)methylbenzoate

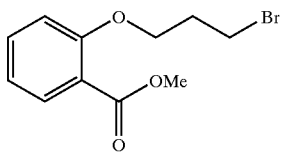

To a stirred solution of methyl salicylate (4.0 g, 26.3 mmol) dry THF (100 mL) under Ar was added Triphenylphosphine (6.9 g, 26.3 mmol) followed by 3-bromopropanol (3.66 g, 26.3 mmol). The rection mixture was cooled to 0° C. in an ice bath and DEAD (4.55 mL, 28.9 mmol) was added in drops over period of 15 min. The reaction mixture was left to stir at room temperature for 15 h. The reaction mixture concentrated under reduced pressure. The resulting crude product was purified by chromatography over SiO₂ (10:1, hexanes/ethyl acetate) to give 4.5 g of the desired product as a pale yellow oil (y: 63%). ¹H NMR (CDCl₃) δ (ppm): 7.83–7.99 (dd, 1H), 7.49–7.44 (t, 1H), 7.00–6.97 (m, 2H), 4.19 (t, 214), 3.89 (s, 3H), 3.71 (t, 2H), 2.36 (p, 2H).

2(3-Pyrrolidinylpropyloxy)methylbenzoate

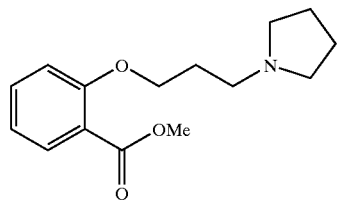

2(3-Bromopropyloxy)methylbenzoate (4.0 g, 11.3 mmol) was dissolved in neat pyrrolidine (40 mL) and stirred at room temperature for 1 h. The reaction mixture was then concentrated under reduced pressure. The isolated residue re-dissolved in DCM and washed with saturated bicarbonate solution (2×50 mL), dried with MgSO₄, filtered and concentrated under reduced pressure to give 3.8 g of colorless oil (y: 99%) ¹H NMR (CDCl₃) δ (ppm): 7.79–7.77 (d, 1H), 7.47 (t, 1H), 6.99–6.94 (m, 2H), 4.11 (t, 2H), 3.89 (s, 2H), 2.67 (t, 2H), 2.57 (br, 4H), 2.06 (p, 2H), 1.87 (br, 4H).

2-(3-Pyrrolidinylpropyloxy)benzylalcohol

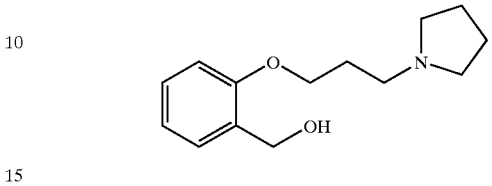

To a suspension of lithium aluminum hydride (0.9 g, 23.6 mmol) in anhydrous THF (100 mL) was added a solution of the methyl ester (3.0 g 11.8 mmol) in THF (10 mL) over a period of 10 min. The reaction mixture was refluxed for 6 h, cooled to 0° C. and quenched with water (0.9 mL) followed by 15% NaOH solution 0.9 mL) and finally with water (2.7 mL of). The crystalline precipitate was filtered through the celite. The filtrate vas concentrated to yield 2.3 g of crude product, which was subsequently purified by chromatography on SiO₂ (hexanes/ethyl acetate 5:1) to afford 2.02 g of product as colorless oil (y: 76%). ¹H NMR (CDCl₃) δ (ppm): 7.26–7.22 (m, 2H), 6.95–6.88 (m, 2H), 4.61 (s, 2H), 4.1 (t, 2H), 2.68 (t, 2H), 2.54 (br, 4H), 2.03 (p, 2H), 1.85–1.81 (m, 4H).

General Procedure for the Synthesis of 4-Cholorobenzenesulfanilides

To 1.0 g of amine dissolved in DCM (20 mL) or 1,2-dichloroethane was added 1.1 equivalent of pyridine and 1.0 equivalent of 4-chlorobenzenesulfonylchloride. The reaction mixture was gently refluxed over night then cooled to room temperature. The reaction mixture was concentrated under reduced pressure and the crude product was recrystallised from DCM/hexanes to give the product in 90–95% yield.

General Procedure for the Preparation of 4-Cholorobenzenesulfonanilides

To a biphasic mixture of alkylamines (11.0 g) in water (20 mL) was added 1.6 equivalent of solid NaHCO₃ followed by 1.0 equivalent of 4-chlorobenzesulfonamide. The heterogeneous mixture was refluxed for 2 h then cooled to room temperature and acidified with 1.0 M HCl to pH 1. The precipitated product was filtered, washed with water and subsequently recrystallized from ethyl acetate/hexanes to give the crystalline sulfonamide in 85–95% yield.

General Procedure for Alkylation of 4-Chlorobenzenesulfonamides

To a stirred solution of 2-(3'-piperidinylpropyloxy)-benzylalcohol (1.0 equivalent) in THF (10 mL/mmol) was added 1.5 equivalent of PPh₃ and 4-chlorobenzenesulfonamides followed by 1.5 equivalent of DEAD. The reaction mixture was stirred at room temperature for 12 h then concentrated under reduced pressure. The crude mixture was purified by chromatography (multiple elution 200 mL of ethyl acetate followed by 0.5% methanol 0.5% triethylamine in ethyl acetate) to give 45–60% yield of product as a colorless oil (free base). The free base was dissolved in DCM and an excess of a 1.0 M solution of HCl in ether was added. The resulting solution was concentrated under reduced pressure to give white solid. The HCl salt was purified by passing through a short column of silica and eluting with 10% methanol in DCM to yield white solid.

The following compounds were prepared according to the scheme described in the previous example.

EXAMPLE 224

4-Chloro-N-[3-(methylsulfanyl)phenyl]-N-{2-[3-(1-piperidinyl)propoxy]benzyl}benzenesulfonamide Hydrochloride

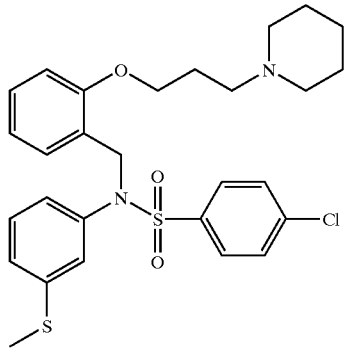

$R_f$ =0.25 (5% methanol/DCM) $^1$H NMR (300 MHz, CDCl$_3$) δ μm): 7.87–7.84 (m, 2H), 7.63–7.50 (m, 3H), 7.33–7.27 (m, 5H), 6.91 (m, 2H), 6.44 (m, 1H), 4.82 (d, 1H), 4.61 (m, 1H), 4.24 (m, 1H), 3.51 (s, 2H), 3.34 (m, 4H), 2.41 (t, 4H), 1.66–1.26 (m, 9H), 0.87 (m, 9H).

EXAMPLE 225

N-{2-[3-(dimethylamino)propoxy]benzyl}4-nitro-N-phenylbenzenesulfonamide

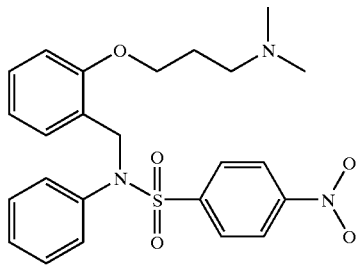

$R_f$=0.32 (9% methanol/DCM) $^1$H NMR (300 MHz, CDCl$_3$) δ (ppm): 8.36–8.22 (m, 3H), 8.06 (m, 1H), 7.80 (m, 2H), 7.23–7.15 (m, 3H), 6.82–6.67 (m, 5H), 4.82 (s, 2H), 4.12 (t, 2H), 3.45 (m, 2H), 2.87 (s, 6H), 2.41 (m, 2H).

EXAMPLE 226

N-{2-[3-(dimethylamino)propoxy]benzyl}-2-nitro-N-phenylbenzenesulfonamide

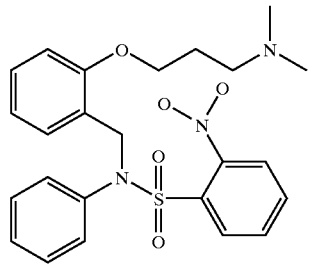

$R_f$=0.16 (9% methanol/DCM) $^1$H NMR (300 MHz, CDCl$_3$) δ (ppm): 7.62 (m, 2H), 7.50–7.42 (m, 2H), 7.29–7.07 (m, 7H), 6.85–6.74 (m, 2H), 5.04 (s, 2H), 3.86 (t, 2H), 2.42 (t, 2H), 2.25 (s, 6H), 1.85 (m, 2H).

EXAMPLE 227

5-(Dimethylamino)-N-{2-[3-(dimethylamino)propoxy]benzyl}-N-phenyl-1-naphthalenesulfonamide

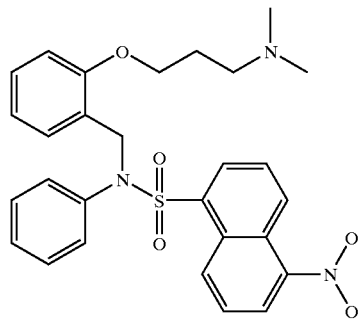

$R_f$=0.16 (9% methanol/DCM) $^1$H NMR (300 MHz, CDCl$_3$) δ (ppm): 8.69–8.23 (m, 15H), 4.99 (s, 2H), 4.12 (t, 2H), 3.60 (m, 2H), 2.85 (s, 6H), 2.50 (m, 2H).

EXAMPLE 228

N-{2-[3-(dimethylamino)propoxy]benzyl}-N-phenylmethanesulfonamide

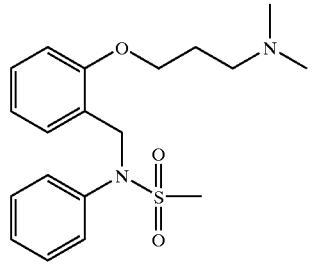

$R_f$=0.16 (9% methanol/DCM) $^1$H NMR (300 MHz, CDCl$_3$) δ (ppm): 7.33–7.15 (m, 6H), 6.91–6.70 (m, 3H), 4.88 (s, 2H), 4.06 (t, 2H), 3.36 (t, 2H), 2.97 (s, 3H), 2.82 (s, 6H) 2.48–2.37 (m, 2H).

EXAMPLE 229

4-Chloro-N-phenyl-N-(2-{2-[3-(1-piperidinyl)propoxy]phenyl}ethyl)benzenesulfonamide Hydrochloride

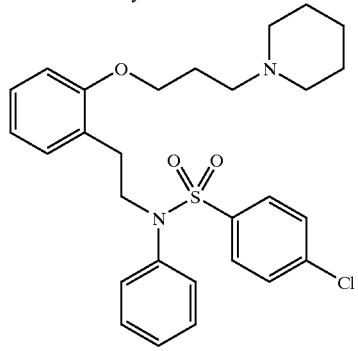

$R_f$=0.17 (5% methanol, 1% triethylamine) $^1$H NMR (300 MHz, CDCl$_3$) δ (ppm): 7.54–7.47 (m, 4H), 7.36–7.34 (m, 2H), 7.17 (dt, 1H), 7.04 (m, 2H), 6.92 (m, 2H), 6.75 (t, 1H), 4.17–4.05 (m, 2H), 3.86–3.81 (m, 2H), 3.6 (br, 2H), 3.45–3.40 (m, 2H), 3.1 (BR, 2H), 2.79–2.74 (m, 2H), 2.34–2.25 (m, 2H), 1.88 (br, 4H), 1.25 (t, 2H). ESI calculated for C$_{28}$H$_{33}$ClN$_2$O$_3$S (MH$^+$) 513, Observed 513.

EXAMPLE 230

4-Chloro-N-{5-chloro-2-[3-(1-piperidinyl)propoxy]benzyl}-N-phenylbenzenesulfonamide Hydrochloride

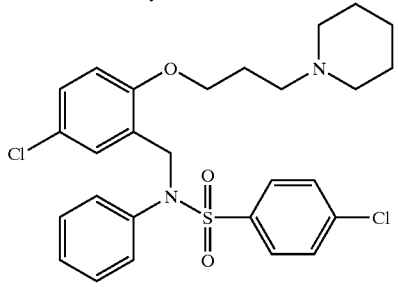

$R_f$=0.43 (3:1;1; nBuOH:H$_2$O:AcOH). $^1$H NMR (CDCl$_3$) δ (ppm): 7.59–7.53 (m, 4H), 7.20–7.17 (m, 3H), 7.10 (dd, 1H), 6.90–6.83 (m, 4H), 4.81 (s, 2H), 4.08 (t, 2H), 3.56–3.50 (m, 4H), 3.06–3.03 (br, 2H), 2.31–2.26 (m, 2H), 1.94–1.80 (m, 6H).

EXAMPLE 231

4-Chloro-N-(2,5-difluorophenyl)-N-{5-fluoro-2-[3-(1-piperidinyl)propoxy]benzyl}benzenesulfonamide Hydrochloride

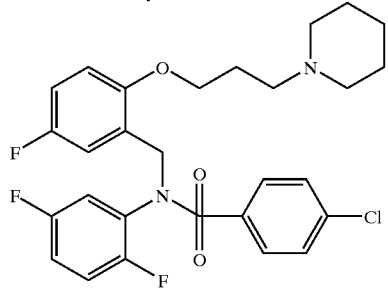

$R_f$=0.47 (9% methanol in DCM), $^1$H NMR (300 MHz, CD$_3$OD) δ (ppm): 7.74 (d, 2H), 7.65 (d, 2H), 7.10–8.05 (m, 2H), 6.99–6.89 (m, 2H), 6.85–6.75 (m, 2H), 4.83 (s, 2H), 4.11 (t, 2H), 3.41 (m, 2H), 3.21 (br, 2H), 2.32–2.23 (m, 2H), 1.87 (m, 4H), 1.58 (br, 2H). LC-MS calculated for C$_{27}$H$_{28}$ClF$_3$N$_2$O$_3$S, [MH+] 553; Observed: 553.

EXAMPLE 232

4-Chloro-N-(2,5-difluorophenyl)-N-{5-methyl-2-[3-(1-piperidinyl)propoxy]benzyl}benzenesulfonamide hydrochloride

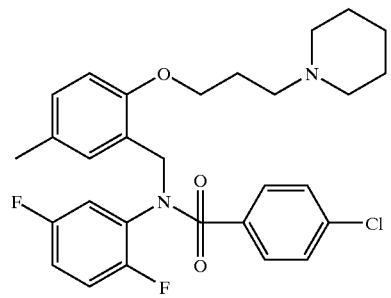

$R_f$=0.45 (9% methanol in DCM), $^1$H NMR (300 MHz, CD$_3$OD) δ (ppm): 7.75 (d, 2H), 7.66 (d, 2H), 7.05 (m, 3H), 6.81 (m, 3H), 4.76 (s, 2H), 4.03 (t, 2H), 3.13–3.00 (m 6H), 2.18 (m, 5H), 1.82 (m, 4H), 1.67 (m, 2H).

EXAMPLE 233

4-Chloro-N-(2,5-difluorophenyl)-N-({3-[3-(1-piperidinyl)propoxy]-2-pyridinyl}methyl)benzenesulfonamide Hydrochloride

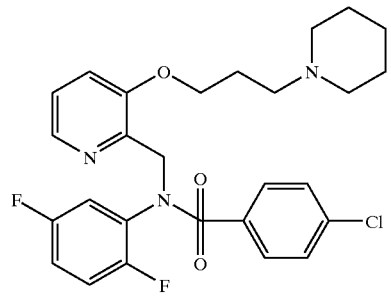

$R_f$=0.33 (10% methanol/DCM) $^1$H NMR (300 MHz, CDCl$_3$) δ (ppm): 7.71 (d, 1H), 7.63–7.51 (m, 4H), 7.31 (d, 1H), 7.15 (m, 1H), 6.90 (m, 2H), 6.62 (m, 1H), 4.87 (s, 2H), 4.08 (t, 2H), 3.28 (m, 2H), 3.07 (m, 4H), 2.21 (m, 2H), 1.74 (m, 4H), 1.55 (m, 2H). $^{13}$C NMR (75 MHz, CD$_3$OD) δ (ppm): 157.1, 146.0, 142.9, 142.5, 139.9, 132.3, 132.1, 129.3, 129.1, 129.0, 127.9, 122.2, 121.7, 121.3, 120.3, 120.1, 120.0, 119.8, 58.5, 57.8, 56.4, 54.3, 27.2, 26.4, 25.0.

EXAMPLE 234

4-Chloro-N-2,5-difluorophenyl-N-({3-[3-(1-piperidinyl)propoxy]-2-naphthylmethyl})benzenesulfonamide hydrochloride

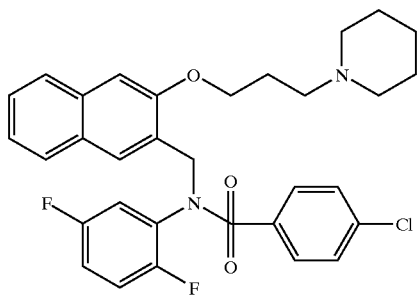

$R_f$=0.55 (9% methanol/DCM) $^1$H NMR (500 MHz, CD$_3$OD) δ (ppm): 7.73–7.67 (dd, 4H), 7.63–7.55 (dd, 3H), 7.43 (s, 1H), 7.38 (m, 1H), 7.24 (t, 1H), 7.18 (s, 1H), 6.95 (m, 2H), 6.81 (m, 1H), ° C. NMR (125 MHz, CD$_3$OD) δ (ppm): 160.3, 159.1, 158.4, 156.5, 141.0, 138.5, 136.3, 132.4, 130.8, 130.5, 129.7, 128.62, 128.0, 127.7, 125.3, 125.2, 120.0, 119.8, 118.4, 118.4, 118.2, 118.2, 107.3, 66.7, 56.7, 55.0, 51.5, 26.0, 25.1, 23.7.

EXAMPLE 235

4-Chloro-N-(3-chlorophenyl)-N-{2-[3-(1-piperidinyl)propoxy]benzyl}benzenesulfonamide Hydrochloride

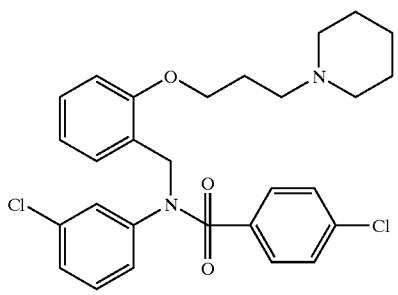

$R_f$=0.13 (1% triethylamine/ethyl acetate) $^1$H NMR (300 MHz, CD$_3$OD) δ (ppm): 7.61 (m, 4H), 7.17 (m, 3H), 6.92–6.84 (m, 4H), 6.67 (t, 1H), 4.84 (s, 2H) 4.15 (br, 2H), 3.67 (m, 4H), 3.06 (t, 2H), 2.34 (br, 2H), 2.02–1.52 (m, 6H). $^{13}$C NMR (75 MHz, CD$_3$OD) δ (ppm): 156.5, 140.3, 139.4, 136.6, 134.0, 130.1, 129.6, 129.2, 129.0, 128.6, 128.0, 127.0, 123.2, 120.4, 111.0, 66.4, 56.0, 54.6, 48.7, 26.7, 26.0, 24.4.

EXAMPLE 236

4-Chloro-N-(2,5-difluorophenyl)-N-(1-{2-[3-(1-piperidinyl)propoxy]phenyl}ethyl)benzenesulfonamide Hydrochloride

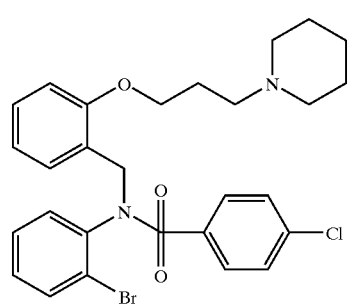

$R_f$=0.19 (1% triethylamine/ethyl acetate) $^1$H NMR (300 MHz, CD$_3$OD) δ (ppm): 7.66 (dd, 4H), 7.45 (d, 1H), 7.15 (m, 3H), 6.85 (dd, 2H), 7.67 (d, 1H), 6.58 (t, 1H), 5.20 (d, 1H), 4.53 (d, 1H), 4.19–4.05 (m, 2H), 3.83 (m, 3H), 3.31 (br, 2H), 2.33 (br, 2H), 2.00–1.78 (m, 6H). $^{13}$C NMR (75 MHz, CD$_3$OD) δ (ppm): 156.5, 140.3, 139.4, 136.6, 134.0, 130.1, 129.6, 129.1, 128.6, 128.0, 127.0, 123.2, 120.4, 111.0, 56.0, 54.6, 48.7, 26.7, 26.0, 24.4.

EXAMPLE 237

N-(3-bromophenyl)-4-chloro-N-{2-[3-(1-piperidinyl)propoxy]benzyl}benzenesulfonamide Hydrochloride

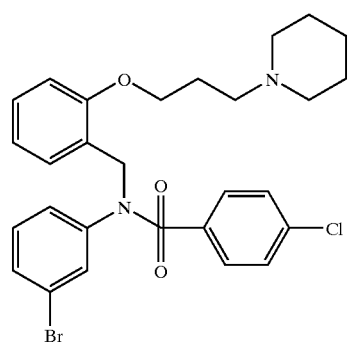

$R_f$=0.59 (10% methanol/DCM) $^1$H NMR (300 MHz, CD$_3$OD) δ (ppm): 7.42 (m, 2H), 7.45 (m, 1H), 7.22–7.06 (m, 3H), 6.93–6.84 (m, 3H), 6.68 (t, 1H), 4.85 (s, 2H), 4.27 (t, 2H), 3.61 (m, 4), 3.07 (br, 2H), 2.34 (m, 2H), 1.92 (m, 6H).

EXAMPLE 238

4-Chloro-N-[2-(methylsulfanyl)phenyl]-N-{2-[3-(1-piperidinyl)propoxy]benzyl}benzenesulfonamide Hydrochloride

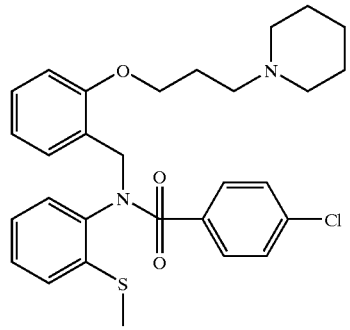

$^1$H NMR (300 MHz, CD$_3$OD) δ (ppm): 7.72–7.75 (m, 2H), 7.65–7.59 (m, 2H), 7.32–7.10 (m, 3H), 6.97 (dt, 1H), 6.85 (d, 1H), 6.69 (d, 1H), 6.57 (dt, 1H), 5.20 (d, 1H), 4.17 (m, 1H), 3.99 (m, 1H), 3.53 (m, 1H), 3.20 (m, 4H), 2.23 (m, 2H), 2.12 (s, 3H), 1.91 (m, 4H), 1.65 (br, 2H). ESI calculated for C$_{28}$H$_{33}$ClN$_2$O$_3$S$_2$ [MH+] 545; Observed: 545.

EXAMPLE 239

4-Chloro-N-[4-methylsulfanyl)phenyl]-N-{2-[3-(1-piperidinyl)propoxy]benzyl}benzenesulfonamide Hydrochloride

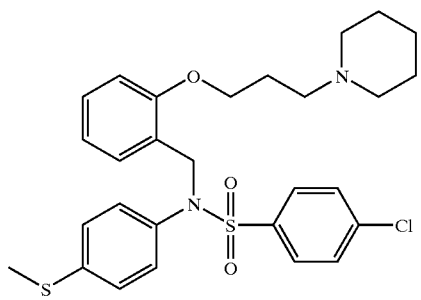

R$_f$=0.40 (10% methanol/DCM) $^1$H NMR (300 MHz, CD$_3$OD) δ (ppm): 7.60 (m, 4H), 7.16 (m, 1H), 7.03 (m, 2H), 6.85–6.77 (m, 3H), 6.66 (m, 1H), 4.81 (s, 2H), 4.10 (m, 4H), 3.06 (m, 2H), 2.39–2.28 (m, 5H), 2.02–1.1.28 (m, 8H). $^{13}$C NMR (75 MHz, CD$_3$OD) δ (ppm): 156.4, 139.1, 138.5, 136.9, 135.8, 130.0, 129.1, 129.1, 129.1, 128.8, 126.1, 123.7, 120.4, 111.0, 66.3, 56.0, 55.8, 54.6, 48.9, 26.7, 26.0, 25.7, 24.4, 15.3, 14.5, 14.2.

EXAMPLE 240

4-Chloro-N-cyclohexyl-N-{2-[3-(1-piperidinyl)propoxy]benzyl}benzenesulfonamide Hydrochloride

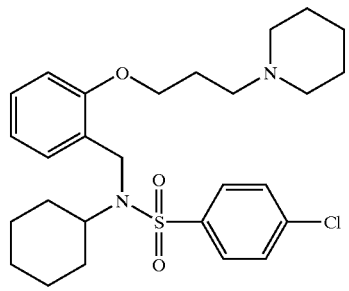

R$_f$ 0.49 (10% methanol/DCM) $^1$H NMR (300 MHz, CD$_3$OD) δ (ppm): 7.84–7.82 (m, 2H), 7.61–7.58 (m, 2H), 7.14–7.25 (m, 2H), 6.97–6.89 (m, 2H), 4.53 (s, 2H), 4.15 (m, 2H), 3.63–3.43 (m, 4H), 2.99 (m, 2H), 2.29 (m, 2H), 1.98–1.12 (m, 16H). $^{13}$C NMR (75 MHz, CD$_3$OD) δ: 158.1, 141.3, 140.0, 131.6, 130.7, 130.3, 129.8, 127.1, 121.7, 112.4, 66.1, 59.9, 56.1, 54.5, 44.8, 32.4, 27.3, 26.4, 25.3, 24.4, 22.8.

EXAMPLE 241

4-Chloro-N-(2-chlorophenyl)-N-{2-[3-(1-piperidinyl)propoxy]benzenesulfonamide Hydrochloride

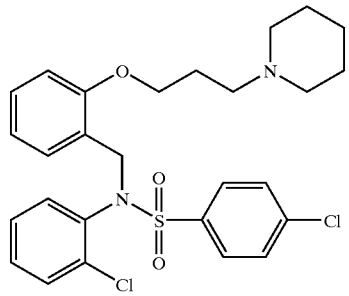

R$_f$=0.44 (10% methanol/DCM) $^1$H NMR (300 MHz, CD$_3$OD) δ (ppm): 7.73–7.69 (m, 2H), 7.64–7.59 (m, 2H), 7.30–7.10 (m, 4H), 6.90–6.80 (m, 3H), 6.64 (dt, 1H), 5.07 (d, 2H), 4.70 (d, 4H), 4.12–3.99 (d, 2H), 3.52 (m, 1H), 3.17 (b, 4H), 2.21 (br, 2H), 1.84 (m, 4H), 1.65 (m, 2H) $^{13}$C NMR (75 MHz, CD$_3$OD) δ (ppm): 156.9, 139.0, 138.7, 135.7, 134.8, 133.4, 134.0, 130.3, 129.5, 129.3, 129.1, 129.0, 127.0, 123.6, 120.2, 110.9, 66.3, 55.9, 54.6, 48.5, 26.5, 26.0, 24.4.

EXAMPLE 242

4-Chloro-N-[2-(methylsulfonyl)phenyl]-N-{2-[3-(1-piperidinyl)propoxy]benzyl}benzenesulfonamide Hydrochloride

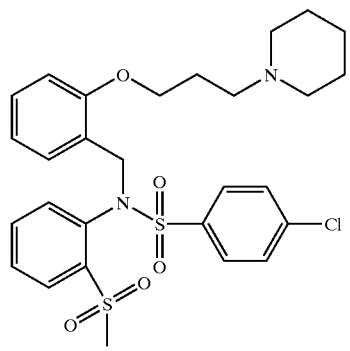

$R_f$ 0.13 (0.2% triethylamine/5% methanol/ethyl acetate) $^1$H NMR (300 MHz, CD$_3$OD) δ (ppm): 8.07 (dd, 1H), 7.78–7.4 (m, 2H), 7.66–7.45 (m, 1H), 7.17 (m, 1H), 6.80 (m, 2H), 6.64 (m, 21H), 5.24 (d, 1H), 4.63 (d, 1H), 3.88 (m, 1H), 3.70 (m, 1H), 3.06 (m, 9H), 1.99 (m, 2H), 1.80 (m, 4H), 1.63 (m, 2H).

EXAMPLE 243

4-Chloro-N-[3-(methylsulfonyl)phenyl]-N-{2-[3-(1-piperidinyl)propoxy]benzyl}benzenesulfonamide Hydrochloride

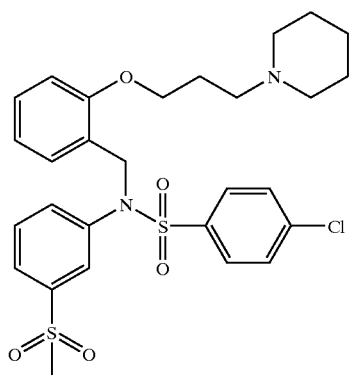

$R_f$=0.19 (5% methanol 0.2% triethylamine in ethyl acetate). $^1$H NMR (CD$_3$OD) δ (ppm): 7.78–7.75 (m, 1H), 7.61 (m, 4H), 7.47 (t, 1H), 7.42 (t, 1H), 7.35–7.32 (ddd, 1H), 7.17–7.11 (dt, 1H), 7.04–7.01 (dd, 1H), 6.86 (d, 1H), 6.71 (dt, 1H), 4.87 (s, 2H), 4.02 (t, 2H), 3.14–3.09 (m, 2H), 2.97–2.95 (s overlaps m, 5H), 2.18–2.12 (m, 2H), 1.82–1.74 (m, 4H), 1.62–1.60 (m, 2H).

EXAMPLE 244

4-Chloro-N-[4-(methylsulfonyl)phenyl]-N-{2-[3-(1-piperidinyl)propoxy]benzyl}benzenesulfonamide Hydrochloride

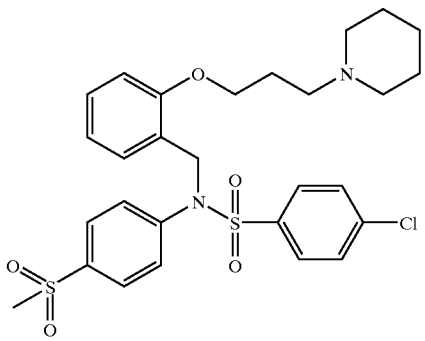

$R_f$=0.18 (93:5:2; ethyl acetate:methanol:triethylamine). $^1$H NMR (300 MHz, CD$_3$OD) δ :7.79 (d, 2H), 7.62 (m, 4H), 7.27–7.14 (m, 3H), 6.96–6.88 (m, 2H), 6.69 (m, 1H), 4.9 (s overlapped by HOD), 2H), 4.12 (m, 2H), 3.70–3.59 (m, 4H), 3.07–3.01 (m overlaps s, 5H), 2.29 (m, 2H), 2.02–1.78 (m, 6H). ESI calculated for C$_{28}$H$_{33}$ClN$_2$O$_5$S$_2$: 576. Observed 577 (MH$^+$).

EXAMPLE 245

4-Chloro-N-[3-(methylsulfanyl)phenyl]-N-{2-[3-(1-piperidinyl)propoxy]benzyl}benzenesulfonamide hydrochloride

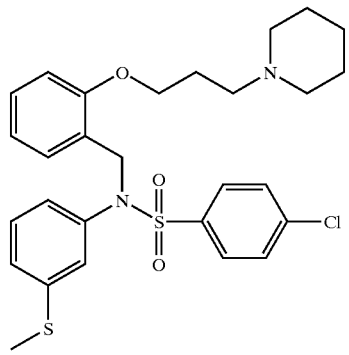

$^1$H NMR (300 MHz, CD$_3$OD) δ (ppm): 7.62 (m, 4H), 7.32–7.05 (m, 3H), 6.95–6.82 (m, 2H), 6.92–6.61 (m, 3H), 4.84 (s, 2H), 4.14 (t, 2H), 3.58 (m, 4H), 3.05 (m, 2H), 2.28 (m, 5H), 1.88 (br, 6H). ESI calculated for C$_{28}$H$_{33}$ClN$_2$O$_3$S$_2$ [MH+] 545; Observed: 545.

EXAMPLE 246

4-Chloro-N-(2,3-dihydro-1H-inden-2-yl)-N-{2-[3-(1-piperidinyl)propoxy]benzyl}benzenesulfonamide Hydrochloride

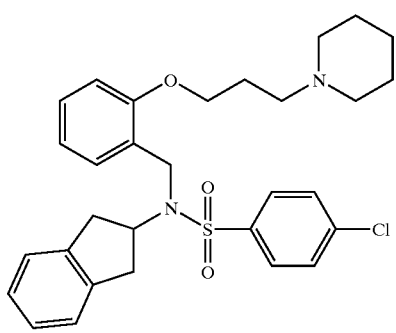

$R_f$=0.24 (10% methanol/DCM) $^1$H NMR (300 MHz, CD$_3$OD) δ (ppm): 7.91–7.87 (m, 2H), 7.64–7.61 (m, 2H), 4.78 (m, 1H), 7.21 (m, 1H), 7.05–0.90 (m, 5H), 6.83 (d, 1H), 4.88 (m, 1H), 4.43 (s, 2H), 3.88 (t, 2H), 3.30 (m, 2H), 2.88–2.59 (m, 10H), 1.67–1.50 (m, 6H). $^{13}$C NMR (75 MHz, CD$_3$OD) δ (ppm): 157.1, 141.4, 140.8, 140.3, 130.8, 130.3, 130.2, 129.7, 127.9, 127.5, 125.3, 121.7, 112.01, 66.8, 60.0, 56.8, 55.2, 43.6, 37.2, 26.6, 25.8, 24.4.

EXAMPLE 247

N-(4-bromophenyl)-4-chloro-N-{2-[3-(1-piperidinyl)propoxy]benzyl}benzenesulfonamide Hydrochloride

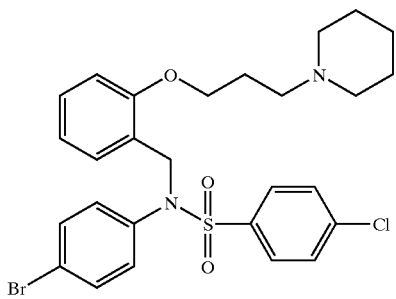

$R_f$=0.18 (19:1 DCM:methanol) $^1$H NMR (300 MHz, CD$_3$OD) δ (ppm): 7.71 (m, 4H), 7.33 (m, 2H), 7.17 (m, 1H), 6.91–6.81 (m, 4H), 6.69 (m, 1H), 4.82 (s, 2H), 4.10 (t, 2H), 3.56 (m, 2H), 3.23 (m, 4H), 2.28 (m, 2H), 1.86 (m, 4H), 1.66 (br, 2H). $^{13}$C NMR (75 MHz, CD$_3$OD) δ (ppm): 158.5, 140.7, 138.9, 137.8, 133.1, 132.2, 131.1, 130.7, 130.6, 124.0, 122.9, 121.5, 112.3, 66.2, 56.4, 54.9, 54.9, 51.4, 25.7, 24.8, 23.2.

EXAMPLE 248

4-Chloro-N-(5-chloro-2-hydroxyphenyl)-N-{2-[3-(1-piperidinyl)propoxy]benzyl)benzenesulfonamide Hydrochloride

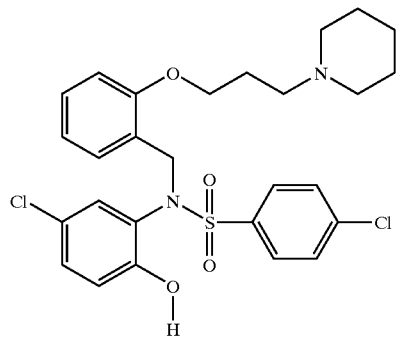

$R_f$ =0.62 (10% methanol/DCM), $^1$H NMR (300 MHz, CD$_3$OD) δ (ppm): 7.68–7.65 (m, 2H), 7.56–7.53 (m, 2H), 7.21–7.16 (m, 1H), 7.0 (dd, 1H), 6.92–6.87 (m, 2H), 6.76 (d, 1H), 6.67 (t, 1H), 6.56 (d, 1H), 4.93 (s, 2H), 4.15 (t, 2H), 3.72–3.60. (m, 4H), 3.12–3.10 (m, 2H), 2.39–2.30 (m, 2H), 2.04–1.73 (m, 5H), 1.61–1.52 (m, 1H). $^{13}$C NMR (75 MHz, CD$_3$OD) δ (ppm): 158.4, 155.4, 140.2, 139.6, 133.9, 132.7, 131.1, 130.7, 130.4, 130.2, 125.9, 124.5, 124.1, 121.5, 118.2, 112.1, 65.9, 56.2, 54.7, 25.5, 24.5, 22.9.

EXAMPLE 249

4-Chloro-N-(2,3-dihydro-1H-inden-1-yl)-N-{2-[3-(1-piperidinyl)propoxy]benzyl}benzenesulfonamide Hydrochloride

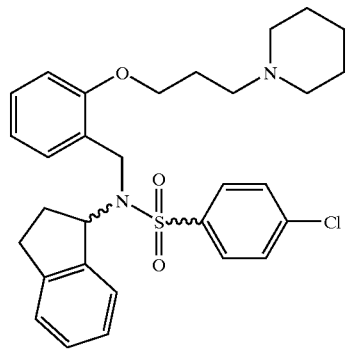

$R_f$=0.40 (10% methanol/DCM) $^1$H NMR (300 MHz, CD$_3$OD) δ (ppm): 7.89 (m, 2H), 7.60 (m, 2H, 7.31 (d, 1H), 7.23–7.07 (m, 3H), 6.91 (m, 1H), 6.80 (t, 1H), 6.71 (d, 1H), 6.56 (d, 1H), 5.57 (t, 1H), 4.49 (d, 1H), 4.12 (m, 1H), 3.80 (t, 2H), 2.86–2.45 (m, 8H), 2.17 (m, 1H), 1.91–1.70 (m, 3H), 1.66–1.49 (m, 6H). $^{13}$C NMR (75 MHz, CD$_3$OD) δ (ppm): 157.6, 145.2, 141.3, 140.8, 140.2, 130.8, 130.7, 130.1, 129.6, 129.36, 127.4, 127.1, 126.1, 125.8, 121.3, 111.8, 67.0, 65.0, 57.1, 55.5, 43.8, 31.5, 31.0, 27.0, 26.3, 25.0.

EXAMPLE 250

4-Chloro-N-cyclopentyl-N-{2-[3-(1-piperidinyl)propoxy]benzyl}benzenesulfonamide Hydrochloride

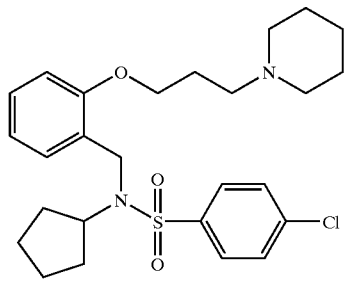

$R_f$=0.60 (9:1; DCM:methanol) $^1$H NMR (300 MHz CD$_3$OD) δ (ppm): 7.84 (m, 2H), 7.73–7.62 (m, 2H), 7.37 (d, 1H), 7.25 (m, 1H), 6.93 (m, 2H), 4.45 (s, 2H), 425 (m, 2H), 4.11 (t, 2H), 2.28 (m, 2H), 2.00–1.71 (m, 4H), 1.56–0.87 (m, 10H). $^{13}$C NMR (75 MHz, CD$_3$OD) δ ppm): 157.2, 140.8, 140.0, 133.2, 133.06, 130.6, 130.5, 130.1, 130.0, 129.8, 127.6, 121.8, 112.2, 66.1, 60.8, 55.9, 54.5, 44.2, 29.86, 25.3, 24.4, 22.8.

EXAMPLE 251

4-Chloro-N-(2,4-dichlorophenyl)-N-{2-[3-(1-piperidinyl)propoxy]benzyl}benzenesulfonamide Hydrochloride

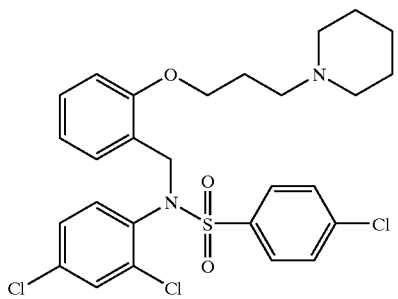

$R_f$=0.31 (10% methanol/DCM) $^1$H NMR (300 MHz, CD$_3$OD) δ (ppm): 7.65–7.52 (m, 4H) 7.28 (d, 1H) 7.14–7.07 (m, 2H), 6.79 (m, 3H), 6.60 (t, 1H), 4.96 (m, 1H), 4.60 (m, 1H), 4.00 (m, 2H), 3.34–3.03 (m, 6H), 2.10 (m, 2H), 1.73 (m, 4H), 1.55 (m, 2H). $^{13}$C NMR (75 MHz, CD$_3$OD) δ (ppm): 160.34, 142.46, 140.79, 139.54, 137.77, 137.42, 136.15, 134.59, 132.99, 132.84, 132.39, 132.26, 130.38, 125.17, 123.08, 113.86, 67.96, 58.22, 56.55, 52.47, 27.56, 26.65, 25.19.

EXAMPLE 252

4-Chloro-N-(2,5-dibromophenyl)-N-{2-[3-(1-piperidinyl)propoxy]benzyl}benzenesulfonamide Hydrochloride

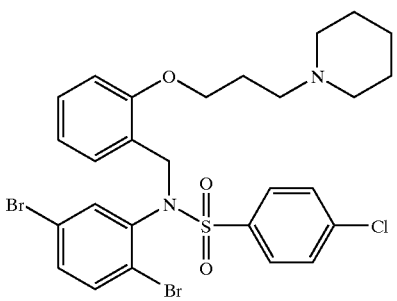

$R_f$=0.26 (10%° methanol/DCM) $^1$H NMR (300 MHz, CD$_3$OD) δ (ppm): 7.64–7.53 (m, 4H), 7.31 (d, 1H), 7.21 (dd, 1H), 7.10 (dt, 1H), 6.86 (d, 1H), 6.79 (d, 1H), 6.61 (t, 1H), 5.40 (d, 1H), 4.58 (d, 1H), 3.95 (m, 2H), 3.22–2.02 (m, 6H), 2.08 (m, 2H), 2.11–1.54 (m, 6H). $^{13}$C NMR (75 MHz, CD$_3$OD) δ (ppm): 154.6, 136.9, 135.6, 134.4, 132.0, 130.2, 129.0, 127.4, 126.7, 126.7, 122.5, 118.9, 117.4, 117.33, 108.0, 61.7, 52.2, 50.6, 50.5, 21.3, 20.3, 18.7. ESI calculated for C$_{27}$H$_{29}$Br$_2$ClN$_2$O$_3$S [MH+] 657; Observed: 657.

EXAMPLE 253

4-Chloro-N-(2,5-dichlorophenyl)-N-{2-[3-(1-piperidinyl)propoxy]benzyl}benzenesulfonamide Hydrochloride

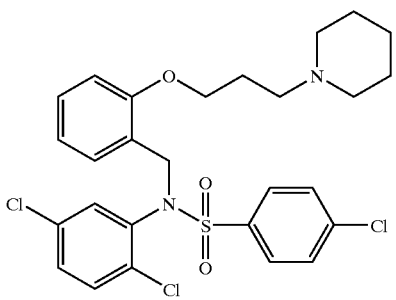

$R_f$=0.35 (10% methanol/CDCl$_3$) $^1$H NMR (300 MHz, CD$_3$OD), δ (ppm): 7.72–7.60 (m, 4H), 7.27–7.15 (m, 3H), 6.87 (m, 2H), 6.78 (dd, 1H), 6.63 (t, 1H) 5.03 (d, 1H), 5.68 (d, 1H), 4.15 (m, 1H), 4.02 (m, 1H) 3.67 (m, 1H) 3.65 (m, 1H), 2.31 (m, 2H), 1.88 (m, 6H). $^{13}$C NMR (75 MHz, CD$_3$OD) δ (ppm): 158.69, 141.00, 138.84, 137.78, 135.68, 133.50, 133.39, 133.02, 132.61, 131.54, 131.27, 130.82, 130.70, 123.27, 121.54, 112.23, 65.98, 56.28, 54.66, 51.00, 25.44, 24.42, 22.93.

EXAMPLE 254

4-Chloro-N-cycloheptyl-N-{2-[3-(1-piperidinyl)propoxy]benzyl}benzenesulfonamide Hydrochloride

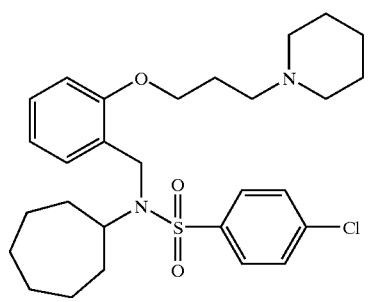

$R_f$=0.37 (10% methanol/DCM) $^1$H NMR (300 MHz, CD$_3$OD) δ (ppm): 7.65 (d, 2H), 7.41 (d, 2H), 7.29 (d, 1H), 7.06 (t, 1H), 6.76 (m, 2H), 4.26 (s, 2H), 3.88 (t, 2H), 3.67 (m, 1H), 2.54–2.40 (m, 6H), 1.88 (m, 2H), 1.49–1.12 (m, 18H). $^{13}$C NMR (75 MHz, CD$_3$OD) δ (ppm): 158.2, 141.9, 140.6, 131.7, 131.3, 130.6, 130.4, 128.5, 122.3, 112.9, 68.1, 62.6, 58.0, 56.2, 44.0, 35.3, 29.2, 28.0, 27.1, 27.0, 25.6.

EXAMPLE 255

4-Chloro-N-(2-chloro-3-pyridinyl)-N-{2-[3-(1-piperidinyl)propoxy]benzyl}benzenesulfonamide Hydrochloride

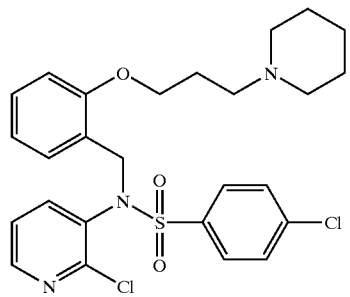

$R_f$=0.37 (10% methanol/DCM) $^1$H NMR (300 MHz, CD$_3$OD) δ (ppm): 7.77–7.73 (4H, m), 7.33–7.20 (3H, m), 6.94–6.90 (m, 3H), 6.75–6.70 (m, 1H), 5.03 (d, 1H), 5.77 (d, 1H), 4.13–4.02 (m, 2H), 3.44–3.16 (m, 6H), 2.24 (m, 2H), 1.89–1.84 (m, 4H), 1.67 (m, 2H). $^{13}$C NMR (75 MHz, CD$_3$OD) δ (ppm): 159.1, 141.0, 139.3, 138.6, 135.2, 133.4, 131.6, 131.6, 131.1, 134.0, 129.4, 127.8, 123.7, 121.6, 112.4, 66.1, 56.7, 54.9, 54.9, 51.6, 25.7, 24.7, 23.2.

EXAMPLE 256

N-[(2S)-bicyclo[2.2.1]hept-2-yl]4-chloro-N-{2-[3-(1-piperidinyl)propoxy]benzyl}benzenesulfonamide Hydrochloride

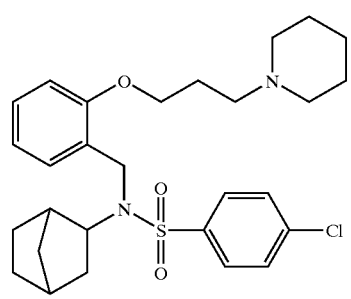

$R_f$=0.33 (10% methanol/DCM) $^1$H NMR (300 MHz, CD$_3$OD) δ (ppm): 7.86–7.81 (m, 2H), 7.62–7.58 (m, 2H), 7.49 (m, 1H), 7.19 (m, 1H), 6.93 (m, 2H), 4.44 (s, 2H), 4.03 (m, 2H), 3.89 (m, 1H), 2.62 (m, 6H), 2.07–0.90 (m, 18H). $^{13}$C NMR (75 MHz, CD$_3$OD) δ (ppm): 158.2, 1423, 141.5, 132.1, 131.5, 131.3, 130.79, 129.4, 123.0, 113.5, 68.6, 64.2, 58.6, 56.9, 44.9, 43.5, 40.0, 38.6, 38.5, 31.8, 29.9, 28.66, 27.6, 26.3.

EXAMPLE 257

4-Chloro-N-(3,5-dichlorophenyl)-N-(2-[3-(1-piperidinyl)propoxy]benzyl}benzenesulfonamide Hydrochloride

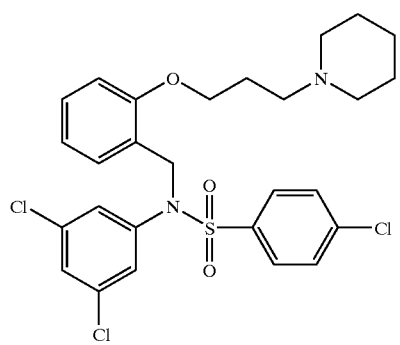

$R_f$=0.6 (10% methanol/DCM) $^1$H NMR (500 MHz, CDCl$_3$) δ (ppm): 7.65 (m, 4H), 7.30 (t, 1H), 7.23–7.18 (m, 1H), 6.98–6.92 (m, 4H), 6.73 (m, 1H), 4.15 (t, 2H) 3.64–3.57 (m, 2H), 3.70–3.67 (m, 2H), 3.09–3.04 (m, 2H), 2.38–2.32 (m, 2H), 2.10–1.98 (m, 2H), 1.88–1.79 (m, 4H) ESI calculated for C$_{27}$H$_{29}$Cl$_3$N$_2$O$_3$S [MH+] 569; Observed: 569.

EXAMPLE 258

4-Chloro-N-(2,5-dichloro-3-pyridinyl)-N-{2-[3-(1-piperidinyl)propoxy]benzyl}benzenesulfonamide Hydrochloride

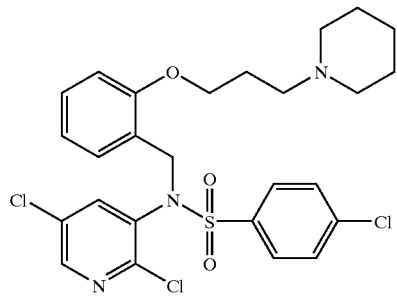

$R_f$ =0.49 (10% methanol/DCM) $^1$H NMR (300 MHz, CD$_3$OD) δ (ppm): 8.28 (d, 1H), 7.77–7.54 (m, 4H), 7.41 (d, 1H), 7.23 (m, 1H), 6.93–6.86 (m, 2H), 6.71 (m, 1H), 5.05 (m, 10H), 4.78 (m, 1H), 4.17–4.04 (m, 2H), 3.69–3.44 (m, 4H), 3.04 (m, 2H), 2.31 (m, 2H), 2.00–1.51 (m, 6H). ESI calculated for C$_{26}$H$_{28}$Cl$_3$N$_3$O$_3$S [MH+] 568; Observed: 568.

EXAMPLE 259

N-{5-[((2,5-dichloro{2-[3-(1-piperidinyl)propoxy]benzyl}anilino)sulfonyl]-4-methyl-1,3-thiazol-2-yl}acetamide Hydrochloride

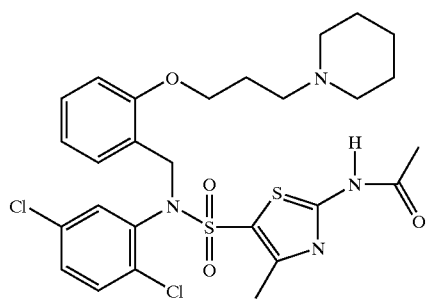

$R_f$=0.70 (3:1:1 n-BuOH/H$_2$O/AcOH) $^1$H NMR (500 MHz, DMSO) δ (ppm): 12.73 (s, 1H), 10.08 (br, 1H), 7.43 (m, 2H), 7.27 (d, 1H), 7.20 (m, 1H), 6.99 (d, 1H), 6.91 (d, 1H), 6.75 (t, 1H), 4.99 (d, 1H), 4.69 (d, 1H), 4.00 (m, 2H), 3.47–3.22 (m, 1H), 2.21–1.70 (m, 9H). ESI calculated for C$_{27}$H$_{32}$Cl$_2$N$_4$O$_4$S [MH+] 611; Observed: 611.

EXAMPLE 260

(E)-N-(2,5-dichlorophenyl)-2-phenyl-N-{2-[3-(1-piperidinyl)propoxy]benzyl}ethenesulfonamide hydrochloride

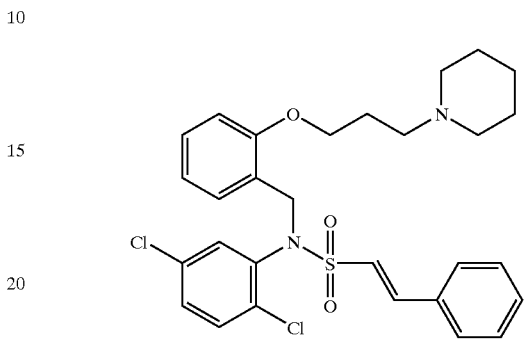

$R_f$=0.62 (3:1:1 n-BuOH/H$_2$O/AcOH) $^1$H NMR (500 MHz, CD$_3$OD) δ (ppm): 7.62 (m, 2H), 7.45 (m, 3H), 7.35–7.32 (dd, 2H), 7.29–7.21 (m, 4H), 6.93 (m, 2H), 6.72 (t, 1H), 4.88 (m, 2H), 4.17 (m, 1H), 4.04 (m, 1H), 3.39 (m, 6H), 2.27 (m, 2H), 1.93 (m, 4H), 1.69 (m, 2H). ESI calculated for C$_{29}$H$_{32}$Cl$_2$N$_2$O$_3$S [MH+] 559; Observed: 559.

EXAMPLE 261

N-(2,5-dichlorophenyl)(phenyl)-N-{2-[3-(1-piperidinyl)propoxy]benzyl}methanesulfonamide Hydrochloride

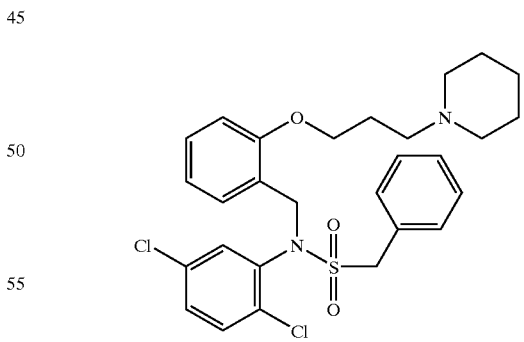

$R_f$=0.67 (3:1:1 n-BuOH/H$_2$O/AcOH) $^1$H NMR (500 MHz, CD$_3$OD) δ (ppm): 7.39–7.28 (m, 8H), 6.96 (m, 2H), 6.80 (t, 2H), 4.88 (m, 2H), 4.51 (s, 2H), 4.05 (d, 2H), 3.31–3.30 (m, 6H), 2.18 (m, 2H), 1.78 (m, 4H), 1.61 (br, 2H). ESI calculated for C$_{28}$H$_{32}$Cl$_2$N$_2$O$_3$S [MH+] 547; Observed: 547.

EXAMPLE 262

N-(2,5-difluorophenyl)-4-methyl-N-{2-[3-(1-piperidinyl)propoxy]benzyl}benzenesulfonamide Hydrochloride

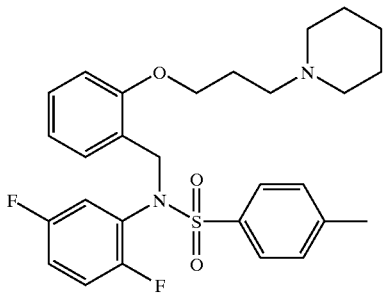

¹H NMR (300 MHz, CD₃OD) δ (ppm): 7.62–7.50 (m, 3H), 7.37 (m, 2H), 7.13 (t, 1H), 6.93–6.84 (m, 2H), 6.76 (d, 1H), 6.63–6.58 (m, 2H), 4.71 (s, 2H), 4.12–4.05 (m, 2H), 3.63–3.57 (m, 2H), 3.03 (t, 2H), 2.42 (s, 3H), 2.30 (m, 2H), 1.97–1.68 (m, 6H).

EXAMPLE 263

4-Bromo-N-(2,5-difluorophenyl)-N-{2-[3-(1-piperidinyl)propoxy]benzyl}benzenesulfonamide Hydrochloride

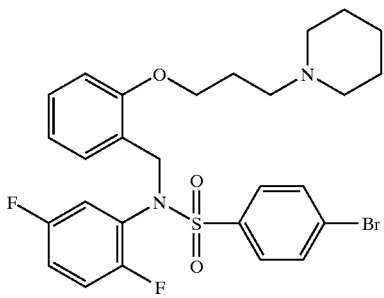

¹H NMR (300 MHz, CD₃OD) δ (ppm): 7.79 (d, 2H), 7.63 (d, 2H), 7.19 (t, 1H), 7.00 (m, 2H), 6.90 (d, 1H), 6.85 (d, 1H), 6.73 (m, 1H), 6.65 (m, 1H), 4.83 (s, 2H), 4.15 (m, 2H), 3.68 (d, 2H), 3.60 (m, 2H), 3.30 (m, 2H), 3.06 (m, 2H), 2.35 (m, 2H), 1.99 (m, 2H), 1.85 (m, 3H), 1.55 (m, 1H).

EXAMPLE 264

4-Chloro-N-cyclopropyl-N-{2-[3-(1-piperidinyl)propoxy]benzyl}benzenesulfonamide Hydrochloride

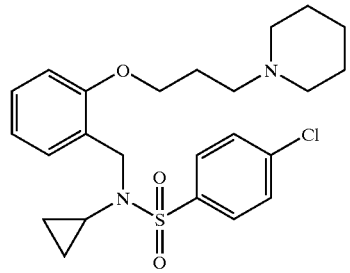

$R_f$=0.32 (10% methanol/DCM) ¹H NMR (500 MHz, CD₃OD) δ μm): 7.88–7.86 (d, 2H), 7.67–7.65 (d, 2H), 7.31–7.22 (m, 2H), 6.96–6.88 (dt, 2H), 4.38 (s, 2H), 4.11 (s, 2H), 3.31 (s, 1H), 20 (m, 4H), 2.27–2.22 (m, 2H), 1.87–1.78 (m, 6H), 1.66 (m, 2H), 0.47 (m, 4H). ¹³C NMR (125 MHz, CD₃OD) δ (ppm): 158.4, 140.6, 137.5, 133.0, 130.8, 130.8, 130.7, 125.5, 121.7, 112.4, 66.2, 56.3, 54.8, 52.2, 31.86, 25.7, 24.7, 23.2.

EXAMPLE 265

N-[(2S)-bicyclo[2.2.1]hept-2-yl]-4-chloro-N-{2-[3-(1-piperidinyl)propoxy]benzyl}benzenesulfonamide Hydrochloride

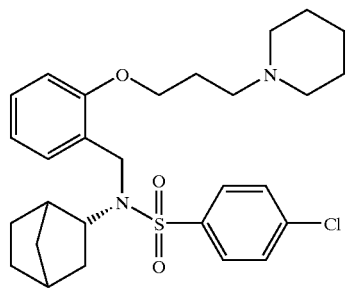

$R_f$=0.52 (10% methanol/DCM) ¹H NMR (300 MHz, CD₃OD) δ (ppm): 7.81 (m, 2H), 7.56 (m, 2H), 7.39 (d, 1H), 7.19 (m, 1H), 6.91 (m, 2), 4.46 (s, 2H), 4.02 (t, 2H), 3.85 (m, 2H), 2.55 (m, 7H), 2.01 (m, 3H), 1.68–0.99 (m, 14H). ESI calculated for C₂₈H₃₁ClN₂O₃S [MH+] 517; Observed: 517.

EXAMPLE 266

4-Chloro-N-(2,5-difluorophenyl)-N-{2-[3-(1-piperidinyl)propoxy]benzyl}benzenesulfonamide Hydrochloride

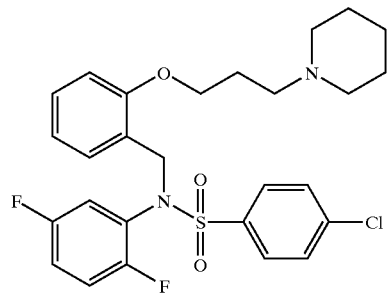

$R_f$=0.38 (10% methanol/DCM) ¹H NMR (300 MHz, CD₃OD) δ (ppm): 7.69–7.58 (m, 4H), 7.18–6.61 (m, 7H), 4.79 (s, 2H), 4.12 (t, 2H), 3.68–3.56 (m, 4H), 3.07–2.99 (m, 2H), 2.33 (m, 2H), 1.98–1.52 (m, 6H). ¹³C NMR (75 MHz, CD₃OD) δ (ppm): 158.6, 141.0, 138.3, 132.9, 131.5, 130.8, 130.5, 127.5, 127.5, 123.4, 121.6, 120.0, 119.7, 118.6, 118.5, 118.4, 118.3, 1182, 118.1, 112.3, 66.0, 56.3, 54.7, 51.2, 51.1, 25.5, 24.5, 22.9.

EXAMPLE 267

4-Chloro-N-(2-methylphenyl)-N-{2-[3-(1-piperidinyl)propoxy]benzyl}benzenesulfonamide Hydrochloride

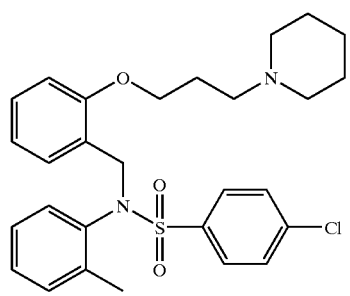

$R_f$=0.59 (15% methanol/DCM) $^1$H NMR (300 MHz, CD$_3$OD) δ (ppm): 7.74–7.65 (m, 4H), 7.24–6.93 (m, 5H), 6.60–6.55 (dd, 3H), 5.47 (d, 1H), 4.14 (m, 4H), 3.80–3.43 (m, 6H), 3.34 (m, 2H), 1.90–1.72 (m, 6H). $^{13}$C NMR (75 MHz, CD$_3$OD) δ (ppm): 158.7, 141.9, 140.7, 138.5, 138.3, 133.5, 132.1, 131.1, 130.8, 130.61, 129.6, 128.9, 127.3, 123.6, 121.3, 111.9, 65.8, 56.2, 54.6, 52.5, 25.5, 24.5, 22.9, 18.5. ESI calculated for C$_{28}$H$_{33}$ClN$_2$O$_3$S [MH+] 513; Observed: 513.

EXAMPLE 268

4-Chloro-N-(3-methylphenyl)-N-{2-[3-(1-piperidinyl)propoxy]benzyl}benzenesulfonamide Hydrochloride

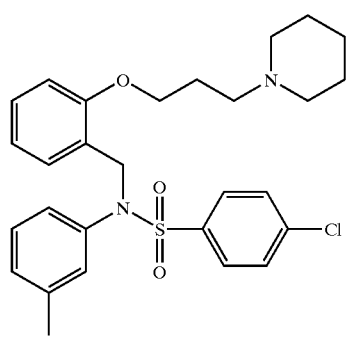

$R_f$=0.32 (10% methanol/DCM) $^1$H NMR (300 MHz, CD$_3$OD) δ (ppm): 7.71–7.49 (m, 4H), 7.20–6.94 (m, 4H), 6.84 (d, 1H), 6.69 (m, 3H), 4.80 (s, 2H), 4.04 (t, 2H), 3.22 (m, 2H), 3.06 (b, 4H), 2.29–2.17 (m, 5H), 1.80 (m, 4H), 1.61 (m, 2H). $^{13}$C NMR (75 MHz, CD$_3$OD) δ (ppm): 156.5, 138.5, 138.1, 137.8, 136.4, 130.7, 129.1, 128.8, 128.7, 128.6, 128.0, 127.8, 125.2, 122.7, 119.5, 110.4, 64.6, 54.7, 53.0, 49.3, 24.2, 23.2, 21.8, 19.4. ESI calculated for C$_2$H$_{33}$ClN$_2$O$_3$S [MH+] 513; Observed: 513.

EXAMPLE 269

2-{2-[3-(1-piperidinyl)propoxy]benzyl}-2H-naphtho[1,8-cd]isothiazole 1,1-Dioxide Hydrochloride

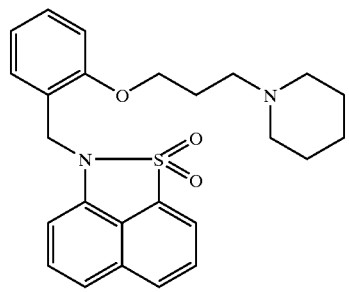

$R_f$=0.48 (10% methanol/DCM) $^1$H NMR (300 MHz, CD$_3$OD) δ μm): 8.11–7.97 (dd, 2H), 7.76 (m, 1H), 7.44–7.23 (m, 4H), 6.98 (d, 1H), 6.87 (t, 1H), 6.68 (m, 1H), 4.95 (s, 2H), 4.10 (t, 2H), 2.60–2.41 (m, 6H), 2.02 (m, 2H), 1.57–1.40 (m, 6H). $^{13}$C NMR (75 MHz, CD$_3$OD) δ (ppm): 160.1, 140.2, 134.8, 134.4, 134.0, 133.0, 132.8, 132.7, 131.8, 126.8, 124.1, 123.1, 121.8, 114.7, 107.4, 69.1, 58.9, 57.2, 44.2, 28.6, 27.6, 26.2. ESI calculated for C$_{25}$H$_{28}$ClN$_2$O$_3$S [MH+] 437; Observed: 437.

EXAMPLE 270

4-Chloro-N-(2,3-dichlorophenyl)-N-(2-[3-(1-piperidinyl)propoxy]benzyl}benzenesulfonamide Hydrochloride

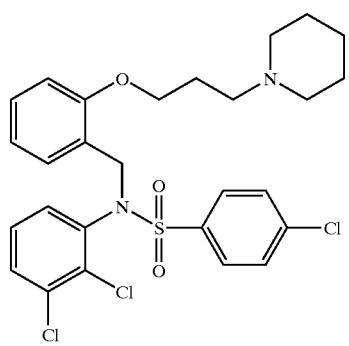

$R_f$=0.38 (10% methanol/DCM) $^1$H NMR (300 MHz, CD$_3$OD) 3 μm): 7.73–7.62 (m, 4H), 7.42 (dd, 1H), 7.22–7.10 (m, 2H) 6.85 (d, 1H) 6.83 (dd, 1H), 6.73 (dd, 1H) 6.63 (t 1H) 5.16 (d, 1H) 4.58 (d, 1H) 4.18 (m, 1H) 4.05 (d, 1H) 3.53–3.30 (m, 6H) 2.36–1.90 (m, 4H). $^{13}$C NMR (75 MHz, CD$_3$OD) δ (ppm): 159.39 141.58, 139.54, 139.42, 136.60, 135.47, 133.69, 132.59, 132.31, 132.15, 131.48, 131.38, 129.32, 123.92, 122.10, 112.87, 66.59, 56.95, 55.31, 51.84, 26.10, 25.07, 23.59. ESI calculated for C$_{27}$H$_{29}$Cl$_3$N$_2$O$_3$S [MH+] 567; Observed: 567.

EXAMPLE 271

4-Chloro-N-{2-[3-(1-piperidinyl)propoxy]benzyl}-N-tetrahydro-2H-pyran-4-ylbenzenesulfonamide hydrochloride

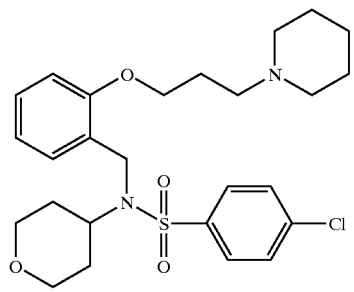

$R_f$=0.42 (10% methanol/DCM), $^1$H NMR (300 MHz, CD$_3$OD) δ (ppm): 7.90–7.86 (m, 2H), 7.63–7.69 (m, 2H), 7.41–7.39 (m, 1H), 7.33–7.27 (m, 1H), 6.97–6.92 (m, 2H), 4.56 (s, 2H), 4.16–4.12 (t, 2H), 3.93–3.87 (m, 1H), 3.80–3.73 (m, 2H), 3.44 3.22 (m, 8H), 2.32–227 (m, 2H), 1.89–1.80 (m, 4H), 1.61–1.53 (m 4H), 1.29–1.25 (m, 2H). $^{13}$C NMR (free base, 75 MHz, CDCl$_3$) δ (ppm): 155.1, 139.5, 138.4, 128.9, 128.6, 127.9, 125.6, 120.0, 110.2, 55.7, 55.1, 54.2, 41.0, 30.8, 26.4, 25.4, 23.9, 14.0.

EXAMPLE 272

4-Chloro-N-(2,5-difluorophenyl)-N-({1-[3-(1-piperidinyl)propoxy]-2-naphthylmethyl)benzenesulfonamide Hydrochloride

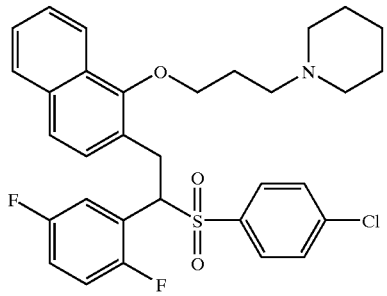

$R_f$=0.6 (10:1 DCM:methanol), $^1$H NMR (CD$_3$OP) δ (ppm): 7.99–7.96 (m, 1H), 7.82–7.76 (m, 3H), 7.66–7.63 (m, 1H), 7.54–7.45 (m, 3H), 7.30–7.28 (m, 1H), 7.05–7.00 (m, 2H), 6.84–6.81 (m, 1H), 5.01–4.91 (m, 2H), 4.04–4.01 (m, 2H), 3.32–3.00 (m, 6H), 2.23–2.26 (m, 2H), 1.81–1.64 (m, 6H). LC-MS calculated for C$_{31}$H$_{31}$ClF$_2$N$_2$O$_3$S: 585: observed 585.

EXAMPLE 273

4-Chloro-N-(2,5-difluorophenyl)-N-({1-[3-(1-piperidinyl)propoxy]-2-naphthyl}methyl)benzenesulfonamide Hydrochloride

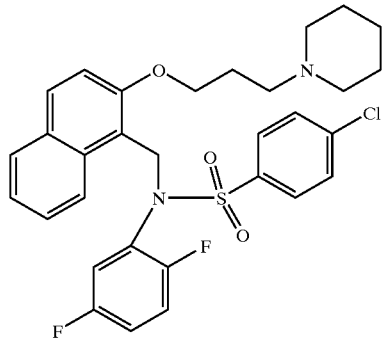

Mp=228° C. (d). $R_f$=0.45 (10:1; DCM:methanol). $^1$H NMR (DMSO) δ (ppm): 8.20–8.17 (m, 1H), 7.87–7.77 (m, 6H), 7.55–7.11 (m, 5H), 6.57 (m, 1H), 5.25 (m, 2H), 3.95 (m, 2H), 3.40–3.36 (m, 2H), 3.15 (m, 2H), 2.85 (m, 2H), 2.12 (m, 2H), 1.80–1.76 (m, 4H), 1.42 (m, 2H). LC-MS calculated for C$_{31}$H$_{31}$ClF$_2$N$_2$O$_3$S: 585: observed 585.

EXAMPLE 274

Using the general synthetic scheme outlined in SCHEME 274, compounds described in Examples 275–283 were prepared.

SCHEME 274

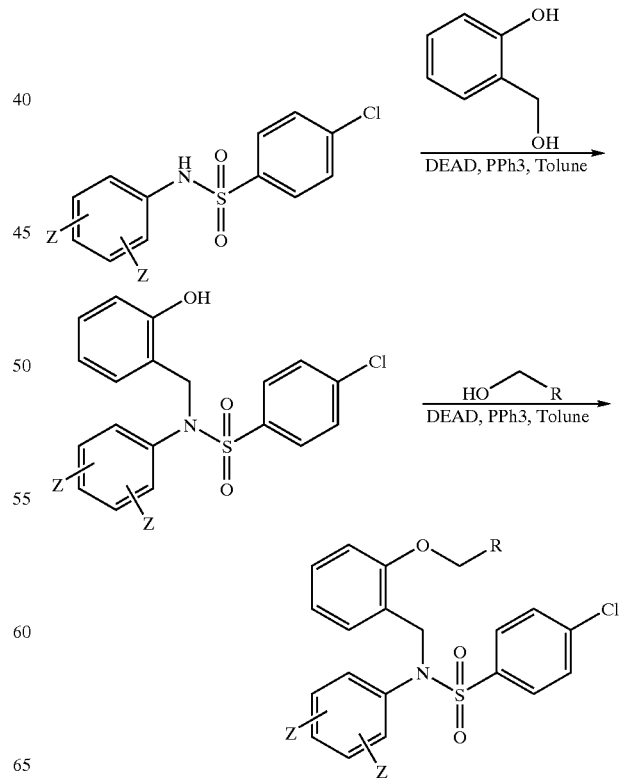

EXAMPLE 275

4-Chloro-N-(2,5-difluorophenyl)-N-(2-hydroxybenzyl)benzenesulfonamide

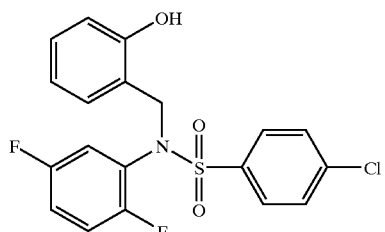

$R_f$=0.50 (3:1; hexanes:ethyl acetate). $^1$H NMR (CDCl$_3$) δ (ppm): 7.74–7.71 (d, 2H, 7.54–7.51 (d, 2H), 7.20–6.96 (m, 1H), 7.00–6.96 (m, 2H), 6.89–6.87 (m, 2H), 6.75–6.67 (m, 2H), 6.45 (s, 1H), 4.70 (s, 2H).

EXAMPLE 276

4-Chloro-N-{2-[2-(1-methyl-2-piperidinyl)ethoxy]benzyl}-N-phenylbenzenesulfonamide Hydrochloride

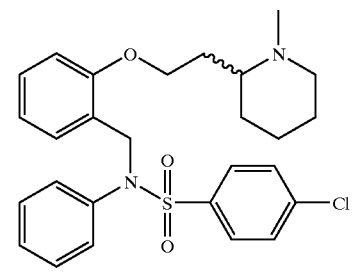

$R_f$=0.23 (10% methanol/DCM) $^1$H NMR (300 MHz, CD$_3$OD) δ (ppm): 7.66–7.60 (m, 4H), 7.22–7.15 (m, 4H), 6.95–6.89 (m, 4H), 6.68 (t, 1H), 5.04 (d, 1H), 4.71 (d, 1H), 4.16 (m, 2H), 3.85 (m, 1H), 3.47 (d, 1H), 3.19 (m, 1H), 2.98 (s, 3H), 2.65 (m, 1H), 2.22 (m, 1H), 2.01–1.64 (m, 6H). $^{13}$C NMR (75 MHz, CD$_3$OD) δ (ppm): 158.7, 140.9, 140.0, 138.4, 133.3, 131.2, 131.0, 130.9, 130.7, 130.3, 130.0, 124.7, 121.9, 112.7, 64.9, 63.4, 57.4, 51.8, 41.1, 31.5, 28.9, 24.5, 23.1. ESI calculated for C$_{27}$H$_{33}$ClN$_2$O$_3$S [MH+] 499; Observed: 499.

EXAMPLE 277

4-Chloro-N-{2-[2-(1-methyl-2-pyrrolidinyl)ethoxy]benzyl}-N-phenylbenzenesulfonamide Hydrochloride

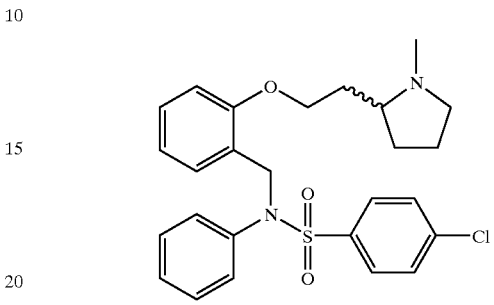

$R_f$=0.24 (10% methanol/DCM) $^1$H NMR (300 MHz, CD$_3$OD) δ (ppm): 7.62 (m, 4H), 7.22–7.16 (m, 4H), 6.96–6.89 (m, 4H), 6.68 (t, 1H), 4.51 (d, 1H), 4.77 (d, 1H), 4.28 (m, 2H), 4.14–4.02 (m, 2H), 3.73 (m, 1H), 3.22 (m, 1H), 3.04 (s, 3H), 2.69–2.44 (m, 2H), 2.28–1.91 (m, 4H). $^{13}$C NMR (75 MHz, CD$_3$OD) δ (ppm): 158.6, 140.8, 139.9, 138.4, 133.4 131.2, 130.9, 130.9 130.7, 130.3, 129.7–124.7, 121.9, 112.7, 67.8, 65.9, 57.8, 51.8, 40.1 31.6 30.5, 22.7.

EXAMPLE 278

4-Chloro-N-phenyl-N-{2-[2-(2-piperidinyl)ethoxy]benzyl}benzenesulfonamide Hydrochloride

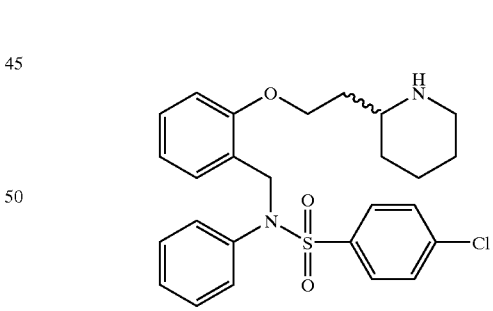

$R_f$=0.40 (14% methanol/DCM) $^1$H NMR (300 MHz, CD$_3$OD) δ (ppm): 7.59–7.52 (m, 4H), 7.15–7.08 (m, 4H), 6.88–6.80 (m, 4H), 6.60 (t, 1H), 4.93 (d, 1H), 4.68 (d, 1H) 4.15–4.05 (m, 2H), 3.79 (m, 1H), 3.37 (m, 1H), 3.10 (m, 1H), 2.26–1.49 (m, 8H). $^{13}$C NMR (75 MHz, CD$_3$OD) δ (ppm): 158.6, 140.8, 140.1, 138.5, 133.1, 131.1, 131.0, 130.9, 130.7, 130.4, 129.7, 124.9, 121.9, 112.9, 64.9, 55.9, 51.8, 46.6, 34.9, 29.9, 23.9, 23.5. ESI calculated for C$_{26}$H$_{29}$ClN$_2$O$_3$S [MH+] 485; Observed: 485.

EXAMPLE 279

N-{2-[3-(3-hydroxy-1-pyrrolidinyl)propoxy]
benzyl}-N-phenylbenzenesulfonamide
Hydrochloride

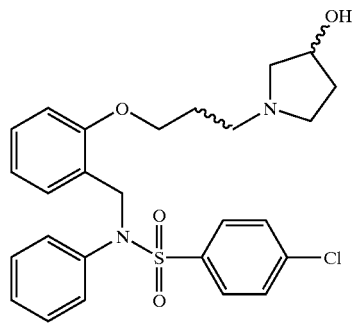

$R_f$=0.15 (9% methanol/DCM) $^1$H NMR (300 MHz, CD$_3$OD) δ (ppm): 7.52–7.46 (m, 4H), 7.10–7.01 (m, 4H), 6.80–6.73 (m, 4H), 6.54 (m, 1H), 4.74 (s, 2H), 4.48–4.46 (m, 1H), 4.02 (t, 2H), 3.58 (m, 3H), 3.39 (m, 3H), 2.28–1.93 (m, 4H). $^{13}$C NMR (75 MHz, CD$_3$OD) δ (ppm): 160.3, 142.4, 141.6, 140.1, 134.8, 132.8, 132.5, 132.4, 131.9, 131.3, 126.4, 123.4, 114.3, 72.4, 67.9, 64.9, 56.9, 55.9, 53.5, 36.0, 29.2. ESI calculated for C$_{27}$H$_{29}$ClN$_2$O$_4$S [MH+] 501; Observed: 501.

EXAMPLE 280

4-Chloro-N-{2-[3-(2-ethyl-1-piperidinyl)propoxy]
benzyl}-N-phenylbenzenesulfonamide
Hydrochloride

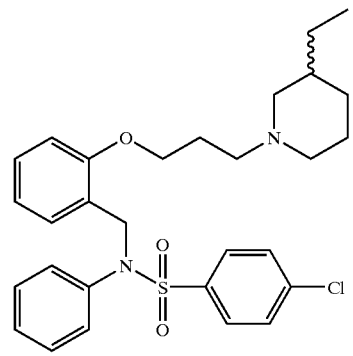

$R_f$=0.23 (10% methanol/DCM) $^1$H NMR (300 MHz, CD$_3$OD) δ (ppm): 7.44–7.59 (m, 4H), 7.24–7.15 (m, 4H), 6.94–6.89 (m, 4H), 6.68 (t, 1H), 4.88 (d, 2H), 4.17 (t, 2H), 3.66–3.52 (d, 3H), 3.25 (m, 2H), 2.33 (m, 2H), 2.03–1.63 (m, 8H), 1.05 (t, 3H), $^{13}$C NMR (75 MHz, CD$_3$OD) δ (ppm): 158.9, 141.0, 140.2, 138.9, 133.4, 131.3, 131.1, 131.0, 130.5, 129.8, 125.0, 122.1, 113.0, 66.9, 65.6, 52.0, 51.9, 51.7, 28.2, 25.8, 24.2, 22.4, 10.8. ESI calculated for C$_{29}$H$_{35}$ClN$_2$O$_3$S [MH+] 527; Observed: 527.

EXAMPLE 281

4-Chloro-N-phenyl-N-[2-(4-pyridinylmethoxy)
benzyl]benzenesulfonamide Hydrochloride

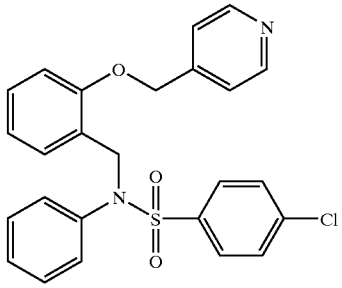

$R_f$=0.63 (5% methanol/DCM) $^1$H NMR (300 MHz, CD$_3$OD) δ (ppm): 8.31 (d, 2H), 7.47–7.38 (m, 4H), 7.25 (d, 2H), 7.11 (m, 1H), 7.02–6.97 (m, 4H), 6.79 (m, 2H), 6.70 (m, 2H), 4.90 (s, 2H), 4.77 (s, 2H).

EXAMPLE 282

4-Chloro-N-phenyl-N-[2-(2-pyridinylmethoxy)
benzyl]benzenesulfonamide Hydrochloride

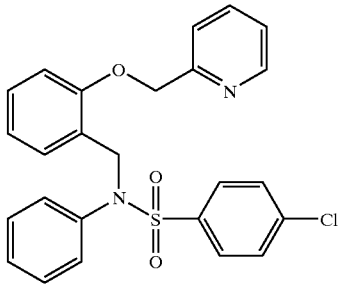

$R_f$=0.57 (5% methanol/DCM) $^1$H NMR (300 MHz, CD$_3$OD) δ (ppm): 8.87 (d, 1H), 9.60 (t, 1H), 8.17 (d, 1H), 8.02 (t, 1H), 7.61 (q, 4H), 7.29–6.86 (m, 9H), 5.47 (s, 2H), 5.00 (s, 2H), $^{13}$C NMR (75 MHz, CD$_3$OD) δ (ppm): 156.2, 153.8, 147.5, 143.6, 140.5, 138.3, 136.9, 134.1, 130.6, 130.5, 130.4, 130.0, 129.3, 127.4, 126.8, 125.7, 123.1, 113.5, 68.7, 51.3. ESI calculated for C$_1$H$_{11}$ClN$_2$O$_3$S [MH+) 465; Observed: 465.

EXAMPLE 283

4-Chloro-N-phenyl-N-[2-(3-pyridinylmethoxy)
benzyl]benzenesulfonamide Hydrochloride

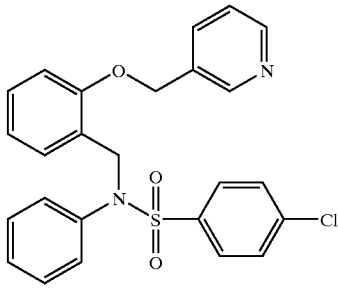

$R_f$=0.61 (5% methanol/DCM) $^1$H NMR (300 MHz, CD$_3$OD) δ (ppm): 8.58–8.51 (m, 2H), 7.89, (d, 1H), 7.62–7.44 (m, 5H), 7.30 (dd, 1H), 7.20–7.16 (m, 4H), 6.98–6.84 (m, 4H), 5.07 (s, 2H), 4.90 (s, 2H).

EXAMPLE 284

The general synthetic scheme set forth in SCHEME 284 can also be used for the preparation of numerous compounds according to the invention.

SCHEME 284

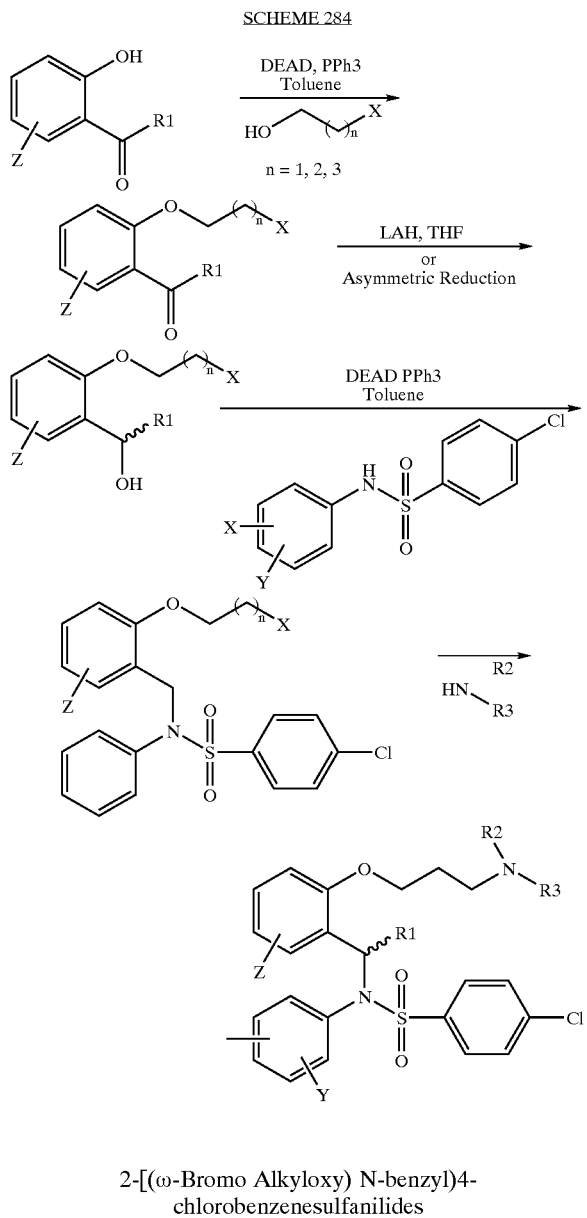

2-[(ω-Bromo Alkyloxy) N-benzyl)4-chlorobenzenesulfanilides

To a stirred suspension of lithium aluminum hydride (1.78 g, 46.8 mmol) in THF (90 mL) at 0° C. was added a solution of salicylanilide (5.0 g, 23.4 mmol) in THF (50 mL) over 0.5 h. The resulting mixture was heated at refluxing for 3 h, then cooled to 0° C., quenched with saturated NaHSO$_4$ solution, filtered through celite pad and the celite pad was washed with ethyl acetate. The filtrate was diluted with ethyl acetate (300 mL), washed with saturated brine (2×100 TL), dried with MgSO$_4$, filtered and concentrated under reduced pressure to give 3.9 g of the desired product as white solid (y: 83%) $R_f$=0.40 (25% ethyl acetate/hexanes) $^1$H NMR (300 MHz, CDCl$_3$) δ (ppm): 7.28–7.15 (m, 4H), 7.95–6.84 (in, 5M), 4.41 (s, 2H).

Sulfonylation of the amine (2.0 g, 10.0 mmol) according to the general procedure described elsewhere provided the desired product (3.40 g, 9.10 mmol, 91%). $R_f$=0.35 (25% ethyl acetate/hexanes) $^1$H NMR (300 MHz, CDCl$_3$) δ (ppm): 7.66–7.49 (m, 4H), 7.28–7.14 (m 4H), 6.97–6.65 (m, 5H), 4.71 (s, 21).

General Procedure for Alkylation of Phenol with ω-Bromoalkanols

Mitsunobu alkylation of phenol with 3-bromo propanol, 4-bromo butanol and 5-bromo pentanol according general procedure described elsewhere gave the corresponding 2-[(O-bromo alkyloxy) N-benzyl]4-chlorobenzenesulfanilides.

General Procedure for the Amination of 2-[(ω-Bromo Alkyloxy) N-benzyl]4-chlorobenzenesulfanilides The bromo compound (1.0 eq) was dissolved in neat amine (5.0 eq) (or in DCM (2.0 mL/mmol) if the amine is a solid), and the solution was allowed stir at room temperature under Ar for 1 h. The reaction mixture was then concentrated under reduced pressure, re-dissolved in ethyl acetate (25 mL/mmol) washed the ethyl acetate solution with saturated bicarbonate solution and water, dried with MgSO$_4$, filtered and concentrated under reduced pressure to give the desired product, as the free base, in near quantitative yield. The free base was converted into the corresponding HCl salt as described elsewhere. The HCl salt was purified by passing through a short plug of SiO$_2$ (10% methanol/DCM) to yield the desired product in >90% yield.

The compounds described in Examples 285–320 were prepared according to the scheme described in the previous example.

EXAMPLE 285

N-[2-(3-bromopropoxy)benzyl]-4-chloro-N-phenylbenzenesulfonamide

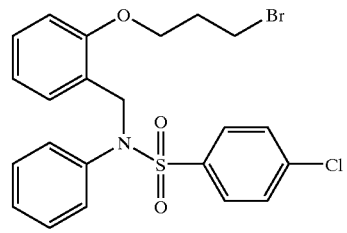

$R_f$=0.35 (20% ethyl acetate/hexanes) $^1$H NMR (300 MHz, CDCl$_3$) δ (ppm): 7.55–7.47 (m, 2H), 7.19–7.17 (m, 4H), 7.27–7.14 (m, 5H), 6.98 (m, 2H), 6.86–6.75 (m, 2H), 4.78 (s, 2H), 3.99 (t, 2H), 3.53 (t, 2H), 2.20 (q, 2H).

EXAMPLE 286

4-Chloro-N-{2-[(5-chloropentyl)oxy]benzyl}-N-phenylbenzenesulfonamide

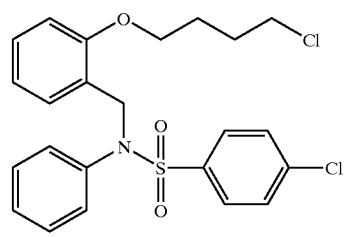

$R_f$=0.17 (6% ethyl acetate/hexanes) $^1$H NMR (300 MHz, CDCl$_3$) δ (ppm): 7.59–6.70 (m, 13H), 3.82 (t, 2H), 3.56 (t, 2H), 1.83–1.54 (m, 6H).

EXAMPLE 287

4-Chloro-N-phenyl-N-{2-[3-(1-pyrrolidinyl)propoxy]benzyl}benzenesulfonamide Hydrochloride

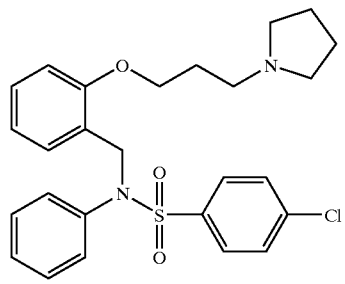

$R_f$=0.60 (6:1:DCM:methanol). $^1$H NMR (300 MHz, CDCl$_3$) δ (ppm): 7.55–7.47 (m, 4H), 7.19–7.17 (m, 3H), 6.79–6.75 (m, 3H), 6.61 (d, 2H), 4.75 (s, 2H), 4.13 (br, 2H), 3.80–3.65 (m, 4H), 3.15 (br, 2H), 2.60 (br, 2H), 2.15 (m, 4H).

EXAMPLE 288

Tert-butyl 4-{3-[2-({[(4 chlorophenyl)sulfonyl}anilino}methyl)phenoxy]propyl}-1-piperazinecarboxylate

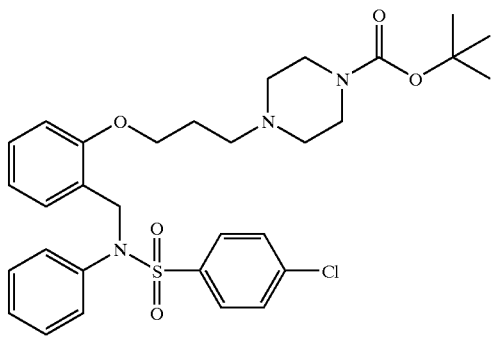

$R_f$=0.13 (5% methanol/DCM) $^1$H NMR (300 MHz, CDCl$_3$) δ (ppm): 7.56 (m, 2H), 7.45 (m, 2H), 7.32–7.12 (m, 5H), 6.99 (m, 2H), 6.83 (t, 1H), 6.73 (d, 1H), 5.30 (s, 2H), 3.89 (t, 2H), 3.44 (t, 4H), 2.50–2.37 (m, 6H), 1.87 (q, 2H), 1.47 (s, 9H).

EXAMPLE 289

4-Chloro-N-{2-[3-(3,6-dihydro-1(2H)pyridinyl)propoxy]benzyl}-N-phenylbenzenesulfonamide Hydrochloride

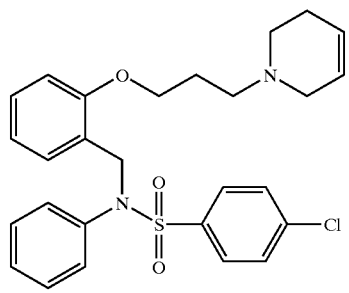

$R_f$=0.45 (5% methanol/DCM) $^1$H NMR (300 MHz, CD$_3$OD) δ (ppm): 7.40 (m, 4H), 6.95 (m, 4H), 6.71–6.60 (m, 4H), 6.43 (m, 1H), 5.82 (m, 1H), 5.59 (m, 1H), 4.65 (s, 2H), 3.97 (t, 2H), 3.71 (m, 2H), 3.55–3.10 (m, 4H), 2.33–1.81 (m, 4H). $^{13}$C NMR (75 MHz, CD$_3$OD) δ (ppm): 158.8, 140.9, 139.9, 138.5, 133.4, 131.2, 130.9, 130.8, 130.3, 129.6, 127.1, 124.7, 121.8, 121.4, 112.6, 66.3, 55.7, 52.0, 52.0, 51.0, 25.9, 24.1.

EXAMPLE 290

N-{2-[3-(4-benzyl-1-piperidinyl)propoxy]benzyl}-4-chloro-N-phenylbenzenesulfonamide Hydrochloride

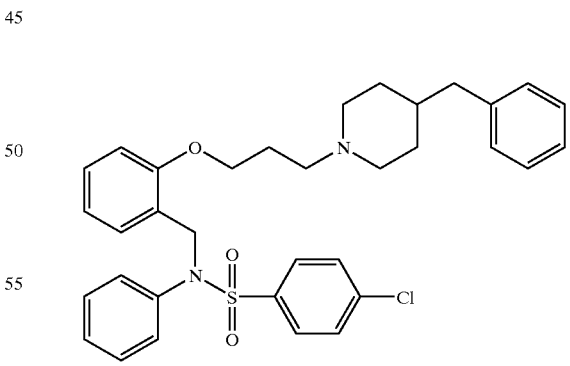

$R_f$=0.60 (14% methanol/DCM) $^1$H NMR (300 MHz, CD$_3$OD) δ (ppm): 7.54 (m, 4H), 7.21–7.06 (m, 9H), 6.82–6.74 (m, 4H), 6.57 (m, 1H), 4.78 (s, 2H), 4.07 (m, 2H), 3.55 (m, 4H), 2.99 (m, 2H), 2.58 (m, 2H), 2.27 (m, 2H), 1.89–1.51 (m, 5H).

EXAMPLE 291

N-{2-[3-(4-benzyl-1-piperidinyl)propoxy]benzyl}4-chloro-N-phenylbenzenesulfonamide Hydrochloride

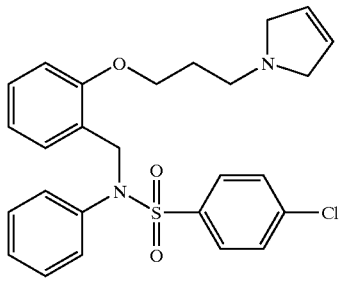

$R_f$=0.32 (9% methanol/DCM) $^1$H NMR (300 MHz CD$_3$OD) δ (ppm): 7.40 (m, 4H), 6.99 (m, 4H), 6.69–6.44 (m, 5H), 5.80 (s, 2H), 4.66 (s, 2H), 4.07–3.96 (m, 6H), 3.62 (m, 2H), 2.11 (m, 2H). $^{13}$C NMR (75 MHz, CD$_3$OD) δ (ppm): 161.0, 143.0, 142.0, 140.6, 135.6, 133.4, 133.0, 132.9, 132.4, 131.8, 128.7, 126.8, 123.9, 114.7, 68.2, 63.7, 56.9, 54.2, 29.6.

EXAMPLE 292

N-{2-[3-(1-azetidinyl)propoxy]benzyl}-4-chloro-N-phenylbenzenesulfonamide Hydrochloride

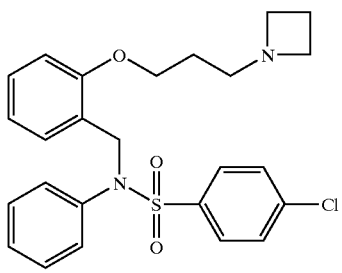

$R_f$=0.54 (14% methanol/DCM) $^1$H NMR (300 MHz, CD$_3$OD) δ (ppm): 7.61–7.54 (m, 4H), 7.16–7.09 (m, 4H), 6.88–6.78 (m, 4H), 6.60 (t, 1H), 4.84 (s, H), 4.25 (t, 4H), 4.08 (m, 2H), 3.67 (m, 2H), 2.52 (m, 2H), 2.10 (m, 2H). $^{13}$C NMR (75 MHz, CD$_3$OD) δ (ppm): 158.8, 140.9, 139.9, 138.4, 133.4, 131.2, 130.9, 130.77, 130.3, 129.6, 124.6, 121.8, 112.6, 65.8, 56.2, 54.1, 52.0, 26.2, 17.6.

EXAMPLE 293

4-Chloro-N-phenyl-N-(2-{[5-(1-piperidinyl)pentyl]oxy}benzyl)benzenesulfonamide Hydrochloride

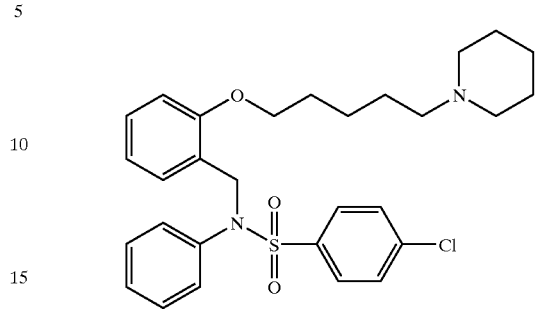

$R_f$=0.17 (20% methanol/ethyl acetate) $^1$H NMR (300 MHz, CD$_3$OD) δ (ppm): 7.89–7.82 (m, 4H), 7.47–7.36 (m, 4H), 7.27–7.09 (m, 4H), 6.96–6.91 (m, 1H), 5.09 (s, 2H), 4.23 (t, 2H), 3.81 (d, 2H), 3.42 (t, 2H), 3.20 (m, 2H), 2.25–1.95 (m, 12H).

EXAMPLE 294

4-Chloro-N-phenyl-N-[2-[4-(1-piperidinyl)butoxy]benzyl}benzenesulfonamide Hydrochloride

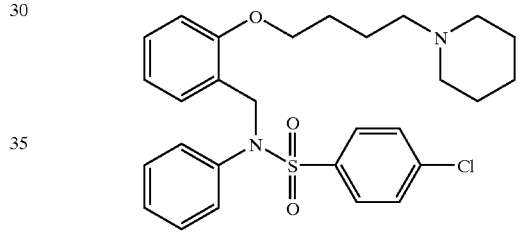

$R_f$=0.20 (5% methanol/DCM) $^1$H NMR (300 MHz, CD$_3$OD) δ (ppm): 7.38 (m, 4H), 6.97 (m, 4H), 6.69 (m, 4H), 6.44 (t, 1H), 4.64 (s, 2H), 3.84 (t, 2H), 2.99 (m, 6H), 1.93–1.68 (m, 10H). $^{13}$C NMR (75 MHz, CD$_3$OD) δ (ppm): 158.5, 140.3, 139.8, 138.3, 132.5, 130.5, 130.4, 130.4, 130.3, 129.8, 129.0, 124.5, 121.1, 112.3, 68.1, 58.1, 54.3, 51.3, 27.6, 25.3, 22.7, 22.3. ESI calculated for C$_{29}$H$_{33}$ClN$_2$O$_3$S [MH+] 511; Observed: 511.

EXAMPLE 295

4-Chloro-N-{2-[3-(3,4-dihydro-2(1H)-isoquinolinyl)propoxy]benzyl})-N-phenylbenzenesulfonamide

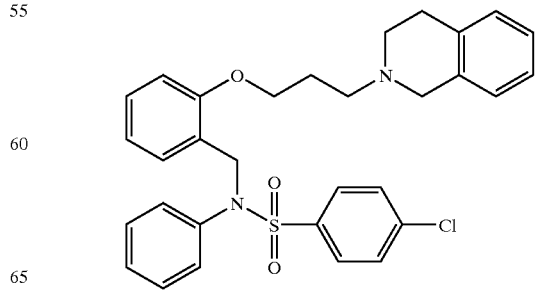

$R_f$=0.50 (50% ethyl acetate/hexanes) $^1$H NMR (300 MHz, CDCl$_3$) δ (ppm): 7.59–7.55 (m, 2H), 7.46–7.42 (m, 2H), 7.44 (dd, 1H), 7.22–6.99 (m, 10H), 6.84 (t, 1H), 6.74 (t, 1H), 3.92 (t, 2H), 3.62 (s, 2H) 2.91 (t, 2H), 2.73 (t, 2H), 2.62 (t, 2H), 1.96 (m, 2H). $^{13}$C NMR (75 MHz, CDCl$_3$) δ (ppm): 159.1, 141.7, 141.6, 139.7, 137.2, 136.8, 132.6, 131.6, 131.4, 131.3, 131.2, 130.4, 129.1, 128.7, 128.2, 126.4, 122.9, 113.6, 68.6, 58.7, 57.4, 53.5, 51.8, 31.7, 29.5. ESI calculated for C$_{31}$H$_{31}$ClN$_2$O$_3$S [MH+] 547; Observed: 547.

EXAMPLE 296

4-Chloro-N-[2-[3-cyclohexylamino)propoxy]benzyl}-N-phenylbenzenesulfonamide Hydrochloride

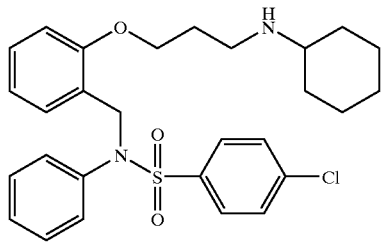

$R_f$=0.20 (14% methanol/DCM) $^1$H NMR (300 MHz, CD$_3$OD) δ (ppm): 7.45–7.37 (m, 4H), 7.45–7.11 (m, 4H), 7.–7.11 (m, 4H), 6.89 (m, 1H), 5.09 (s, 2H), 4.38 (t, 2H), 3.72 (t, 2H), 3.40 (m, 1H), 2.49 (m, 4H), 2.13–1.94 (m, 3H), 1.66–1.48 (m, 5H). $^{13}$C NMR (75 MHz, CD$_3$OD) δ 158.6, 140.7, 140.1, 138.6, 133.0, 131.07, 130.9, 130.9, 130.7, 130.3, 129.6, 124.9, 121.8, 112.8, 66.5, 59.1, 51.6, 44.1, 30.9, 28.1, 26.6, 25.9. ESI calculated for C$_{28}$H$_{33}$ClN$_2$O$_3$S [MH+] 513; Observed: 513.

EXAMPLE 297

4-Chloro-N-{2-[3-(cyclopropylamino)propoxy]benzyl}-N-phenylbenzenesulfonamide Hydrochloride

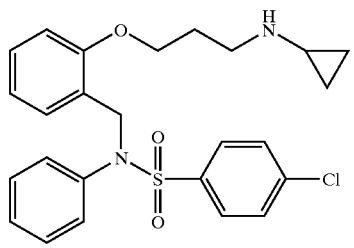

$R_f$=0.32 (10% methanol/DCM) $^1$H NMR (300 MHz, CD$_3$OD) δ (ppm): 7.40–7.32 (m, 4H), 6.99–6.89 (m, 5H), 6.76–6.74 (m, 2H), 6.57 (m, 2H), 4.61 (s, 2H), 3.71 (t, 2H), 2.66 (t, 2H), 1.99 (m, 1H), 1.71 (m, 2H), 0.30–0.15 (m, 4H). $^{13}$C NMR (75 MHz, CD$_3$OD) δ (ppm): 159.0, 141.1, 139.3, 132.6, 131.3, 131.2, 131.1, 130.7, 129.8, 125.8, 122.2, 113.2, 68.1, 51.2, 48.4, 32.6, 30.8, 6.8. ESI calculated for C$_{25}$H$_{27}$ClN$_2$O$_3$S [MH+] 471; Observed: 471.

EXAMPLE 298

4-Chloro-N-{2-[3-(4-hydroxy-1-piperidinyl)propoxy]benzyl}-N-phenylbenzenesulfonamide Hydrochloride

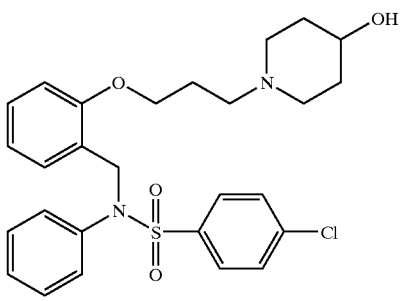

$R_f$ =0.19 (10% methanol/DCM) $^1$H NMR (300 MHz, CD$_3$OD) δ (ppm): 7.50–7.43 (m, 4H), 7.07–6.98 (m, 4H), 6.78–6.72 (m, 4H), 6.54–6.49 (m, 1H), 4.17 (s, 2H), 3.98 (t, H), 3.81 (m, 1H), 3.39–3.08 (m, 6H), 2.20–2.11 (m, 2H), 1.98–1.91 (m, 2H), 1.70 (m, 2H). $^{13}$C NMR (75 MHz, CD$_3$OD) δ (ppm): 158.7, 140.8, 140.1, 138.6, 133.2, 131.2, 130.9, 130.9, 130.8, 130.3, 129.6, 124.8, 121.8, 112.7, 66.6, 56.3, 51.8, 51.3, 32.6, 26.2. ESI calculated for C$_{27}$H$_{31}$ClN$_2$O$_4$S [MH+] 515; Observed: 515.

EXAMPLE 299

4-Chloro-N-phenyl-N-{2-[3-(1-piperazinyl)propoxy]-benzyl}benzenesulfonamide Dihydrochloride

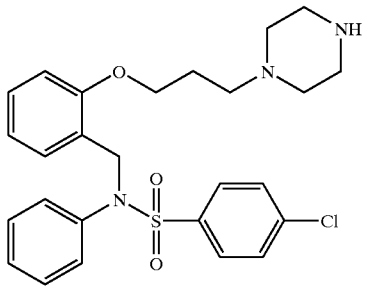

$R_f$=0.15 (14% methanol/DCM) $^1$H NMR (300 MHz, CD$_3$OD) δ (ppm): 7.80–7.65 (m, 5H), 7.33–7.27 (m, 4H), 7.07–6.91 (m, 4H), 6.77 (t, 1H), 5.01 (s, 2H), 4.34 (t, 2H), 4.02–3.68 (m, 10H), 2.59 (m, 2H). $^{13}$C NMR (75 MHz, CD$_3$OD) δ (ppm): 158.7, 140.8, 139.8, 138.5, 13.3, 133.1, 131.2, 130.9, 130.9, 130.8, 130.3, 129.7, 124.7, 121.8, 112.7, 66.1, 56.5, 52.0, 50.3, 50.3, 42.4, 25.6. ESI calculated for C$_{21}$H$_{30}$ClN$_3$O$_3$SCl [MH+] 500; Observed: 500.

EXAMPLE 300

4-Chloro-N-(2-{[(2S)-7-methyl-7-azabicyclo[2.2.1]hept-2-yl]methoxy]benzyl)-N-phenylbenzenesulfonamide Hydrochloride

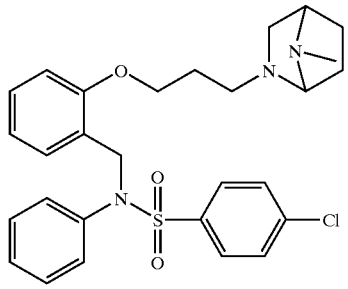

$R_f$=0.20 (10% methanol/DCM) $^1$H NMR (300 MHz, CD$_3$OD) δ (ppm): 7.65–7.59 (m, 4H), 7.25–7.16 (m, 4l), 7.00–6.93 (m, 4H), 6.73 (m, 1H), 4.88 (q, 2H), 4.10 (m, 1H), 3.97 (m, 3H), 2.76 (s, 3H), 2.54 (m, 1H), 2.23–1.78 (m, 6H). $^{13}$C NMR (75 MHz, CD$_3$OD) δ (ppm): 158.7, 140.8, 140.3, 138.7, 133.0, 131.1, 130.9, 130.8, 130.7, 1303, 129.6, 125.2, 122.0, 113.2, 70.5, 68.1, 66.1, 51.7, 43.3, 34.4, 33.8, 3.1, 25.8. ESI calculated for C$_{27}$N$_2$O$_3$SClH$_{29}$ [MH+] 497; Observed: 497.

EXAMPLE 301

N-phenyl-N-{2-[4-(1-piperidinyl)butyl]benzyl}benzenesulfonamide

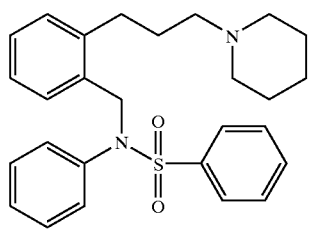

$R_f$=0.33 (5% methanol/DCM) $^1$H NMR (300 MHz, CDCl$_3$) δ (ppm): 7.67–7.62 (m, 2H), 7.55–7.50 (m, 2H), 7.21–7.11 (m, 5H), 6.94–6.83 (m, 4H), 4.75 (s, 2H), 2.99–2.80 (m; 8H), 2.05–1.62 (m, 10H). $^{13}$C NMR (75 MHz, CDCl$_3$) δ (ppm): 141.5, 138.5, 137.9, 133.4, 132.6, 131.4, 130.0, 129.4, 129.2, 129.2, 128.7, 128.5, 128.1, 126.2, 57.9, 53.7, 53.0, 31.9, 29.1, 24.5, 23.5, 22.9.

EXAMPLE 302

4-Chloro-N-{2-[3-(1H-imidazol-1-yl)propoxy]benzyl}-N-phenylbenzenesulfonamide Hydrochloride

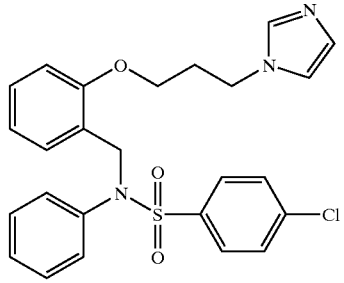

$R_f$=0.38 (10% methanol/DCM) $^1$H NMR (300 MHz, CD$_3$OD) δ (ppm): 7.53–7.38 (m, 5H), 7.04–6.93 (m, 5H), 6.85–6.75 (m, 4H), 6.55 (m, 1H), 6.50 (t, 1H), 4.70 (s, 2H), 4.18 (t, 2H), 3.72 (t, 2H), 2.06 (m, 2H). $^{13}$C NMR (75 MHz, CD$_3$OD) δ (ppm): 157.6, 139.6, 139.4, 137.7, 131.9, 129.9, 129.8, 129.7, 129.6, 429.2, 128.5, 124.0, 120.6, 111.4, 64.7, 50.5, 44.4, 31.3. ESI calculated for C$_{25}$H$_{29}$ClN$_3$O$_3$S [MH+] 482; Observed: 482.

EXAMPLE 303

4-Chloro-N-{2-[3-(3,5-dimethyl-1-piperidinyl)propoxy]benzyl}-N-phenylbenzenesulfonamide Hydrochloride

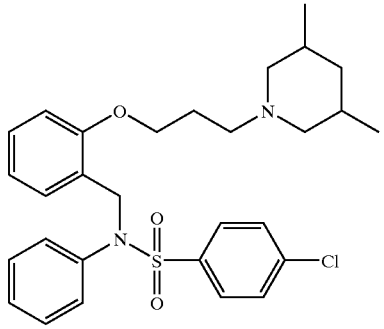

$R_f$=0.35 (9% methanol/DCM) $^1$H NMR (300 MHz, CD$_3$OD) δ (ppm): 7.66–7.58 (m, 4H), 7.23–7.14 (m, 4H), 6.99–6.88 (m, 4H), 6.70 (t, 1H), 4.87 (s, 2H), 4.09 (t, 2H), 3.44–2.83 (m, 4H), 2.39–1.85 (m, 6H), 1.11–0.77 (m, 8H). $^{13}$C NMR (75 MHz, CD$_3$OD) δ (ppm): 158.9, 140.9, 140.3, 138.7, 133.2, 131.2, 131.1, 131.02, 130.9, 130.4, 129.7, 125.0, 121.9, 112.8, 67.0, 66.9, 60.8, 57.5, 56.8, 51.7, 41.7, 38.5, 31.3, 26.4, 26.3, 19.7, 19.3.

EXAMPLE 304

4-Chloro-N-{2-[3-(1,4-dioxa-8-azaspiro[4.5]dec-8-yl)propoxy]benzyl}-N-phenylbenzenesulfonamide

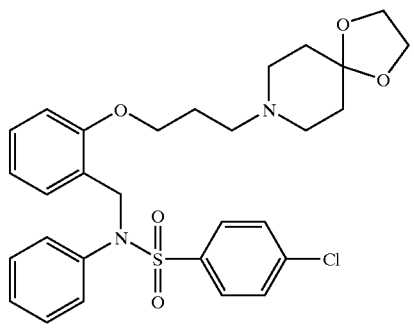

R$_f$=0.38 (9% methanol/DCM) $^1$H NMR (300 MHz, CDCl$_3$) δ (ppm): 7.58–7.55 (m, 2H), 7.4 & 7.36 (m, 3H), 7.23–7.11 (m, 4H), 7.00 (dd, 2H), 6.85 (t, 1H), 6.72 (d, 1H), 4.79 (s, 2H), 3.83 (t, 2H), 2.52–2.44 (m, 6H), 1.90–1.74 (m, 6H). $^{13}$C NMR (75 MHz, CDCl$_3$) δ (ppm): 156.8, 139.6, 139.4, 137.5, 130.4, 129.5, 129.50, 129.2, 128.2, 124.3, 120.8, 111.4, 107.6, 66.7, 64.6, 55.2, 51.8, 49.5, 35.2, 27.4.

EXAMPLE 305

N-{2-[3-(1-azepanyl)propoxy]benzyl}-4-chloro-N-phenylbenzenesulfonamide Hydrochloride

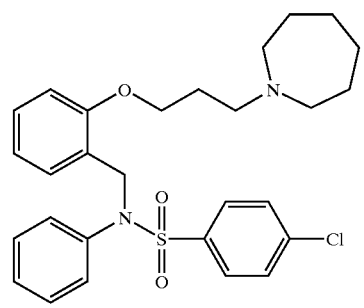

R$_f$=0.19 (9% methanol/DCM) $^1$H NMR (300 MHz, CD$_3$OD) δ (ppm): 7.68–7.61 (m, 4H), 7.25–7.16 (m, 4H), 6.97–6.86 (m, 4H), 6.68 (m, 1H), 4.89 (s, 2H), 4.18 (t, 2H), 3.69 (m, 2H), 3.50 (t, H), 2.37 (m, 2H), 2.00 (b, 4H), 1.79 (m, 4H). $^{13}$C NMR (75 MHz, CD$_3$OD) δ (ppm): 161.0, 143.0, 142.2, 140.7, 135.5, 133.4, 133.1, 133.0, 132.5, 131.9, 126.9, 124.0, 114.8, 68.7, 59.3, 58.7, 54.1, 30.2, 28.4, 27.6.

EXAMPLE 306

4-Chloro-N-(2-{3-[(2R,6S)-2,6-dimethylpiperidinyl]propoxy}benzyl)-N-phenylbenzenesulfonamide Hydrochloride

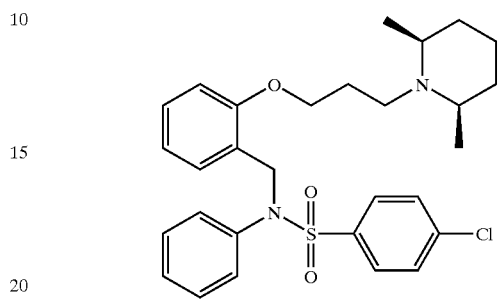

R$_f$=0.23 (9% methanol/DCM) $^1$H NMR (300 MHz, CD$_3$OD) δ (ppm): 7.44 (m, 4H), 7.06–7.99 (m, 4H), 6.85–6.72 (m, 4H), 6.57 (m, 1H), 4.70 (s, 2H), 3.96 (t, 2H), 3.43–3.23 (m, 6H), 2.11–1.51 (m, 8H), 1.29 (d, 6H). $^{13}$C NMR (75 MHz, CD$_3$OD) δ (ppm): 158.4, 140.8, 140.3, 138.7, 132.6, 130.9, 130.7, 130.4, 129.6, 125.2, 122.1, 113.1, 66.8, 61.2, 51.1, 24.0, 19.2. ESI calculated for C$_{29}$H$_{35}$ClN$_2$O$_3$S [MH+] 527; Observed: 527.

EXAMPLE 307

4-Chloro-N-{2-[3-(4-oxo-1-piperidinyl)propoxy]benzyl}-N-phenylbenzenesulfonamide Hydrochloride

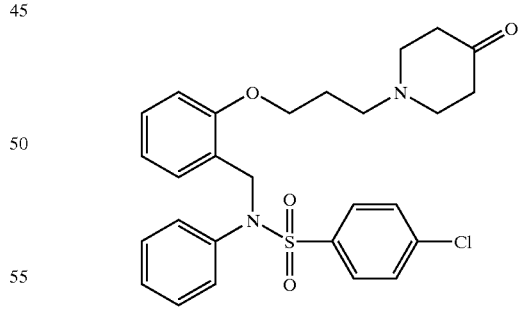

R$_f$=0.25 (5% methanol/DCM) $^1$H NMR (300 MHz, CD$_3$OD) δ (ppm): 7.76–7.64 (m, 4H), 7.33–7.18 (m, 5H), 7.06 (dd, 2H), 6.94 (d, 1H), 6.84 (t, 1H), 4.82 (s, 2H), 3.99 (t, 2H), 2.72 (t, 4H), 2.60 (m, 2H), 2.39 (t, 4H), 1.87 (m, 2H). $^{13}$C NMR (75 MHz, CD$_3$OD) δ (ppm): 212.0, 159.4, 141.9, 141.8, 139.9, 139.2, 131.9, 131.8, 131.7, 131.6, 130.7, 126.6, 123.1, 113.8, 68.7, 56.8, 55.9, 52.3, 44.0, 30.0.

EXAMPLE 308

4-Chloro-N-phenyl-N-{2-[3-(4-thiomorpholinyl)propoxy]benzyl}benzenesulfonamide Hydrochloride

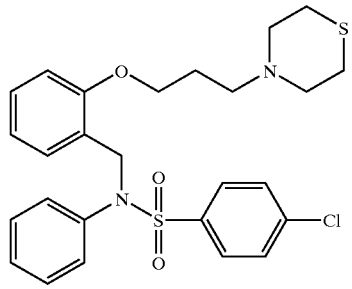

$R_f$=0.40 (5% methanol/DCM) $^1$H NMR (300 MHz, DMSO) δ (ppm): 7.40 (dd, 4H), 7.04–6.88 (m, 4H), 6.77 (m, 2H), 6.57 (dt, 3H), 4.51 (s, 2H), 3.63 (t, 2H), 2.35–2.25 (m, 10H), 1.51 (m, 2H). $^{13}$C NMR (75 MHz, CDCl$_3$) δ (ppm): 156.9, 139.4, 139.4, 137.5, 130.6, 129.4, 129.2, 129.2, 128.2, 124.18, 120.7, 111.3, 66.3, 56.1, 55.4, 49.7, 28.3, 26.6.

EXAMPLE 309

4-Chloro-N-{5-chloro-2-[3-(4-hydroxy-1-piperidinyl)propoxy]benzyl}-N-phenylbenzenesulfonamide Hydrochloride

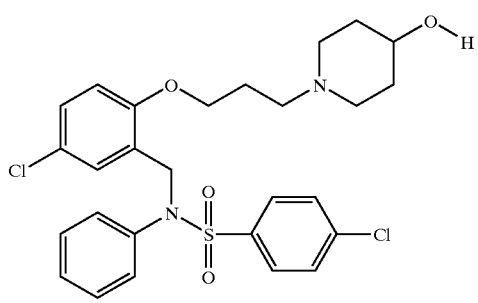

$R_f$=0.18 (10:1; DCM:methanol). $^1$H NMR (CD$_3$OD) δ (ppm): 7.44–7.37 (m, 4H), 7.06–7.03 (m, 3H), 6.95 (dd, 1H), 6.76–6.67 (m, 4H), 4.63 (s, 2H), 3.88 (t, 2H), 3.71 (br, 1H), 3.21–3.11 (m, 4H), 2.86 (br, 2H), 2.08–1.99 (m, 2H), 1.89–1.73 (m, 2H), 1.62 (m, 2H).

EXAMPLE 310

4-Chloro-N-{2-[3-(3-hydroxy-1-piperidinyl)propoxy]benzyl}-N-phenylbenzenesulfonamide Hydrochloride

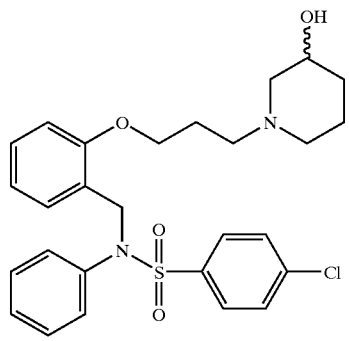

$R_f$=0.23 (9% methanol/DCM) $^1$H NMR (300 MHz, CD$_3$OD) δ (ppm): 7.66–7.59 (m, 4H), 7.23–7.14 (m, 4H), 7.03–6.87 (m, 4H), 6.72 (t, 1H), 4.87 (s, 2H), 4.06 (t, 2H), 3.94 (b, 1H), 3.21–3.03 (m, 6H), 2.18–1.56 (m, 6H). $^{13}$C NMR (75 MHz, CD$_3$OD) δ (ppm): 157.7, 139.8, 139.2, 137.6, 131.9, 130.0, 129.9, 129.8, 129.7, 129.2, 128.5, 124.0, 120.7, 111.7, 66.0, 65.1, 59.6, 55.9, 53.8, 50.4, 31.4, 25.5, 20.3.

EXAMPLE 311

4-Chloro-N-(2-{3-[4-(hydroxymethyl)-1-piperidinyl]propoxy}benzyl)-N-phenylbenzenesulfonamide Hydrochloride

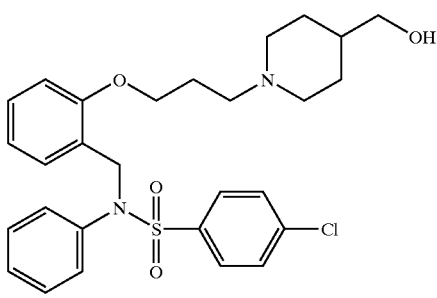

$R_f$=0.20 (9% methanol/DCM) $^1$H NMR (300 MHz, CD$_3$OD) δ (ppm): 7.41–7.34 (m, 4H), 6.99–6.90 (m, 4H), 6.71–6.63 (m, 4H), 6.43 (m, 1H), 4.63 (s, 2H), 3.90 (t, 2H), 3.47–3.24 (m, 6H), 2.82 (m, 2H), 2.09 (m, 2H), 1.81–1.33 (m, 5H). $^{13}$C NMR (75 MHz, CD$_3$OD) δ (ppm): 158.6, 140.7, 139.8, 138.3, 133.1, 131.0, 130.7, 130.56, 130.1, 129.4, 124.5, 121.6, 112.4, 66.8, 66.3, 56.2, 54.1, 51.6, 37.9, 27.7, 26.0.

EXAMPLE 312

4-Chloro-N-{2-[3-(4-hydroxy-4-methyl-1-piperidinyl)propoxy]benzyl}-N-phenylbenzenesulfonamide Hydrochloride

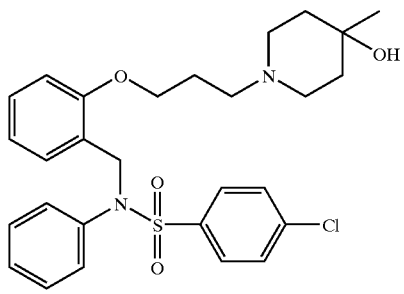

$R_f$=0.3 (1:10; methanol:DCM) $^1$H NMR (300 MHz, CD$_3$OD) δ (ppm): 7.52–7.45 (m, 4H), 7.09–7.01 (m, 4H), 6.91–6.73 (m, 4H), 6.53 (m, 1H), 4.74 (s, 2H), 4.01 (s, 2H), 3.46–3.22 (m, 6H), 2.19 (m, 2M), 1.84–1.68 (m, 4H), 1.18 (s, 3H). $^{13}$C NMR (75 MHz, CD$_3$OD) δ (ppm): 159.4, 141.4, 140.6, 139.2, 133.9, 131.8, 131.5, 131.5, 131.4, 130.9, 130.3, 125.4, 122.4, 113.3, 67.1, 66.9, 56.7, 52.5, 51.4, 37.6, 30.7, 26.8.

EXAMPLE 313

4-Chloro-N-{2-[3-(1,1-dioxido-4-thiomorpholinyl)propoxy]benzyl}-N-phenylbenzenesulfonamide Hydrochloride

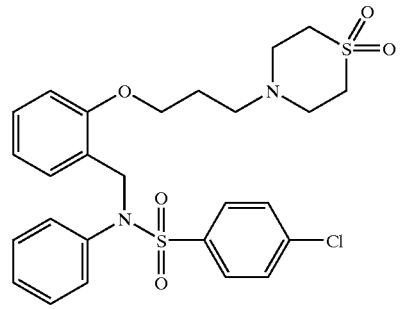

$R_f$=0.45 (67% ethyl acetate/hexanes) $^1$H NMR (300 MHz, DMSO) δ (ppm): 7.72–7.60 (m, 4H), 7.30–7.13 (m, 5H), 7.01 (dd, 2H), 6.89 (d, 1H), 6.79 (t, 1H), 4.77 (s, 2H), 3.92 (t, 2H), 3.09 (m, 4H), 2.88 (m, 4H), 2.62 (t, 2H), 1.78 (m, 2H). $^{13}$C NMR (75 MHz, CDCl$_3$) δ (ppm): 155.9, 138.3, 138.1, 136.3, 130.0, 128.4, 128.3, 128.3, 128.2, 128.1, 127.2, 122.8, 119.5, 110.2, 64.7, 52.6, 52.5, 49.9, 49.1. ESI calculated for C$_{26}$H$_{29}$ClN$_2$S$_2$O$_5$ [MH+] 549; Observed: 549.

EXAMPLE 314

4-Chloro-N-(2-{3-[4-hydroxy-4-(trifuoromethyl)-1-piperidinyl]propoxy}benzyl)-N-phenylbenzenesulfonamide Hydrochloride

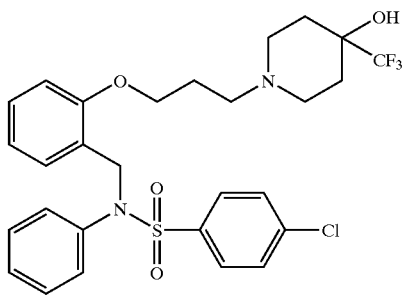

$R_f$=0.23 (5% methanol/DCM) $^1$H NMR (300 MHz, CD$_3$OD) δ (ppm): 7.4–7.35 (m, 4H), 7.01–6.91 (m, 5H), 6.78–6.74 (m, 2H), 6.58–6.52 (m, 2H) 4.63 (s, 2H), 3.73 (t, 2H), 2.68 (m, 2H), 2.42 (m, 2H), 2.19 (dt, 2H), 1.79–1.53 (m, 6H). $^{13}$C NMR (75 MHz, CD$_3$OD) δ (ppm): 160.9, 142.9, 141.1, 134.5, 133.1, 133.0, 132.90, 132.8, 132.4, 131.6, 127.6, 123.9, 114.9, 73.9, 73.6, 69.9, 58.9, 53.1, 51.5, 32.9, 30.0. ESI calculated for C$_{28}$H$_{30}$ClF$_3$N$_2$O$_4$S [MH+] 583; Observed: 583.

EXAMPLE 315

4-Chloro-N-(2,5-difluorophenyl)-N-{2-[3-(1-pyrrolidinyl)propoxy]benzyl}benzenesulfonamide Hydrochloride

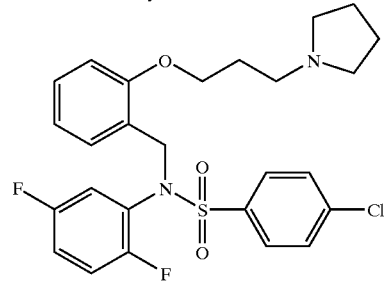

$R_f$=0.40 (10:1;DCM:methanol). $^1$H NMR (300 MHz, CD$_3$OD) δ (ppm): 7.85–7.74 (m, 4H), 7.31 (dt, 1H), 7.16–6.76 (m, 6H), 4.96 (s, 2H), 4.26 (t, 2H), 3.80 (m, 2H), 3.58 (br m, 4H), 2.48–2.39 (m, 2H), 2.57–2.11 (m, 4H).

EXAMPLE 316

4-Chloro-N-(2,5-difluorophenyl)-N-{2-[3-(1H-imidazol-1-yl)propoxy]-6-methoxybenzyl}benzenesulfonamide Hydrochloride

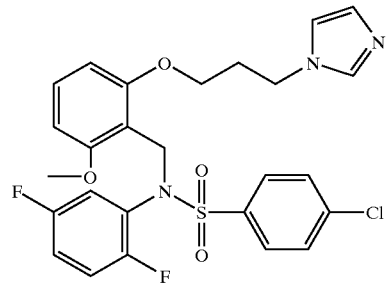

$R_f$=0.5 (93:7; DCM:methanol). $^1$H NMR (CDCl$_3$) δ (ppm): 7.77–7.34 (m, 3H), 7.63–7.60 (m, 2H), 722–7.19 (m, 1H), 7.12 (t, 1H), 7.00–6.95 (m, 2H), 6.60–6.54 (m, 1H), 6.49–6.46 (m, 1H), 6.37–6.35 (m, 1H), 4.94–4.90 (m, 2H), 4.43 (t, 2H), 3.91 (t, 3H), 3.47 (s, 3H), 229 (m, 2H). LC-MS Calculated for C$_{26}$H$_{24}$ClF$_2$N$_3$O$_4$S: 547. Observed: 548 (MH$^+$).

EXAMPLE 317

4-Chloro-N-{2-[3-(diethylamino)propoxy]benzyl}-N-(2,5-difluorophenyl)benzenesulfonamide Hydrochloride

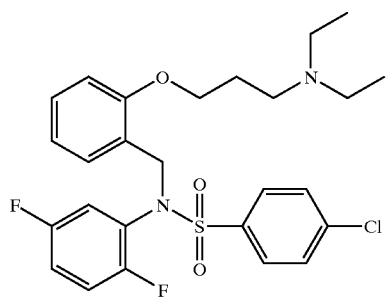

$R_f$=0.49 (9% methanol in DCM), $^1$H NMR (300 MHz, CD$_3$OD) δ (ppm): 7.71 (d, 2H), 7.62 (d, 2H), 7.20 (t, 1H), 7.02–6.98 (m, 2H), 6.90 (d, 1H), 6.88 (d, 1H), 6.76 (m, 1H), 6.69 (t, 1H), 4.84 (s, 2H), 4.16 (t, 2H), 3.64–3.61 (m, 2H), 3.37–3.31 (m, 4H), 2.34–2.31 (m, 2H), 1.38 (t, 6H).

EXAMPLE 318

4-Chloro-N-(2,5-difluorophenyl)-N-{1-[3-(1,3-dioxo-1,3-dihydro-2H-isoindol-2-yl)propoxy]benzyl}benzenesulfonamide

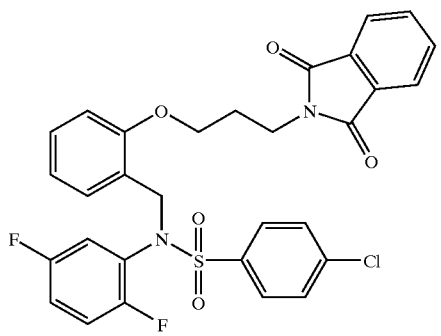

$R_f$=0.33 (2:1 hexanes:ethyl acetate), $^1$H NMR (300 MHz, CDCl$_3$) δ (ppm): 7.85–7.26 (m, 2H), 7.74–7.67 (m, 4H), 7.48 (d, 2H), 7.31 (d, 1H), 7.17 (t, 1H), 6.94–6.83 (m, 4H), 6.70 (d, 1H), 4.82 (s, 1H), 3.86–3.81 (m, 4H), 2.10–2.01 (m, 2H).

EXAMPLE 319

4-Chloro-N-(2,5-difluorophenyl)-N-{2-[3-(2,5-dioxo-1-pyrrolidinyl)propoxy]benzyl}benzenesulfonamide

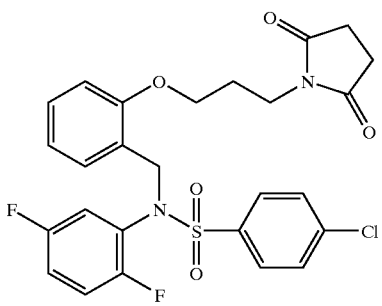

$R_f$=0.73 (5% methanol in CH$_2$Cl$_2$) 3H NMR (300 MHz CDCl$_3$) δ (ppm): 7.70–7.67 (d, 2H), 7.49–7.46 (d, 2H), 7.31–7.15 (m, 2H), 6.94–6.83 (4H), 6.72–6.69 (d, 1H), 4.89–4.82 (br, 2H), 3.83–3.79 (t, 2H), 3.68–3.63 (t, 2H), 2.77–2.64 (br, 4H), 2.05–1.92 (m, 2H). LC-MS calculated for C$_{26}$H$_{23}$ClF$_2$N$_2$O$_5$S [MH$^+$] 549; Observed: 549.

EXAMPLE 320

4-Chloro-N-(2,5-difluorophenyl)-N-{2-[3-(2,6-dioxo-1-piperidinyl)propoxy]benzyl}benzenesulfonamide

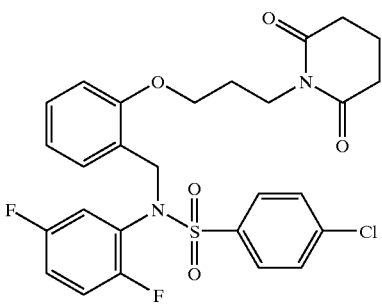

$R_f$=0.43 (1:1 hexanes:ethyl acetate), $^1$H NMR (300 MHz, CDCl$_3$) δ (ppm): 7.68 (d, 2H), 7.48 (d, 2H), 7.36 (d, 1H), 7.17 (m, 1H), 6.94–6.85 (m, 4H), 6.69 (d, 1H), 4.85 (s, 2H), 3.86 (t, 2H), 3.77 (t, 2H), 2.65 (t, 4H), 1.98–1.82 (m, 4H). MS calculated for C$_{27}$H$_{25}$ClF$_2$N$_2$O$_5$S, [MH+] 563; Observed: 563.

EXAMPLE 321

4-Chloro-N-(2,5-difluorophenyl)-N-1-{2-[3-(1H-imidazol-1-yl)propoxy]phenyl}ethyl)benzenesulfonamide Hydrochloride The general synthetic scheme set forth in SCHEME 321 can also be used for the preparation of numerous compounds according to the invention.

SCHEME 321

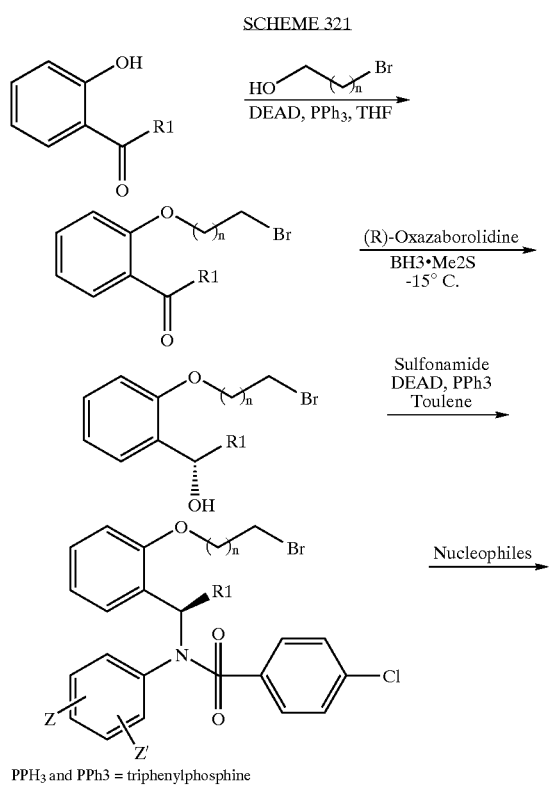

PPH3 and PPh3 = triphenylphosphine

To a solution of 2'-hydroxy acetophenone (3.0 g, 22 mmol) under Ar, in anhydrous THF (100 mL) was added triphenylphosphine (8.7 g, mm mmol), 3-bromopropanol (3.8 g, 27 mmol) and DEAD (5.2 mL, 33 mmol). The reaction mixture was stirred at room temperature for 14 h, concentrated under reduced pressure and the product isolated by $SiO_2$ chromatography (hexanes/ethyl acetate 7:1) to give 4.0 g of product (yield: 71%). $^1$H NMR (300 MHz, $CD_3OD$) δ (ppm): 7.72 (dd, 1H), 7.46 (dt, 1H), 7.02–6.95 (m, 2H), 4.22 (t, 2H), 3.61 (t, 2H), 2.60 (s, 3H), 2.38, (p, 2H).

A solution of 2'(3-bromopropyloxy) acetophenone (3.2 g, 12.5 mmol) in methanol (50 mL) was cooled to 0° C. under Ar atmosphere. Solid $NaBH_4$ (0.475 g, 12.5 mmol) was added in one portion and the reaction mixture was stirred at 0° C. for 1 h, diluted with 100 mL of water and the product extracted with 3×50 mL of ethyl acetate. The combined organic phase was washed with 100 mL of water, dried with anhydrous $MgSO_4$, filtered and concentrated under reduced pressure to give 3.1 g of product (y: 97%). $^1$H NMR (300 MHz $CD_3OD$) δ (ppm): 7.38 (dd, 1H), 7.23 (dt, 1H), 6.98 (t, 1H), 6.89 (d, 1H), 5.13 (q, 1H), 4.17 (t, 2H), 3.61 (t, 2H), 2.36 (p, 2H), 1.50 (d, 3H).

Synthesis of R-Alcohol

To a stirred solution of commercially available (Strem) (R)— methyl oxazaborolidine (127 M solution in toluene, 3.9 mL, 4.95 mmol) at room temperature under Ar was added a solution $BH_3.Me_2S$ (10.5 M, 5.63 mL, 59.1 mmol) over a period of 10 min. The reaction mixture was left stirred at room temperature for 10 min after which time cooled to −20° C. To this cooled solution was added a solution of the ketone (25 33 g, 98.5 mmol) in dry DCM (11 mL) via syringe pump over a period of 4 h. The reaction mixture was left stirred for another 2 h at −20° C. and carefully quenched with pre cooled methanol. The solvent was removed by concentrating under reduced pressure to yield the crude product which was subsequently purified by $SiO_2$ chromatography(ethyl acetate:hexanes, 1:10) to yield the chiral product as a colorless oil (24 g, 94%, >98% ee by chiral HPLC). The stereochemistry is assigned S, based on the literature precedents. $^1$H NMR (300 MHz, $CD_3OD$) δ (ppm): 7.72 (dd, 1H), 7.46 (dt, 1H), 7.02–6.95 (m, 2H), 4.22 (t, 2H), 3.61 (t, 2H), 2.60 (s, 3H), 2.38, (p, 2H).

The procedure was repeated with (S)-methyl oxazaborolidine solution to yield the corresponding (R)-alcohol.

To a stirred solution of the racemic alcohol (0.5 g, 1.9 mmol) in dry THF (10 mL) under Ar was added triphenylphosphine (0.75 g, 2.85 mmol) followed by the sulfonamide (0.91 g, 2.85 mmol). The reaction mixture was cooled to 0° C. in an ice bath and DEAD (0.45 mL, 2.85 mmol) was added over period of 5 min. The reaction mixture was left to stir at room temperature for 15 h then concentrated under reduced pressure to give the crude product mixture which was subsequently purified by chromatography over $SiO_2$ (10:1 hexanes/ethyl acetate) to give 465 mg (y: 63%) to afford a pale yellow oil. $^1$H NMR (500 MHz $CDCl_3$) δ(ppm): 7.62–7.61 (m, 2H), 7.39–7.36 (m, 2H), 7.20 (t, 1H), 6.93 (br, 1H), 6.86 (d overlaps br, 3H), 6.77 (br d, 1H), 6.68 (t, 1H), 6.08 (br, 1H), 4.19–4.09 (m, 2H), 3.77 (br, 2H), 2.47–2.35 (m, 2H), 1.56 (overlapping d, 3H).

The R and S alcohols were similarly converted to the S and R bromoalkyl sulfonamide derivative respectively.

The racemic bromo alkyl sulfonamide derivative (115 mg, 0.21 mmol) was dissolved in dry piperidine (2 mL) under Ar and stirred at room temperature for 1 h. The reaction mixture was concentrated under reduced pressure, re-dissolved in 20 mL of ethyl acetate, washed with saturated bicarbonate solution (2×10 mL of), water (2×10 mL), dried with $MgSO_4$, filtered and concentrated under reduce pressure to give 110 mg of product as colorless oil (free base). The free base was converted to the HCl salt as described before, passed through a short plug of $SiO_2$ (10% methanol in DCM) to yield 85 mg of product as white solid. (y: 70%) $^1$H NMR (500 MHz $CDCl_3$) δ (ppm): 7.68–7.54 (m, 4H), 7.23, 7.01, 6.81, 6.67 (br, 6H), 6.25 (q overlaps br, 2H), 4.32–4.21 (m, 2H), 3.70–3.60 (m, 4H), 3.10–3.56 (br, 2H), 2.43–2.40 (m, 2H), 2.01–1.75 (m, 5H), 1.55–1.51 (m, 4H). ESI calculated for $C_{28}H_{32}ClF_2N_2O_3S$ [MH+] 549; Observed: 549. The R and S bromoalkylsulfonamides were similarly converted to give enantiomerically enriched products.

To a stirred solution of imidazole (82 mg, 1.2 mmol) in anhydrous THF (5.0 mL) was added 2.0 M n-BuLi Solution in hexanes (600 μL 1.2 mmol). The reaction mixture was stirred at room temperature for 30 min, and a solution of bromoalkyl sulfonamide derivative (220 mg, 0.34 mmol in 5 mL of THF) was added. The reaction mixture was stirred at room temperature for 6 h, then quenched with saturated bicarbonate solution, extracted with ethyl acetate (2×25 mL), the combined organic layer were washed with water (2×20 mL), dried with $MgSO_4$, filtered and concentrated to give 200 mg of crude product which was purified by $SiO_2$ chromatography (5% methanol in DCM) to yield 188 mg of product. $R_f$=0.62 (9:1 DCM/methanol). $^1$H NMR ($CDCl_3$, 300 MHz) δ (ppm): 7.63–6.65 (m, 14H), 6.25–6.23 (m, 1H), 4.52–4.32 (m, 2H), 4.08–3.88 (m, 2H), 2.44–2.27 9m, 2H), 1.25–1.21 (overlapping d, 3H). $^{13}$C NMR (75 z) (partial list of resolved lines) δ (ppm): 159.0, 155.81 139.3, 130.1, 137.4, 129.7, 129.4, 128.9, 119.1, 117.6 (d), 117.4 (d), 110.9, 64.1, 52.7, 43.6, 30.9, 18.4.LC-MS calculated for $C_{26}H_{24}ClF_2N_3O_3S$: 532; Observed: 532.

The compounds described in Examples 322–331 were prepared according to the scheme described in the previous example.

EXAMPLE 322

4-Chloro-N-(2,5-difluorophenyl)-N-(1-{2-[3-(1-piperidinyl)propoxy]phenyl}propyl)benzenesulfonamide Hydrochloride

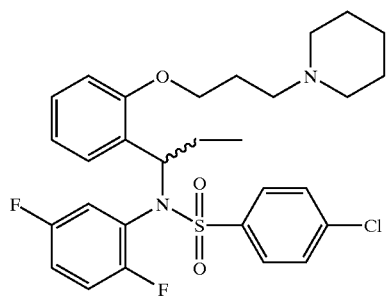

$R_f$=0.38 (10% methanol in DCM), $^1$H NMR (300 MHz, CD$_3$OD) δ (ppm): (t, 4H), 7.26–7.03 (m, 3H), 6.81 (br, 1H), 6.67–6.55 (m, 2H), 6.13–6.04 (m, 2H), 4.32–4.22 (m, 2H), 3.68–3.35 (m, 4H), 3.06 (br, 2H), 2.39–2.38 (m, 2H), 1.99–1.55 (m, 8H), 0.80 (d, 3H). MS calculated for C$_{29}$H$_{33}$ClF$_2$N$_2$O$_3$S, [MH$^+$]563: Observed: 563.

EXAMPLE 323

4-Chloro-N-2,5-difluorophenyl)-N-((1R)-1-{2-[3-(1H-imidazol-1-yl)propoxy]phenyl}ethyl)benzenesulfonamide Hydrochloride

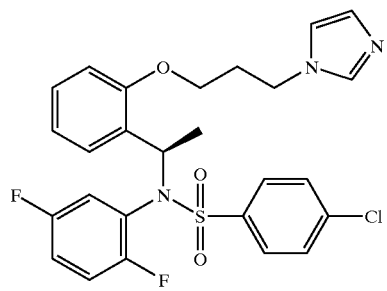

$R_f$=0.46 (10% methanol in DCM), $^1$H NMR (300 MHz, CDCl$_3$) δ (ppm): 8.21 (s, 1H), 7.73–7.42 (m, 6H), 7.20–6.68 (m, 7H), 6.25 (m, 1H), 4.64 (m, 2H), 4.10 (br, 2H), 2.44 (m, 2H), 1.55 (br, 3H). LC-MS calculated for C$_{21}$H$_{24}$ClF$_2$N$_3$O$_3$S, [MH$^+$] 532; Observed: 532.

EXAMPLE 324

4-Chloro-N-(2,5-difluorophenyl)-N-((1R)-1-{2-[3-(1H-tetraazol-1-yl)propoxy]phenyl}ethyl)benzenesulfonamide

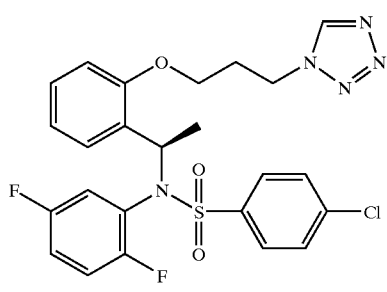

$R_f$=0.57 (19:1; DCM:methanol). $^1$H NMR (CDCl$_3$) δ (ppm): 8.98 (s, 1H), 7.67–7.62 (m, 2H), 7.48–7.42 (m, 2H), 7.21–7.19 (m, 1H), 695–6.52 (m, 5.5H), 6.35–6.28 (m, 1.5H), 5.29–5.06 (m, 1H), 4.95–4.87 (m, 1H), 4.17–3.95 (m, 1H), 2.68–2.50-(m, 2H), 1.54–1.46 (br, 3H). LC-MS calculated for C$_{24}$H$_{22}$ClF$_2$N$_5$O$_3$S: 534. Observed: 536 (MNa+).

EXAMPLE 325

4-Chloro-N-(5-chloro-2-fluorophenyl)-N-((1R)-1-{2-[3-(1H-imidazol-1-yl)propoxy]phenyl}ethyl)benzenesulfonamide Hydrochloride

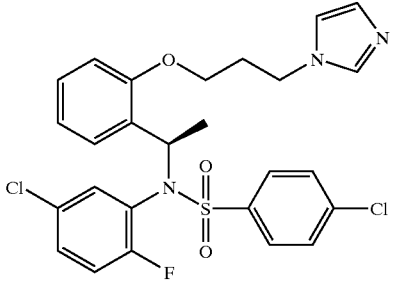

$R_f$=0.15 (5% methanol in DCM), $^1$H NMR (300 MHz, CD$_3$OD) δ (ppm): 7.81–6.59 (m, 14H), 6.20 (s, 1H), 4.54–4.29 (m, 2H), 4.08–3.90 (m, 2H), 2.39–2.14 (m, 2H), 1.63 (br, 3H)). LC-MS calculated for C$_{26}$H$_{24}$Cl$_2$FN$_3$O$_3$S, [MH$^+$] 548; Observed: 548.

EXAMPLE 326

4-Chloro-N-(2,5-dichlorophenyl)-N-((1R)-1-{2-[3-(1H-imidazol-1-yl)propoxy]phenyl}ethyl)benzenesulfonamide Hydrochloride

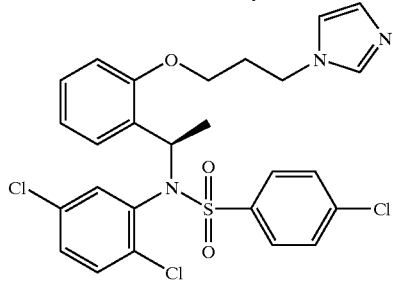

$R_f$=0.72 (10% methanol in DCM), $^1$H NMR (300 MHz, CD$_3$OD) δ (ppm): 7.64 (d, 2H), 7.53 (d, 2H), 7.41–6.66 (m, 10H), 6.14 (m, 1H), 4.32 (m, 2H), 3.94 (m, 2H), 2.30 (m, 2H), 1.63–1.49 (dd, 3H). LC-MS calculated for C$_{26}$H$_{24}$Cl$_3$N$_3$O$_3$S, [MH$^+$] 564; Observed: 564.

EXAMPLE 327

4-Chloro-N-(2,5-difluorophenyl)-N-((1R)-1-{2-[3-(4-methyl-1H-pyrazol-1-yl)propoxy]phenyl}ethyl)benzenesulfonamide

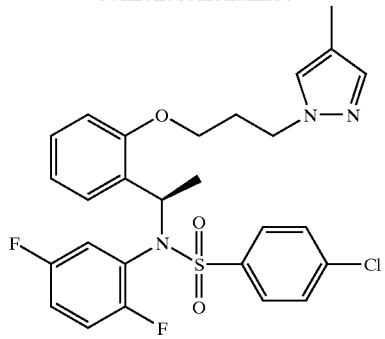

$R_f$=0.32 (19:1 DCM:methanol). $^1$H NMR (CDCl$_3$) δ (ppm): 7.65–7.62 (d, 2H), 7.53 (s, 0.5H), 7.47 (s, 0.5H), 7.40–7.38 (d, 2H), 7.21–7.16 (t, 1H), 6.92–6.67 (m, 5.5H), 6.28–6.23 (m, 1.5H), 4.42–4.25 (m, 2H), 4.07–3.89 (m, 2H), 2.45–2.27 (m, 2H), 2.24 (s, 1.5H), 2.22 (s, 1.5H), 1.53 (d, 3H), LC-MS calculated for C$_{27}$H$_{26}$ClF$_2$N$_3$O$_3$S: 546. Observed: 546.2.

EXAMPLE 328

4-Chloro-N-(2,5-difluorophenyl)-N-(1-{2-[3-(1H-1,2,3-triazol-1-yl)propoxy]phenyl}ethyl)benzenesulfonamide

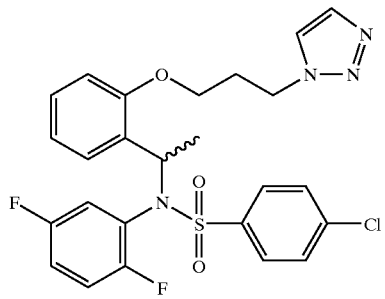

$R_f$=0.32 (3:1; hexanes:ethyl acetate). $^1$H NMR (CDCl$_3$) δ (ppm): 7.66–7.61 (m, 4H), 7.39–7.35 (m, 2H), 7.19–7.10 (m, 1H), 6.92–6.65 (5.5H), 6.15–6.11 (m, 1.5H), 4.89–4.81 (m, 2H), 4.10–4.02 (m, 1H), 3.95–3.87 (m, 1H), 2.58–2.47 (m, 2H), 1.57 (d, 3H). LC-MS calculated for C$_{25}$H$_{23}$ClF$_2$N$_4$O$_3$S: 533. Observed: 230 (M$^+$-303).

EXAMPLE 329

4-Chloro-N-(2,5-difluorophenyl)-N-((1R)-1-{2-[3-(2-methyl-1H-imidazol-1-yl)propoxy]phenyl}ethyl)benzenesulfonamide Hydrochloride

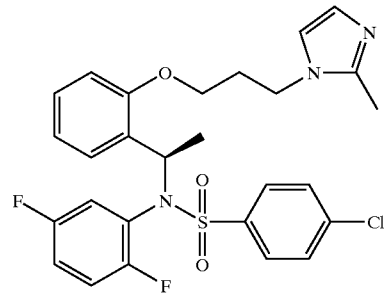

$R_f$=0.31 (19:1; DCM:methanol), $^1$H NMR (CD$_3$OD) δ (ppm): 7.42–7.01 (m, 6H), 6.79–6.44 (m, 5.5H), 6.07–6.00 (m, 1.5H), 4.43–4.34 (m, 2H), 4.08–3.95 (m, 2H), 2.50 (s, 3H), 2.35–2.24 (m, 214), 1.30 (m, 3H). LC-MS calculated for C$_{27}$H$_{26}$ClF$_2$N$_3$O$_3$S: 546. Observed: 546 (M$^+$).

EXAMPLE 330

4-Chloro-N-(2,5-difluorophenyl)-N-(1-[2-[3-(4H-1,2,4-triazol-4-yl)propoxy]phenyl}ethyl)benzenesulfonamide Hydrochloride

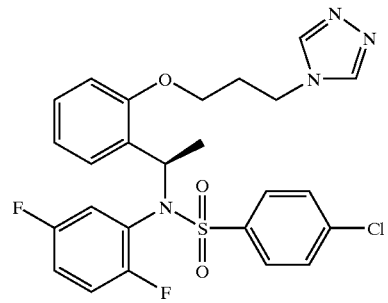

$R_f$=0.28 (19:1; DCM:methanol). $^1$H NMR (CD$_3$OD) δ (ppm): 9.43 (s, 1H), 8.66 (s, 1H), 7.68–7.54 (m, 4H), 7.19–6.66 (m, 5.5H), 6.25–6.18 (m, 1.5H), 4.85–4.76 (m, 2H), 4.14–4.09 (m, 2H), 2.59–02.54 (m, 2H), 1.54 (br, 3H). LC-MS calculated for C$_{25}$H$_{23}$ClF$_2$N$_4$O$_3$S: 532. Observed 532 (M$^+$).

EXAMPLE 331

4-Chloro-N-(2,5-difluorophenyl)-N-((1R)-1-{2-[3-(2H-tetraazol-2-yl)propoxy]phenyl}ethyl)benzenesulfonamide

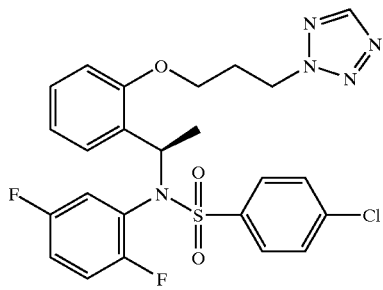

$R_f$=0.25 (4:1; hexanes:ethyl acetate), $^1$H NMR (CDCl$_3$) δ (ppm): 8.89 (s, 1H), 7.67–7.61 (d, 2H), 7.41–7.33 (d, 2H), 7.13–7.10 (m, 1H), 6.93–6.66 (m, 6H), 6.23–6.21 (m, 1H), 5.23–5.09 (m, 2H), 4.19–4.09 (m, 1H), 4.00–3.93 (m, 1H), 2.66–2.56 (m, 2H), 1.56 (d, 3H). LC-MS calculated for C$_{24}$H$_{22}$ClF$_2$N$_5$O$_3$S: 533; observed 566 (MNa$^+$).

EXAMPLE 332

4-Chloro-N-[5-chloro-2-(hydroxymethyl)phenyl]-N-((1R)-1-{2-[3-(1H-imidazol-1-yl)propoxy]phenyl}ethyl)benzenesulfonamide

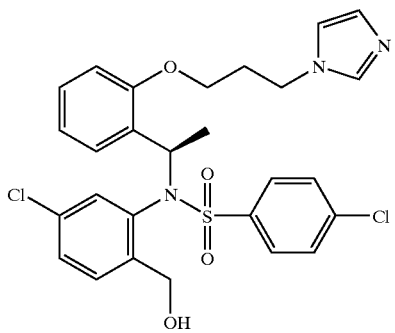

$R_f$=0.33 (19:1; DCM:methanol). $^1$H NMR (CDCl$_3$) δ (ppm): 7.66–7.63 (m, 3H), 7.58–7.50 (m, 2H), 7.39 (m, 2H), 7.18 (m, 1H), 7.08 (m, 2H), 6.84 (d, 1H), 6.64 (t, 1H), 6.58 (s, 1H), 6.43–6.34 (m, 1H), 4.51–4.41 (m, 2H), 4.15–3.91 (m, 3H), 3.53 (d, 10H), 2.42 (m, 2H), 1.88 (m, 1H), 1.42 (d, 3H). LC-MS calculated for C$_{27}$H$_{27}$Cl$_2$N$_3$O$_4$S: 565; Observed: 565 (Me).

EXAMPLE 333

4-Chloro-N-(2,5-difluorophenyl)-N-[1-(2-hydroxyphenyl)ethyl]benzenesulfonamide

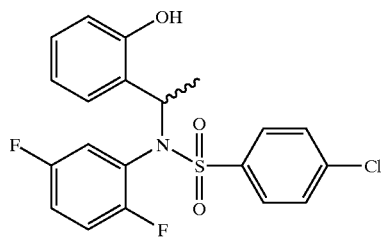

$R_f$=0.30 (6:1;hexanes:ethyl acetate). $^1$H NMR (CDCl$_3$) δ (ppm): 7.82–7.79 (m, 2H), 7.60–7.50 (m, 2H), 7.33–6.91 (m, 6.5H), 6.33–6.19 (m, 0.5H), 5.30 (q, 1H), 1.36–1.25 (br, 3H). LC-MS calculated for C$_{20}$H$_{16}$ClF$_2$NO$_3$S: 423. Observed 446 (MNa$^+$).

EXAMPLE 334

4-Chloro-N-(2,5-difluorophenyl)-N-[(1R)-1-(2-methoxyphenyl)ethyl]benzenesulfonamide

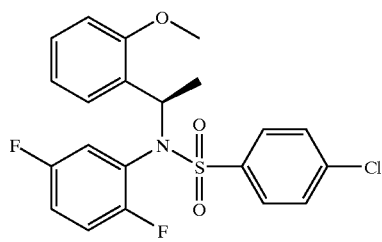

$R_f$=0.32 (15:1 hexanes:ethyl acetate). $^1$H NMR (CDCl$_3$) δ (ppm): 7.66–7.63 (m, 2H0, 7.39–7.37 (m, 2H), 7.18–7.15 (m, 1H), 6.96–6.66 (m, 5.5H), 5.81 (br, 1.5H), 1.67 (s, 1.5H), 1.57 (s, 1.5H).

EXAMPLE 335

4-Chloro-N-(2,5-difluorophenyl)-N-((1R)-1-{2-[3-(2,5-dioxo-1-pyrrolidinyl)propoxy]phenyl}ethyl)benzenesulfonamide

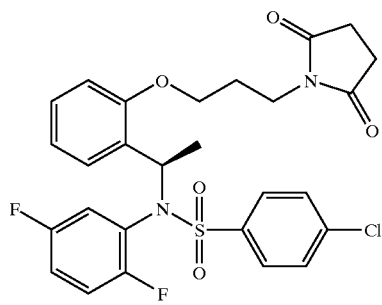

$R_f$=0.46 (3:1; hexanes:ethyl acetate). $^1$H NMR CDCl$_3$) δ: 7.65–7.63 (d, 2H), 7.39–7.36 (d, 2H), 7.20–7.14 (m, 1H), 6.95–6.37 (m, 6H), 6.05 (m, 1H), 4.06–3.74 (m, 4H), 2.73 (s, 4H), 2.20–2.12 (p, 2H), 1.56 (d, 3H), LC-MS calculated for C$_{27}$H$_{25}$ClF$_2$N$_2$O$_5$S: 563.01. Observed 260 (M$^+$-303).

EXAMPLE 336

4-Chloro-N-(4-fluorophenyl)-N-((1R)-1-{2-[3-(1H-imidazol-1-yl)propoxy]phenyl}ethyl)benzenesulfonamide Hydrochloride

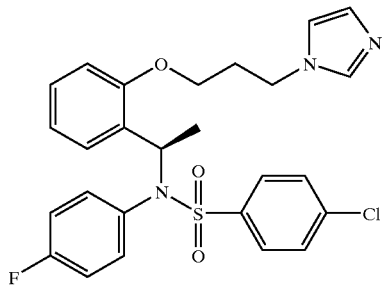

$R_f$=0.34 (5% methanol in DCM), $^1$H NMR (300 MHz, CD$_3$OD) δ (ppm): 7.60 (s, 1H), 7.51 (d, 2H), 7.35 (d, 2H), 7.08–6.94 (m, 2H), 6.89–6.76 (m, 3H), 6.54–6.46 (m, 2H), 6.35 (d, 1H), 6.24 (dt, 1H), 6.12 (q, 1H), 4.44–4.24 (m, 2H), 4.03–3.97 (m, 1H), 3.86–3.79 (m, 1H), 2.39–2.16 (m, 2H), 1.43 (d, 314). LC-MS calculated for C$_{26}$H$_{25}$ClFN$_3$O$_3$S, [MH$^+$]514; Observed: 514.

EXAMPLE 337

4-Chloro-N-(2,4-difluorophenyl)-N-((1R)-1-(2-[3-(1H-imidazol-1-yl)propoxy)phenyl}ethyl)benzenesulfonamide Hydrochloride

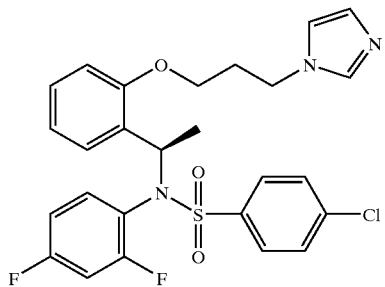

$R_f$=0.43 (5% methanol in CH$_2$Cl$_2$) $^1$H NMR (300 MHz CD$_3$OD) δ (ppm): 7.88 (s, 1H), 7.72–7.69 (m, 2H), 7.51–7.48 (m, 2H), 7.40–7.27 (m, 2H), 7.17–7.11 (m, 1H), 7.04 (br, 1H), 7.00–6.94 (m, 1H), 6.84–6.49 (m, 4H)., 6.28–6.21 (q, 1H), 4.56–4.37 (m, 2H), 4.01–3.89 (m, 2H), 2.3&2.27 (m, 2H), 1.46–1.43 (m, 3H). LC-MS calculated for C$_{26}$H$_{24}$ClF$_2$N$_3$O$_3$S [MH+] 532; Observed: 532.

EXAMPLE 338

4-Chloro-N-(3-fluorophenyl)-N-((1R)-1-{2-[3-(1H-imidazol-1-yl)propoxy]phenyl}ethyl)benzenesulfonamide Hydrochloride

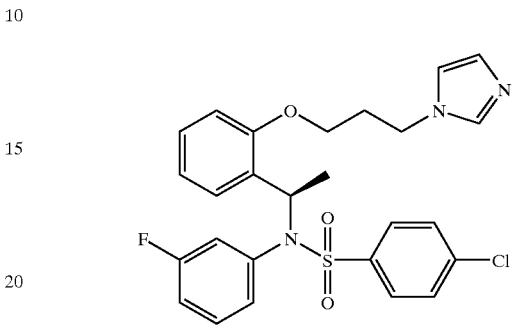

$R_f$=0.29 (5% methanol in CH$_2$Cl$_2$) $^1$H NMR (300 MHz CD$_3$OD) δ (ppm): 7.80 (s, 1H), 7.70–7.65 (m, 2H), 7.56–7.52 (m, 2H), 7.27 (s, 1H), 7.24–7.17 (m, 1H), 7.01–6.85 (m, 4H), 6.71–6.66 (m, 4H), 6.36–6.29 (q, 1H), 4.64–4.43 (m, 2H), 4.21–4.14 (m, 1H), 4.05–3.98 (m, 1H), 2.58–2.30 (m, 2H), 1.68–1.51 (m 3H). LC-MS calculated for C$_{26}$H$_{25}$ClFN$_3$O$_3$S [α]+] 514; Observed: 514.

EXAMPLE 339

4-Chloro-N-(2-fluorophenyl)-N-((1R)-1-{2-[3-(1H-imidazol-1-yl)propoxy]phenyl}ethyl)benzenesulfonamide Hydrochloride $R_f$=0.33 (5% methanol in CH$_2$Cl$_2$) $^1$H NMR (300 MHz CD$_3$OD) δ (ppm): 7.68–6.47 (m, 15H), 6.27–6.08 (q, 1H), 4.43–4.27 (m, 2H), 3.88 (br, 2H), 2.27–2.14 (m, 2H), 1.41 (br, 3H). LC-MS calculated for C$_{26}$H$_{25}$ClFN$_3$O$_3$S [MH+] 514; Observed: 514.

EXAMPLE 340

4-Chloro-N-(2,6-difluorophenyl)-N-((1R)-1-{2-[3-(1H-imidazol-1-yl)propoxy]phenyl}ethyl)benzenesulfonamide Hydrochloride

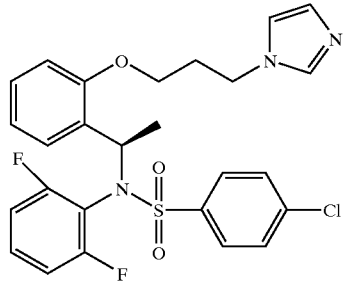

$R_f$=0.35 (5% methanol in $CH_2Cl_2$) $^1$H NMR (300 MHz $CD_3OD$) δ (ppm): 7.54–7.25 (m, 6H), 7.08–6.34 (in, 8H), 6.13–5.97 (q, 1H), 4.36–4.23 (m, 2H), 3.97–3.78 (br, 2H), 2.20–2.10 (br, 2H), 1.35–1.25 (m, 3H). LC-MS calculated for $C_{26}H_{24}ClF_2N_3O_3S$ [H+] 532; Observed: 532.

EXAMPLE 341

S{3-[2-({[(4-chlorophenyl)sulfonyl]anilino}methyl)phenoxy]propyl}ethanethioate

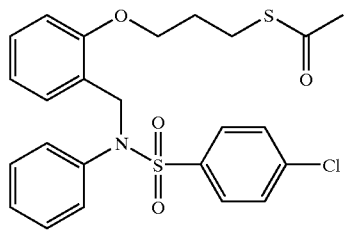

To a stirred solution of N-2-(3-bromopropyloxy)benzyl 4-chlorobenzenesulfanilide (200 mg, 0.4 mmol) in DMF (5 mL) was added the potassium salt of thio acetic acid (92 mg, 0.81 mmol). The reaction mixture was then warmed to 60° C. After 3 h, the reaction mixture was cooled to room temperature, diluted with ethyl acetate (25 mL), washed with saturated bicarbonate solution (3×10 mL) and saturated brine (2×10 mL), dried with $MgSO_4$, filtered and concentrated under reduced pressure to isolate a colorless oil which was purified by $SiO_2$ chromatography (7:1, hexanes:ethyl acetate) to afforded the desired product (130 mg, y: 63%). $R_f$=0.25 (20% ethyl acetate/hexanes) $^1$H NMR (300 MHz, $CDCl_3$) δ (ppm): 7.60–7.56 (m, 2H), 7.46–7.42 (m, 2H), 7.36 (dd, 1H), 7.23–7.7.12 (dd, 2H), 6.85 (t, 1H), 6.70 (d, 1H), 4.82 (s, 2H), 3.85 (t, 2H), 2.95 (t, 2H), 2.33 (s, 3H), 1.92 (q, 2H), $^{13}$C NMR (75 MHz, $CDCl_3$) δ (ppm): 196.0, 156.7, 139.6, 139.4, 137.5, 130.7, 129.5, 129.3, 129.3, 128.3, 124.5, 121.0, 111.3, 66.4, 49.8, 31.1, 29.6, 26.2.

EXAMPLE 342

4-Chloro-N-phenyl-N-[2-(3-sulfanylpropoxy)benzyl]benzenesulfonamide

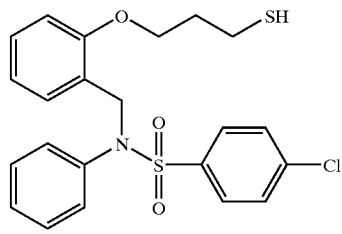

A stirred solution of thio acetate analog prepared above (100 mg, 0.2 mmol) at ° C. in ethanol (5 mL) was vigorously degassed for 0.5 h, then a solution of degassed 1.0 N NaOH (0.4 mL, 0.4 mmol) vas added. The reaction mixture was allowed stir at 0° C. for 1 h warmed to room temperature stirred at room temperature for 1 h, then diluted with degassed ethyl acetate (20 mL), washed with saturated bicarbonate solution (3×10 mL), 10% aqueous HCl (3×10 mL), dried with $MgSO_4$, filtered and concentrated under reduced pressure to isolate a white solid. The crude material was purified by chromatography on $SiO_2$ (4:1 hexanes:ethyl acetate) to give 40 mg of product (y: 44°%). $R_f$=0.25 (20% ethyl acetate/hexanes) $^1$H NMR (300 MHz, $CDCl_3$) δ (ppm): 7.58–7.56 (m, 2H), 7.47–7.54 (m, 2H), 7.34–7.14 (m, 5H), 6.99 (m, 2H), 6.87–6.73 (dt, 2H), 4.78 (s, 2H), 3.92 (t, 2H), 2.63 (q, 2H), 1.96 (q, 2H), 1.35 (t, 1H). $^{13}$C NMR (75 MHz, $CDCl_3$) δ (ppm): 159.1, 141.9, 141.8, 139.9, 133.1, 131.8, 131.8, 131.7, 131.6, 130.6, 126.7, 123.2, 113.7, 68.2, 52.2, 35.8, 24.0.

The following compounds were prepared according to the scheme described in the previous example.

EXAMPLE 343

N-(2,5-difluorophenyl)-4-(phenylsulfanyl)-N-{2-[3-(phenylsulfanyl)propoxy]benzyl}benzenesulfonamide

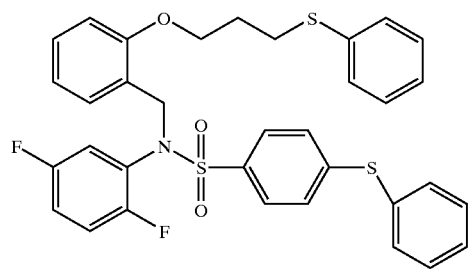

$R_f$=0.54 (4:1 hexanes:ethyl acetate), $^1$H NMR (300 MHz, $CDCl_3$) δ (ppm): 7.63 (d, 2H), 7.54–7.50 (m, 5H), 7.33–7.26 (m, 6H), 7.18 (t, 5H), 6.97 (m, 1H), 6.87–6.79 (m, 2H), 4.70 (s, 2H), 3.94 (t, 2H), 3.08 (t, 2H), 1.90–1.86 (m, 2H).

EXAMPLE 344

4-Chloro-N-(2,5-difluorophenyl)-N-{2-[3-(phenylsulfanyl)propoxy]benzyl}benzenesulfonamide

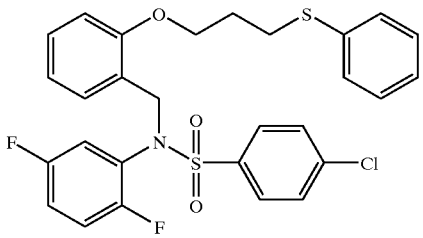

$R_f$=0.45 (6:1 hexanes:ethyl acetate), $^1$H NMR (300 MHz, DMSO) δ (ppm): 7.72 (q, 4H), 7.34–7.18 (m, 8H), 7.00–6.98 (m, 2H), 6.89–6.80 (m, 2H), 4.73 (s, 2H), 3.95 (t, 2H), 3.09 (t, 2H), 1.91–1.87 (m, 2H).

EXAMPLE 345

4-Chloro-N-(2,5-difluorophenyl)-N-{2-[3-(phenylsulfonyl)propoxy]benzyl}benzenesulfonamide

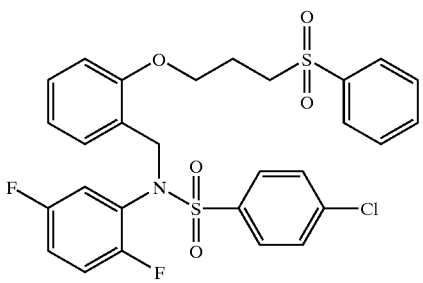

$R_f$=0.40 (3:1 hexanes:ethyl acetate), $^1$H NMR (300 MHz, CDCl$_3$) δ (ppm): 7.96 (d, 2H), 7.68–7.54 (m, 5H), 7.47 (d, 2H), 7.19–7.10 (m, 2H), 6.93–6.68 (m, 5H), 4.77 (s, 2H), 3.97 (t, 2H), 3.38 (t, 2H), 2.24–2.15 (m, 2H).

EXAMPLE 346

4-Chloro-N-{2-[3-(cyclohexylsulfanyl)propoxy]benzyl}-N-(2,5-difluorophenyl)benzenesulfonamide

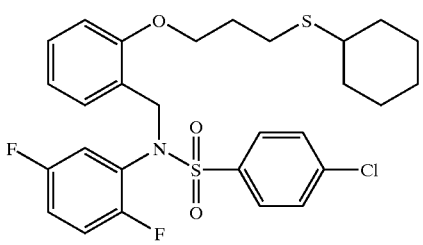

$R_f$=0.26 (5% methanol in DCM), $^1$H NMR (300 MHz, CDCl$_3$) δ (ppm): 7.66 (d, 2H), 7.47 (m, 2H), 7.28–7.15 (m, 1H), 7.00 (d, 1H), 6.90 (m, 2H), 6.75 (m, 3H), 4.81 (s, 214), 3.92 (m, 2H), 2.66 (m, 3H), 1.94 (m, 4H), 1.75 (m, 2H), 1.60 (m, 2H), 1.28 (m, 4H).

EXAMPLE 347

4-Chloro-N-{2-[3-(cyclohexylsulfonyl)propoxy]benzyl}-N-(2,5-difluorophenyl)benzenesulfonamide

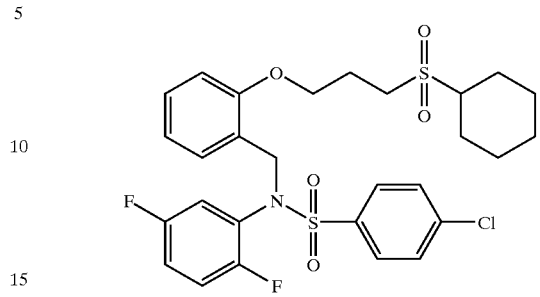

$R_f$=0.29 (3:1 hexanes:ethyl acetate), $^1$H NMR (300 MHz, CDCl$_3$) δ (ppm): 7.65 (d, 2H), 7.48 (d, 2H), 7.18 (t, 1H), 7.80 (d, 2H), 6.90 (m, 21H), 6.76 (m, 3H), 4.78 (s, 2H), 4.10 (t, 2H), 3.29 (t, 2H), 2.94 (m, 1H), 2.35 (m, 2H), 2.22 (d, 2H), 1.90 (m, 2H), 1.72–1.19 (m, 6H). MS calculated for C$_{28}$H$_{30}$ClF$_2$NO$_5$S$_2$, [MNa$^+$] 620; Observed: 620.

EXAMPLE 348

4-Chloro-N-{2-[3-(cyclohexylsulfinyl)propoxy]benzyl}-N-(2,5-difluorophenyl)benzenesulfonamide

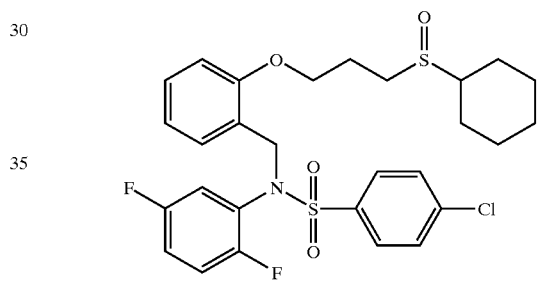

$R_f$=0.32 (1:1 hexanes:ethyl acetate), $^1$H NMR (300 MHz, CDCl$_3$) δ (ppm): 7.64 (d, 2H), 7.47 (d, 2H), 7.19 (t, 1H), 7.08 (d, 2H), 6.92–6.87 (m, 2H), 6.80–6.76 (m, 3H), 4.79 (s, 2H), 4.16–3.98 (m, 2H), 3.12–3.03 (m, 1H), 2.87–2.78 (m, 1H), 2.67–2.60 (m, 1H), 2.34 (m, 2H), 2.14 (d, 1H), 1.95–1.69 (m, 3H), 1.57–1.24 (m, 6H). MS calculated for C$_{28}$H$_{30}$ClF$_2$NO$_4$S$_2$, [MH+] 582; Observed: 582.

EXAMPLE 349

4-Chloro-N-(2,5-difluorophenyl)-N-(2-{3-[(4-methoxyphenyl)sulfanyl]propoxy}benzyl)benzenesulfonamide

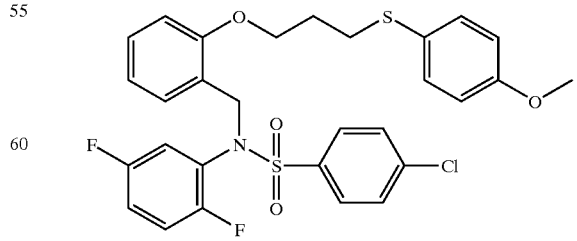

$R_f$=0.44 (6:1 hexanes:ethyl acetate), $^1$H NMR (300 MHz, CDCl$_3$) δ (ppm): 7.67–7.64 (m, 2H), 7.48–7.44 (m, 2H), 7.35–7.32 (m, 2H), 7.31–7.15 (m, 3H), 6.91–6.70 (m, 8H), 4.77 (m, 2H), 3.94–3.86 (m, 2H), 3.77 (m, 3H), 2.97–2.92 (m, 2H), 1.97–1.88 (m, 2H). MS calculated for $C_{29}H_{26}ClF_2NO_4S_2$, [MNa$^+$]612; Observed: 612.

EXAMPLE 350

4-Chloro-N-(2,5-difluorophenyl)-N-(2-{3-[(4-methoxyphenyl)sulfonyl]propoxy}benzyl)benzenesulfonamide

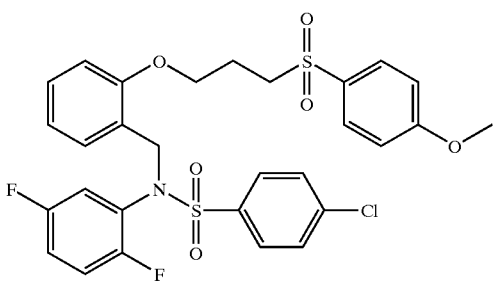

$R_f$=0.42 (2:1 hexanes:ethyl acetate), $^1$H NMR (300 MHz, CDCl$_3$) δ (ppm): 7.87 (d, 2H), 7.63 (d, 2H), 7.47 (d, 2H), 7.26–7.11 (m, 2H), 7.00 (d, 2H), 6.91–6.75 (m, 4H), 6.69 (d, 1H), 4.74 (s, 2H), 3.96 (t, 2H), 3.86 (s, 3H), 3.36–3.31 (m, 2H), 2.22–2.13 (n, 2H). MS calculated for $C_{29}H_{26}ClF_2NO_6S_2$, [MNa$^+$] 644; Observed: 644.

EXAMPLE 351

4-Chloro-N-(2,5-difluorophenyl)-N-(2-{3-[(4-nitrophenyl)sulfanyl]propoxy}benzyl)benzenesulfonamide

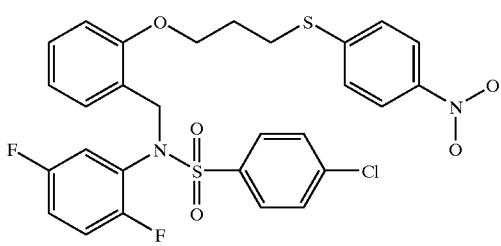

$R_f$=0.40 (6:1 hexanes:ethyl acetate), $^1$H NMR (300 MHz, CDCl$_3$) δ Ppm): 8.12–8.09 (m, 2H), 7.67–7.63 (m, 2H), 7.49–7.45 (m, 2H), 7.41–7.37 (m, 2H), 7.22–7.16 (m, 1H), 7.12–7.09 (m, 1H), 6.91–6.74 (m, 5H), 4.82 (s, 2H), 4.05 (t, 2H), 332 (t, 2H), 2.19 (m, 2H).

EXAMPLE 352

4-Chloro-N-(2,5-difluorophenyl)-N-(2-{3-[(4-methoxyphenyl)sulfinyl]propoxy}benzyl)benzenesulfonamide

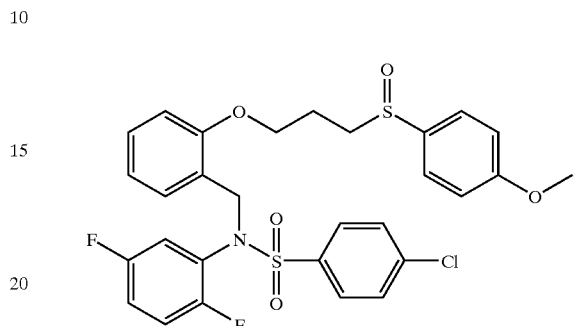

$R_f$=0.23 (1:1 hexanes:ethyl acetate), $^1$H NMR (300 MHz, CDCl$_3$) δ (ppm): 7.66–7.54 (m, 4H), 7.49 (d, 2H), 7.20–7.11 (m, 2H), 7.03 (d, 2H), 6.94–6.76 (m, 4H), 6.71 (d, 1H), 4.76 (s, 2H), 4.05–3.84 (m, 5H), 3.15–2.90 (m, 2H), 2.26–2.00 (m, 2H). MS calculated for $C_{29}H_{26}ClF_2NO_5S_2$, [MNa$^+$] 628; Observed: 628.

EXAMPLE 353

4-Chloro-N-(2,5-difluorophenyl)-N-(2-{3-[(4-nitrophenyl)sulfonyl]propoxy}benzyl)benzenesulfonamide

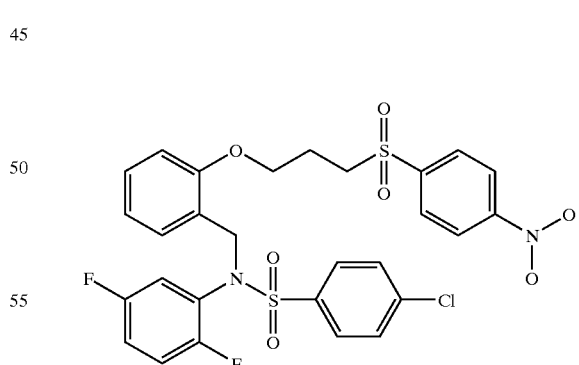

$R_f$=0.56 (2:1 hexanes:ethyl acetate), $^1$H NMR (300 MHz, CDCl$_3$) δ (ppm):8.40 (d, 2H), 8.25 (d, 2H), 7.59 (d, 2H), 7.48 (d, 2H), 7.19–7.14 (t, 1H), 6.89–6.82 (m, 3H), 6.75–6.64 (m, 3H), 4.73 (s, 2H), 4.1 (t, 2H), 3.65 (m, 2H), 2.38–2.33 (m, 2H).

EXAMPLE 354

4-Chloro-N-(2,5-difluorophenyl)-N-(2-{3-[(4-nitrophenyl)sulfinyl]propoxy}benzyl)benzenesulfonamide

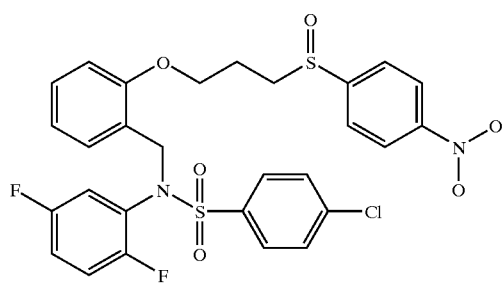

$R_f$=0.53 (1:1 hexanes:ethyl acetate), $^1$H NMR (300 MHz, CDCl$_3$) δ (ppm): 8.36 (d, 2H), 7.93 (d, 2H), 7.64 (d, 2H), 7.50 (d, 2H), 7.17 (m, 1H), 6.91–6.80 (m, 3H), 6.74–6.65 (m, 31H), 4.76 (s, 2H), 4.19–4.02 (m, 2H), 0.356–3.47 (n, 1H), 3.23–3.14 (m, 1H), 2.47–2.41 (m, 1H0, 2.17–2.13 (m, 1H).

EXAMPLE 355

4-Chloro-N-(2-[2-(cyclohexylsulfinyl)ethoxy}benzyl-N-(2,5-difluorophenyl)benzenesulfonamide

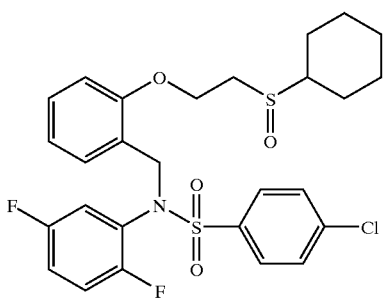

$R_f$=0.35 (1:2 hexanes:ethyl acetate), $^1$H NMR (300 MHz, CDCl$_3$) δ (ppm): 7.65 (d, 2H), 7.47 (d, 2H), 7.22–7.11 (m, 2H), 6.94–6.80 (m, 5H), 4.84 (d, 1H), 4.70 (d, 1H), 4.47–4.27 (m, 2H), 3.19–3.10 (m, 1H), 2.94 (dt, 1H), 2.65 (tt, 1H), 2.14 (d, 1H), 2.04–1.88 (m, 3H), 1.73 (m, 1H), 1.59–1.25 (m, 4H).

EXAMPLE 356

4-Chloro-N-(2-[2-(cyclohexylsulfonyl)ethoxy]benzyl]-N-(2,5-difluorophenyl)benzenesulfonamide

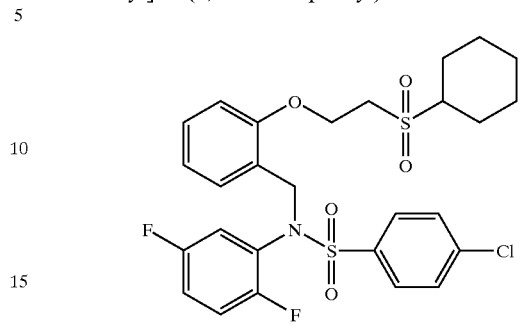

$R_f$=0.30 (3:1 hexanes:ethyl acetate), $^1$H NMR (300 MHz, CDCl$_3$) δ (ppm): 7.65 (d, 2H), 7.47 (d, 2H), 7.26–7.18 (m, 2H), 6.97–6.81 (m, 5H), 4.78 (s, 2H), 4.35 (t, 2H), 3.38 (t, 2H), 2.92 (tr, 1H), 2.20 (d, 2H), 2.05 (m, 2H), 1.74–1.55 (m, 3H), 1.334–1.20 (m, 3H).

EXAMPLE 357

4-Chloro-N-{2-[2-(cyclohexylsulfanyl)ethoxy]benzyl}-N-(2,5-difluorophenyl)benzenesulfonamide

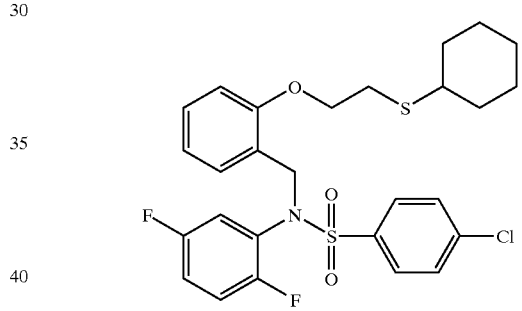

$R_f$=0.30 (15:1 hexanes:ethyl acetate), $^1$H NMR (300 MHz, CDCl$_3$) δ (ppm): 7.67 (d, 2H), 7.56 (d, 2H), 7.34 (d, 1H), 7.19 (t, 1H), 6.95–6.86 (m, 4H), 6.72 (d, 1H), 4.79 (s, 2H), 3.93 (t, 2H), 2.74 (t, 2H), 2.67 (m, 1H), 1.95 (br, 2H), 1.77 (br, 2H), 1.63–1.27 (m, 6H).

EXAMPLE 358

The compounds described in Examples 359–373 were prepared according to the preparative scheme outlined in the previous example.

SCHEME 358

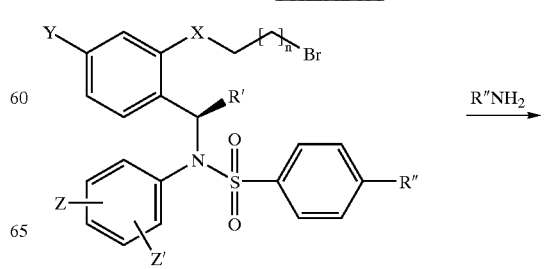

-continued

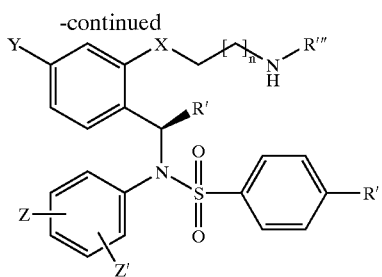

acid chlorides
solid phase base

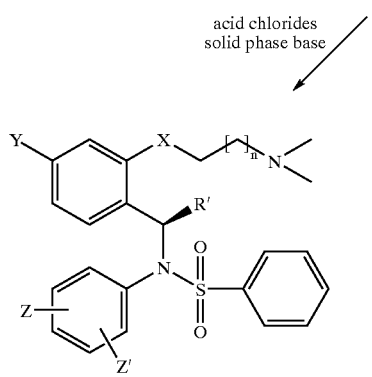

X = O, CH₂  
n = 0, 1, 2, or 3  
Y = H, F  
R' = H, CH₃, CH₂CH₃  
R'' = F, Cl, Br  
R''' = H, CH₃, CH₂CH₃

EXAMPLE 359

N-{3-[2-(1-{[(4-chlorophenyl)sulfonyl]-2,5-difluoroanilino}ethyl)phenoxy]propyl}nicotinamide

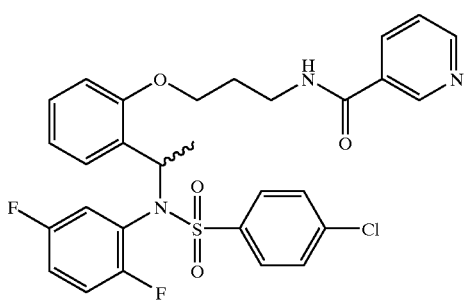

$R_f$=0.43 (19:1; DCM:methanol). $^1$H NMR(CDCl₃) δ (ppm): 9.08 (s, 1H), 8.68 (m, 1H), 8.19–8.15 (m, 1H), 7.63–7.60 (m, 2H), 7.42–7.47 (m, 4H), 6.91–6.66 (m, 6H), 6.20 (q, 1H), 4.22–4.13 (m, 2H), 3.89–3.85 (m, 2H), 2.46–2.43 (m, 1H), 2.28–2.19 (m, 1H), 1.44 (d, 3H). LC-MS calculated for $C_{29}H_{26}ClF_2N_3O_4S$: 586; observed: 586 (M+).

EXAMPLE 360

N-{3-[2-(1-{[(4-chlorophenyl)sulfonyl]-2,5-difluoroanilino}ethyl)phenoxy]propyl}-N-methylnicotinamide

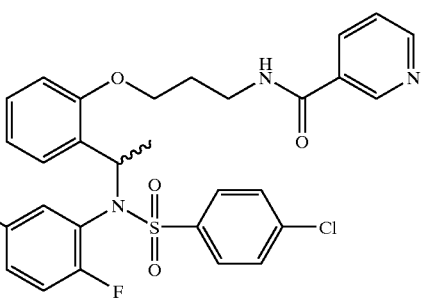

$R_f$=0.60 (9:1 CH₂Cl₂:methanol) $^1$H NMR (300 MHz CDCl₃) δ (ppm): 8.69–8.59 (m, 2H), 7.79–6.11 (m, 13H), 5.80–5.68 (m, 1H), 4.28–3.41 (m, 4H), 3.25–2.97 (d, 3H), 2.50–1.98 (br, 2H), 1.66–1.35 (m, 3H). LC-MS calculated for $C_{30}H_{28}ClF_2N_3O_4S$ [MH+] 600; Observed [MH+] 600.

EXAMPLE 361

N-{3-[2-((1R)-1-{[(4-chlorophenyl)sulfonyl]-2,5-difluoroanilino}ethyl)phenoxy]propyl}-N,2,2-trimethylpropanamide

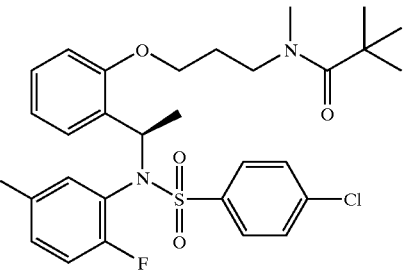

$R_f$=0.28 (3:1; hexanes:ethyl acetate) $^1$H NMR (CDCl₃) δ (ppm): 7.64–7.61 (m, 2H), 7.39–7.36 (m, 2H), 7.21–7.16 (m, 1H), 6.92–6.65 (m, 5.5H), 6.36–6.14 (m, 1.5H), 4.16–3.95 (m, 2H), 3.75–3.57 (m, 2H), 3.18 (m, 3H), 2.23–2.05 (m, 2H), 1.57 (d, 3H), 1.29 (s, 9H). LC-MS—calculated for $C_{29}H_{33}ClF_2N_2O_4S$: 579. Observed: 579 (M+).

EXAMPLE 362

4-Chloro-N-(2,5-difluorophenyl)-N-[(1R)-1-(2-{3-{methyl(methylsulfonyl)amino}propoxy}phenyl)ethyl]benzenesulfonamide

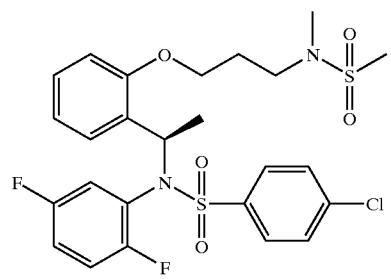

$R_f$=0.25 (2:1 hexanes:ethyl acetate) $^1$H NMR (CDCl$_3$) δ (ppm): 7.65–7.62 (d, 2H), 7.42–7.39 (d, 2H), 7.20–7.17 (m, 1H), 6.91–6.34 (m, 6H), 6.19 (q, 1H), 4.20–4.06 (m, 2H), 3.64–3.55 (m, 2H), 2.96 (s, 3H), 2.84 (s, 3H), 2.25–2.19 (m, 2H), 1.53 (d, 3H). LC-MS calculated for C$_{25}$H$_{27}$ClF$_2$N$_2$O$_5$S$_2$: 573; Observed: 573 (M+).

EXAMPLE 363

N-{3-[2-((1R)-1-{[(4-chlorophenyl)sulfonyl]-2,5-difluoroanilino}ethyl)phenoxy]propyl}-N-methylnicotinamide Hydrochloride

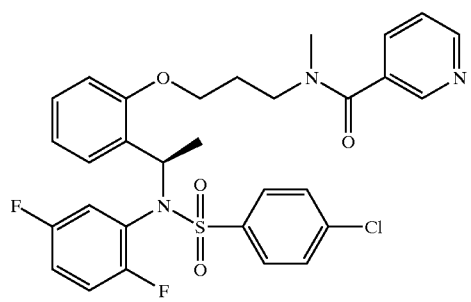

$R_f$=0.56 (19:1; DCM:methanol). $^1$H NMR (CD$_3$OD) δ (ppm): 8.55–8.45 (m, 2H), 7.92–6.08 (overlapping m, 12H), 5.45 (q, 1H), 4.08–3.45 (m, 4H), 3.10 (s, 1.5H), 2.99 (s, 1.5H), 2.19–2.06 (m, 2H), 1.47 (d, 1.5H), 1.34 (d, 1.5H).). LC-MS calculated for C$_{30}$H$_{28}$ClF$_2$N$_3$O$_4$S: 600; Observed: 600 (M+).

EXAMPLE 364

Tert-butyl 6-[{3-[2-({[(4-chlorophenyl)sulfonyl]-2,5-difluoroanllino}methyl)phenoxy]propyl}(methyl)amino-6-oxohexylcarbamate

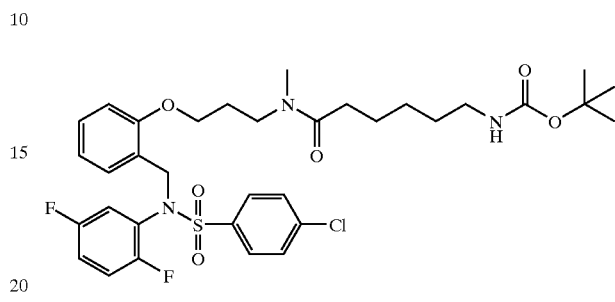

$R_f$=0.33 (1:1;hexanes:ethyl acetate). $^1$H NMR (CDCl$_3$) δ (ppm): 7.67–7.64 (d, 2H), 7.48–7.45 (d, 2H), 7.22–7.08 (m, 2H), 6.91–6.73 (m, 5H), 4.81 (s, 2H), 4.53 (br, 1H), 3.94–3.86 (m, 2H), 3.58–5.53 (m, 2H), 3.12–2.95 (m overlaps d, 5H), 2.30 (t, 2H), 2.04–2.96 (m, 2H), 1.69–1.23 (m, 13H).

EXAMPLE 365

N-{3-[2-({[(4-chlorophenyl)sulfonyl]-2,5-difluoroanilino}methyl)phenoxy]propyl}-N-methyl-5-(2-oxohexahydro-1H-thieno[3,4-d]imidazol-4-yl)pentanamide

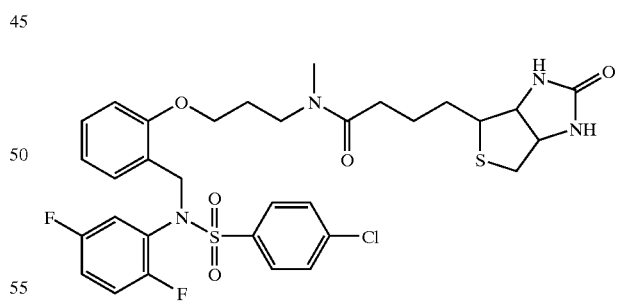

$R_f$=0.57 (10:1; DCM:methanol). $^1$H NMR (CDCl$_3$) δ (ppm): 7.68–7.65 (d, 2H), 7.49–7.46 (m, 2H), 7.22–7.05 (m, 2H), 6.90–6.73 (m, 5H), 5.13 (br, 0.5H), 5.06 (br, 0.5H), 4.82–4.81 (d, 2H), 4.63–4.59 (m, 1H), 4.49–4.47 (m, 1H), 4.31–4.24 (m, 1H), 3.96–3.87 (m, 2H), 3.59–3.56 (m, 2H), 3.17–2.87 (m, 5H), 2.73–2.67 (m, 1H), 2.40–2.32 (m, 2H), 2.08–1.96 (m, 2H), 1.70–1.65 (m, 6H).

EXAMPLE 366

6-Amino-N-{3-[2-({[(4-chlorophenyl)sulfonyl]-2,5-difluoroanilino}methyl)phenoxy]propyl]-N-methylhexanamide Hydrochloride

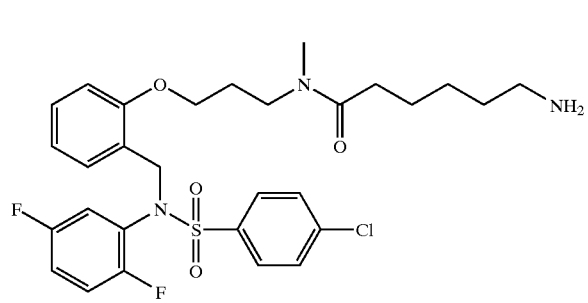

$R_f$=0.56 (6:1;DCM:methanol). $^1$H NMR (CD$_3$OD) δ (ppm): 7.76–7.52 (m, 2H), 7.65–7.61 (m, 2H), 7.22–7.02 (m, 4H), 6.93–6.75 (m, 3H), 4.88 (d overlaps HOD, 2H), 4.01 (t, 1H), 3.93 (t, 1H), 3.71 (t, 1H), 3.63 (t, 1H), 3.12 (s, 1.5H), 2.99 (s, 1.5H), 2.93 (t, 1H), 2.86 (t, 1H), 2.49–2.42 (m, 2H), 2.12–2.00 (m, 2H), 1.71–1.60 (m, 4H), 1.35–1.32 (m, 2H).

EXAMPLE 367

N-{3-[2-((1R)-1-{[(4-chlorophenyl)sulfonyl]-2,5-difluoroanilino}ethyl)phenoxy]propyl}-N-methylacetamide

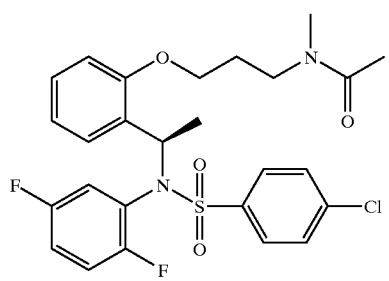

$R_f$=0.38 (1:1; hexanes:ethyl acetate). $^1$H NMR (CDCl$_3$) δ (ppm): 7.65–7.62 (m, 2H), 7.40–7.37 (m, 2H), 7.22–7.16 (m, 1H), 6.91–6.64 (m, 5.5H), 6.35–6.16 (m, 15H), 4.12–3.95 (m, 2H), 3.77–3.57 (m, 2H), 3.10 (s, 1.5H), 3.0 o (s, 1.5H), 2.17–2.10 (m overlaps two s, 5H), 1.58–1.53 (m, 3H). LC-MS calculated for C$_{26}$H$_{21}$ClF$_2$N$_2$O$_4$S: 537. Observed 537 (M+).

EXAMPLE 368

N-{4-[2-((1R)-1-{[(4-chlorophenyl)sulfonyl]-2,5-difluoroanilino}ethyl)phenoxy]butyl}-N-methylpropanamide

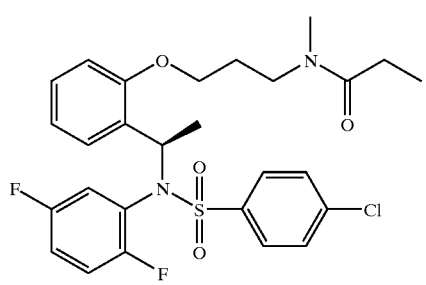

$R_f$=0.4 (1:1 hexanes:ethyl acetate). $^1$H NMR (CDCl$_3$) δ (ppm): 7.63–7.62 (d, 2H), 7.39–7.35 (m, 3H), 7.19–7.15 (m, 2H) 6.91–6.64 (m, 5H), 6.06 (m, 1H), 4.13–4.00 (m, 2H), 3.49–3.39 (m, 2H), 3.01–2.97 (d, 3H), 2.43–2.33 (m, 2H), 1.85–1.83 (m, 4H), 1.57 (d, 3H), 1.17–1.11 (dt, 3H). LC-MS calculated for C$_{28}$H$_{31}$ClF$_2$N$_2$O$_4$S: 565; Observed: 565 (M+).

EXAMPLE 369

N-{3-[2-({[(4-chlorophenyl)sulfonyl]-2,5-difluoroanilino}methyl)phenoxy]propyl}-N-methylcyclohexanecarboxamide

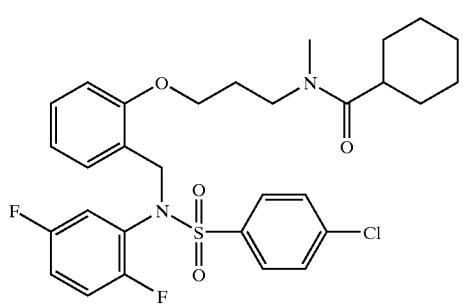

$R_f$=0.26 (2:1 hexanes:ethyl acetate), $^1$H NMR (300 MHz, CDCl$_3$) δ (ppm): 7.65 (m, 2H), 7.44 (d, 2H), 7.19–7.11 (m, 2H), 6.90–6.70 (m, 5H), 4.80 (d, 2H), 3.90–3.82 (m, 2), 3.58–3.50 (m, 2H), 2.91 (d, 3H), 2.49–2.42 (m, 1H), 2.02–1.90 (m, 2H), 1.77–0.83 (m, 11H). MS calculated for C$_{30}$H$_{33}$ClFN$_2$O$_4$S, [MNa$^+$] 613; Observed: 613.

EXAMPLE 370

N-{3-[2-({[(4-chlorophenyl)sulfonyl]-2,5-difluoroanilino}methyl)phenoxy]propyl}-N-methylnicotinamide

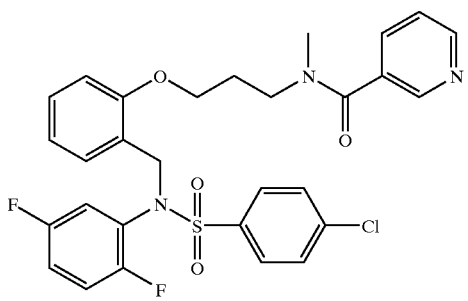

$R_f$=0.66 (9:1 CH$_2$Cl$_2$:methanol) $^1$H NMR (300 MHz CDCl$_3$) δ (ppm): 8.65–8.55 (m, 2H), 7.74–7.59 (m, 3H), 7.46–7.43 (d, 2H), 7.35–7.31 (m, 1H), 7.19–7.14 (m, 1H), 7.06–6.98 (m, 1H), 6.87–6.61 (m, 5H), 4.80–4.76 (br, 1H), 4.45 (br, 1H), 4.01–3.98 (t, 1H), 3.81–3.76 (m, 2H), 3.61–3.57 (m, 1H), 3.13–3.04 (d, 3H), 2.18–2.01 (m, 2H). LC-MS calculated for C$_{29}$H$_{26}$ClF$_2$N$_3$O$_4$S [MH$^+$]586; Observed: 586.

EXAMPLE 371

4-Chloro-N-(2,5-difluorophenyl)-N-(2-{2-[1-(3-pyridinylcarbonyl)-2-piperidinyl]ethoxy}benzyl)benzenesulfonamide

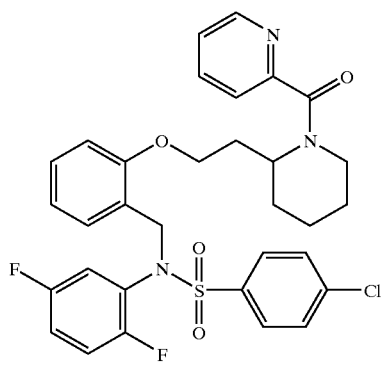

$R_f$=0.50 (1:3 hexanes:ethyl acetate), $^1$H NMR (300 MHz, CDCl$_3$) δ (ppm): 8.57 (m, 2H), 7.62–6.89 (m, 13), 5.30–2.88 (m, 15H), 2.30–1.48 (m, 8H). MS calculated for C$_{32}$H$_{30}$ClF$_2$N$_3$O$_4$S, [MH$^+$] 626; Observed: 626.

EXAMPLE 372

4-[2-(1-{[(4-Chlorophenyl)sulfonyl]-2,5-difluoroanilino}ethyl)phenoxy]-N-(3-pyridinylmethyl)butanamide Hydrochloride

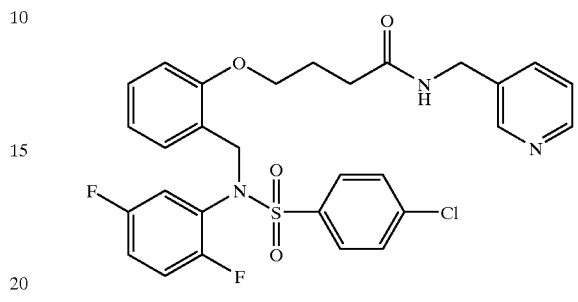

$R_f$=0.53 (5% methanol in CH$_2$Cl$_2$) $^1$H NMR (300 MHz CD$_3$OD) δ (ppm): 8.78 (s, 1H), 8.69–8.68 (d, 1H), 8.54–8.51 (d, 1H), 7.96–7.92 (m, 1H), 7.66–7.63 (d, 2H), 7.52–7.49 (d, 2H), 7.20–6.62 (m, 6H), 6.15–6.09 (q, 1H), 4.58 (br, 2H), 4.09–3.99 (m, 2H), 2.75–2.61 (m, 2H), 2.24–2.17 (m, 2H), 1.57–1.54 (d, 3H). LC-MS calculated for C$_{30}$H$_{28}$ClF$_3$N$_3$O$_4$S [MH$^+$] 600; Observed: 600.

EXAMPLE 373

4-benzoyl-N-((1S)-1-{[{3-[2-({[(4-chlorophenyl)sulfonyl]-2, difluoroanilino}methyl)phenoxy]propyl}(methyl)amino]carbonyl}-5-{[5-(2-oxohexahydro-1H-thieno[3,4-d]imidazol-4-yl)pentanoyl]amino}pentyl)benzamide

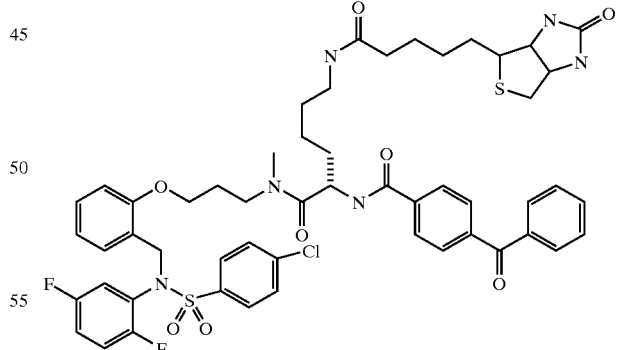

$R_f$=0.37 (7% Methanol in DCM), $^1$H NMR (300 MHz, CDCl$_3$) δ (ppm): 8.15–7.78 (m, 6H), 7.70–7.59 (m, 3H), 7.52–7.45 (m, 4H), 7.15 (t, 1H), 7.03 (d, 1H), 6.89–6.72 (m, 5H), 6.443–6.19 (m, 2H), 5.37 (m, 1H), 5.33 (s, 2H), 5.12 (m, 1H), 4.86–4.82 (m, 1H), 4.44 (m, 1H), 4.26 (m, 1H), 4.01–3.93 (m, 2H), 3.82–3.67 (m, 2H), 3.22–2.65 (m, 9H), 2.17–1.26 (m, 24H).

EXAMPLE 374

Numerous compounds according to the invention can be prepared employing the synthetic scheme set forth in SCHEME 374.

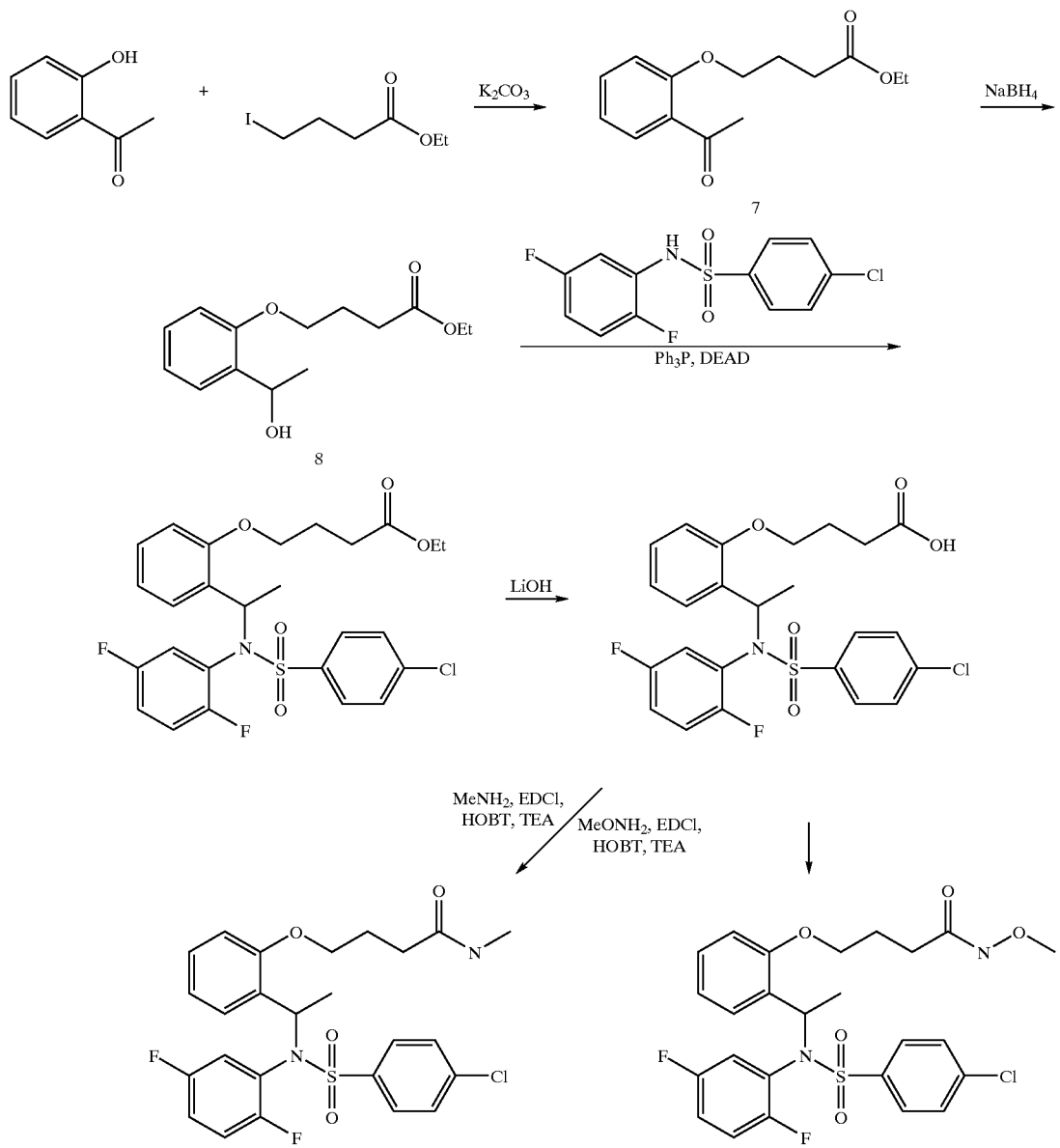

EXAMPLE 375

A suspension of 2-hydroxyphenone (10 mL, 83 mmol), 4-bromobutyric acid (16.6 mL, 116 mmol) and $K_2CO_3$ (14.4 g, 104 mmol) in acetone was refluxed at 56° C. for 64 h. The reaction mixture was acidified with 1 N HCl solution and the acidic solution was extracted with ethyl acetate (3×50 mL). The combined organic phase was washed with $H_2O$ and sat. NaCl aqueous solution, dried over $MgSO_4$. The solution was filtered, concentrated the filtrate to obtain the crude product that purified by $SiO_2$ chromatography to isolate the desired product 7 (15.5 g, 75%) as white solid: $R_f$ 0.46 (10:5, hexane-ethyl acetate); $^1H$ NMR ($CDCl_3$, 300 MHz) δ 7.72 (dd, 1H, J=7.6 Hz, J=1.4 Hz), 7.43 (td, 1H, J=7.6 Hz, J=1.2 Hz), 6.96 (m, 2H), 4.13 (m, 4H), 2.62 (s, 3H), 2.54 (t, 2H, J=6.6 Hz), 2.18 (m, 2H), 2.26 (t, 3H, J=7.2 Hz).

Compound 7 in the reaction scheme outlined above (3.0 g, 12.0 mmol) was treated with $NaBH_4$ (227 mg, 6.0 mmol) in methanol (24 mL) solution in the presence of $CeCl_3 \cdot 7H_2O$ (89 mg, 0.24 mmol) at 25° C. for 10 min. The reaction was quenched with 5% HCl solution. The aqueous phase was extracted with ethyl acetate. The combined organic phase was washed with $H_2O$ and sat NaCl aqueous solution, then dried over $MgSO_4$. Concentration and chromatography afforded compound 8 (3.0 g, 100%) as colorless gum: $R_f$ 0.29 (10:5, hexane-ethyl acetate); $^1H$ NMR ($CDCl_3$, 300

M}z) δ 7.48 (d, 1H, J=7.5 Hz), 7.26 (t, 1H, J=7.6 Hz), 7.05 (t, 1H, J=7.6 Hz), 6.80 (d, 1H, J=8.1 Hz), 5.26 (br s, 1H), 4.68 (s, 2H), 4.28 (q, 2H, J=7.2 Hz), 4.06 (br s, 1H), 1.59 (d, 3H, J=6.6 Hz), 1.33 (t, 3H, J=7.2 Hz).

EXAMPLE 376

Ethyl-4-[2-(1-{[(4-(4-chlorophenyl)sulfonyl]-2,5-difluoroanilino}ethyl)phenoxy]butanoate DEAD (567 μL, 3.6 mmol) was added dropwise to a solution of alcohol 8 (666 mg, 3.0 mmol), Triphenylphosphine (944 mg, 3.6 mmol) and sulfonamide (910 mg, 3.0 mmol) in toluene (10 mL) at 25° C. under Ar. The mixture was stirred for 40 h, then diluted with hexane-ethyl acetate solution (10:3). The generated precipitates were filtered and the filtrate was concentrated in vacuo. Chromatography afforded the compound (1.16 g, 72%) as colorless gum: $R_f$ 0.29 (10:2, hexane-thyl acetate); $^1$H NMR (CDCl$_3$, 300 MHz) δ 7.62 (d, 2H, J=8.7 Hz), 7.36 (d, 2H, J=8.7 Hz), 7.18 (m, 1H), 6.38–6.95 (m, 6H), 6.01 (m, 1H), 4.17 (q, 2H, J=7.2 Hz), 4.04 (m, 1H), 3.98 (m, 1H), 2.61 (t, 2H, J=7.0 Hz), 2.17 (m, 2H), 1.58 (d, 3H, J=6.9 Hz), 1.27 (t, 3H, J=7.0 Hz); LCMS 3.86 min, m/z 556 (M+H$^+$+H$_2$O, $C_{26}H_{26}ClF_2NO_5S$ requires 538.01).

EXAMPLE 377

4-[2-(1-{[(4-Chlorophenyl)sulfonyl]-2,5-difluoroanilino}ethyl)phenoxy]butanoic Acid A solution of ethyl-4-[2-(1-{[(4-chlorophenyl)sulfonyl]-2,5-difluoroanilino}ethyl)phenoxy]butanoate (1.16 g, 2.2 mmol) in THF (5.2 mL), methanol (1.7 mL) and H$_2$O (1.7 mL) was treated with LiOH.H$_2$O (91 mg, 2.2 mmol) at 25° C. for 3 h. The reaction was then quenched with 1 N HCl solution. The aqueous phase was extracted with ethyl acetate. The combined organic phase was washed with H$_2$O and sat. NaCl aqueous solution, then dried over MgSO$_4$. Concentration and chromatography afforded the desired product (457 mg, 41%) as white crystal: m.p. 141.0–142.0° C.; $R_f$ 0.14 (10:10, hexane-ethyl acetate); $^1$H NMR (CDCl$_3$, 300 MHz) δ 11.08 (br s, 1H), 7.62 (d, 2H, J=8.4 Hz), 7.35 (d, 2H, J=8.7 Hz), 7.16 (t, 1H, J=7.5 Hz), 6.38–6.93 (m, 6H), 6.03 (br s, 1H), 4.06 (m, 2H), 2.70 (t, 2H, J=7.0 Hz), 2.17 (m, 2H), 1.57 (d, 3H, J=6.9 Hz); LCMS 3.05 min, m/z 527.2 ($C_{24}H_{22}ClF_2NO_5S$ requires 509.95).

EXAMPLE 378

4-[2-(1-{[(4-Chlorophenyl)sulfonyl]-2,5-difluoroanilino}ethyl)phenoxy]-N-methylbutanamide A mixture of acid 4-[2-(1-([(4-chlorophenyl)sulfonyl]-2,5-difluoroanilino}ethyl)phenoxy]butanoic acid (107 mg, 0.21 mmol), HOBT (31 mg, 0.23 mmol), EDCI (44 mg, 0.23 mmol), Et$_3$N (88 μL, 0.63 mmol) and CH$_3$NH$_2$.HCl (16 mg, 0.23 mmol) in CH$_2$Cl$_2$ (1.0 mL) was stirred at 25° C. for 13 h. The mixture was diluted with ethyl acetate. The organic solution was washed with H$_2$O and sat. NaCl solution then dried over MgSO$_4$. Concentration and chromatography afforded the amide (107 mg, 97%) as colorless gum: $R_f$ 0.32 (10:20, hexane-ethyl acetate); $^1$H NMR (CDCl$_3$, 300 MHz) δ 7.64 (d, 2H, J=6.9 Hz), 7.42 (d, 2H, J=7.8 Hz), 7.18 (t, 1H, J=8.7 Hz), 6.36–6.91 (m, 7H), 6.26 (q, 1H, 1=6.9 Hz), 4.13 (m, 1H), 4.05 (m, 1H), 2.78 (m, 4H), 2.57 (m, 1H), 2.23 (m, 2H), 1.55 (br s, 3H); LCMS m/z 524 (M+H+, $C_{25}H_{25}ClF_2N_2O_4S$ requires 522.99).

EXAMPLE 379

4-[2-(1-{[(4-Chlorophenyl)sulfonyl]-2,5-difluoroanilino}ethyl)phenoxy]-N-methoxybutanamide A mixture of 4-[2-(1-{[(4-chlorophenyl)sulfonyl]-2,5-difluoroanilino}ethyl)phenoxy]butanoic acid (107 mg, 0.21 mmol), HOBT (31 mg, 0.23 mmol), EDCI (44 mg, 0.23 mmol), Et$_3$N (88 μL, 0.63 mmol) and CH$_3$ONH$_2$.HCl (19 mg, 0.23 mmol) in CH$_2$Cl$_2$ (1.0 mL) was stirred at 25° C. for 13 h. The reaction mixture was diluted with ethyl acetate. The organic solution was washed with H$_2$O and sat. NaCl solution then dried over MgSO$_4$. Concentration and chromatography afforded the compound (94 mg, 83%) as colorless gum: $R_f$ 0.20 (10:10, hexane-ethyl acetate); $^1$H NMR (CDCl$_3$, 300 MHz) δ 9.50 (br s, 1H), 7.64 (br s, 2H), 7.43 (br s, 2H), 7.16 (m, 1H), 6.34–6.87 (m, 6H), 627 (q, 1H, J=6.9 Hz), 4.14 (m, 1H), 4.06 (m, 1H), 3.74 (s, 3H), 2.72 (m, 1H), 2.51 (m, 1H), 2.26 (m, 2H), 1.54 (br s, 3H); LCMS 2.95, m/z 562 (M+Na$^+$, $C_{25}H_{25}ClF_2N_2O_5S$ requires 538.99).

EXAMPLE 380

Numerous compounds according to the invention can be prepared employing the general synthetic scheme set forth in SCHEME 380.

SCHEME 380

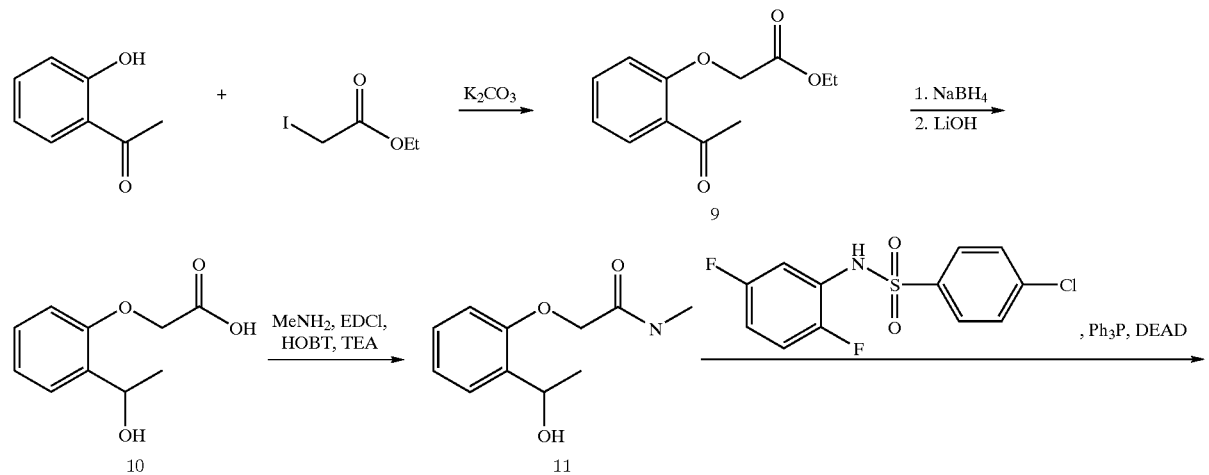

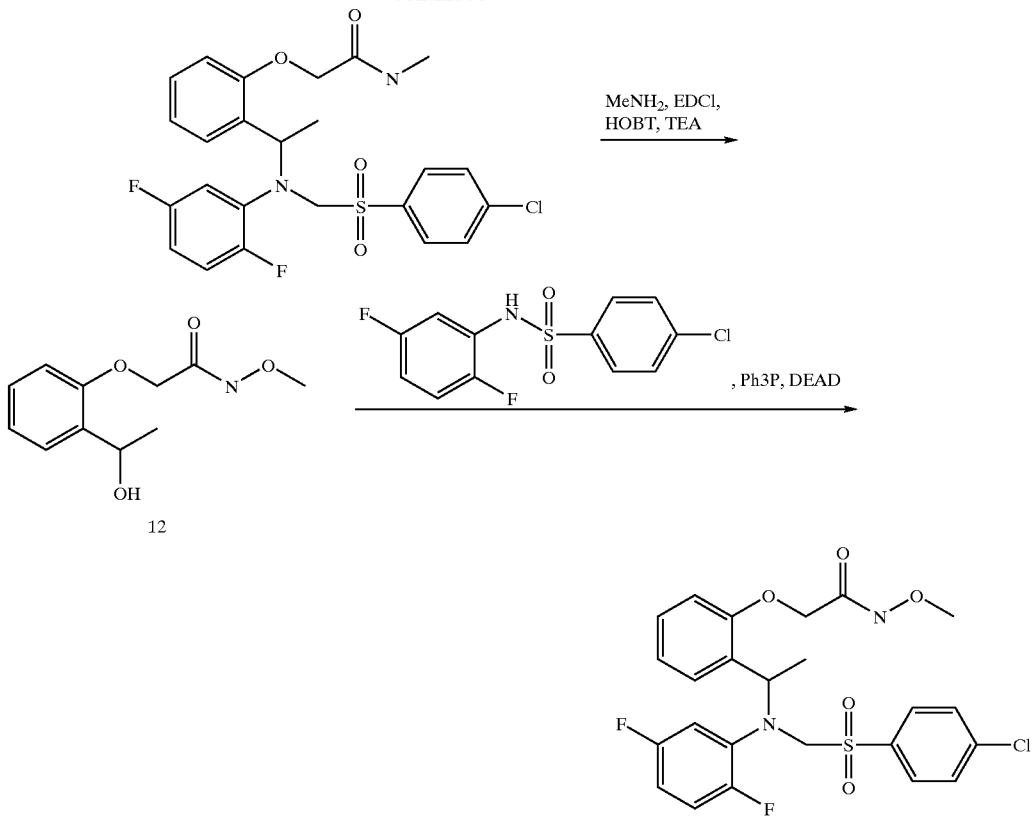

A suspension of 2-hydroxyphenone (10 mL, 83 mmol), ethyl iodoacetate (25.0 g, 117 mmol) and $K_2CO_3$ (12.6 g, 91 mmol) in acetone was refluxed at 60° C. for 28 h. The reaction mixture was then diluted with ether. The ether solution was washed with 1 N NaOH solution, $H_2O$ and sat. NaCl aqueous solution, then dried over $MgSO_4$. Concentration and chromatography afforded compound 9 (8.76 g, 47%) as white solid: $R_f$ 0.19 (10:2, hexane-ethyl acetate); $^1$H NMR (CDCl$_3$, 300 MHz) δ 7.76 (m, 1H), 7.42 (m, 1H), 7.04 (m, 1H), 6.82 (m, 1H), 4.70 (m, 2H), 4.28 (q, 2H, J=4.2 Hz), 2.72 (s, 3H), 1.31 (t, 3H, J=7.2 Hz).

Compound 9 in the reaction scheme above (4.6 g, 21 mmol) was treated with excess of NaBH$_4$ in methanol (40 mL) solution in the presence of CeCl$_3$.7H$_2$O (155 mg, 0.40 mmol) at 25° C. for 10 min. The reaction was then quenched with 5% HCl solution. The aqueous phase was extracted with ethyl acetate. The combined organic phase was washed with $H_2O$ and sat. NaCl aqueous solution, then dried over $MgSO_4$.

The residue was dissolved in a solution of THF-methanol-$H_2O$ (3:1:1, 20 mL) and treated with LiOH.H$_2$O (1.0 g, 25 mmol) at 25° C. for 3 h. The reaction mixture was then acidified and extracted with ethyl acetate. The combined organic phase was dried over $MgSO_4$. Concentration and chromatography afforded compound 10 (3.3 g, 82%) as white solid: $R_f$ 0.34 (10:1, CH$_2$Cl$_2$-methanol); $^1$H NMR (CD$_3$OD, 300 MHz) δ 7.52 (dd, 1H, J=7.6 Hz, J=1.4 Hz), 7.28 (td, 1H, J=7.8 Hz, J=1.5 Hz), 7.06 (t, 1H, J=7.5 Hz), 6.92 (d, 1H, J=8.1 Hz), 5.33 (q, 1H, J=6.6 Hz), 5.03 (br s, 2H), 4.79 (s, 2H), 1.51 (d, 3H, J=7.2 Hz).

A mixture of hydroxy acid 10 (980 mg, 5.0 mmol), HOBT (743 mg, 5.5 mmol), EDCI (1.05 g, 5.5 mmol), NaHCO$_3$ (1.26 g, 15.0 mmol) and CH$_3$NH$_2$.HCl (371 mg, 5.5 mmol) in DMF (10 mL) was stirred at 25° C. for 23 h. The reaction mixture was diluted with ethyl acetate. The organic solution was washed with $H_2O$ and sat NaCl solution then dried over $MgSO_4$. Concentration afforded alcohol 11 (664 mg, 64%/o) as colorless syrup: $R_f$ 0.21 (10:05, CH$_2$Cl$_2$-methanol); $^1$H NMR (CD$_3$OD, 300 MHz) δ 7.50 (dd, 1H, J=7.6 Hz, J=1.6 Hz), 7.27 (m, 1H), 7.05 (t, 1H, I=7.5 Hz), 6.90 (d, 1H, J=8.1 Hz), 5.34 (q, 1H, J=7.2 Hz), 5.01 (br s, 2H), 4.57 (d, 2H, J=3.0 Hz), 2.85 (s, 3H), 1.54 (d, 3H, J=7.0 Hz).

EXAMPLE 381

[2-(1-{[(4-Chlorophenyl)sulfonyl]-2,5-difluoroanilino}ethyl)phenoxy]-N-methylacetamide DEAD (352 μL, 2.2 mmol) was added dropwise to a solution of alcohol 11 (312 mg, 1.5 mmol), Triphenylphosphine (586 mg, 2.2 mmol) and sulfonamide 3 (452 mg, 1.5 mmol) in THF (6 mL) at 25° C. under Ar. The mixture was stirred at 25° C. for 22 h, then concentrated in vacuo. Small amount of crude product was purified by HPLC to afford the compound (34 mg) as white foam: $R_f$ 0.35 (10:10, hexane-ethyl acetate); $^1$H NMR (CDCl, 300 MHz) δ 7.95 (m, 1H), 7.68 (br s, 2H), 7.44 (br s, 2H), 7.26 (br s, 1H), 6.24–6.95 (m, 6H), 6.32 (q, 1H, J=7.2 Hz), 4.69 (m, 1H), 4.52 (m, 1H), 2.95 (s, 3H), 1.50 (d, 3H, J=7.2 Hz); LCMS 3.46 min, m/z 517.1 (M+Na$^+$, $C_{23}H_{21}ClF_2N_2O_4S$ requires 494.94).

A mixture of hydroxy acid 10 (980 mg, 5.0 mmol), HOBT (743 mg, 5.5 mmol), EDCI (1.05 g, 5.5 mmol), NaHCO$_3$ (1.26 g, 15 mmol) and CH$_3$ONH$_2$HCl (459 mg, 5.5 mmol) in DMF (20 mL) was stirred at 25° C. for 23 h. The reaction mixture was diluted with ethyl acetate. The organic solution was washed with $H_2O$ and sat. NaCl solution then dried over $MgSO_4$. Concentration afforded the desired product (340 mg, 30%) as colorless syrup: $R_f$ 0.19 (10:0.5, $CH_2Cl_2$-methanol); $^1H$ NMR ($CDCl_3$, 300 MHz) δ 7.44 (d, 1H, J=7.8 Hz), 7.24 (t, 1H, J=7.2 Hz), 7.00 (t, 1H, J=7.4 Hz), 6.88 (d, 1H, J=8.1 Hz), 5.23 (m, 1H), 4.90 (s, 2H), 4.57 (d, 2H, J=2.7 Hz), 3.70 (s, 3H), 1.48 (d, 3H, J=6.6 Hz).

EXAMPLE 382

[2-(1-{[(4-Chlorophenyl)sulfonyl]-2,5-difluoroanilino}ethyl)phenoxy]-N-methoxyacetamide DEAD (357 µL, 2.3 mmol) was added dropwise to a solution of alcohol 12 (340 mg, 1.5 mmol), Triphenylphosphine (595 mg, 2.3 mmol) and sulfonamide 3 (458 mg, 1.5 mmol) in THF (6 mL) at 25° C. under Ar. The mixture was stirred at 25° C. for 22 h, then concentrated in vacuo. Crude product was purified by HPLC to afford the desired product (144 mg) as white foam: $R_f$ 0.38 (10:10, hexane-ethyl acetate); $^1H$ NMR ($CDCl_3$, 300 MHz) δ 10.81 (m, 1H), 7.72 (m, 2H), 7.47 (m, 2H), 7.27 (m, 1H), 6.24–6.97 (m, 7H), 4.80 (m, 1H), 4.60 (m, 1H), 3.88 (s, 3H), 1.48 (d, 3H, J=6.9 Hz); LCMS 3.19 min, m/z 533 (M+Na$^+$, $C_{23}H_{21}ClF_2N_2O_5S$ requires 510.94).

EXAMPLE 383

Numerous compounds according to the present invention can be prepared employing the general scheme set forth in SCHEME 383.

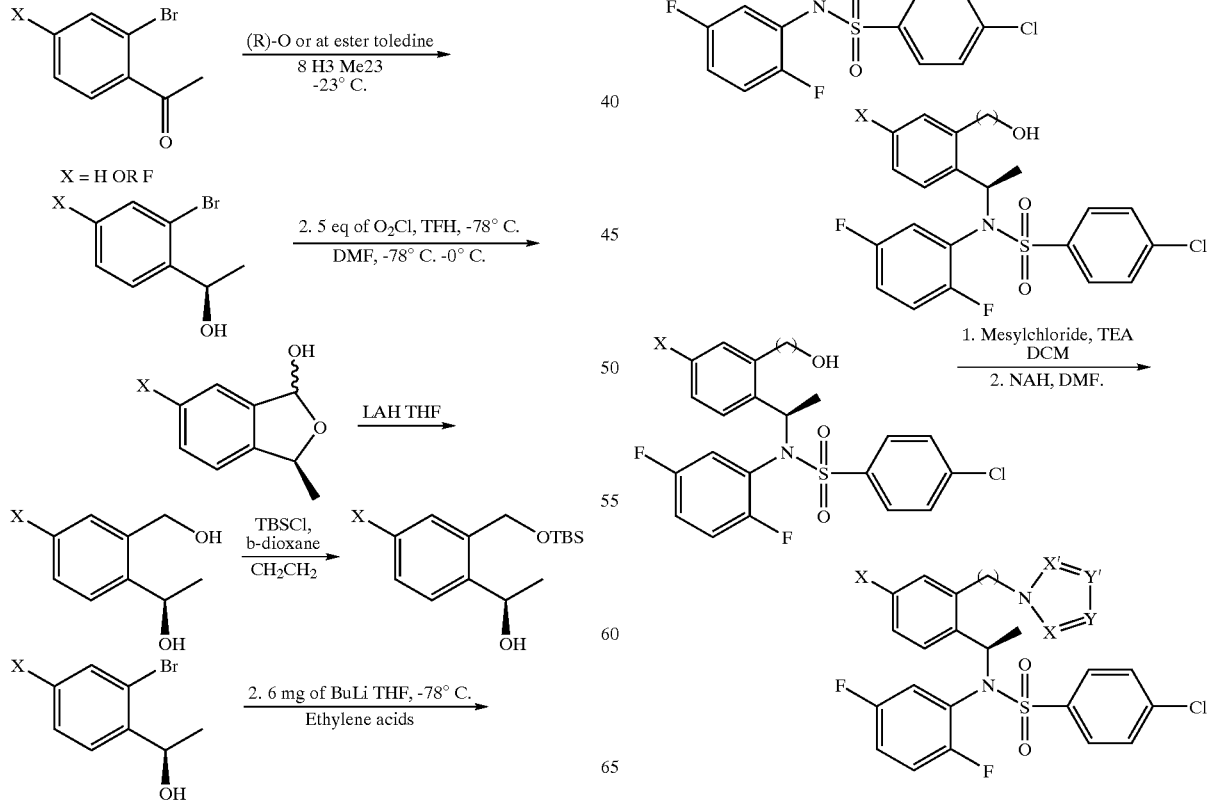

EXAMPLE 384

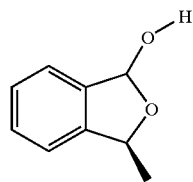

$R_f$=0.25 (3:1 hexanes:ethyl acetate), $^1$H NMR (300 MHz, CDCl$_3$) δ: 7.46–7.21 (m, 4H), 6.51–6.40 (dd, 1H), 5.52 (dq, 1H), 2.93–2.89 (m, 1H), 1.60–1.33 (dd, 3H).

EXAMPLE 385

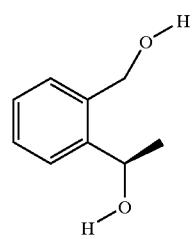

$R_f$=0.23 (2:1 hexanes:ethyl acetate), $^1$H NMR (300 MHz, CDCl$_3$) δ: 7.66–7.16 (m, 4H), 5.16 (q, 1H), 4.87–4.60 (dd, 2H), 3.13 (b, 2H), 1.59 (d, 3H).

EXAMPLE 386

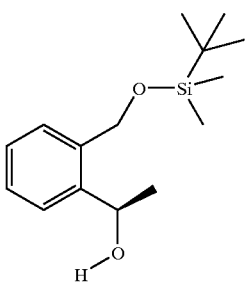

$R_f$=0.25 (15:1 hexanes:ethyl acetate), $^1$H NMR (300 MHz, CDCl$_3$) δ: 7.43–7.14 (m, 4H), 5.06 (m, 1H), 4.86–4.56 (dd, 2H), 3.07 (s, 3.07), 1.48 (d, 3H), 0.85 (s, 9H), 0.00 (m, 6H).

EXAMPLE 387

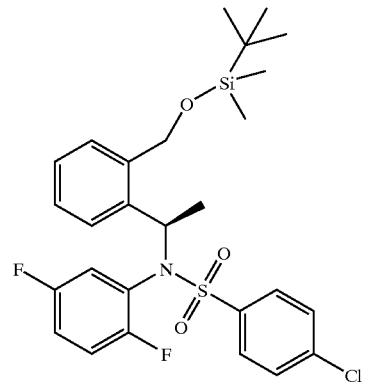

$R_f$=0.30 (20:1 hexanes:ethyl acetate), $^1$H NMR (300 MHz, CDCl$_3$) δ: 7.64–6.22 (m, 11H), 5.87 (q, 1H), 5.10 (m, 1H), 4.84 (m, 1H), 1.50 (m, 3K), 0.97 (s, 91), 0.10 (d, 6H).

EXAMPLE 388

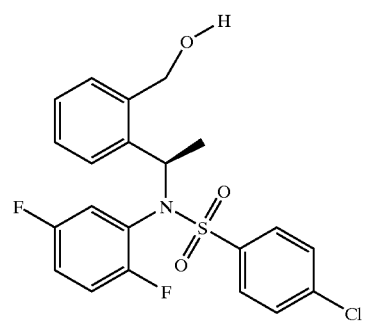

$R_f$=0.25 (3:1 hexanes:ethyl acetate), $^1$H NMR (300 MHz, CDCl$_3$) δ: 7.63–7.72 (m, 1H), 6.02 (b, 1H), 5.01–4.85 (m, 2H), 2.53–2.16 (bb, 1H), 1.49–1.38 (m, 3H).

EXAMPLE 389

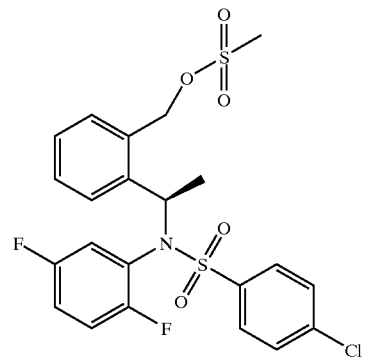

$R_f$=0.25 (3:1 hexanes:ethyl acetate), $^1$H NMR (300 MHz, CDCl$_3$) δ: 7.69–6.75 (m, 1H), 5.89 (m, 2H), 5.42–5.30 (m, 1H), 3.09 (s, 3H), 1.51–1.39 (m, 3H).

EXAMPLE 390

4-Chloro-N-(2,5-difluorophenyl)-N-[2-(1H-tetraazol-1-ylmethyl)benzyl]benzenesulfonamide

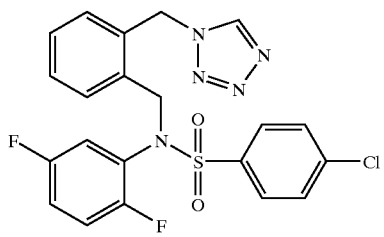

$R_f$=0.48 (1:1; ethyl acetate:hexanes). $^1$H NMR (CDCl$_3$) δ μm): 8.96 (s, 1H), 7.76–7.74 (d, 2H), 7.60–7.58 (d, 2H), 7.35–7.09 (m, 3H0, 6.99–6.90 (m, 3H), 6.75–6.69 (m, 1H), 5.93 (s, 2H), 4.82 (s, 2H). LC-MS calculated for C$_{21}$H$_{16}$ClF$_2$N$_5$O$_2$S 476; Observed: 476.

EXAMPLE 391

4-Chloro-N-(2,5-difluorophenyl)-N-[2-(2H-tetraazol-2-ylmethyl)benzyl]benzenesulfonamide

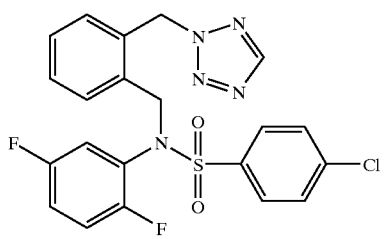

$R_f$=0.50 (2:1; hexanes:ethyl acetate) δ (ppm): 8.515 (s, 1H), 7.76–7.72 (m, 2H), 7.54–7.51 (m, 2H), 7.23–6.69 (m, 7H), 6.08 (s, 2H0, 4.93 (s, 2H). LC-MS calculated for C$_{21}$H16ClF2N5O2S: 476; Observed: 476.

EXAMPLE 392

4-Chloro-N-(2,5-difluorophenyl)-N-[2-(1H-1,2,4-triazol-1-ylmethyl)benzyl]benzenesulfonamide

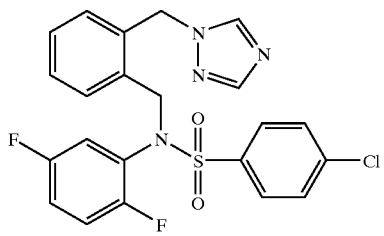

Mp=147–148 (ethyl acetate/hexanes). $R_f$=0.28 (19:1; DCM:methanol). $^1$H NMR δ (ppm): 8.26 (s, 1H), 8.08 (s, 1H), 7.71–7.68 (m, 2H), 7.54–7.51 (m, 2H), 7.25–6.71 (m, 7H), 5.60 9s, 2H0, 4.80 (s, 2H). LC-MS calculated for C$_{22}$H$_{17}$ClF$_2$N$_4$S: 475. Observed: 475.

EXAMPLE 393

4-Chloro-N-(2,5-difluorophenyl)-N-[2-(1H-imidazol-1-ylmethyl)benzyl]benzenesulfonamide

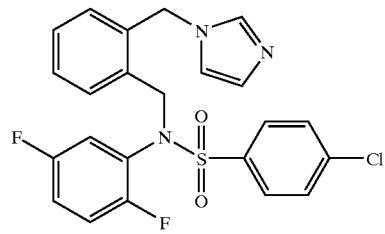

Mp=166–167 (DCM/hexanes). $R_f$=0.31 (191; DCM:methanol). $^1$H NMR δ (ppm): 7.65–7.50 (m, 5H), 7.33–7.07 (m, 3H), 6.99–6.87 (m, 4H), δ 72–6.71 (m, 1H), 5.40 (s, 2H), 4.69 (s, 21). LC-MS calculated for C$_{23}$H$_{17}$ClF$_2$N$_3$O$_2$S: 474. Observed 474.

EXAMPLE 394

4-Chloro-N-(2,5-difluorophenyl)-N-{(1R)-1-[2-(1H-imidazol-1-ylmethyl)phenyl ethyl}benzenesulfonamide Hydrochloride

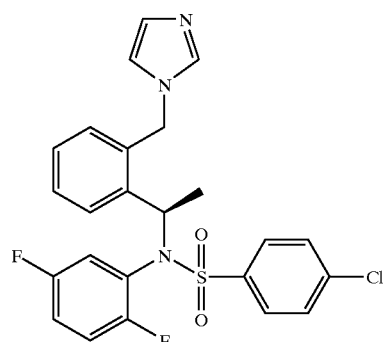

$R_f$=0.50 (10:1 DCM:methanol). $^1$H NMR (CD$_3$OD) δ (ppm): 7.77–7.75 (m, 2H), 7.63–7.52 (m, 3H), 7.30–6.80 (8.53H), 6.55 (m, 0.5H), 5.88–5.81 (m, 2H), 5.49–5.34 (m, 1H), 1.46–1.26 (m, 3H). LC-MS calculated for C$_{23}$H$_{20}$ClF$_2$NO$_2$S: 487. Observed 488 (MH$^+$).

EXAMPLE 395

4-Chloro-N-(2,5-difluorophenyl)-N-{(1R)-1-[2-(1H-1,2,4-triazol-1-ylmethyl)phenyl]ethyl}benzenesulfonamide

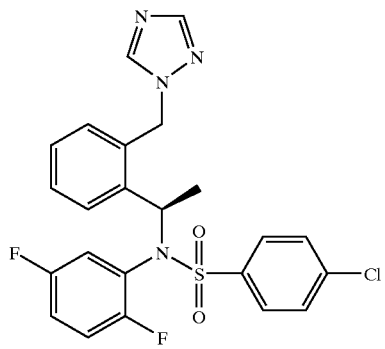

$R_f$=0.25 (97:3; DCM:methanol). $^1$H NMR (CD$_3$OD) δ (ppm): 8.26 (s, 1H), 8.00 (s, 1H), 7.70–6.41 (m, 13H), 6.09–5.91 (m, 2H), 5.44 (d, 1H), 1.42–1.25 (dd 3H). LC-MS calculated for C23H19ClF2N4O2S: 488. Observed 489 (MH+).

EXAMPLE 396

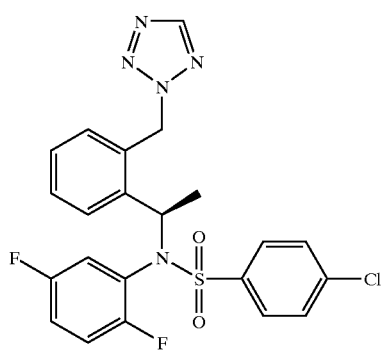

$R_f$=0.34 (6:1; hexanes:ethyl acetate). $^1$H NMR (CDCl$_3$) δ (ppm): 8.53 (s, 1H), 7.74–6.59 (m, 13H), 6.29–6.22 (m, 1H), 5.84 (d, 1H), 1.42–1.25 (dd, 3H). LC-MS calculated for $C_{22}H_{18}ClF_2N_5O_2S$ 489. Observed 490 (MH+).

EXAMPLE 397

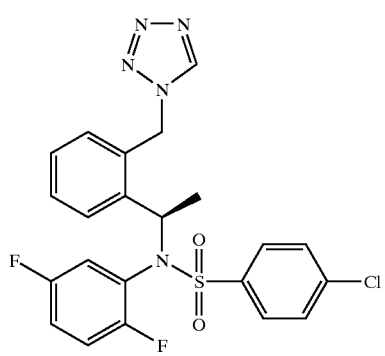

$R_f$=0.25 (2:1;hexanes:ethyl acetate). $^1$H NMR (CDCl$_3$) δ (ppm):8.34 (s, 1H), 7.72–7.69 (m, 2H), 7.53–6.35 (m, 10H), 6.37 (d, 1H), 5.91 (q, 1H), 5.74 (d, 1H), 1.40–1.24 (dd, 3H).). LC-MS calculated for $C_{22}H_{18}ClF_2N_5O_2S$: 489. Observed 490 (MH$^+$).

EXAMPLE 398

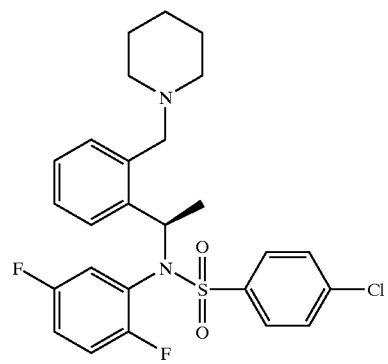

$R_f$=0.50 (10:1 DCM:methanol). $^1$H NMR (CDCl$_3$) δ (ppm):7.66–6.82 (m, 11H), 6.14 (br, 1H), δ 3.30–3.14 (m, 6H), 1.83–1.48 (m, 9H). LC-MS calculated for $C_{26}H_{27}ClF_2N_2O_2S$: 504. Observed 505 (MH+).

EXAMPLE 399

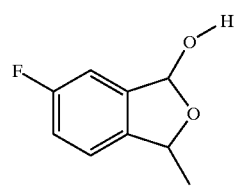

$R_f$=0.25 (3:1 hexanes:ethyl acetate), $^1$H NMR (300 M}, CDCl$_3$) c: 7.18–7.06 (m, 3H), 6.37 (d, 1H), 5.23 (q, 1H), 3.01 (d, 1H), 1.58 (t, 3H).

EXAMPLE 400

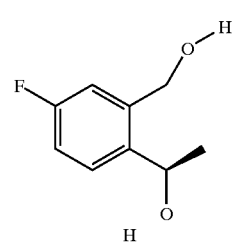

$R_f$=0.23 (2:1 hexanes:ethyl acetate), $^1$H NMR (300 MHz, CDCl$_3$) δ: 7.46–7.41 (m, 1H), 7.08–6.98 (m, 2H), 5.10 (q, 1H), 4.80–4.59 (dd, 2H), 3.08 (s, 1H), 3.93 (s, 1H), 1.53 (d, 3H).

EXAMPLE 401

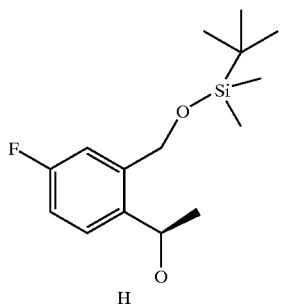

$R_f$=0.25 (15:1 hexanes:ethyl acetate), $^1$H NMR (300 MHz, CDCl$_3$) δ: 7.37–7.31 (m, 1H), 6.99–6.82 (m, 2H), 4.97 (q, 1H), 4.79–4.52 (dd, 2H), 2.76 (b, 1H), 1.39 (d, 3H), 0.79 (s, 9H), 0.00 (d, 6H).

EXAMPLE 402

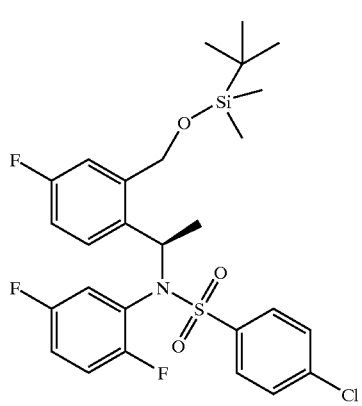

$R_f$=0.30 (20:1 hexanes:ethyl acetate), $^1$H NMR (300 MHz, CDCl$_3$) δ:7.63–6.16 (m, 10H), 5.58 (q, 1H), 4.79 (m, 2H), 1.36 (m, 3H), 0.79 (s, 9H), –0.06 (d, 6H).

EXAMPLE 403

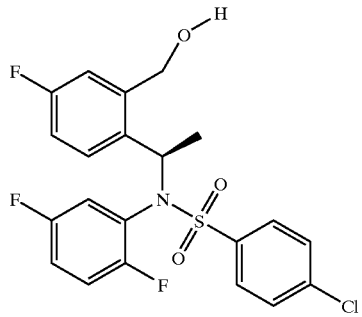

$R_f$=0.25 (3:1 hexanes:ethyl acetate), $^1$H NMR (300 MHz, CDCl$_3$) 7.66–7.27 (m, 4H), 7.03–6.47 (m, 6H), 5.94 (d, 1H), 4.94 (m, 2H), 2.56–2.26 (bb, 1H), 1.50–1.40 (m, 3H).

EXAMPLE 404

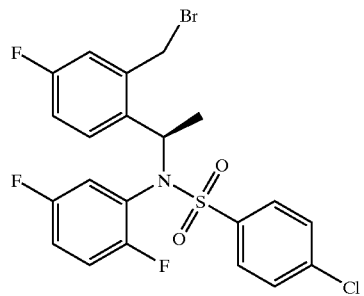

$R_f$=0.30 (15:1 hexanes:ethyl acetate), $^1$H NMR (300 M&, CDCl$_3$) δ 7.72–7.41 (m, 4H), 7.10–6.42 (m, 6H), 5.93 (m, 1H), 5.29–5.10 (m, 1H), 4.47–4.39 (m, 1H), 1.48–1.23 (m, 3H).

EXAMPLE 405

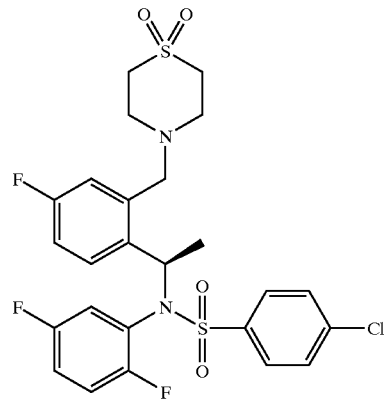

$R_f$=0.19 (3:1; hexanes:ethyl acetate). $^1$H NMR (CDCl$_3$) δ (ppm): 7.66–7.74 (m, 2H), 7.56–7.40 (m, 2H), 7.06–6.37 (m, 6H), 6.44–6.37 (m, 1H), 4.49 (d overlaps d, 1H), 3.52 (d, 1H), 3.18–3.03 (m, 8H), 1.44 (d, 3H). LC-MS calculated for C$_{25}$H$_{24}$ClF$_3$N$_2$O$_4$S$_2$: 572. Observed 572.

EXAMPLE 406

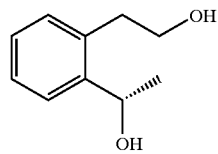

A solution of n-BuLi in THF (2.5 M, 17.6 mL, 44 mmol) was added dropwise within 30 min to a solution of (s)-(–)-2-bromo-α-methylbenzyl alcohol (3.9 g, 19.4 mmol) in THF at –78° C. under Ar. After having been stirred for 40 min, the generated suspension was warmed to 0° C., and ethylene oxide ((5 mL, 100 mmol) was added. The mixture was stirred at 0° C. for 1 h. The reaction was quenched with 1 N HCl aqueous solution. The aqueous phase was extracted with ethyl acetate. The combined organic solution was washed with water and sat. NaCl solution, then dried over Na$_2$SO$_4$. Concentration and flush column chromatography afforded the diol (1.4 g, 44%) as colorless liquid: $R_f$ 0.16 (10:10, hexanes:ethyl acetate); $^1$H NMR (CDCl$_3$, 300 MHz)

& 7.50 (m, 1H), 7.25 (m, 2H), 7.17 (m, 1H), 5.13 (q, 1H, J=6.6 Hz), 3.90 (m, 1H), 3.76 (m, 1H), 3.00 (m, 1H), 2.86 (m, 1H), 2.94 (br s, 1H), 1.52 (d, 3H, J=6.6 Hz).

EXAMPLE 407

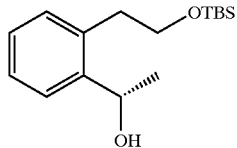

A solution of the diol prepared according to the previous example (890 mg, 5.4 mmol) in CH$_2$Cl$_2$ (21 mL) was treated with TBSCl (848 mg, 5.6 mmol) in the presence of imidazole (803 mg, 11.8 mmol) at 25° C. under Ar for 40 min. The reaction was quenched with H$_2$O. The aqueous phase was extracted with CH$_2$Cl$_2$. The combined organic phase was dried over Na$_2$SO$_4$. Concentration afforded product (1.5 g, 100%) as colorless liquid: R$_f$ 0.21 (10:1, hexanes:ethyl acetate); $^1$H NMR (CDCl$_3$, 300 MHz) d: 7.50 (m, 1H), 7.27 (m, 2H), 7.22 (m, 1H), 5.18 (m, q, 1H, I=6.3 Hz), 3.94 (m, 1H), 3.87 (m, 1H), 3.28 (m, 1H), 3.01 (m, 2H), 1.56 (d, 3H, 3=6.3 Hz), 0.85 (s, 9H), 0.00 (s, 6H).

EXAMPLE 408

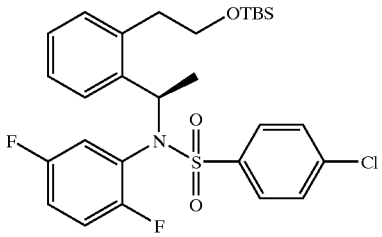

To a solution of the alcohol prepared according to the previous example (4.4 g, 16 mmol) in toluene (53 mL) at 25° C. under Ar, were added triphenylphosphine (5.4 g, 20.5 mmol) and sulfonamide 3 (5.3 g, 17.4 mmol). The mixture was cooled to 0° C., and DEAD (3.0 mL, 19 mmol) was added dropwise. After the addition, the mixture was stirred at 25° C. for 36 h. Concentration and chromatography afforded product 4 (6.66 g, 75%) as colorless syrup: R$_f$ 0.39 (10:1, hexanes:ethyl acetate); $^1$H NMR (CDCl$_3$, 300 MHz) δ 7.62 (m, 2H), 7.38 (m, 2H), 7.16 (m, 2), 6.29–7.07 (m, 5H), 5.94 (m, 1H), 3.86 (m, 2H), 3.26 (m, 1H), 2.79 (m, 1H), 1.53 (m, 3H), 0.88 (s, 9H), 0.02 (s, 3H), 0.00 (s, 3H).

EXAMPLE 409

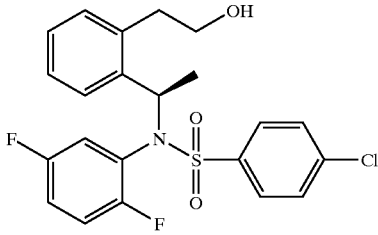

A solution of product prepared according to the previous example (6.6 g, 11.7 mmol) in THF (55 mL) was treated with TBAF solution (1.0 M in THF, 12 mL, 12.2 mmol) at 25° C. under Ar for 40 min. The reaction was quenched with H$_2$O. The aqueous phase was extracted with ethyl acetate and the combined organic solution was washed with sat. NaCl aqueous solution, then dried over MgSO$_4$. Concentration and chromatography afforded 4-chloro-N-(2,5-difluorophenyl)-N-{((1R)-1-[2-(2-hydroxyethyl)phenyl] ethyl}benzenesulfonamide (4.8 g, 92%) as colorless gum: R$_f$ 0.28 (10:4, hexanes:ethyl acetate); $^1$H NMR (CDCl$_3$, 300 MHz) δ7.62 (m, 2H), 7.43 (m, 2H), 7.19 (m, 2H), 6.40–7.00 (m, 5H), 5.99 (m, 1H), 3.95 (t, 2H, 3=6.6 Hz), 3.34 (m, 1H), 3.00 (m, 1H), 1.92 (s, 1H), 1.48 (m, 3H); LCMS 3.36 min, m/z 469.0 (M+H+H$_2$O, C$_{22}$H$_{20}$ClF$_2$NO$_3$S requires 451.91).

EXAMPLE 410

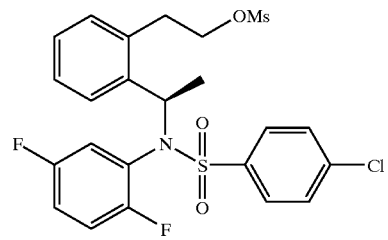

A solution of 4-chloro-N-(2,5-difluorophenyl)-N-{(1R)-1-[2-(2-hydroxyethyl)phenyl]ethyl}-benzenesulfonamide (422 mg, 0.94 mmol) in triethylamine (5.0 mL) was treated with MsCl (109 μL, 1.4 mmol) at 0° C. under Ar for 3 h. The reaction mixture was diluted with ethyl acetate. The organic solution was washed with H$_2$O and sat. NaCl aqueous solution, then dried over MgSO$_4$. Concentration in vacuo afforded the mesylate (450 mg, 91%) as light yellow syrup: R$_f$ 0.25 (10:4, hexanes:ethyl acetate).

A solution of 4-chloro-N-(2,5-difluorophenyl)-N-{(1R)-1-[2-(2-hydroxyethyl)phenyl]ethyl}-benzenesulfonamide (422 mg, 0.94 mmol) in triethylamine (5.0 mL) was treated with MsCl (109 μL, 1.4 mmol) at 0° C. under Ar for 3 h. The reaction mixture was diluted with ethyl acetate. The organic solution was washed with H$_2$O and sat. NaCl aqueous solution, then dried over MgSO$_4$. Concentration in vacuo afforded mesylate (450 mg, 91%) as light yellow syrup: R$_f$ 0.25 (10:4, hexanes:ethyl acetate).

EXAMPLE 411

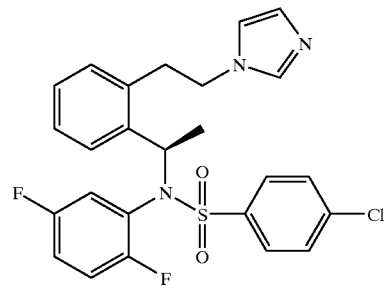

Imidazole (82 mg, 1.2 mmol) was added slowly to a suspension of NaH (60%, 58 mg, 1.4 mmol) in DMF (2.0 mL) at 25° C. under Ar. After having been stirred at 25° C. for 20 min, the generated solution was added to a solution of mesylate 5 (420 mg, 0.80 mmol) in THF (6.0 mL). The mixture was stirred at 25° C. overnight. The reaction was quenched with H$_2$O and the aqueous phase was extracted

217 with ethyl acetate. The dried organic solution was concentrated in vacuo. Chromatography afforded 4-chloro-N-(2,5-difluorophenyl)-N-((1R)-1-{2-[2-(1H-imidazol-1-yl)ethyl]phenyl}ethyl)benzenesulfonamide hydrochloride as colorless syrup (211 mg, 53%) as colorless gum: $R_f$ 0.31 (10:0.5 $CH_2Cl_2$-methanol); $^1H$ NMR ($CDCl_3$, 300 MHz) δ 7.40–7.66 (m, 5H), 6.22–7.30 (m, 9H), 5.62 (m, 1H), 4.42 (m, 1H), 4.18 (m, 1H), 3.61 (m, 1H), 3.22 (m, 1H), 1.34 (d, 3H, J=6.3 Hz); LCMS calculated for $C_{21}H_{22}ClF_2N_3O_2S$ 502. Observed: 502.

EXAMPLE 412

4-Chloro-N-(2,5-difluorophenyl)-N-((1R)-1-{2-[2-(1H-imidazol-1-yl)ethyl]phenyl}ethyl)benzenesulfonamide Hydrochloride A solution of HCl in $Et_2O$ (1.0 M, 398 μL, 0.40 mmol) was added dropwise to a solution of 4-chloro-N-(2,5-difluorophenyl)-N-(1R)-1-{2-[2-(1H-imidazol-1-yl)ethyl]phenyl}ethyl) benzenesulfonamide hydrochloride (100 mg, 0.20 mmol) in $CH_2Cl_2$ (2.0 mL) at 25° C. under Ar. After having been stirred for 30 min, the solvents were removed in vacuo. The residue was purified by chromatography to afforded 4-chloro-N-(2,5-difluorophenyl)-N-((1R)-1-{2-[2-(1H-imidazol-1-yl)ethyl]phenyl)ethyl)benzenesulfonamide hydrochloride (99 mg, 92%) as white solid. m.p. 205.0–206.0° C.; $R_f$ 0.32 (10:0.5, $CH_2Cl_2$-methanol); $^1H$ NMR ($CD_3OD$, 300 MHz) δ 9.22 (s, 1H), 7.76–8.07 (m, 6H), 6.57–7.52 (m, 7H), 6.23 (m, 1H), 4.93 (m, 2H), 3.91 (m, 1H), 3.78 (m, 1H), 1.69 (d, 3H, J=6.9 Hz); LCMS 3.04 min, m/z 502.05 (M+H$^+$–HCl, $C_{25}H_{22}ClF_2N_3O_2S$·HCl requires 501.98 36.46).

EXAMPLE 413

4-Chloro-N-(2,5-difluorophenyl-N-((1R)-1-{2-[2-(1H-1,2,4-triazol-1-yl)ethyl]phenyl}ethyl) Benzenesulfonamide

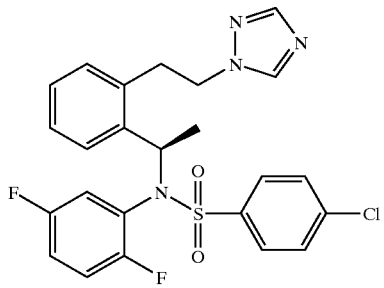

1,2,4-Triazole (101 mg, 1.5 mmol) was treated with NaH (60%, 70 mg, 1.8 mmol) in THF (7.0 mL) and DMF (0.5 mL) at 25° C. under Ar for 30 min. The generated suspension was added slowly to a solution of mesylate 5 (0.97 mmol) in THF (3.0 mL) and the mixture was stirred for 48 h. The reaction was quenched with $H_2O$ and the aqueous phase was extracted with ethyl acetate. The dried organic solution was concentrated and chromatography afforded 4-chloro-N-(2,5-difluorophenyl)-N-((1R)-1-{2-[2-(1H-1,2,4-triazol-1-yl)ethyl]phenyl}ethyl)benzenesulfonamide (260 mg, 53%) as white crystal: m.p. 116–118° C.; $R_f$ 0.28 (10:10, hexanes:ethyl acetate); $^1H$ NMR ($CDCl_3$, 300 MHz) δ 8.01 (br 2H), 7.39–73 (m, 4H), 6.32–7.11 (m, 7H), 5.83 (m, 1H), 4.65 (m, 1H), 4.89 (m, 1H), 3.29–3.68 (m, 2H), 1.35 (m, 3H); LCMS 3.43 min, m/z 503.05 (M+H, $C_{24}H_{21}ClF_2N_4O_2S$ requires 502.96).

218

EXAMPLE 414

4-Chloro-N-(2,5-difluorophenyl)-N-((1R)-1-{2-[2-(2-methyl-1H-imidazol-1-yl)ethyl]phenyl}ethyl)benzenesulfonamide Hydrochloride

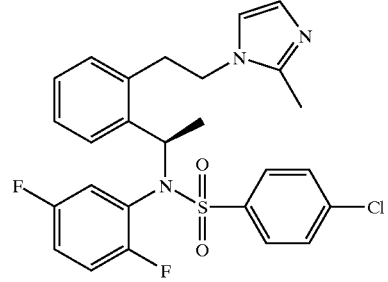

2-Methylimidazole (77 mg, 0.94 mmol) was treated with NaH (60%, 27 mg, 1.1 mmol) in DMF (1.0 mL) at 25° C. under Ar for 30 min. The generated solution was added slowly to a solution of mesylate 5 (250 mg, 0.47 mmol) in THF and the mixture was stirred at 25° C. for 26 h. The reaction was quenched with $H_2O$ and the aqueous phase was extracted with ethyl acetate. The dried organic solution was concentrated in vacuo. Chromatography afforded the desired product (39 mg, 16%) as a colorless gum: $R_f$ 0.28 (10:0.5, $CH_2Cl_2$-methanol); $^1H$ NMR ($CDCl_3$, 300 MHz) δ 7.60 (m, 2H), 7.42 (m, 2H), 7.15 (m, 2H), 6.20–6.98 (m, &H), 5.52 (m, 1H), 4.30 (m, 1H), 4.06 (m, 1H), 3.69 (m, 1H), 3.12 (m, 1H), 2.10 (m, 3H), 1.27 (m, 3H); LCMS 3.07 min, m/z 516.10 (M+H+, $C_{26}H_{24}ClF_2N_3O_2S$ requires 516.00).

4-chloro-N-(2,5-difluorophenyl)-N-((1R)-1-{2-[2-(2-methyl-1H-imidazol-1-yl)ethyl]phenyl}ethyl)benzenesulfonamide (39 mg, 0.075 mmol) was dissolved in $CH_2Cl_2$ (2.0 mL) and treated with HCl—$Et_2O$ solution (1.0 M, 83 μL) at 25° C. for 15 min. Solvents were removed in vacuo and chromatography afforded 4-chloro-N-(2,5-difluorophenyl)-N-((1R)-1-(2-[2-(2-methyl-1H-imidazol-1-yl)ethyl]phenyl}ethyl)benzenesulfonamide hydrochloride (26 mg, 61%) as white solid: m.p. 190.5–192.0° C.; $R_f$ 0.38 (10:1, $CH_2Cl_2$-methanol); $^1H$ NMR ($CD_3OD$, 300 MHz) δ 7.39–7.67 (m, 5H), 7.29 (m, 1H), 6.18–7.12 (m, 7H), 5.67 (q, 1H, J=6.9 Hz), 4.44 (m, 1H), 4.35 (m, 1H), 3.59 (m, 1H), 3.25 (m, 1H), 2.27 (m, 3H), 1.31 (d, 3H, I=6.6 Hz); LCMS 3.07 min, m/z 516.05 (M+H$^+$–HCl, $C_{26}H_{24}ClF_2N_3O_2S$ HCl requires 516.00).

The following compounds were prepared using the preparative schemes described in the previous Examples.

EXAMPLE 415

4-Chloro-N-(2,5-difluorophenyl)-N-((1R)-1-{2-[2-(1H-tetraazol-1-yl)ethyl]phenyl}ethyl)benzenesulfonamide

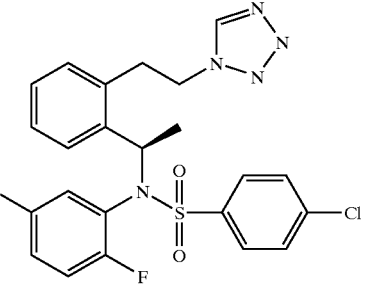

$R_f$ 0.16 (10:5, hexanes:ethyl acetate); $^1H$ NMR ($CDCl_3$, 300 MHz) δ 8.75 (s, 1H), 7.42–7.74 (m, 4H), 6.30–7.20 (m, 7H), 5.94 (m, 1H), 4.98 (m, 1H), 4.75 (m, 1H), 3.56 (m, 2H), 1.40 (d, 3H, J=6.9 Hz); LCMS 3.56 min, m/z 504.05 (M+H, $C_{23}H_{20}ClF_2N_5O_2S$ requires 503.95).

EXAMPLE 416

4-Chloro-N-(2,5-difluorophenyl)-N-((1R)-1-{2-[2-(2H-tetraazol-2-yl)ethyl]phenyl}ethyl)benzenesulfonamide

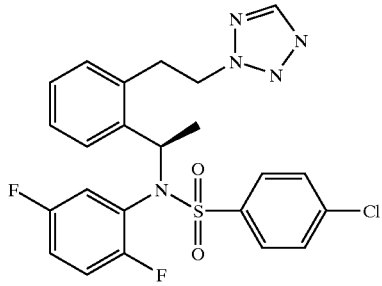

$R_f$ 0.40 (10:4, hexanes:ethyl acetate); $^1$H NMR (CDCl$_3$, 300 MHz) δ: 8.55 (s, 1H), 7.63 (m, 2H), 7.41 (m, 2H), 6.45–7.14 (m, 7H), 5.88 (m, 10H), 5.01 (m, 2H), 3.80 (m, 1H), 3.52 (m, 1H), 1.45 (m, 3H); LCMS 4.37 min, m/z 526.05 (M+Na$^+$, C$_{23}$H$_{20}$ClF$_2$N$_5$O$_2$S requires 503.95).

EXAMPLE 417

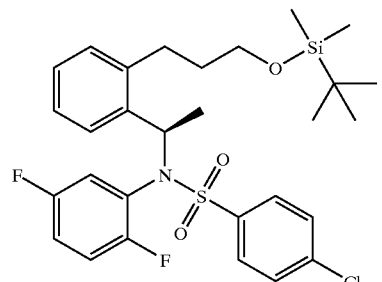

$R_f$=0.25 (15:1 hexanes:ethyl acetate), $^1$H NMR (300 MHz, CDCl$_3$) o: 7.45–6.61 (m, 1H), 5.78 (q, 1H), 3.65–3.52 (m, 2H), 3.00 (m, 1H), 2.66–2.55 (m, 1H), 1.79–1.59 (m, 2H), 1.43–1.30 (m, 3H), 0.84 (d, 9H), 0.01 (d, 6H).

EXAMPLE 418

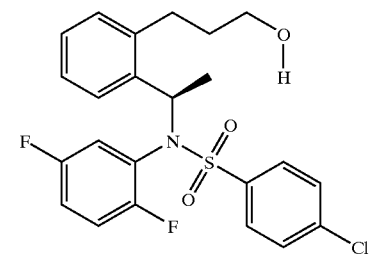

$R_f$=0.23 (3:1 hexanes:ethyl acetate), $^1$H NMR (300 MHz, CDCl$_3$) δ: 7.66–7.60 (m, 2H), 7.42–7.40 (m, 2H), 7.19–6.59 (m, 7H), 5.94 (q, 1H), 3.83–3.76 (m, 2H), 3.21–3.11 (m, 1H), 2.87–2.77 (m, 1H), 2.01–1.88 (m, 2H), 1.72 (t, 1H), 1.53 (m, 3H).

EXAMPLE 419

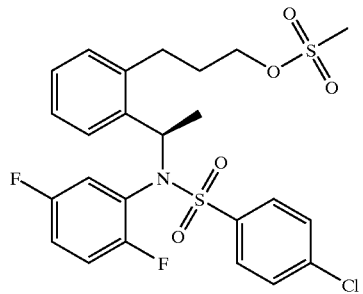

$R_f$=0.30 (3:1 hexanes:ethyl acetate), $^1$H NMR (300 MHz, CDCl$_3$) δ: 7.65 (m, 2H), 7.42 (m, 2H), 7.18–6.29 (m, 7H), 6.93 (m, 1H), 4.36 (m, 2H), 3.24 (m, 1H), 3.10 (s, 3H), 2.87 (m, 1H), 2.14 (m, 2H), 1.53 (m, 3H).

EXAMPLE 420

4-Chloro-N-(2,5-difluorophenyl)-N-{2-[3-(1-piperidinyl)propyl]benzyl}benzenesulfonamide

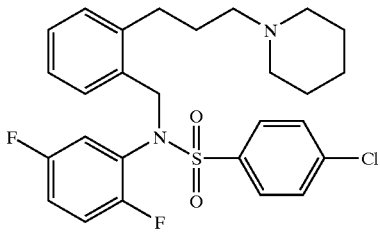

$R_f$=0.25 (9:1;DCM:methanol). $^1$H NMR (CD$_3$OD)δ(ppm) :7.75–7.62 (m, 4H), 7.19–6.89 (m, 7H), 4.76 (s, overlaps HOD, 2H), 2.95–2.85 (m, 8H), 2.11–1.95 (m, 2H), 1.81–1.75 (m, 4H), 1.65–1.55 (m, 2H). LC-MS calculated for C$_{27}$H$_{30}$ClF$_2$N$_2$O$_2$S: 519. Observed 519 (M+).

EXAMPLE 421

4-Chloro-N-(2,5-difluorophenyl)-N-((1R)-1-{2-[3-(1H-imidazol-1-yl)propyl]phenyl}ethyl)benzenesulfonamide Hydrochloride

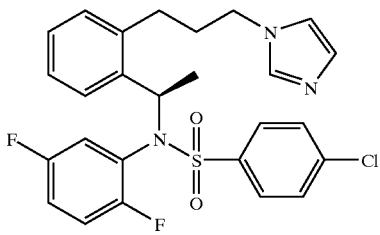

$R_f$=0.34 (19:1;DCM:methanol). $^1$H NMR (CD$_3$OD) δ (ppm):7.74 (s, 1H), 7.70–7.57 (m, 4H), 7.24 (s, 1H), 7.22–6.61 (m, 8.5H), 6.3 (br m, 0.5H), 5.87 (q, 1H), 4.19 (t, 2H), 3.02–2.81 (m, 2H), 2.21–2.11 (m, 2H), 1.51–1.49 (m, 3H). LC-MS calculated for C$_{26}$H$_{24}$ClF$_2$N$_3$O$_2$S: 516. Observed 516 (M+).

EXAMPLE 422

4-Chloro-N-(2,5-difluorophenyl)-N-((1R)-1-{2-[3-(1H-1,2,4-triazol-1-yl)propyl]phenyl}ethyl)benzenesulfonamide

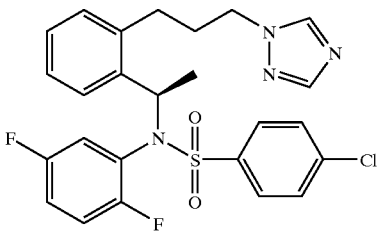

$R_f$=0.29 (19:1;DCM:methanol). $^1$H NMR (CDCl$_3$) δ (ppm): 8.19 (s, 1H), 8.00 9s, 1H), 7.67–6.30 (m, 11H), 5.92 (q, 1H), 4.36 (t, 2H), 3.17–3.07 (m, 1H), 2.91–2.82 (m, 1H), 2.38–2.22 (m, 2H), 1.49 (br, 3H). LC-MS calculated for C$_{25}$H$_{23}$ClF$_2$N$_4$O$_2$S: 517. Observed 517 (M+).

EXAMPLE 423

4-Chloro-N-(2,5-difluorophenyl)-N-((1R)-1-{2-[3-(2H-tetraazol-2-yl)propyl]phenyl}ethyl)benzenesulfonamide

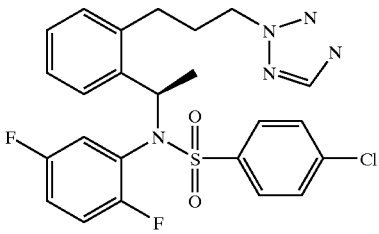

$R_f$=0.50 (3:1 hexanes:ethyl acetate). $^1$H NMR (CDCl$_3$) δ (ppm): 8.81 (Ss, 1H), 7.69–6.24 (m, 11), 5.93 (q, 1H), 4.65 (t, 2H), 3.15–2.85 (m, 2H), 2.55–2.25 (m, 2H), 1.31 (d, 3H). LC-MS calculated for C$_{24}$H$_{22}$ClF$_2$N$_5$O$_2$S: 518. Observed 215 (M$^+$-303).

EXAMPLE 424

4-Chloro-N-(2,5-difluorophenyl)-N-((1R)-1-{2-[3-(1H-tetraazol-1-yl)propyl]phenyl}ethyl)benzenesulfonamide

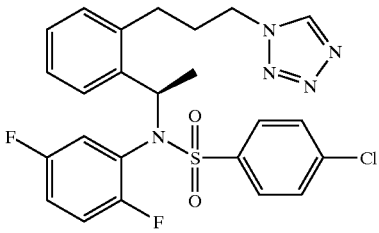

$R_f$=0.20 (2:1 hexanes:ethyl acetate). $^1$H NMR (CDCl$_3$) δ (ppm): 9.23 (s, 1H), 7.70–0.27 (m, 1H), 5.92 (q, 1H), 4.65 (t, 2H), 3.20–2.90 (m, 2H), 2.54–2.33 (m, 2H), 1.46 (d, 3H). LC-MS calculated for C$_{21}$H$_{22}$ClF$_2$N$_5$O$_2$S: 518. Observed 518 (M+).

EXAMPLE 425

4-Chloro-N-[5-chloro-2-(hydroxymethyl)phenyl]-N-((1R)-1-{2-[3-(1H-imidazol-1-yl)propyl]phenyl}ethyl)benzenesulfonamide

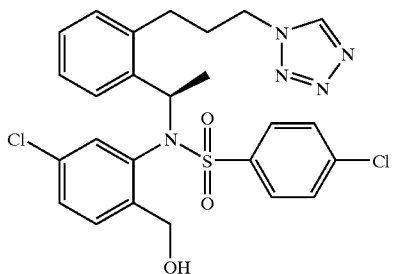

$R_f$=0.29 (19:1 DCM:methanol). $^1$H NMR (CDCl$_3$) δ (ppm):7.74–6.57 (m, 13H0, 6.28–6.19 (m, 1H), 6.01–5.94 (m, 1H), 0004.19–4.03 (m, 2H), 3.86–3.75 (m, 1H), 3.42–3.16 (m, 2H), 2.93–2.83 (m, 1H), 2.28–1.98 (m, 4H), 1.39 (d, 3H). LC-MS calculated for C$_{27}$H$_{27}$Cl$_2$N$_3$O$_3$S: 544.5. Observed: 544.5 (M+).

EXAMPLE 426

4-Chloro-2-[[(4-chlorophenyl)sulfonyl]((1R)-1-{2-[3-(1H-imidazol-1-yl)propyl]phenyl}ethyl)amino]benzyl Acetate

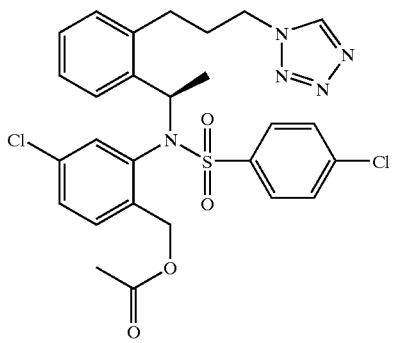

$R_f$=0.26 (19:1 DCM:methanol). $^1$H NMR (CDCl$_3$) δ (ppm): 7.68–6.76 (m, 14H), 6.23 (d, 1H), 5.97 (q, 1H), 4.36 (d, 1H), 4.15 (t, 2H), 3.58 (d, 1H), 3.18–3.09 (m, 1H), 2.97–2.88 (m, 1H), 2.34–2.21 (m, 2H), 1.89 (s, 3H), 1.43 (d, 3H).

EXAMPLE 427

4-Chloro-N-(2,5-difluorophenyl)-N-((1R)-1-{2-[3-(1-piperidinyl)propyl]phenyl}ethyl)benzenesulfonamide Hydrochloride

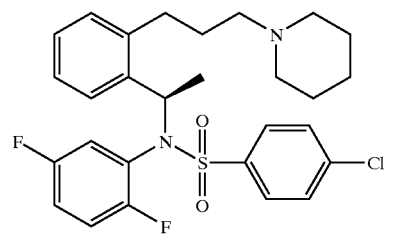

$R_f$=0.68 (9:1 DCM:methanol). $^1$H NMR (CD$_3$OD) δ (ppm): 7.57–7.28 (m, 5H), 7.09–6.93 (m, 3H), 6.68–6.10 (m, 3H), 5.74 9q, 1H{), 3.87–2.58 (m, 8H), 0.1.98–1.85 (m, 2H), 1.71–1.61 (m, 4H), 1.49–1.16 (m, 5H).). LC-MS calculated for C$_{28}$H$_{31}$ClF$_2$N$_2$O$_2$S: 533. Observed: 533 (M+).

EXAMPLE 428

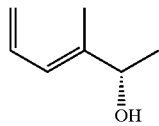

A solution of 9-BBN in THF (0.5 M, 91 mL, 45 mmol) was added dropwise to a solution of allyloxy-tert-butyldimethylsilane (8.7 g, 50 mmol) in THF (25 mL) at 0° C. under Ar. The mixture was stirred at 0° C. for 1 h, then at 60° C. for additional 1 h. the solution was then cooled to 25° C. To the generated solution at 25° C., were added compound 19 (8.85 g, 40 mmol), PdCl$_2$(dppf) (990 mg, 1.2 mmol) and 3 M NaOH aqueous solution (13.5 mL, 40.4 mmol). The mixture was refluxed at 60° C. for 12 h. The solution was extracted with CH$_2$Cl$_2$ and the combined organic solution was washed with sat. NH$_4$Cl solution and sat. NaCl solution, then dried over MgSO$_4$. Chromatography afforded the desired product (21) (11.4 g, 90%) as colorless syrup: R$_f$ 0.12 (10:1, hexanes:ethyl acetate); $^1$H NMR (CDCl$_3$, 300 MHz) δ 7.41 (m, 1H), 7.69 (m, 2H), 5.09 (m, 1H), 3.58 (m, 2H), 2.66 (m, 2H), 2.1] (s, 1H), 1.73 (m, 2H), 1.39 (m, 3H), 0.84 (s, 9H), −0.01 (s, 3H), −0.02 (s, 3H).

EXAMPLE 429

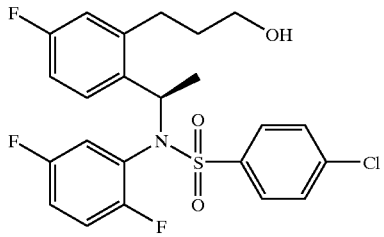

R$_f$=0.30 (10:5, hexanes:ethyl acetate); $^1$H NMR (CDCl$_3$, 300 MHz) δ 7.65 (m, 2H), 7.42 (d, 2H), 7.00 (m, 2H), 6.91 (m, 1H), 6.33–6.74 (m, 3H), 5.92 (q, 1H, J=6.6 Hz), 3.79 (s, 2H), 3.15 (m, 10H), 2.82 (m, 1H), 2.68 (s, 1H), 1.92 (m, 2H), 1.51 (m, 3H); LCMS 3.55 min, m/z 501.15 (M+H+H$_2$O, C$_{23}$H$_{21}$ClF$_3$NO$_3$S requires 483.94).

EXAMPLE 430

4-Chloro-N-(2,5-difluorophenyl)-N-(1-{4-fluoro-2-[3-(1H-imidazol-1-yl)propyl]phenyl}ethyl) benzenesulfonamide Hydrochloride

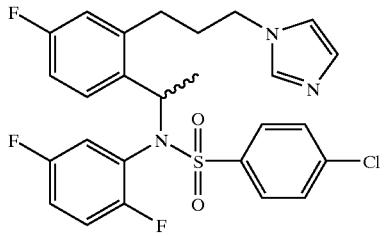

R$_f$=0.44 (10:1;DCM:methanol). $^1$H NMR (CD$_3$OD) δ (ppm):7.93–6.37 (m, 13H), 5.89 (m, 1H), 4.16 (t, 2H), 3.10–2.85 (m, 2H), 2.31–2.17 (m, 2H), 1.52–1.50 (m, 3H). LC-MS calculated for C$_{26}$H$_{23}$ClF$_3$N$_5$O$^2$S: 534. Observed 534 (M+).

EXAMPLE 431

4-Chloro-N-(2,5-difluorophenyl)-N-((1R)-1-{4-fluoro-2-[3-(1H-imidazol-1-yl)propyl]phenyl}ethyl) benzenesulfonamide Hydrochloride

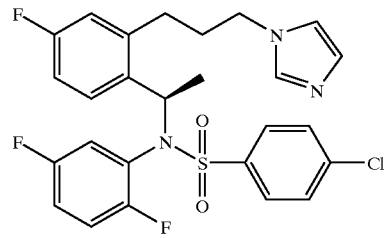

R$_f$=0.38 (19:1;DCM:methanol). $^1$H NMR (CDCl$_3$) δ (ppm): 9.64 (s, 0.4H), 9.56 (s, 0.6H), 7.71–7.40 (m, 6H), 7.02–6.20 (m, 6H), 5.92 (q, 1H), 4.62–4.47 (m, 2H), 3.15–2.95 (m, 2H), 2.57–2.22 (m, 2H), 1.41 (d, 3H). LC-MS calculated for C$_{26}$H$_{23}$ClF$_3$N$_3$O$_2$S: 534. Observed 534 (M+).

EXAMPLE 432

4-Chloro-N-2,5-difluorophenyl)-N-((1R)-1-{4-fluoro-2-[3-(1H-1,2,4-triazol-1-yl)propyl] phenyl}ethyl)benzenesulfonamide

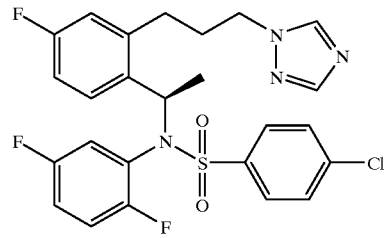

R$_f$=0.38 (1:1 hexanes:ethyl acetate). $^1$H NMR (CDCl$_3$) δ (ppm): 8.19 (s, 1H), 8.01 (s, 1H), 7.67–7.45 (m, 4H), 6.70–6.28 (m, 6H), 5.87 (q, 1H), 4.34 (t, 2H), 3.11–2.98 (m, 1H), 2.91–2.80 (m, 1H), 238–2.22 (m, 2H), 1.46 (d, 3H). LC-MS calculated for C$_2$H$_{12}$ClF$_3$N$_4$O$_2$S: 535. Observed 535 (M+).

EXAMPLE 433

4-Chloro-N-(2-difluorophenyl)-N-((1R)-1-{4-fluoro-2-[3-(2H-tetraazol-2-yl)propyl]phenyl}ethyl) benzenesulfonamide

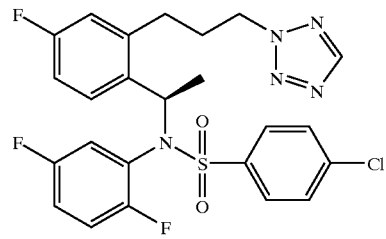

R$_f$=0.33 (3:1 hexanes:ethyl acetate). $^1$H NMR (CDCl$_3$) δ (ppm): 8.58 (s, 1H), 7.66–7.32 (m, 4H0, 7.01–6.31 (m, 6H), 5.84 (q, 1H), 4.83 (dt, 2H), 3.17–3.07 (m, 1H), 2.88–2.78 (m, 1H), 2.43 (p, 2H), 1.52 (d, 3H). LC-MS calculated for C$_{24}$H$_{21}$ClF$_3$N$_5$O$_2$S: 536. Observed 233 (M$^+$−303).

EXAMPLE 434

4-Chloro-N-(2,5-difluorophenyl)-N-((1R)-1-[4-fluoro-2-[3-(1H-tetraazol-1-yl)propyl]phenyl}ethyl)benzenesulfonamide

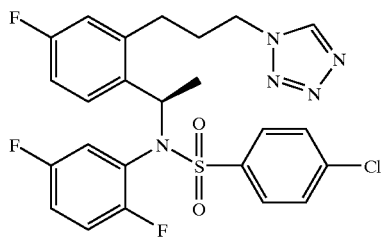

$R_f$=0.50 (1:1 hexanes:ethyl acetate). $^1$H NMR (CDCl$_3$) δ (ppm): 8.79 (s, 1H), 7.69–7.46 (m, 4H0, 7.02–6.23 (m, 6H), 5.92–5.84 (m, 1H), 4.66 (t, 2H), 2.39 (t, 2H), 2.49–2.31 9m, 2H), 1.43 (d, 3H).). LC-MS calculated for $C_{24}H_{21}ClF_3N_5O_2S$: 536. Observed 233. (M$^+$-303).

EXAMPLE 435

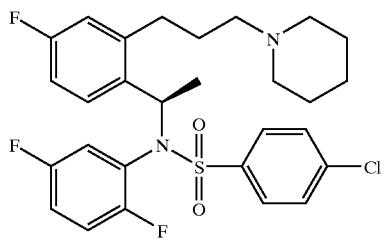

$R_f$ =0.42 (19:1 DCM:methanol). $^1$H NMR (CDCl$_3$) δ (ppm): 7.62 (m, 2H), 7.47–7.37 (m, 2H), 7.00–6.50 (m, 6H), 5.90 (q, 1H), 3.08–2.98 (m, 1H), 2.70–2.60 (m, 1H), 2.53–2.38 (m, 6H), 1.92–1.82 (m, 2H), 1.70–1.63 (m, 4H), 1.51 (d, 3H0, 1.50–1.44 (m, 2H). LC-MS calculated for $C_{28}H_{30}ClF_3N_2O_2S$: 551. Observed 551 (M+).

EXAMPLE 436

4-Chloro-N-(2,5-difluorophenyl)-N-((1R)-1-{4-fluoro-2-[3-(4-methyl-1-piperazinyl)propyl]phenyl}ethyl)benzenesulfonamide

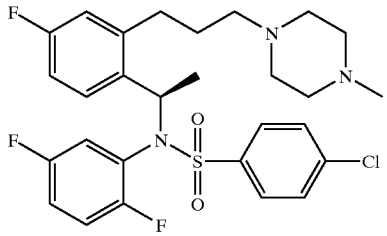

$R_f$=0.4 (9:1 DCM:methanol). $^1$H NMR (CDCl$_3$) δ (ppm): 7.76–7.51 9m, 2H), 7.42–7.37 (m, 2H), 7.02–6.55 (m, 6H), 5.87 (q, 1H), 3.10–3.00 9m, 1H), 2.67–2.28 (m, 12H), 1.87–1.75 (m, 2H), 1.58–1.45 (m, 3H). LC-MS calculated for $C_{29}H_{31}ClF_2N_3O_2S$: 566. Observed 566 (M+).

EXAMPLE 437

4-Chloro-N-(2,5-difluorophenyl)-N-[(1R)-1-(4-fluoro-2-{3-[2-(trifluoroethyl)-1H-imidazol-1-yl]propyl]phenyl)ethyl]benzenesulfonamide

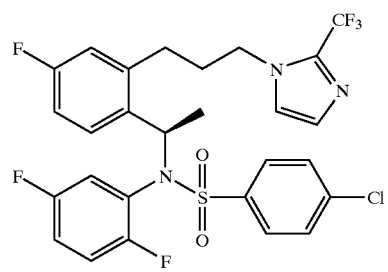

$R_f$=0.32 (5:2; hexanes:ethyl acetate). $^1$H NMR (CDCl$_3$) δ (ppm): 7.74–7.40 (m, 6H), 7.01–6.23 (m, 6H), 5.87 (q, 1H), 4.19 (t, 2H), 3.01–2.96 (m, 2H), 2.32–2.16 (m, 2H), 1.44 (d, 3H). LC-MS calculated for $C_{27}H_{22}ClF_6N_3O_2S$: 602. Observed: 602 (M+).

EXAMPLE 438

Numerous compounds according to the invention can be prepared employing the general scheme set forth in SCHEME 438.

SCHEME 438

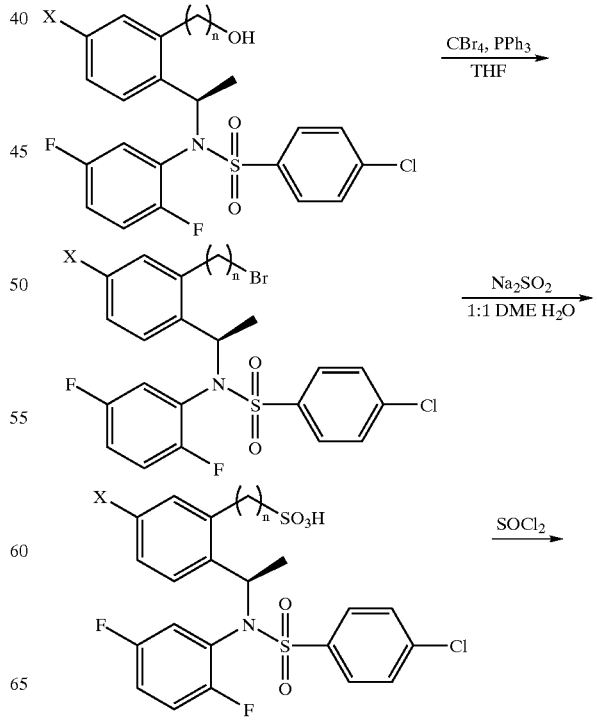

-continued

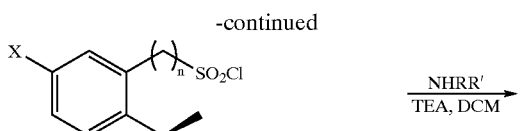

Using the preparative scheme outlined in Example 438, the compounds of Examples 439–448 were prepared.

EXAMPLE 439

4-Chloro-N-(2,5-difluorophenyl)-N-[(1R)-1-(4-fluoro-2-{4-[(methylamino)sulfonyl]butyl}phenyl)ethyl]benzenesulfonamide

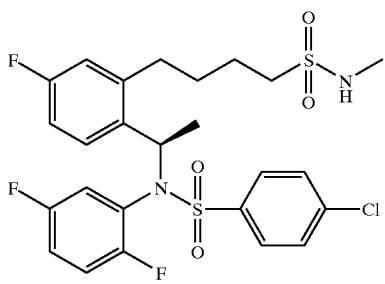

$R_f$=0.19 (2:1; hexanes:ethyl acetate). $^1$H NMR (300 MHz CDCl$_3$) δ: 7.70–7.45 (m, 4H), 7.01–6.32 (m, 6H), 5.89 (q, 1H), 4.95 (m, 2H), 322–3.07 (m, 3H), 2.81–2.80 (m overlaps d, 4H), 2.03–1.84 (m, 4H), 1.49 (br, 3H). LC-MS calculated for C$_{25}$H$_{26}$ClF$_3$N$_2$O$_4$S$_2$ [M+] 575 Observed 272 (M$^+$-303).

EXAMPLE 440

4-Chloro-N-(2,5-difluorophenyl)-N-[(1R)-1-(2-{4-[(ethylamino)sulfonyl]butyl}-4-fluorophenyl)ethyl]benzenesulfonamide

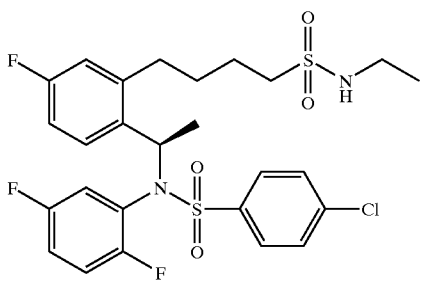

$R_f$=0.23 (3:1; hexanes:ethyl acetate). $^1$H NMR (300 MHz CDCl$_3$) δ: 7.70–7.42 9m, 4H), 7.01–6.29 (m, 6H), 5.88 (q, 1H), 4.61 (t, 1H), 3.31–3.07 (m, 5H), 2.86–2.72 (m, 1H), 2.03–1.78 (m, 4H), 1.48 (r, 3H), 1.21 (t, 3H). LC-MS calculated for C$_{25}$H$_{28}$ClF$_3$N$_2$O$_4$S$_2$ [M+] 589; Observed: 286 (M$^+$-303).

EXAMPLE 441

4-Chloro-N-(2,5-difluorophenyl)-N-((1R)-1-{4-fluoro-2-[4-(4-thiomorpholinylsulfonyl)butyl]phenyl}ethyl)benzenesulfonamide

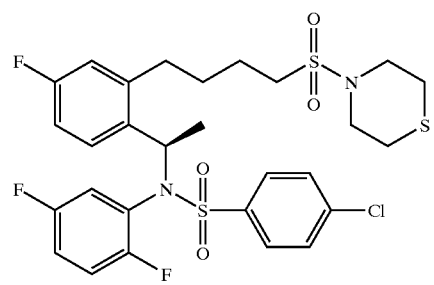

$R_f$=0.41 (3:1; hexanes:ethyl acetate). $^1$H NMR (300 MHz CDCl$_3$) δ: 7.70–7.40 (m, 4H), 7.01–6.28 (m, 6H), 5.88 (q, 1H), 3.65–0.660 (m, 4H), 3.17–3.05 (m, 3H0, 2.83–2.69 (m, 5H), 2.10–1.81 (m, 4H), 1.50 (br d, 3H). LC-MS calculated for C$_{26}$H$_{30}$ClF$_3$N$_2$O$_4$S$_3$ [M+] 647.2; Observed: 647.

EXAMPLE 442

4-Chloro-N-(2,5-difluorophenyl)-N-[(1R)-1-(2-{4-[(1,1-dioxido-4-thiomorpholinyl)sulfonyl]butyl}-4-fluorophenyl)ethyl]benzenesulfonamide

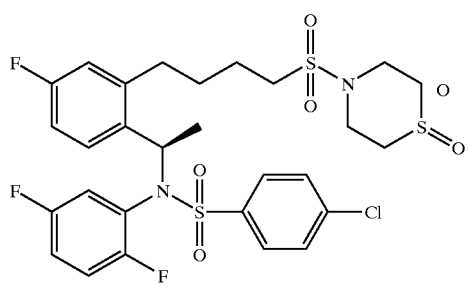

$R_f$=0.32 (2:1; hexanes:ethyl acetate). $^1$H NMR (300 MHz CDCl$_3$) δ: 7.70–7.38 (m, 4H), 6.90–6.31 (m, 6H), 6.00 (m, 1H), 4.10–3.98 (m, 4H), 3.41–2.92 (m, 8H), 2.22–1.93 (m, 4H), 1.58 (d, 3H). LC-MS calculated for C$_{28}$H$_{30}$ClF$_3$N$_2$O$_6$S$_3$ [M+] 679.2; Observed: 376 (M$^+$-303).

EXAMPLE 443

4-Chloro-N-(2,5-difluorophenyl)-N-[(1R)-1-(4-fluoro-2-{3-[(methylamino)sulfonyl]propyl}phenyl)ethyl]benzenesulfonamide

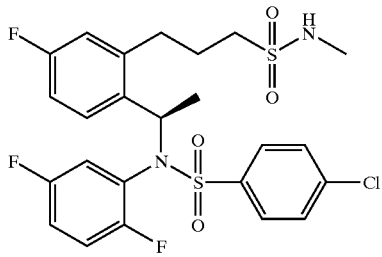

$R_f$=0.18 (3:1 hexanes:ethyl acetate) $^1$H NMR (300 MHz CDCl$_3$) δ: 7.71–7.47 (m, 4H), 7.01–6.30 (m, 6H), 5.94–5.91 (br, 1H), 4.73 (br, 1H), 3.24–3.22 (m, 3H), 3.05–2.83 (m, 4H), 2.20 (br, 2H), 1.45 (s, 3H). LC-MS calculated for $C_{24}H_{24}ClF_3N_2O_4S_2$ [M+] 561; Observed: 258 (M$^+$-303).

EXAMPLE 444

4-Chloro-N-(2,5-difluorophenyl)-N-[(1R)-1-(2-(3-[(ethylamino)sulfonyl]propyl}-4-fluorophenyl)ethyl]benzenesulfonamide

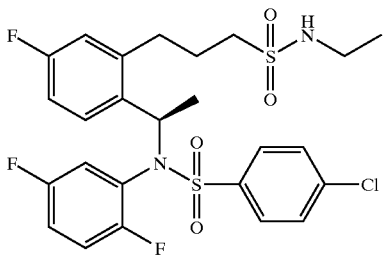

$R_f$=0.30 (3:1 hexanes:ethyl acetate) $^1$H NMR (300 MHz CDCl$_3$) δ: 7.72–7.60 (m, 2H), 7.49–7.42 (m, 2H), 7.05–6.30 (m, 6H), 5.95–5.88 (q, 1H), 4.79–4.75 (t, 1H), 3.25–3.17 (m, 5H), 3.00–2.92 (m, 1H), 2.24–2.14 (m, 2H), 1.48–1.46 (m, 3H), 1.25–1.18 (m, 3H). LC-MS calculated for $C_{25}H_{26}ClF_3N_2O_4S_2$ [M+] 575; Observed: 272 (M-303).

EXAMPLE 445

4-Chloro-N-(2,5-difluorophenyl)-N-[(1R)-1-(2-{3-[(dimethylamino)sulfonyl]propyl}-4-fluorophenyl)ethyl]benzenesulfonamide

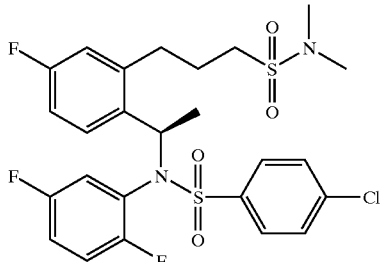

$R_f$=0.26 (3:1 hexanes:ethyl acetate) $^1$H NMR (300 MHz CDCl$_3$) δ (ppm): 7.68–7.47 (m, 4H), 7.08–6.30 (m, 6H), 5.89 (br, 1H), 3.14–2.88 (m, 10H), 2.22 (m, 2H) 1.48–1.46 (br, 3H). LC-MS calculated for $C_{25}H_{26}ClF_3N_2O_4S$ % [M+] 575; Observed: 575.

EXAMPLE 446

4-Chloro-N-[(1R)-1-(2-{3-[(diethylamino)sulfonyl]propyl)}-4-fluorophenyl)ethyl]-N-(2,5-difluorophenyl)benzenesulfonamide

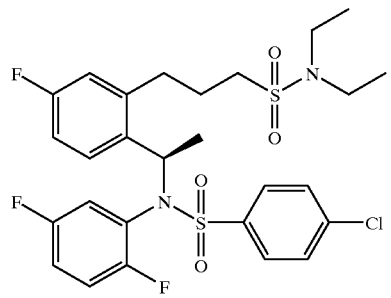

$R_f$=0.35 (3:1 hexanes:ethyl acetate) $^1$H NMR (300 MHz CDCl$_3$) δ (ppm): 7.69–7.44 (m, 4H), 7.03–6.31 (m, 6H), 5.88–5.86 (q, 1H), 3.37–3.09 (m, 8H), 2.20–2.15 (m, 2H), 1.49–1.47 (m, 3H), 1.25–1.1.9 (m, 6H). LC-MS calculated for $C_{27}H_{30}ClF_3N_2O_4S_2$ [M+] 603; Observed: 603.

EXAMPLE 447

4-Chloro-N-(2,5-dichlorophenyl)-N-[(1R)-1-(4-fluoro-2-{4-[(methylamino)sulfonyl]butyl}phenyl)ethyl]benzenesulfonamide

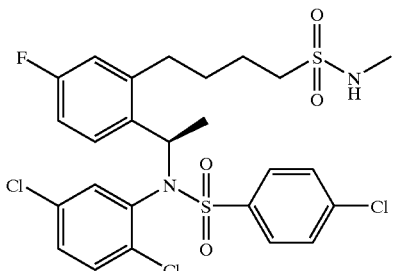

$R_f$=0.27 (2:1 hexanes:ethyl acetate) $^1$H NMR (300 MHz CDCl$_3$) δ (ppm): 7.71 (d, 2H), 7.50–7.47 (d, 2H), 7.36–7.15 (m, 2H), 6.91–6.72 (m, 2H), 6.56–6.37 (m, 2H), 5.92–5.77 (m, 1H), 4.60–4.48 (m, 1H), 3.24–3.12 (m, 3H), 2.84–2.69 (m, 4H), 2.06–1.74 (m, 4H), 1.44–1.37 (m, 3H). LC-MS cacld for $C_{25}H_{26}Cl_3FN_2O_4S_2$ [MH+] 608; Observed: 608.

EXAMPLE 448

4-Chloro-N-(5-chloro-2-fluorophenyl)-N-[(1R)-1-(4-fluoro-2-{4-[[(methylamino)sulfonyl]butyl}phenyl)ethyl]benzenesulfonamide

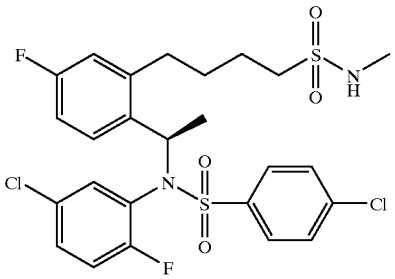

$R_f$=0.22 (2:1 hexanes:ethyl acetate) $^1$H NMR (300 MHz CDCl$_3$) δ (ppm): 7.68–7.58 (m, 2H), 7.49–7.41 (m, 2H), 7.25–6.51 (m, 6H), 5.91–5.89 (m, 1H), 4.50–4.48 (br, 1H), 3.21–3.01 (m, 3H), 2.84–2.82 (m, 4H), 2.01–1.83 (m, 4H), 1.49–1.47 (r, 3H). LC-MS calculated for $C_{25}H_{26}Cl_2F_2N_2O_4S_2$ [M+] 591; Observed: 288 (M$^+$-303).

EXAMPLE 449

4-Chloro-N-phenyl-N-[2-(3-sulfanylpropoxy)benzyl]benzenesulfonamide

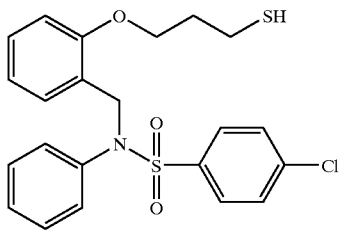

Numerous compounds according to the invention can be prepared employing the general scheme set forth in SCHEME 449.

SCHEME 449

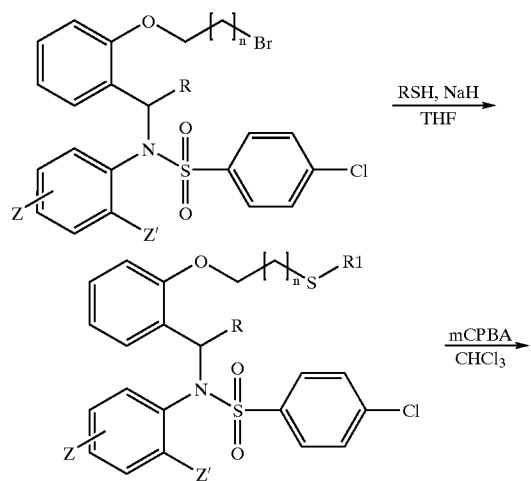

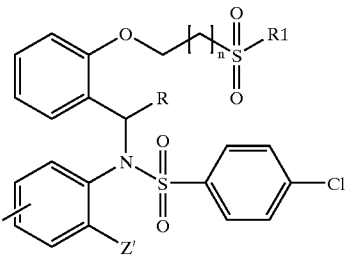

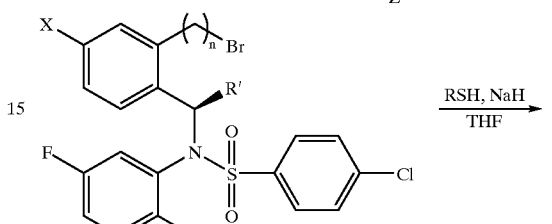

R' = H, CH$_3$
n = 1–4
x = H, F

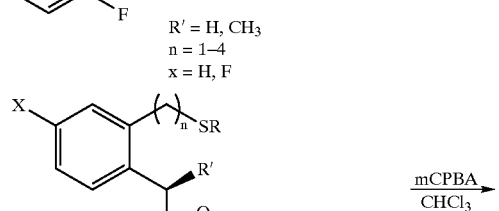

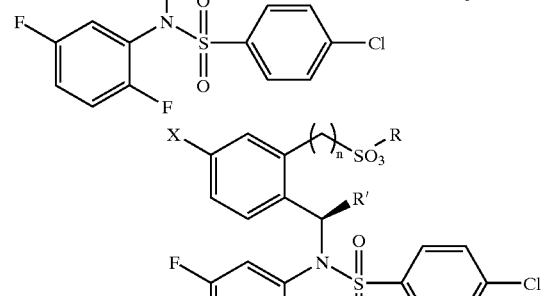

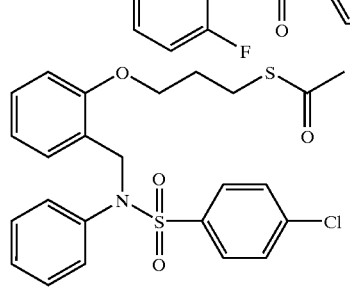

To a stirred solution of N-2-(3-bromopropyloxy)benzyl 4-chlorobenzenesulfanilide (200 mg, 0.4 mmol) in DMF (5 mL) was added the potasium salt of thio acetic acid (92 mg, 0.81 mmol). The reaction mixture was then warmed to 60° C. After 3 h, the reaction mixture was cooled to room temperature, diluted with ethyl acetate (25 mL), washed with saturated bicarbonate solution (3×10 mL) and saturated brine (2×10 mL), dried with MgSO$_4$, filtered and concentrated under reduced pressure to isolate a colorless oil which was purified by SiO$_2$ chromatography (7:1, hexanes:ethyl acetate) to afforded the desired product (130 mg, y: 63%). $R_f$=0.25 (20% ethyl acetate/exanes) $^1$H NMR (300 MHz, CDCl$_3$) δ (ppm): 7.60–7.56 (m, 2H), 7.46–7.42 (m, 2H), 7.36 (dd, 1H), 7.23–7.7.12 (dd, 2H), 6.85 (t, 1H), 6.70 (d, 1H), 4.82 (s, 2H), 3.85 (t, 2H), 2.95 (t, 2H), 2.33 (s, 3H), 1.92 (q, 2H), $^{13}$C NMR (75 MHz, CDCl$_3$) δ (ppm): 196.0, 156.7, 139.6, 139.4, 137.5, 130.7, 129.5, 129.3, 129.3, 128.3, 124.5, 121.0, 111.3, 66.4, 49.8, 31.1, 29.6, 26.2.

A stirred solution of thio acetate analog prepared above (100 mg, 0.2 mmol) at ° C. in ethanol (5 mL) was vigorously degassed for 0.5 h, then a solution of degassed 1.0 N NaOH (0.4 mL, 0.4 mmol) was added. The reaction mixture was allowed stir at 0° C. for 1 h, warmed to room temperature and stirred at room temperature for 1 h, then diluted with degassed ethyl acetate (20 mL), washed with saturated bicarbonate solution (3×10 mL), 10% aqueous HCl (3×10 mL), dried with MgSO$_4$, filtered and concentrated under reduced pressure to isolate a white solid. The crude material was purified by chromatography on SiO$_2$ (4:1 hexanes:ethyl acetate) to give 40 mg of product (y: 44%). R$_f$=0.25 (20% ethyl acetate/hexanes) $^1$H NMR (300 MHz, CDCl$_3$) δ (ppm): 7.58–7.56 (m, 2H), 7.47–7.54 (m, 2H), 7.34–7.14 (m, 5H), 6.99 (m, 2H), 6.87–6.73 (dt, 2H), 4.78 (s, 2H), 3.92 (t, 2H), 2.63 (q, 2H), 1.96 (q, 2H), 1.35 (t, 1H). $^{13}$C NMR (75 MHz, CDCl$_3$) δ (ppm): 159.1, 141.9, 141.8, 139.9, 133.1, 131.8, 131.8, 131.7, 131.6, 130.6, 126.7, 123.2, 113.7, 68.2, 52.2, 35.8, 24.0.

Using the preparative scheme outlined above, the compounds of Examples 450–464 were prepared.

EXAMPLE 450

N-(2,5-difluorophenyl)-4-(phenylsulfanyl)-N-{2-[3-(phenylsulfanyl)propoxy]benzyl}benzenesulfonamide

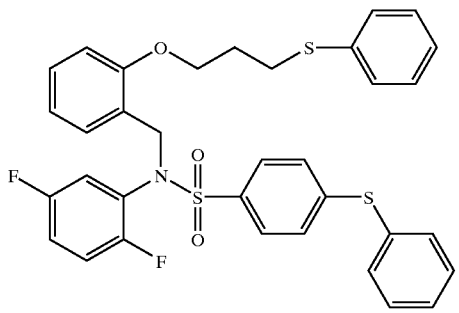

R$_f$=0.54 (4:1 hexanes:ethyl acetate), $^1$H NMR (300 MHz, CDCl$_3$) δ (ppm): 7.63 (d, 2H), 7.54–7.50 (m, 5H), 7.33–7.26 (r, 6H), 7.18 (t, 5H), 6.97 (m, 1H), 6.87–6.79 (m, 2H), 4.70 (s, 2H), 3.94 (t, 2H), 3.08 (t, 2H), 1.90–1.86 (m, 2H).

EXAMPLE 451

4-Chloro-N-(2,5-difluorophenyl)-N-{2-[3-(phenylsulfanyl)propoxy]benzyl}benzenesulfonamide

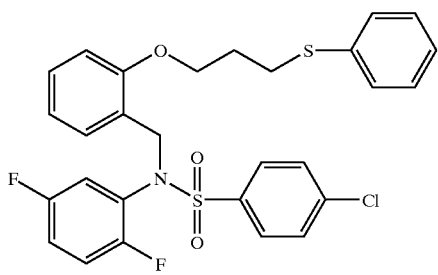

R$_f$=0.45 (6:1 hexanes:ethyl acetate), $^1$H NMR (300 MHz, DMSO) δ (ppm): 7.72 (q, 4H), 7.34–7.18 (m, 8H), 7.00–6.98 (m, 2H), 6.89–6.80 (m, 2H), 4.73 (s, 2H), 3.95 (t, 2H), 3.09 (t, 2H), 1.91–1.87 (m, 2H).

EXAMPLE 452

4-Chloro-N-(2,5-difluorophenyl)-N-{2-[3-(phenylsulfonyl)propoxy]benzyl}benzenesulfonamide

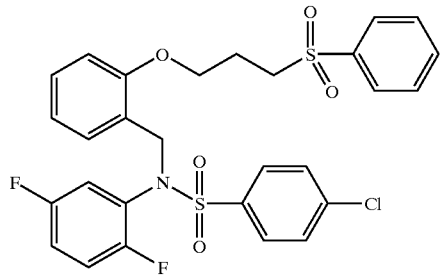

R$_f$=0.40 (3:1 hexanes:ethyl acetate), $^1$H NMR (300 MHz, CDCl$_3$) δ (ppm): 7.96 (d, 2H), 7.68–7.54 (m, 5H), 7.47 (d, 2H), 7.19–7.10 (m, 2H), 6.93–6.68 (m, 5H), 4.77 (s, 2H), 3.97 (t, 2H), 3.38 (t, 2H), 2.24–2.15 (m, 2H).

EXAMPLE 453

4-Chloro-N-{2-[3-(cyclohexylsulfanyl)propoxy]benzyl}-N-(2,5-difluorophenyl)benzenesulfonamide

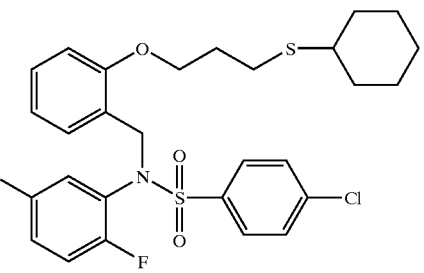

R$_f$=0.26 (5% methanol in DCM), $^1$H NMR (300 MHz, CDCl$_3$) δ (ppm): 7.66 (d, 2H), 7.47 (m, 2H), 7.28–7.15 (m, 1H), 7.00 (d, 1H), 6.90 (m, 2H), 6.75 (m, 3H), 4.81 (s, 2H), 3.92 (m, 2H), 2.66 (m, 3H), 1.94 (m, 4H), 1.75 (m, 2H), 1.60 (m, 2H), 1.28 (m, 4H).

EXAMPLE 454

4-Chloro-N-{2-[3-(cyclohexylsulfonyl)propoxy]benzyl}-N-(2,5-difluorophenyl)benzenesulfonamide

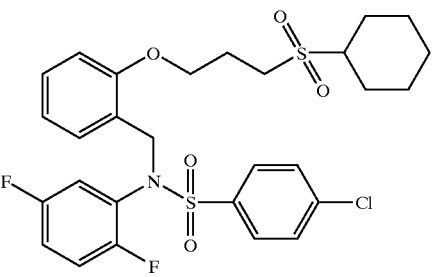

R$_f$=0.29 (3:1 hexanes:ethyl acetate), $^1$H NMR (300 MHz, CDCl$_3$) δ (ppm): 7.65 (d, 2H), 7.48 (d, 2H), 7.18 (t, 1H), 7.80 (d, 2H), 6.90 (m, 2H), 6.76 (m, 3H), 4.78 (s, 2H), 4.10 (t, 2H), 3.29 (t, 2H), 2.94 (m, 1H), 2.35 (m, 2H), 2.22 (d, 2H), 1.90 (m, 2H), 1.72–1.19 (m, 6H). MS calculated for C$_{28}$H$_{30}$ClF$_2$NO$_5$S$_2$, [MNa$^+$] 620; Observed: 620.

EXAMPLE 455

4-Chloro-N-{2-[3-(cyclohexylsulfinyl)propoxy]benzyl}-N-(2,5-difluorophenyl)benzenesulfonamide

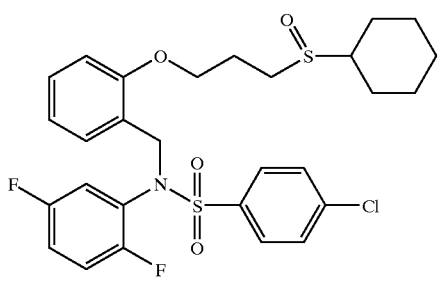

R$_f$=0.32 (1:1 hexanes:ethyl acetate), $^1$H NMR (300 MHz, CDCl$_3$) δ (ppm): 7.64 (d, 2H), 7.47 (d, 2H), 7.19 (t, 1H), 7.08 (d, 2H), 6.92–6.87 (m, 2H), 6.80–6.76 (m, 3H), 4.79 (s, 2H), 4.16–3.98 (m, 2H), 3.12–3.03 (m, 1H), 2.87–2.78 (m, 1H), 2.17–2.60 (m, 1H), 2.34 (m, 2H), 2.14 (d, 1H), 1.95–1.69 (m, 3H), 1.57–1.24 (m, 6H). MS calculated for C$_{28}$H$_{30}$ClF$_2$NO$_4$S$_2$, [MH] 5682; Observed: 682.

EXAMPLE 456

N-(4-bromophenyl)-4-chloro-N-{2-[3-(1-piperidinyl)propoxy]benzenesulfonamide Hydrochloride

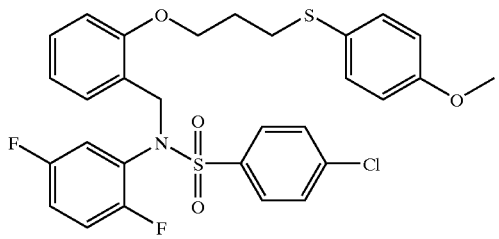

R$_f$=0.44 (6:1 hexanes:ethyl acetate), $^1$H NMR (300 MHz, CDCl$_3$) δ (ppm): 7.67–7.64 (m, 2H), 7.48–7.44 (m, 2H), 7.35–7.32 (m, 2H), 7.31–7.15 (m, 3H), 6.96–6.70 (m, 8H), 4.77 (m, 2H), 3.94–3.86 (m, 2H), 3.77 (m, 3H), 2.97–2.92 (m, 2H), 1.97–1.88 (m, 2H). MS calculated for C$_{29}$H$_{26}$ClF$_2$NO$_4$S$_2$, [MNa$^+$] 612; Observed: 612.

EXAMPLE 457

4-Chloro-N-(2,5-difluorophenyl)-N-(2-{3-[(4-methoxyphenyl)sulfonyl]propoxy}benzyl)benzenesulfonamide

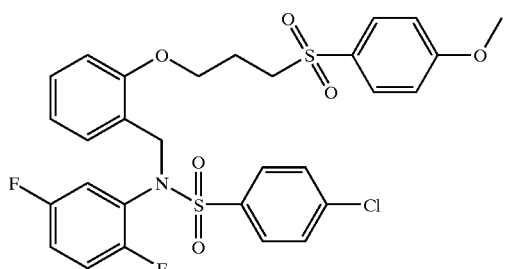

R$_f$=0.42 (2:1 hexanes:ethyl acetate), $^1$H NMR (300 MHz, CDCl$_3$) δ (ppm): 7.87 (d, 2H), 7.63 (d, 2H), 7.47 (d, 2H), 7.26–7.11 (m, 2H), 7.00 (d, 2H), 6.91–6.75 (m, 4H), 6.69 (d, 1H), 4.74 (s, 2H), 3.96 (t, 2H), 3.86 (s, 3H), 3.36–3.31 (m, 2H), 2.22–2.13 (m, 2H). MS calculated for C$_{29}$H$_{26}$ClF$_2$NO$_6$S$_2$, [MNa$^+$]644; Observed: 644.

EXAMPLE 458

4-Chloro-N-(2,5-difluorophenyl)-N-(2-{3-[(4-methoxyphenyl)sulfinyl]propoxy}benzyl)benzenesulfonamide

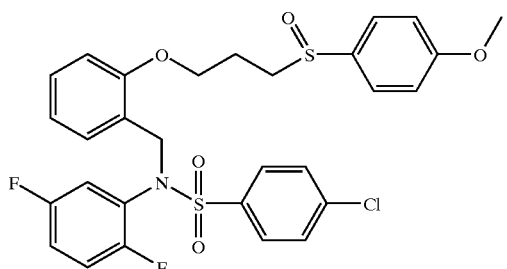

R$_f$=0.23 (1:1 hexanes:ethyl acetate), $^1$H NMR (300 MHz, CDCl$_3$) δ (ppm): 7.66–7.54 (m, 4H), 7.49 (d, 2H), 7.20–7.11 (m, 2H), 7.03 (d, 2H), 6.94–6.76 (m, 4H), 6.71 (d, 10H), 4.76 (s, 2H), 4.05–3.84 (m, 5H), 3.15–2.90 (m, 2H), 2.26–2.00 (m, 2H).). MS calculated for C$_{29}$H$_{26}$ClF$_2$NO$_5$S$_2$, [a+] 628; Observed: 628.

EXAMPLE 459

4-Chloro-N-(2,5-difluorophenyl)-N-(2-{3-[(4-nitrophenyl)sulfonyl]propoxy}benzyl)benzenesulfonamide

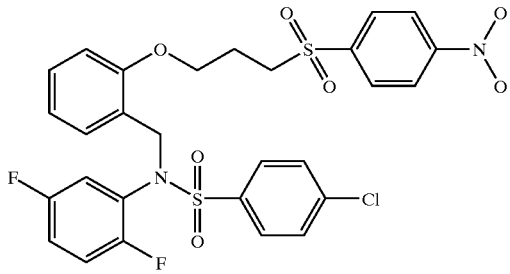

R$_f$=0.56 (2:1 hexanes:ethyl acetate), $^1$H NMR (300 MHz, CDCl$_3$) δ (ppm):8.40 (d, 2H), 8.25 (d, 2H), 7.59 (d, 2H), 7.48 (d, 2H), 7.19–7.14 (t, 111, 6.89–6.82 (m, 3H), 6.75–6.64 (m, 3H), 4.73 (s, 2H), 4.1 (t, 2H), 3.65 (m, 2H), 2.38–2.33 (m, 2H).

EXAMPLE 460

4-Chloro-N-2,5-difluorophenyl)-N-(2-{3-[(4-nitrophenyl)sulfanyl]propoxy}benzyl)benzenesulfonamide

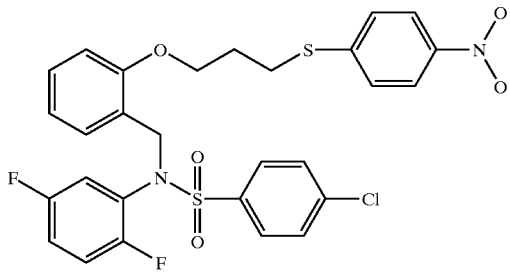

R$_f$=0.40 (6:1 hexanes:ethyl acetate), $^1$H NMR (300 MHz, CDCl$_3$) δ (Ppm): 8.12–8.09 (m, 2H), 7.67–7.63 (m, 2H), 7.49–7.45 (m, 2H), 7.41–7.37 (m, 2H), 7.22–7.16 (m, 1H), 7.12–7.09 (m, 1H), 6.91–6.74 (m, 5H), 4.82 (s, 2H), 4.05 (t, 2H), 3.32 (t, 2H), 2.19 (m, 2H).

EXAMPLE 461

4-Chloro-N-(2,5-difluorophenyl)-N-(2-{3-[(4-nitrophenyl)sulfinyl]propoxy}benzyl)benzenesulfonamide

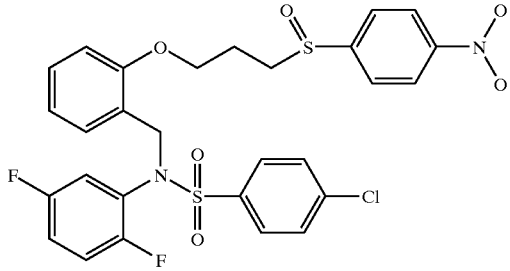

R$_f$=0.53 (1:1 hexanes:ethyl acetate), $^1$H NMR (300 MHz, CDCl$_3$) δ (ppm): 8.36 (d, 2H), 7.93 (d, 2H), 7.64 (d, 2H), 7.50 (d, 2H), 7.17 (m, 1H), 6.91–6.80 (m, 3H), 6.74–6.65 (m, 3H), 4.76 (s, 2H), 4.19–4.02 (m, 2H), 0.356–3.47 (m, 1H), 3.23–3.14 (m, 1H), 2.47–2.41 (m, 1H0, 2.17–2.13 (m, 1H).

EXAMPLE 462

4-Chloro-N-{2-[2-(cyclohexylsulfinyl)ethoxy]benzyl)-N-(2,5-difluorophenyl)benzenesulfonamide

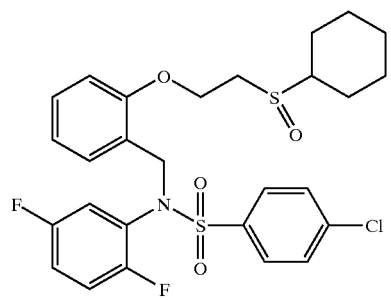

R$_f$=0.35 (1:2 hexanes:ethyl acetate), $^1$H NMR (300 MHz, CDCl$_3$) δ (ppm): 7.65 (d, 2H), 7.47 (d, 2H), 7.22–7.11 (m, 2H), 6.94–6.80 (m, 5H), 4.84 (d, 1H), 4.70 (d, 1H), 4.47–4.27 (m, 2H), 3.19–3.10 (m, 1H), 2.94 (dt, 1H), 2.65 (tt, 1H), 2.14 (d, 1H), 2.04–1.88 (m, 31), 1.73 (m, 1H), 1.59–1.25 (m, 4H).

EXAMPLE 463

4-Chloro-N-{2-[2-(cyclohexylsulfonyl)ethoxy]benzyl}-N-(2,5-difluorophenyl)benzenesulfonamide

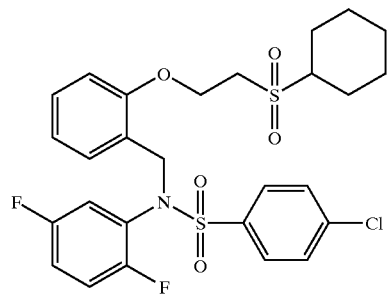

R$_f$=0.30 (3:1 hexanes:ethyl acetate), $^1$H NMR (300 MHz, CDCl$_3$) δ (ppm): 7.65 (d, 2H), 7.47 (d, 2H), 7.26–7.18 (m, 2H), 6.97–6.81 (m, 5H), 4.78 (s, 2H), 4.35 (t, 2H), 3.38 (t, 2H), 2.92 (tr, 1H), 2.20 (d, 2H), 2.05 (m, 2H), 1.74–1.55 (m, 3H), 1.334–1.20 (m, 3H).

EXAMPLE 464

4-Chloro-N-{2-[2-cyclohexylsulfanyl)ethoxy]benzyl}-N-(2,5-difluorophenyl)benzenesulfonamide

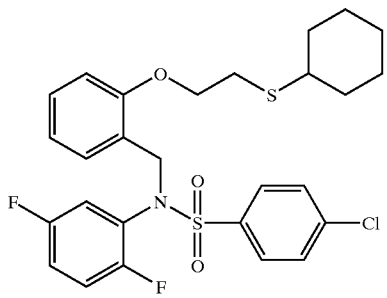

$R_f$=0.30 (15:1 hexanes:ethyl acetate), $^1$H NMR (300 MHz, CDCl$_3$) δ (ppm): 7.67 (d, 2H), 7.56 (d, 2H), 7.34 (d, 1H), 7.19 (t, 1H), 6.95–6.86 (m, 4H), 6.72 (d, 1H), 4.79 (s, 2H), 3.93 (t, 2H), 2.74 (t, 2H), 2.67 (m, 1H), 1.95 (br, 2H), 1.77 (br, 2H), 1.63–1.27 (m, 6H).

EXAMPLE 465

4-Chloro-N-(2,5-difluorophenyl)-N-(1R)-1-{2-[(ethylsulfonyl)methyl]4-fluorophenyl}ethyl)benzenesulfonamide

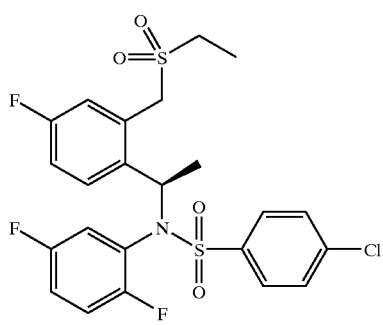

$R_f$=0.4 (3:1;hexanes:ethyl acetate). $^1$H NMR (CDCl$_3$) δ (ppm): 7.75–7.65 (m, 2H), 7.55–7.44 (m, 2H), 7.17–6.24 (m, 6H), 6.08 (q, 1H), 5.56 (overlapping doublets, 1H), 4.17 (overlapping doubletes, 1H), 3.30–3.20 9m, 2H), 1.61–1.55 (m, 3H), 1.34 (d, 3H). LC-MS calculated for C$_{23}$H$_{21}$ClF$_3$NO$_4$S$_2$ [M+] 532; Observed: 229 (M$^+$-303).

EXAMPLE 466

Methyl 3-{[2-((1R)-1-{[(4-chlorophenyl)sulfonyl]-2,5-difluoroanilino}ethyl)-5-fluorobenzyl]sulfonyl}propanoate

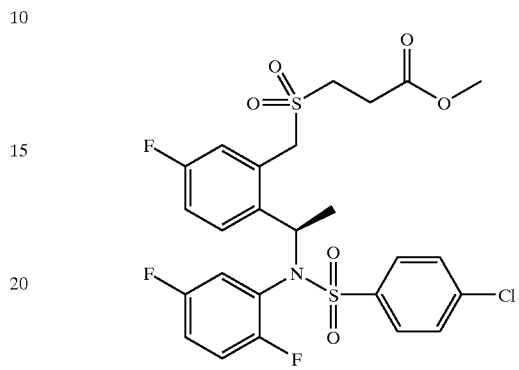

$R_f$=0.50 (2:1;hexanes:ethyl acetate). $^1$H NMR (CDCl$_3$) δ (ppm): 7.81–7.67 (m, 2H), 7.57–7.47 (m, 2H), 7.17–6.27 (m, 6H), 6.15–6.03 (m, 1H), 5.62–5.58 (overlapping doublets, 1H), 4.26–4.22 (overlapping doublets, 1 μl), 3.80 (s, 3H), 3.72–3.51 (m, 2H), 3.12–3.05 (m, 2H), 1.39–1.25 (br, 3H). LC-MS cacld for C$_{25}$H$_{23}$ClF$_3$NO$_6$S$_2$: 590. Observed: 608 (M$^+$+H$_2$O).

EXAMPLE 467

3-{[2-((1R)-1-{[(4-chlorophenyl)sulfonyl]-2,5-difluoroanilino}ethyl)-5-fluorobenzyl]sulfonyl}propanoic Acid

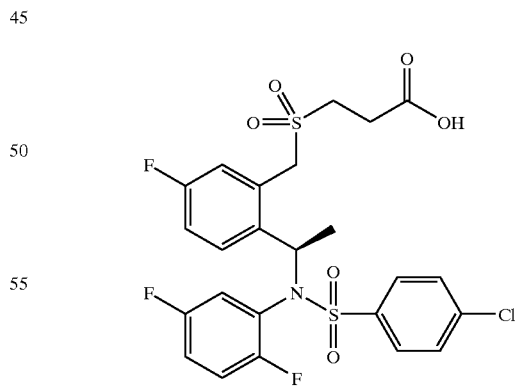

$R_f$=0.55 (6:1;DCM:methanol). $^1$H NMR (CD$_3$OD) δ (ppm):7.83–7.54 (m, 4H), 721–6.32 (m, 6H), 6.10–6.07 (m, 1H), 5.49–5.44 (m, 1H), 4.64–4.53 (m, 1H), 3.64–3.51 (m, 2H), 3.05–2.93 (m, 2H) 1.38 (d, 3H). LC-MS cacld for C$_{24}$H$_{21}$ClF$_3$NO$_6$S$_2$: 576. Observed: 576 (Me).

EXAMPLE 468

Methyl (2R)-2-[(tert-butoxycarbonyl)amino]-3-{[2-((1R)-1-{[(4-chlorophenyl)sulfonyl]-2,5-difluoroanilino}ethyl)-5-fluorobenzyl]sulfanyl}propanoate

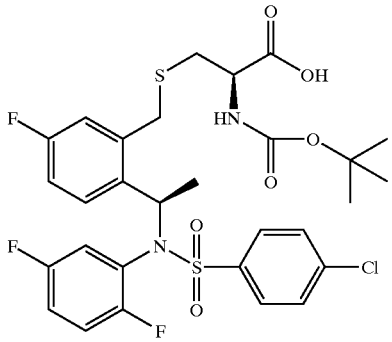

$R_f$=0.47 (3:1;hexanes:ethyl acetate). $^1$H NMR (CDCl$_3$) δ (ppm): 7.74–7.63 (m, 2H), 7.49–7.39 (m, 2H), 7.05–6.41 (m, 6H), 6.05 (br, 1H), 5.53 (br, 1H), 4.68–4.62 (m, 1H), 4.47–4.38 (m, 1H), 3.81–3.76 9m, 4H0, 3.07–2.97 (m, 2H), 1.48–1.37 (br overlaps s, 12H). LC-MS cacld for C$_{30}$H$_{32}$ClF$_3$N2O$_6$S$_2$: 673. Observed: 573 (M$^+$-Boc).

EXAMPLE 469

Methyl (2R)-2-[(tert-butoxycarbonyl)amino]-3-{[2-((1R)-1-{[(4-chlorophenyl)sulfonyl]-2,5-difluoroanilino}ethyl)-5-fluorobenzyl]sulfonyl}propanoate

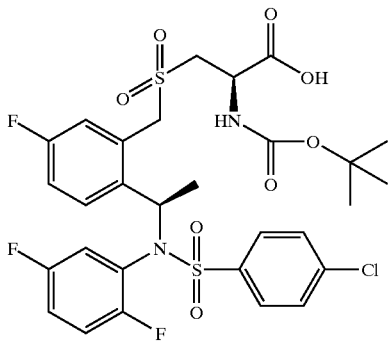

$R_f$=0.25 (3:1;hexanes:ethyl acetate). $^1$H NMR (CDCl$_3$) δ (ppm): 7.80–7.69 (m, 2H), 7.58–7.47 (m, 2H), 7.16–7.01 (m, 2H), 6.89–6.62 (m, 3H), 6.31–5.91 (m, 2H), 5.61 (br, 1H), 4.91 (br, 1H), 4.31–4.21 (m, 1H), 3.92–3.84 (m overlaps s, 5H), 1.50 (s, 9H), 1.36–1.34 (br, 3H). LC-MS cacld for C$_{30}$H$_{32}$ClF$_3$N2O$_8$S$_2$: 705. Observed: 605 (M$^+$-Boc).

EXAMPLE 470

Methyl 2-amino-3-{[2-(1R)-1-{[(4-chlorophenyl)sulfonyl]-2,5-difluoroanilino}ethyl)-5-fluorobenzyl]sulfonyl}propanoate Hydrochloride

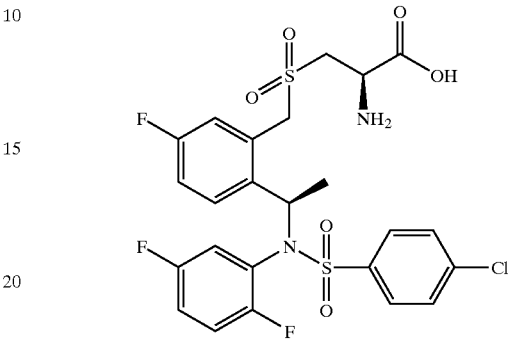

$R_f$=0.50 (2:1;hexanes:ethyl acetate). $^1$H NMR (CDCl$_3$) δ (ppm): 7.76–7.64 (m, 2H), 7.53–7.43 (m, 2H), 7.24–7.16 (m, 1H), 7.05–6.33 (m, 5H), 6.13 (br, 1H), 5.57 9d, 1H), 4.82–4.68 (r, 2H), 3.84–3.0 (br overlaps s, 7H), 137–1.35 (br, 31.1). LC-MS cacld for C$_{25}$H$_{24}$ClF$_3$N$_2$O$_6$S$_2$: 604. Observed: 605 (MH$^+$).

EXAMPLE 471

Methyl (2S)-2-[(tert-butoxycarbonyl)amino]-3-{[2-((1R)-1-{[(4-chlorophenyl)sulfonyl]-2,5-difluoroanilino}ethyl)-5-fluorobenzyl]sulfonyl}propanoate

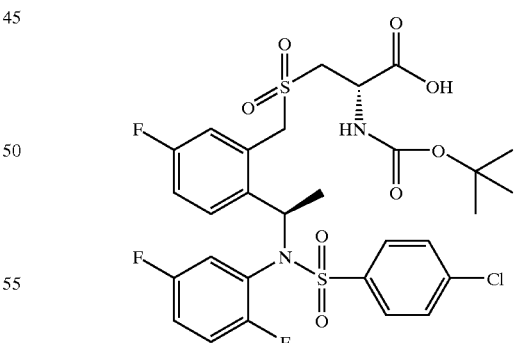

$R_f$=0.25 (2:1;hexanes:ethyl acetate). $^1$H NMR (CDCl$_3$) δ (ppm): 7.76–7.63 (m, 2H), 7.53–7.41 (m 2H), 7.71–7.00 (m, 3H), 6.87–6.32 (m, 3H), 6.11–5.81 (m, 2H), 5.63 (m, 1H), 4.81 {br, 1H), 4.59–4.23 (m, 1H), 3.94–3.88 (m, 2H), 3.85 (s, 3H), 1.48 (s, 9H), 1.37–1.35 (br, 3H). LC-MS cacld for C$_{30}$H$_{32}$ClF$_3$N$_2$O$_8$S$_2$: 705. Observed: 605 (M$^+$-Boc).

EXAMPLE 472

4-Chloro-N-(2,5-difluorophenyl)-N-((1R)-1-[2-[2-(ethylsulfonyl)ethyl]-4-fluorophenyl}ethyl)benzenesulfonamide

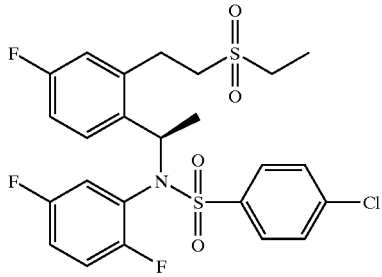

$R_f$=0.28 (3:1;hexanes:ethyl acetate). $^1$H NMR (CDCl$_3$) δ (ppm): 7.68–7.58 (m, 2H), 7.49–7.48 (m, 2H), 7.05–6.41 (m, 6H), 5.89 (q, 1H), 3.54–3.20 (m, 6H), 1.50–1.41 (m, 6H).). LC-MS calculated for $C_{24}H_{23}ClF_3NO_4S_2$ 546; Observed: 242 (M$^+$-303).

EXAMPLE 473

Methyl 3-({2-[2-((1R)-1-{1 (4-chlorophenyl)sulfonyl]-2,5-difluoroanilino}ethyl)-5-fluorophenyl]ethyl}sulfanyl)propanoate

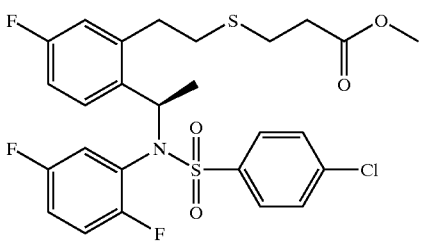

$R_f$=0.33 (6:1;hexanes:ethyl acetate). $^1$H NMR (CDCl$_3$) δ μm): 7.67–7.54 (m, 2H), 7.44–7.35 (m, 2H), 7.00–6.28 (m, 6H), 5.93–5.81 (m, 1H), 3.68 (s, 3H), 3.40–3.28 9m, 1H), 2.99–2.65 (m, 7H), 1.53 (br 3H). LC-MS cacld for $C_{26}H_{25}ClF_3NO_4S_2$: 572. Observed: 269 (M$^+$-303).

EXAMPLE 474

Methyl 3-({2-[2-((1R)-1-{[(4-chlorophenyl)sulfonyl]-2,5-difluoroanilino}ethyl)-5-fluorophenyl]ethyl}sulfonyl)propanoate

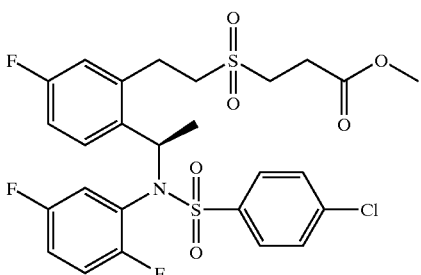

$R_f$=0.50 (2:1;hexanes:ethyl acetate). $^1$H NMR (CDCl$_3$) (ppm): 7.72–7.59 (m, 2H), 7.50–7.40 9m, 2H), 7.08–6.42 (m, 6H), 5.97–5.83 (m, 1H), 3.72 (s, 3H), 3.57–3.34 (m, 6l), 2.98 (t, 3H), 1.50–1.38 (br, 3H). LC-MS cacld for $C_{26}H_{25}ClF_3NO_6S_2$: 640. Observed: 621 (M$^+$+H$_2$O).

EXAMPLE 475

3-({2-[2-((1R)-1-{[(4-chloro-phenyl)sulfonyl]-2,5-difluoroanilino}ethyl)-5-fluorophenyl]ethyl}sulfonyl)propanoic Acid

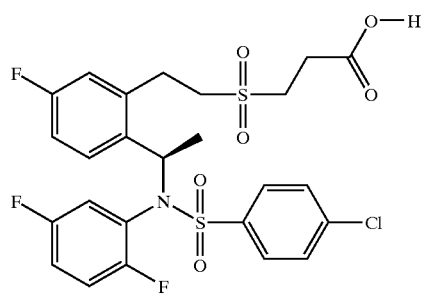

$R_f$=0.48 (10:1;DCM:methanol). $^1$H NMR (CD$_3$OD) δ (ppm): 7.89–7.63 (m, 2H), 7.58–7.51 (m, 2H), 7.21–7.00 (m, 3H), 6.89–6.45 (m, 3H), 5.95–5.90 (m, 1H), 3.60–3.50 (m, 4H), 3.23–3.22 (m, 2H), 2.91–2.83 (m, 2H), 1.55–1.42 (br, 3H). LC-MS cacld for $C_{25}H_{23}ClF_3NO_6S_2$: 589. Observed: 589 (M+).

EXAMPLE 476

Methyl ({2-[2-((1R)-1-{[(4-chlorophenyl)sulfonyl]-2,5-difluoroanilino}ethyl)-5-fluorophenyl]ethyl}sulfinyl)acetate

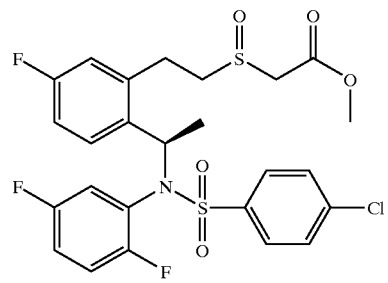

$R_f$=0.45 (1:1;hexanes:ethyl acetate). $^1$H NMR (CDCl$_3$) δ (ppm): 7.75–7.58 (m, 2H), 7.50–7.40 (m, 2H), 7.08–6.88 (m, 3H), 6.88–6.42 (m, 3H), 5.92–5.87 (r, 1H), 3.98–3.79 (m overlaps s, 5H), 3.59–3.21 (m, 4H), 1.49–1.44 (m, 3H). LC-MS cacld for $C_{25}H_{23}ClF_3NO_5S_2$: 574. Observed: 271 (M$^+$-303).

EXAMPLE 477

Methyl ({2-[2-((1R)-1-[[(4-chlorophenyl)sulfonyl]-2,5-difluoroanilino}ethyl)-5-fluorophenyl]ethyl}sulfanyl)acetate

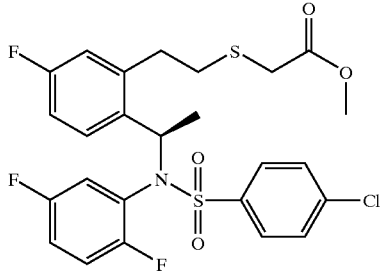

$R_f$=0.40 (6:1;hexanes:ethyl acetate). $^1$H NMR (CDCl$_3$) δ (ppm): 7.71–7.58 (m, 2H), 7.48–7.39 (m, 2H), 7.01–6.33 (m, 6H), 5.90 (q, 1H), 3.78 (s, 3H), 3.47–3.45 (m, 3H), 3.00–2.91 (m, 3H), 1.55–1.47 (br, 3H). LC-MS cacld for $C_{25}H_{23}ClF_3NO_4S_2$: 558. Observed: 255 (M$^+$-303).

EXAMPLE 478

Methyl ({2-[2-((1R)-1-{[(4-chlorophenyl)sulfonyl]-2,5-difluoroanilino}ethyl)-5-fluorophenyl]ethyl}sulfonyl)acetate

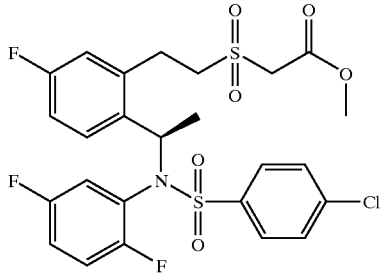

$R_f$=0.45 (2:1;hexanes:ethyl acetate). $^1$H NMR (CDCl$_3$) δ (ppm): 7.71–7.61 (m, 2H), 7.51–7.39 (m, 2H), 7.07–6.37 (m, 6H), 5.95–5.89 (m, 1H), 4.39–4.34 (m, 1H), 4.15–4.10 (m, 1H), 3.87 (s, 3H), 3.75–3.61 (m, 3H), 3.41–3.31 (m, 1H), 1.51–1.41 (br, 3H). LC-MS cacld for $C_{25}H_{23}ClF_3NO_6S_2$: 590. Observed: 287 (M$^+$-303).

EXAMPLE 479

Methyl ({2-[2-((1R)-1-{[(4-chlorophenyl)sulfonyl]-2,5-difluoroanilino}ethyl)-5-fluorophenyl]ethyl}sulfonyl)acetate

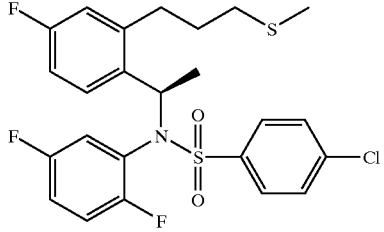

$R_f$=0.30 (10:1;hexanes:ethyl acetate). $^1$H NMR (CDCl$_3$) δ (ppm): 7.71–7.57 (m, 2H), 7.44–7.37 (m, 2H), 7.00–6.31 (m, 6H), 5.88 (q, 1H), 3.21–3.09 (m, 1H), 2.83–2.73 (m, 1H), 2.62 (m, 2H), 2.16 (s, 3H), 1.99–1.89 (m, 2H), 1.54 (br, 3H).). LC-MS calculated for $C_{24}H_{23}ClF_3NO_2S_2$ [M+] 514; Observed: 211 (M$^+$-303).

EXAMPLE 480

N-(2,5-difluorophenyl)-N-((1R)-1-{4-fluoro-2-[3-(methylsulfanyl)propyl]phenyl}ethyl)-4-(methylsulfanyl)benzenesulfonamide

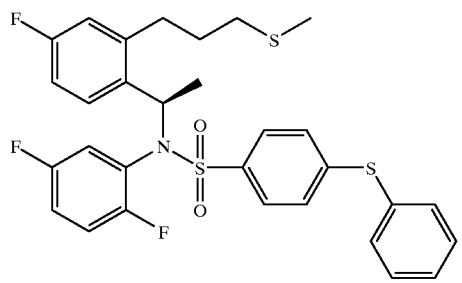

$R_f$=0.39 (5:1;hexanes:ethyl acetate). $^1$H NMR (CDCl) δ (ppm): 7.64–7.50-(m, 2H), 7.23–7.15 (m, 2H), 7.00–6.84 (m, 3H), 6.69–6.33 (m, 3H), 5.88–5.79 (m, 1H), 2.21–3.10 (m, 1H), 2.78–2.72 (m, 1H0, 2.61 9t, 2H), 2.49 9s, 3H0, 2.14 (s, 3H), 1.98–1.90 (m, 2H), 1.54–1.50 (br, 3H).). LC-MS calculated for $C_{25}H_{26}F_3NO_2S_3$ [M+] 525; Observed: 548 (M+Na).

EXAMPLE 481

4-Chloro-N-(2,5-difluorophenyl)-N-((1R)-1-}4-fluoro-2-[3-(methylsulfonyl)propyl]phenyl}ethyl)benzenesulfonamide

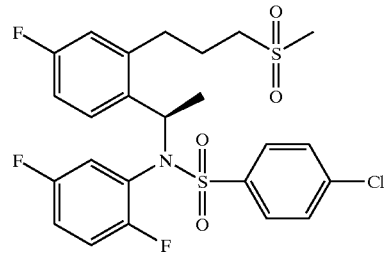

$R_f$=0.19 (2:1;hexanes:ethyl acetate). $^1$H NMR (CDCl$_3$) δ (ppm): 7.73–7.59 (m, 2H), 7.51–7.41 (m, 2H), 7.05–6.30- (m, 6H), 5.91 (q, 1H), 3.24–3.03 (m, 4H), 2.98 (s, 3H), 2.27–2.23 (m, 2H), 1.45 (d, 3H). LC-MS calculated for $C_{24}H_{23}ClF_3NO_4S_2$ [M+] 546; Observed: 243 (M$^+$-303).

EXAMPLE 482

4-Chloro-N-(2,5-difluorophenyl)-N-((1R)-1-{2-[3-(ethylsulfanyl)propyl]-4-fluorophenyl}ethyl)benzenesulfonamide

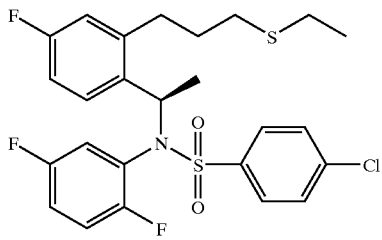

$R_f$=0.31 (10:1;hexanes:ethyl acetate). $^1$H NMR (CDCl$_3$) δ (ppm): 7.68–7.54 (m, 2H), 7.44–7.38 (m, 2H), 7.00–6.28 (m, 6H), 5.87 (q, 1H), 3.22–3.08 (m, 1H), 2.82–2.53 (m, 5H), 1.98–1.86 (m, 2H), 1.55 (br, 3H), 1.30 (t, 3H). LC-MS calculated for $C_{25}H_{25}ClF_3NO_2S_2$ [M+] 528; Observed: 225 (M$^+$-303).

EXAMPLE 483

4-Chloro-N-(2,5-difluorophenyl)-N-((1R)-1-[2-[3-(ethylsulfonyl)propyl]-4-fluorophenyl}ethyl)benzenesulfonamide

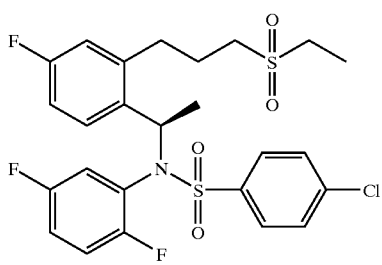

$R_f$=0.45 (2:1;hexanes:ethyl acetate). $^1$H NMR (CDCl$_3$) δ (ppm): 7.71–7.60 (m, 2H), 7.52–7.40 (m, 2H), 7.01–6.31 (m, 6H), 5.90 (q, 1H), 3.22–2.87 (m, 6H), 2.33–2.19 (m, 2H), 1.45–1.40 (m, 6H). LC-MS calculated for $C_{25}H_{25}ClF_3NO_4S_2$ [M+] 560; Observed: 257 (M$^+$-303).

EXAMPLE 484

N-(2,5-difluorophenyl)-4-(ethylsulfanyl-N-((1R)-{2-[3-(ethylsulfanyl)propyl]-4-fluorophenyl}ethylbenzenesulfonamide

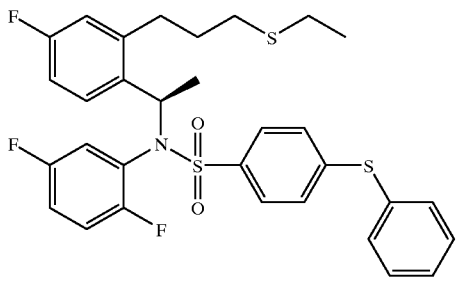

$R_f$=0.49 (5:1;hexanes:ethyl acetate). $^1$H NMR (CDCl$_3$) δ (ppm): 7.68–7.50 (m, 2H), 7.29–7.21 (m, 2H0, 7.04–6.33 (m, 6H), 5.88–5.76 (m, 1H), 3.21–3.11 9m, 1H0, 2.98 9q, 2H0, 2.83–2.71 (m, 1H), 2.68–2.56 (m overlaps q, 4H), 1.95–1.93 9m, 2H), 1.52–1.49 (br, 3H0, 1.33 (t, 3H), 1.27 (t, 3H). LC-MS cacld for $C_{27}H_{30}F_3NO_2S_3$: 553. Observed: 576 (M++Na).

EXAMPLE 485

Methyl (2R)-2-[(tert-butoxycarbonyl)amino]-3-({3-[2-(1R)-1-{[(4-chlorophenyl)sulfonyl]-2,5-difluoroanilino}ethyl)-5-fluorophenyl]propyl}sulfanyl)propanoate

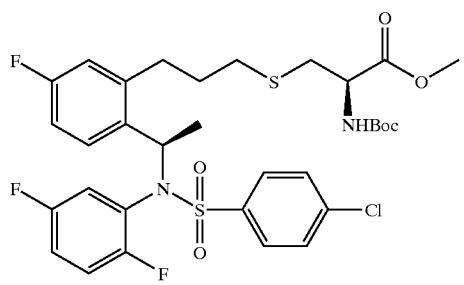

$R_f$=0.50 (3:1;hexanes:ethyl acetate). $^1$H NMR (CDCl$_3$) δ (ppm): 7.71–7.58 (m, 2H), 7.45–7.40 (m, 2H), 7.00–6.45 (m, 6H), 5.87 (q, 1H), 4.45–5.40 (br, 1H), 4.61 (br, 1H), 3.78, 3.76 (s, rotomers, 3H), 3.30–3.00 (m, 3H), 2.81–2.65 (m, 3H), 1.94–1.88 (m, 2H), 1.52–1.38 (br overlaps s, 12H). LC-MS cacld for $C_{32}H_{36}ClF_3N_2O_6S_2$: 701. Observed: 398 (MW-303).

EXAMPLE 486

Methyl (2R)-2-[(tert-butoxycarbonyl)amino]-3-{3-[2-(1R)-1-{[(4-chlorophenyl)sulfonyl]-2,5-difluoroanilino}ethyl)-5-fluorophenyl]propyl]sulfonyl)propanoate

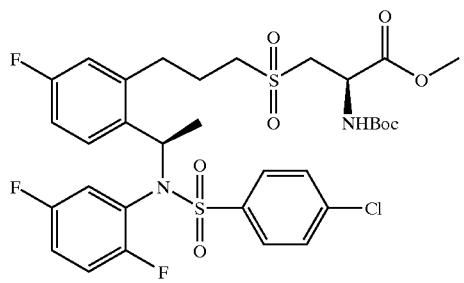

$R_f$=0.38 (2:1; hexanes:ethyl acetate). $^1$H NMR (CDCl$_3$) δ (ppm): 7.71–7.61 (m, 2H), 7.50–7.41 (m, 2H), 7.11–6.49 (m, 6H), 5.89 (q, 1H), 5.71 (br, 1H), 3.81, 3.79 (s, rotomers, 3H), 3.74–3.70 (m, 2H), 3.24–3.20 9m, 3H), 2.91 (br, 1H), 2.28–2.17 (m, 2H0, 1.45–1.45 (br overlaps s, 12H). LC-MS cacld for $C_{32}H_{36}ClF_3N_2OS_2$: 733. Observed: 633 (M$^+$-Boc).

EXAMPLE 487

Methyl (2R)-2-amino-3-({3-[2-((1R)-1-{[(4-chlorophenyl)sulfonyl]-2,5-difluoroanilino}ethyl)-5-fluorophenyl]propyl}sulfonyl)propanoate Hydrochloride

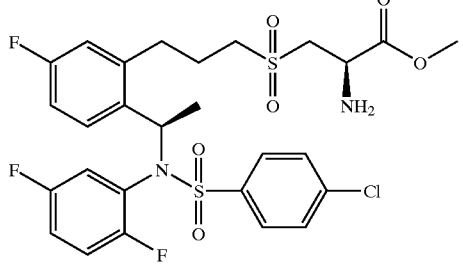

$R_f$=0.43 (2:1; hexanes:ethyl acetate). $^1$H NMR (CD$_3$OD) δ (ppm): 7.81–7.51 (m, 4H), 7.70–6.85 (m, 4H), 6.66–6.45 (m, 2H), 5.94–5.89 (m, 1H), 4.2 9br, 1H), 3.76–2.92 (s overalaps m, 9H), 2.21–2.11 (m, 2H), 1.51–1.46 (br, 3H). LC-MS cacld for $C_{27}H_{26}ClF_3N_2O_6S_2$: 632. Observed: 633 (MH$^+$).

EXAMPLE 488

4-Chloro-N-(2,5-difluorophenyl)-N-((1R)-1-{4-fluoro-2-[4-(methylsulfanyl)butyl]phenyl}ethyl)benzenesulfonamide

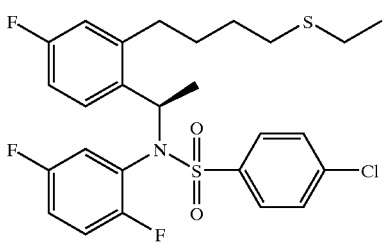

$R_f$=0.33 (9:1;hexanes:ethyl acetate). $^1$H NMR (CDCl$_3$) δ (ppm): 7.67–7.57 (m, 2H), 7.43–7.37 (m, 2H), 7.02–6.312 (m, 6H), 5.86 (q, 1H), 3.1 (br, 1H), 2.70–2.59 (m, 3H), 2.14 (s, 3H), 1.77–1.75 (m, 4H), 1.55–1.53 (br, 3H). LC-MS cacld for $C_{25}H_{25}ClF_3NO_2S_2$: 528. Observed: 225 (M$^+$-303).

EXAMPLE 489

4-Chloro-N-(2,5-difluorophenyl)-N-((1R)-1-{4-fluoro-2-[4-(methylsulfonyl)butyl]phenyl}ethyl)benzenesulfonamide

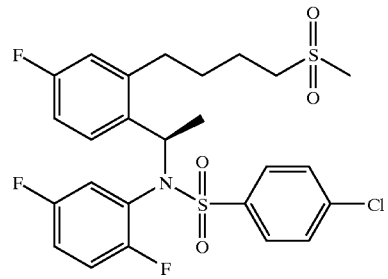

$R_f$=0.52 (1:1;hexanes:ethyl acetate). $^1$H NMR (CDCl$_3$) δ (ppm): 7.70–7.62 (m, 2H), 7.49–7.38 (m, 2H), 7.02–6.24 (m, 6H), 5.88 (q, 1H), 3.30–3.07 (m, 3H), 2.96 (s, 3H), 2.88–2.70 (m, 1H), 2.10–1.86 (m, 4H), 1.52 (d, 3H). LC-MS cacld for $C_{25}H_{25}ClF_3NO_4S$: 560. Observed: 578 (M$^+$+H$_2$O).

EXAMPLE 490

4-Chloro-N-(2,5-difluorophenyl)-N-((1R)-1-{2-[4-(ethylsulfanyl)butyl]-4-fluorophenyl}ethyl)benzenesulfonamide

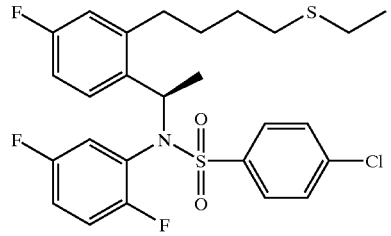

$R_f$=0.33 (9:1;hexanes:ethyl acetate). $^1$H NMR (CDCl$_3$) δ (ppm):7.68–7.58 (m, 2H), 7.45–7.38 (m, 2H), 6.99–6.31 (m, 6H), 5.85 (q, 1H), 3.1 (br, 1H), 2.70–2.61 (m, 3H), 2.57 (q, 2H), 1.78–1.73 (m, 2H), 1.53 (br, 3H), 1.28 (t, 3H). LC-MS cacld for $C_{26}H_{27}ClF_3NO_2S_2$: 542. Observed: 239 (M$^+$-303).

EXAMPLE 491

4-Chloro-N-(2,5-difluorophenyl)-N-((1R)-1-}2-[4-(ethylsulfonyl)butyl]-4-fluorophenyl}ethyl)benzenesulfonamide

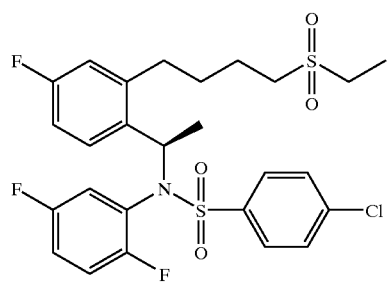

$R_f$=0.14 (3:1;hexanes:ethyl acetate). $^1$H NMR (CDCl$_3$) δ (ppm): 7.71–7.63 (m, 21H), 7.48–7.36 (m, 2H), 7.02–6.31 (m, 6H), 5.87 (q, 1H), 3.31–3.22 (m, 3H), 3.06 (q, 2H), 2.17–1.67 (m, 4H), 1.48 (d, 3H), 1.41 (t, 3H). LC-MS cacld for $C_{26}H_{27}ClF_3NO_4S_2$: 574. Observed: 592 (M$^+$+1120).

EXAMPLE 492

Numerous compounds according to the invention can be prepared employing the general scheme set forth in SCHEME 492.

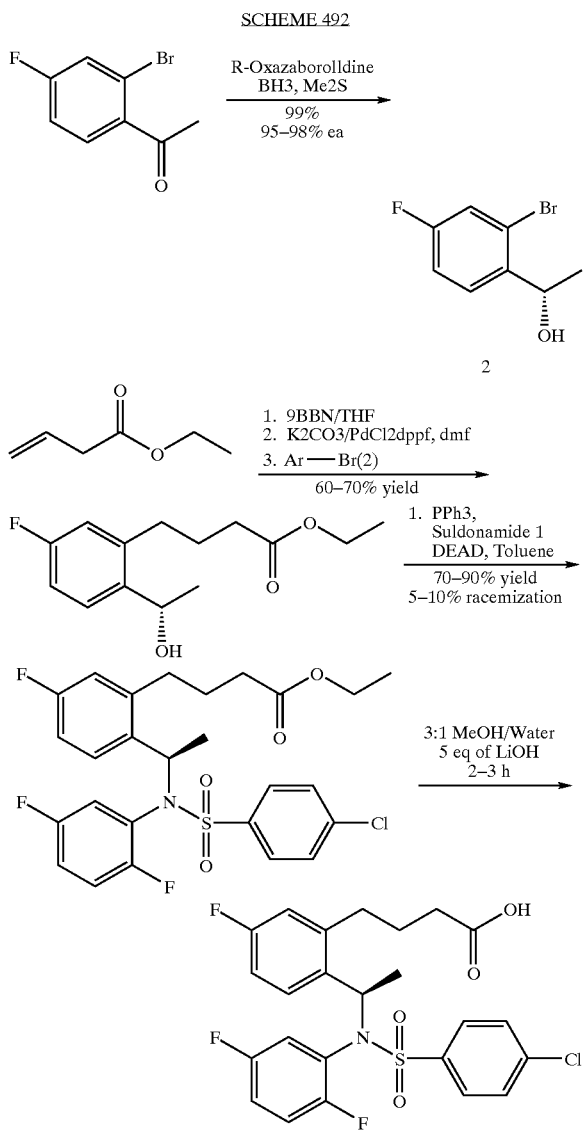

In an oven-dried two necked 100 mL round bottom flask under a vigorous stream of Ar was placed a solution of (R)—Oxazaborolidine in toluene (5.5 mL 1.27 M, 7 mmol, Strem). To this solution was slowly added $BH_3.Me_2S$ solution (8.3 mL, 83 mmol, 10.0 M, Aldrich). The reaction mixture was then cooled to −20° C. and neat ketone (30.0 g, 138 mmol, Marshalton) was added through a syringe pump over a period of 4–5 h while keeping the bath temperature at −20° C. After the addition was complete the reaction mixture was allowed to stir at −20° C. until the reaction was complete by GC (about 2 h). The reaction mixture was then carefully quenched by adding to pre-cooled methanol (−20° C.) and stirred for 1 h. The reaction mixture was then concentrated under reduced pressure and the crude product was purified by filtration through silica gel by eluting with 10:1–1:6 hexanes:ethyl acetate to separate the product from the catalyst. Isolated quantitative yield of the product. $R_f$ (10:1 hexanes:ethyl acetate) 0.32. $^1H$ NMR ($CDCl_3$) δ 7.60–7.57 (dd, 1H), 7.27–7.31 (m, 2H), 7.10–7.00 (m, 1H), 5.30–5.17 (dq, 1H), 1.99 (s, 1H), 1.49 (d, 3H).

Ethyl vinylacetate (27.98 g, 218.3 mmol) was dissolved in 100 mL of dry THF, in an oven dried flask. The flask was cooled in an ice bath and a solution of 9-BBN (0.5 M, 437 mL, 218.5 mmol, Aldrich) was added over a period of 1 h. The reaction mixture was allowed to stir at room temperature for 8 h and then added $K_2CO_3$ (70.0 g, 506 mmol), DMF (700 mL), alcohol (40 g, 182 mmol) and $PdCl_2dppf$ (4.0 g, 2.7 mol %, Aldrich). The reaction mixture was heated to 60° C. for 21 h at which time TLC shows complete consumption of the alcohol. The reaction mixture was then cooled to room temperature, filtered through celite and concentrated. The crude reaction mixture was purified by chromatography over $SiO_2$ (1.0 Kg of $SiO_2$, 5:1 hexanes:ethyl acetate) to isolate 37 g of pale yellow oil (95% pure). $^1H$ NMR ($CDCl_3$) δ 7.52–7.50 (dd, 1H), 6.96–6.82 (m, 3H), 5.15–5.11 (br q, 1H), 4.13–4.06 (q, 2H), 2.75–2.63 (m, 2H), 2.35 (t, 2H), 1.93 (p, 2H), 1.48 (d, 3H), 1.23 (t, 3H).

EXAMPLE 493

Ethyl 4-[2-((1R)-1-{[(4-chlorophenyl)sulfonyl]-2,5-difluoroanilino}ethyl)$_5$-fluorophenyl]butanoate To a solution of $PPh_3$ (41.2 g, 157 mmol, Aldrich), in 180 mL of dry toluene was added solid sulfonamide 1 (47.6 g, 157 mmol). The solution was stirred at room temperature for 30 min (sulfonamide dissolves only partially) and cooled to 0° C. in an ice-bath. Neat DEAD (24.7 mL, 157 mmol, Aldrich) was slowly added to the reaction mixture. The sulfonamide dissolves as the addition of DEAD progresses. After the addition was over, the reaction mixture was allowed to warm to room temperature and a solution of the alcohol (37 g, 131 mmol) in 80 mL of dry toluene was added through a syringe pump over a period of 5 h The reaction mixture was then allowed to stir at room temperature until TLC shows complete consumption of starting material (21 h). The reaction mixture was then concentrated under reduced pressure. The phosphine oxide was crystallized from 6:1 hexanes:ethyl acetate and the mother liquor was concentrated and purified by chromatography (7:1 hexanes:ethyl acetate) to isolate 51 g of product as pale yellow oil. $R_f$ (10:1 hexanes:ethyl acetate) 0.33 $^1H$ NMR ($CDCl_3$) δ7.65–7.58 (m, 2H), 7.41–7.39 (m, 2H), 7.15–6.31 (m, 6H), 5.82 (q, 1H), 4.16 (q, 2H), 3.10 (m, 1H), 2.68 (m, 1H), 2.4 (t, 2H), 1.93 (m, 2H), 1.52–1.45 (br 3H), 1.45 (t, 3H).

EXAMPLE 494

4-[2-((1R)-1-{[(4-chlorophenyl)sulfonyl]-2,5-difluoroanilino}ethyl) 5-fluorophenyl]butanoic Acid

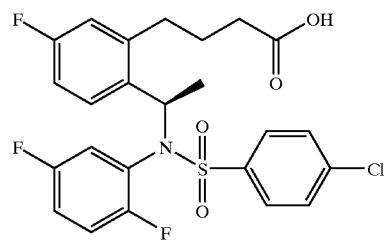

A solution of the ester (48 g, in 700 mL of methanol) was cooled to 0° C. and 230 mL of LiOH solution (10.2 g of LiOH in 230 mL of water) was added slowly. The reaction mixture turned turbid, and a pale yellow precipitate separates. The reaction mixture was mechanically stirred at 0° C. for 1 h and at room temperature for 2 h. The reaction mixture was then cooled to 0° C. and carefully adjusted to pH1 with 6 N HCl. Extracted the product with 4×250 mL of ethyl acetate, washed the ethyl acetate solution with dilute brine (3×200 mL), dried the organic layer with MgSO$_4$, filtered and concentrated to yield crude product. The crude product was purified by SiO$_2$ chromatography (1:1 hexanes:ethyl acetate) and the product was recrystallized from 4:1 hexanes:ethyl acetate (10 mL/g) to >98% ee. R$_f$ (10:4 hexanes-:ethyl acetate) 0.15. $^1$H NMR (CDCl$_3$) 5.66–7.59 (m, 2H), 7.43–7.40 (m, 2H), 6.99–6.33 (m, 6H), 5.85 (q, 1H), 3.15–3.11 (m, 1H), 2.78–2.68 (m, 1H), 2.54 (t, 2H), 2.02 (m, 2H), 1.54–1.52 (br d, 3H).

EXAMPLE 495

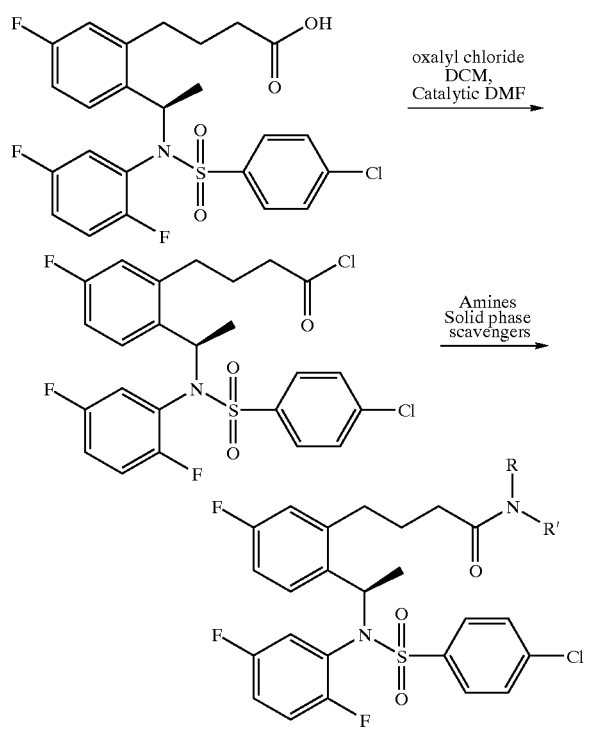

Using the scheme outlined in the preparative scheme in this example, the of Example 496–503 compounds were prepared.

EXAMPLE 496

4-[2-((1R)-1-{[(4-chlorophenyl)sulfonyl]-2,5-difluoroanilino}ethyl)-5-fluorophenyl]-N-cyclohexylbutanamide

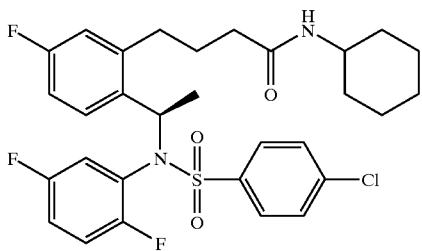

R$_f$=0.39 (2:1 hexanes:ethyl acetate) $^1$H NMR (300 MHz, CDCl$_3$) δ (ppm): 7.70–7.59 (m, 2H), 7.47–7.41 (m, 2H), 7.01–6.32 (m, 6H), 5.92–5.85 (q, 1H), 5.62 (br, 1H), 3.86–3.74 (m, 1H), 3.12–3.03 (m, 1H), 2.80–2.70 (m, 1H), 2.38–2.28 (m, 2H), 2.01–1.92 (br, 4H), 1.73–1.07 (m, 1H). LC-MS calculated for C$_{30}$H$_{32}$ClF$_3$N$_2$O$_3$S [MH+] 593; Observed: 290 (–303).

EXAMPLE 497

4-[2-((1R)-1-{[(4-chlorophenyl)sulfonyl]-2,5-difluoroanilino}ethyl)-5-fluorophenyl]-N,N-diethylbutanamide

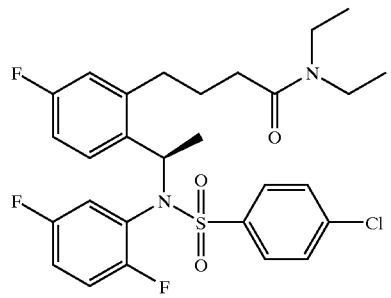

R$_f$=0.35 (2:1 hexanes:ethyl acetate) $^1$H NMR (300 MHz CDCl$_3$) δ (ppm): 7.70–7.61 (m, 2H), 7.45–7.43 (br, 2H), 7.00–6.32 (br, 6H), 5.93–5.87 (q, 1H), 3.46–3.32 (m, 4H), 3.18–3.11 (m, 1H), 2.75–2.70 (m, 1H), 2.51–2.46 (t, 2H) 2.05–1.95 (m, 2H), 1.51–1.49 (br, 3H), 1.26–1.12 (m, 6H). LC-MS calculated for C$_{28}$H$_{30}$ClF$_3$N$_2$O$_3$S [H+] 567; Observed: 567.

EXAMPLE 498

4-[2-((1R)-1-{[(4-chlorophenyl)sulfonyl]-2,5-difluoroanilino}ethyl)-5-fluorophenyl]-N-methylbutanamide

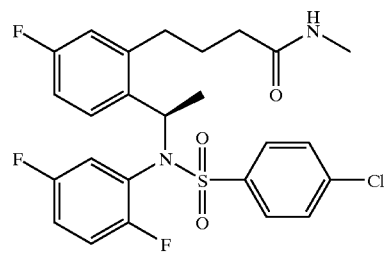

R$_f$=0.17 (1:1 hexanes:ethyl acetate) $^1$H NMR (300 MHz CDCl$_3$) δ: 7.71–7.60 (m, 2H), 7.48–7.41 (m, 2H), 7.00–6.30 (m, 6H), 5.93–5.86 (q, 1H), 5.80 (br, 1H), 3.13–3.03 (m, 1H), 2.85–2.74 (m, 4H), 2.40–2.35 (t, 2H), 2.02 (br, 2H), 1.50–1.47 (hr, 3H). LC-MS calculated for C$_{25}$H$_{24}$ClF$_3$N$_2$O$_3$S [MH+] 525; Observed: MH-303.

EXAMPLE 499

4-[2-((1R)-1-{[(4 chlorophenyl)sulfonyl]-2,5-difluoroanilno}ethyl)-5-fluorophenyl]-N-ethylbutanamide

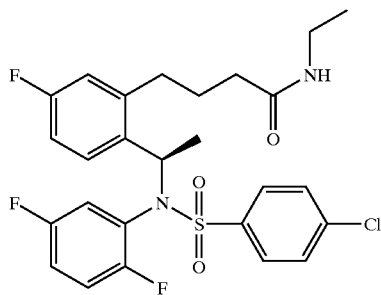

$R_f$=0.31 (1:1 hexanes:ethyl acetate) $^1$H NMR (300 MHz CDCl$_3$) δ: 7.70–7.60 (m, 2H), 7.48–7.41 (m, 2H), 7.00–6.31 (m, 6H), 5.93–5.86 (q, 1H), 5.73 (br, 1H), 3.38–3.28 (m, 2H), 3.13–3.03 (m, 1H), 2.78–2.73 (m, 1H), 2.38–2.33 (t, 2H), 2.02–2.01 (br, 2H), 1.50–1.47 (br, 3H), 1.18–1.13 (t, 3H). LC-MS calculated for $C_{26}H_{26}ClF_3N_2O_3S$ MH+] 539; Observed: MH-303.

EXAMPLE 500

4-[2-((1R)-1-{[(4-chlorophenyl)sulfonyl]-2,5-difluoroanilino}ethyl)-5-fluorophenyl]-N,N-dipropylbutanamide

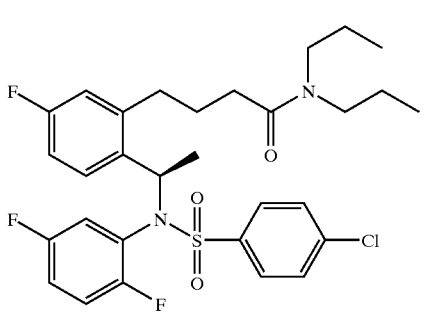

$R_f$=0.46 (3:1 hexanes:ethyl acetate) $^1$H NMR (300 MHz CDCl$_3$) δ: 7.70–7.61 (m, 2H), 7.45–7.43 (m, 2H), 7.00–6.31 (m, 6H), 5.93–5.86 (q, 1H), 3.34–3.11 (m, 5H), 2.75–2.70 (m, 1H), 2.51–2.46 (t, 2H), 2.04–1.97 (m, 2H), 1.65–1.49 (m, 7H), 0.95–0.88 (m, 6H). LC-MS calculated for $C_{30}H_{34}ClF_3N_2O_3S$ [MH+] 595; Observed: 595.

EXAMPLE 501

4-Chloro-N-(2,5-difluorophenyl)-N-((1R)-1-{4-fluoro-2-[4-oxo-4'-(1-piperidinyl)butyl]phenyl}ethyl)benzenesulfonamide

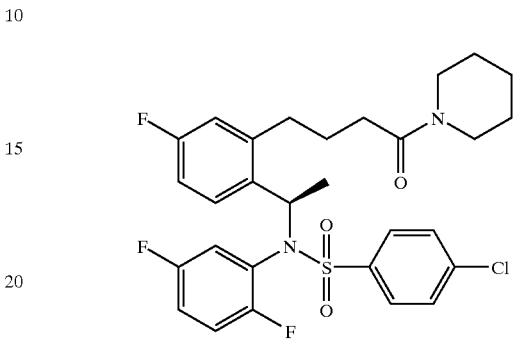

$R_f$=0.31 (2:1 hexanes:ethyl acetate) $^1$H NMR (300 MHz CDCl$_3$) δ7.70–7.60 (m, 2H), 7.46–7.43 (m, 2H), 7.00–6.32 (m, 6H), 5.92–5.85 (q, 1H), 3.62–3.58 (t, 2H), 3.47–3.43 (t, 2H), 3.15–3.11 (m, 1H), 2.78–2.68 (m, 1H), 2.52–2.47 (t, 2H), 2.03–1.93 (m, 2H), 1.66–1.49 (m, 9H). LC-MS calculated for $C_{29}H_{30}ClF_3N_2O_3S$ [MH+] 579; Observed: 579.

EXAMPLE 502

4-Chloro-N-(2,5-difluorophenyl-N-((1R)-1-{4-fluoro-2-[4-oxo-4-(4-thiomorpholinyl)butyl]phenyl}ethyl)benzenesulfonamide

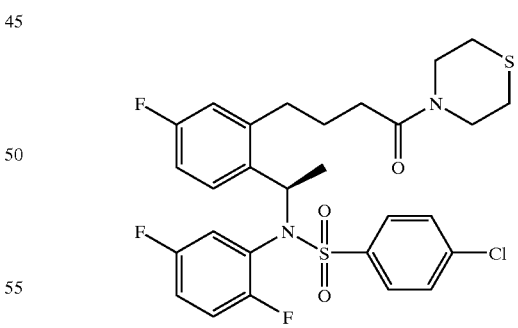

$R_f$=0.38 (2:1 hexanes:ethyl acetate) $^1$H NMR (300 MHz CDCl$_3$) δ7.70–7.60 (m, 2H), 7.47–740 (m, 2H), 7.01–6.31 (m, 6H), 5.94–5.87 (q, 1H), 3.94–3.91 (t, 2H), 3.81–3.78 (t, 2H), 3.12–3.10 (m, 1H), 2.84–2.71 (m, 1H), 2.65–2.64 (br, 4H), 2.53–2.49 (t, 2H), 2.06–1.96 (m, 2H), 1.49–1.47 (br, 3H). LC-MS calculated for $C_{28}H_{28}ClF_3N_2O_3S_2$ [MH+] 597, Observed 597.

EXAMPLE 503

4-Chloro-N-(2,5-difluorophenyl)-N-((1R)-1-{4-fluoro-2-[4-(4-thiomorpholinylsulfonyl)butyl]phenyl}ethyl)benzenesulfonamide

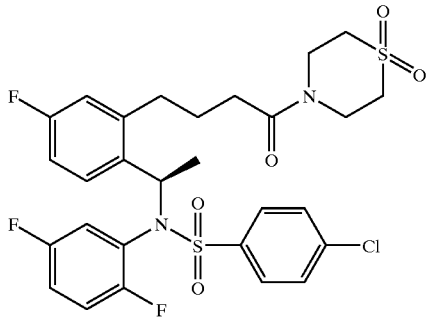

$R_f$=0.46 (1:1 hexanes:ethyl acetate) $^1$H NMR (300 MHz CDCl$_3$) δ: 7.71–7.59 (m, 2H), 7.51–7.41 (m, 2H), 7.07–6.29 (m, 6H), 5.96–5.94 (br, 1H), 4.14–4.04 (d, 4H), 3.07–2.83 (m, 6H), 2.64–2.59 (t, 2H), 2.08–2.03 (m, 2H), 1.44–1.42 (d, 3H). LC-MS calculated for $C_{29}H_{28}ClF_3N_2O_5S_2$ [MH+] 629; Observed. MH-303.

EXAMPLE 504

General Procedure for the Synthesis of Amine Oxides

The free base (0.5 g) was dissolved in methanol (5 mL) and 30% $H_2O_2$ in water (5 mL) was added. The mixture was stirred at room temperature for 14 h then concentrated under reduced pressure. The resulting crude product was purified by chromatography on $SiO_2$ to yield the desired N-oxide product in >90% yield.

Using the preparative scheme described in the previous example, the following compounds were prepared.

EXAMPLE 505

4-Chloro-N-{2-[3-(1-hydroxy-1~lambda~5~piperidin-1-yl)propoxy]benzyl}-N-phenylbenzenesulfonamide $R_f$=0.15 (1% triethylamine/5% methanol/ethyl acetate) $^1$H NMR (300 MHz, CDCl$_3$) δ (ppm): 7.55 (m, 4H), 7.21 (m, 4H), 6.78 (m, 4H), 6.60 (m, 1H), 4.74 (s, 2H), 4.53 (m, 2H), 4.19 (m, 4), 3.53 (t, 2H), 2.67 (m, 2H), 2.35 (m, 2H), 1.87–1.27 (m, 4H). $^{13}$C NMR (75 MHz, CDCl$_3$) δ (ppm): 156.9, 139.6, 137.2, 136.0, 131.9, 130.1, 129.4, 129.0, 128.9, 128.8, 128.5, 121.5, 1202, 110.7, 66.5, 64.6, 63.6, 51.3, 29.7, 22.1, 21.3, 20.3. ESI calculated for $C_{27}H_{31}ClN_2O_4S$ [MH+] 515; Observed: 515.

EXAMPLE 506

4-Chloro-N-2,5-dichlorophenyl)-N-{2-[3-(1-oxido-1-piperidinyl)propoxy]benzyl}benzenesulfonamide $R_f$=0.42 (10% methanol/DCM) $^1$H NMR (300 MHz, CDCl$_3$) δ (ppm): 7.64–751 (m, 4H), 7.26–7.14 (m, 4H,), 6.81–6.03 (m, 3H), 4.97–4.80 (dd, 2H), 4.47–4.17 (m, 6H), 3.45 (m, 2H), 2.64 (m, 2H), 2.28 (m, 2H), 1.86 (m, 3H), 1.49 (m, 1H). $^{13}$C NMR (75 MHz, CDCl$_3$) δ (ppm): 157.3, 140.3, 137.3, 135.8, 134.1, 132.8, 132.4, 131.8, 131.6, 131.0, 130.5, 129.9, 129.3, 121.2, 120.8, 111.2, 66.9, 65.1, 64.6, 63.5, 50.42, 22.5, 21.6, 20.7.

EXAMPLE 507

4-Chloro-N-(2,5-difluorophenyl-N-{2-[3-(1-oxido-1-pyrrolidinyl)propoxy]benzyl}benzenesulfonamide $R_f$=0.38 (9% methanol/DCM) $^1$H NMR (500 MHz, CD$_3$OD) δ (ppm): 7.69–7.61 (m, 4H), 7.18 (m, 1H), 7.01–6.89 (m, 4H), 6.77–6.67 (m, 2H), 4.13 (t, 2H), 3.81 (m, 2H), 3.64–3.48 (m, 4H), 2.52–2.33 (m, 4), 2.09 (m, 2H). $^{13}$C NMR (125 MHz, CD$_3$OD) δ (ppm): 160.4, 159.1, 158.7, 158.4, 157.1, 140.9, 138.5, 132.8, 131.4, 130.8, 130.5, 127.6, 123.5, 121.4, 120.1, 119.9, 118.5, 118.4, 118.4, 118.3, 118.2, 118.1, 112.3, 69.1, 66.8, 66.4, 51.0, 25.6, 22.7. ESI calculated for $C_{26}H_{27}ClF_2N_1O_4S$ [MH+] 537; Observed: 537.

EXAMPLE 508

4-Chloro-N-(2,5-difluorophenyl)-N-[2-[3-(1,1,4-trioxido-4-thiomorpholinyl)propoxy]benzyl}benzenesulfonamide $R_f$=0.53 (9% methanol/DCM) $^1$H NMR (300 MHz, CDCl$_3$) δ (ppm): 7.65–7.48 (m, 4H), 7.32–7.16 (m, 1H), 6.91–6.58 (m, 6H), 4.78 (s, 2H), 4.39–3.92 (m, 8H), 3.65 (m, 2H), 2.96 (m, 2H), 2.64 (m, (2H), $^{13}$C NMR (75 MHz, CDCl$_3$) δ (ppm): 159.3, 157.9, 156.9, 156.1, 154.5, 139.7, 136.6, 131.4, 130.3, 129.4, 128.7, 125.7, 125.6, 125.4, 121.5, 120.4, 118.9, 118.5, 117.2, 117.1, 117.0, 116.9, 116.8, 116.7, 110.8, 69.4, 65.5, 63.4, 50.0, 46.3, 23.0. ESI calculated for $C_{26}H_{27}ClF_2O_6S_2N_2$ [MH+] 601; Observed: 601.

EXAMPLE 509

4-Chloro-N-(2,5-difluorophenyl)-N-{2-[3-(1-oxido-1-piperidinyl)propoxy]benzyl}benzenesulfonamide $R_f$=0.45 (9% methanol/DCM) $^1$H NMR (300 MHz, CD$_3$OD) δ (ppm): 7.68–7.54 (m, 4H), 7.23–6.67 (m, 6H), 6.29–6.22 (m, 2H), 4.26 (m, 2H), 3.70–3.48 (m, 4H), 3.06 (m, 2H), 2.41 (m, 2H), 2.01–1.51 (m, 9H). $^{13}$C NMR (75 MHz, CD$_3$OD) δ (ppm): 158.9 (dd), 157.2, 155.6, (dd), 140.2, 137.0, 131.8, 130.8, 129.9, 129.1, 125.7 (dd), 121.5, 120.7, 118.8 (d), 117.7, (t), 11.4 (t), 111.2, 66.8, 65.0, 64.5, 50.6, 22.5, 21.6, 20.7. ESI calculated for $C_{27}H_{29}ClF_2N_2O_4S$ [MH+] 551; Observed: 551.

EXAMPLE 510

4-Chloro-N-{2-[3-(diethylnitroryl)propoxy]benzyl}-N-(2,5-difluorophenyl)benzenesulfonamide $R_f$=0.49 (9% methanol in DCM), $^1$H NMR (300 MHz, CD$_3$OD) δ (ppm) (d, 2H), 7.61 (d, 2H), 7.19 (t, 1H), 7.02–6.99 (m, 2H), 6.95 (d, 1H), 6.89 (d, 1H), 6.78–6.70 (m, 2H), 4.83 (s, 2H), 4.12 (t, 2H0, 3.69–3.66 (m, 2H), 3.44–3.40 (m, 4H), 2.37–2.34 (m, 2H), 1.37 (t, 6H). MS calculated for $C_{26}H_{29}ClF_2N_2O_4S$: 539; Observed: 539.

EXAMPLE 511

General Procedure for the Synthesis of Quaternary Ammonium Compounds

The free base was dissolved in DCM (2 mL/mmol) and excess of MeI (4.0 eq) was added. The reaction mixture was stirred at room temperature for 1 h then concentrated under reduced pressure to give pure quaternary ammonium compounds.

EXAMPLE 512

1-{3-[2-({[(4-chlorophenyl)sulfonyl]-2,5-difluoroanilino}methyl)phenoxy]propyl}-1-methylpiperidinium Iodide $R_f$=0.42 (3:1:1 n-BuOH/H$_2$O/AcOH) $^1$H NMR (300 MHz, CD$_3$OD) δ (ppm): 7.69–7.57 (m, 4H), 7.18–6.59 (m, 7H), 4.80 (s, 2H), 4.16 (t, 2H), 3.88 (m, 2H), 3.59 (m, 4H), 3.18 (s, 2H), 2.37 (m, 2H), 1.93–1.60 (m, 6H).

EXAMPLE 513

1-{3-[2-({2,5-dichloro[(4-chlorophenyl)sulfonyl]anilino}methyl)phenoxy]propyl}-1-methylpiperidinium Iodide $R_f$=0.32 (10:1;DCM:methanol). $^1$H NMR (300 MHz, CD$_3$OD) δ (ppm):7.74–7.63 (m, 4H), 7.28–7.18 (m, 3H), 6.93 (d, 1H), 6.86 (d, 1H), 6.75 (dd, 1H), 6.64 (dt, 1H), 5.13 (d, 1H), 4.67 (d, 1H), 4.27–4.26 (m, 1H), 4.11–4.02 (m, 2H), 3.86–3.79 (m, 1H), 3.52 (br m, 4H), 3.22 9s, 3H), 2.40-(br m, 2H), 1.99–1.64 (m, 6H). MS ESI calculated for C$_{29}$H$_{32}$Cl$_3$N$_2$O$_3$S: 581. Observed 581.

EXAMPLE 514

Compounds of the present invention can be prepared using the following general schemes.

In Schemes 514a, 514b and 514c, R$^1$ is halogen, methyloxytetrahydropyranyl, or a methyloxyacyl moiety such as —CH$_2$OAc. R$^2$ is hydrogen or halogen; R$^3$ is hydrogen, halogen or substituted or unsubstituted alkyl; R$^4$ and R$^5$ are substituted or unsubstituted hydrocarbyl, substituted or unsubstituted heterocycle optionally having one or more double bonds, alkoxy, ether, ester, amide, R$^6$ is substituted or unsubstituted hydrocarbyl, or substituted or unsubstituted heterocycle optionally having one or more double bonds; n is an integer from 1 up to 4, and Z is heterocycle optionally having one or more double bonds.

Scheme 514a illustrates a general process and shows the production of chiral compounds of a key intermediate of Formula II.

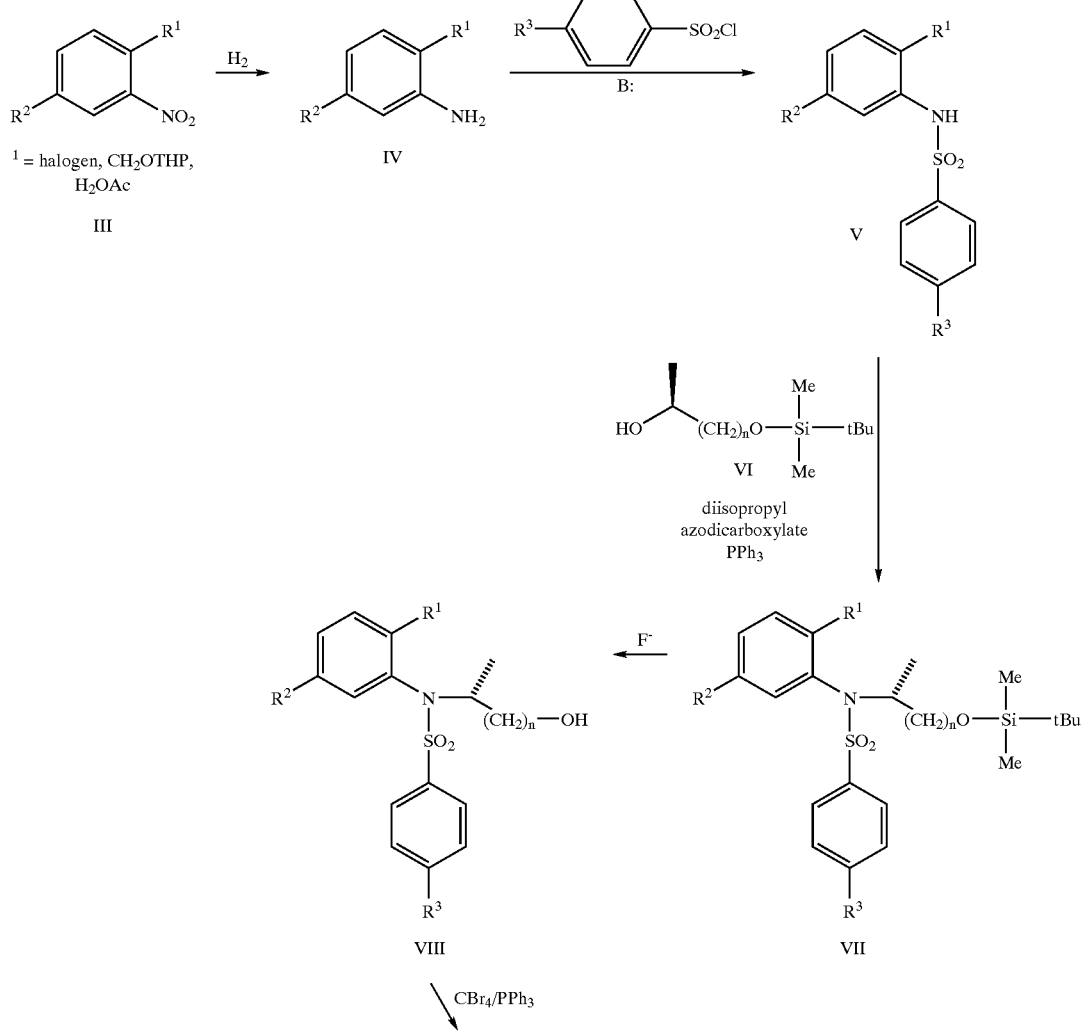

Scheme 514a

Synthesis of Intermediate II

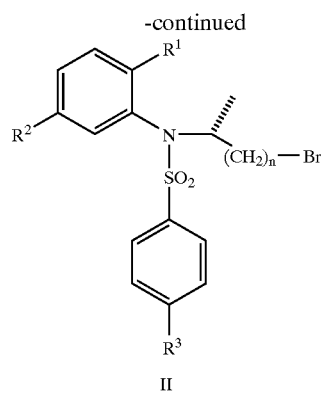

The Scheme process begins with reduction of 2,5-disubstituted-nitrobenzene (III) to the corresponding substituted aniline (IV) which is reacted with an Re-substituted benzenesulfonyl halide to provide intermediate (V). Treatment of (V) with (S)₄[[dimethyl(1,1-dimethylethyl)silyl]oxy]-2-alkanol gives compound VII which is converted, in turn, to the corresponding alcohol (VIII) and then to the halide (II) with bromide being the preferred halide.

Scheme 514b illustrates several methods of producing some of the Formula I products; i.e., when R¹ is halogen, —CH₂O-2-tetrahydropyran or —CH₂OAc.

Scheme 514b

Preparation of Formula Ia Products

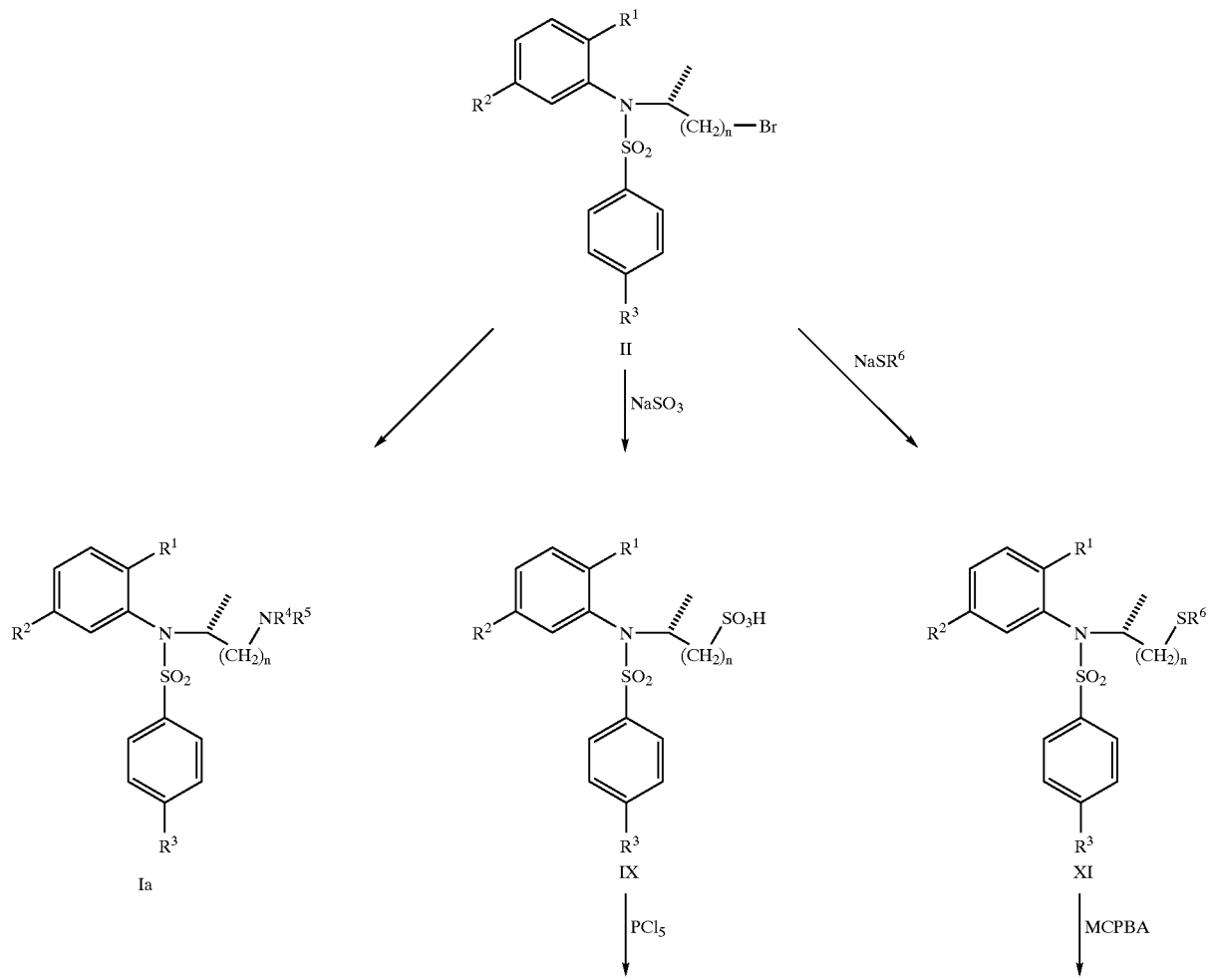

-continued

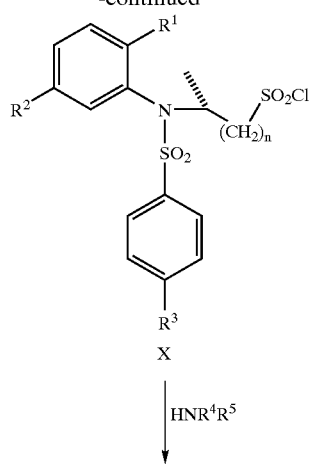
X

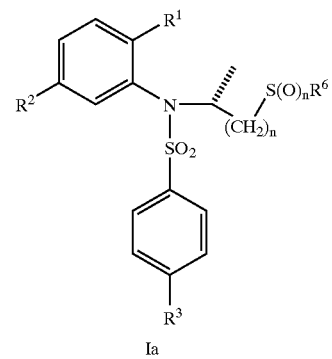
Ia

HNR⁴R⁵ ↓

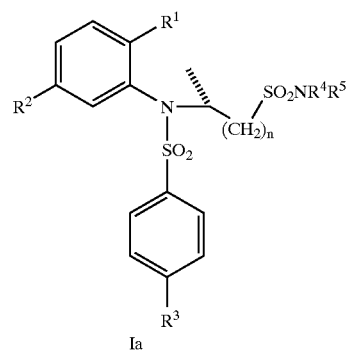
Ia

In Scheme 514b, products (Ia) can be obtained starting with intermediate compound (II). Products (Ia) can be formed directly from intermediate compound (II) by reaction with nucleophilic heterocyclics. Alternatively, intermediate compound (II) can be converted into compounds (X and XI), which can then be used to produce products (Ia) as shown in Scheme 2.

Scheme 514c shows preparation of Formula I products wherein $R^1$ is —$CH_2OH$.

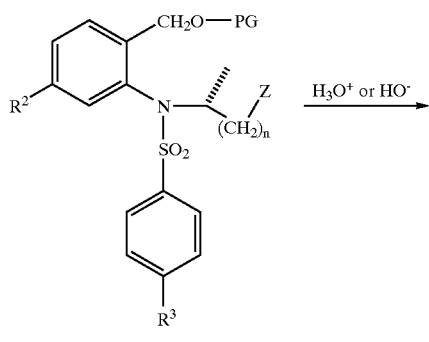
Ia: PG = OAc, OTHP $H_3O^+$ or $HO^-$ →

-continued

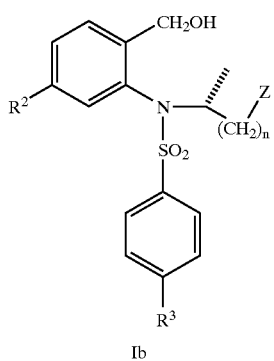
Ib

In Scheme 514c, cleavage of acetyl or tetrahydropyran groups from compounds of Formula Ia provide Formula Ib products wherein $R^1$ is —$CH_2OH$.

EXAMPLE 515

In the following examples, intermediate alcohols were prepared via a Mitsunobu reaction between a secondary sulfonamide and a commercially available TBDMS protected chiral diol, followed by HF deprotection as described herein.

265

4-Chloro-N-(2,5-difluorophenyl)-N-[(R)-1-methyl-2-hydroxyethyl]benzenesulfonamide

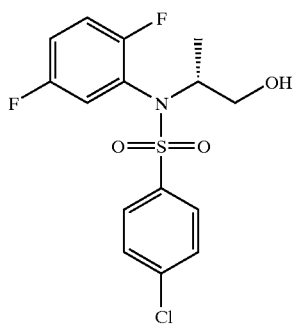

Yield=70%; Colorless viscous oil: IR (neat, CH$_2$Cl$_2$) 1504, 1346, 1164, 1093, 755, 625 cm$^{-1}$; MS (ESI+), 362 (M+H)$^+$.

EXAMPLE 516

4-Chloro-N-2,5-difluorophenyl)-N-[2-[[[[4-nitrophenyl]oxy]carbonyl]oxy](—R)-1-methylethyl]benzenesulfonamide

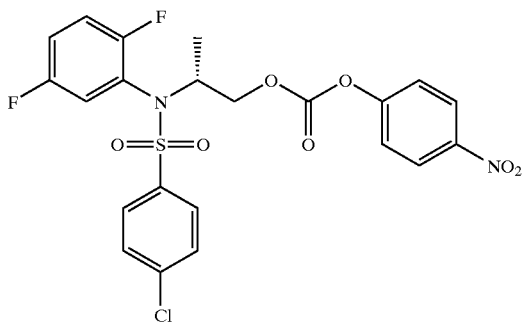

To a solution of 4-chloro-N-(2,5-difluorophenyl)-N-[(R)-1-methyl-2-hydroxyethyl]benzenesulfonamide (958 mg, 2.65 mmol) in THF (13 mL) and acetonitrile (2 ml) was added pyridine (209 mg, 2.65 mmol) followed by 4-nitrophenyl chloroformate (586 mg, 2.92 mmol). The resulting mixture was allowed to stir at 22° C. for 16 h. The solvents were removed and the product was dissolved in ether, washed with water, then brine. The ether layer was dried over MgSO$_4$, filtered, and concentrated under reduced pressure. Silica gel chromatography (ethyl acetate:hexane, 5–20% ethyl acetate gradient) of the concentrate afforded the title compound (1.23 g, yield 88%) as a colorless viscous oil.

266

EXAMPLE 517

4-Chloro-N-(2,5-difluorophenyl)-N-[2-[[N'-[3-(1 h-imidazol-1-yl)propylamino]carbonyl]oxy]-(r)-1-methylethyl]benzenesulfonamide

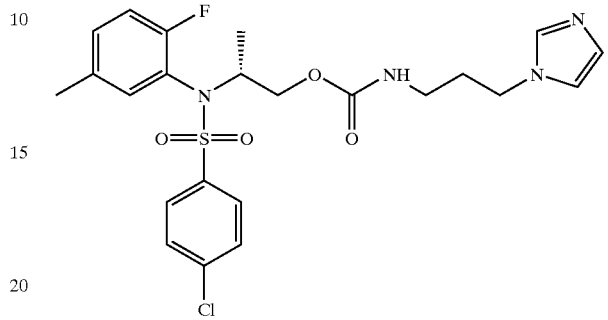

To a solution of 4-chloro-N-2,5-diflurophenyl)-N-[2-[[[[4-nitrophenyl]oxy)carbonyl]oxy]-1(R)-methylethyl]benzenesulfonamide (580 mg, 1.10 mmol) in methanol (5 ml) was added 3-aminopropyl-(1H)imidazole (276 mg, 2.20 mmol). The resulting mixture was allowed to stir at 22° C. for 16 h, then concentrated under reduced pressure. Silica gel chromatography (methanol in CH$_2$Cl$_2$ with 0.5% NH$_4$OH, 5–10% methanol gradient) of the concentrate afforded the title compound (344 mg, 61%) as a pale yellow powder. IR (KBr) 1722, 1506, 1345, 1261, 1183, 623 cm$^{-1}$; MS (ESI+), 513 (M+H)$^+$.

Non basic carbamates shown in the following examples were prepared in an analogous manner as described above but were purified via silica gel chromatography (ethyl acetate:hexane 5–50% ethyl acetate gradient) of the concentrate.

EXAMPLE 518

4-Chloro-N-(2,5-difluorophenyl)-N-[2-[[[pyrrolidin-1-yl]carbonyl]oxy]-(R)-1-methylethyl]benzenesulfonamide

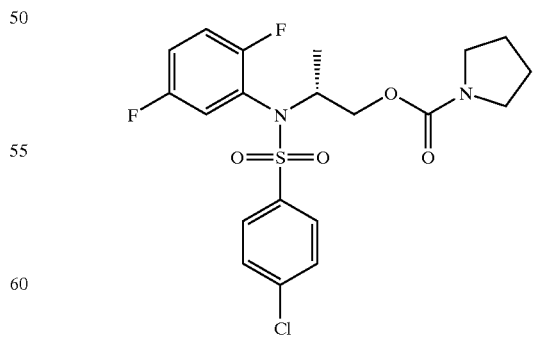

Yield=87%; Colorless viscous oil: IR (neat, CH$_2$Cl$_2$) 1704, 1504, 1424, 1352, 1165, 1092 cm$^{-1}$; MS (ESI+), 459 (M+H)$^+$.

EXAMPLE 519

4-Chloro-N-(2,5-dichlorophenyl-N-[2-[[N'-[3-(1H-imidazol-1-yl)propylamino]carbonyl]oxy]-(R)-1-methylethyl]benzenesulfonamide

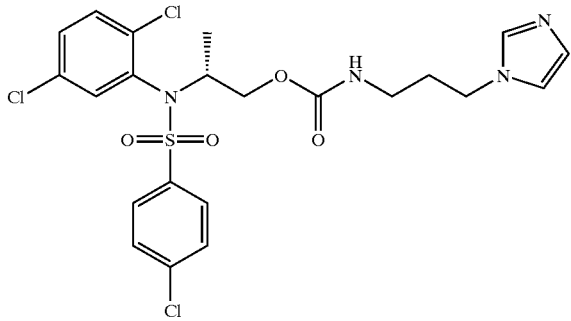

Yield=81%; pale yellow powder: IR (neat, CH$_2$Cl$_2$) 1718, 1467, 1250, 1169, 1085, 622 cm$^{-1}$; MS (ESI+), 545 (M+H)$^+$.

EXAMPLE 520

4-Chloro-N-(2,5-dichlorophenyl)-N-[2-[[[pyrrolidin-1-yl]carbonyl]oxy]-(R)-1-methylethyl]benzenesulfonamide

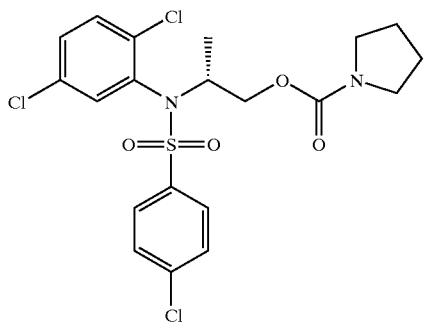

Yield=81%; White solid: IR (KBr) 1702, 1430, 1352, 1174, 1099, 620 cm$^{-1}$; MS (ESI+), 491 (M+H)$^+$.

EXAMPLE 521

4-Chloro-N-(2,5-dichlorophenyl)-N-[2-[[[(S)-2-(hydroxymethyl)pyrrolidin-1-yl)]carbonyl]oxy]-(R)-1-methylethyl]benzenesulfonamide

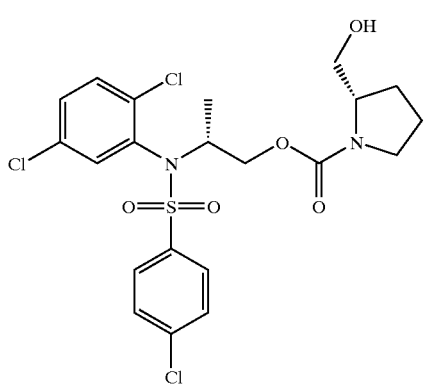

Yield=81%; Colorless glassine solid: IR (KBr) 1699, 1421, 1356, 1170, 1095, 622 cm$^{-1}$; MS (ESI+), 521 (M+H)$^+$.

EXAMPLE 522

4-Chloro-N-(2,5-dichlorophenyl)-N-[2-[[N'-[2-(piperidin-1-yl)ethylamino]carbonyl]oxy]-(R)-1-methylethyl]benzenesulfonamide

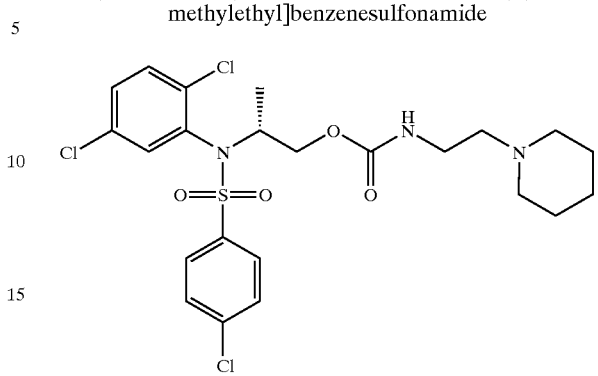

Yield=73%; Colorless glassine solid: IR (neat, CH$_2$Cl$_2$) 1723, 1468, 1352, 1170, 1095, 622 cm$^{-1}$; MS (ESI+), 548 (M+H)$^+$.

EXAMPLE 523

4-Chloro-N-(2,5-dichlorophenyl)-N-[2-[[[N'-[3-(1h-imidazol-1-yl)propyl-N'-Ethylamino]carbonyl]oxy]-(R)-1-methylethyl]benzenesulfonamide

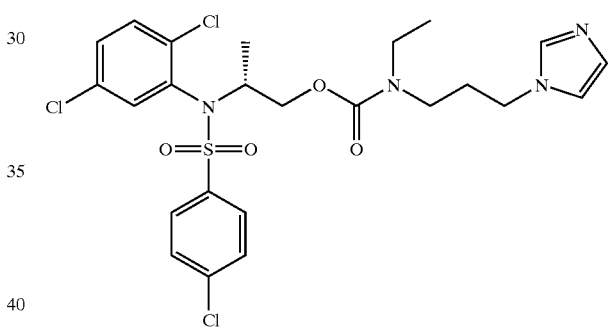

Yield=48%; Pale yellow viscous oil: IR (neat, CH$_2$Cl$_2$) 1699, 1467, 1352, 1170, 1095, 623 cm$^{-1}$; MS (ESI+), 573 (M+H)$^+$.

EXAMPLE 524

4-Chloro-N-(2,5-dichlorophenyl)-N-[2-[[N'-[3-(1H-tetrazol-1-yl)-propylamino]carbonyl]oxy]-(R)-1-methylethyl]benzenesulfonamide

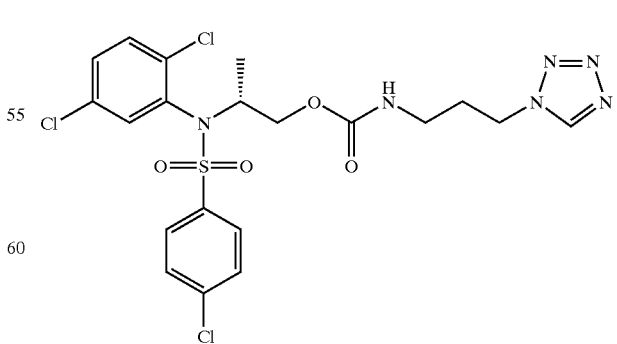

Yield=46%; White powder: IR (KBr) 1718, 1467, 1348, 1168, 1095, 622 cm$^{-1}$; MS (ESI+), 547 (M+H)$^+$.

EXAMPLE 525

4-Chloro-N-(2,5-dichlorophenyl)-N-[2-[[N'-[2-(hydroxyethyl)-N'-methyl]amino]carbonyl]oxy](R)-1-methylethyl]benzenesulfonamide

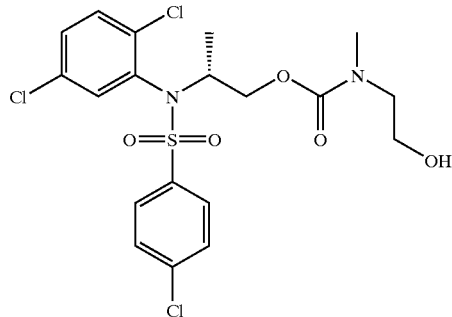

Yield=80%; Pale yellow viscous oil: IR (neat, CH$_2$Cl$_2$) 1699, 1466, 1354, 1170, 1095, 623 cm$^{-1}$; MS (ESI+), 495 (M+H)$^+$.

EXAMPLE 526

4-Chloro-N-(2,5-dichlorophenyl)-N-[2-[[[N'-[3-(1H-imidazol-1-yl)propyl]-N'-methylamino]carbonyl]oxy]-(R)-1-methylethyl]benzenesulfonamide

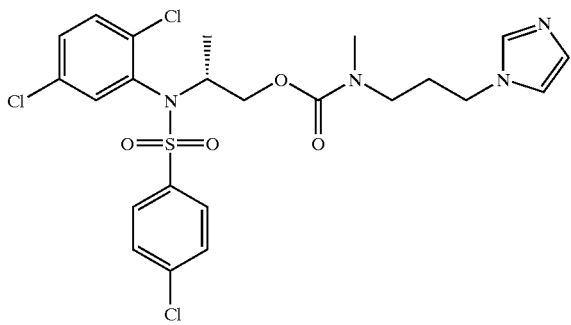

Yield=50%; Pale yellow gummy solid: IR (neat, CH$_2$Cl$_2$) 1699, 1467, 1352, 1170, 1095, 622 cm$^{-1}$; MS (ESI+), 559 (M+H)$^+$.

EXAMPLE 527

4-Chloro-N-(2-fluoro-5-chlorophenyl)-N-[(R)-1-methyl-2-hydroxyethyl]benzenesulfonamide

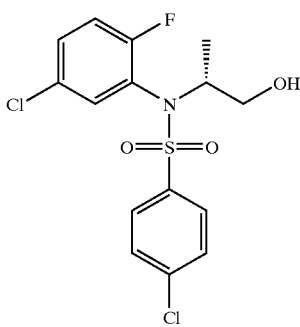

Yield=83%; Colorless viscous oil: IR (neat, CH$_2$Cl$_2$) 1493, 1345, 1166, 1054, 758, 622 cm$^{-1}$; MS (ESI+), 378 (M+H)$^+$.

EXAMPLE 528

4-Chloro-N-(2-fluoro-5-chlorophenyl)-N-[2-[[[pyrrolidin-1-yl]carbonyl]oxy]-(R)-1-methylethyl]benzenesulfonamide

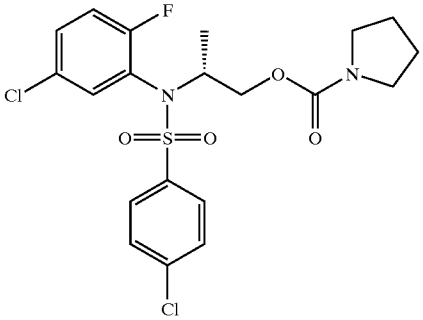

Yield=71%; White powder: IR (neat, CH$_2$Cl$_2$) 1704, 1494, 1424, 1352, 1171, 622 cm$^{-1}$; MS (ESI+), 475 (M+H)$^+$.

EXAMPLE 529

4-Chloro-N-(2-fluoro-5-chlorophenyl)-N-[2-[[N'-[3-(1H-imidazol-1-yl)propylamino]carbonyl]oxy]-(R)-1-methylethyl]benzenesulfonamide

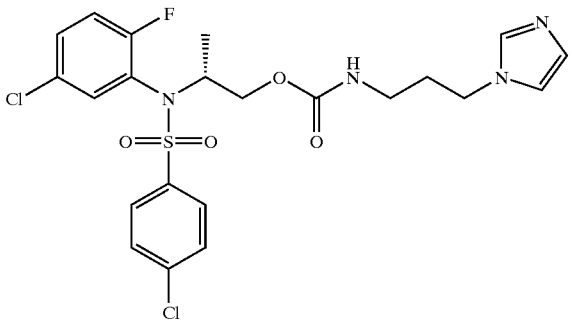

Yield=81%; White powder: IR (KBr) 1720, 1345, 1263, 1171, 758, 620 cm$^{-1}$; MS (ESI+), 529 (M+H)$^+$.

EXAMPLE 530

4-Chloro-N-(2-fluoro-5-chlorophenyl)-N-[2-[[N'-[2-(1H-imidazol 4-yl)ethylamino]carbonyl]oxy]-(R)-1-methylethyl]benzenesulfonamide

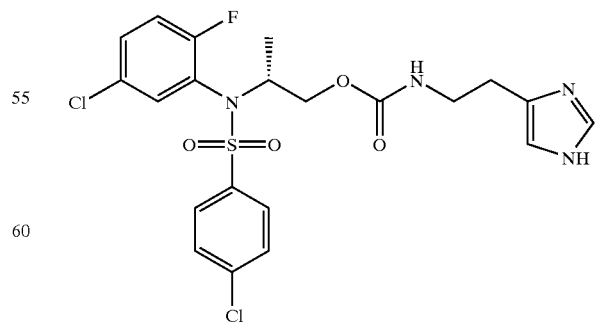

Yield-74%; White powder: IR (KBr) 1716, 1494, 1262, 1169, 1091, 758 cm$^{-1}$; MS (ESI+), 515 (M+H)$^+$.

EXAMPLE 531

4-Chloro-N-[5-chloro-2-(hydroxymethyl)phenyl]-N-
[2-[[N'-[3-(1H-imidazol-1-yl)propylamino]carbonyl]
oxy]-(1R)-(2R)-dimethylethyl]benzenesulfonamide

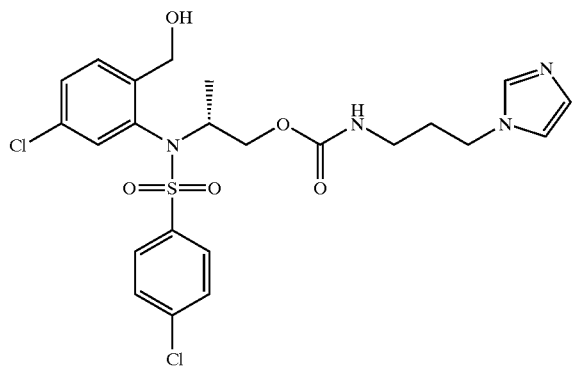

Yield=77%; White solid: IR (KBr) 1716, 1347, 1168, 1091, 757, 627 cm⁻¹; MS (ESI+), 55 (M+H)⁺.

EXAMPLE 532

4-Chloro-N-[5-chloro-2-(hydroxymethyl)phenyl]-N-
[2-[[[N'-[3-(1H-imidazol-1-yl)propyl]-N'-
cyclopropylmethylamino]carbonyl]oxy]-(R)-1-
methylethyl]benzenesulfonamide

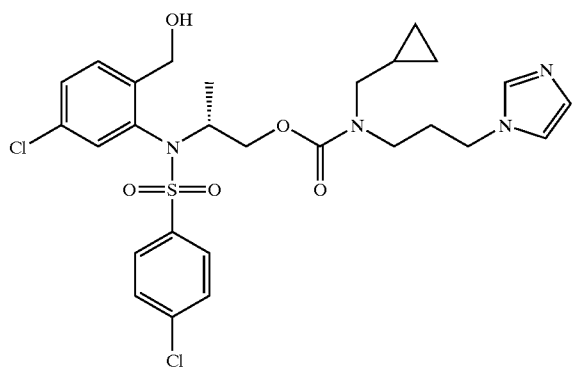

Yield=32%; Colorless glassine solid: IR (KBr) 1697, 1477, 1167, 1092, 758, 622 cm⁻¹; MS (ESI+), 595 (M+H)⁺.

EXAMPLE 533

4-Chloro-N-[5-chloro-2-(hydroxymethyl)phenyl]-N-
[2-[[[N'-[3-(1H-imidazol-1-yl)propyl]-N'-(2-
methylethyl)amino]carbonyl]oxy]-(R)-1-
methylethyl]benzenesulfonamide

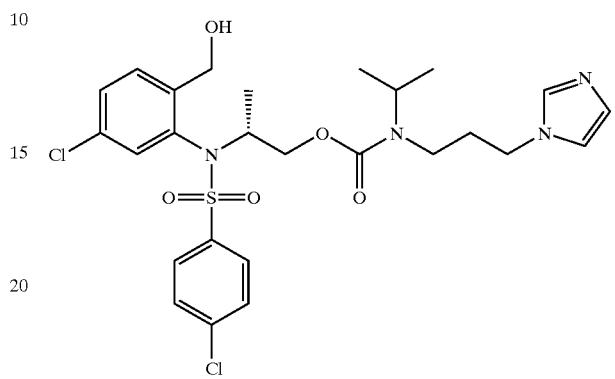

Yield=43%; Beige solid: IR (neat, CH₂Cl₂) 1342, 1166, 1092, 1055, 757, 622 cm⁻¹; MS (ESI+), 583 (M+H)⁺.

EXAMPLE 534

4-Chloro-N-(2 dichlorophenyl)-N-[1-(S)-[1-[2-
(methylsulfonyl)ethyl]pyrrolidin-2-yl]ethyl]
benzenesulfonamide

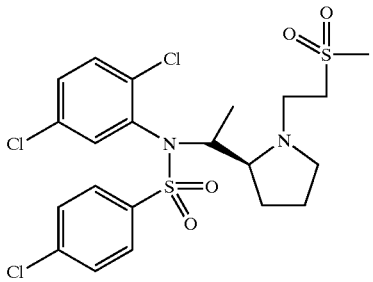

The above-named compound was prepared using the preparative scheme described below.

α-Methyl-[N-(tert-butoxycarbonyl)]-L-prolinol

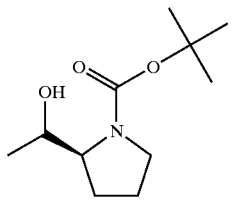

To a solution of (S)-2-acetyl-1-pyrrolidinecarboxylic acid 1,1-dimethylethyl ester [CA 91550-08-2] (5.600 g, 26.400 mmol) in ethanol (40 mL) was added sodium borohydride (2.0 g, 53 mmol) under nitrogen at 0° C. The reaction was stirred for 2 h. Ethanol was removed under reduced pressure.

The concentrate was diluted with ethyl ether (100 mL) and washed with H₂O (2×100 mL). The organic extract was dried over Na₂SO₄, filtered, and concentrated. Silica gel chromatography (1:5 to 1:4 gradient; ethyl acetate/hexanes) of the concentrate afforded two isomers, designated A, the first eluting isomer, (2.050 g, 40%) and the more polar B (1.537 g, yield=30%), of the title compound. Isomer B was used in the subsequent reaction.

4-Chloro-N-(2,5-dichlorophenyl)-N-[1-(S)-[1-[(1,1-dimethylethoxy)carbonyl]pyrrolidin-2-yl]ethyl]benzenesulfonamide

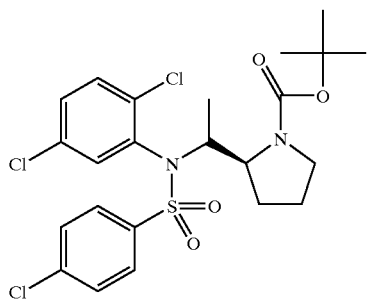

To a solution of 4-chloro-N-(2,5-dichlorophenyl)benzenesulfonamide (0.100 g, 0.298 mmol), triphenylphosphine (0.230 g, 0.890 mmol), α-methyl-[N-(tert-butoxycarbonyl)]-L-prolinol, (isomer B, 0.200 g, 0.890 mmol) in toluene (2 mL) was added diisopropylazodicarboxylate (0.180 g, 0.890 mmol) dropwise at 0° C. under nitrogen atmosphere. The resulting mixture was allowed to warm to 22° C. with stirring. After 18 h the mixture was washed with sat NaHCO₃ (4 mL), brine (4 mL) and extracted with ethyl ether (4 mL). The organic extract was dried over Na₂SO₄ and filtered. Silica gel chromatography (1:4 ethyl acetate/hexanes) of the concentrate afforded the title compound (0.095 g, yield=60%), MS (ESI) 532.

4-Chloro-N-(2,5-dichlorophenyl)-N-[1-(S)-pyrrolidin-2-yl]ethyl]benzene Sulfonamide

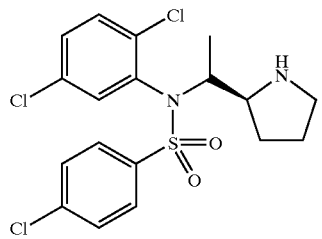

To a solution of 4-chloro-N-(2,5-dichlorophenyl)-N-[1-(S)-[1-[(1,1-dimethylethoxy)carbonyl]pyrrolidin-2-yl]ethyl]benzenesulfonamide (0.095 g, 0.178 mmol) was added a solution of 1:1 trifluoroacetic acid/CH₂Cl₂ (2 mL) at 22° C. The mixture was stirred for 1 h at 22° C. The solvent and trifluoroacetic acid were removed by reduced pressure to afford the title compound (0.075 g, yield=98%), MS (ESI) 432.

4-Chloro-N-2,5-dichlorophenyl)-N-[1-(S)-[1-[2-(methylsulfonyl ethyl]pyrrolidin-2-yl]ethyl]benzenesulfonamide

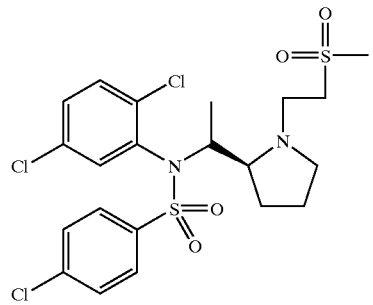

To a solution of 4-chloro-N-(2,5-dichlorophenyl)-N-[1-[(S)-pyrrolidin-2-yl]ethyl]benzenesulfonamide (0.075 g, 0.174 mmol) in THF (1 mL) was added methyl vinyl sulfone (0.060 g, 0.530 mmol) at 22° C. The reaction was stirred for 18 h. The resulting mixture was washed with sat. K₂CO₃ (2 mL), brine (2 mL) and extracted with ethyl ether (2 mL). The organic solution was dried over Na₂SO₄, filtered and evaporated. Silica gel chromatography (1:5 ethyl acetate/hexanes) of the concentrate afforded the title compound (0.533 g, yield=57%), MS (ESI) 538.

EXAMPLE 535

(R)-Chloro-N-(5-chloro-2-fluorophenyl)-N-[5-[N-(S)-[1-(methoxycarbonyl)-2-methylpropyl]amino]-1-methyl-5-oxopentyl]benzenesulfonamide

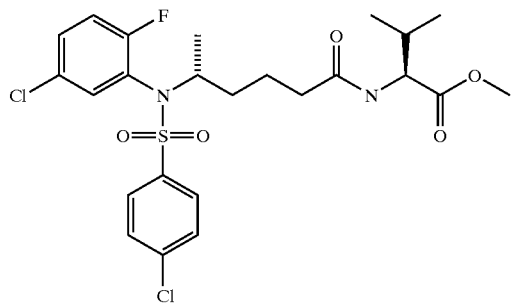

To a solution of (5R)—S-[N-[5-chloro-2-fluorophenyl][(4-chlorophenyl)sulfonyl]amino]-hexanoyl chloride (0.265 g, 0.584 mmol) in THF (3 mL) was added Hunig's base (0.305 mL, 1.75 mmol) and L-valine methyl ester hydrochloride (0.294 g, 1.75 mmol) at 22° C. The reaction was stirred at 22° C. temperature for 12 h. The reaction was treated with sat. NaHCO₃ (6 mL) and the aqueous phase extracted with ether (3×15 mL). The combined organic extracts were dried over MgSO₄, filtered, and concentrated under reduced pressure. Silica gel chromatography (3:7 ethyl acetate:Hexanes) of the concentrate afforded the title compound as a light yellow wax (0.233 g, yield=73%). MS (ESI) 547 (M+H).

EXAMPLE 536

(R)-4-Chloro-N-(5-chloro-2-fluorophenyl)-N-[5-[N-(S)-[1-(carboxy)-2-methylpropyl]amino]-1-methyl-5-oxopentyl]benzenesulfonamide

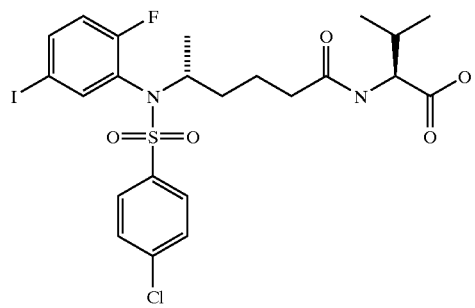

To a solution of (R)$_4$-chloro-N-(5-chloro-2-fluorophenyl)-N-[5-[N-(S)-[1-(methoxycarbonyl)-2-methylpropyl]amino]-1-methyl-5-oxopentyl]benzenesulfonamide (0.170 g, 0.310 mmol) in methanol (3.5 mL) was added NaOH (1N, 0.450 mL, 0.931 mmol) at 22° C. The resulting mixture was heated at reflux with stirring for 1.5 h. The mixture was acidified with 1N HCl and was extracted with chloroform (3×20 mL). The combined organic extracts were dried over MgSO$_4$, filtered, and concentrated under reduced pressure to afford the title compound (0.161 g, 97%) as a white powder. MS (ESI) 533 (M+H).

EXAMPLE 537

(R)-4-Chloro-N-(5-chloro-2-fluorophenyl)-N-[4-[N-(S)-[1-(methoxycarbonyl)-2-methylpropyl]amino]1-methyl-4-oxobutyl]benzenesulfonamide

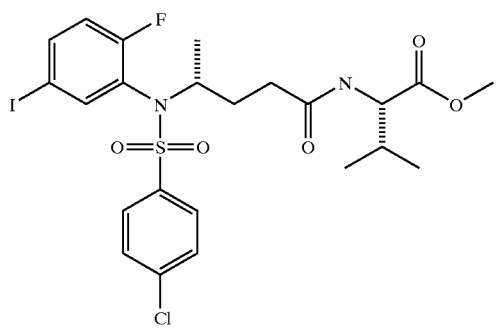

In a manner similar to the previous example, the title compound was prepared by reacting (4R)-4-[N-[5-chloro-2-fluorophenyl][(4-chlorophenyl)sulfonyl]amino]pentanoyl chloride with L-valine methyl ester hydrochloride (71% yield). MS (EST) 533 (M+H).

EXAMPLE 538

(R)-4-Chloro-N-(5-chloro-2-fluorophenyl)-N-[4-[N-(S)-[1-methoxycarbonyl)-3-methylbutyl]amino]-1-methyl-4-oxobutyl]benzenesulfonamide

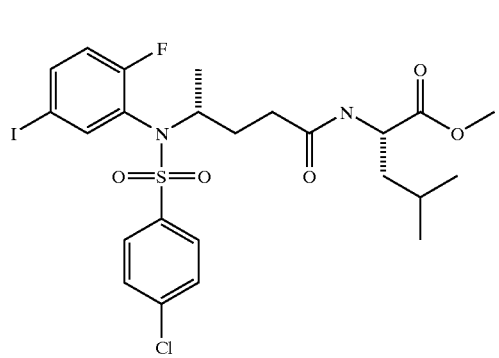

In a manner similar to the previous example, the title compound was prepared by reacting (4R)-4-[N-[5-chloro-2-fluorophenyl][(4-chlorophenyl)sulfonyl]amino]pentanoyl chloride with L-leucine methyl ester hydrochloride (70% yield). MS (ES) 547 (M+H).

EXAMPLE 539

(R)-4-Chloro-N-(5-chloro-2-fluorophenyl)-N-[5-[N-(R)-[1-(methoxycarbonyl)-2-methylpropyl]amino]-1-methyl-5-oxopentyl]benzenesulfonamide

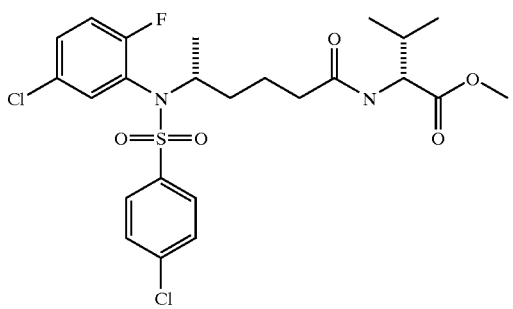

In a manner similar to the previous example, the title compound was prepared by reacting (5R)-5-N-[5-chloro-2-fluorophenyl][(4-chlorophenyl)sulfonyl]amino]hexanoyl chloride with D-valine methyl ester hydrochloride (82% yield). MS (ESI) 547 (M+H).

EXAMPLE 540

(R)-4-Chloro-N-(5-chloro-2-fluorophenyl)-N-[5-[N-(R)-[1-(methoxycarbonyl)-3-methylbutyl]amino]-1-methyl-5-oxopentyl]benzenesulfonamide

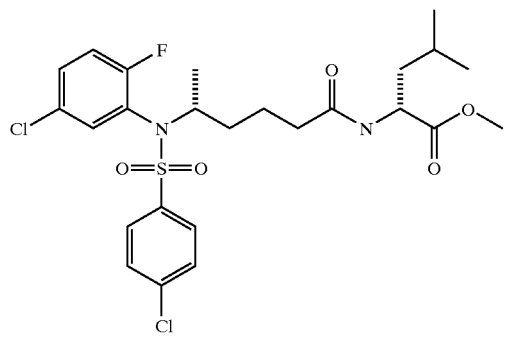

In a manner similar to the previous example, the title compound was prepare by reacting (5R)-5-[N-[5-chloro-2-fluorophenyl][(4-chlorophenyl)sulfonyl]amino]hexanoyl chloride with D-leucine methyl ester hydrochloride (73% yield). MS (ESI) 561 (M+H).

EXAMPLE 541

(R)-4-Chloro-N-(5-chloro-2-fluorophenyl)-N-[5-[N-(S)-[1-methoxycarbonyl)-3-methylbutyl]amino]-1-methyl-5-oxopentyl]benzenesulfonamide

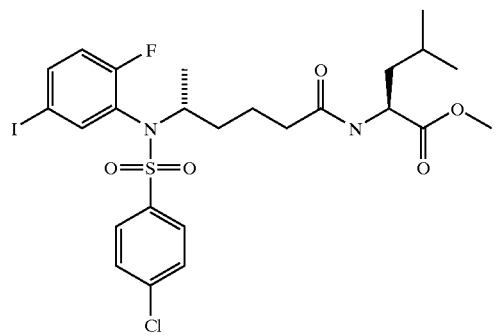

In a manner described herein, the title compound was prepared by reacting (5R)-5-[N-[5-chloro-2-fluorophenyl][(4-chlorophenyl)sulfonyl]amino]hexanoyl chloride with L-leucine methyl ester hydrochloride to afford the title compound (71% yield). MS (ESI) 561 (M+H).

EXAMPLE 542

(R)-4-Chloro-N-(5-chloro-2-fluorophenyl)-N-[6-[N-(S)-[1-(methoxycarbonyl)-2-methylpropyl]amino]-1-methyl-6-oxohexyl]benzenesulfonamide

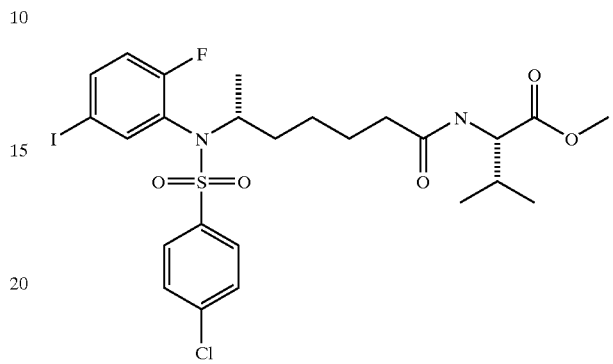

In a manner described herein, the title compound was prepared by reacting (6R)-6-[N-[5-chloro-2-fluorophenyl][(4-chlorophenyl)sulfonyl]amino]heptanoyl chloride with L-valine methyl ester hydrochloride (85% yield). MS (ESI) 561 (M+H).

EXAMPLE 543

(R)-4-Chloro-N-(5-chloro-2-fluorophenyl)-N-[6-[N-(S)-[1-(methoxycarbonyl)-3-methylbutyl]amino]-1-methyl-6-oxohexyl]benzenesulfonamide

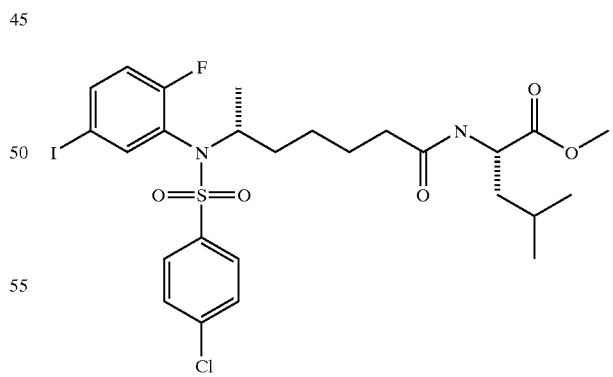

In a manner described herein, the title compound was prepared by reacting (6R)-6-[N-[5-chloro-2-fluorophenyl][(4-chlorophenyl)sulfonyl]amino]heptanoyl chloride with L-leucine methyl ester hydrochloride (89% yield). MS (ESI) 575 (M+H).

EXAMPLE 544

(R)-4-Chloro-N-(5-chloro-2-fluorophenyl)-N-[5-[N-(R)-[1-(carboxy)-2-methylpropyl]amino]-1-methyl-5-oxopentyl]benzenesulfonamide

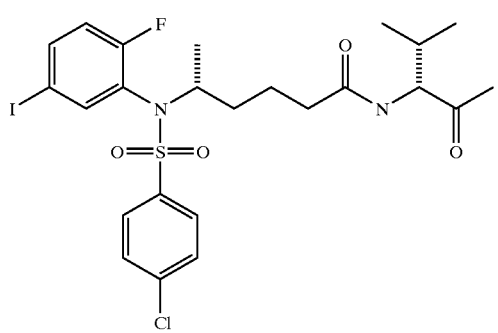

In a manner described herein, the title compound was prepared by hydrolysis of (R)-4-chloro-N-(5-chloro-2-fluorophenyl)-N-[5-[N—(R)-[1-(methoxycarbonyl)-2-methylpropyl]amino]-1-methyl-5-oxopentyl]benzenesulfonamide (90% yield). MS (ESI) 533 (M+H).

EXAMPLE 545

(R)-4-Chloro-N-(5-chloro-2-fluorophenyl)-N-[5-[N-(R)[1-(carboxy)-3-methylpropyl]amino]-1-methyl-5-oxopentyl]benzenesulfonamide

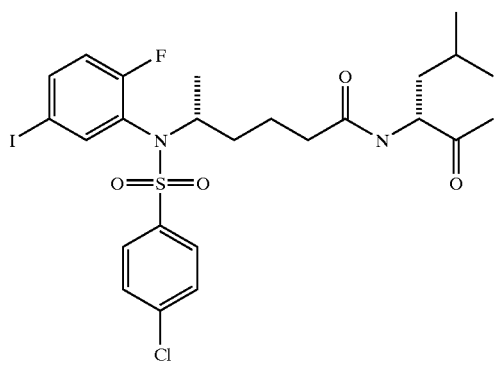

In a manner described herein, the title compound was prepared by hydrolysis of (R)-4-chloro-N-(5-chloro-2-fluorophenyl)-N-[5-[N-(R)-[1-(methoxycarbonyl)-3-methylbutyl]amino]-1-methyl-5-oxopentyl]benzenesulfonamide (89% yield). MS (ESI) 547 (M+H).

EXAMPLE 546

(R)-4-Chloro-N-(5-chloro-2-fluorophenyl)-N-[5-[N-(S)-[1-(carboxy)-3-methylbutyl]amino]-1-methyl-5-oxopentyl]benzenesulfonamide

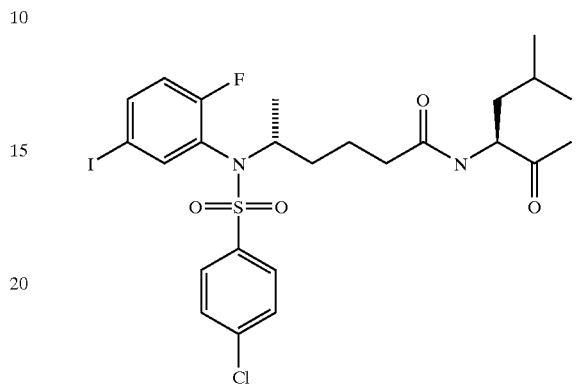

In a manner described herein, the title compound was prepared by hydrolysis of $(R)_4$-chloro-N-(5-chloro-2-fluorophenyl)-N-[5-[N-(S)-[1-(methoxycarbonyl)-3-methylbutyl]amino]-1-methyl-5-oxopentyl]benzenesulfonamide (90% yield). MS (ESI) 547 (M+H).

EXAMPLE 547

(R)-4-Chloro-N-(5-chloro-2-fluorophenyl)-N-[6-[N-(S)-[1-(carboxy)-2-methylpropyl]amino]-1-methyl-6-oxohexyl]benzenesulfonamide

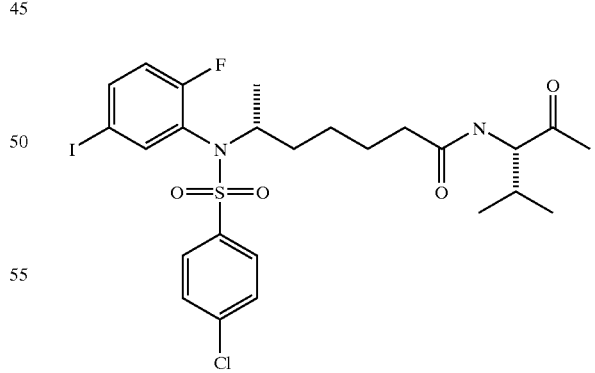

In a manner described herein, the title compound was prepared by hydrolysis of (R)-4-chloro-N-(5-chloro-2-fluorophenyl)-N-[6-[N-(S)-[1-(methoxycarbonyl)-2-methylpropyl]amino]-1-methyl-6-oxohexyl]benzenesulfonamide (85% yield). MS (ESI) 547 (M+H).

EXAMPLE 548

(R)-4-Chloro-N-(5-chloro-2-fluorophenyl)-N-[6-[N-(S)-[1-(carboxy)-3-methylbutyl]amino]-1-methyl-6-oxohexyl]benzenesulfonamide

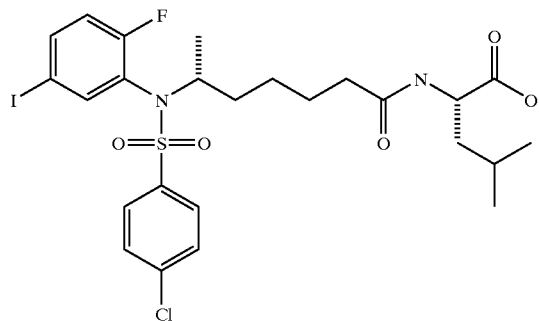

In a manner described herein, the title compound was prepared by hydrolysis of (R)-4-chloro-N-(5-chloro-2-fluorophenyl)-N-[6-[N-(S)-[1-(methoxycarbonyl)-3-methylbutyl]amino]-1-methyl-6-oxohexyl]benzenesulfonamide (83% yield). MS (ESI) 561 (M+H).

EXAMPLE 549

4-Chloro-N-[5-chloro-2-(hydroxymethyl)phenyl]-N-[2-[[[(methylamino)carbonyl]oxy]-(R)-1-methylethyl]benzenesulfonamide

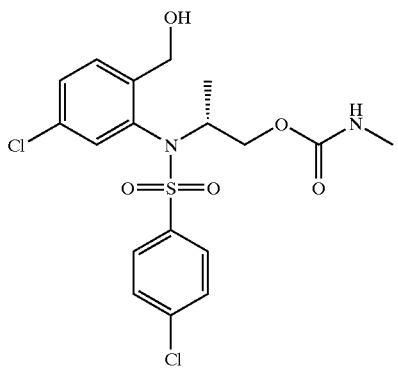

To a solution of 4-chloro-N-[5-chloro-2-(acetoxymethyl)phenyl]-N-[2-[[[[4-nitrophenyl]oxy]carbonyl]oxy]-(R)-1-methylethyl]benzenesulfonamide (50 mg, 0.08 mmol) in DMF (2.0 mL) in a 15 mL HDPE cartridge was added methylamine (5.2 mg,). The mixture was shaken for 12 h at 22° C. in a 48 well reactor. The mixture was filtered, rinsed with ether to a test tube and concentrated by speed vacuum to afford crude 4-chloro-N-[5-chloro-2-(acetoxymethyl)phenyl]-N-[2-[[[methylamino]carbonyl]oxy]-(R)-1-methylethyl]benzenesulfonamide. The molecular weight of the intermediate product was determined by LC/MS. The residue was diluted with methanol (2.0 mL) in a test tube and K$_2$CO$_3$ was added. The mixture was shaken for 2 hours and filtered. The methanol was removed by speed vacuum and the residue was purified by preparative HPLC with 90% methanol/H$_2$O at 4 mL/min. The desired product was concentrated by speed vacuum to afford the title compound. Yield=32% colorless oil: LC/MS, 448 (M+H); Retention Time, 3.71 min.

The following carbamates were prepared as described in the previous example. They were all analyzed by LC/MS.

EXAMPLE 550

4-Chloro-N-[5-chloro-2-(hydroxymethyl)phenyl]-N-[2-[[[propylamino]carbonyl]oxy]-(R)-1-methylethyl]benzenesulfonamide

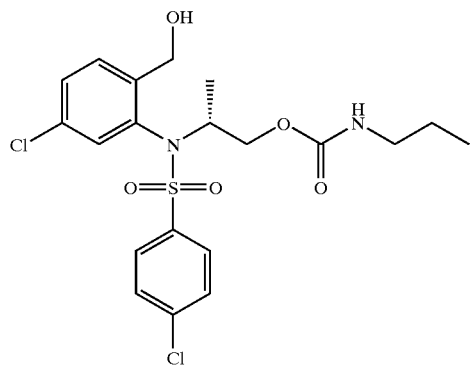

Yield=32% colorless oil: LC/MS, 476 (M+H); Retention time, 3.93 min.

EXAMPLE 551

4-Chloro-N-[5-chloro-2-(hydroxymethyl)phenyl]-N-[2-[[[(1,1-dimethyl)ethylamino]carbonyl]oxy]-(R)-1-methylethyl]benzenesulfonamide

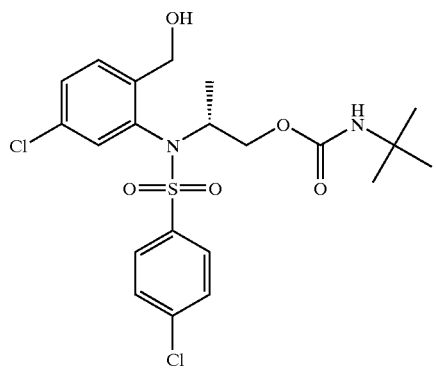

Yield-35% colorless oil: LC/MS, 490 (M+H); Retention time, 4.09 min.

EXAMPLE 552

4-Chloro-N-[5-chloro-2-hydroxymethyl)phenyl]-N-[2-[[[diethylamino]carbonyl]oxy]-(R)-1-methylethyl]benzenesulfonamide

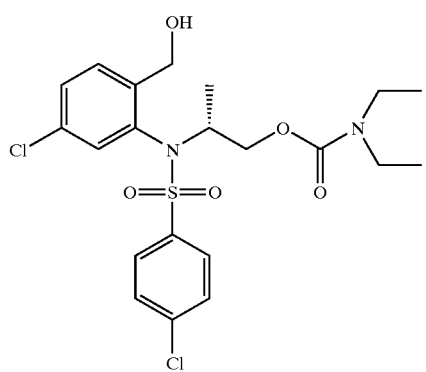

Yield=26% colorless oil: LC/MS, 490 (M+H); Retention time, 4.08 min.

EXAMPLE 553

4-Chloro-N-[5-chloro-2-(hydroxymethyl)phenyl]-N-[2-[[[cyclohexylamino]carbonyl]oxy]-(R)-1-methylethyl]benzenesulfonamide

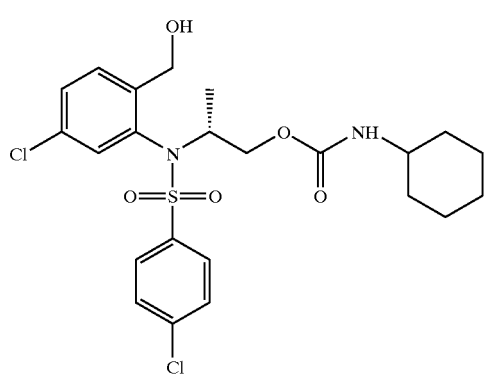

Yield=15% colorless oil: LC/MS, 516 (M+H); Retention time, 4.23 min.

EXAMPLE 554

4-Chloro-N-[5-chloro-2-(hydroxymethyl)phenyl]-N-[2-[[N'-[3-(1H-imididazol-1-yl) propylamino]carbonyl]oxy](R)-1-methylethyl]benzenesulfonamide

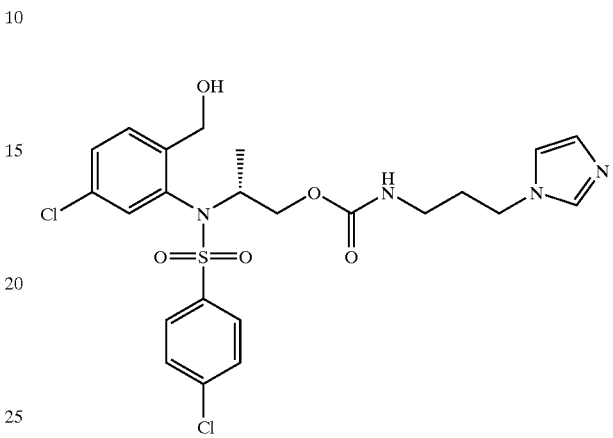

Yield=30% colorless oil: LC/MS, 542 (M+H); Retention time, 4.80 min.

EXAMPLE 555

4-Chloro-N-[5-chloro-2-hydroxymethyl)phenyl]-N-[2-[[[isopropylamino]carbonyl]oxy]-(R)-1-methylethyl]benzenesulfonamide

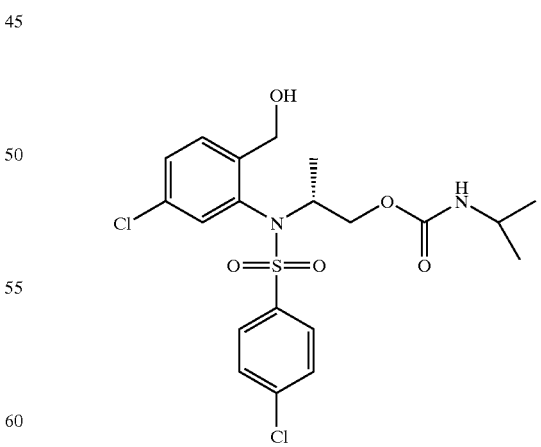

Yield=30% colorless oil: LC/MS, 476 (M+H); Retention time, 3.92 min.

EXAMPLE 556

4-Chloro-N-[5-chloro-2-(hydroxymethyl)phenyl]-N-[2-[[[pyrrolidin-1-yl]carbonyl]oxy]-(R)-1-methylethyl]benzenesulfonamide

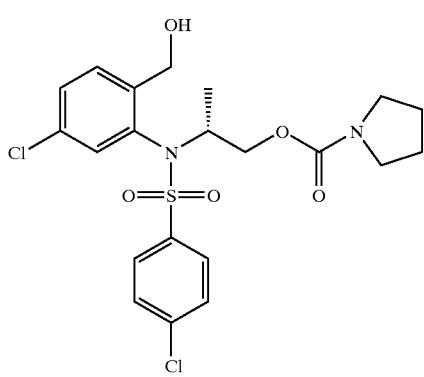

Yield=32% colorless oil: LC/MS, 488 (M+H); Retention time, 4.20 min.

EXAMPLE 557

4-Chloro-N-[5-chloro-2-(hydroxymethyl)phenyl]-N-[2-[[[(1-methyl)propylamino]carbonyl]oxy]-(R)-1-methylethyl]benzenesulfonamide

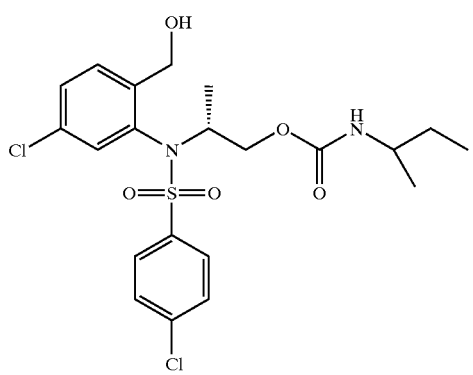

Yield=33% colorless oil: LC/MS, 490 (M+H); Retention time, 4.05 min.

EXAMPLE 558

4-Chloro-N-[5-chloro-2-(hydroxymethyl)phenyl]-N-[2-[[[ethylamino]carbonyl]oxy]-(R)-1-methylethyl]benzenesulfonamide

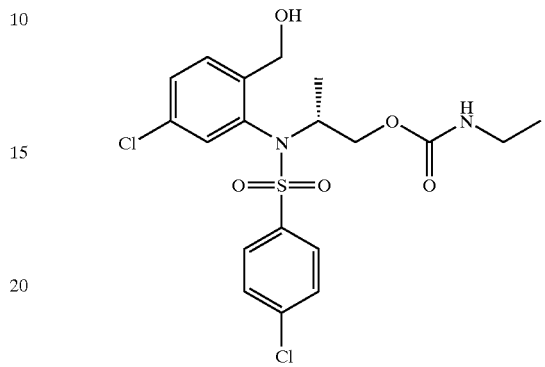

To a solution of 4-chloro-N-[5-chloro-2-(acetoxymethyl)phenyl]-N-[2[[[[4-nitrophenyl]oxy]carbonyl]oxy]-(R)-methylethyl]benzenesulfonamide (0.85 g, 0.14 mmol) was added ethylamine (0.13 g, 0.28 mmol) in DMF (2 mL). The resulting mixture was allowed to stir at 22° C. for 12 h and concentrated under reduced pressure. The mixture was diluted with methanol/H$_2$O (2 mL), followed by the addition of K$_2$CO$_3$. The mixture was filtered and the solvent was removed. Silica gel chromatography (30% ethyl acetate/hexanes) of the concentrate afforded the title compound. Yield=900/o colorless oil: MS (ESI+), 462 (M+H).

The following carbamates were prepared as described in the previous example.

EXAMPLE 559

4-Chloro-N-[5-chloro-2-(hydroxymethyl)phenyl]-N-[3-[[N'-[3-(1H-imidazol-1-yl) propylamino]carbonyl]oxy]-(R)-1-methylpropyl]benzenesulfonamide

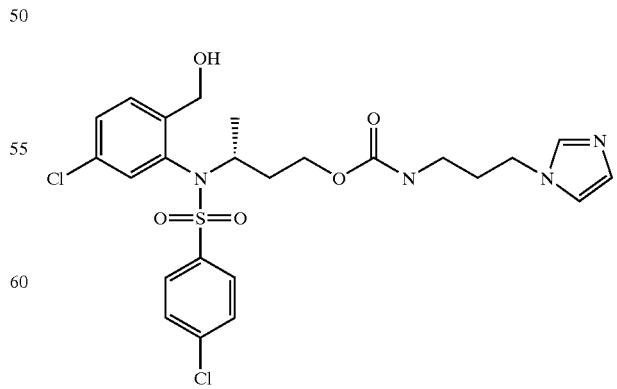

Yield=70% colorless oil: MS (ESI+), 556 (M+H).

EXAMPLE 560

4-Chloro-N-[5-chloro-2-(hydroxymethyl)phenyl]-N-[3-[[N'-[2-(1H-imidazol-1-yl) ethylamino]carbonyl]oxy]-(R)-1-methylpropyl]benzenesulfonamide

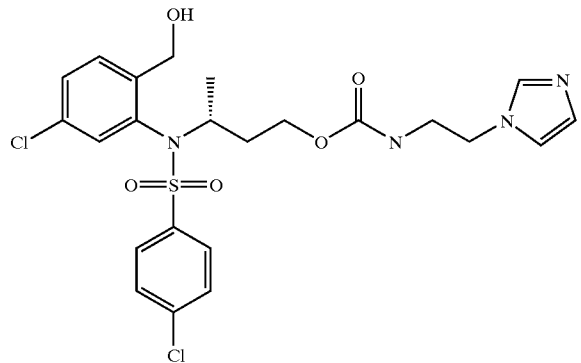

Yield=75% colorless oil: MS (ESI+), 542 (M+H).

EXAMPLE 561

4-Chloro-N-[5-chloro-2-(hydroxymethyl)phenyl]-N-[4-[[N'-[2-(1H-imidazol-1-yl) ethylamino]carbonyl]oxy]-(R)-1-methylbutyl]benzenesulfonamide

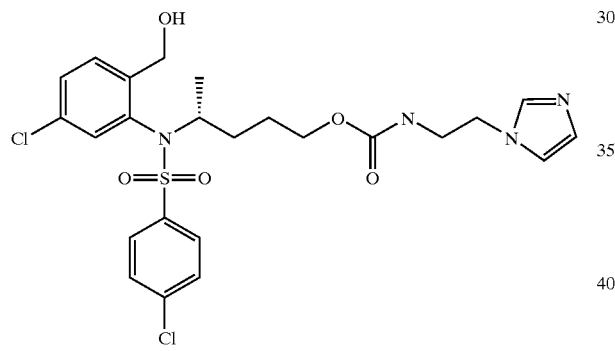

Yield=70% colorless oil: MS (ESI+), 556 (M+H).

EXAMPLE 562

4-Chloro-N-[5-chloro-2-(hydroxymethyl)phenyl)]-N-[4-[[N'-[3-(1H-imidazol-1-yl) propylamino]carbonyl]oxy]-(R)-1-methylbutyl]benzenesulfonamide

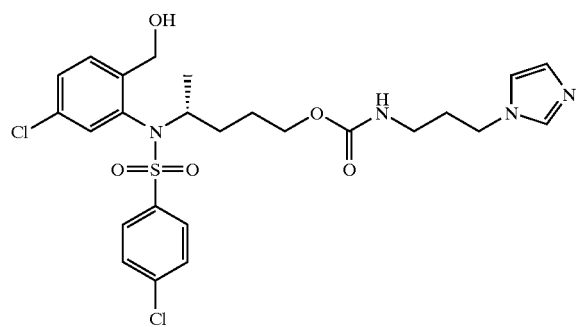

Yield=75% colorless oil: MS (ESI+), 570 (M+H).

EXAMPLE 563

4-Chloro-N-[5-chloro-2-(hydroxymethyl)phenyl]-N-[2-[[[N'-[3-(1H-imidazol-1-yl)propyl]-N'-ethylamino]carbonyl]oxy]-(R)-1-methylethyl]benzenesulfonamide

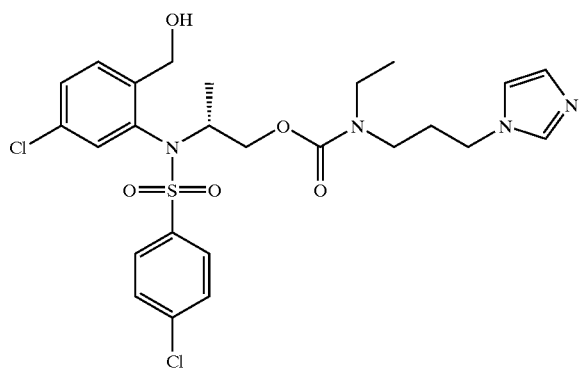

Yield=70% colorless oil: MS (ESI−), 567 (M−H).

EXAMPLE 564

4-Chloro-N-[5-chloro-2-(hydroxymethyl)phenyl]-N-[4-[[[pyrrolidin-1-yl]carbonyl]oxy]-(R)-1-methylbutyl]benzenesulfonamide

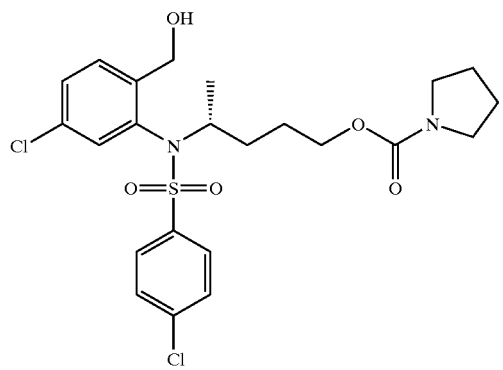

Yield=70% colorless oil: MS (ESI+), 516 (M+H).

EXAMPLE 565

4-Chloro-N-[5-chloro-2-(hydroxymethyl)phenyl]-N-[4-[[N'-[2-(hydroxyethyl)-N'-methylamino]carbonyl]oxy]-(R)-1-methylbutyl]benzenesulfonamide

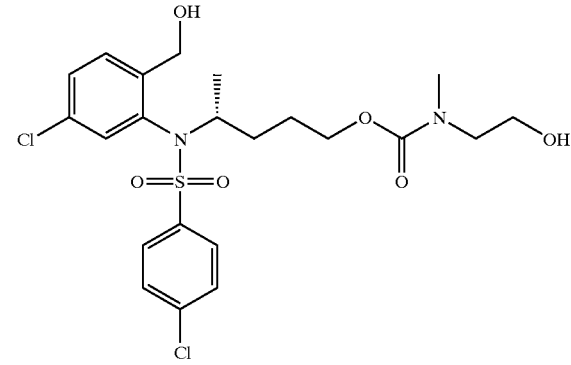

Yield=65% colorless oil: MS (ESI+), 520 (M+H).

EXAMPLE 566

4-Chloro-N-(2-fluoro-5-chlorophenyl)-N-[2-[[N'-[3-(1H-tetrazol-1-yl)propylamino]carbonyl]oxy]-(R)-1-methylethyl]benzenesulfonamide

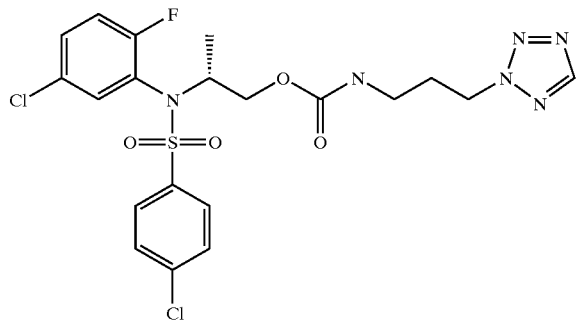

Yield=76% colorless oil: MS (ESI+), 532 (M+H).

EXAMPLE 567

4-Chloro-N-(2-fluoro-5-chlorophenyl)-N-[2-[[N'-[3-(1H-tetrazol-2-yl)propylamino]carbonyl]oxy]-(R)-1-methylethyl]benzenesulfonamide

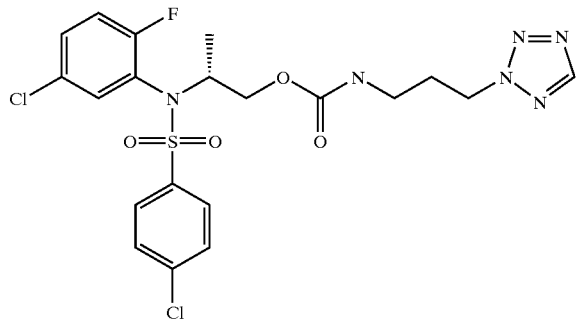

Yield=70% colorless oil: MS (ESI+), 532 (M+H).

EXAMPLE 568

4-Chloro-N-(5-chloro-2-fluorophenyl)-N-[[(1R)-1-(chlorocarbonyl)]ethyl]benzenesulfonamide

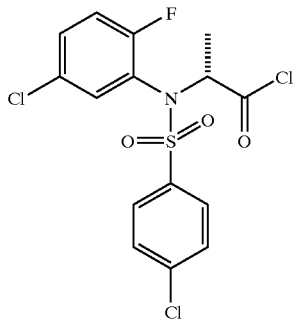

To a stirred solution of 4-chloro-N-(5-chloro-2-fluorophenyl)sulfoanilide (10 g, 31.23 mmol), triphenylphosphine (12.5 g, 45.99 mmol), and ethyl-(s)-lactate (5.43 g, 45.99 mmol) in THF (300 mL) was added diethylazodicarboxylate (11.94, 68.62 mmol) dropwise at 0° C. under nitrogen. The reaction mixture was allowed to warm to room temp and stirred for 18 h. and further diluted with ethyl acetate (1 L) and washed with water (2×500 mL), brine (1×500 mL) and dried over MgSO$_4$. Filtration and concentration in vacuo, followed by silica gel chromatography (5% ethyl acetate/hexane) of the concentrate produced the 4-chloro-N-(5-chloro-2-fluorophenyl)-N-[[(1R)-1-(ethoxycarbonyl)ethyl]-benzenesulfonamide compound, in 80% yield (10.5 g).

To the solution of above ester (2 g, 4.76 mmol) in THF:MeOH:H$_2$O/50:20:5 was added Lithium hydroxide (0.29 g, 7.14 mmol) and further stirred the reaction mixture for 2 h. The reaction mixture was diluted with 1N HCl (100 mL) and then extracted with ethyl acetate (2×150 mL). The organic layer was washed with brine and dried over MgSO$_4$, filtered, and concentrated to give 4-chloro-N-(5-chloro-2-fluorophenyl)-N-[(1R)-1-(carboxyethyl)]benzenesulfonamide as white solid in 75% yield (1.4 g). $^1$H NMR (DMSO) 7.92–7.29 (m, 7H), 4.60–4.58 (d, 1H), 4.04–4.01 (q, 1H), 1.11–1.09 (d, 2H), MS (ESI+) 391.87 (M+H)$^+$. Further, the resulting carboxylic acid (1.3 g, 3.31 mmoL) was dissolved in CH$_2$Cl$_2$ (50 mL) and DMF (0.3 mL) and oxalyl chloride (0.34 mL, 3.97 mmoL) was added to it. The resulting reaction mixture was stirred at rt for 1 h. It was then concentrated under reduced pressure to provide the title compound in 95% yield.

EXAMPLE 569

4-Chloro-N-5-chloro-2-fluorophenyl)-N-[(1R)-1-[(butylamino)carbonyl]ethyl]benzenesulfonamide

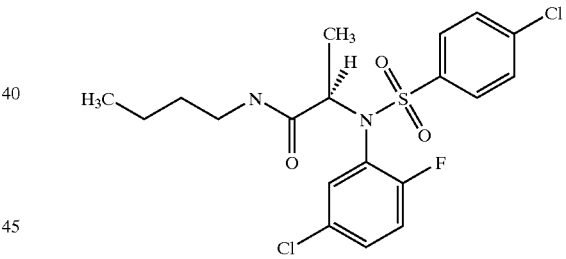

To the solution of N-butylamine (5.5 mg, 0.075 mmol) in 1,2 dichloroethane (0.75 mL) in a minireactors was added 2% cross linked poly(4-vinyl pyridine) (12.00 ng, 0.105 mmol) resin and solution (0.1 M) of 4-chloro-N-(5-chloro-2-fluorophenyl)-N-[[(R)-1 chlorocarbonyl)]ethyl] benzenesulfonamide (12.30 mg, 0.030 mmol) in 1,2 dichloromethane. The mini reactor was stirred on the shaker for 12 h, followed by quenching the reaction mixture with SCX (92 mg, 0.06 mmol) resin and further stirred on the shaker for additional 18 h. Filtered off the resin and washed the resin 1,2 dichloroethane (2×0.2 mL) and combined solvent was collected in microtube and evaporated and the product was analyzed by HPLC using the column YMC S7 C18 (3.0×50 mm) with a flow rate of 5.0 mL/min and gradient time of 2.0 min., using the solvent composition of 10% MeOH —90% H$_2$O—0.1% TFA, 90% MeOH—10% H$_2$O—0.1% TFA. The title compound was obtained with 77% purity in 54% yield; MS (ESI) 446.98 (M+H); R$_f$ =1.87.

EXAMPLE 570

4-Chloro-N-(5-chloro-2-fluorophenyl)-N-[(1R)-1-
[[[2-(4-morpholinyl)ethyl]amino]carbonyl]ethyl]
benzenesulfonamide

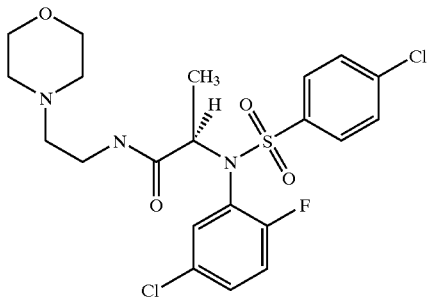

In a manner described herein, the title compound was prepared by the reaction of 4-chloro-N-(5-chloro-2-fluorophenyl)-N-[[(1R)-1-(chlorocarbonyl)]ethyl]benzenesulfonamide with 4-(2-aminoethyl)morpholine (25% yield); MS (ES) 503.99 (M+H); $R_f$ 1.70.

EXAMPLE 571

4-Chloro-N-(5-chloro-2-fluorophenyl)-N-[(1R)-1-
[[(3,3-diphenylpropyl)amino]carbonyl]ethyl]
benzenesulfonamide

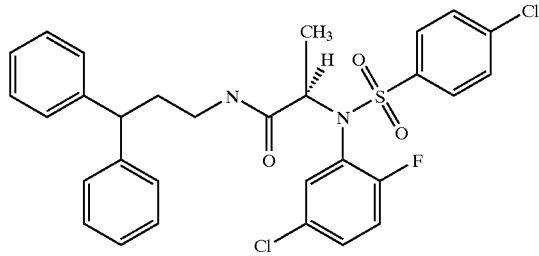

In a manner described herein, the title compound was prepared by the reaction of 4-chloro-N-(5-chloro-2-fluorophenyl)-N-[[(1R)-1-(chlorocarbonyl)]ethyl]benzenesulfonamide with 3,3-diphenylpropylamine (94% yield); MS (ESI) 584.96 (M+H); $R_f$ 2.1.

EXAMPLE 572

4-Chloro-N-(5-chloro-2-fluorophenyl)-N-[(1R)-1-
[[(cyclopropylmethyl)amino]carbonyl]ethyl]
benzenesulfonamide

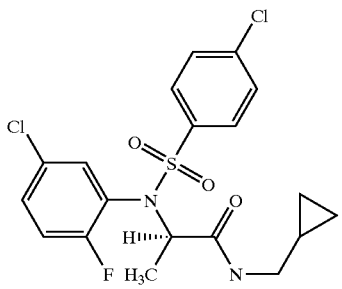

In a manner described herein, the title compound was prepared by the reaction of 4-chloro-N-(5-chloro-2-fluorophenyl)-N-[[(1R)-1-(chlorocarbonyl)]ethyl]benzenesulfonamide with (aminomethyl)cyclopropane (47% yield); MS ESI) 444.95 (M+H); $R_f$ 1.80.

EXAMPLE 573

4-Chloro-N-(5-chloro-2-fluorophenyl)-N-[(1R)-1-
[[[2-(4-pyridinyl)ethyl]amino]carbonyl]ethyl]
benzenesulfonamide

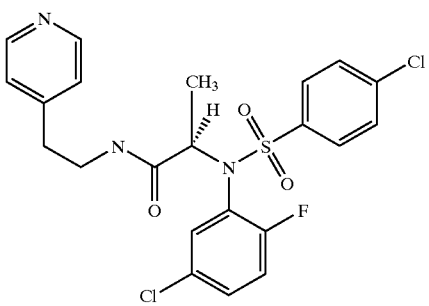

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 4-(2-aminoethyl)pyridine (30% yield) MS (ESI) 495.92 (M+H); $R_f$ 1.49.

EXAMPLE 574

4-Chloro-N-(5-chloro-2-fluorophenyl)-N-[(1R)-1-
[[[2-(2,4-dichlorophenylethyl]amino]carbonyl]ethyl]
benzenesulfonamide

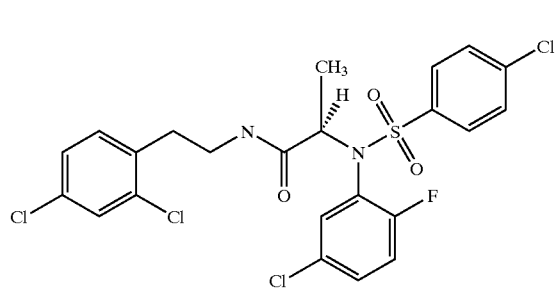

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 2,4-dichlorophenethylamine. (>95% yield); MS (ESI) 562.84 (M+H); $R_f$ 2.12.

EXAMPLE 575

4-Chloro-N-(5-chloro-2-fluorophenyl)-N-[(1R)-1-
[[(adamantylmethyl)amino]carbonyl]ethyl]
benzenesulfonamide

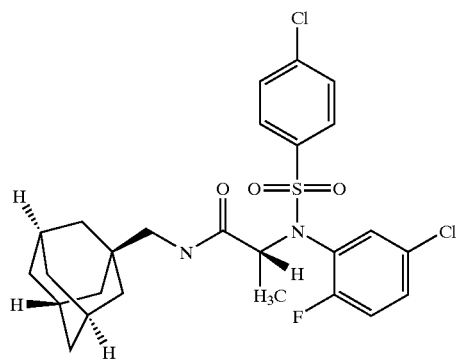

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 1-adamantanemethylamine (>95% yield); MS (ESI) 538.98 (M+H); $R_f$ 2.17.

EXAMPLE 576

4-Chloro-N-5-chloro-2-fluorophenyl)-N-[(1R)-1-
[(cyclopentylamino)carbonyl]ethyl]
benzenesulfonamide

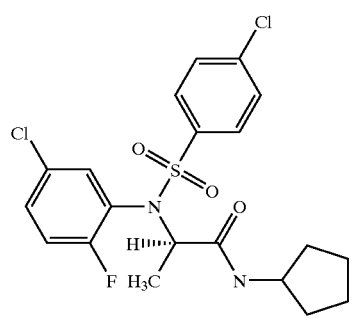

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with cyclopentylamine (61% yield) MS (ESI) 458.98 (M+H); $R_f$ 1.88.

EXAMPLE 577

4-Chloro-N-(5-chloro-2-fluorophenyl)-N-[(1R)-1-
[(cyclohexylamino)carbonyl]ethyl]
benzenesulfonamide

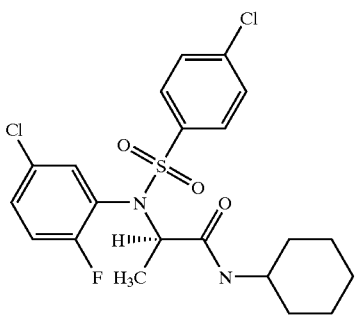

In a manner similar to previous examples, the title compound was prepared by the reaction of 4-chloro-N-(5-chloro-2-fluorophenyl)-N-[[(1R)-1-chlorocarbonyl)]ethyl]benzenesulfonamide with cyclohexylamine (>95% yield); MS (ESI) 473.00 (M+H); $R_f$ 1.95.

EXAMPLE 578
4-Chloro-N-(5-chloro-2-fluorophenyl)-N-[(1R)-1-[[(1,2,3,4-tetrahydro-1-naphthalenyl)amino]carbonyl]ethyl]benzenesulfonamide

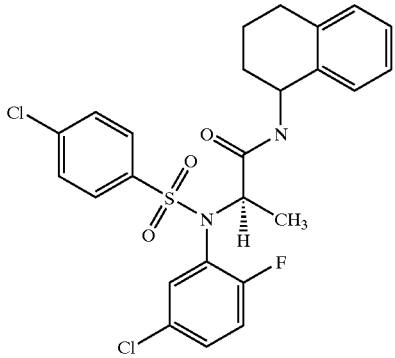

In a manner similar to previous examples, the title compound was prepared by the reaction of 4-chloro-N-5-chloro-2-fluorophenyl)-N-[[(1R)-1-(chlorocarbonyl)]ethyl]benzenesulfonamide 1,2,3,4-tetrahydro-1-naphthylamine (>95% yield); MS (ESI) 520.96 (M+H); $R_f$ 2.02.

EXAMPLE 579
4-Chloro-N-(5-chloro-2-fluorophenyl)-N-[(1R)-1-[[(2,3-dihydro-1H-indenyl)amino]carbonylethyl]benzenesulfonamide

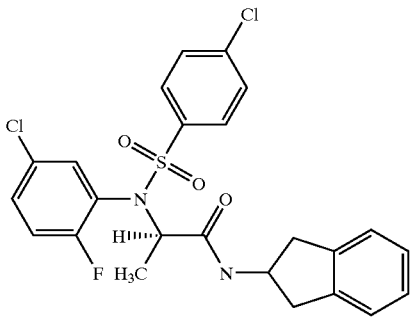

In a manner similar to previous examples, the title compound was prepared by the reaction of 4-chloro-N-5-chloro-2-fluorophenyl)-N-[[(1R)-1-(chlorocarbonyl)]ethyl]benzenesulfonamide with 2-aminoindan (86% yield); MS (ESI) 506.96 (M+H); $R_f$ 1.97.

EXAMPLE 580
4-Chloro-N-(5-chloro-2-fluorophenyl)-N-[(1R)-1-[[(1H-indazol-5-yl) amino]carbonylethyl]benzenesulfonamide

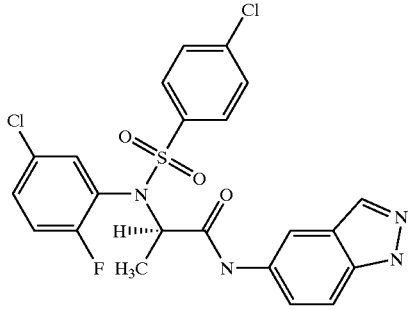

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 5-aminoindazole (97% yield); MS (ESI) 506.95 (M+H); $R_f$ 1.74.

EXAMPLE 581
4-Chloro-N-(5-chloro-2-fluorophenyl)-N-[(1R)-1-[[[4-(N,N-diethylamino)-1-methylbutyl]amino]carbonyl]ethyl]benzenesulfonamide

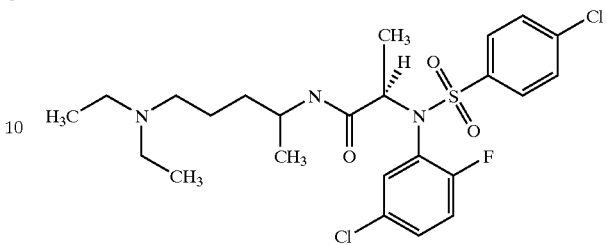

In a manner similar to previous examples, the title compound was prepared by the reaction of 4-chloro-N-5-chloro-2-fluorophenyl)-N-[[(1R)-1-(chlorocarbonyl)]ethyl]benzenesulfonamide with 2-amino-5-diethylaminopentane (<95% yield); MS (ESI) 532.03 (M+H); $R_f$ 1.58.

EXAMPLE 582
4-Chloro-N-(5-chloro-2-fluorophenyl)-N-[(1R)-1-[[[(4-pyridinyl)methyl]amino]carbonyl]ethyl]benzenesulfonamide

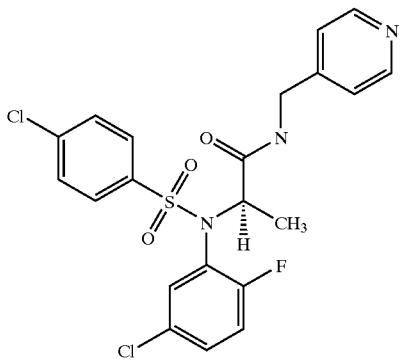

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 4-(aminomethyl)pyridine (28% yield);MS (ESI) 481.93 (M+H); $R_f$ 1.69.

EXAMPLE 583
4-Chloro-N-(chloro-2-fluorophenyl)-N-[(1R)-1-[[[(2,6-dichlorophenyl)ethyl]amino]carbonyl]ethyl]benzenesulfonamide

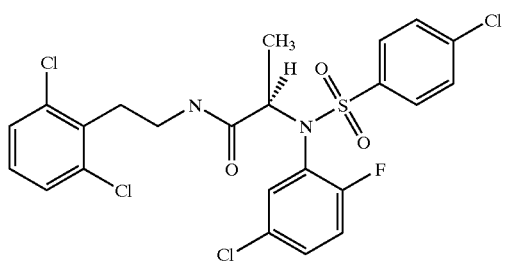

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 2,6-dichlorophenethylamine (94% yield); MS (ESI) 562.98 (M+H); $R_f$ 2.04.

EXAMPLE 584

4-Chloro-N-(5-chloro-2-fluorophenyl)-N-[(1R)-1-[[2-[N-ethyl-N-(3-methylphenyl)amino]ethyl]carbonyl]ethyl]benzenesulfonamide

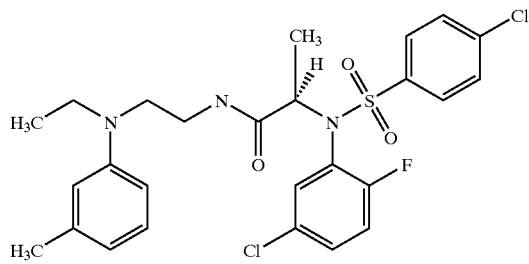

In a manner similar to previous examples, the title compound was prepared by the reaction of 4-chloro-N-(5-chloro-2-fluorophenyl)-N-[[(1R)-1-chlorocarbonyl)]ethyl] benzenesulfonamide with N-(2-aminoethyl)-N-ethyl-M-toluidine (<95% yield); MS (ESI) 551.99 (M+H); $R_f$ 1.72.

EXAMPLE 585

4-Chloro-N-(5-chloro-2-fluorophenyl)-N-[(1R)-1-[[(4-tert-butylcyclohexyl) amino]carbonyl]ethyl]benzenesulfonamide

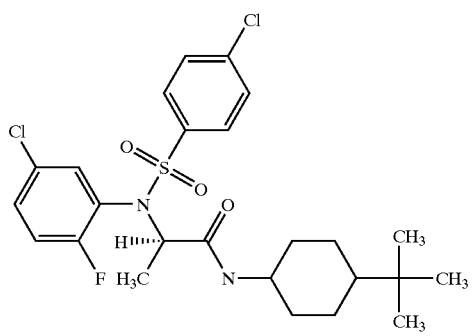

In a manner similar to previous examples, the title compound was prepared by the reaction of 4-chloro-N-(5-chloro-2-fluorophenyl)-N-[[(1R)-1-(chlorocarbonyl)]ethyl] benzenesulfonamide with 4-tert-butylcyclohexylamine (>95% yield); MS (ESI) 529.03 (M+H); $R_f$ 2.20.

EXAMPLE 586

4-Chloro-N-(5-chloro-2-fluorophenyl)-N-[(1R)-1-[[[2-(2-thienyl)ethyl]amino]carbonyl]ethyl]benzenesulfonamide

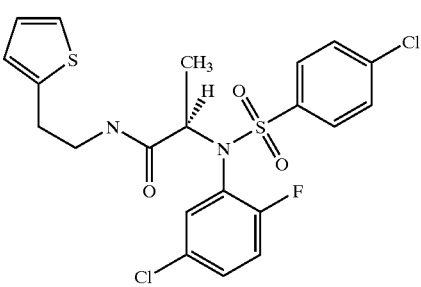

In a manner similar to previous examples, the title compound was prepared by the reaction of 4-chloro-N-(5-chloro-2-fluorophenyl)-N-[[(1R)-1-(chlorocarbonyl)]ethyl] benzenesulfonamide with 2-thiopheneethylamine (>95% yield); MS (ESI) 500.91 (M+H); $R_f$ 1.90.

EXAMPLE 587

4-Chloro-N-(5-chloro-2-fluorophenyl)-N-[(1R)-1-[[(2-phenoxyethyl)amino]carbonyl]ethyl]benzenesulfonamide

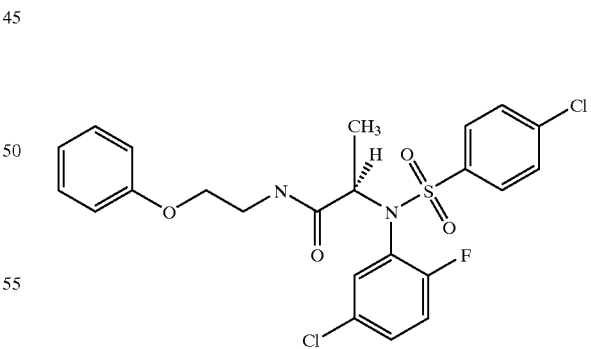

In a manner similar to previous examples, the title compound was prepared by the reaction of 4-chloro-N-(5-chloro-2-fluorophenyl)-N-[[(1R)-(chlorocarbonyl)]ethyl] benzenesulfonamide with 2-phenoxyethylamine (>95% yield); MS (ESI) 510.95 (M+H); $R_f$ 1.92.

EXAMPLE 588

4-Chloro-N-(5-chloro-2-fluorophenyl)-N-[(1R)-1-[[[(1,3-benzodioxol-5-yl)methyl]amino]carbonyl]ethyl]benzenesulfonamide

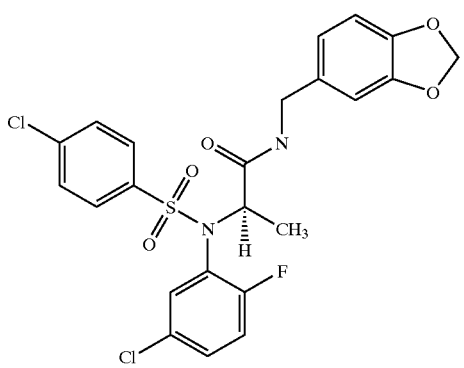

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 3,4-methylenedioxybenzylamine (>95% yield); MS (ESI) 524.93 (M+H); $R_f$ 1.84.

EXAMPLE 589

4-Chloro-N-(5-chloro-2-fluorophenyl)-N-[(1R)-1-[[(3-ethoxypropyl)amino]carbonyl]ethyl]benzenesulfonamid

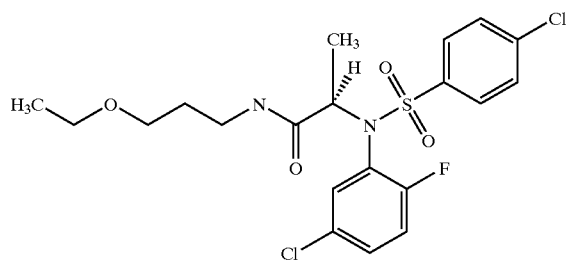

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 3-ethoxypropylamine (>95% yield); MS (ESI) 476.99 (M+H); $R_f$ 1.79.

EXAMPLE 590

4-Chloro-N-(5-chloro-2-fluorophenyl)-N-[(1R)-1-[[[(2-tetrahydrofuranyl)methyl]amino]carbonyl]ethyl]benzenesulfonamide

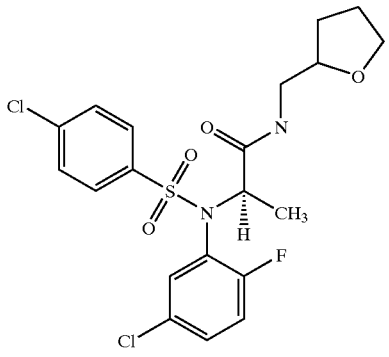

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with tetrahydrofurfurylamine (93% yield); MS (ESI) 474.99 (M+H); $R_f$ 1.75.

EXAMPLE 591

4-Chloro-N-(5-chloro-2-fluorophenyl)-N-[(1R)-1-[[[3-(4-morpholinyl)propyl]amino]carbonyl]ethyl]benzenesulfonamide

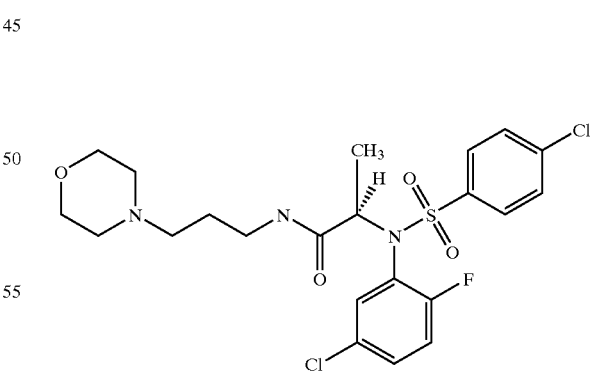

In a manner similar to previous examples, the title compound was prepared by the reaction of 4-chloro-N-(5-chloro-2-fluorophenyl)-N-[[(1R)—(chlorocarbonyl)]ethyl]benzenesulfonamide with 4-(3-aminopropyl)morpholine (44% yield); MS (ESI) 518.00 (M+H); $R_f$ 1.51.

EXAMPLE 592

4-Chloro-N-5-chloro-2-fluorophenyl)-N-[(1R)-1-[[[[(2R)-6,7-dimethylbicyclo]3.1.1]heptan-2-yl]methyl]amino]carbonyl]ethyl]benzenesulfonamide

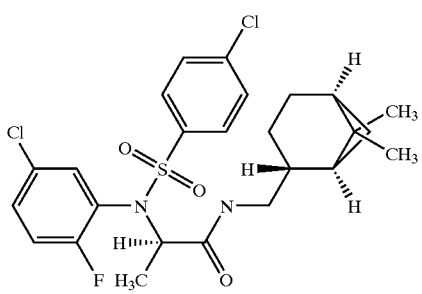

In a manner similar to previous examples, the title compound was prepared by the reaction of 4-chloro-N-(5-chloro-2-fluorophenyl)-N-[[(1R)-1-chlorocarbonyl)]ethyl]benzenesulfonamide with (−)-cis-myrtanylamine (>95% yield); MS (ESI) 527.01 (M+H); $R_f$, 2.14.

EXAMPLE 593

4-Chloro-N-(5-chloro-2-fluorophenyl)-N-[(1R)-1-[[(4-phenylbutyl)amino]carbonyl]ethyl]benzenesulfonamide

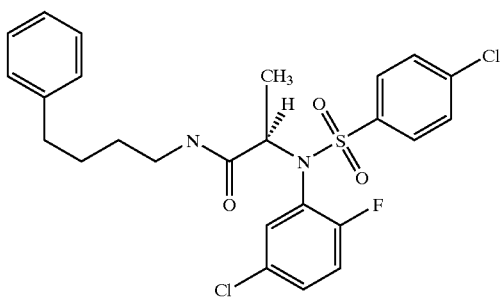

In a manner similar to previous examples, the title compound was prepared by the reaction of 4-chloro-N-5-chloro-2-fluorophenyl)-N-[[(1R)-1-(chlorocarbonyl)]ethyl]benzenesulfonamide with 4-phenylbutylamine (>95% yield); MS (ESI) 522.98 (M+H); $R_f$ 2.03.

EXAMPLE 594

4-Chloro-N-(5-chloro-2-fluorophenyl)-N-[(1R)-1-[[[2-(4-methylphenyl)ethyl amino]carbonyl]ethyl]benzenesulfonamide

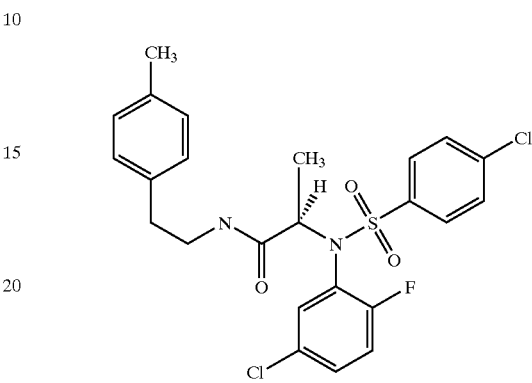

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 2-(p-tolyl)ethylamine (69% yield); MS (ESI) 508.95 (M+H); $R_f$ 2.01.

EXAMPLE 595

4-Chloro-N-(5-chloro-2-fluorophenyl)-N-[(1R)-1-[[[2-(4-flurophenyl)ethyl]amino]carbonyl]ethyl]benzenesulfonamide

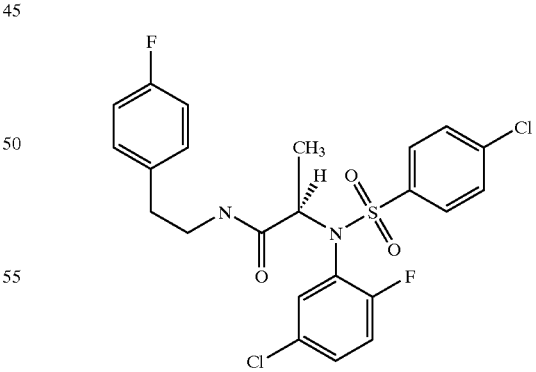

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 4-fluorophenethylamine (68% yield); MS (ESI) 512.94 (M+H); $R_f$ 1.94.

EXAMPLE 596

4-Chloro-N-(5-chloro-2-fluorophenyl)-N-[(1R)-1-[[(2,6-difluorophenylmethyl) amino]carbonyl]ethyl]benzenesulfonamide

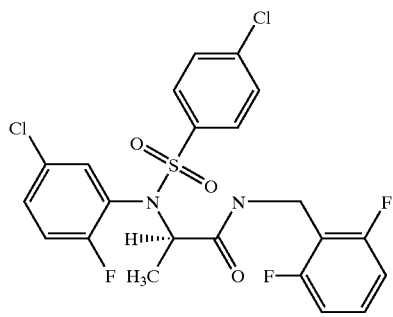

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 2,6-difluorobenzylamine (75% yield); MS (ESI) 516.93 (M+H); $R_f$ 1.86.

EXAMPLE 597

4-Chloro-N-(5-chloro-2-fluorophenyl)-N-[(1R)-1-[[(3-hydroxy-2,2-dimethylpropyl)amino]carbonyl]ethyl]benzenesulfonamide

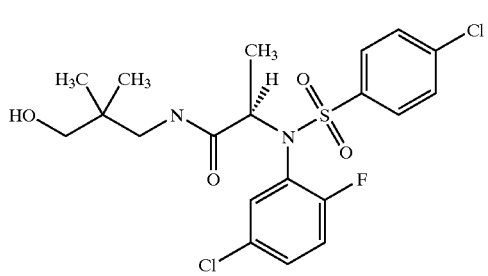

In a manner similar to previous examples, the title compound was prepared by the reaction of 4-chloro-N-(5-chloro-2-fluorophenyl)-N-[[(R)-1-(chlorocarbonyl)]ethyl]benzenesulfonamide with neopentanolamine (73% yield); MS (ESI) 476.99 (M+H); $R_f$ 1.74.

EXAMPLE 598

4-Chloro-N-(5-chloro-2-fluorophenyl-N-[(1R)-1-[[N-(2-aminoethyl)-N-phenylamino]carbonyl]ethyl]benzenesulfonamide

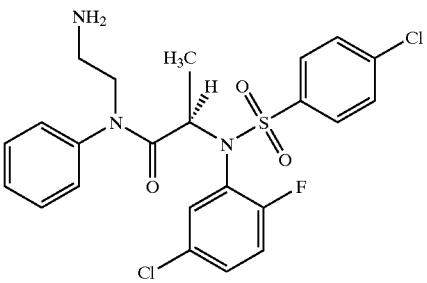

In a manner similar to previous examples, the title compound was prepared by the reaction of 4-chloro-N-5-chloro-2-fluorophenyl)-N-[[(1R)-1-chlorocarbonyl)]ethyl]benzenesulfonamide with N-phenylethylenediamine (>95% yield); MS (ESI) 509.97 (M+H); $R_f$ 1.72.

EXAMPLE 599

4-Chloro-N-(5-chloro-2-fluorophenyl)-N-[(1R)-1-[[(3-iodophenylmethyl) amino]carbonyl]ethyl]benzenesulfonamide

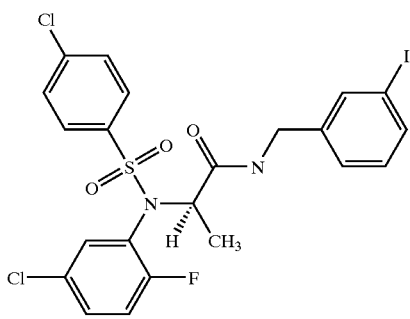

In a manner similar to previous examples, the title compound was prepared by the reaction of 4-chloro-N-(5-chloro-2-fluorophenyl)-N-[[(R)-1-(chlorocarbonyl)]ethyl]benzenesulfonamide with 3-iodobezylamine (>95% yield); MS (ESI) 606.78 (M+H); $R_f$ 2.01.

EXAMPLE 600

4-Chloro-N-(5-chloro-2-fluorophenyl)-N-[(1R)-1-[[[2-(4-hydroxyphenyl)ethyl]amino]carbonyl]ethyl]benzenesulfonamide

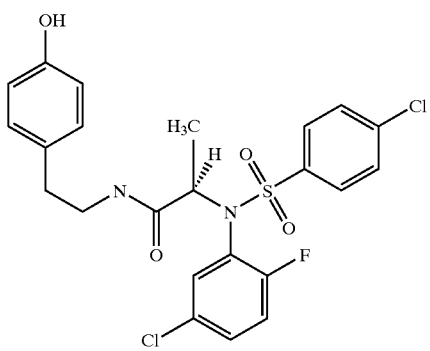

In a manner similar to previous examples, the title compound was prepared by the reaction of 4-chloro-N-(5-chloro-2-fluorophenyl)-N-[[(R)-1-(chlorocarbonyl)]ethyl]benzenesulfonamide with tyramine (44% yield); MS (ESI) 510.94 (M+H); $R_f$ 1.73.

EXAMPLE 601

4-Chloro-N-(5-chloro-2-fluorophenyl)-N-[(1R)-1-[[[(3-pyridinyl)methyl]amino]carbonyl]ethyl]benzenesulfonamide

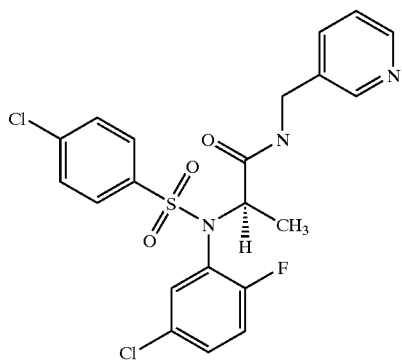

In a manner similar to previous examples, the title compound was prepared by the reaction of 4-chloro-N-5-chloro-2-fluorophenyl)-N-[[(1R)-1-(chlorocarbonyl)]ethyl]benzenesulfonamide with 3-(aminomethyl)pyridine (15% yield); MS (ESI) 481.95 (M+H); $R_f$ 1.49.

EXAMPLE 602

4-Chloro-N-(5-chloro-2-fluorophenyl)-N-[(1R)-1-[[[(3-(N,N-dibutylamino)propyl]amino]carbonyl]ethyl]Benzenesulfonamide

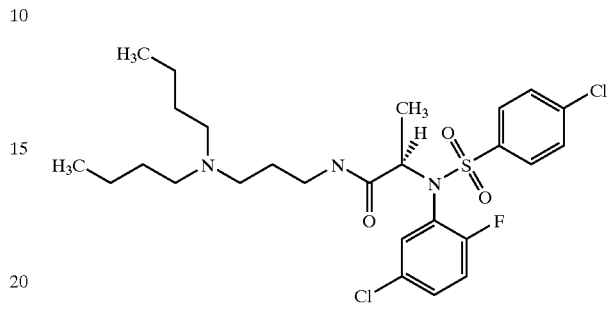

In a manner similar to previous examples, the title compound was prepared by the reaction of 4-chloro-N-5-chloro-2-fluorophenyl)-N-[[(1R)-1-(chlorocarbonyl)]ethyl]benzenesulfonamide with 3-(dibutylamino)propylamine (>95% yield); MS (ESI) 560.04 (M+H); $R_f$ 1.74.

EXAMPLE 603

4-Chloro-N-(5-chloro-2-fluorophenyl)-N-[(1R)-1-[[[(3,4-difluorophenylmethyl)amino]carbonyl]ethyl]benzenesulfonamide

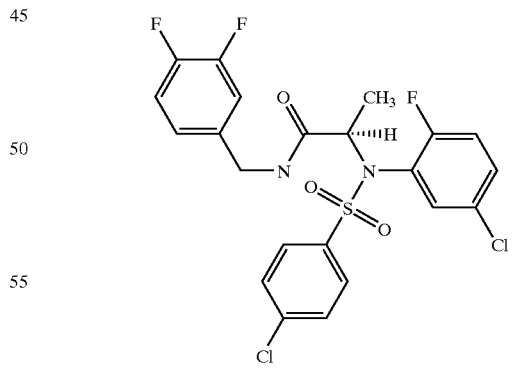

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 3,4-difluorobenzylamine (>95% yield); MS (ESI) 516.93 (M+H); $R_f$ 1.91.

EXAMPLE 604

4-Chloro-N-(5-chloro-2-fluorophenyl)-N-[(1R)-1-[[(5-hydroxy-1,5-dimethylhexyl)amino]carbonyl]ethyl]benzenesulfonamide

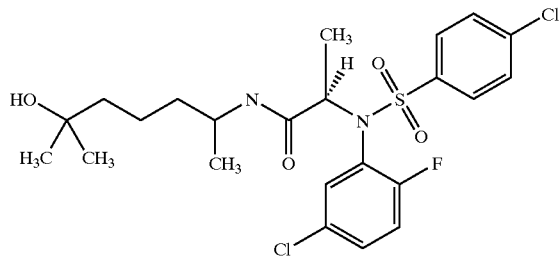

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with heptaminol hydrochloride (22% yield); MS (ESI) 519.01 (M+H); $R_f$ 1.69.

EXAMPLE 605

4-Chloro-N-(5-chloro-2-fluorophenyl)-N-[(1R)-1-[[(5-chloro-2-hydroxyphenyl)amino]carbonyl]ethyl]benzenesulfonamide

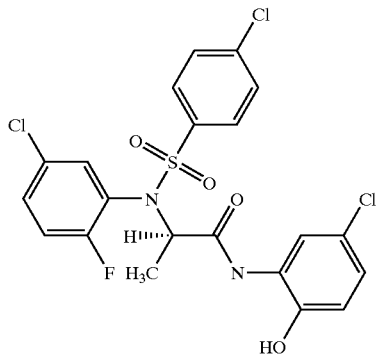

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 2-amino-4-chlorophenol (50% yield); MS (ESI) 516.87 (M+H); $R_f$ 1.93.

EXAMPLE 606

4-Chloro-N-5-chloro-2-fluorophenyl)-N-[(1R)-1-[(tetradecylamino)carbonyl]ethyl]benzenesulfonamide

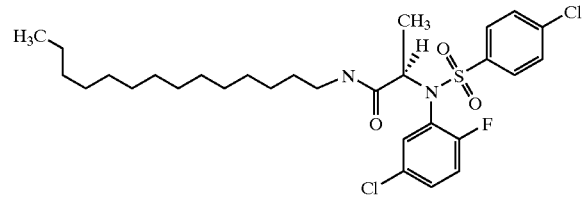

In a manner similar to previous examples, the title compound was prepared by the reaction of 4-chloro-N-(5-chloro-2-fluorophenyl-N-[[(1R)-1-(chlorocarbonyl)]ethyl]benzenesulfonamide with 1-tetradecylamine (38% yield); MS (ESI) 587.07 (M+H); $R_f$ 2.73.

EXAMPLE 607

4-Chloro-N-(5-chloro-2-fluorophenyl)-N-[(1R)-1-[[(trans-4hydroycyclohexyl)amino]carbonyl]ethyl]benzenesulfonamide

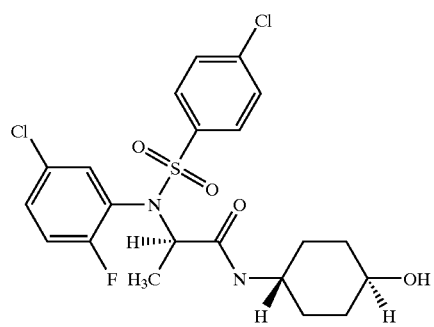

In a manner similar to previous examples, the title compound was prepared by the reaction of 4-chloro-N-5-chloro-2-fluorophenyl)-N-[[(1R)-1-(chlorocarbonyl)]ethyl]benzenesulfonamide with trans-4-aminocyclohexanol hydrochloride (29% yield); MS (ESI) 488.99 (M+H); $R_f$ 1.69.

EXAMPLE 608

4-Chloro-N-(5-chloro-2-fluorophenyl)-N-[(1R)-1-[[[2-(2-pyridinyl) amino]carbonyl]ethyl]benzenesulfonamide

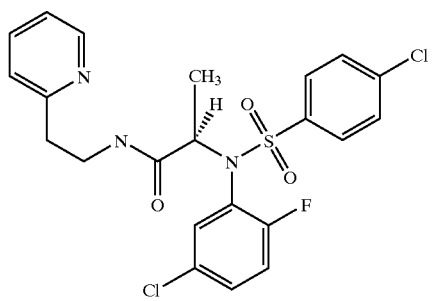

In a manner similar to previous examples, the title compound was prepared by the reaction of 4-chloro-N-(5-chloro-2-fluorophenyl)-N-[[(1R)-1-chlorocarbonyl)]ethyl]benzenesulfonamide with 2-(2-aminoethyl)pyridine (>95% yield); MS (ESI) 495.96 (M+H); $R_f$ 1.69.

EXAMPLE 609

4-Chloro-N-(5-chloro-2-fluorophenyl)-N-[(1R)-1-[[[3-(2-methyl-1-piperidinyl) amino]carbonyl]ethyl]benzenesulfonamide

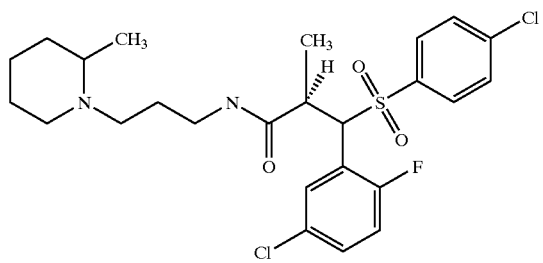

In a manner similar to previous examples, the title compound was prepared by the reaction of 4-chloro-N-(5-chloro-2-fluorophenyl-N-[[(1R)-1-(chlorocarbonyl)ethyl]benzenesulfonamide with 1-(3-aminopropyl)-2-pipecoline (>95% yield); MS (ESI) 529.98 (M+H); $R_f$ 1.68.

EXAMPLE 610

4-Chloro-N-(5-chloro-2-fluorophenyl)-N-[(1R)-1-[[[(2-pyridinyl)methyl amino]carbonyl]ethyl]benzenesulfonamid

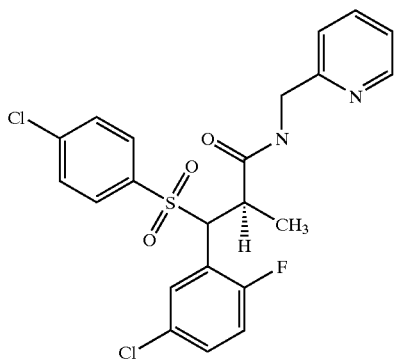

In a manner similar to previous examples, the title compound was prepared by the reaction of 4-chloro-N-(5-chloro-2-fluorophenyl)-N-[[(1R)-1-(chlorocarbonyl)ethyl]benzenesulfonamide with 2-(aminomethyl)pyridine (>95% yield); MS (ESI) 482.04 (M+H); $R_f$ 1.69.

EXAMPLE 611

4-Chloro-N-(5-chloro-2-fluorophenyl)-N-[(1R)-1-[[(4-methylcyclohexyl)amino]carbonyl]ethyl]benzenesulfonamide

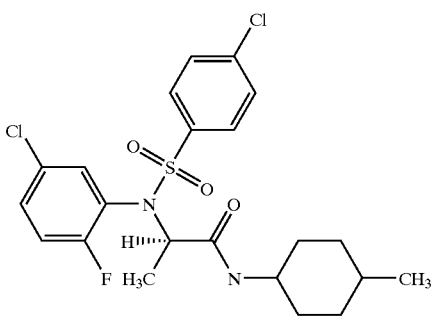

In a manner similar to previous examples, the title compound was prepared by the reaction of 4-chloro-N-(5-chloro-2-fluorophenyl)-N-[[(1R)-1-(chlorocarbonyl)ethyl]benzenesulfonamide with 4-methylcyclohexylamine (>95% yield); MS (ESI) 487.00 (M+H); $R_f$ 2.01.

EXAMPLE 612

4-Chloro-N-(5-chloro-2-fluorophenyl)-N-1-[[[(1R)-1-(hydroxymethyl)-2-[(phenylmethyl)thio]-ethyl]amino]carbonyl]benzenesulfonamide

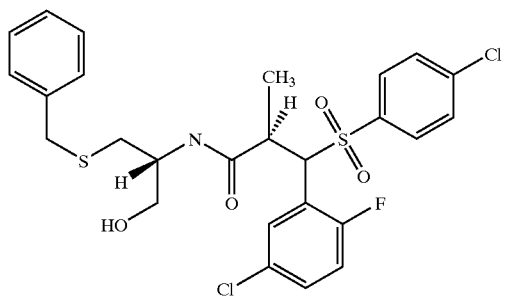

In a manner similar to previous examples, the title compound was prepared by the reaction of 4-chloro-N-(5-chloro-2-fluorophenyl)-N-[[(1R)-1-(chlorocarbonyl)ethyl]benzenesulfonamide with S-benzyl-L-cysteinol (75% yield); MS (ESI) 570.93 (M+H); $R_f$ 1.95.

EXAMPLE 613

4-Chloro-N-(5-chloro-2-fluorophenyl)-N-[(1R)-1-
[[(2-hydroxy-1,1-dimethylethyl) amino]carbonyl]
ethyl]benzenesulfonamide

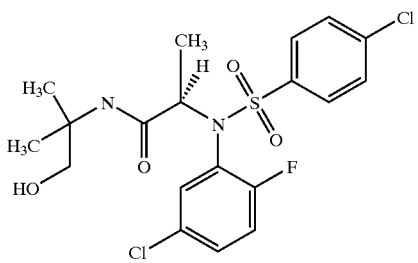

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 2-amino-2-methyl-1-propanol (58% yield); MS (ESI) 462.96 (M+H); $R_f$ 1.71.

EXAMPLE 614

4-Chloro-N-(5-chloro-2-fluorophenyl)-N-[(1R)-1-
[(cycloheptylamino)]carbonyl]ethyl]
Benzenesulfonamide

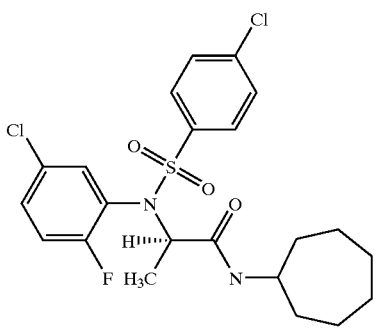

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with cycloheptylamine (83% yield); MS (ESI) 487.00 (M+H); $R_f$ 2.00.

EXAMPLE 615

4-Chloro-N-(5-chloro-2-fluorophenyl)-N-[(1R)-1-
[[(4-oxapentyl)amino]carbonyl]ethyl]
benezenesulfonamide

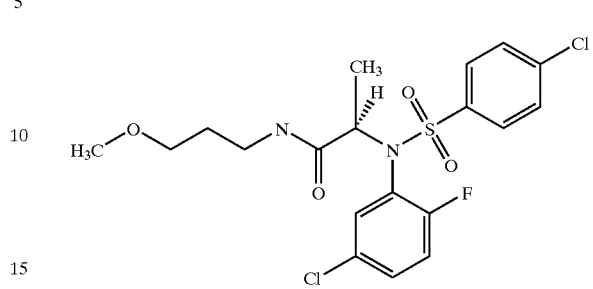

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 3-methoxypropylamine (96% yield); MS (ESI) 462.97 (M+H); $R_f$ 1.73.

EXAMPLE 616

4-Chloro-N-(5-chloro-2-fluorophenyl)-N-[(1R)-1-
[[(3-methylcyclohexyl)amino]carbonyl]ethyl]
benezenesulfonamide

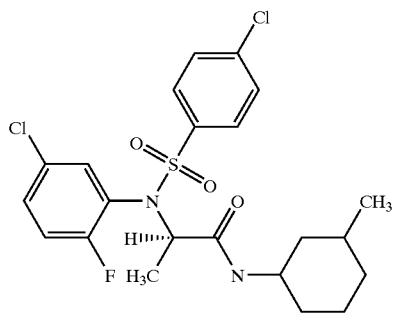

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 3-methylcyclohexylamine (76% yield); MS (ESI) 487.01 (M+H); $R_f$ 2.01.

EXAMPLE 617

4-Chloro-N-(5-chloro-2-fluorophenyl)-N-[(1R)-1-
[[[4-[2,4-bis(1,1-dimethylpropyl)-phenoxy]butyl]
amino]carbonyl]ethyl]benzenesulfonamide

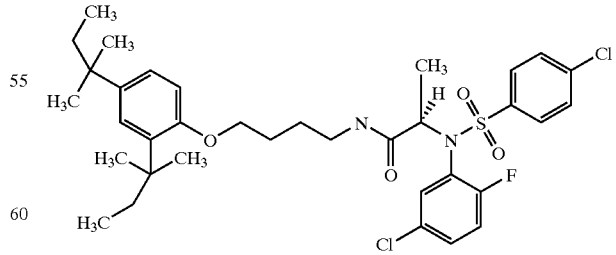

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 4-(2,4-di-tert-amylphenoxy)butylamine (94% yield); MS (ESI) 679.1 (M+H); $R_f$ 2.60.

EXAMPLE 618

4-Chloro-N-(5-chloro-2-fluorophenyl)-N-[(1R)-1-[[[1-(hyroxymethyl)-2-methylpropyl]amino]carbonyl]ethyl]benzenesulfonamide

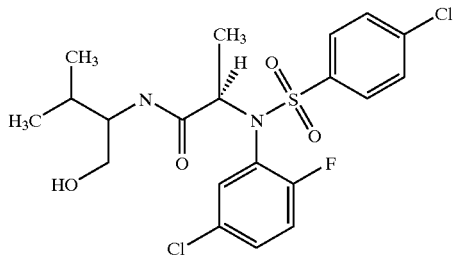

In a manner similar to previous examples, the title compound was prepared by the reaction of 4-chloro-N-(5-chloro-2-fluorophenyl)-N-[[(1R)-1-chlorocarbonyl)]ethyl]benzenesulfonamide with DL-valinol (66% yield); MS (ESI) 477.00 (M+H); $R_f$ 1.77.

EXAMPLE 619

4-Chloro-N-(5-chloro-2-fluorophenyl)-N-[(1R)-1-[[(6-hydroxyhexyl)amino]carbonyl]ethyl]benzenesulfonamide

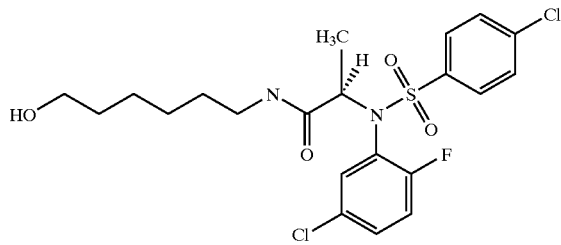

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 6-amino-1-hexanol (39% yield); MS (ESI) 490.98 (M+H); $R_f$ 1.72.

EXAMPLE 620

4-Chloro-N-(5-chloro-2-fluorophenyl)-N-[(1R)-1-[[(1R)-(1-cyclohexylethyl)amino]carbonyl]ethyl]benzenesulfonamide

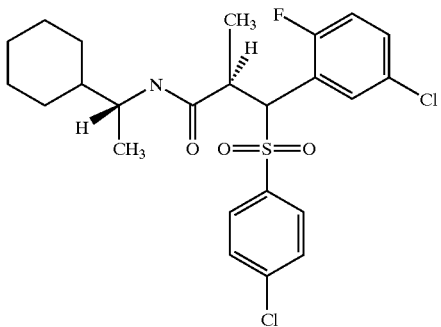

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with (R)-(–)-1-cyclohexylethylamine (76% yield); MS (ESI) 501.00 (M+H); $R_f$ 2.07.

EXAMPLE 621

4-Chloro-N-(5-chloro-2-fluorophenyl)-N-[(1R)-1-[[[(2-(piperidinyl)ethyl]amino]carbonyl)ethyl]benzenesulfonamide

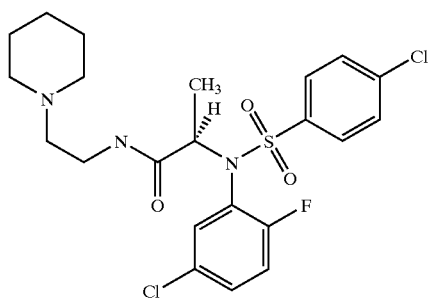

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 1-(2-aminoethyl)piperidine (20% yield); MS (ESI) 502.05 (M+H); $R_f$ 1.69.

EXAMPLE 622

4-Chloro-N-(5-chloro-2-fluorophenyl)-N-[(1R)-1-[[[2-(4-methoxyphenyl)ethyl]amino]carbonyl]ethyl]benzenesulfonamide

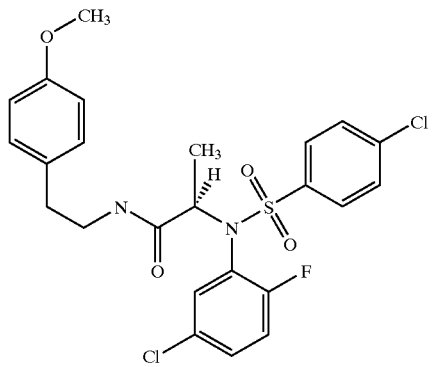

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 4-methoxyphenethylamine (64% yield); MS (ESI) 524.97 (M+H); $R_f$ 1.91.

EXAMPLE 623

4-Chloro-N-(5-chloro-2-fluorophenyl)-N-[(1R)-1-[[N-(2-aminoethyl)-N-(5-nitro-2-pyridinyl) amino]carbonyl]ethyl]benzenesulfonamide

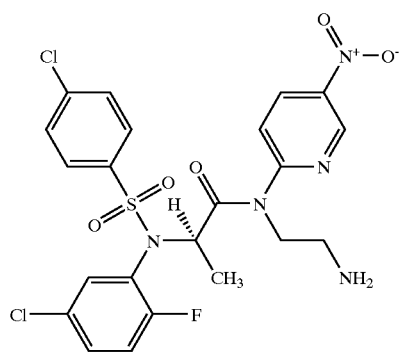

In a manner similar to previous examples, the title compound was prepared by the reaction of 4-chloro-N-(5-chloro-2-fluorophenyl)-N-[[(R)-1-(chlorocarbonyl)]ethyl]benzenesulfonamide with 2-(2-aminoethylamino)-5-nitropyridine (>95% yield); MS (ESI) 555.93 (M+H); $R_f$ 1.80.

EXAMPLE 624

4-Chloro-N-(5-chloro-2-fluorophenyl)-N-[(1R)-1-[[[(1S)-2-hydroxy-1-(phenylmethyl)ethyl]amino]carbonyl]ethyl]benzenesulfonamide

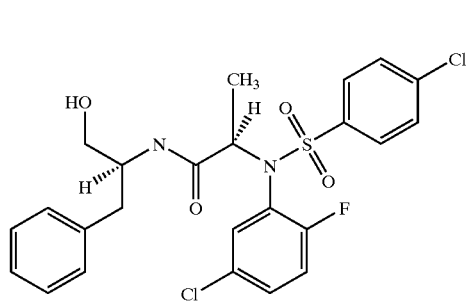

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with L-phenylalaninol (75% yield); MS (ESI) 524.96 (M+H); $R_f$ 1.87.

EXAMPLE 625

4-Chloro-N-(5-chloro-2-fluorophenyl)-N-[(1R)-1-[[[(2,5-difluorophenylmethyl)amino]carbonyl]ethyl]benzenesulfonamide

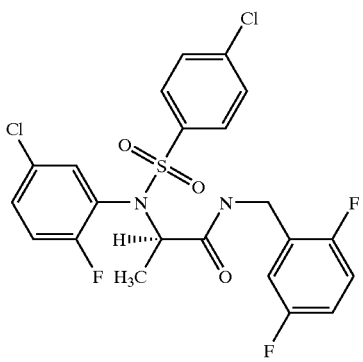

In a manner similar to previous examples, the title compound was prepared by the reaction of 4-chloro-N-(5-chloro-2-fluorophenyl)-N-[(1R)-1-(chlorocarbonyl)]ethyl]benzenesulfonamide with 2,5-difluorobenzylamine (93% yield); MS (ESI) 516.93 (M+H); $R_f$ 1.88.

EXAMPLE 626

4-Chloro-N-(5-chloro-2-fluorophenyl)-N-[(1R)-[[[(2-thienyl)methyl]amino]carbonyl]ethyl]benzenesulfonamide

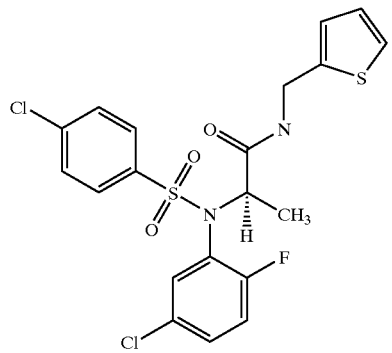

In a manner similar to previous examples, the title compound was prepared by the reaction of 4-chloro-N-5-chloro-2-fluorophenyl)-N-[[(1R)-1-(chlorocarbonyl)]ethyl]benzenesulfonamide with 2-aminomethylthiophene (67% yield); MS (ESI) 486.91 (M+H); $R_f$ 1.84.

EXAMPLE 627

4-Chloro-N-(5-chloro-2-fluorophenyl)-N-(1R)-1-[[(2R)-bicyclo[2.2.1]hept-2-yl)amino]carbonyl]ethyl]benzenesulfonamide

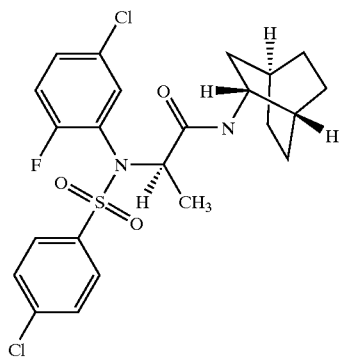

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with exo-2-aminononobornane (77% yield); MS (ESI) 485.00 (M+H); $R_f$ 1.96.

EXAMPLE 628

4-Chloro-N-(5-chloro-2-fluorophenyl)-N-[(1R)-1-[[[(2-fluorophenyl)ethyl]amino]carbonyl]ethyl]benzenesulfonamide

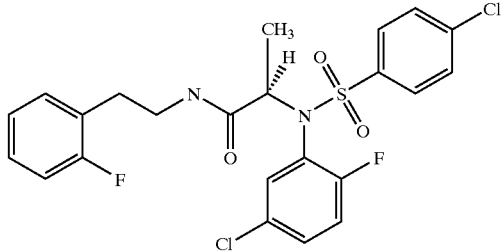

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 2-fluorophenethylamine (80% yield); MS (ESI) 512.94 (M+H); $R_f$ 1.93.

EXAMPLE 629

4-Chloro-N-(5-chloro-2-fluorophenyl)-N-[(1R)-1-[[(4-hydroxybutyl) amino]carbonyl]ethyl]benzenesulfonamide

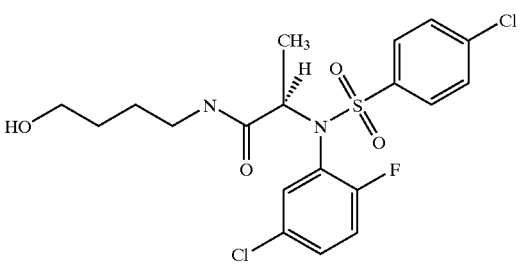

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 4-amino-1-butanol (24% yield); MS (ESI) 462.97 (M+H); $R_f$ 1.63.

EXAMPLE 630

4-Chloro-N-(5-chloro-2-fluorophenyl)-N-[(1R)-1-[[(4-methoxyphenylmethyl)amino]carbonyl]ethyl]benzenesulfonamide

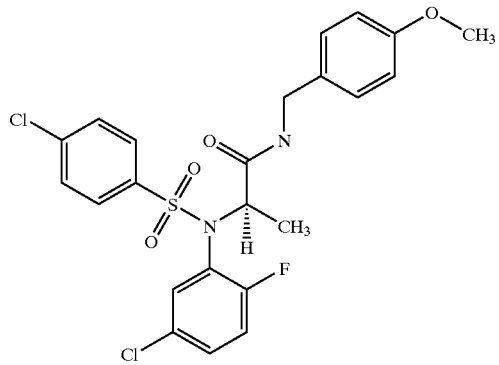

In a manner similar to previous examples, the title compound was prepared by the reaction of 4-chloro-N-(5-chloro-2-fluorophenyl)-N-[[(1R)-1-(chlorocarbonyl)]ethyl]benzenesulfonamide with 4-methoxybenzylamine (60% yield); MS (ESI) 510.95 M+H); $R_f$ 1.86.

EXAMPLE 631

4-Chloro-N-(5-chloro-2-fluorophenyl)-N-[(1R)-1-[[(3,4,5-trimethoxyphenylmethyl) amino]carbonyl] ethyl]benzenesulfonamide

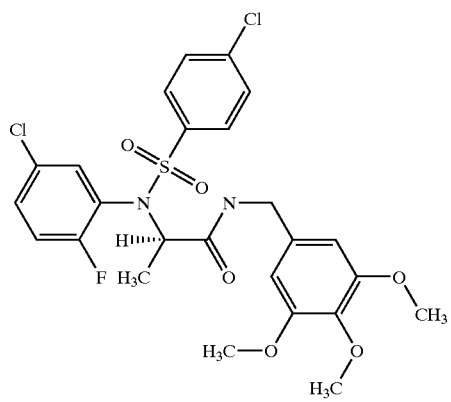

In a manner similar to previous examples, the title compound was prepared by the reaction of 4-chloro-N-(5-chloro-2-fluorophenyl)-N-[[(1R)-1-(chlorocarbonyl)]ethyl] benzenesulfonamide with 3,4,5-trimethoxybenzylamine (94% yield); MS (ESI) 570.95 M+H); $R_f$ 1.80.

EXAMPLE 632

4-Chloro-N-(5-chloro-2-fluorophenyl)-N-[(1R)-1-[[[2-[[2-(hydromethyl)phenyl]thio]-phenylmethyl] amino]carbonyl]ethyl]benzenesulfonamide

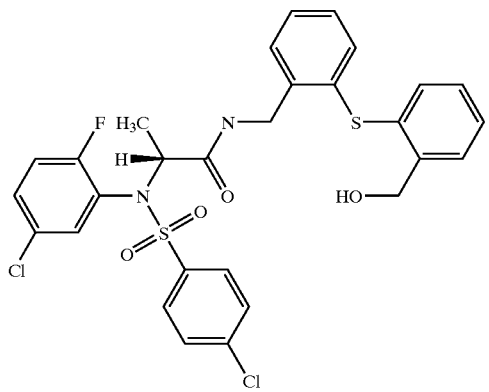

In a manner similar to previous examples, the title compound was prepared by the reaction of 4-chloro-N-(5-chloro-2-fluorophenyl)-N-[[(1R)-1-(chlorocarbonyl)]ethyl] benzenesulfonamide with 2-(2-(aminomethyl)phenylthio) benzylalcohol (>95% yield); MS (ESI) 618.95 (M+H); $R_f$ 1.97.

EXAMPLE 633

4-Chloro-N-(5-chloro-2-fluorophenyl)-N-[(1R)-1-[[(2,6-dimethoxyphenylmethyl) amino]carbonyl] ethyl]benzenesulfonamide

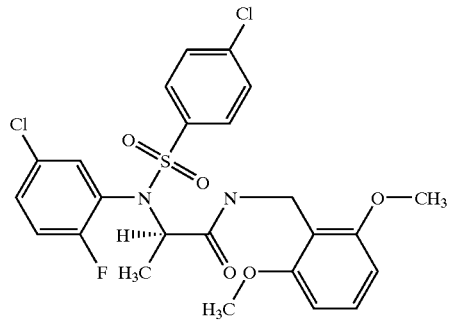

In a manner similar to previous examples, the title compound was prepared by the reaction of 4-chloro-N-(5-chloro-2-fluorophenyl)-N-[[(1R)-1-(chlorocarbonyl)]ethyl] benzenesulfonamide with 2,6-dimethoxybenzylamine (>95% yield); MS (ESI) 540.96 (M+H); $R_f$ 1.95.

EXAMPLE 634

4-Chloro-N-5-chloro-2-fluorophenyl)-N-[(1R)-[[(3,5-dichorophenylmethyl) amino]carbonyl]ethyl] benzenesulfonamide

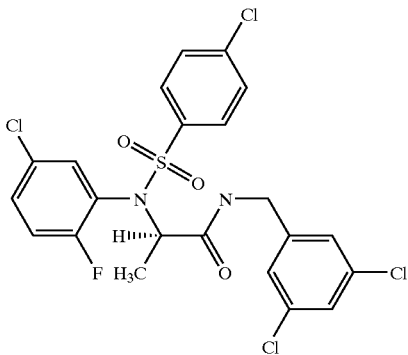

In a manner similar to previous examples, the title compound was prepared by the reaction of 4-chloro-N-(5-chloro-2-fluorophenyl)-N-[[(1R)-1-(chlorocarbonyl)]ethyl] benzenesulfonamide with 3,5-dichlorobenzylamine (65% yield); MS (ESI) 548.81 (M+H); $R_f$ 2.07.

EXAMPLE 635

4-Chloro-N-(5-chloro-2-fluorophenyl)-N-[(1R)-1-[[[4-(1,2,3-thiadiazol-4-yl)phenylmethyl]amino] carbonyl]ethyl]benzenesulfonamide In a manner similar to previous examples, the title compound was prepared by the reaction of 4-chloro-N-(5-chloro-2-fluorophenyl)-N-[[(1R)-1-chlorocarbonyl)]ethyl] benzenesulfonamide with R4-(1,2,3-thiadiazol-4-yl) benzylamine (84% yield); MS (ESI) 564.91 (M+H); $R_f$ 1.82.

EXAMPLE 636

In Vitro Cell-Based Assay of Inhibitors of Amyloid β Production

Transfected H4 (human neuroglioma) cells stably expressing APP constructs are used to identify and assess inhibitors of Aβ production. In brief, cells lines are exposed to compounds, and the effect of each compound on amyloid β production is determined by measuring the amount of amyloid β produced using an enzyme linked immunosorbent assay (ELISA) that detects amyloid β (see, for example, Seubert et al., (1992) *Nature,* 359:325–327).

Transfected cells that stably express wild-type and variant forms of APP are plated in 96-well format plates at a density sufficient for the rapid detection of the secreted amyloid β (experimentally predetermined for a particular stable cell population). Cells are plated at least six hours prior to the introduction of the test compound at which time the growth medium is replaced by fresh medium containing the compound to be tested. All synthetic agents are initially screened at doses ranging from 10–100 μM. Higher dilutions of agents can be used to minimize cytotoxicity. Incubation of cells with a test compound continues for approximately 16 hours at which time aliquots of medium from each well are removed and assayed for amyloid β.

ELISA is carried out by methods known in the art (see, e.g., Haass et al., *Antibodies: A Laboratory Manual,* Harlow and lane, Editors, Cold Spring Harbor Press, 1988) The capture antibody is typically a mouse monoclonal (IgG1/kβ-APPa) which recognizes the carboxyl terminal epitope of amyloid β. The specificity of the capture antibody insures measurement of amyloid β without interference from other secreted APP fragments that share amino acid sequence (amyloid β 1–16) homology with amyloid β but lack the carboxy-terminal region. The detecting antibody is typically an affinity-purified rabbit polyclonal antibody that is specific for the amino terminus of amyloid β.

Results from test compounds are compared to results obtained when cells are treated with control agents. Amyloid β levels are determined by comparison to a standard curve obtained by subjecting a range of known amounts of amyloid β to the ELISA.

A compound is identified as "active" when it inhibits cellular production of amyloid β relative to levels in control samples by at least 50% at the initial tested concentration without significant cytotoxicity. Active compounds are then assayed in dose-response experiments to determine the lowest dose of compound necessary for inhibition of amyloid β production. The results obtained when invention compounds are subjected to the above described assay results are summarized in Table B. In the table, an inhibitory concentration ($IC_{50}$) of less than or equal to 25 nM is represented by +++++; 50 nM≧$IC_{50}$>25 nM, by ++++; 100 nM≧$IC_{50}$>50 nM, by +++; 500 nM≧$IC_{50}$>100 nM by ++; $IC_{50}$>500 nM is represented by +. Compounds which did not display measurable activity in this assay are represented by –.

| NUMBER | ACTIVITY | COMPOUND |
|---|---|---|
| 1 | +++++ | 4-chloro-N-(2,5-difluorophenyl)-N-((1R)-1-{2-[4-(1,1-dioxido-4-thiomorpholinyl)-4-oxobutyl]-4-fluorophenyl}ethyl)benzenesulfonamide |
| 2 | +++++ | 4-chloro-N-(2,5-difluorophenyl)-N-((1R)-1-{2-[4-(1,1-dioxido-4-thiomorpholinyl)-4-oxobutyl]-4-fluorophenyl}ethyl)benzenesulfonamide |
| 3 | +++++ | 4-chloro-N-(2,5-difluorophenyl)-N-((1R)-1-{4-fluoro-2-[4-oxo-4-(4-thiomorpholinyl)butyl]phenyl}ethyl)benzenesulfonamide |
| 4 | +++++ | 4-chloro-N-(2,5-difluorophenyl)-N-((1R)-1-{4-fluoro-2-[3-(4-methyl-1-piperazinyl)-3-oxopropyl]phenyl}ethyl)benzenesulfonamide hydrochloride |
| 5 | +++++ | 4-chloro-N-(2,5-difluorophenyl)-N-((1R)-1-{4-fluoro-2-[3-oxo-3-(4-thiomorpholinyl)propyl]phenyl}ethyl)benzenesulfonamide |
| 6 | +++++ | 4-chloro-N-(2,5-difluorophenyl)-N-((1R)-1-{4-fluoro-2-[3-(1-piperidinyl)propyl]phenyl}ethyl)benzenesulfonamide |
| 7 | +++++ | 4-chloro-N-(2,5-difluorophenyl)-N-(1-{2-[3-(1H-imidazol-1-yl)propoxy]phenyl}ethyl)-benzenesulfonamide |
| 8 | +++++ | 4-chloro-N-(2,5-difluorophenyl)-N-{2-[3-(1-piperidinyl)propoxy]benzyl}benzenesulfonamide hydrochloride |
| 9 | +++++ | 4-chloro-N-(2,5-difluorophenyl)-N-{2-[3-(1-piperidinyl)propoxy]benzyl}benzenesulfonamide hydrochloride |
| 10 | +++++ | 4-chloro-N-(2,5-difluorophenyl)-N-{2-[3-(1-piperidinyl)propoxy]benzyl}benzenesulfonamide hydrochloride |
| 11 | +++++ | 4-chloro-N-(2,5-difluorophenyl)-N-{2-[3-(1-piperidinyl)propoxy]benzyl}benzenesulfonamide hydrochloride |
| 12 | +++++ | methyl (2R)-2-[(tert-butoxycarbonyl)amino]-3-{[2-((1R)-1-{[(4-chlorophenyl)sulfonyl]-2,5-difluoroanilino}ethyl)-5-fluorobenzyl]sulfonyl}propanoate |
| 13 | +++++ | 4-chloro-N-(2,5-difluorophenyl)-N-((1R)-1-{2-[3-(1-piperidinyl)propyl]phenyl}ethyl)-benzenesulfonamide hydrochloride |
| 14 | +++++ | ethyl 4-[2-((1R)-1-{[(4-chlorophenyl)sulfonyl]-2,5-difluoroanilino}ethyl)-5-fluorophenyl]butanoate |
| 15 | +++++ | 4-chloro-N-(2,5-difluorophenyl)-N-((1R)-1-{4-fluoro-2-[3-(4-methyl-1-piperazinyl)-3-oxopropyl]phenyl}ethyl)benzenesulfonamide |
| 16 | +++++ | 4-chloro-N-(2,5-difluorophenyl)-N-((1R)-1-{4-fluoro-2-[3-(2H-tetraazol-2-yl)propyl]phenyl}ethyl)benzenesulfonamide |
| 17 | +++++ | 4-[2-((1R)-1-{5-chloro[(4-chlorophenyl)-sulfonyl]-2-fluoroanilino}ethyl)-5-fluorophenyl]butanoic acid |
| 18 | +++++ | 4-chloro-N-(2,5-difluorophenyl)-N-((1R)-1-{4-fluoro-2-[2-(3-pyridinylmethoxy)ethyl]phenyl}ethyl)benzenesulfonamide hydrochloride |
| 19 | +++++ | 4-chloro-N-(2,5-difluorophenyl)-N-[(1R)-1-(4-fluoro-2-{4-[(methylamino)sulfonyl]butyl}-phenyl)ethyl]benzenesulfonamide |
| 20 | +++++ | 4-chloro-N-(2,5-difluorophenyl)-N-[(1R)-1-(4-fluoro-2-{4-[(methylamino)sulfonyl]butyl}-phenyl)ethyl]benzenesulfonamide |
| 21 | +++++ | 4-chloro-N-(2,5-difluorophenyl)-N-((1R)-1-{4-fluoro-2-[3-(methylsulfonyl)propyl]phenyl}-ethyl)benzenesulfonamide |
| 22 | +++++ | 4-chloro-N-(2,5-difluorophenyl)-N-[(1R)-1-(4-fluoro-2-{4-[(methylamino)sulfonyl]butyl}-phenyl)ethyl]benzenesulfonamide |
| 23 | +++++ | 4-[2-((1R)-1-{[(4-chlorophenyl)sulfonyl]-2,5-difluoroanilino}ethyl)-5-fluorophenyl]butanoic acid |
| 24 | +++++ | 4-chloro-N-(2,5-difluorophenyl)-N-((1R)-1-{4-fluoro-2-[3-(1-piperidinyl)butyl]phenyl}-ethyl)benzenesulfonamide hydrochloride |
| 25 | +++++ | 2-((1R)-1-{[(4-chlorophenyl)sulfonyl]-2,5-difluoroanilino}ethyl)benzyl 4-thiomorpholine-carboxylate |
| 26 | +++++ | 4-chloro-N-(2,5-difluorophenyl)-N-((1R)-1-{2-[3-(ethylsulfonyl)propyl]-4-fluorophenyl}-ethyl)benzenesulfonamide |
| 27 | +++++ | 4-chloro-N-(2,5-difluorophenyl)-N-((1R)-1-{2-[3-(ethylsulfonyl)propyl]-4-fluorophenyl}-ethyl)benzenesulfonamide |
| 28 | +++++ | 4-chloro-N-(2,5-difluorophenyl)-N-((1R)-1-{4-fluoro-2-[4-(4-methyl-1-piperazinyl)-4-oxobutyl]phenyl}ethyl)benzenesulfonamide hydrochloride |

-continued

| NUMBER | ACTIVITY | COMPOUND |
|---|---|---|
| 29 | +++++ | 4-chloro-N-(2,5-difluorophenyl)-N-((1R)-1-{4-fluoro-2-[2-(4-pyridinylmethoxy)ethyl]-phenyl}ethyl)benzenesulfonamide hydrochloride |
| 30 | +++++ | 5-[2-((1R)-1-{[(4-chlorophenyl)sulfonyl]-2,5-difluoroanilino}ethyl)-5-fluorophenyl]-pentanoic acid |
| 31 | +++++ | 4-chloro-N-[5-chloro-2-(hydroxymethyl)-phenyl]-N-((1R)-1-{2-[3-(1H-imidazol-1-yl)-propyl]phenyl}ethyl)benzenesulfonamide |
| 32 | +++++ | 4-chloro-N-(2,5-difluorophenyl)-N-((1R)-1-{4-fluoro-2-[3-(1H-1,2,4-triazol-1-yl)propyl]-phenyl}ethyl)benzenesulfonamide |
| 33 | +++++ | 4-chloro-N-(2,5-difluorophenyl)-N-((1R)-1-{4-fluoro-2-[4-(1H-imidazol-1-yl)butyl]phenyl}-ethyl)benzenesulfonamide hydrochloride |
| 34 | +++++ | 4-[2-((1R)-1-{[(4-chlorophenyl)sulfonyl]-2,5-difluoroanilino}ethyl)-5-fluorophenyl]butanoic acid |
| 35 | +++++ | 4-chloro-N-(2,5-difluorophenyl)-N-[(1R)-1-(4-fluoro-2-{3-[(methylamino)sulfonyl]propyl}-phenyl)ethyl]benzenesulfonamide |
| 36 | +++++ | methyl (2R)-2-[(tert-butoxycarbonyl)amino]-3-{(2-((1R)-1-{[(4-chlorophenyl)sulfonyl]-2,5-difluoroanilino}ethyl)-5-fluorobenzyl]-sulfanyl}propanoate |
| 37 | +++++ | 4-chloro-N-(2,5-difluorophenyl)-N-((1R)-1-{4-fluoro-2-[4-oxo-4-(1-piperidinyl)butyl]-phenyl}ethyl)benzenesulfonamide |
| 38 | +++++ | 3-[2-((1R)-1-{[(4-chlorophenyl)sulfonyl]-2,5-difluoroanilino}ethyl)-5-fluorophenyl]-propanoic acid |
| 39 | +++++ | 3-[2-((1R)-1-{[(4-chlorophenyl)sulfonyl]-2,5-difluoroanilino}ethyl)-5-fluorophenyl]-propanoic acid |
| 40 | +++++ | N-(tert-butoxy)-4-[2-((1R)-1-{[(4-chloro-phenyl)sulfonyl]-2,5-difluoroanilino}ethyl)-5-fluorophenyl]butanamide |
| 41 | +++++ | 4-chloro-N-(2,5-difluorophenyl)-N-((1R)-1-{2-[3-(1H-imidazol-1-yl)propyl]phenyl}ethyl)-benzenesulfonamide hydrochloride |
| 42 | +++++ | 4-chloro-N-(2,5-difluorophenyl)-N-((1R)-1-{2-[3-(1H-imidazol-1-yl)propyl]phenyl}ethyl)-benzenesulfonamide hydrochloride |
| 43 | +++++ | 4-chloro-N-(2,5-difluorophenyl)-N-((1R)-1-{2-[3-(1H-imidazol-1-yl)propyl]phenyl}ethyl)-benzenesulfonamide hydrochloride |
| 44 | +++++ | 4-chloro-N-(2,5-difluorophenyl)-N-((1R)-1-{2-[3-(1H-imidazol-1-yl)propyl]phenyl}ethyl)-benzenesulfonamide hydrochloride |
| 45 | +++++ | 4-chloro-N-(2,5-difluorophenyl)-N-((1R)-1-{4-fluoro-2-[4-(methylsulfonyl)butyl]phenyl}-ethyl)benzenesulfonamide |
| 46 | +++++ | 4-chloro-N-(2,5-difluorophenyl)-N-((1R)-1-{4-fluoro-2-[4-(methylsulfonyl)butyl]phenyl}-ethyl)benzenesulfonamide |
| 47 | +++++ | 4-chloro-N-(2,5-difluorophenyl)-N-[(1R)-1-(2-{3-[(dimethylamino)sulfonyl]propyl}-4-fluorophenyl)ethyl]benzenesulfonamide |
| 48 | +++++ | 4-chloro-N-(2,5-difluorophenyl)-N-((1R)-1-{4-fluoro-2-[4-(1-piperidinyl)butyl]phenyl}-ethyl)benzenesulfonamide hydrochloride |
| 49 | +++++ | 4-chloro-N-(2,5-difluorophenyl)-N-(1-{2-[3-(4H-1,2,4-triazol-4-yl)propoxy]phenyl}ethyl)-benzenesulfonamide hydrochloride |
| 50 | +++++ | 4-chloro-N-(2,5-difluorophenyl)-N-[(1R)-1-(2-{3-[(ethylamino)sulfonyl]propyl}-4-fluoro-phenyl)ethyl]benzenesulfonamide |
| 51 | +++++ | 4-chloro-N-(2,5-difluorophenyl)-N-((1R)-1-{4-fluoro-2-[3-(1H-tetrazol-1-yl)propyl]phenyl}-ethyl)benzenesulfonamide |
| 52 | +++++ | 4-chloro-N-(2,5-difluorophenyl)-N-((1R)-1-{2-[(ethylsulfonyl)methyl]-4-fluorophenyl}-ethyl)benzenesulfonamide |
| 53 | +++++ | 4-chloro-N-(2,5-difluorophenyl)-N-((1R)-1-{4-fluoro-2-[3-(1H-imidazol-1-yl)propyl]phenyl}-ethyl)benzenesulfonamide hydrochloride |
| 54 | +++++ | 4-chloro-N-(2,5-difluorophenyl)-N-((1R)-1-{4-fluoro-2-[3-(1H-imidazol-1-yl)propyl]phenyl}-ethyl)benzenesulfonamide hydrochloride |
| 55 | +++++ | 4-chloro-N-(2,5-difluorophenyl)-N-((1R)-1-{4-fluoro-2-[3-(1H-imidazol-1-yl)propyl]phenyl}-ethyl)benzenesulfonamide hydrochloride |
| 56 | +++++ | 4-[2-((1R)-1-{[(4-chlorophenyl)sulfonyl]-2,5-difluoroanilino}ethyl)-5-fluorophenyl]-N-methoxybutanamide |
| 57 | +++++ | N-(3-{2-((1R)-1-{[(4-chlorophenyl)sulfonyl]-2,5-difluoroanilino}ethyl)phenoxy]propyl)-N,2,2-trimethylpropanamide |
| 58 | +++++ | 4-chloro-N-(2,5-difluorophenyl)-N-{(1R)-1-[4-fluoro-2-(3-hydroxybutyl)phenyl]ethyl}-benzenesulfonamide |
| 59 | +++++ | 4-chloro-N-(2,5-difluorophenyl)-N-[(1R)-1-(2-{4-[(ethylamino)sulfonyl]butyl}-4-fluoro-phenyl)ethyl]benzenesulfonamide |
| 60 | +++++ | 4-chloro-N-(2,5-difluorophenyl)-N-(1-{4-fluoro-2-[3-(1H-imidazol-1-yl)propyl]phenyl}-ethyl)benzenesulfonamide hydrochloride |
| 61 | +++++ | N-{4-[2-((1R)-1-{[(4-chlorophenyl)sulfonyl]-2,5-difluoroanilino}ethyl)phenoxy]butyl}-2-methoxy-N-methylacetamide |
| 62 | +++++ | methyl 3-{[2-((1R)-1-{[(4-chlorophenyl)-sulfonyl]-2,5-difluoroanilino}ethyl)-5-fluoro-benzyl]sulfonyl}propanoate |
| 63 | +++++ | 2-[2-((1R)-1-{[(4-chlorophenyl)sulfonyl]-2,5-difluoroanilino}ethyl)phenyl]ethyl 4-thio-morpholinecarboxylate |
| 64 | +++++ | 4-chloro-N-(2,5-difluorophenyl)-N-((1R)-1-{2-[3-(ethylsulfanyl)propyl]-4-fluorophenyl}-ethyl)benzenesulfonamide |
| 65 | +++++ | 4-chloro-N-(2,5-difluorophenyl)-N-((1R)-1-{2-[4-(ethylsulfonyl)butyl]-4-fluorophenyl}-ethyl)benzenesulfonamide |
| 66 | +++++ | 4-chloro-N-(2,5-difluorophenyl)-N-((1R)-1-{2-[4-(ethylsulfonyl)butyl]-4-fluorophenyl}-ethyl)benzenesulfonamide |
| 67 | +++++ | 4-chloro-N-(2,5-difluorophenyl)-N-((1R)-1-{2-[3-(1H-imidazol-1-yl)propoxy]phenyl}-ethyl)benzenesulfonamide hydrochloride |
| 68 | +++++ | 4-[2-(1-{[(4-chlorophenyl)sulfonyl]-2,5-difluoroanilino}ethyl)-5-fluorophenyl]butanoic acid |
| 69 | +++++ | 4-chloro-N-(2,5-difluorophenyl)-N-{(1R)-1-[4-fluoro-2-(4-hydroxypentyl)phenyl]ethyl}-benzenesulfonamide |
| 70 | +++++ | methyl (2R)-2-[(tert-butoxycarbonyl)amino]-3-({3-[2-((1R)-1-{[(4-chlorophenyl)sulfonyl]-2,5-difluoroanilino}ethyl)-5-fluorophenyl]propyl}-sulfanyl)propanoate |
| 71 | +++++ | 4-chloro-N-(2,5-difluorophenyl)-N-((1R)-1-{2-[3-(1H-tetraazol-1-yl)propoxy]phenyl}-ethyl)benzenesulfonamide |
| 72 | +++++ | 4-chloro-N-(2,5-difluorophenyl)-N-((1R)-1-{2-[3-(1H-imidazol-1-yl)propoxy]phenyl}-ethyl)benzenesulfonamide hydrobromide |
| 73 | +++++ | 4-chloro-N-(2,5-difluorophenyl)-N-((1R)-1-{4-fluoro-2-[3-oxo-3-(1-piperidinyl)-propyl]phenyl}ethyl)benzenesulfonamide |
| 74 | +++++ | 4-[2-((1R)-1-{[(4-chlorophenyl)sulfonyl]-2,5-difluoroanilino}ethyl)-5-fluorophenyl]-N-methoxy-N-methylbutanamide |
| 75 | +++++ | methyl (2R)-2-[(tert-butoxycarbonyl)amino]-3-({3-[2-((1R)-1-{[(4-chlorophenyl)sulfonyl]-2,5-difluoroanilino}ethyl)-5-fluorophenyl]-propyl}sulfonyl)propanoate |
| 76 | +++++ | 4-chloro-N-(2,5-dichlorophenyl)-N-{2-[3-(1-oxido-1-piperidinyl)propoxy]benzyl}-benzenesulfonamide |
| 77 | +++++ | 4-chloro-N-(2,5-dichlorophenyl)-N-{2-[3-(1-oxido-1-piperidinyl)propoxy]benzyl}-benzenesulfonamide |
| 78 | +++++ | 4-chloro-N-(2,5-difluorophenyl)-N-{2-[3-(1-oxido-1-piperidinyl)propoxy]benzyl}-benzenesulfonamide |

-continued

| NUMBER | ACTIVITY | COMPOUND |
|---|---|---|
| 79 | +++++ | 4-chloro-N-(2,5-difluorophenyl)-N-{2-[3-(1,1,4-trioxido-4-thiomorpholinyl)propoxy]-benzyl}benzenesulfonamide |
| 80 | +++++ | 4-chloro-N-(2,5-difluorophenyl)-N-((1R)-1-{2-[3-(1-piperidinyl)propoxy]phenyl}ethyl)-benzenesulfonamide hydrochloride |
| 81 | +++++ | methyl ({2-[2-((1R)-1-{[(4-chlorophenyl)-sulfonyl]-2,5-difluoroanilino}ethyl)-5-fluoro-phenyl]ethyl}sulfinyl)acetate |
| 82 | +++++ | 4-chloro-N-(5-chloro-2-fluorophenyl)-N-((1R)-1-{2-[3-(1H-imidazol-1-yl)propoxy]phenyl}-ethyl)benzenesulfonamide hydrochloride |
| 83 | +++++ | methyl 3-({2-[2-((1R)-1-{[(4-chlorophenyl)-sulfonyl]-2,5-difluoroanilino}ethyl)-5-fluoro-phenyl]ethyl}sulfanyl)propanoate |
| 84 | +++++ | 4-bromo-N-(2,5-difluorophenyl)-N-{2-[3-(1-piperidinyl)propoxy]benzyl}benzene-sulfonamide hydrochloride |
| 85 | +++++ | 4-chloro-N-{2-[3-(diethylnitroryl)propoxy]-benzyl}-N-(2,5-difluorophenyl)benzene-sulfonamide |
| 86 | +++++ | 4-chloro-N-{2-[3-(diethylnitroryl)propoxy]-benzyl}-N-(2,5-difluorophenyl)benzene-sulfonamide |
| 87 | +++++ | 2-((1R)-1-{[(4-chlorophenyl)sulfonyl]-2,5-difluoroanilino}ethyl)-5-fluorobenzyl 4-methyl-1-piperazinecarboxylate |
| 88 | +++++ | 4-chloro-N-(2,5-difluorophenyl)-N-((1R)-1-{2-[3-(2H-tetraazol-2-yl)propoxy]phenyl}ethyl)-benzenesulfonamide |
| 89 | +++++ | 4-chloro-N-(2,5-difluorophenyl)-N-({1-[3-(1-piperidinyl)propoxy]-2-naphthyl}methyl)-benzenesulfonamide hydrochloride |
| 90 | +++++ | 4-chloro-N-(2,5-difluorophenyl)-N-((1R)-1-{2-[3-(4-methyl-1H-pyrazol-1-yl)propoxy]-phenyl}ethyl)benzenesulfonamide |
| 91 | +++++ | 4-chloro-N-(2,5-difluorophenyl)-N-((1R)-1-{4-fluoro-2-[2-(2-pyridinylmethoxy)ethyl]-phenyl}ethyl)benzenesulfonamide hydro-chloride |
| 92 | +++++ | 4-[2-((1R)-1-{[(4-chlorophenyl)sulfonyl]-2,5-difluoroanilino)ethyl)-5-fluorophenyl]-N-methylbutanamide |
| 93 | +++++ | N-(allyloxy)-4-[2-((1R)-1-{[(4-chlorophenyl)-sulfonyl]-2,5-difluoroanilino}ethyl)-5-fluorophenyl]butanamide |
| 94 | +++++ | 4-chloro-N-(2,5-difluorophenyl)-N-((1R)-1-{4-fluoro-2-[4-(4-thiomorpholinylsulfonyl)butyl]-phenyl}ethyl)benzenesulfonamide |
| 95 | +++++ | methyl ({2-[2-((1R)-1-{[(4-chlorophenyl)-sulfonyl]-2,5-difluoroanilino}ethyl)-5-fluoro-phenyl]ethyl}sulfanyl)acetate |
| 96 | +++++ | 4-chloro-N-(2,5-difluorophenyl)-N-((1R)-1-{4-fluoro-2-[3-(methylsulfanyl)propyl]phenyl}-ethyl)benzenesulfonamide |
| 97 | +++++ | 2-((1R)-1-{[(4-chlorophenyl)sulfonyl]-2,5-difluoroanilino}ethyl)-5-fluorobenzyl 4-thio-morpholinecarboxylate |
| 98 | +++++ | 4-chloro-N-(2,5-difluorophenyl)-N-((1R)-1-{2-[3-(1H-tetraazol-1-yl)propyl]phenyl}ethyl)-benzenesulfonamide |
| 99 | +++++ | 4-chloro-N-(2,5-difluorophenyl)-N-[(1R)-1-(4-fluoro-2-{4-[methoxy(methyl)amino]-butyl}phenyl)ethyl]benzenesulfonamide |
| 100 | +++++ | 4-chloro-N-(2,5-difluorophenyl)-N-((1R)-1-{2-[3-(1H-tetraazol-1-yl)propyl]phenyl}ethyl)-benzenesulfonamide |
| 101 | +++++ | 3-[2-((1R)-1-{[(4-chlorophenyl)sulfonyl]-2,5-difluoroanilino}ethyl)-5-fluorophenyl]-N-[2-(4-morpholinyl)ethyl]propanamide |
| 102 | +++++ | 4-chloro-N-(2,5-difluorophenyl)-N-{(1R)-1-[4-fluoro-2-(4-oxopentyl)phenyl]ethyl}-benzenesulfonamide |
| 103 | +++++ | 4-chloro-N-(2,5-difluorophenyl)-N-{(1R)-1-[4-fluoro-2-(4-oxobutyl)phenyl]ethyl}-benzenesulfonamide |
| 104 | +++++ | 4-[2-((1R)-1-{[(4-chlorophenyl)sulfonyl]-2,5-difluoroanilino}ethyl)-5-fluorophenyl]-N-ethoxybutanamide |
| 105 | +++++ | 4-chloro-N-(2,5-difluorophenyl)-N-(1-{2-[3-(1H-imidazol-1-yl)propyl]phenyl}ethyl)-benzenesulfonamide |
| 106 | +++++ | 4-[2-((1R)-1-{[(4-chlorophenyl)sulfonyl]-2,5-difluoroanilino}ethyl)-5-fluorophenyl]-N-ethylbutanamide |
| 107 | +++++ | methyl 3-({2-[2-((1R)-1-{[(4-chlorophenyl)-sulfonyl]-2,5-difluoroanilino}ethyl)-5-fluoro-phenyl]ethyl}sulfonyl)propanoate |
| 108 | +++++ | 4-chloro-N-(2,5-difluorophenyl)-N-((1R)-1-{2-[3-oxo-3-(4-thiomorpholinyl)propyl]phenyl}-ethyl)benzenesulfonamide |
| 109 | +++++ | 4-chloro-N-(2,5-difluorophenyl)-N-[(1R)-1-(2-{3-[methyl(methylsulfonyl)amino]propoxy}-phenyl)ethyl]benzenesulfonamide |
| 110 | +++++ | N-{3-[2-((1R)-1-{[(4-chlorophenyl)sulfonyl]-2,5-difluoroanilino}ethyl)phenoxy]propyl}-N-methylnicotinamide hydrochloride |
| 111 | +++++ | 4-chloro-N-[(1R)-1-(2-{3-[(diethylamino)-sulfonyl]propyl}-4-fluorophenyl)ethyl]-N-(2,5-difluorophenyl)benzenesulfonamide |
| 112 | +++++ | 3-[2-((1R)-1-{[(4-chlorophenyl)sulfonyl]-2,5-difluoroanilino}ethyl)-5-fluorophenyl]-N-isobutylpropanamide |
| 113 | +++++ | methyl 2-amino-3-{[2-((1R)-1-{[(4-chloro-phenyl)sulfonyl]-2,5-difluoroanilino}ethyl)-5-fluorobenzyl]sulfonyl}propanoate hydro-chloride |
| 114 | +++++ | 4-chloro-N-(2,5-difluorophenyl)-N-{(1R)-1-[4-fluoro-2-(5,5,5-trifluoro-4-oxopentyl)phenyl]-ethyl}benzenesulfonamide |
| 115 | +++++ | 4-chloro-N-(2,5-difluorophenyl)-N-((1R)-1-{2-[2-(ethylsulfonyl)ethyl]-4-fluorophenyl}-ethyl)benzenesulfonamide |
| 116 | +++++ | 4-chloro-N-(2,5-difluorophenyl)-N-((1R)-1-{4-fluoro-2-[3-(4-methyl-1-piperazinyl)propyl]-phenyl}ethyl)benzenesulfonamide |
| 117 | +++++ | 3-[2-((1R)-1-{[(4-chlorophenyl)sulfonyl]-2,5-difluoroanilino}ethyl)-5-fluorophenyl]-N-(tetrahydro-2-furanylmethyl)propanamide |
| 118 | +++++ | 3-[2-((1R)-1-{[(4-chlorophenyl)sulfonyl]-2,5-difluoroanilino}ethyl)-5-fluorophenyl]-N-cyclohexylpropanamide |
| 119 | +++++ | 4-chloro-N-(2,5-difluorophenyl)-N-((1R)-1-{2-[3-(2-methyl-1H-imidazol-1-yl)propoxy]-phenyl}ethyl)benzenesulfonamide hydro-chloride |
| 120 | +++++ | 3-({2-[2-((1R)-1-{[(4-chlorophenyl)sulfonyl]-2,5-difluoroanilino}ethyl)-5-fluorophenyl]-ethyl}sulfonyl)propanoic acid |
| 121 | +++++ | 4-chloro-N-(2,5-difluorophenyl)-N-((1R)-1-{2-[3-(2,5-dioxo-1-pyrrolidinyl)propoxy]-phenyl}ethyl)benzenesulfonamide |
| 122 | +++++ | 3-[2-((1R)-1-{[(4-chlorophenyl)sulfonyl]-2,5-difluoroanilino}ethyl)phenyl]propyl 4-thiomorpholinecarboxylate |
| 123 | +++++ | tert-butyl 4-{3-[2-((1R)-1-{[(4-chlorophenyl)-sulfonyl]-2,5-difluoroanilino}ethyl)-5-fluorophenyl]propanoyl}-1-piperazine-carboxylate |
| 124 | +++++ | N-{4-[2-((1R)-1-{[(4-chlorophenyl)sulfonyl]-2,5-difluoroanilino}ethyl)phenoxy]butyl}-N-methylpropanamide |
| 125 | +++++ | 4-[2-((1R)-1-{[(4-chlorophenyl)sulfonyl]-2,5-difluoroanilino}ethyl)-5-fluorophenyl]-N-cyclohexylbutanamide |
| 126 | +++++ | 4-chloro-N-(2,5-difluorophenyl)-N-((1R)-1-{2-[4-(ethylsulfanyl)butyl]-4-fluorophenyl}-ethyl)benzenesulfonamide |
| 127 | +++++ | 3-{[2-((1R)-1-{[(4-chlorophenyl)sulfonyl]-2,5-difluoroanilino}ethyl)-5-fluorobenzyl]sulfonyl}-propanoic acid |
| 128 | +++++ | 2-[2-((1R)-1-{[(4-chlorophenyl)sulfonyl]-2,5-difluoroanilino}ethyl)-5-fluorophenyl]ethyl nicotinate hydrochloride |

| NUMBER | ACTIVITY | COMPOUND |
|---|---|---|
| 129 | +++++ | N-[2-(4-chlorophenyl)ethyl]-3-[2-((1R)-1-{[(4-chlorophenyl)sulfonyl]-2,5-difluoroanilino}-ethyl)-5-fluorophenyl]propanamide |
| 130 | +++++ | N-{3-[2-(1-{[(4-chlorophenyl)sulfonyl]-2,5-difluoroanilino}ethyl)phenoxy]propyl}-N,2,2-trimethylpropanamide |
| 131 | +++++ | methyl ({2-[2-((1R)-1-{[(4-chlorophenyl)-sulfonyl]-2,5-difluoroanilino}ethyl)-5-fluoro-phenyl]ethyl}sulfonyl)acetate |
| 132 | +++++ | 2-[2-((1R)-1-{[(4-chlorophenyl)sulfonyl]-2,5-difluoroanilino}ethyl)-5-fluorophenyl]ethyl 4 thiomorpholinecarboxylate |
| 133 | +++++ | 4-chloro-N-(2,5-difluorophenyl)-N-((1R)-1-{4-fluoro-2-[3-(1H-imidazol-1-yl)butyl]phenyl}-ethyl)benzenesulfonamide hydrochloride |
| 134 | +++++ | 4-[2-((1R)-1-{[(4-chlorophenyl)sulfonyl]-2,5-difluoroanilino}ethyl)-5-fluorophenyl]-N-isobutoxybutanamide |
| 135 | +++++ | 1-tert-butyl 4-{2-[2-((1R)-1-{[(4-chloro-phenyl)sulfonyl]-2,5-difluoroanilino}ethyl)-5-fluorophenyl]ethyl} 1,4-piperazine-dicarboxylate |
| 136 | +++++ | 4-chloro-N-(2,5-difluorophenyl)-N-((1R)-1-{4-fluoro-2-[3-(4-morpholinyl)-3-oxopropyl]-phenyl}ethyl)benzenesulfonamide |
| 137 | +++++ | 4-chloro-N-(2,5-difluorophenyl)-N-((1R)-1-{2-[3-(4-methyl-1-piperazinyl)-3-oxopropyl]-phenyl}ethyl)benzenesulfonamide |
| 138 | +++++ | 4-chloro-N-(2,5-difluorophenyl)-N-((1R)-1-{4-fluoro-2-[(3E)-3-(hydroxyimino)butyl]phenyl}-ethyl)benzenesulfonamide |
| 139 | +++++ | 4-chloro-N-(2,5-dichlorophenyl)-N-{2-[3-(1-piperidinyl)propoxy]benzyl}benzene-sulfonamide hydrochloride |
| 140 | +++++ | 4-chloro-N-(2,5-dichlorophenyl)-N-{2-[3-(1-piperidinyl)propoxy]benzyl}benzene-sulfonamide |
| 141 | +++++ | 4-chloro-N-(2,5-dichlorophenyl)-N-{2-[3-(1-piperidinyl)propoxy]benzyl}benzene-sulfonamide hydrochloride |
| 142 | +++++ | 2-[2-((1R)-1-{[(4-chlorophenyl)sulfonyl]-2,5-difluoroanilino}ethyl)phenyl]ethyl nicotinate |
| 143 | +++++ | 4-[2-((1R)-1-{2,5-dichloro[(4-chlorophenyl)-sulfonyl]anilino}ethyl)-5-fluorophenyl]butanoic acid |
| 144 | +++++ | 2-[2-((1R)-1-{[(4-chlorophenyl)sulfonyl]-2,5-difluoroanilino}ethyl)phenyl]ethyl 4-morpholinecarboxylate |
| 145 | +++++ | 4-[2-(1-{[(4-chlorophenyl)sulfonyl]-2,5-difluoroanilino}ethyl)phenoxy]-N-methyl-butanamide |
| 146 | +++++ | N-benzyl-3-[2-((1R)-1-{[(4-chlorophenyl)-sulfonyl]-2,5-difluoroanilino}ethyl)-5-fluoro-phenyl]-N-[2-(dimethylamino)ethyl]-propanamide |
| 147 | +++++ | 4-chloro-N-(2,5-difluorophenyl)-N-((1R)-1-{2-[3-(2H-tetraazol-2-yl)propyl]phenyl}ethyl)-benzenesulfonamide |
| 148 | +++++ | 4-chloro-N-(2,5-difluorophenyl)-N-((1R)-1-{4-fluoro-2-[4-(methylsulfanyl)butyl]phenyl}-ethyl)benzenesulfonamide |
| 149 | +++++ | 4-chloro-N-(5-chloro-2-fluorophenyl)-N-[(1R)-1-(4-fluoro-2-{4-[(methylamino)sulfonyl]-butyl}phenyl)ethyl]benzenesulfonamide |
| 150 | +++++ | 3-[2-((1R)-1-{[(4-chlorophenyl)sulfonyl]-2,5-difluoroanilino}ethyl)-5-fluorophenyl]-N-[3-(1H-imidazol-1-yl)propyl]propanamide |
| 151 | +++++ | 4-chloro-N-(2,5-difluorophenyl)-N-(1-{2-[3-(1-piperidinyl)propoxy]phenyl}ethyl)benzene-sulfonamide hydrochloride |
| 152 | +++++ | 2-[2-((1R)-1-{[(4-chlorophenyl)sulfonyl]-2,5-difluoroanilino}ethyl)-5-fluorophenyl]ethyl 3 pyridinylmethylcarbamate |
| 153 | +++++ | N-butyl-3-[2-((1R)-1-{[(4-chlorophenyl)-sulfonyl]-2,5-difluoroanilino}ethyl)-5-fluoro-phenyl]-N-methylpropanamide |
| 154 | +++++ | 2-[2-((1R)-1-{[(4-chlorophenyl)sulfonyl]-2,5-difluoroanilino}ethyl)-5-fluorophenyl]ethyl isonicotinate |
| 155 | +++++ | 3-[2-((1R)-1-{[(4-chlorophenyl)sulfonyl]-2,5-difluoroanilino}ethyl)-5-fluorophenyl]-N-[2-(2-pyridinyl)ethyl]propanamide |
| 156 | +++++ | N-benzyl-3-2-((1R)-1-{[(4-chlorophenyl)-sulfonyl]-2,5-difluoroanilino}ethyl)-5-fluorophenyl]propanamide |
| 157 | +++++ | 3-[2-((1R)-1-{[(4-chlorophenyl)sulfonyl]-2,5-difluoroanilino}ethyl)-5-fluorophenyl]-N-(3-fluorobenzyl)propanamide |
| 158 | +++++ | methyl (2R)-2-amino-3-({3-[2-((1R)-1-{[(4-chlorophenyl)sulfonyl]-2,5- |
| 159 | +++++ | 2-[2-((1R)-1-{[(4-chlorophenyl)sulfonyl]-2,5-difluoroanilino}ethyl)phenyl]ethyl isonicotinate |
| 160 | +++++ | N-(1,3-benzodioxol-5-ylmethyl)-3-[2-((1R)-1-{[(4-chlorophenyl)sulfonyl]-2,5-difluoro-anilino}ethyl)-5-fluorophenyl]propanamide |
| 161 | +++++ | N-(tert-butyl)-3-[2-((1R)-1-{[(4-chlorophenyl)-sulfonyl]-2,5-difluoroanilino}ethyl)-5-fluoro-phenyl]propanamide |
| 162 | +++++ | 4-chloro-N-(2,5-difluorophenyl)-N-{5-fluoro-2-[3-(1-piperidinyl)propoxy]benzyl}benzene-sulfonamide hydrochloride |
| 163 | +++++ | 4-chloro-N-(2,5-difluorophenyl)-N-[(1R)-1-(4-fluoro-2-{3-[2-(trifluoromethyl)-1H-imidazol-1-yl]propyl}phenyl)ethyl]benzenesulfonamide |
| 164 | +++++ | 3-[2-((1R)-1-{[(4-chlorophenyl)sulfonyl]-2,5-difluoroanilino}ethyl-5-fluorophenyl]-N-(2-furylmethyl)propanamide |
| 165 | +++++ | 4-chloro-N-(2,4-difluorophenyl)-N-((1R)-1-{2-[3-(1H-imidazol-1-yl)propoxy]phenyl}ethyl)-benzenesulfonamide hydrochloride |
| 166 | +++++ | 4-chloro-N-(2,5-difluorophenyl)-N-((1R)-1-{2-[2-(2H-tetraazol-2-yl)ethyl]phenyl}ethyl)-benzenesulfonamide |
| 167 | +++++ | 3-[2-((1R)-1-{[(4-chlorophenyl)sulfonyl]-2,5-difluoroanilino}ethyl)-5-fluorophenyl]-N-[2-(diethylamino)ethyl]propanamide |
| 168 | +++++ | 3-[2-((1R)-1-{[(4-chlorophenyl)sulfonyl]-2,5-difluoroanilino}ethyl)-5-fluorophenyl]-N-(2-pyridinylmethyl)propanamide |
| 169 | +++++ | 4-chloro-N-(2,5-difluorophenyl)-N-{(1S)-1-{2-[3-(1-piperidinyl)propoxy]phenyl}ethyl)-benzenesulfonamide hydrochloride |
| 170 | +++++ | 4-chloro-N-(2,5-difluorophenyl)-N-(1-{2-[3-(1H-imidazol-1-yl)propoxy]phenyl}ethyl)-benzenesulfonamide hydrochloride |
| 171 | +++++ | 3-[2-((1R)-1-{[(4-chlorophenyl)sulfonyl]-2,5-difluoroanilino}ethyl)-5-fluorophenyl]-N-(4-methylcyclohexyl)propanamide |
| 172 | +++++ | N-{2-[2-(1-{[(4-chlorophenyl)sulfonyl]-2,5-difluoroanilino}ethyl)phenoxy]ethyl}-N,2-dimethylpropanamide |
| 173 | +++++ | 4-chloro-N-(2,5-difluorophenyl)-N-{(1R)-1-[4-fluoro-2-(3-oxobutyl)phenyl]ethyl}benzene-sulfonamide |
| 174 | +++++ | 4-chloro-N-(2,5-difluorophenyl)-N-((1R)-1-{2-[2-(1H-tetraazol-1-yl)ethyl]phenyl}ethyl)-benzenesulfonamide |
| 175 | +++++ | 4-chloro-N-[5-chloro-2-(hydroxymethyl)-phenyl]-N-((1R)-1-{2-[3-(1H-imidazol-1-yl)-propoxy]phenyl}ethyl)benzenesulfonamide |
| 176 | +++++ | 4-chloro-N-(2,5-difluorophenyl)-N-((1R)-1-{2-[2-(1H-tetraazol-1-yl)ethyl]phenyl}ethyl)-benzenesulfonamide |
| 177 | +++++ | 4-chloro-N-(2,5-difluorophenyl)-N-{2-[3-(1-pyrrolidinyl)propoxy]benzyl}benzene-sulfonamide hydrochloride |
| 178 | +++++ | 4-chloro-N-(2,5-difluorophenyl)-N-{2-[3-(1-pyrrolidinyl)propoxy]benzyl}benzene-sulfonamide hydrochloride |
| 179 | +++++ | 4-chloro-N-(2,5-difluorophenyl)-N-[(1R)-1-phenylethyl]benzenesulfonamide |
| 180 | +++++ | 4-chloro-N-(2,5-difluorophenyl)-N-{2-[3-(1-piperidinyl)propyl]benzyl}benzene-sulfonamide hydrochloride |

-continued

| NUMBER | ACTIVITY | COMPOUND |
|---|---|---|
| 181 | +++++ | 2-((1R)-1-{[(4-chlorophenyl)sulfonyl]-2,5-difluoroanilino}ethyl)-5-fluorobenzyl 2-(4-morpholinyl)ethylcarbamate |
| 182 | ++++ | 4-chloro-N-(2,5-difluorophenyl)-N-{(1R)-1-[4-fluoro-2-(5,5,5-trifluoro-4-hydroxypentyl)-phenyl]ethyl}benzenesulfonamide |
| 183 | ++++ | 3-[2-((1R)-1-{[(4-chlorophenyl)sulfonyl]-2,5-difluoroanilino}ethyl)-5-fluorophenyl]-N-[2-(1H-indol-3-yl)ethyl]propanamide |
| 184 | ++++ | N-[1-(2-{4-[(aminocarbonyl)(methyl)amino]-butoxy}phenyl)ethyl]-4-chloro-N-(2,5-difluorophenyl)benzenesulfonamide |
| 185 | ++++ | 2-((1R)-1-{[(4-chlorophenyl)sulfonyl]-2,5-difluoroanilino}ethyl)benzyl 4-morpholinecarboxylate |
| 186 | ++++ | 3-[3-((1R)-1-{[(4-chlorophenyl)sulfonyl]-2,5-difluoroanilino}ethyl)phenyl]propanoic acid |
| 187 | ++++ | 3-[2-((1R)-1-{[(4-chlorophenyl)sulfonyl]-2,5-difluoroanilino}ethyl)-5-fluorophenyl]-N-(3-pyridinylmethyl)propanamide |
| 188 | ++++ | 4-[2-(1-{[(4-chlorophenyl)sulfonyl]-2,5-difluoroanilino}ethyl)phenoxy]-N-methoxy-butanamide |
| 189 | ++++ | methyl (2S)-2-[(tert-butoxycarbonyl)amino]-3-{[2-((1R)-1-{[(4-chlorophenyl)sulfonyl]-2,5-difluoroanilino}ethyl)-5-fluorobenzyl]-sulfonyl}propanoate |
| 190 | ++++ | 4-[2-({[(4-chlorophenyl)sulfonyl]-2,5-difluoroanilino}methyl)-5-fluorophenyl]-butanoic acid |
| 191 | ++++ | N-{3-[2-(1-{[(4-chlorophenyl)sulfonyl]-2,5-difluoroanilino}ethyl)phenoxy]propyl}-N-methylnicotinamide |
| 192 | ++++ | 3-[2-((1R)-1-{[(4-chlorophenyl)sulfonyl]-2,5-difluoroanilino}ethyl)-5-fluorophenyl]-N-(3-pyridinyl)propanamide |
| 193 | ++++ | N-{4-[2-(1-{[(4-chlorophenyl)sulfonyl]-2,5-difluoroanilino}ethyl)phenoxy]butyl}-N-methylpropanamide |
| 194 | ++++ | 2-[2-((1R)-1-{[(4-chlorophenyl)sulfonyl]-2,5-difluoroanilino}ethyl)-5-fluorophenyl]ethyl 4 morpholinecarboxylate |
| 195 | ++++ | 4-chloro-N-(2,5-difluorophenyl)-N-((1R)-1-{4-fluoro-3-[3-(1H-imidazol-1-yl)propyl]phenyl}-ethyl)benzenesulfonamide hydrochloride |
| 196 | ++++ | 4-chloro-N-{(1R)-1-[2-(3-cyanopropyl)-4-fluorophenyl]ethyl}-N-(2,5-difluorophenyl)-benzenesulfonamide |
| 197 | ++++ | 2-[2-((1R)-1-{[(4-chlorophenyl)sulfonyl]-2,5-difluoroanilino}ethyl)phenyl]ethyl 2-(2-pyridinyl)ethylcarbamate |
| 198 | ++++ | 2-[2-((1R)-1-{[(4-chlorophenyl)sulfonyl]-2,5-difluoroanilino}ethyl)-5-fluorophenyl]ethyl 3 pyridinylcarbamate |
| 199 | ++++ | 4-chloro-N-(4-fluorophenyl)-N-((1R)-1-{2-[3-(1H-imidazol-1-yl)propoxy]phenyl}ethyl)-benzenesulfonamide hydrochloride |
| 200 | ++++ | 2-((1R)-1-{[(4-chlorophenyl)sulfonyl]-2,5-difluoroanilino}ethyl)-5-fluorobenzyl isonicotinate |
| 201 | ++++ | 4-chloro-N-(2,5-difluorophenyl)-N-((1R)-1-{2-[3-(4-morpholinyl)-3-oxopropyl]phenyl}ethyl)-benzenesulfonamide |
| 202 | ++++ | 2-((1R)-1-{[(4-chlorophenyl)sulfonyl]-2,5-difluoroanilino}ethyl)-5-fluorobenzyl nicotinate |
| 203 | ++++ | 3-[2-((1R)-1-{[(4-chlorophenyl)sulfonyl]-2,5-difluoroanilino}ethyl)-5-fluorophenyl]-N-(2-methoxyethyl)propanamide |
| 204 | ++++ | 2-[2-((1R)-1-{[(4-chlorophenyl)sulfonyl]-2,5-difluoroanilino}ethyl)-5-fluorophenyl]ethyl 1 piperidinecarboxylate |
| 205 | ++++ | 4-[3-((1R)-1-{[(4-chlorophenyl)sulfonyl]-2,5-difluoroanilino}ethyl)phenyl]butanoic acid |
| 206 | ++++ | 3-[2-((1R)-1-{[(4-chlorophenyl)sulfonyl]-2,5-difluoroanilino}ethyl)-5-fluorophenyl]-N-(4-fluorobenzyl)propanamide |
| 207 | ++++ | 4-chloro-N-(2,5-difluorophenyl)-N-{(1R)-1-[4-fluoro-2-(5-methyl-4-oxo-5-hexenyl)phenyl]-ethyl}benzenesulfonamide |
| 208 | ++++ | 2-((1R)-1-{[(4-chlorophenyl)sulfonyl]-2,5-difluoroanilino}ethyl)-5-fluorobenzyl 2-phenyl-propylcarbamate |
| 209 | ++++ | 2-((1R)-1-{[(4-chlorophenyl)sulfonyl]-2,5-difluoroanilino}ethyl)benzyl tert-butyl-carbamate |
| 210 | ++++ | 3-[2-((1R)-1-{[(4-chlorophenyl)sulfonyl]-2,5-difluoroanilino}ethyl)-5-fluorophenyl]-N-[4-(trifluoromethyl)benzyl]propanamide |
| 211 | ++++ | 3-[2-((1R)-1-{[(4-chlorophenyl)sulfonyl]-2,5-difluoroanilino}ethyl)-5-fluorophenyl]-N,N-diethylpropanamide |
| 212 | ++++ | 4-chloro-N-(2,5-difluorophenyl)-N-[1-(2-{3-[[(ethylamino)carbonyl](methyl)amino]-propoxy}phenyl)ethyl]benzenesulfonamide |
| 213 | ++++ | N-{4-[2-(1-{[(4-chlorophenyl)sulfonyl]-2,5-difluoroanilino}ethyl)phenoxy]butyl}-2-methoxy-N-methylacetamide |
| 214 | ++++ | N-{2-[2-(1-{[(4-chlorophenyl)sulfonyl]-2,5-difluoroanilino}ethyl)phenoxy]ethyl}-N-methylacrylamide |
| 215 | ++++ | 2-((1R)-1-{[(4-chlorophenyl)sulfonyl]-2,5-difluoroanilino}ethyl)-5-fluorobenzyl 3-(1H-imidazol-1-yl)propylcarbamate |
| 216 | ++++ | N-{3-[2-({[(4-chlorophenyl)sulfonyl]-2,5-difluoroanilino}methyl)phenoxy]propyl}-N-methylnicotinamide |
| 217 | ++++ | N-{3-[2-(1-{[(4-chlorophenyl)sulfonyl]-2,5-difluoroanilino}ethyl)phenoxy]propyl}-N-methylacetamide |
| 218 | ++++ | 2-[2-((1R)-1-{[(4-chlorophenyl)sulfonyl]-2,5-difluoroanilino}ethyl)-5-fluorophenyl]ethyl isopropylcarbamate |
| 219 | ++++ | 2-[2-((1R)-1-{[(4-chlorophenyl)sulfonyl]-2,5-difluoroanilino}ethyl)-5-fluorophenyl]ethyl benzylcarbamate |
| 220 | ++++ | N-{4-[2-(1-{[(4-chlorophenyl)sulfonyl]-2,5-difluoroanilino}ethyl)phenoxy]butyl}-N-methylacetamide |
| 221 | ++++ | 4-[2-(1-{[(4-chlorophenyl)sulfonyl]-2,5-difluoroanilino}ethyl)phenoxy]butanoic acid |
| 222 | ++++ | N-{4-[2-(1-{[(4-chlorophenyl)sulfonyl]-2,5-difluoroanilino}ethyl)phenoxy]butyl}-N-methyl-4-morpholinecarboxamide |
| 223 | ++++ | 4-[2-((1R)-1-{[(4-chlorophenyl)sulfonyl]-2,5-difluoroanilino}ethyl)-5-fluorophenyl]-N,N-diethylbutanamide |
| 224 | ++++ | methyl 4-[{3-[2-(1-{[(4-chlorophenyl)-sulfonyl]-2,5-difluoroanilino}ethyl)phenoxy]-propyl}(methyl)amino]-4-oxobutanoate |
| 225 | ++++ | 4-chloro-N-(2,5-difluorophenyl)-N-((1R)-1-{2-[(1,1-dioxido-4-thiomorpholinyl)methyl]-4-fluorophenyl}ethyl)benzenesulfonamide |
| 226 | ++++ | 2-((1R)-1-{[(4-chlorophenyl)sulfonyl]-2,5-difluoroanilino}ethyl)benzyl 4-methyl-1-piperazinecarboxylate |
| 227 | ++++ | N,N-diallyl-3-[2-((1R)-1-{[(4-chlorophenyl)-sulfonyl]-2,5-difluoroanilino}ethyl)-5-fluorophenyl]propanamide |
| 228 | ++++ | 3-[2-((1R)-1-{[(4-chlorophenyl)sulfonyl]-2,5-difluoroanilino}ethyl)-5-fluorophenyl]-N-(2,2 dimethoxyethyl)propanamide |
| 229 | ++++ | 3-[2-((1R)-1-{[(4-chlorophenyl)sulfonyl]-2,5-difluoroanilino}ethyl)-5-fluorophenyl]-N-(2-phenylpropyl)propanamide |
| 230 | ++++ | 4-chloro-N-(2,5-dibromophenyl)-N-{2-[3-(1-piperidinyl)propoxy]benzyl}benzene-sulfonamide hydrochloride |
| 231 | ++++ | N-{3-[2-(1-{[(4-chlorophenyl)sulfonyl]-2,5-difluoroanilino}ethyl)phenoxy]propyl}-acetamide |
| 232 | ++++ | 4-chloro-N-(2,5-difluorophenyl)-N-{1-[2-(3-{methyl[(methylamino)carbonyl]amino}-propoxy)phenyl]ethyl}benzenesulfonamide |

-continued

| NUMBER | ACTIVITY | COMPOUND |
|---|---|---|
| 233 | ++++ | 2-[2-((1R)-1-{[(4-chlorophenyl)sulfonyl]-2,5-difluoroanilino}ethyl)-5-fluorophenyl]ethyl 2 pyridinylmethylcarbamate |
| 234 | ++++ | N-{3-[2-(1-{[(4-chlorophenyl)sulfonyl]-2,5-difluoroanilino}ethyl)phenoxy]propyl}-N-methylcyclopropanecarboxamide |
| 235 | ++++ | 2-[2-((1R)-1-{[(4-chlorophenyl)sulfonyl]-2,5-difluoroanilino}ethyl)-5-fluorophenyl]ethyl 2 (2-pyridinyl)ethylcarbamate |
| 236 | ++++ | 3-[2-((1R)-1-{[(4-chlorophenyl)sulfonyl]-2,5-difluoroanilino}ethyl)phenyl]-N-[3-(1H-imidazol-1-yl)propyl]propanamide |
| 237 | ++++ | 4-chloro-N-(2,5-difluorophenyl)-N-((1R)-1-{2-[3-oxo-3-(1-piperidinyl)propyl]phenyl}ethyl)-benzenesulfonamide |
| 238 | ++++ | N-{3-[2-(1-{[(4-chlorophenyl)sulfonyl]-2,5-difluoroanilino}ethyl)phenoxy]propyl}-nicotinamide |
| 239 | ++++ | methyl (2S)-2-{[2-((1R)-1-{[(4-chlorophenyl)-sulfonyl]-2,5-difluoroanilino}ethyl)benzyl]-amino}propanoate |
| 240 | ++++ | 4-chloro-N-(2,5-difluorophenyl)-N-[(1S)-2-hydroxy-1-methylethyl]benzenesulfonamide |
| 241 | ++++ | 2-[2-((1R)-1-{[(4-chlorophenyl)sulfonyl]-2,5-difluoroanilino}ethyl)-5-fluorophenyl]ethyl 2 (diethylamino)ethylcarbamate |
| 242 | ++++ | 3-[2-((1R)-1-{[(4-chlorophenyl)sulfonyl]-2,5-difluoroanilino}ethyl)phenyl]-N-cyclooctyl-propanamide |
| 243 | ++++ | 2-{{2-[2-(1-{[(4-chlorophenyl)sulfonyl]-2,5-difluoroanilino}ethyl)phenoxy]ethyl}(ethyl)-amino]-1,1-dimethyl-2-oxoethyl acetate |
| 244 | ++++ | N-(2-{3-[(aminocarbonyl)(methyl)amino]-propoxy}benzyl)-4-chloro-N-(2,5-difluoro-phenyl)benzenesulfonamide |
| 245 | ++++ | 4-chloro-N-(2,5-difluorophenyl)-N-(1-{2-[3-(1H-1,2,3-triazol-1-yl)propoxy]phenyl}ethyl)-benzenesulfonamide |
| 246 | ++++ | 2-[2-((1R)-1-{[(4-chlorophenyl)sulfonyl]-2,5-difluoroanilino}ethyl)phenyl]ethyl 2,2-dimethoxyethylcarbamate |
| 247 | ++++ | 2-[2-((1R)-1-{[(4-chlorophenyl)sulfonyl]-2,5-difluoroanilino}ethyl)-5-fluorophenyl]ethyl diethylcarbamate |
| 248 | ++++ | N-[5-chloro-2-(hydroxymethyl)phenyl]-4-methyl-N-[(1S)-1-methylbutyl]benzene-sulfonamide |
| 249 | ++++ | tert-butyl 4-{3-[2-((1R)-1-{[(4-chlorophenyl)-sulfonyl]-2,5-difluoroanilino}ethyl)phenyl]-propanoyl}-1-piperazinecarboxylate |
| 250 | ++++ | 2-[2-((1R)-1-{[(4-chlorophenyl)sulfonyl]-2,5-difluoroanilino}ethyl)phenyl]ethyl 4-methyl-1-piperazinecarboxylate |
| 251 | ++++ | N-(2,5-difluorophenyl)-4-fluoro-N-{2-[3-(1-piperidinyl)propoxy]benzyl}benzene-sulfonamide hydrochloride |
| 252 | ++++ | 2-((1R)-1-{[(4-chlorophenyl)sulfonyl]-2,5-difluoroanilino}ethyl)-5-fluorobenzyl 2-pyridinecarboxylate |
| 253 | ++++ | N-{2-[2-(1-{[(4-chlorophenyl)sulfonyl]-2,5-difluoroanilino}ethyl)phenoxy]ethyl}-2-methoxy-N-methylacetamide |
| 254 | ++++ | 2-[2-((1R)-1-{[(4-chlorophenyl)sulfonyl]-2,5-difluoroanilino}ethyl)-5-fluorophenyl]ethyl 4 methyl-1-piperazinecarboxylate |
| 255 | ++++ | N-(tert-butyl)-3-[2-((1R)-1-{[(4-chlorophenyl)-sulfonyl]-2,5-difluoroanilino}ethyl)phenyl]-propanamide |
| 256 | ++++ | 2-[2-((1R)-1-{[(4-chlorophenyl)sulfonyl]-2,5-difluoroanilino}ethyl)phenyl]ethyl 3-pyridinyl-methylcarbamate |
| 257 | ++++ | 3-[2-((1R)-1-{[(4-chlorophenyl)sulfonyl]-2,5-difluoroanilino}ethyl)phenyl]-N-[2-(4-morpholinyl)ethyl]propanamide |
| 258 | ++++ | 4-[2-(1-{[(4-chlorophenyl)sulfonyl]-2,5-difluoroanilino}ethyl)phenoxy]-N-(3-pyridinyl-methyl)butanamide hydrochloride |
| 259 | ++++ | N-{4-[2-(1-{[(4-chlorophenyl)sulfonyl]-2,5-difluoroanilino}ethyl)phenoxy]butyl}-N-ethylacetamide |
| 260 | ++++ | N-{3-[2-(1-{[(4-chlorophenyl)sulfonyl]-2,5-difluoroanilino}ethyl)phenoxy]propyl}-N-methyl-2-furamide |
| 261 | ++++ | N-{3-[2-(1-{[(4-chlorophenyl)sulfonyl]-2,5-difluoroanilino}ethyl)phenoxy]propyl}-N-methylcyclobutanecarboxamide |
| 262 | ++++ | 4-chloro-N-cyclohexyl-N-{2-[3-(1-piperidinyl)-propoxy]benzyl}benzenesulfonamide hydrochloride |
| 263 | ++++ | 4-chloro-N-cyclohexyl-N-{2-[3-(1-piperidinyl)-propoxy]benzyl}benzenesulfonamide hydrochloride |
| 264 | ++++ | 4-chloro-N-cyclohexyl-N-{2-[3-(1-piperidinyl)-propoxy]benzyl}benzenesulfonamide hydrochloride |
| 265 | ++++ | 4-chloro-N-(2,5-difluorophenyl)-N-[1-(2-{3-[{[(7,7-dimethyl-2-oxobicyclo[2.2.1]hept-1-yl)methyl]sulfonyl}(methyl)amino]propoxy}-phenyl)ethyl]benzenesulfonamide |
| 266 | ++++ | 2-[2-((1R)-1-{[(4-chlorophenyl)sulfonyl]-2,5-difluoroanilino}ethyl)phenyl]ethyl tetrahydro 2-furanylmethylcarbamate |
| 267 | ++++ | 2-[2-((1R)-1-{[(4-chlorophenyl)sulfonyl]-2,5-difluoroanilino}ethyl)-5-fluorophenyl]ethyl bis(2-methoxyethyl)carbamate |
| 268 | ++++ | 3-[2-((1R)-1-{[(4-chlorophenyl)sulfonyl]-2,5-difluoroanilino}ethyl)phenyl]-N-[2-(1H-indol 3-yl)ethyl]propanamide |
| 269 | ++++ | 4-chloro-N-(2,5-dichlorophenyl)-N-[(1R)-1-(4-fluoro-2-{4-[(methylamino)sulfonyl]butyl}-phenyl)ethyl]benzenesulfonamide |
| 270 | ++++ | 2-[2-((1R)-1-{[(4-chlorophenyl)sulfonyl]-2,5-difluoroanilino}ethyl)-5-fluorophenyl]ethyl 2 (4-morpholinyl)ethylcarbamate |
| 271 | ++++ | 4-chloro-N-(2,5-difluorophenyl)-N-((1R)-1-{2-[3-(4,5-dihydro-1H-imidazol-2-yl)propyl]-4 fluorophenyl}ethyl)benzenesulfonamide hydrochloride |
| 272 | ++++ | 3-[2-((1R)-1-{[(4-chlorophenyl)sulfonyl]-2,5-difluoroanilino}ethyl)-5-fluorophenyl]-N-(1,2,3,4-tetrahydro-1-naphthalenyl)-propanamide |
| 273 | ++++ | N-{3-[2-(1-{[(4-chlorophenyl)sulfonyl]-2,5-difluoroanilino}ethyl)phenoxy]propyl}-2,2-dimethylpropanamide |
| 274 | ++++ | 4-tert-butyl-N-{3-[2-(1-{[(4-chlorophenyl)-sulfonyl]-2,5-difluoroanilino}ethyl)phenoxy]-propyl}benzamide |
| 275 | ++++ | 2-[2-((1R)-1-{[(4-chlorophenyl)sulfonyl]-2,5-difluoroanilino}ethyl)phenyl]ethyl bis(2-methoxyethyl)carbamate |
| 276 | ++++ | N-{3-[2-(1-{[(4-chlorophenyl)sulfonyl]-2,5-difluoroanilino}ethyl)phenoxy]propyl}-N-methyl-1-adamantanecarboxamide |
| 277 | ++++ | 4-chloro-N-(2,5-difluorophenyl)-N-(1-{2-[3-(1H-tetraazol-5-yl)propoxy]phenyl}ethyl)-benzenesulfonamide |
| 278 | ++++ | 4-chloro-N-(2,5-difluorophenyl)-N-{1-[2-(4-{ethyl[(methylamino)carbonyl]amino}butoxy)-phenyl]ethyl}benzenesulfonamide |
| 279 | ++++ | 2-[2-((1R)-1-{[(4-chlorophenyl)sulfonyl]-2,5-difluoroanilino}ethyl)-5-fluorophenyl]ethyl 1 benzyl-4-piperidinylcarbamate |
| 280 | ++++ | (2E)-3-[3-((1R)-1-{[(4-chlorophenyl)sulfonyl]-2,5-difluoroanilino}ethyl)phenyl]-2-propenoic acid |
| 281 | ++++ | 4-chloro-N-(2,5-difluorophenyl)-N-{1-[2-(4-{methyl[(methylamino)carbonyl]amino}-butoxy)phenyl]ethyl}benzenesulfonamide |
| 282 | ++++ | 4-chloro-N-(2,5-difluorophenyl)-N-{(1R)-1-[2-(1H-tetraazol-1-ylmethyl)phenyl]ethyl}-benzenesulfonamide |
| 283 | ++++ | N-{3-[2-(1-{[(4-chlorophenyl)sulfonyl]-2,5-difluoroanilino}ethyl)phenoxy]propyl}-N,3- |

| NUMBER | ACTIVITY | COMPOUND |
|---|---|---|
| | | dimethyl-2-butenamide |
| 284 | ++++ | 2-((1R)-1-{[(4-chlorophenyl)sulfonyl]-2,5-difluoroanilino}ethyl)benzyl 1-piperidine-carboxylate |
| 285 | ++++ | 4-chloro-N-(2-fluorophenyl)-N-((1R)-1-{2-[3-(1H-imidazol-1-yl)propoxy]phenyl}ethyl)-benzenesulfonamide hydrochloride |
| 286 | ++++ | 4-[2-({[(4-chlorophenyl)sulfonyl]-2,5-difluoroanilino}methyl)phenyl]butanoic acid |
| 287 | ++++ | 2-[2-((1R)-1-{[(4-chlorophenyl)sulfonyl]-2,5-difluoroanilino}ethyl)-5-fluorophenyl]ethyl tetrahydro-2-furanylmethylcarbamate |
| 288 | ++++ | 3-[2-((1R)-1-{[(4-chlorophenyl)sulfonyl]-2,5-difluoroanilino}ethyl)-5-fluorophenyl]-N-(2,5 difluorobenzyl)propanamide |
| 289 | ++++ | N-(4-{[3-[2-(1-{[(4-chlorophenyl)sulfonyl]-2,5-difluoroanilino}ethyl)phenoxy]propyl}-(methyl)amino]sulfonyl}phenyl)acetamide |
| 290 | ++++ | 3-[2-((1R)-1-{[(4-chlorophenyl)sulfonyl]-2,5-difluoroanilino}ethyl)phenyl]-N-[2-(2-pyridinyl)ethyl]propanamide |
| 291 | ++++ | N-{4-[2-(1-{[(4-chlorophenyl)sulfonyl]-2,5-difluoroanilino}ethyl)phenoxy]butyl}-N-ethyl-2-methoxyacetamide |
| 292 | ++++ | 4-chloro-N-(2,5-difluorophenyl)-N-{2-[3-(1-oxido-1-pyrrolidinyl)propoxy]benzyl}benzene-sulfonamide |
| 293 | +++ | N-{2-[2-(1-{[(4-chlorophenyl)sulfonyl]-2,5-difluoroanilino}ethyl)phenoxy]ethyl}-N,2,2-trimethylpropanamide |
| 294 | +++ | 4-chloro-N-(2,5-difluorophenyl)-N-{1-[2-(2-{ethyl[(methylamino)carbonyl]amino}ethoxy)-phenyl]ethyl}benzenesulfonamide |
| 295 | +++ | 2-((1R)-1-{[(4-chlorophenyl)sulfonyl]-2,5-difluoroanilino}ethyl)-5-fluorobenzyl 3-pyridinylcarbamate |
| 296 | +++ | 2-[2-((1R)-1-{[(4-chlorophenyl)sulfonyl]-2,5-difluoroanilino}ethyl)-5-fluorophenyl]ethyl benzyl(methyl)carbamate |
| 297 | +++ | N-[1-(2-{3-[[(tert-butylamino)carbonyl]-(methyl)amino]propoxy}phenyl)ethyl]-4-chloro-N-(2,5-difluorophenyl)benzenesulfonamide |
| 298 | +++ | 2-[2-((1R)-1-{[(4-chlorophenyl)sulfonyl]-2,5-difluoroanilino}ethyl)-5-fluorophenyl]ethyl 3 (1H-imidazol-1-yl)propylcarbamate |
| 299 | +++ | N-{2-[2-(1-{[(4-chlorophenyl)sulfonyl]-2,5-difluoroanilino}ethyl)phenoxy]ethyl}-N-methylpropanamide |
| 300 | +++ | 3-[2-((1R)-1-{[(4-chlorophenyl)sulfonyl]-2,5-difluoroanilino}ethyl)phenyl]-N-(2-pyridinyl-methyl)propanamide |
| 301 | +++ | 3-[2-((1R)-1-{[(4-chlorophenyl)sulfonyl]-2,5-difluoroanilino}ethyl)phenyl]propyl 3-(1H-imidazol-1-yl)propylcarbamate |
| 302 | +++ | 4-chloro-N-{2-[2-(cyclohexylsulfinyl)ethoxy]-benzyl}-N-(2,5-difluorophenyl)benzene-sulfonamide |
| 303 | +++ | 2-[2-((1R)-1-{[(4-chlorophenyl)sulfonyl]-2,5-difluoroanilino}ethyl)-5-fluorophenyl]ethyl diallylcarbamate |
| 304 | +++ | 3-[2-((1R)-1-{[(4-chlorophenyl)sulfonyl]-2,5-difluoroanilino}ethyl)-5-fluorophenyl]-N-(1-phenylethyl)propanamide |
| 305 | +++ | 4-chloro-N-(2,5-difluorophenyl)-N-((1R)-1-{2-[2-(2-methyl-1H-imidazol-1-yl)ethyl]phenyl}-ethyl)benzenesulfonamide hydrochloride |
| 306 | +++ | 2-[2-((1R)-1-{[(4-chlorophenyl)sulfonyl]-2,5-difluoroanilino}ethyl)-5-fluorophenyl]ethyl 1,2,3,4-tetrahydro-1-naphthalenylcarbamate |
| 307 | +++ | 2-((1R)-1-{[(4-chlorophenyl)sulfonyl]-2,5-difluoroanilino}ethyl)benzyl 2-(4-morpholinyl)-ethylcarbamate |
| 308 | +++ | N-{3-[2-(1-{[(4-chlorophenyl)sulfonyl]-2,5-difluoroanilino}ethyl)phenoxy]propyl}-N-methyl-2-(phenylsulfanyl)acetamide |
| 309 | +++ | N-{3-[2-(1-{[(4-chlorophenyl)sulfonyl]-2,5-difluoroanilino}ethyl)phenoxy]propyl}-3-cyano-N-methylbenzamide |
| 310 | +++ | 3-[2-((1R)-1-{[(4-chlorophenyl)sulfonyl]-2,5-difluoroanilino}ethyl)phenyl]-N-(2,2-dimethoxyethyl)propanamide |
| 311 | +++ | 2-((1R)-1-{[(4-chlorophenyl)sulfonyl]-2,5-difluoroanilino}ethyl)-5-fluorobenzyl cyclo-octylcarbamate |
| 312 | +++ | 2-[2-((1R)-1-{[(4-chlorophenyl)sulfonyl]-2,5-difluoroanilino}ethyl)-5-fluorophenyl]ethyl cyclooctylcarbamate |
| 313 | +++ | 4-chloro-N-(2,3-dichlorophenyl)-N-{2-[3-(1-piperidinyl)propoxy]benzyl}benzene-sulfonamide hydrochloride |
| 314 | +++ | N-{3-[2-(1-{[(4-chlorophenyl)sulfonyl]-2,5-difluoroanilino}ethyl)phenoxy]propyl}-N-methyl-2-thiophenesulfonamide |
| 315 | +++ | 2-[2-((1R)-1-{[(4-chlorophenyl)sulfonyl]-2,5-difluoroanilino}ethyl)phenyl]ethyl methyl-(phenyl)carbamate |
| 316 | +++ | 3-[2-((1R)-1-{[(4-chlorophenyl)sulfonyl]-2,5-difluoroanilino}ethyl)-5-fluorophenyl]-N,N-bis(2-methoxyethyl)propanamide |
| 317 | +++ | 2-((1R)-1-{[(4-chlorophenyl)sulfonyl]-2,5-difluoroanilino}ethyl)-5-fluorobenzyl 1,2,3,4-tetrahydro-1-naphthalenylcarbamate |
| 318 | +++ | 2-[2-((1R)-1-{[(4-chlorophenyl)sulfonyl]-2,5-difluoroanilino}ethyl)phenyl]ethyl 2-(4-morpholinyl)ethylcarbamate |
| 319 | +++ | N-{2-[2-(1-{[(4-chlorophenyl)sulfonyl]-2,5-difluoroanilino}ethyl)phenoxy]ethyl}-N-methyl-4-morpholinecarboxamide |
| 320 | +++ | N-{3-[2-(1-{[(4-chlorophenyl)sulfonyl]-2,5-difluoroanilino}ethyl)phenoxy]propyl}-2,6-dimethoxybenzamide |
| 321 | +++ | N-{3-[2-({[(4-chlorophenyl)sulfonyl]-2,5-difluoroanilino}methyl)phenoxy]propyl}-N-methylacetamide |
| 322 | +++ | 2-[2-((1R)-1-{[(4-chlorophenyl)sulfonyl]-2,5-difluoroanilino}ethyl)-5-fluorophenyl]ethyl 2 (1-methyl-2-pyrrolidinyl)ethylcarbamate |
| 323 | +++ | 2-{[4-[2-(1-{[(4-chlorophenyl)sulfonyl]-2,5-difluoroanilino}ethyl)phenoxy]butyl}(methyl)-amino]-1,1-dimethyl-2-oxoethyl acetate |
| 324 | +++ | 4-chloro-N-(2,5-dichlorophenyl)-N-((1R)-1-{2-[3-(1H-imidazol-1-yl)propoxy]phenyl}ethyl)-benzenesulfonamide hydrochloride |
| 325 | +++ | 2-[2-((1R)-1-{[(4-chlorophenyl)sulfonyl]-2,5-difluoroanilino}ethyl)-5-fluorophenyl]ethyl 2,2-dimethoxyethylcarbamate |
| 326 | +++ | 2-[2-((1R)-1-{[(4-chlorophenyl)sulfonyl]-2,5-difluoroanilino}ethyl)phenyl]ethyl 1,3-benzodioxol-5-ylmethylcarbamate |
| 327 | +++ | N-{2-[2-(1-{[(4-chlorophenyl)sulfonyl]-2,5-difluoroanilino}ethyl)phenoxy]ethyl}-N-methylcyclobutanecarboxamide |
| 328 | +++ | 2-[2-((1R)-1-{[(4-chlorophenyl)sulfonyl]-2,5-difluoroanilino}ethyl)-5-fluorophenyl]ethyl 3 fluorobenzylcarbamate |
| 329 | +++ | 4-chloro-N-(2,5-difluorophenyl)-N-{2-[3-(1-piperidinyl)propyl]benzyl}benzenesulfonamide hydrochloride |
| 330 | +++ | N-{4-[2-(1-{[(4-chlorophenyl)sulfonyl]-2,5-difluoroanilino}ethyl)phenoxy]butyl}-N-ethylpropanamide |
| 331 | +++ | N-{2-[2-(1-{[(4-chlorophenyl)sulfonyl]-2,5-difluoroanilino}ethyl)phenoxy]ethyl}-N-methylacetamide |
| 332 | +++ | 2-[2-((1R)-1-{[(4-chlorophenyl)sulfonyl]-2,5-difluoroanilino}ethyl)phenyl]ethyl 2-(1-pyrrolidinyl)ethylcarbamate |
| 333 | +++ | 3-[2-((1R)-1-{[(4-chlorophenyl)sulfonyl]-2,5-difluoroanilino}ethyl)-5-fluorophenyl]-N-(3,4 difluorobenzyl)propanamide |
| 334 | +++ | 2-[2-((1R)-1-{[(4-chlorophenyl)sulfonyl]-2,5-difluoroanilino}ethyl)-5-fluorophenyl]ethyl 4 methylcyclohexylcarbamate |

| NUMBER | ACTIVITY | COMPOUND |
|---|---|---|
| 335 | +++ | 3-((1R)-1-{[(4-chlorophenyl)sulfonyl]-2,5-difluoroanilino}ethyl)benzoic acid |
| 336 | +++ | 4-chloro-N-(2,5-difluorophenyl)-N-((1R)-1-[2-(1H-1,2,4-triazol-1-ylmethyl)phenyl]ethyl}-benzenesulfonamide |
| 337 | +++ | 3-[2-((1R)-1-{[(4-chlorophenyl)sulfonyl]-2,5-difluoroanilino}ethyl)-5-fluorophenyl]-N-methyl-N-phenylpropanamide |
| 338 | +++ | N,N-diallyl-3-[2-((1R)-1-{[(4-chlorophenyl)sulfonyl]-2,5-difluoroanilino}ethyl)phenyl]-propanamide |
| 339 | +++ | 4-chloro-N-(2,5-difluorophenyl)-N-((1R)-1-{2-[2-(1H-1,2,4-triazol-1-yl)ethyl]phenyl}ethyl)-benzenesulfonamide |
| 340 | +++ | 4-butoxy-N-{3-[2-(1-{[(4-chlorophenyl)-sulfonyl]-2,5-difluoroanilino}ethyl)phenoxy]-propyl}benzamide |
| 341 | +++ | N-{4-[2-(1-{[(4-chlorophenyl)sulfonyl]-2,5-difluoroanilino}ethyl)phenoxy]butyl}-N,2,2-trimethylpropanamide |
| 342 | +++ | 3-[2-((1R)-1-{[(4-chlorophenyl)sulfonyl]-2,5-difluoroanilino}ethyl)phenyl]-N-[4-(trifluoro-methyl)benzyl]propanamide |
| 343 | +++ | 2-[2-((1R)-1-{[(4-chlorophenyl)sulfonyl]-2,5-difluoroanilino}ethyl)phenyl]ethyl 2-(diethyl-amino)ethylcarbamate |
| 344 | +++ | N-{3-[2-(1-{[(4-chlorophenyl)sulfonyl]-2,5-difluoroanilino}ethyl)phenoxy]propyl}-N-methyl-2-(2-thienyl)acetamide |
| 345 | +++ | 2-[2-((1R)-1-{[(4-chlorophenyl)sulfonyl]-2,5-difluoroanilino}ethyl)-5-fluorophenyl]ethyl 2 (1H-indol-3-yl)ethylcarbamate |
| 346 | +++ | 2-((1R)-1-{[(4-chlorophenyl)sulfonyl]-2,5-difluoroanilino}ethyl)benzyl methyl(phenyl)-carbamate |
| 347 | +++ | N-{3-[2-(1-{[(4-chlorophenyl)sulfonyl]-2,5-difluoroanilino}ethyl)phenoxy]propyl}-N-methyl-2-nitro-4-(trifluoromethyl)benzene-sulfonamide |
| 348 | +++ | 4-chloro-N-(2,5-difluorophenyl)-N-[1-(2-{3-[methyl(phenylsulfonyl)amino]propoxy}-phenyl)ethyl]benzenesulfonamide |
| 349 | +++ | 2-[2-((1R)-1-{[(4-chlorophenyl)sulfonyl]-2,5-difluoroanilino}ethyl)-5-fluorophenyl]ethyl phenylcarbamate |
| 350 | +++ | 2,6-dichloro-N-{3-[2-(1-{[(4-chlorophenyl)-sulfonyl]-2,5-difluoroanilino}ethyl)phenoxy]-propyl}benzamide |
| 351 | +++ | methyl 3-[2-(1-{[(4-chlorophenyl)sulfonyl]-2,5-difluoroanilino}ethyl)phenoxy]propyl(methyl)-carbamate |
| 352 | +++ | 3-[2-((1R)-1-{[(4-chlorophenyl)sulfonyl]-2,5-difluoroanilino}ethyl)-5-fluorophenyl]-N-phenylpropanamide |
| 353 | +++ | 3-[2-((1R)-1-{[(4-chlorophenyl)sulfonyl]-2,5-difluoroanilino}ethyl)phenyl]-N-(tetrahydro-2-furanylmethyl)propanamide |
| 354 | +++ | 2-[2-((1R)-1-{[(4-chlorophenyl)sulfonyl]-2,5-difluoroanilino}ethyl)phenyl]ethyl 3-(1H-imidazol-1-yl)propylcarbamate |
| 355 | +++ | N-{4-[2-(1-{[(4-chlorophenyl)sulfonyl]-2,5-difluoroanilino}ethyl)phenoxy]butyl}-N-methylcyclobutanecarboxamide |
| 356 | +++ | 4-chloro-2-[[(4-chlorophenyl)sulfonyl]((1R)-1-{2-[3-(1H-imidazol-1-yl)propyl]phenyl}ethyl)-amino]benzyl acetate |
| 357 | +++ | 4-chloro-N-(2,5-difluorophenyl)-N-{1-[2-(4-{ethyl[(isopropylamino)carbonyl]amino}-butoxy)phenyl]ethyl}benzenesulfonamide |
| 358 | +++ | 2-[2-((1R)-1-{[(4-chlorophenyl)sulfonyl]-2,5-difluoroanilino}ethyl)-5-fluorophenyl]ethyl 2,5-difluorobenzylcarbamate |
| 359 | +++ | 4-chloro-N-(2,5-difluorophenyl)-N-((1R)-1-{4-fluoro-2-[(4-pyridinylmethoxy)methyl]phenyl}-ethyl)benzenesulfonamide |
| 360 | +++ | 2-((1R)-1-{[(4-chlorophenyl)sulfonyl]-2,5-difluoroanilino}ethyl)-5-fluorobenzyl 2-(diethylamino)ethylcarbamate |
| 361 | +++ | 2-((1R)-1-{[(4-chlorophenyl)sulfonyl]-2,5-difluoroanilino}ethyl)-5-fluorobenzyl methyl-(phenyl)carbamate |
| 362 | +++ | 2-chloro-N-{3-[2-(1-{[(4-chlorophenyl)-sulfonyl]-2,5-difluoroanilino}ethyl)phenoxy]-propyl}benzamide |
| 363 | +++ | methyl [{4-[2-(1-{[(4-chlorophenyl)-sulfonyl]-2,5-difluoroanilino}ethyl)phenoxy]-butyl}(methyl)amino](oxo)acetate |
| 364 | +++ | 2-[{2-[2-(1-{[(4-chlorophenyl)sulfonyl]-2,5-difluoroanilino}ethyl)phenoxy]ethyl}(methyl)-amino]-1,1-dimethyl-2-oxoethyl acetate |
| 365 | +++ | 2-((1R)-1-{[(4-chlorophenyl)sulfonyl]-2,5-difluoroanilino}ethyl)-5-fluorobenzyl cyclo-hexylcarbamate |
| 366 | +++ | 2-[2-(1-{[(4-chlorophenyl)sulfonyl]-2,5-difluoroanilino}ethyl)phenoxy]-N-methoxy-acetamide |
| 377 | +++ | N-{3-[2-(1-{[(4-chlorophenyl)sulfonyl]-2,5-difluoroanilino}ethyl)phenoxy]propyl}-2-nitrobenzamide |
| 378 | +++ | 3-[2-((1R)-1-{[(4-chlorophenyl)sulfonyl]-2,5-difluoroanilino}ethyl)phenyl]propyl 1-piperidinecarboxylate |
| 379 | +++ | 2-[2-((1R)-1-{[(4-chlorophenyl)sulfonyl]-2,5-difluoroanilino}ethyl)phenyl]ethyl isopropyl-carbamate |
| 380 | +++ | 4-chloro-N-(2,5-difluorophenyl)-N-((1R)-1-{4-fluoro-2-[(3-pyridinylmethoxy)methyl]phenyl}-ethyl)benzenesulfonamide |
| 381 | +++ | N-{2-[2-(1-{[(4-chlorophenyl)sulfonyl]-2,5-difluoroanilino}ethyl)phenoxy]ethyl}-N-methyl-2-(2-thienyl)acetamide |
| 382 | +++ | 4-chloro-N-(2,5-difluorophenyl)-N-{1-[2-(2-{methyl[(methylamino)carbonyl]amino}-ethoxy)phenyl]ethyl}benzenesulfonamide |
| 383 | +++ | 3-[2-((1R)-1-{[(4-chlorophenyl)sulfonyl]-2,5-difluoroanilino}ethyl)phenyl]-N-(2,5-difluoro-benzyl)propanamide |
| 384 | +++ | N-{4-[2-(1-{[(4-chlorophenyl)sulfonyl]-2,5-difluoroanilino}ethyl)phenoxy]butyl}-N-methyl-2-(phenylsulfanyl)acetamide |
| 385 | +++ | 2-[2-((1R)-1-{[(4-chlorophenyl)sulfonyl]-2,5-difluoroanilino}ethyl)-5-fluorophenyl]ethyl 1 phenylethylcarbamate |
| 386 | +++ | N-{3-[2-{[(4-chlorophenyl)sulfonyl]-2,5-difluoroanilino}methyl)phenoxy]propyl}-2-methoxy-N-methylacetamide |
| 387 | +++ | N-{3-[2-(1-{[(4-chlorophenyl)sulfonyl]-2,5-difluoroanilino}ethyl)phenoxy]propyl}-N,4,7,7 tetramethyl-3-oxo-2-oxabicyclo[2.2.1]heptane-1-carboxamide |
| 388 | +++ | N-(1,3-benzodioxol-5-ylmethyl)-3-[2-((1R)-1-{[(4-chlorophenyl)sulfonyl]-2,5-difluoro-anilino}ethyl)phenyl]propanamide |
| 389 | +++ | 2-[2-((1R)-1-{[(4-chlorophenyl)sulfonyl]-2,5-difluoroanilino}ethyl)phenyl]ethyl benzyl-carbamate |
| 390 | +++ | 3-[2-((1R)-1-{[(4-chlorophenyl)sulfonyl]-2,5-difluoroanilino}ethyl)-5-fluorophenyl]-N-(2-phenylethyl)propanamide |
| 391 | +++ | 4-chloro-N-(2-chloro-3-pyridinyl)-N-{2-[3-(1-piperidinyl)propoxy]benzyl}benzene-sulfonamide hydrochloride |
| 392 | +++ | 2-[2-((1R)-1-{[(4-chlorophenyl)sulfonyl]-2,5-difluoroanilino}ethyl)phenyl]ethyl 2-methoxy-ethylcarbamate |
| 393 | +++ | 3-[2-((1R)-1-{[(4-chlorophenyl)sulfonyl]-2,5-difluoroanilino}ethyl)phenyl]-N-[2-(1-pyrrolidinyl)ethyl]propanamide |
| 394 | +++ | N-{3-[2-(1-{[(4-chlorophenyl)sulfonyl]-2,5-difluoroanilino}ethyl)phenoxy]propyl}-N-methylcyclopentanecarboxamide |
| 395 | +++ | 2-((1R)-1-{[(4-chlorophenyl)sulfonyl]-2,5-difluoroanilino}ethyl)-5-fluorobenzyl 2,2-dimethoxyethylcarbamate |

| NUMBER | ACTIVITY | COMPOUND |
|---|---|---|
| 396 | +++ | 2-[2-((1R)-1-{[(4-chlorophenyl)sulfonyl]-2,5-difluoroanilino}ethyl)-5-fluorophenyl]ethyl 2 methoxyethylcarbamate |
| 397 | +++ | 4-chloro-N-(2,5-difluorophenyl)-N-[1-(2-{2-[[(dimethylamino)carbonyl](methyl)amino]-ethoxy}phenyl)ethyl]benzenesulfonamide |
| 398 | +++ | 2-((1R)-1-{[(4-chlorophenyl)sulfonyl]-2,5-difluoroanilino}ethyl)-5-fluorobenzyl isobutylcarbamate |
| 399 | +++ | 4-chloro-N-(2,5-difluorophenyl)-N-{2-[3-(2,5-dioxo-1-pyrrolidinyl)propoxy]benzyl}-benzenesulfonamide |
| 400 | +++ | 4-chloro-N-(2,5-difluorophenyl)-N-((1R)-1-{4-fluoro-2-[(2-pyridinylmethoxy)methyl]phenyl}-ethyl)benzenesulfonamide |
| 401 | +++ | 3-[2-((1R)-1-{[(4-chlorophenyl)sulfonyl]-2,5-difluoroanilino}ethyl)phenyl]-N-cyclohexyl-propanamide |
| 402 | +++ | 2-[2-((1R)-1-{[(4-chlorophenyl)sulfonyl]-2,5-difluoroanilino}ethyl)phenyl]ethyl 2-phenyl-propylcarbamate |
| 403 | +++ | 3-[2-((1R)-1-{[(4-chlorophenyl)sulfonyl]-2,5-difluoroanilino}ethyl)phenyl]-N-phenyl-propanamide |
| 404 | +++ | 3-[2-((1R)-1-{[(4-chlorophenyl)sulfonyl]-2,5-difluoroanilino}ethyl)phenyl]-N-(2-furyl-methyl)propanamide |
| 405 | +++ | 2-[2-((1R)-1-{[(4-chlorophenyl)sulfonyl]-2,5-difluoroanilino}ethyl)-5-fluorophenyl]-ethanesulfonic acid |
| 406 | +++ | 3-[2-((1R)-1-{[(4-chlorophenyl)sulfonyl]-2,5-difluoroanilino}ethyl)phenyl]-N-(1,2,3,4-tetrahydro-1-naphthalenyl)propanamide |
| 407 | +++ | 4-chloro-N-{2-[3-(cyclohexylsulfinyl)propoxy]-benzyl}-N-(2,5-difluorophenyl)benzene-sulfonamide |
| 408 | +++ | N-{3-[2-(1-{[(4-chlorophenyl)sulfonyl]-2,5-difluoroanilino}ethyl)phenoxy]propyl}-2,6-difluorobenzamide |
| 409 | +++ | 4-butyl-N-{3-[2-(1-{[(4-chlorophenyl)-sulfonyl]-2,5-difluoroanilino}ethyl)phenoxy]-propyl}benzamide |
| 410 | +++ | 4-chloro-N-(2,5-difluorophenyl)-N-{1-[2-(3-{methyl[(4-nitrophenyl)sulfonyl]amino}-propoxy)phenyl]ethyl}benzenesulfonamide |
| 411 | +++ | 3-[2-((1R)-1-{[(4-chlorophenyl)sulfonyl]-2,5-difluoroanilino}ethyl)phenyl]propyl isopropyl-carbamate |
| 412 | +++ | N-{2-[2-(1-{[(4-chlorophenyl)sulfonyl]-2,5-difluoroanilino}ethyl)phenoxy]ethyl}-N-ethyl-2,2-dimethylpropanamide |
| 413 | +++ | 4-chloro-N-(2,5-difluorophenyl)-N-[2-(3-hydroxypropyl)benzyl]benzenesulfonamide |
| 414 | +++ | 1-tert-butyl 4-[2-((1R)-1-{[(4-chlorophenyl)-sulfonyl]-2,5-difluoroanilino}ethyl)-5-fluorobenzyl] 1,4-piperazinedicarboxylate |
| 415 | +++ | methyl [{3-[2-(1-{[(4-chlorophenyl)sulfonyl]-2,5-difluoroanilino}ethyl)phenoxy]propyl}-(methyl)amino](oxo)acetate |
| 416 | +++ | [[2-((1R)-1-{[(4-chlorophenyl)sulfonyl]-2,5-difluoroanilino}ethyl)benzyl](methyl)amino]-acetic acid hydrochloride |
| 417 | +++ | N-{2-[2-(1-{[(4-chlorophenyl)sulfonyl]-2,5-difluoroanilino}ethyl)phenoxy]ethyl}-N-ethyl-2-(phenylsulfanyl)acetamide |
| 418 | +++ | 2-((1R)-1-{[(4-chlorophenyl)sulfonyl]-2,5-difluoroanilino}ethyl)-5-fluorobenzyl 2-(1-methyl-2-pyrrolidinyl)ethylcarbamate |
| 419 | +++ | 2-[2-((1R)-1-{[(4-chlorophenyl)sulfonyl]-2,5-difluoroanilino}ethyl)-5-fluorophenyl]ethyl 4 fluorobenzylcarbamate |
| 420 | +++ | 4-chloro-N-(2,5-difluorophenyl)-N-({3-[3-(1-piperidinyl)propoxy]-2-naphthyl}methyl)-benzenesulfonamide hydrochloride |
| 421 | +++ | 4-chloro-N-(2,5-difluorophenyl)-N-({3-[3-(1-piperidinyl)propoxy]-2-naphthyl}methyl)-benzenesulfonamide hydrochloride |
| 422 | +++ | 2-[2-((1R)-1-{[(4-chlorophenyl)sulfonyl]-2,5-difluoroanilino}ethyl)-5-fluorophenyl]ethyl 2 phenylethylcarbamate |
| 423 | +++ | N-{3-[2-(1-{[(4-chlorophenyl)sulfonyl]-2,5-difluoroanilino}ethyl)phenoxy]propyl}-4-propylbenzamide |
| 424 | +++ | N-{3-[2-(1-{[(4-chlorophenyl)sulfonyl]-2,5-difluoroanilino}ethyl)phenoxy]propyl}-2-methoxy-N-methylbenzamide |
| 425 | +++ | 2-[2-((1R)-1-{[(4-chlorophenyl)sulfonyl]-2,5-difluoroanilino}ethyl)phenyl]ethyl benzyl[2-(dimethylamino)ethyl]carbamate |
| 426 | +++ | 3-[2-((1R)-1-{[(4-chlorophenyl)sulfonyl]-2,5-difluoroanilino}ethyl)phenyl]-N-methyl-N-phenylpropanamide |
| 427 | +++ | 3-[2-((1R)-1-{[(4-chlorophenyl)sulfonyl]-2,5-difluoroanilino}ethyl)phenyl]-N-(2-phenyl-propyl)propanamide |
| 428 | +++ | N-{3-[2-(1-{[(4-chlorophenyl)sulfonyl]-2,5-difluoroanilino}ethyl)phenoxy]propyl}-3-cyclopentyl-N-methylpropanamide |
| 429 | +++ | 2-((1R)-1-{[(4-chlorophenyl)sulfonyl]-2,5-difluoroanilino}ethyl)-5-fluorobenzyl tetrahydro 2-furanylmethylcarbamate |
| 430 | +++ | 3-[2-((1R)-1-{[(4-chlorophenyl)sulfonyl]-2,5-difluoroanilino}ethyl)phenyl]-N-(3,4-difluorobenzyl)propanamide |
| 431 | +++ | 3-[2-((1R)-1-{[(4-chlorophenyl)sulfonyl]-2,5-difluoroanilino}ethyl)phenyl]-N-(1-phenyl-ethyl)propanamide |
| 432 | +++ | N-{3-[2-(1-{[(4-chlorophenyl)sulfonyl]-2,5-difluoroanilino}ethyl)phenoxy]propyl}-acrylamide |
| 433 | +++ | N-{4-[2-(1-{[(4-chlorophenyl)sulfonyl]-2,5-difluoroanilino}ethyl)phenoxy]butyl}-N,3-dimethyl-2-butenamide |
| 434 | +++ | N-{2-[2-(1-{[(4-chlorophenyl)sulfonyl]-2,5-difluoroanilino}ethyl)phenoxy]ethyl}-N-ethyl-2-methoxyacetamide |
| 435 | +++ | 2-[2-((1R)-1-{[(4-chlorophenyl)sulfonyl]-2,5-difluoroanilino}ethyl)-5-fluorophenyl]ethyl 2 furylmethylcarbamate |
| 436 | +++ | 2-[2-((1R)-1-{[(4-chlorophenyl)sulfonyl]-2,5-difluoroanilino}ethyl)phenyl]ethyl 2-(1H-indol-3-yl)ethylcarbamate |
| 437 | +++ | 2-((1R)-1-{[(4-chlorophenyl)sulfonyl]-2,5-difluoroanilino}ethyl)-5-fluorobenzyl isopropylcarbamate |
| 438 | +++ | 4-chloro-N-(2,5-difluorophenyl)-N-{(1R)-1-[2-(1H-imidazol-1-ylmethyl)phenyl]ethyl}-benzenesulfonamide hydrochloride |
| 439 | +++ | 4-chloro-N-(2,5-difluorophenyl)-N-{(1R)-1-[2-(1H-tetraazol-1-ylmethyl)phenyl]ethyl}-benzenesulfonamide |
| 440 | +++ | 4-tert-butyl-N-{3-[2-(1-{[(4-chlorophenyl)-sulfonyl]-2,5-difluoroanilino}ethyl)phenoxy]-propyl}-N-methylbenzamide |
| 441 | +++ | 2-[2-((1R)-1-{[(4-chlorophenyl)sulfonyl]-2,5-difluoroanilino}ethyl)-5-fluorophenyl]ethyl butyl(methyl)carbamate |
| 442 | +++ | N-{2-[2-(1-{[(4-chlorophenyl)sulfonyl]-2,5-difluoroanilino}ethyl)phenoxy]ethyl}-N-methylcyclopentanecarboxamide |
| 443 | +++ | 3-[2-((1R)-1-{[(4-chlorophenyl)sulfonyl]-2,5-difluoroanilino}ethyl)phenyl]-N-(2-phenyl-ethyl)propanamide |
| 444 | +++ | N-benzyl-3-[2-((1R)-1-{[(4-chlorophenyl)-sulfonyl]-2,5-difluoroanilino}ethyl)-5-fluoro-phenyl]-N-methylpropanamide |
| 445 | +++ | 4-chloro-N-(2,5-difluorophenyl)-N-{1-[2-(4-{ethyl[(ethylamino)carbonyl]amino}butoxy)-phenyl]ethyl}benzenesulfonamide |
| 446 | +++ | 3-[2-((1R)-1-{[(4-chlorophenyl)sulfonyl]-2,5-difluoroanilino}ethyl)phenyl]-N-(3-pyridinyl-methyl)propanamide |
| 447 | +++ | 6-amino-N-{3-[2-({[(4-chlorophenyl)sulfonyl]-2,5-difluoroanilino}methyl)phenoxy]propyl}- |

-continued

| NUMBER | ACTIVITY | COMPOUND |
|---|---|---|
| | | N-methylhexanamide hydrochloride |
| 448 | +++ | 6-amino-N-{3-[2-({[(4-chlorophenyl)sulfonyl]-2,5-difluoroanilino}methyl)phenoxy]propyl}-N-methylhexanamide hydrochloride |
| 449 | +++ | N-{4-[2-(1-{[(4-chlorophenyl)sulfonyl]-2,5-difluoroanilino}ethyl)phenoxy]butyl}-N-ethyl-cyclobutanecarboxamide |
| 450 | +++ | 4-chloro-N-(2,5-difluorophenyl)-N-(2-{2-[1-(2-pyridinylcarbonyl)-2-piperidinyl]ethoxy}-benzyl)benzenesulfonamide |
| 451 | +++ | 4-chloro-N-(2,5-difluorophenyl)-N-(2-{2-[1-(3-pyridinylcarbonyl)-2-piperidinyl]ethoxy}-benzyl)benzenesulfonamide |
| 452 | +++ | N-benzyl-3-[2-((1R)-1-{[(4-chlorophenyl)-sulfonyl]-2,5-difluoroanilino}ethyl)phenyl]-N-methylpropanamide |
| 453 | +++ | N-{2-[2-(1-{[(4-chlorophenyl)sulfonyl]-2,5-difluoroanilino}ethyl)phenoxy]ethyl}-N-ethyl-acetamide |
| 454 | +++ | N-{4-[2-(1-{[(4-chlorophenyl)sulfonyl]-2,5-difluoroanilino}ethyl)phenoxy]butyl}-N-ethyl-2-methylpropanamide |
| 455 | +++ | 2-((1R)-1-{[(4-chlorophenyl)sulfonyl]-2,5-difluoroanilino}ethyl)-5-fluorobenzyl 1-benzyl-4-piperidinylcarbamate |
| 456 | +++ | 2-[2-((1R)-1-{[(4-chlorophenyl)sulfonyl]-2,5-difluoroanilino}ethyl)phenyl]ethyl 3-pyridinylcarbamate |
| 457 | +++ | 2-[2-((1R)-1-{[(4-chlorophenyl)sulfonyl]-2,5-difluoroanilino}ethyl)-5-fluorophenyl]ethyl 2 phenylpropylcarbamate |
| 458 | +++ | N-{3-[2-({[(4-chlorophenyl)sulfonyl]-2,5-difluoroanilino}methyl)phenoxy]propyl}-N,2,2-trimethylpropanamide |
| 459 | +++ | 2-[2-((1R)-1-{[(4-chlorophenyl)sulfonyl]-2,5-difluoroanilino}ethyl)-5-fluorophenyl]ethyl 2 (4-chlorophenyl)ethylcarbamate |
| 460 | +++ | 4-chloro-N-(2-chlorophenyl)-N-{2-[3-(1-piperidinyl)propoxy]benzyl}benzene-sulfonamide hydrochloride |
| 461 | +++ | N-{3-[2-({[(4-chlorophenyl)sulfonyl]-2,5-difluoroanilino}methyl)phenoxy]propyl}-N-methylpropanamide |
| 462 | +++ | N-{3-[2-(1-{[(4-chlorophenyl)sulfonyl]-2,5-difluoroanilino}ethyl)phenoxy]propyl}-N-methyl-3-nitrobenzenesulfonamide |
| 463 | +++ | N-{4-[2-(1-{[(4-chlorophenyl)sulfonyl]-2,5-difluoroanilino}ethyl)phenoxy]butyl}-N-methylbutanamide |
| 464 | +++ | N-{3-[2-(1-{[(4-chlorophenyl)sulfonyl]-2,5-difluoroanilino}ethyl)phenoxy]propyl}-2-fluorobenzamide |
| 465 | +++ | 4-chloro-N-(2,5-difluorophenyl)-N-({3-[3-(1-piperidinyl)propoxy]-2-pyridinyl}methyl)-benzenesulfonamide hydrochloride |
| 466 | +++ | N-{3-[2-(1-{[(4-chlorophenyl)sulfonyl]-2,5-difluoroanilino}ethyl)phenoxy]propyl}-N-methylbenzamide |
| 467 | +++ | N-{3-[2-(1-{[(4-chlorophenyl)sulfonyl]-2,5-difluoroanilino}ethyl)phenoxy]propyl}-2,2,2,3,3,4,4,5,5,6,6,7,7,8,8,8-pentadecafluoro-N-methyloctanamide |
| 468 | +++ | methyl 4-[{2-[2-(1-{[(4-chlorophenyl)-sulfonyl]-2,5-difluoroanilino}ethyl)phenoxy]-ethyl}(methyl)amino]-4-oxobutanoate |
| 469 | +++ | N-{4-[2-(1-{[(4-chlorophenyl)sulfonyl]-2,5-difluoroanilino}ethyl)phenoxy]butyl)-N-methyl-2-(2-thienyl)acetamide |
| 470 | +++ | N-{4-[2-(1-{[(4-chlorophenyl)sulfonyl]-2,5-difluoroanilino}ethyl)phenoxy]butyl}-N-ethylbutanamide |
| 471 | +++ | N-{3-[2-(1-{[(4-chlorophenyl)sulfonyl]-2,5-difluoroanilino}ethyl)phenoxy]propyl}-4-ethyl N-methylbenzamide |
| 472 | +++ | 3-[2-((1R)-1-{[(4-chlorophenyl)sulfonyl]-2,5-difluoroanilino}ethyl)phenyl]propyl methyl-(phenyl)carbamate |
| 473 | +++ | 2-((1R)-1-{[(4-chlorophenyl)sulfonyl]-2,5-difluoroanilino}ethyl)-5-fluorobenzyl 2-(1H-indol-3-yl)ethylcarbamate |
| 474 | ++ | N-{4-[2-(1-{[(4-chlorophenyl)sulfonyl]-2,5-difluoroanilino}ethyl)phenoxy]butyl}-N-methylcyclopentanecarboxamide |
| 475 | ++ | N-{3-[2-(1-{[(4-chlorophenyl)sulfonyl]-2,5-difluoroanilino}ethyl)phenoxy]propyl}-N-methyl-2-thiophenecarboxamide |
| 476 | ++ | 4-chloro-N-(2,5-difluorophenyl)-N-[1-(2-{3-[[(4-fluorophenyl)sulfonyl](methyl)amino]-propoxy}phenyl)ethyl]benzenesulfonamide |
| 477 | ++ | N-{3-[2-(1-{[(4-chlorophenyl)sulfonyl]-2,5-difluoroanilino}ethyl)phenoxy]propyl}-N-methyl-1,3-benzodioxole-5-carboxamide |
| 478 | ++ | 3-[2-((1R)-1-{[(4-chlorophenyl)sulfonyl]-2,5-difluoroanilino}ethyl)phenyl]-N-(2-methoxy-ethyl)propanamide |
| 479 | ++ | 3-[2-((1R)-1-{[(4-chlorophenyl)sulfonyl]-2,5-difluoroanilino}ethyl)phenyl]propyl diethylcarbamate |
| 480 | ++ | 2-((1R)-1-{[(4-chlorophenyl)sulfonyl]-2,5-difluoroanilino}ethyl)benzyl 2-(1H-indol-3-yl)ethylcarbamate |
| 481 | ++ | 2-((1R)-1-{[(4-chlorophenyl)sulfonyl]-2,5-difluoroanilino}ethyl)-5-fluorobenzyl 3-pyridinylmethylcarbamate |
| 482 | ++ | N-{3-[2-(1-{[(4-chlorophenyl)sulfonyl]-2,5-difluoroanilino}ethyl)phenoxy]propyl}-N-methyl-2-nitrobenzenesulfonamide |
| 483 | ++ | methyl {[2-((1R)-1-{[(4-chlorophenyl)-sulfonyl]-2,5-difluoroanilino}ethyl)benzyl]-amine}acetate |
| 484 | ++ | N-{2-[2-(1-{[(4-chlorophenyl)sulfonyl]-2,5-difluoroanilino}ethyl)phenoxy]ethyl}-N-methylbutanamide |
| 485 | ++ | N-{4-[2-(1-{[(4-chlorophenyl)sulfonyl]-2,5-difluoroanilino}ethyl)phenoxy]butyl}-N-ethyl-3-methylbutanamide |
| 486 | ++ | 1-tert-butyl 4-[2-((1R)-1-{[(4-chlorophenyl)-sulfonyl]-2,5-difluoroanilino}ethyl)benzyl] 1,4-piperazinedicarboxylate |
| 487 | ++ | N-[2-(4-chlorophenyl)ethyl]-3-[2-((1R)-1-{[(4-chlorophenyl)sulfonyl]-2,5-difluoroanilino}-ethyl)phenyl]propanamide |
| 488 | ++ | N-{2-[2-(1-{[(4-chlorophenyl)sulfonyl]-2,5-difluoroanilino}ethyl)phenoxy]ethyl}-N-methylbenzamide |
| 489 | ++ | 3-[2-((1R)-1-{[(4-chlorophenyl)sulfonyl]-2,5-difluoroanilino}ethyl)-5-fluorophenyl]-N,N-dipropylbutanamide |
| 490 | ++ | N-{4-[2-(1-{[(4-chlorophenyl)sulfonyl]-2,5-difluoroanilino}ethyl)phenoxy]butyl}-N,3-dimethylbutanamide |
| 491 | ++ | 4-chloro-N-(2,5-difluorophenyl)-N-[2-(1H-tetraazol-1-ylmethyl)benzyl]benzene-sulfonamide |
| 492 | ++ | 4-chloro-N-{2-[3-(1,1-dioxido-4-thio-morpholinyl)propoxy]benzyl}-N-phenyl-benzenesulfonamide hydrochloride |
| 493 | ++ | 2-[2-((1R)-1-{[(4-chlorophenyl)sulfonyl]-2,5-difluoroanilino}ethyl)phenyl]ethyl diallylcarbamate |
| 494 | ++ | N-{2-[2-(1-{[(4-chlorophenyl)sulfonyl]-2,5-difluoroanilino}ethyl)phenoxy]ethyl}-N-methyl-2-(phenylsulfanyl)acetamide |
| 495 | ++ | (2E)-N-{4-[2-(1-{[(4-chlorophenyl)sulfonyl]-2,5-difluoroanilino}ethyl)phenoxy]butyl}-N-methyl-2-butenamide |
| 496 | ++ | N-{3-[2-(1-{[(4-chlorophenyl)sulfonyl]-2,5-difluoroanilino}ethyl)phenoxy]propyl}[1,1'-biphenyl]-4-carboxamide |
| 497 | ++ | N-{3-[2-(1-{[(4-chlorophenyl)sulfonyl]-2,5-difluoroanilino}ethyl)phenoxy]propyl}-2,3,6-trifluorobenzamide |
| 498 | ++ | 3-[2-((1R)-1-{[(4-chlorophenyl)sulfonyl]-2,5-difluoroanilino}ethyl)phenyl]propyl benzyl- |

-continued

| NUMBER | ACTIVITY | COMPOUND |
|---|---|---|
| | | carbamate |
| 499 | ++ | ethyl 4-[2-(1-{[(4-chlorophenyl)sulfonyl]-2,5-difluoroanilino}ethyl)phenoxy]butanoate |
| 500 | ++ | N-(sec-butyl)-3-[2-((1R)-1-{[(4-chlorophenyl)sulfonyl]-2,5-difluoroanilino}ethyl)phenyl]-propanamide |
| 501 | ++ | N-{2-[2-(1-{[(4-chlorophenyl)sulfonyl]-2,5-difluoroanilino}ethyl)phenoxy]ethyl}-N,3-dimethyl-2-butenamide |
| 502 | ++ | N-{3-[2-(1-{[(4-chlorophenyl)sulfonyl]-2,5-difluoroanilino}ethyl)phenoxy]propyl}-2,4-difluoro-N-methylbenzamide |
| 503 | ++ | (2E)-N-(2-[2-(1-{[(4-chlorophenyl)sulfonyl]-2,5-difluoroanilino}ethyl)phenoxy]ethyl}-N-methyl-2-butenamide |
| 504 | ++ | N-{2-[2-(1-{[(4-chlorophenyl)sulfonyl]-2,5-difluoroanilino}ethyl)phenoxy]ethyl}-N-ethylpropanamide |
| 505 | ++ | 2-bromo-N-{3-[2-(1-{[(4-chlorophenyl)sulfonyl]-2,5-difluoroanilino}ethyl)phenoxy]-propyl}-N-methylbenzamide |
| 506 | ++ | N-{2-[2-(1-{[(4-chlorophenyl)sulfonyl]-2,5-difluoroanilino}ethyl)phenoxy]ethyl}-N-ethyl-4-morpholinecarboxamide |
| 507 | ++ | 2-((1R)-1-{[(4-chlorophenyl)sulfonyl]-2,5-difluoroanilino}ethyl)-5-fluorobenzyl 2,5-difluorobenzylcarbamate |
| 508 | ++ | 2-[2-((1R)-1-{[(4-chlorophenyl)sulfonyl]-2,5-difluoroanilino}ethyl)phenyl]ethyl 2,5-difluorobenzylcarbamate |
| 509 | ++ | 1-((1R)-1-{[(4-chlorophenyl)sulfonyl]-2,5-difluoroanilino}ethyl)benzyl 3-(1H-imidazol-1-yl)propylcarbamate |
| 510 | ++ | N-{2-[2-(1-{[(4-chlorophenyl)sulfonyl]-2,5-difluoroanilino}ethyl)phenoxy]ethyl}-N-methyl-1-adamantanecarboxamide |
| 511 | ++ | N-{2-[2-(1-{[(4-chlorophenyl)sulfonyl]-2,5-difluoroanilino}ethyl)phenoxy]ethyl}-N-methylcyclohexanecarboxamide |
| 512 | ++ | 3-[2-((1R)-1-{[(4-chlorophenyl)sulfonyl]-2,5-difluoroanilino}ethyl)phenyl]-N-[2-(1-methyl 2-pyrrolidinyl)ethyl]propanamide |
| 513 | ++ | 2-chloro-N-{[2-(1-{[(3-chlorophenyl)sulfonyl]-2,5-difluoroanilino}ethyl)phenoxy]propyl}-N-methylbenzamide |
| 514 | ++ | (2E)-N-{4-[2-(1-{[(4-chlorophenyl)sulfonyl]-2,5-difluoroanilino}ethyl)phenoxy]butyl}-N-ethyl-2-butenamide |
| 515 | ++ | N-benzyl-3-[2-((1R)-1-{[(4-chlorophenyl)-sulfonyl]-2,5-difluoroanilino}ethyl)phenyl]-propanamide |
| 516 | ++ | 3-[2-((1R)-1-{[(4-chlorophenyl)sulfonyl]-2,5-difluoroanilino}ethyl)phenyl]-N-[2-(diethylamino)ethyl]propanamide |
| 517 | ++ | N-butyl-2-[2-((1R)-1-{[(4-chlorophenyl)-sulfonyl]-2,5-difluoroanilino}ethyl)phenyl]-N-methylpropanamide |
| 518 | ++ | N-{3-[2-(1-{[(4-chlorophenyl)sulfonyl]-2,5-difluoroanilino}ethyl)phenoxy]propyl}-2,6-dimethoxy-N-methylbenzamide |
| 519 | ++ | 3-[2-((1R)-1-{[(4-chlorophenyl)sulfonyl]-2,5-difluoroanilino}ethyl)phenyl]-N-(3-fluorobenzyl)propanamide |
| 520 | ++ | N-{3-[2-(1-{[(4-chlorophenyl)sulfonyl]-2,5-difluoroanilino}ethyl)phenoxy]propyl}-2,5-difluorobenzamide |
| 521 | ++ | 2-((1R)-1-{[(4-chlorophenyl)sulfonyl]-2,5-difluoroanilino}ethyl)benzyl bis(2-methoxyethyl)carbamate |
| 522 | ++ | N-{2-[2-(1-{[(4-chlorophenyl)sulfonyl]-2,5-difluoroanilino}ethyl)phenoxy]ethyl}-N,3-dimethylbutanamide |
| 523 | ++ | N-{3-[2-(1-{[(4-chlorophenyl)sulfonyl]-2,5-difluoroanilino}ethyl)phenoxy]propyl}-2,3-difluoro-N-methylbenzamide |
| 524 | ++ | 4-chloro-N-(2,5-difluorophenyl)-N-((1R)-1-{2-[3-(2H-tetrazol-2-yl)propyl]phenyl}ethyl)-benzenesulfonamide |
| 525 | ++ | 2-[2-((1R)-1-{[(4-chlorophenyl)sulfonyl]-2,5-difluoroanilino}ethyl)phenyl]ethyl 3-fluorobenzylcarbamate |
| 526 | ++ | 4-chloro-N-(2,5-difluorophenyl)-N-((1R)-1-{2-[2-(1H-imidazol-1-yl)ethyl]phenyl}ethyl)-benzenesulfonamide hydrochloride |
| 527 | ++ | methyl 4-({3-[2-(1-{[(4-chlorophenyl)-sulfonyl]-2,5-difluoroanilino}ethyl)phenoxy]-propyl}amino)-4-oxobutanoate |
| 528 | ++ | 4-butoxy-N-{3-[2-(1-{[(4-chlorophenyl)-sulfonyl]-2,5-difluoroanilino}ethyl)phenoxy]-propyl}-N-methylbenzamide |
| 529 | ++ | 2-((1R)-1-{[(4-chlorophenyl)sulfonyl]-2,5-difluoroanilino}ethyl)benzyl 3-pyridinyl-methylcarbamate |
| 530 | ++ | 2-[{3-[2-({[(4-chlorophenyl)sulfonyl]-2,5-difluoroanilino}methyl)phenoxy]propyl}-(methyl)amino]-1,1-dimethyl-2-oxoethyl acetate |
| 531 | ++ | 3-[2-((1R)-1-{[(4-chlorophenyl)sulfonyl]-2,5-difluoroanilino}ethyl)phenyl]-N-(3-pyridinyl)-propanamide |
| 532 | ++ | 3-[2-((1R)-1-{[(4-chlorophenyl)sulfonyl]-2,5-difluoroanilino}ethyl)phenyl]-N-isobutyl-propanamide |
| 533 | ++ | N-{3-[2-(1-{[(4-chlorophenyl)sulfonyl]-2,5-difluoroanilino}ethyl)phenoxy]propyl}-N-methyl-9-oxo-9H-fluorene-4-carboxamide |
| 534 | ++ | 4-chloro-N-(2,5-difluorophenyl)-N-{(1R)-1-[2-(2H-tetraazol-2-ylmethyl)phenyl]ethyl}-benzenesulfonamide |
| 535 | ++ | 2-((1R)-1-{[(4-chlorophenyl)sulfonyl]-2,5-difluoroanilino}ethyl)-5-fluorobenzyl benzyl[2-(dimethylamino)ethyl]carbamate |
| 536 | ++ | N-{3-[2-(1-{[(4-chlorophenyl)sulfonyl]-2,5-difluoroanilino}ethyl)phenoxy]propyl}-2,4-difluorobenzamide |
| 537 | ++ | 2-[2-((1R)-1-{[(4-chlorophenyl)sulfonyl]-2,5-difluoroanilino}ethyl)-5-fluorophenyl]ethyl sec-butylcarbamate |
| 538 | ++ | 2-((1R)-1-{[(4-chlorophenyl)sulfonyl]-2,5-difluoroanilino}ethyl)-5-fluorobenzyl 2-(2-pyridinyl)ethylcarbamate |
| 539 | ++ | 2-((1R)-1-{[(4-chlorophenyl)sulfonyl]-2,5-difluoroanilino}ethyl)-5-fluorobenzyl 1-phenylethylcarbamate |
| 540 | ++ | 4-chloro-N-(2,5-difluorophenyl)-N-[1-(2-{3-[methyl(4-toluidinocarbonyl)amino]propoxy}-phenyl)ethyl]benzenesulfonamide |
| 541 | ++ | N-{4-[2-(1-{[(4-chlorophenyl)sulfonyl]-2,5-difluoroanilino}ethyl)phenoxy]butyl}-N-ethyl-2-(2-thienyl)acetamide |
| 542 | ++ | 2-((1R)-1-{[(4-chlorophenyl)sulfonyl]-2,5-difluoroanilino}ethyl)benzyl 2-(2-pyridinyl)-ethylcarbamate |
| 543 | ++ | N-[1-(2-{3-[[(4-tert-butylphenyl)sulfonyl]-(methyl)amino]propoxy}phenyl)ethyl]-4-chloro-N-(2,5-difluorophenyl)benzene-sulfonamide |
| 544 | ++ | N-benzyl-3-[2-((1R)-1-{[(4-chlorophenyl)-sulfonyl]-2,5-difluoroanilino}ethyl)phenyl]-N-[2 (dimethylamino)ethyl]propanamide |
| 545 | ++ | N-{3-[2-(1-{[(4-chlorophenyl)sulfonyl]-2,5-difluoroanilino}ethyl)phenoxy]propyl}-1-naphthamide |
| 546 | ++ | 3-[2-((1R)-1-{[(4-chlorophenyl)sulfonyl]-2,5-difluoroanilino}ethyl)phenyl]propyl butyl-(methyl)carbamate |
| 547 | ++ | 4-chloro-N-(2,5-difluorophenyl)-N-[(1R)-1-(2,3,4,5,6-pentafluorophenyl)ethyl]benzene-sulfonamide |
| 548 | ++ | N-{4-[2-(1-{[(4-chlorophenyl)sulfonyl]-2,5-difluoroanilino}ethyl)phenoxy]butyl}-N-ethyl-3-methyl-2-butenamide |
| 549 | ++ | 2-((1R)-1-{[(4-chlorophenyl)sulfonyl]-2,5-difluoroanilino}ethyl)-5-fluorobenzyl 3,4- |

| NUMBER | ACTIVITY | COMPOUND |
|---|---|---|
| | | difluorobenzylcarbamate |
| 550 | ++ | 2-[2-((1R)-1-{[(4-chlorophenyl)sulfonyl]-2,5-difluoroanilino}ethyl)phenyl]ethyl diethyl-carbamate |
| 551 | ++ | N-{3-2-({[(4-chlorophenyl)sulfonyl]-2,5-difluoroanilino}methyl)phenoxy]propyl}-N,2-dimethylpropanamide |
| 552 | ++ | 3-[2-((1R)-1-{[(4-chlorophenyl)sulfonyl]-2,5-difluoroanilino}ethyl)phenyl]-N-(4-fluoro-benzyl)propanamide |
| 553 | ++ | 3-chloro-N-(2,5-difluorophenyl)-N-[1-(2-{4-[[(ethylamino)carbonyl](methyl)amino]-butoxy}phenyl)ethyl]benzenesulfonamide |
| 554 | ++ | 2-[2-((1R)-1-{[(4-chlorophenyl)sulfonyl]-2,5-difluoroanilino}ethyl)phenyl]ethyl benzyl-(methyl)carbamate |
| 555 | ++ | 3-[2-((1R)-1-{[(4-chlorophenyl)sulfonyl]-2,5-difluoroanilino}ethyl)phenyl]propyl 3,4-difluorobenzylcarbamate |
| 556 | ++ | 2-((1R)-1-{[(4-chlorophenyl)sulfonyl]-2,5-difluoroanilino}ethyl)-5-fluorobenzyl 1-piperidinecarboxylate |
| 557 | ++ | 2-((1R)-1-{[(4-chlorophenyl)sulfonyl]-2,5-difluoroanilino}ethyl)-5-fluorobenzyl 4-methyl-cyclohexylcarbamate |
| 558 | ++ | N-{3-[2-(1-{[(4-chlorophenyl)sulfonyl]-2,5-difluoroanilino}ethyl)phenoxy]propyl}-N,4-dimethyl-2-nitrobenzamide |
| 559 | ++ | N-{2-[2-(1-{[(4-chlorophenyl)sulfonyl]-2,5-difluoroanilino}ethyl)phenoxy]ethyl}-N-ethyl-2-methylpropanamide |
| 560 | ++ | methyl 4-[{2-[2-(1-{[(4-chlorophenyl)-sulfonyl]-2,5-difluoroanilino}ethyl)phenoxy]-ethyl}(ethyl)amino]-4-oxobutanoate |
| 561 | ++ | N-{4-[2-(1-{[(4-chlorophenyl)sulfonyl]-2,5-difluoroanilino}ethyl)phenoxy]butyl}-N-methylbenzamide |
| 562 | ++ | allyl 3-[2-(1-{[(4-chlorophenyl)sulfonyl]-2,5-difluoroanilino}ethyl)phenoxy]propyl-(methyl)carbamate |
| 563 | ++ | 2-((1R)-1-{[(4-chlorophenyl)sulfonyl]-2,5-difluoroanilino}ethyl)benzyl 2,2-dimethoxy-ethylcarbamate |
| 564 | ++ | 4-chloro-N-(2,5-difluorophenyl)-N-[1-(2-{2-[methyl(methylsulfonyl)amino]ethoxy}-phenyl)ethyl]benzenesulfonamide |
| 565 | ++ | 2-((1R)-1-{[(4-chlorophenyl)sulfonyl]-2,5-difluoroanilino}ethyl)-5-fluorobenzyl 2-(4-chlorophenyl)ethylcarbamate |
| 566 | ++ | 2-((1R)-1-{[(4-chlorophenyl)sulfonyl]-2,5-difluoroanilino}ethyl)-5-fluorobenzyl benzyl-(methyl)carbamate |
| 567 | ++ | 2-((1R)-1-{[(4-chlorophenyl)sulfonyl]-2,5-difluoroanilino}ethyl)-5-fluorobenzyl benzyl-carbamate |
| 568 | ++ | 2-((1R)-1-{[(4-chlorophenyl)sulfonyl]-2,5-difluoroanilino}ethyl)-5-fluorobenzyl 2-pyridinylmethylcarbamate |
| 569 | ++ | 2-[2-((1R)-1-{[(4-chlorophenyl)sulfonyl]-2,5-difluoroanilino}ethyl)phenyl]ethyl 2-phenylethylcarbamate |
| 570 | ++ | N-{3-[2-(1-{[(4-chlorophenyl)sulfonyl]-2,5-difluoroanilino}ethyl)phenoxy]propyl}-N-methyl-2-nitrobenzamide |
| 571 | ++ | N-{3-[2-(1-{[(4-chlorophenyl)sulfonyl]-2,5-difluoroanilino}ethyl)phenoxy]propyl}-3,4-difluoro-N-methylbenzamide |
| 572 | ++ | 4-chloro-N-[1-(2-{2-[[(diethylamino)carbonyl]-(methyl)amino]ethoxy}phenyl)ethyl]-N-(2,5 difluorophenyl)benzenesulfonamide |
| 573 | ++ | N-{2-[2-(1-{[(4-chlorophenyl)sulfonyl]-2,5-difluoroanilino}ethyl)phenoxy]ethyl}-N-methyl-2-furamide |
| 574 | ++ | (2S)-2-{[2-((1R)-1-{[(4-chlorophenyl)-sulfonyl]-2,5-difluoroanilino}ethyl)benzyl]-amino}propanoic acid |
| 575 | ++ | 4-chloro-N-(2,5-difluorophenyl)-N-[1-(2-{3-[[(4-methoxyphenyl)sulfonyl](methyl)amino]-propoxy}phenyl)ethyl]benzenesulfonamide |
| 576 | ++ | 2-[2-((1R)-1-{[(4-chlorophenyl)sulfonyl]-2,5-difluoroanilino}ethyl)phenyl]ethyl 4-fluoro-benzylcarbamate |
| 577 | ++ | N-[1-(2-{4-[[(tert-butylamino)carbonyl](ethyl)-amino]butoxy}phenyl)ethyl]-4-chloro-N-(2,5 difluorophenyl)benzenesulfonamide |
| 578 | ++ | N-benzyl-4-chloro-N-(2,5-difluorophenyl)-benzenesulfonamide |
| 579 | ++ | N-{2-[2-(1-{[(4-chlorophenyl)sulfonyl]-2,5-difluoroanilino}ethyl)phenoxy]ethyl}-N-methyl-2-thiophenecarboxamide |
| 580 | ++ | N-{3-[2-(1-{[(4-chlorophenyl)sulfonyl]-2,5-difluoroanilino}ethyl)phenoxy]propyl}-4-cyano-N-methylbenzamide |
| 581 | ++ | 2-((1R)-1-{[(4-chlorophenyl)sulfonyl]-2,5-difluoroanilino}ethyl)benzyl tetrahydro-2-furanylmethylcarbamate |
| 582 | ++ | 2,5-dichloro-N-{3-[2-(1-{[(4-chlorophenyl)-sulfonyl]-2,5-difluoroanilino}ethyl)phenoxy]-propyl}-N-methylbenzenesulfonamide |
| 583 | ++ | 2-chloro-N-{3-[2-(1-{[(4-chlorophenyl)-sulfonyl]-2,5-difluoroanilino}ethyl)phenoxy]-propyl}-N-methylbenzamide |
| 584 | ++ | 4-butyl-N-{3-[2-(1-{[(4-chlorophenyl)-sulfonyl]-2,5-difluoroanilino}ethyl)phenoxy]-propyl} N-methylbenzamide |
| 585 | ++ | 4-chloro-N-(2,5-difluorophenyl)-N-[2-(1H-1,2,4-triazol-1-ylmethyl)benzyl]benzene-sulfonamide |
| 586 | ++ | N-[1-(2-{4-[[(tert-butylamino)carbonyl]-(methyl)amino]butoxy}phenyl)ethyl]-4-chloro-N-(2,5-difluorophenyl)benzenesulfonamide |
| 587 | ++ | 2-((1R)-1-{[(4-chlorophenyl)sulfonyl]-2,5-difluoroanilino}ethyl)benzyl 2-(1-methyl-2-pyrrolidinyl)ethylcarbamate |
| 588 | ++ | N-{4-[2-(1-{[(4-chlorophenyl)sulfonyl]-2,5-difluoroanilino}ethyl)phenoxy]butyl}-N-methylpentanamide |
| 589 | ++ | N-{3-[2-(1-{[(4-chlorophenyl)sulfonyl]-2,5-difluoroanilino}ethyl)phenoxy]propyl}-benzamide |
| 590 | ++ | N-{3-[2-(1-{[(4-chlorophenyl)sulfonyl]-2,5-difluoroanilino}ethyl)phenoxy]propyl}-2-methylbenzamide |
| 591 | ++ | N-{2-[2-(1-{[(4-chlorophenyl)sulfonyl]-2,5-difluoroanilino}ethyl)phenoxy]ethyl}-N-ethylbenzamide |
| 592 | ++ | N-{2-[2-(1-{[(4-chlorophenyl)sulfonyl]-2,5-difluoroanilino}ethyl)phenoxy]ethyl}-N-ethyl-2-thiophenecarboxamide |
| 593 | ++ | 2-((1R)-1-{[(4-chlorophenyl)sulfonyl]-2,5-difluoroanilino}ethyl)benzyl 4-(trifluoro-methyl)benzylcarbamate |
| 594 | ++ | 4-chloro-N-(2,5-difluorophenyl)-N-{1-[2-(2-{ethyl[(ethylamino)carbonyl]amino}ethoxy)-phenyl]ethyl}benzenesulfonamide |
| 595 | ++ | {[2-((1R)-1-{[(4-chlorophenyl)sulfonyl]-2,5-difluoroanilino}ethyl)benzyl]amino}acetic acid hydrochloride |
| 596 | ++ | N-{3-[2-({[(4-chlorophenyl)sulfonyl]-2,5-difluoroanilino}methyl)phenoxy]propyl}-N-methyl-4-morpholinecarboxamide |
| 597 | ++ | 4-chloro-N-(2,5-difluorophenyl)-N-(2-{3-[[(dimethylamino)carbonyl](methyl)amino]-propoxy}benzyl)benzenesulfonamide |
| 598 | ++ | 2-[2-((1R)-1-{[(4-chlorophenyl)sulfonyl]-2,5-difluoroanilino}ethyl)phenyl]ethyl 2-(4-chlorophenyl)ethylcarbamate |
| 599 | ++ | 4-chloro-N-(2,5-difluorophenyl)-N-(1-{2-[3-(methyl{[4-(trifluoromethyl)phenyl]sulfonyl}-amino)propoxy]phenyl}ethyl)benzene-sulfonamide |
| 600 | ++ | N-{2-[2-(1-{[(4-chlorophenyl)sulfonyl]-2,5-difluoroanilino}ethyl)phenoxy]ethyl}-N-ethylcyclobutanecarboxamide |

-continued

| NUMBER | ACTIVITY | COMPOUND |
|---|---|---|
| 601 | ++ | 2-((1R)-1-{[(4-chlorophenyl)sulfonyl]-2,5-difluoroanilino}ethyl)-5-fluorobenzyl diethylcarbamate |
| 602 | ++ | N-{3-[2-(1-{[(4-chlorophenyl)sulfonyl]-2,5-difluoroanilino}ethyl)phenoxy]propyl}-N-methyl-4-nitrobenzamide |
| 603 | ++ | N-{3-[2-(1-{[(4-chlorophenyl)sulfonyl]-2,5-difluoroanilino}ethyl)phenoxy]propyl}-2-cyclohexyl-N-methylacetamide |
| 604 | ++ | 4-chloro-N-{2-[3-(cyclohexylsulfonyl)-propoxy]benzyl}-N-(2,5-difluorophenyl)-benzenesulfonamide |
| 605 | ++ | N-{3-[2-({[(4-chlorophenyl)sulfonyl]-2,5-difluoroanilino}methyl)phenoxy]propyl}-4-cyano-N-methylbenzamide |
| 606 | ++ | N-{3-[2-(1-{[(4-chlorophenyl)sulfonyl]-2,5-difluoroanilino}ethyl)phenoxy]propyl}-4-cyanobenzamide |
| 607 | ++ | N-{3-[2-(1-{[(4-chlorophenyl)sulfonyl]-2,5-difluoroanilino}ethyl)phenoxy]propyl}-3,5-dinitrobenzamide |
| 608 | ++ | N-(2,5-difluorophenyl)-4-methyl-N-{2-[3-(1-piperidinyl)propoxy]benzyl}benzenesulfonamide hydrochloride |
| 609 | ++ | N-{4-[2-(1-{[(4-chlorophenyl)sulfonyl]-2,5-difluoroanilino}ethyl)phenoxy]butyl}-N-ethylpentanamide |
| 610 | ++ | 2-((1R)-1-{[(4-chlorophenyl)sulfonyl]-2,5-difluoroanilino}ethyl)benzyl 2-(1-pyrrolidinyl)-ethylcarbamate |
| 611 | ++ | 4-chloro-N-(2,5-difluorophenyl)-N-[6-(1-piperidinyl)hexyl]benzenesulfonamide hydrochloride |
| 612 | ++ | 2-((1R)-1-{[(4-chlorophenyl)sulfonyl]-2,5-difluoroanilino}ethyl)benzyl isobutylcarbamate |
| 613 | ++ | tert-butyl 6-[{3-[2-({[(4-chlorophenyl)-sulfonyl]-2,5-difluoroanilino}methyl)phenoxy]-propyl}(methyl)amino]-6-oxohexylcarbamate |
| 614 | ++ | 2-((1R)-1-{[(4-chlorophenyl)sulfonyl]-2,5-difluoroanilino}ethyl)-5-fluorobenzyl 1,3-benzodioxol-5-ylmethylcarbamate |
| 615 | ++ | 2-((1R)-1-{[(4-chlorophenyl)sulfonyl]-2,5-difluoroanilino}ethyl)-5-fluorobenzyl 4-morpholinecarboxylate |
| 616 | ++ | N-{3-[2-(1-{[(4-chlorophenyl)sulfonyl]-2,5-difluoroanilino}ethyl)phenoxy]propyl}-3,5-difluoro-N-methylbenzamide |
| 617 | ++ | N-{3-[2-(1-{[(4-chlorophenyl)sulfonyl]-2,5-difluoroanilino}ethyl)phenoxy]propyl}-N,2,4,6-tetramethylbenzenesulfonamide |
| 618 | ++ | S-methyl 4-[2-(1-{[(4-chlorophenyl)sulfonyl]-2,5-difluoroanilino}ethyl)phenoxy]butyl-(methyl)thiocarbamate |
| 619 | ++ | 2-((1R)-1-{[(4-chlorophenyl)sulfonyl]-2,5-difluoroanilino}ethyl)-5-fluorobenzyl 4-fluoro-benzylcarbamate |
| 620 | ++ | 3-[2-((1R)-1-{[(4-chlorophenyl)sulfonyl]-2,5-difluoroanilino}ethyl)phenyl]propyl 4-fluoro-benzylcarbamate |
| 621 | ++ | 4-chloro-N-(2,5-difluorophenyl)-N-[2-(3-hydroxy-1-propynyl)benzyl]benzene-sulfonamide |
| 622 | ++ | 2-[2-((1R)-1-{[(4-chlorophenyl)sulfonyl]-2,5-difluoroanilino}ethyl)phenyl]ethyl (1S)-1-phenylethylcarbamate |
| 623 | ++ | N-{3-[2-(1-{[(4-chlorophenyl)sulfonyl]-2,5-difluoroanilino}ethyl)phenoxy]propyl}-2,3,6-trifluoro-N-methylbenzamide |
| 624 | ++ | 2-[2-((1R)-1-{[(4-chlorophenyl)sulfonyl]-2,5-difluoroanilino}ethyl)phenyl]ethyl butyl-(methyl)carbamate |
| 625 | ++ | N-{2-[2-(1-{[(4-chlorophenyl)sulfonyl]-2,5-difluoroanilino}ethyl)phenoxy]ethyl}-N-ethyl-2-furamide |
| 626 | ++ | 2-((1R)-1-{[(4-chlorophenyl)sulfonyl]-2,5-difluoroanilino}ethyl)-5-fluorobenzyl diallylcarbamate |
| 627 | ++ | N-{3-[2-({[(4-chlorophenyl)sulfonyl]-2,5-difluoroanilino}methyl)phenoxy]propyl}-N-methylcyclohexanecarboxamide |
| 628 | ++ | N-{3-[2-(1-{[(4-chlorophenyl)sulfonyl]-2,5-difluoroanilino}ethyl)phenoxy]propyl}-N-methyl-2,2-diphenylacetamide |
| 629 | ++ | 4-chloro-N-phenyl-N-{2-[3-(1-piperidinyl)-propyl]benzyl}benzenesulfonamide hydrochloride |
| 630 | ++ | N-{3-[2-(1-{[(4-chlorophenyl)sulfonyl]-2,5-difluoroanilino}ethyl)phenoxy]propyl}-2-fluoro-N-methylbenzamide |
| 631 | ++ | 2-((1R)-1-{[(4-chlorophenyl)sulfonyl]-2,5-difluoroanilino}ethyl)benzyl diallylcarbamate |
| 632 | ++ | 2-((1R)-1-{[(4-chlorophenyl)sulfonyl]-2,5-difluoroanilino}ethyl)benzyl 3-pyridinylcarbamate |
| 633 | ++ | S-methyl 3-[2-({[(4-chlorophenyl)sulfonyl]-2,5-difluoroanilino}methyl)phenoxy]propyl-(methyl)thiocarbamate |
| 634 | ++ | 3-[2-((1R)-1-{[(4-chlorophenyl)sulfonyl]-2,5-difluoroanilino}ethyl)phenyl]propyl (1S)-1-phenylethylcarbamate |
| 635 | ++ | 2-((1R)-1-{[(4-chlorophenyl)sulfonyl]-2,5-difluoroanilino}ethyl)benzyl phenylcarbamate |
| 636 | ++ | 4-chloro-N-{3-[2-(1-{[(4-chlorophenyl)-sulfonyl]-2,5-difluoroanilino}ethyl)phenoxy]-propyl}-N-methyl-2-nitrobenzamide |
| 637 | ++ | N-{3-[2-(1-{[(4-chlorophenyl)sulfonyl]-2,5-difluoroanilino}ethyl)phenoxy]propyl}-2-iodo-N-methylbenzamide |
| 638 | ++ | N-{3-[2-({[(4-chlorophenyl)sulfonyl]-2,5-difluoroanilino}methyl)phenoxy]propyl}-N-methylbutanamide |
| 639 | ++ | 2-((1R)-1-{[(4-chlorophenyl)sulfonyl]-2,5-difluoroanilino}ethyl)benzyl 2,5-difluoro-benzylcarbamate |
| 640 | ++ | 2-((1R)-1-{[(4-chlorophenyl)sulfonyl]-2,5-difluoroanilino}ethyl)-5-fluorobenzyl 2-phenyl-ethylcarbamate |
| 641 | ++ | 2-bromo-N-{3-(2-({[(4-chlorophenyl)-sulfonyl]-2,5-difluoroanilino}methyl)-phenoxy]propyl}-N-methylbenzamide |
| 642 | ++ | N-{2-[2-(1-{[(4-chlorophenyl)sulfonyl]-2,5-difluoroanilino}ethyl)phenoxy]ethyl}-N-ethyl-3-methyl-2-butenamide |
| 643 | ++ | N-{3-[2-(1-{[(4-chlorophenyl)sulfonyl]-2,5-difluoroanilino}ethyl)phenoxy]propyl}-3,4-dimethoxy-N-methylbenzamide |
| 644 | ++ | 2-[2-((1R)-1-{[(4-chlorophenyl)sulfonyl]-2,5-difluoroanilino}ethyl)phenyl]ethyl 1,2,3,4-tetrahydro-1-naphthalenylcarbamate |
| 645 | ++ | 4-chloro-N-{2-[3-(4-hydroxy-1-piperidinyl)-propoxy]benzyl}-N-phenylbenzenesulfonamide hydrochloride |
| 646 | ++ | N-{2-[2-(1-{[(4-chlorophenyl)sulfonyl]-2,5-difluoroanilino}ethyl)phenoxy]ethyl}-N-ethylbutanamide |
| 647 | ++ | 2,4-dichloro-N-{3-[2-(1-{[(4-chlorophenyl)-sulfonyl]-2,5-difluoroanilino}ethyl)phenoxy]-propyl}-N-methylbenzenesulfonamide |
| 648 | ++ | 4-chloro-N-(2,5-difluorophenyl)-N-{2-[2-[1-(4-ethoxybenzoyl)-2-piperidinyl]ethoxy]-benzyl}benzenesulfonamide |
| 649 | ++ | (2E)-N-{2-[2-(1-{[(4-chlorophenyl)sulfonyl]-2,5-difluoroanilino}ethyl)phenoxy]ethyl}-N-ethyl-2-butenamide |
| 650 | ++ | 2-[2-((1R)-1-{[(4-chlorophenyl)sulfonyl]-2,5-difluoroanilino}ethyl)phenyl]ethyl sec-butyl-carbamate |
| 651 | ++ | N-{3-[2-(1-{[(4-chlorophenyl)sulfonyl]-2,5-difluoroanilino}ethyl)phenoxy]propyl}-3,4,5-trimethoxybenzamide |
| 652 | ++ | N-{3-[2-(1-{[(4-chlorophenyl)sulfonyl]-2,5-difluoroanilino}ethyl)phenoxy]propyl}-4-methoxy-N-methylbenzamide |

| NUMBER | ACTIVITY | COMPOUND |
|---|---|---|
| 653 | ++ | N-{2-[2-(1-{[(4-chlorophenyl)sulfonyl]-2,5-difluoroanilino}ethyl)phenoxy]ethyl}-3-cyclopentyl-N-methylpropanamide |
| 654 | ++ | N-{3-[2-(1-{[(4-chlorophenyl)sulfonyl]-2,5-difluoroanilino}ethyl)phenoxy]propyl}-4-fluoro-N-methylbenzamide |
| 655 | ++ | 3-[2-((1R)-1-{[(4-chlorophenyl)sulfonyl]-2,5-difluoroanilino}ethyl)phenyl]-N-isopropylpropanamide |
| 656 | ++ | N-{3-[2-(1-{[(4-chlorophenyl)sulfonyl]-2,5-difluoroanilino}ethyl)phenoxy]propyl}-N-methyl-4-propylbenzamide |
| 657 | ++ | N-{3-[2-(1-{[(4-chlorophenyl)sulfonyl]-2,5-difluoroanilino}ethyl)phenoxy]propyl}-N-methyl-3-(trifluoromethyl)benzamide |
| 658 | ++ | 2-((1R)-1-{[(4-chlorophenyl)sulfonyl]-2,5-difluoroanilino}ethyl)-5-fluorobenzyl 4-(trifluoromethyl)benzylcarbamate |
| 659 | ++ | (2S)-2-[[2-((1R)-1-{[(4-chlorophenyl)sulfonyl]-2,5-difluoroanilino}ethyl)benzyl]-(methyl)amino]propanoic acid hydrochloride |
| 660 | ++ | 2-((1R)-1-{[(4-chlorophenyl)sulfonyl]-2,5-difluoroanilino}ethyl)benzyl 1,2,3,4-tetrahydro-1-naphthalenylcarbamate |
| 661 | ++ | 4-chloro-N-(2,5-difluorophenyl)-N-(2-{2-[1-(3-fluorobenzoyl)-2-piperidinyl]ethoxy}benzyl)-benzenesulfonamide |
| 662 | ++ | 2-((1R)-1-{[(4-chlorophenyl)sulfonyl]-2,5-difluoroanilino}ethyl)benzyl 2-(diethylamino)-ethylcarbamate |
| 663 | ++ | 4-chloro-N-(3-chlorophenyl)-N-{2-[3-(1-piperidinyl)propoxy]benzyl}benzenesulfonamide hydrochloride |
| 664 | ++ | N-{2-[2-(1-{[(4-chlorophenyl)sulfonyl]-2,5-difluoroanilino}ethyl)phenoxy]ethyl}-N-methylpentanamide |
| 665 | ++ | N-{3-[2-({[(4-chlorophenyl)sulfonyl]-2,5-difluoroanilino}methyl)phenoxy]propyl}-2,3-difluoro-N-methylbenzamide |
| 666 | ++ | N-{3-[2-({[(4-chlorophenyl)sulfonyl]-2,5-difluoroanilino}methyl)phenoxy]propyl}-N-methyl-5-(2-oxohexahydro-1H-thieno[3,4-d]-imidazol-4-yl)pentamide |
| 667 | ++ | 2-((1R)-1-{[(4-chlorophenyl)sulfonyl]-2,5-difluoroanilino}ethyl)benzyl 2-furylmethylcarbamate |
| 668 | ++ | N-{3-[2-(1-{[(4-chlorophenyl)sulfonyl]-2,5-difluoroanilino}ethyl)phenoxy]propyl}-N-methyl-3,5-dinitrobenzamide |
| 669 | ++ | 2-((1R)-1-{[(4-chlorophenyl)sulfonyl]-2,5-difluoroanilino}ethyl)benzyl 2-methoxy-ethylcarbamate |
| 670 | ++ | N-{3-[2-(1-{[(4-chlorophenyl)sulfonyl]-2,5-difluoroanilino}ethyl)phenoxy]propyl}-2,3,4-trifluoro-N-methylbenzamide |
| 671 | ++ | N-{3-[2-(1-{[(4-chlorophenyl)sulfonyl]-2,5-difluoroanilino}ethyl)phenoxy]propyl}-N-methyl-2-naphthalenesulfonamide |
| 672 | ++ | 4-chloro-N-(2,5-difluorophenyl)-N-(2-{2-[1-(2-iodobenzyl)-2-piperidinyl]ethoxy}benzyl)-benzenesulfonamide |
| 673 | ++ | 2-((1R)-1-{[(4-chlorophenyl)sulfonyl]-2,5-difluoroanilino}ethyl)benzyl 1,3-benzodioxol-5-ylmethylcarbamate |
| 674 | ++ | 2-((1R)-1-{[(4-chlorophenyl)sulfonyl]-2,5-difluoroanilino}ethyl)benzyl isopropylcarbamate |
| 675 | ++ | 2-((1R)-1-{[(4-chlorophenyl)sulfonyl]-2,5-difluoroanilino}ethyl)benzyl cyclohexylcarbamate |
| 676 | ++ | N-{4-[2-(1-{[(4-chlorophenyl)sulfonyl]-2,5-difluoroanilino}ethyl)phenoxy]butyl}-2-ethyl-N-methylhexanamide |
| 677 | ++ | isobutyl 3-[2-(1-{[(4-chlorophenyl)sulfonyl]-2,5-difluoroanilino}ethyl)phenoxy]propyl-(methyl)carbamate |
| 678 | ++ | benzyl 3-[2-(1-{[(4-chlorophenyl)sulfonyl]-2,5-difluoroanilino}ethyl)phenoxy]propyl-(methyl)carbamate |
| 679 | ++ | N-{3-[2-(1-{[(4-chlorophenyl)sulfonyl]-2,5-difluoroanilino}ethyl)phenoxy]propyl}-4-fluorobenzamide |
| 680 | ++ | N-{3-[2-({[(4-chlorophenyl)sulfonyl]-2,5-difluoroanilino}methyl)phenoxy]propyl}-N,2-dimethylbenzamide |
| 681 | ++ | 2-({[(4-chlorophenyl)sulfonyl]-2,5-difluoroanilino}methyl)phenyl acrylate |
| 682 | ++ | 2,4-dichloro-N-{3-[2-(1-{[(4-chlorophenyl)-sulfonyl]-2,5-difluoroanilino}ethyl)phenoxy]-propyl}-5-fluorobenzamide |
| 683 | ++ | 4-bromo-N-{3-[2-(1-{[(4-chlorophenyl)-sulfonyl]-2,5-difluoroanilino}ethyl)phenoxy]-propyl}-N-methylbenzamide |
| 684 | ++ | 3-chloro-N-{3-[2-(1-{[(4-chlorophenyl)-sulfonyl]-2,5-difluoroanilino}ethyl)phenoxy]-propyl}-N-methylbenzenesulfonamide |
| 685 | ++ | 2-[2-((1R)-1-{3-[2-(1-{[(4-chlorophenyl)-sulfonyl]-2,5-difluoroanilino}ethyl)phenyl]-ethyl cyclohexylcarbamate |
| 686 | ++ | N-{3-[2-(1-{3-[2-(1-{[(4-chlorophenyl)-sulfonyl]-2,5-difluoroanilino}ethyl)phenoxy]-butyl}-2-cyclohexyl-N-methylacetamide |
| 687 | ++ | N-{3-[2-(1-{3-[2-(1-{[(4-chlorophenyl)-sulfonyl]-2,5-difluoroanilino}ethyl)phenoxy]-propyl}-3-methylbenzamide |
| 688 | ++ | 3-chloro-N-{3-[2-(1-{[(4-chlorophenyl)-sulfonyl]-2,5-difluoroanilino}ethyl)phenoxy]-propyl}-N-methylbenzamide |
| 689 | ++ | 4-chloro-N-(2,5-difluorophenyl)-N-(2-{3-[(4-nitrophenyl)sulfinyl]propoxy}benzyl)benzene-sulfonamide |
| 690 | ++ | N-{3-[2-(1-{[(4-chlorophenyl)sulfonyl]-2,5-difluoroanilino}ethyl)phenoxy]propyl}-3-methoxybenzamide |
| 691 | ++ | 2-((1R)-1-{[(4-chlorophenyl)sulfonyl]-2,5-difluoroanilino}ethyl)-5-fluorobenzyl 2-furylmethylcarbamate |
| 692 | ++ | 4-chloro-N-(2,5-difluorophenyl)-N-[1-(2-{3-[[(4-iodophenyl)sulfonyl](methyl)amino]-propoxy}phenyl)ethyl]benzenesulfonamide |
| 693 | ++ | N-{3-[2-(1-{[(4-chlorophenyl)sulfonyl]-2,5-difluoroanilino}ethyl)phenoxy]propyl}-N,2-dimethylbenzamide |
| 694 | ++ | N-{2-[2-(1-{[(4-chlorophenyl)sulfonyl]-2,5-difluoroanilino}ethyl)phenoxy]ethyl}-N-ethyl-3-methylbutanamide |
| 695 | ++ | 4-chloro-N-(2,5-difluorophenyl)-N-[1-(2-{2-[[(isopropylamino)carbonyl](methyl)amino]-ethoxy}phenyl)ethyl]benzenesulfonamide |
| 696 | ++ | N-{3-[2-({[(4-chlorophenyl)sulfonyl]-2,5-difluoroanilino}methyl)phenoxy]propyl}-N,3-dimethylbenzamide |
| 697 | ++ | N-{3-[2-(1-{[(4-chlorophenyl)sulfonyl]-2,5-difluoroanilino}ethyl)phenoxy]ethyl}-N-methyl-2-(trifluoromethyl)benzamide |
| 698 | ++ | 4-chloro-N-[1-(2-{2-[[(diethylamino)carbonyl]-(ethyl)amino]ethoxy}phenyl)ethyl]-N-(2,5-difluorophenyl)benzenesulfonamide |
| 699 | ++ | N-{3-[2-(1-{[(4-chlorophenyl)sulfonyl]-2,5-difluoroanilino}ethyl)phenoxy]propyl}-3-fluoro-N-methylbenzamide |
| 700 | ++ | N-{4-[2-(1-{[(4-chlorophenyl)sulfonyl]-2,5-difluoroanilino}ethyl)phenoxy]butyl}-N,2,4-trimethylpentanamide |
| 701 | ++ | 4-chloro-N-(2,5-difluorophenyl)-N-{1-[2-(2-{methyl[(2,2,2-trifluorophenyl)sulfonyl]-amino}ethoxy)phenyl]ethyl}benzene-sulfonamide |
| 702 | ++ | 4-chloro-N-(2,5-difluorophenyl)-N-{2-[3-(phenylsulfinyl)propoxy]benzyl}benzene-sulfonamide |
| 703 | ++ | N-{3-[2-(1-{[(4-chlorophenyl)sulfonyl]-2,5-difluoroanilino}ethyl)phenoxy]propyl}-N-methyl-4-(trifluoromethyl)benzamide |

-continued

| NUMBER | ACTIVITY | COMPOUND |
|---|---|---|
| 704 | ++ | 4-chloro-N-(2,5-difluorophenyl)-N-{2-[3-(2,6-dioxo-1-piperidinyl)propoxy]benzyl}benzenesulfonamide |
| 705 | ++ | N-{2-[2-(1-{[(4-chlorophenyl)sulfonyl]-2,5-difluoroanilino}ethyl)phenoxy]ethyl}-N-ethyl-2-(2-thienyl)acetamide |
| 706 | ++ | 4-chloro-N-(2,4-dichlorophenyl)-N-{2-[3-(1-piperidinyl)propoxy]benzyl}benzenesulfonamide hydrochloride |
| 707 | ++ | N-{3-[2-(1-{[(4-chlorophenyl)sulfonyl]-2,5-difluoroanilino}ethyl)phenoxy]propyl}-4-methylbenzamide |
| 708 | ++ | N-{3-[2-(1-{[(4-chlorophenyl)sulfonyl]-2,5-difluoroanilino}ethyl)phenoxy]butyl}-N-ethyl-2-furamide |
| 709 | ++ | N-[1-(2-{2-{[(tert-butylamino)carbonyl]-(ethyl)amino]ethoxy}phenyl)ethyl]-4-chloro-N-(2,5 difluorophenyl)benzenesulfonamide |
| 710 | ++ | N-{3-[2-(1-{[(4-chlorophenyl)sulfonyl]-2,5-difluoroanilino}ethyl)phenoxy]propyl}-2,4,5-trifluoro-N-methylbenzamide |
| 711 | ++ | 4-chloro-N-(2,5-difluorophenyl)-N-{2-[3-(1-piperidinyl)-1-propynyl]benzyl}benzenesulfonamide hydrochloride |
| 712 | ++ | N-{3-[2-(1-{[(4-chlorophenyl)sulfonyl]-2,5-difluoroanilino}ethyl)phenoxy]butyl}-3-cyclopentyl-N-methylpropanamide |
| 713 | ++ | 2,4,6-trichloro-N-{3-[2-(1-{[(4-chlorophenyl)sulfonyl]-2,5-difluoroanilino}ethyl)phenoxy]-propyl}-N-methylbenzamide |
| 714 | ++ | S-methyl 4-[2-(1-{3-[2-(1-{[(4-chlorophenyl)sulfonyl]-2,5-difluoroanilino}ethyl)phenoxy]butyl(ethyl)thiocarbamate |
| 715 | ++ | 2-((1R)-1-{[(4-chlorophenyl)-sulfonyl]-2,5-difluoroanilino}ethyl)benzyl benzyl(methyl)-carbamate |
| 716 | ++ | N-{3-[2-({[(4-chlorophenyl)sulfonyl]-2,5-difluoroanilino}methyl)phenoxy]propyl}-2-iodo-N-methylbenzamide |
| 717 | ++ | N-{3-[2-({[(4-chlorophenyl)sulfonyl]-2,5-difluoroanilino}methyl)phenoxy]propyl}-N-methylpentamide |
| 718 | ++ | 4-chloro-N-phenyl-N-{2-[3-(1-pyrrolidinyl)-propoxy]benzyl}benzenesulfonamide hydrochloride |
| 719 | ++ | N-{3-[2-(1-{[(4-chlorophenyl)sulfonyl]-2,5-difluoroanilino}ethyl)phenoxy]propyl}-4-iodo-N-methylbenzamide |
| 720 | ++ | 2-((1R)-1-{[(4-chlorophenyl)sulfonyl]-2,5-difluoroanilino}ethyl)benzyl butyl(methyl)-carbamate |
| 721 | ++ | N-{2-[2-(1-{[(4-chlorophenyl)sulfonyl]-2,5-difluoroanilino}ethyl)phenoxy]ethyl}-N-ethylcyclopentanecarboxamide |
| 722 | ++ | 4-chloro-N-{3-[2-(1-{[(4-chlorophenyl)-sulfonyl]-2,5-difluoroanilino}ethyl)phenoxy]-propyl}-N-methylbenzamide |
| 723 | ++ | N-{3-[2-(1-{[(4-chlorophenyl)sulfonyl]-2,5-difluoroanilino}ethyl)phenoxy]propyl}-3-nitrobenzamide |
| 724 | ++ | N-[1-(2-{2-[[(tert-butylamino)carbonyl]-(methyl)amino]ethoxy}phenyl)ethyl]-4-chloro-N-(2,5-difluorophenyl)benzenesulfonamide |
| 725 | ++ | 4-chloro-N-(2,5-difluorophenyl)-N-{1-[2-(2-{ethyl[(isopropylamino)carbonyl]amino}-ethoxy)phenyl]ethyl}benzenesulfonamide |
| 726 | ++ | 2-[2-((1R)-1-{[(4-chlorophenyl)sulfonyl]-2,5-difluoroanilino}ethyl)phenyl]ethyl 3,4-difluorobenzylcarbamate |
| 727 | ++ | N-{3-[2-(1-{[(4-chlorophenyl)sulfonyl]-2,5-difluoroanilino}ethyl)phenoxy]propyl}-2,5-difluoro-N-methylbenzamide |
| 728 | ++ | 2,4,6-trichloro-N-{3-[2-(1-{[(4-chlorophenyl)sulfonyl]-2,5-difluoroanilino}ethyl)phenoxy]propyl}benzamide |
| 729 | ++ | 2-((1R)-1-{[(4-chlorophenyl)sulfonyl]-2,5-difluoroanilino}ethyl)-5-fluorobenzyl 2-methoxyethylcarbamate |
| 730 | ++ | 3-[2-((1R)-1-{[(4-chlorophenyl)sulfonyl]-2,5-difluoroanilino}ethyl)phenyl]propyl phenylcarbamate |
| 731 | ++ | 2-((1R)-1-{[(4-chlorophenyl)sulfonyl]-2,5-difluoroanilino}ethyl)benzyl 2-(4-chlorophenyl)ethylcarbamate |
| 732 | ++ | (2Z)-N-{3-[2-(1-{[(4-chlorophenyl)sulfonyl]-2,5-difluoroanilino}ethyl)phenoxy]propyl}-3-phenyl-2-propenamide |
| 733 | ++ | N-{3-[2-(1-{[(4-chlorophenyl)sulfonyl]-2,5-difluoroanilino}methyl)phenoxy]propyl}-2-fluoro-N-methylbenzamide |
| 734 | ++ | 4-chloro-N-(2,5-difluorophenyl)-N-(2-{3-[[(isopropylamino)carbonyl](methyl)amino]-propoxy}benzyl)benzenesulfonamide |
| 735 | ++ | 4-chloro-N-(2,5-difluorophenyl)-N-[1-(2-{2-[(isopropylsulfonyl)(methyl)amino]ethoxy}-phenyl)ethyl]benzenesulfonamide |
| 736 | ++ | N-{3-[2-(1-{[(4-chlorophenyl)sulfonyl]-2,5-difluoroanilino}ethyl)phenoxy]propyl}-2,5-bis(trifluoromethyl)benzamide |
| 737 | ++ | N-{3-[2-(1-{[(4-chlorophenyl)sulfonyl]-2,5-difluoroanilino}ethyl)phenoxy]propyl}-N-methyl-3-nitrobenzamide |
| 738 | ++ | (2Z)-N-{3-[2-(1-{[(4-chlorophenyl)sulfonyl]-2,5-difluoroanilino}ethyl)phenoxy]propyl}-N methyl-3-phenyl-2-propenamide |
| 739 | ++ | N-{4-[2-(1-{[(4-chlorophenyl)sulfonyl]-2,5-difluoroanilino}ethyl)phenoxy]butyl}-N-ethylacrylamide |
| 740 | ++ | 4-chloro-N-(2,5-dichlorophenyl)-N-{2-[3-(1H-imidazol-1-yl)propoxy]benzyl}benzenesulfonamide hydrochloride |
| 741 | ++ | N-{3-[2-(1-{[(4-chlorophenyl)sulfonyl]-2,5-difluoroanilino}ethyl)phenoxy]propyl}-N,4-dimethylbenzamide |
| 742 | ++ | N-{3-[2-(1-{[(4-chlorophenyl)sulfonyl]-2,5-difluoroanilino}ethyl)phenoxy]propyl}-2,3,4,5,6-pentafluorobenzamide |
| 743 | ++ | 2-((1R)-1-{[(4-chlorophenyl)sulfonyl]-2,5-difluoroanilino}ethyl)benzyl 2-phenyl-ethylcarbamate |
| 744 | ++ | 2,2,2-trichloro-N-{2-[2-(1-{[(4-chlorophenyl)-sulfonyl]-2,5-difluoroanilino}ethyl)phenoxy]-ethyl}-N-ethylacetamide |
| 745 | ++ | N-{2-[2-(1-benzoyl-2-piperidinyl)ethoxy]-benzyl}-4-chloro-N-(2,5-difluorophenyl)benzenesulfonamide |
| 746 | ++ | 4-chloro-N-(2-{2-[1-(3,5-difluorobenzyl)-2-piperidinyl]ethoxy}benzyl)-N-(2,5-difluorophenyl)benzenesulfonamide |
| 747 | ++ | N-{3-[2-({[(4-chlorophenyl)sulfonyl]-2,5-difluoroanilino}methyl)phenoxy]propyl}-4-fluoro-N-methylbenzamide |
| 748 | ++ | 2-((1R)-1-{[(4-chlorophenyl)sulfonyl]-2,5-difluoroanilino}ethyl)benzyl 4-fluoro-benzylcarbamate |
| 749 | ++ | 4-chloro-N-{2-[3-(3,6-dihydro-1(2H)-pyridinyl)-propoxy]benzyl}-N-phenylbenzenesulfonamide hydrochloride |
| 750 | ++ | 2,4-dichloro-N-{3-[2-(1-{[(4-chlorophenyl)-sulfonyl]-2,5-difluoroanilino}ethyl)phenoxy]-propyl}-5-fluoro-N-methylbenzamide |
| 751 | ++ | 4-chloro-N-(2,5-difluorophenyl)-N-[2-(2H-tetraazol-2-ylmethyl)benzyl]benzenesulfonamide |
| 752 | ++ | N-{3-[2-({[(4-chlorophenyl)sulfonyl]-2,5-difluoroanilino}methyl)phenoxy]propyl}-N-methyl[1,1'-biphenyl]-4-carboxamide |
| 753 | ++ | N-{3-[2-(1-{[(4-chlorophenyl)sulfonyl]-2,5-difluoroanilino}ethyl)phenoxy]propyl}-2,4-dimethoxy-N-methylbenzamide |
| 754 | ++ | 4-chloro-N-{2-[2-(cyclohexylfulfonyl)ethoxy]-benzyl}-N-(2,5-difluorophenyl)benzenesulfonamide |
| 755 | ++ | N-{3-[2-(1-{[(4-chlorophenyl)sulfonyl]-2,5- |

-continued

| NUMBER | ACTIVITY | COMPOUND |
|---|---|---|
| 756 | ++ | difluoroanilino}ethyl)phenoxy]propyl}-2,6-difluoro-N-methylbenzamide N-{4-[2-(1-{[(4-chlorophenyl)sulfonyl]-2,5-difluoroanilino}ethyl)phenoxy]butyl}-N-ethyl-2-thiophenecarboxamide |
| 757 | ++ | S-ethyl-3-[2-({[(4-chlorophenyl)sulfonyl]-2,5-difluoroanilino}methyl)phenoxy]propyl-(methyl)thiocarbamate |
| 758 | ++ | 2-((1R)-1-{[(4-chlorophenyl)sulfonyl]-2,5-difluoroanilino}ethyl)benzyl sec-butylcarbamate |
| 759 | ++ | N-{3-[2-(1-{[(4-chlorophenyl)sulfonyl]-2,5-difluoroanilino}methyl)phenoxy]propyl}-N-methyl-2-phenylcyclopropanecarboxamide |
| 760 | ++ | 2-((1R)-1-{[(4-chlorophenyl)sulfonyl]-2,5-difluoroanilino}ethyl)-5-fluorobenzyl bis(2-methoxyethyl)carbamate |
| 761 | ++ | N-{3-[2-(1-{[(4-chlorophenyl)sulfonyl]-2,5-difluoroanilino}ethyl)phenoxy]propyl}-3-fluorobenzamide |
| 762 | ++ | 2-[2-((1R)-1-{[(4-chlorophenyl)sulfonyl]-2,5-difluoroanilino}ethyl)phenyl]ethyl phenylcarbamate |
| 763 | ++ | 3-[2-((1R)-1-{[(4-chlorophenyl)sulfonyl]-2,5-difluoroanilino}ethyl)phenyl]propyl benzyl(methyl)carbamate |
| 764 | ++ | 2-((1R)-1-{[(4-chlorophenyl)sulfonyl]-2,5-difluoroanilino}ethyl)-5-fluorobenzyl 3-fluorobenzylcarbamate |
| 765 | ++ | N-{3-[2-({[(4-chlorophenyl)sulfonyl]-2,5-difluoroanilino}methyl)phenoxy]propyl}-4-iodo-N-methylbenzamide |
| 766 | ++ | N-{3-[2-(1-{[(4-chlorophenyl)sulfonyl]-2,5-difluoroanilino}ethyl)phenoxy]propyl-N,3-dimethylbenzamide |
| 767 | ++ | N-{4-[2-(1-{[(4-chlorophenyl)sulfonyl]-2,5-difluoroanilino}ethyl)phenoxy]butyl}-N-ethylbenzamide |
| 768 | ++ | N-{3-[2-(1-{[(4-chlorophenyl)sulfonyl]-2,5-difluoroanilino}ethyl)phenoxy]propyl}-4-ethoxy-N-methylbenzamide |
| 769 | ++ | N-{2-[2-(1-{[(4-chlorophenyl)sulfonyl]-2,5-difluoroanilino}ethyl)phenoxy]ethyl}-N-ethyl-1-adamantanecarboxamide |
| 770 | ++ | N-{3-[2-(1-{[(4-chlorophenyl)sulfonyl]-2,5-difluoroanilino}ethyl)phenoxy]propyl}-N-methyl-4-(trifluoromethoxy)benzamide |
| 771 | ++ | S-methyl 2-[2-(1-{[(4-chlorophenyl)sulfonyl]-2,5-difluoroanilino}ethyl)phenoxy]ethyl(ethyl)-thiocarbamate |
| 772 | ++ | 4-chloro-N-(2,5-difluorophenyl)-N-[2-(1H-imidazol-1-ylmethyl)benzyl]benzene-sulfonamide |
| 773 | ++ | 4-chloro-N-(2,5-difluorophenyl)-N-(1-{2-[3-(methyl{[(E)-2-phenylethyl]sulfonyl}amino)-propoxy]phenyl}ethyl)benzenesulfonamide |
| 774 | ++ | 2-chloro-N-{3-[2-(1-{[(4-chlorophenyl)-sulfonyl]-2,5-difluoroanilino}methyl)phenoxy]-propyl}-N-methylbenzamide |
| 775 | ++ | N-{3-[2-({[(4-chlorophenyl)sulfonyl]-2,5-difluoroanilino}methyl)phenoxy]propyl}-2-methoxy-N-methylbenzamide |
| 776 | ++ | N-{3-[2-(1-{[(4-chlorophenyl)sulfonyl]-2,5-difluoroanilino}ethyl)phenoxy]propyl}-N-methyl-1-naphthalenesulfonamide |
| 777 | ++ | N-{2-[2-(1-{[(4-chlorophenyl)sulfonyl]-2,5-difluoroanilino}ethyl)phenoxy]propyl}-N-ethylpentamide |
| 778 | ++ | N-{3-[2-(1-{[(4-chlorophenyl)sulfonyl]-2,5-difluoroanilino}ethyl)phenoxy]propyl}-2,3,4,5 tetrafluoro-N-methylbenzamide |
| 779 | ++ | methyl (2S)-2-[[2-((1R)-1-{[(4-chlorophenyl)-sulfonyl]-2,5-difluoroanilino}ethyl)benzyl]-(methyl)amino]propanoate |
| 780 | ++ | 4-chloro-N-(2,5-difluorophenyl)-N-[2-(2-{1-[(2-phenylcyclopropyl)carbonyl]-2- |
| 781 | ++ | piperidinyl}ethoxy)benzyl]benzenesulfonamide 4-chloro-N-(1-methylbutyl)-N-{2-[3-(1-piperidinyl)propoxy]benzyl}benzene-sulfonamide hydrochloride |
| 782 | ++ | 4-chloro-N-(1-methylbutyl)-N-{2-[3-(1-piperidinyl)propoxy]benzyl}benzene-sulfonamide hydrochloride |
| 783 | ++ | (2E)-1-N-{3-[2-({[(4-chlorophenyl)sulfonyl]-2,5-difluoroanilino}methyl)phenoxy]propyl}-N methyl-2-butenamide |
| 784 | ++ | N-{3-[2-(1-{[(4-chlorophenyl)sulfonyl]-2,5-difluoroanilino}ethyl)phenoxy]propyl}-2,2-diphenylacetamide |
| 785 | ++ | N-{4-[2-(1-{[(4-chlorophenyl)sulfonyl]-2,5-difluoroanilino}ethyl)phenoxy]butyl}-2-cyclohexyl-N-ethylacetamide |
| 786 | ++ | N-{3-[2-(1-{[(4-chlorophenyl)sulfonyl]-2,5-difluoroanilino}ethyl)phenoxy]propyl}-3-methoxy-N-methylbenzamide |
| 787 | ++ | 4-chloro-N-(2,5-difluorophenyl)-N-[2-(2-{1-[(2-fluorobenzoyl)-2-piperidinyl]ethoxy}-benzyl)benzenesulfonamide |
| 788 | ++ | N-{3-[2-(1-{[(4-chlorophenyl)sulfonyl]-2,5-difluoroanilino}ethyl)phenoxy]propyl}-N-methyl-3-(trifluoromethyl)benzenesulfonamide |
| 789 | ++ | N-{3-[2-(1-{[(4-chlorophenyl)sulfonyl]-2,5-difluoroanilino}ethyl)phenoxy]propyl}-2-phenylcyclopropanecarboxamide |
| 790 | ++ | S-ethyl 4-[2-(1-{[(4-chlorophenyl)sulfonyl]-2,5-difluoroanilino}ethyl)phenoxy]butyl-(ethyl)thiocarbamate |
| 791 | ++ | N-{3-[2-({[(4-chlorophenyl)sulfonyl]-2,5-difluoroanilino}methyl)phenoxy]propyl}-N,3-dimethylbutamide |
| 792 | ++ | 4-chloro-N-(2,5-difluorophenyl)-N-(2-{1-(1-naphthoyl)-2-piperidinyl]ethoxy}benzyl)-benzenesulfonamide |
| 793 | ++ | N-{2-[2-(1-{[(4-chlorophenyl)sulfonyl]-2,5-difluoroanilino}ethyl)phenoxy]ethyl}-2-ethyl-N-methylhexanamide |
| 794 | ++ | 4-chloro-N-[1-(2-{3-[[(4-chlorophenyl)-sulfonyl](methyl)amino]propoxy}phenyl)-ethyl]-N-(2,5-difluorophenyl)benzene-sulfonamide |
| 795 | ++ | 2-((1R)-1-{[(4-chlorophenyl)sulfonyl]-2,5-difluoroanilino}ethyl)-5-fluorobenzyl sec-butylcarbamate |
| 796 | ++ | N-{2-[2-(1-{[(4-chlorophenyl)sulfonyl]-2,5-difluoroanilino}ethyl)phenoxy]ethyl}-2,2,3,3,4,4,4-heptafluoro-N-methylbutanamide |
| 797 | ++ | 4-chloro-N-(2,5-difluorophenyl)-N-(2-{2-[1-(2,3,4-trifluorobenzoyl)-2-piperidinyl]ethoxy}-benzyl)benzenesulfonamide |
| 798 | ++ | methyl [[2-((1R)-1-{[(4-chlorophenyl)-sulfonyl]-2,5-difluoroanilino}ethyl)benzyl]-(methyl)amino]acetate |
| 799 | ++ | 2-((1R)-1-{[(4-chlorophenyl)sulfonyl]-2,5-difluoroanilino}ethyl)benzyl 2-phenylpropyl-carbamate |
| 800 | ++ | N-{3-[2-({[(4-chlorophenyl)sulfonyl]-2,5-difluoroanilino}methyl)phenoxy]propyl}-N-methylbenzamide |
| 801 | ++ | 4-chloro-N-(2,5-difluorophenyl)-N-[1-(2-{3-[[(ethylamino)carbonyl](methyl)amino]-ethoxy}phenyl)ethyl]benzenesulfonamide |
| 802 | ++ | N-{3-[2-(1-{[(4-chlorophenyl)sulfonyl]-2,5-difluoroanilino}ethyl)phenoxy]propyl}-3,5-dimethoxy-N-methylbenzamide |
| 803 | ++ | 4-chloro-N-(2,5-difluorophenyl)-N-(2-{3-[(4-methoxyphenyl)sulfinyl]propoxy}benzyl)-benzenesulfonamide |
| 804 | ++ | N-(3-bromophenyl)-4-chloro-N-{2-[3-(1-piperidinyl)propoxy]benzyl}benzene-sulfonamide hydrochloride |
| 805 | ++ | N-{3-[2-(1-{[(4-chlorophenyl)sulfonyl]-2,5-difluoroanilino}ethyl)phenoxy]propyl}-4-nitrobenzamide |

| NUMBER | ACTIVITY | COMPOUND |
|---|---|---|
| 806 | ++ | 3-bromo-N-{3-[2-(1-{[(4-chlorophenyl)-sulfonyl]-2,5-difluoroanilino}ethyl)phenoxy]-propyl}-N-methylbenzenesulfonamide |
| 807 | ++ | 4-chloro-N-{3-[2-(1-{[(4-chlorophenyl)-sulfonyl]-2,5-difluoroanilino}ethyl)phenoxy]-propyl}-N-methyl-3-nitrobenzenesulfonamide |
| 808 | ++ | N-{3-[2-(1-{[(4-chlorophenyl)sulfonyl]-2,5-difluoroanilino}ethyl)phenoxy]propyl}-2-naphthamide |
| 809 | ++ | N-{2-[3-(3-hydroxy-1-pyrrolidinyl)propoxy]-benzyl}-N-phenylbenzenesulfonamide hydrochloride |
| 810 | ++ | N-{3-[2-({[(4-chlorophenyl)sulfonyl]-2,5-difluoroanilino}methyl)phenoxy]propyl}-N-methyl-2-naphthamide |
| 811 | ++ | 4-chloro-N-{3-[2-(1-{[(4-chlorophenyl)-sulfonyl]-2,5-difluoroanilino}ethyl)phenoxy]-propyl}benzamide |
| 812 | ++ | 4-chloro-N-(2-{3-[(2R, 6S)-2,6-dimethyl-piperidinyl]propoxy}benzyl)-N-phenylbenzene-sulfonamide hydrochloride |
| 813 | ++ | N-{3-[2-({[(4-chlorophenyl)sulfonyl]-2,5-difluoroanilino}methyl)phenoxy]propyl}-2,4,5-trifluoro-N-methylbenzamide |
| 814 | ++ | N-{3-[2-({[(4-chlorophenyl)sulfonyl]-2,5-difluoroanilino}methyl)phenoxy]propyl}-3-methoxy-N-methylbenzamide |
| 815 | ++ | N-{3-[2-(1-{[(4-chlorophenyl)sulfonyl]-2,5-difluoroanilino}ethyl)phenoxy]propyl}-3,5-difluorobenzamide |
| 816 | ++ | 4-chloro-N-(3,5-dichlorophenyl)-N-{2-[3-(1-piperidinyl)propoxy]benzyl}benzene-sulfonamide hydrochloride |
| 817 | ++ | 4-butoxy-N-{3-[2-({[(4-chlorophenyl)sulfonyl]-2,5-difluoroanilino}methyl)phenoxy]propyl}-N-methylbenzamide |
| 818 | ++ | 4-chloro-N-(2,5-difluorophenyl)-N-{2-[3-(phenylsulfonyl)propoxy]benzyl}benzene-sulfonamide |
| 819 | ++ | N-{3-[2-(1-{[(4-chlorophenyl)sulfonyl]-2,5-difluoroanilino}ethyl)phenoxy]propyl}-4-methoxybenzamide |
| 820 | ++ | 3-bromo-N-{3-[2-(1-{[(4-chlorophenyl)-sulfonyl]-2,5-difluoroanilino}ethyl)phenoxy]-propyl}-N-methylbenzamide |
| 821 | ++ | N-{3-[2-({[(4-chlorophenyl)sulfonyl]-2,5-difluoroanilino}methyl)phenoxy]propyl}-N-methyl-1-naphthamide |
| 822 | ++ | 3,4-dichloro-N-{3-[2-(1-{[(4-chlorophenyl)-sulfonyl]-2,5-difluoroanilino}ethyl)phenoxy]-propyl}-N-methylbenzenesulfonamide |
| 823 | ++ | 2-((1R)-1-{[(4-chlorophenyl)sulfonyl]-2,5-difluoroanilino}ethyl)benzyl (1S)-1-phenyl-ethylcarbamate |
| 824 | ++ | N-{3-[2-(1-{[(4-chlorophenyl)sulfonyl]-2,5-difluoroanilino}ethyl)phenoxy]propyl}-4-iodobenzamide |
| 825 | ++ | 2-((1R)-1-{[(4-chlorophenyl)sulfonyl]-2,5-difluoroanilino}ethyl)benzyl benzylcarbamate |
| 826 | ++ | phenyl 3-[2-(1-{[(4-chlorophenyl)sulfonyl]-2,5-difluoroanilino}ethyl)phenoxy]propyl(methyl)-carbamate |
| 827 | ++ | 4-chloro-N-(cyclobutylmethyl)-N-{2-[3-(1-piperidinyl)propoxy]benzyl}benzene-sulfonamide hydrochloride |
| 828 | ++ | N-{3-[2-(1-{[(4-chlorophenyl)sulfonyl]-2,5-difluoroanilino}ethyl)phenoxy]propyl}-2,3,4,5,6-pentafluoro-N-methylbenzamide |
| 829 | ++ | 3-bromo-N-{3-[2-(1-{[(4-chlorophenyl)-sulfonyl]-2,5-difluoroanilino}ethyl)phenoxy]-propyl}benzamide |
| 830 | ++ | S-ethyl 4-[2-(1-{[(4-chlorophenyl)sulfonyl]-2,5-difluoroanilino}ethyl)phenoxy]ethyl(ethyl)-thiocarbamate |
| 831 | ++ | N-{2-[2-(1-{[(4-chlorophenyl)sulfonyl]-2,5-difluoroanilino}ethyl)phenoxy]ethyl}-N,2-diethylhexanamide |
| 832 | ++ | 4-chloro-N-(2,5-difluorophenyl)-N-[2-(2-{1-[(2Z)-3-phenyl-2-propenoyl]-2-piperidinyl}-ethoxy)benzyl]benzenesulfonamide |
| 833 | ++ | 4-chloro-N-(2-{3-[4-hydroxy-4-(trifluoro-methyl)-1-piperidinyl]propoxy}benzyl)-N-phenylbenzenesulfonamide hydrochloride |
| 834 | ++ | N-{3-[2-({[(4-chlorophenyl)sulfonyl]-2,5-difluoroanilino}methyl)phenoxy]propyl}-2,4-dimethoxy-N-methylbenzamide |
| 835 | ++ | 4-chloro-N-cyclopentyl-N-{2-[3-(1-piperidinyl)propoxy]benzyl}benzene-sulfonamide hydrochloride |
| 836 | ++ | N-{(1R)-1-[2-(3-aminopropoxy)phenyl]ethyl}-3-chloro-N-(2,5-difluorophenyl)benzene-sulfonamide |
| 837 | ++ | N-{3-[2-({[(4-chlorophenyl)sulfonyl]-2,5-difluoroanilino}methyl)phenoxy]propyl}-2-ethyl N-methylhexanamide |
| 838 | ++ | 2-((1R)-1-{[(4-chlorophenyl)sulfonyl]-2,5-difluoroanilino}ethyl)benzyl benzyl[2-(dimethylamino)ethyl]carbamate |
| 839 | ++ | 2,4-dichloro-N-{3-[2-(1-{[(4-chlorophenyl)-sulfonyl]-2,5-difluoroanilino}ethyl)phenoxy]-propyl}-N-methylbenzamide |
| 840 | ++ | N-{3-[2-(1-{[(4-chlorophenyl)sulfonyl]-2,5-difluoroanilino}ethyl)phenoxy]propyl}-N-methyl[1,1'-biphenyl]-4-carboxamide |
| 841 | ++ | (2Z)-N-{3-[2-({[(4-chlorophenyl)sulfonyl]-2,5-difluoroanilino}methyl)phenoxy]propyl}-N-methyl-3-phenyl-2-propenamide |
| 842 | ++ | 4-chloro-N-(4-hexynyl)-N-{2-[3-(1-piperidinyl)propoxy]benzyl}benzene-sulfonamide hydrochloride |
| 843 | ++ | N-{4-[2-(1-{[(4-chlorophenyl)sulfonyl]-2,5-difluoroanilino}ethyl)phenoxy]butyl}-N-methylacrylamide |
| 844 | ++ | N-{2-[2-(1-{[(4-chlorophenyl)sulfonyl]-2,5-difluoroanilino}ethyl)phenoxy]ethyl}-2-cyclohexyl-N-methylacetamide |
| 845 | ++ | N-(2-{2-[1-([1,1'-biphenyl]-4-ylcarbonyl)-2-piperidinyl]ethoxy}benzyl)-4-chloro-N-(2,5-difluorophenyl)benzenesulfonamide |
| 846 | ++ | N-{4-[2-(1-{[(4-chlorophenyl)sulfonyl]-2,5-difluoroanilino}ethyl)phenoxy]butyl}-N-methyl-1-adamantanecarboxamide |
| 847 | ++ | 3,4-dichloro-N-{3-[2-(1-{[(4-chlorophenyl)-sulfonyl]-2,5-difluoroanilino}ethyl)phenoxy]-propyl}-N-methylbenzamide |
| 848 | ++ | 4-chloro-N-(cyclopentylmethyl)-N-{2-[3-(1-piperidinyl)propoxy]benzyl}benzene-sulfonamide hydrochloride |
| 849 | ++ | 4-chloro-N-(2-{3-[[(diethylamino)carbonyl]-(methyl)amino]propoxy}benzyl)-N-(2,5-difluorophenyl)benzenesulfonamide |
| 850 | ++ | 4-chloro-N-{2-[2-(cyclohexylsulfanyl)ethoxy]-benzyl}-N-(2,5-difluorophenyl)benzene-sulfonamide |
| 851 | ++ | N-{2-[3-(1-azepanyl)propoxy]benzyl}-4-chloro-N-phenylbenzenesulfonamide hydro-chloride |
| 852 | ++ | 4-chloro-N-cyclohexyl-N-{2-[3-(1-piperidinyl)propoxy]benzyl}benzenesulfonamide hydrochloride |
| 853 | ++ | 2,2,2-trichloro-N-{3-[2-({[(4-chlorophenyl)-sulfonyl]-2,5-difluoroanilino}methyl)phenoxy]-propyl}-N-methylacetamide |
| 854 | ++ | N-{2-[2-(1-{[(4-chlorophenyl)sulfonyl]-2,5-difluoroanilino}ethyl)phenoxy]ethyl}-N-methyltetradecanamide |
| 855 | ++ | N-[(1R)-1-(2-bromophenyl)ethyl]-4-chloro-N-(2,5-difluorophenyl)benzenesulfonamide |
| 856 | ++ | S-ethyl 2-(1-{[(4-chlorophenyl)sulfonyl]-2,5-difluoroanilino}ethyl)phenoxy]ethyl-(methyl)thiocarbamate |
| 857 | ++ | N-{2-[2-(1-{[(4-chlorophenyl)sulfonyl]-2,5-difluoroanilino}ethyl)phenoxy]ethyl}-3-cyclopentyl-N-ethylpropanamide |

-continued

| NUMBER | ACTIVITY | COMPOUND |
|---|---|---|
| 858 | ++ | N-{3-[2-(1-{[(4-chlorophenyl)sulfonyl]-2,5-difluoroanilino}ethyl)phenoxy]propyl}-N-methyl-2-naphthamide |
| 859 | ++ | 4-chloro-N-{2-[3-(4-morpholinyl)propoxy]-benzyl}-N-phenylbenzenesulfonamide hydrochloride |
| 860 | ++ | 4-chloro-N-(2,5-difluorophenyl)-N-(2-{2-[1-(3-methylbenzoyl)-2-piperidinyl]ethoxy}benzyl)benzenesulfonamide |
| 861 | ++ | 4-chloro-N-(2,5-difluorophenyl)-N-((1S)-1-{2-[3-(1H-imidazol-1-yl)propoxy]phenyl}ethyl)-benzenesulfonamide hydrochloride |
| 862 | ++ | N-{3-[2-({[(4-chlorophenyl)sulfonyl]-2,5-difluoroanilino}methyl)phenoxy]propyl}-3-fluoro-N-methylbenzamide |
| 863 | ++ | N-{3-[2-(1-{[(4-chlorophenyl)sulfonyl]-2,5-difluoroanilino}ethyl)phenoxy]propyl}-2,3,4,5 tetrafluorobenzamide |
| 864 | ++ | N-{3-[2-({[(4-chlorophenyl)sulfonyl]-2,5-difluoroanilino}methyl)phenoxy]propyl}-2,3,4-trifluoro-N-methylbenzamide |
| 865 | ++ | 4-chloro-N-{2-[3-(2-ethyl-1-piperidinyl)-propoxy]benzyl}-N-phenylbenzenesulfonamide hydrochloride |
| 866 | ++ | N-(2-bromophenyl)-4-chloro-N-{2-[3-(1-piperidinyl)propoxy]benzyl}benzene-sulfonamide hydrochloride |
| 867 | ++ | 4-chloro-N-[(1R)-1-methylbutyl]-N-{2-[3-(1-piperidinyl)propoxy]benzyl}benzene-sulfonamide hydrochloride |
| 868 | ++ | 4-chloro-N-(2,5-difluoroanilino)-N-[(1S)-2-hydroxy-1-phenylethyl]benzenesulfonamide |
| 869 | ++ | 4-chloro-N-{2-[3-(cyclohexylsulfanyl)-propoxy]benzyl}-N-(2,5-difluorophenyl)-benzenesulfonamide |
| 870 | ++ | 4-chloro-N-{2-[3-(cyclohexylsulfanyl)-propoxy]benzyl}-N-(2,5-difluorophenyl)-benzenesulfonamide |
| 871 | ++ | 4-chloro-N-(2,5-difluoroanilino)-N-(2-{3-[(4-methoxyphenyl)sulfonyl]propoxy}benzyl)-benzenesulfonamide |
| 872 | ++ | N-{3-[2-({[(4-chlorophenyl)sulfonyl]-2,5-difluoroanilino}methyl)phenoxy]propyl}-N-methyl-4-nitrobenzamide |
| 873 | ++ | N-{3-[2-({[(4-chlorophenyl)sulfonyl]-2,5-difluoroanilino}methyl)phenoxy]propyl}-N-methyl-4-(trifluoromethoxy)benzamide |
| 874 | ++ | 4-chloro-N-(2,5-difluorophenyl)-N-[(1R)-1-(2-vinylphenyl)ethyl]benzenesulfonamide |
| 875 | ++ | 4-chloro-N-(2-methylphenyl)-N-{2-[3-(1-piperidinyl)propoxy]benzyl}benzene-sulfonamide hydrochloride |
| 876 | ++ | 2,2,2-trichloro-N-{3-[2-({[(4-chlorophenyl)-sulfonyl]-2,5-difluoroanilino}ethyl)phenoxy]-propyl(methyl)carbamate |
| 877 | ++ | 4-chloro-N-{2-[3-(1,4-dioxa-8-azaspiro[4.5]-dec-8-yl)propoxy]benzyl}-N-phenylbenzene-sulfonamide |
| 878 | + | 4-chloro-N-(2,5-difluorophenyl)-N-(1-{2-[3-(1-piperidinyl)propoxy]phenyl}propyl)benzene-sulfonamide hydrochloride |
| 879 | + | N-(2,5-difluorophenyl)-4-methoxy-N-{2-[3-(1-piperidinyl)propoxy]benzyl}benzene-sulfonamide hydrochloride |
| 880 | + | N-{2-[3-(4-benzyl-1-piperidinyl)propoxy]-benzyl}-4-chloro-N-phenylbenzenesulfonamide hydrochloride |
| 881 | + | 3-[2-((1R)-1-{[(4-chlorophenyl)sulfonyl]-2,5-difluoroanilino}ethyl)-5-fluorophenyl]-1-propanesulfonic acid |
| 882 | + | 4-chloro-N-{2-[3-(1H-imidazol-1-yl)propoxy]-benzyl}-N-phenylbenzenesulfonamide hydrochloride |
| 883 | + | 4-chloro-N-{2-[3-(1-hydroxy-[lambda~5~piperidin-1-yl)propoxy]benzyl}-N-phenyl-benzenesulfonamide |
| 884 | + | 4-chloro-N-(2,5-difluorophenyl)-N-(2-{2-[1-(4-methylbenzoyl)-2-piperidinyl]ethoxy}benzyl)-benzenesulfonamide |
| 885 | + | 4-chloro-N-[1-(2-{2-[[(4-chlorophenyl)-sulfonyl](methyl)amino]propoxy}phenyl)-ethyl]-N-(2,5-difluorophenyl)benzene-sulfonamide |
| 886 | + | N-benzyl-4-chloro-N-{2-[3-(1-piperidinyl)-propoxy]benzyl}benzenesulfonamide hydrochloride |
| 887 | + | 4-chloro-N-(5-chloro-2-hydroxyphenyl)-N-{2-[3-(1-piperidinyl)propoxy]benzyl}benzene-sulfonamide hydrochloride |
| 888 | + | 4-chloro-N-(2,5-difluorophenyl)-N-[1-(2-{2-[[(diisopropylamino)carbonyl](methyl)amino]-ethoxy}phenyl)ethyl]benzenesulfonamide |
| 889 | + | 4-chloro-N-{2-[2-(1-methyl-2-piperidinyl)-ethoxy]benzyl}-N-phenylbenzenesulfonamide hydrochloride |
| 890 | + | 4-chloro-N-(2,5-difluorophenyl)-N-(2-{2-[1-(3,4-dimethoxybenzoyl)-2-piperidinyl]ethoxy}-benzyl)benzenesulfonamide |
| 891 | + | N-{3-[2-({[(4-chlorophenyl)sulfonyl]-2,5-difluoroanilino}methyl)phenoxy]propyl}-N-methyl-3-(trifluoromethyl)benzamide |
| 892 | + | N-{3-[2-(1-{[(4-chlorophenyl)sulfonyl]-2,5-difluoroanilino}ethyl)phenoxy]propyl}-N-methyl-2,5-bis(trifluoromethyl)benzamide |
| 893 | + | N-{3-[2-({[(4-chlorophenyl)sulfonyl]-2,5-difluoroanilino}methyl)phenoxy]propyl}-N,4-dimethylbenzamide |
| 894 | + | 2-((1R)-1-{[(4-chlorophenyl)sulfonyl]-2,5-difluoroanilino}ethyl)benzyl diethylcarbamate |
| 895 | + | 4-chloro-N-(3-fluorophenyl)-N-((1R)-1-{2-[3-(1H-imidazol-1-yl)propoxy]phenyl}ethyl)-benzenesulfonamide hydrochloride |
| 896 | + | 2,4-dichloro-N-{3-[2-({[(4-chlorophenyl)-sulfonyl]-2,5-difluoroanilino}methyl)phenoxy]-propyl}-5-fluoro-N-methylbenzamide |
| 897 | + | 4-chloro-N-cycloheptyl-N-{2-[3-(1-piperidinyl)propoxy]benzyl}benzene-sulfonamide hydrochloride |
| 898 | + | N-{3-[2-({[(4-chlorophenyl)sulfonyl]-2,5-difluoroanilino}methyl)phenoxy]propyl}-N-methyl-4-(trifluoromethyl)benzamide |
| 899 | + | N-(2-{2-[1-(4-butoxybenzoyl)-2-piperidinyl]-ethoxy}benzyl)-4-chloro-N-(2,5-difluoro-phenyl)benzenesulfonamide |
| 900 | + | 3-chloro-N-{3-[2-(1-{[(4-chlorophenyl)-sulfonyl]-2,5-difluoroanilino}ethyl)phenoxy]-propyl}benzamide |
| 901 | + | 4-chloro-N-(2,5-difluorophenyl)-N-(2-{2-[1-(4-iodobenzoyl)-2-piperidinyl]ethoxy}benzyl)-benzenesulfonamide |
| 902 | + | 4-chloro-N-(2,5-difluorophenyl)-N-(2-{2-[1-(2-methoxybenzoyl)-2-piperidinyl]ethoxy}-benzyl)benzenesulfonamide |
| 903 | + | N-{3-[2-({[(4-chlorophenyl)sulfonyl]-2,5-difluoroanilino}methyl)phenoxy]propyl}-N-methyl-1,3-benzodioxole-5-carboxamide |
| 904 | + | (2S)-2-{[(4-chlorophenyl)sulfonyl]-2,5-difluoroanilino}-2-henylethyl isonicotinate |
| 905 | + | 4-chloro-N-(2,5-difluorophenyl)-N-(2-{3-[(4-nitrophenyl)sulfonyl]propoxy}benzyl)benzene-sulfonamide |
| 906 | + | 4-chloro-N-(2,5-dichloro-3-pyridinyl)-N-{2-[3-(1-piperidinyl)propoxy]benzyl}benzene-sulfonamide hydrochloride |
| 907 | + | N-{3-[2-({[(4-chlorophenyl)sulfonyl]-2,5-difluoroanilino}methyl)phenoxy]propyl}-N,4-dimethyl-3-nitrobenzamide |
| 908 | + | 4-chloro-N-(2,5-difluorophenyl)-N-((1R)-1-{2-[3-(1H-imidazol-1-yl)propoxy]phenyl}ethyl)-benzenesulfonamide hydrochloride |
| 909 | + | 4-chloro-N-(2,5-difluorophenyl)-N-(2-{2-[1-(3-methoxybenzoyl)-2-piperidinyl]ethoxy}-benzyl)benzenesulfonamide |
| 910 | + | 2-((1R)-1-{[(4-chlorophenyl)sulfonyl]-2,5- |

-continued

| NUMBER | ACTIVITY | COMPOUND |
|---|---|---|
| | | difluoroanilino}ethyl)benzyl 3-fluorobenzyl-carbamate |
| 911 | + | 4-chloro-N-(2,5-difluorophenyl)-N-((1R)-1-{2-[3-(1H-imidazol-1-yl)propoxy]-6-methoxy-benzyl}benzenesulfonamide hydrochloride |
| 912 | + | N-(2,5-difluorophenyl)-N-((1R)-1-{4-fluoro-2-[3-(methylsulfanyl)propyl]phenyl}ethyl)-4-(methylsulfanyl)benzenesulfonamide |
| 913 | + | N-{3-[2-({[(4-chlorophenyl)sulfonyl]-2,5-difluoroanilino}ethyl)phenoxy]propyl}-3,4,5-trimethoxy-N-methylbenzamide |
| 914 | + | 2-((1R)-1-{[(4-chlorophenyl)sulfonyl]-2,5-difluoroanilino}ethyl)-5-fluorobenzyl 2-(1-pyrrolidinyl)ethylcarbamate |
| 915 | + | 4-chloro-N-{2-[3-(3-hydroxy-1-piperidinyl)-propoxy]benzyl}-N-phenylbenzenesulfonamide hydrochloride |
| 916 | + | 4-chloro-N-(2,5-difluorophenyl)-N-{2-[3-(1,3-dioxo-1,3-dihydro-2H-isoindol-2-yl)propyl]-benzyl}benzenesulfonamide |
| 917 | + | N-{3-[2-({[(4-chlorophenyl)sulfonyl]-2,5-difluoroanilino}methyl)phenoxy]propyl}-N-methyl-2-phenylcyclopropanecarboxamide |
| 918 | + | N-{2-[2-(1-azetidinyl)propoxy]benzyl}-4-chloro-N-phenylbenzenesulfonamide hydro-chloride |
| 919 | + | 4-chloro-N-(3-methylphenyl)-N-{2-[3-(1-piperidinyl)propoxy]benzyl}benzene-sulfonamide hydrochloride |
| 920 | + | N-{3-[2-(1-{[(4-chlorophenyl)sulfonyl]-2,5-difluoroanilino}ethyl)phenoxy]propyl}-4-(trifluoromethoxy)benzamide |
| 921 | + | N-(2-{2-[1-(1,3-benzodioxol-5-ylcarbonyl)-2-piperidinyl]ethoxy}benzyl)-4-chloro-N-(2,5-difluorophenyl)benzenesulfonamide |
| 922 | + | 4-chloro-N-(2-{3-[4-(hydroxymethyl)-1-piperidinyl]propoxy}benzyl)-N-phenylbenzene-sulfonamide hydrochloride |
| 923 | + | N-chloro-N-{2-[(1E)-3-oxo-3-(1-pyrrolidinyl)-1-propenyl]benzyl}-N-phenylbenzene-sulfonamide |
| 924 | + | 4-chloro-N-[2-(methylsulfanyl)phenyl]-N-{2-[3-(1-piperidinyl)propoxy]benzyl}benzene-sulfonamide hydrochloride |
| 925 | + | 4-chloro-N-[2-(methylsulfanyl)phenyl]-N-{2-[3-(1-piperidinyl)propoxy]benzyl}benzene-sulfonamide hydrochloride |
| 926 | + | 4-chloro-N-{2-[3-(3,5-dimethyl-1-piperidinyl)-propoxy]benzyl}-N-phenylbenzenesulfonamide hydrochloride |
| 927 | + | N-{2-[3-(4-benzyl-1-piperidinyl)propoxy]-benzyl}-4-chloro-N-phenylbenzenesulfonamide hydrochloride |
| 928 | + | N-{2-[2-(1-{[(4-chlorophenyl)sulfonyl]-2,5-difluoroanilino}ethyl)phenoxy]ethyl}-N-ethyltetradecanamide |
| 929 | + | methyl [{2-[2-(1-{[(4-chlorophenyl)sulfonyl]-2,5-difluoroanilino}ethyl)phenoxy]ethyl}-(methyl)amino](oxo)acetate |
| 930 | + | N-{2-[2-(1-{[(4-chlorophenyl)sulfonyl]-2,5-difluoroanilino}ethyl)phenoxy]ethyl}-N,2,4-trimethylpentamide |
| 931 | + | N-{3-[2-(1-{[(4-chlorophenyl)sulfonyl]-2,5-difluoroanilino}ethyl)phenoxy]ethyl}-N-methyl-3,5-bis(trifluoromethyl)benzamide |
| 932 | + | 3,4-dichloro-N-{3-2-({[(4-chlorophenyl)-sulfonyl]-2,5-difluoroanilino}methyl)phenoxy]-propyl}-N-methylbenzamide |
| 933 | + | 4-chloro-N-(2-{2-[1-(2,3-difluorobenzyl)-2-piperidinyl]ethoxy}benzyl)-N-(2,5-difluoro-phenyl)benzenesulfonamide |
| 934 | + | N-{3-[2-(1-{[(4-chlorophenyl)sulfonyl]-2,5-difluoroanilino}ethyl)phenoxy]propyl}-N-methyl-3,5-bis(trifluoromethyl)benzamide |
| 935 | + | 4-[2-((1R)-1-{4-chloro-2-[[(4-chlorophenyl)-sulfonyl](methyl)amino]phenoxy}ethyl)-5-fluorophenyl]butanoic acid |
| 936 | + | N-(2,5-difluorophenyl)-4-(ethylsulfanyl)-N-((1R)-1-{2-[3-(ethylsulfanyl)propyl]-4-fluoro-phenyl}ethyl)benzenesulfonamide |
| 937 | + | 4-chloro-N-phenyl-N-{2-[3-(4-thio-morpholinyl)propoxy]benzyl}benzene-sulfonamide hydrochloride |
| 938 | + | 4-chloro-N-(2,5-difluorophenyl)-N-(2-{2-[1-(3,4,5-trimethoxybenzoyl)-2-piperidinyl]-ethoxy}benzyl)benzenesulfonamide |
| 939 | + | 4-chloro-N-(2,5-difluorophenyl)-N-{(1R)-1-[2-(1-piperidinylmethyl)phenyl]ethyl}benzene-sulfonamide hydrochloride |
| 940 | + | 3-[2-(2-{[(4-chlorophenyl)sulfonyl]-2,5-difluoroanilino}-1-methylethyl)-5-fluoro-phenyl]butanoic acid |
| 941 | + | 4-chloro-N-(2-{[(2S)-7-methyl-7-azabicyclo-[2.2.1]hept-2-yl]methoxy}benzyl)-N-phenyl-benzenesulfonamide hydrochloride |
| 942 | + | N-(2-{2-[1-(2-bromobenzoyl)-2-piperidinyl]-ethoxy}benzyl)-4-chloro-N-(2,5-difluoro-phenyl)benzenesulfonamide |
| 943 | + | N-{4-[2-(1-{[(4-chlorophenyl)sulfonyl]-2,5-difluoroanilino}ethyl)phenoxy]butyl}-3-cyclopentyl-N-ethylpropanamide |
| 944 | + | 4-chloro-N-phenyl-N-{2-[3-(1-piperazinyl)-propoxy]benzyl}benzenesulfonamide dihydro-chloride |
| 945 | + | 4-chloro-N-{2-[3-(1-piperidinyl)propoxy]-benzyl}-N-(3-pyridinylmethyl)benzene-sulfonamide hydrochloride |
| 946 | + | 4-chloro-N-(2,5-difluorophenyl)-N-(2-{2-[1-(4-fluorobenzoyl)-2-piperidinyl]ethoxy}benzyl)-benzenesulfonamide |
| 947 | + | 4-chloro-N-{3-[2-(1-{[(4-chlorophenyl)-sulfonyl]-2,5-difluoroanilino}ethyl)phenoxy]-propyl}-2-nitrobenzamide |
| 948 | + | 2-chloro-5-{2-[3-(1-piperidinyl)propoxy]-benzyl}-6H-dibenzo[c,e][1,2]thiazine 5,5-dioxide hydrochloride |
| 949 | + | N-{2-[2-(1-{[(4-chlorophenyl)sulfonyl]-2,5-difluoroanilino}ethyl)phenoxy]ethyl}-N-ethylacrylamide |
| 950 | + | 3,5-dichloro-N-{3-[2-(1-{[(4-chlorophenyl)-sulfonyl]-2,5-difluoroanilino}ethyl)phenoxy]-propyl}-N-methylbenzamide |
| 951 | + | 4-chloro-N-(4-methylpentyl)-N-{2-[3-(1-piperidinyl)propoxy]benzyl}benzene-sulfonamide hydrochloride |
| 952 | + | 4-chloro-N-[3-(methylsulfanyl)phenyl]N-{2-[3-(1-piperidinyl)propoxy]benzyl}benzene-sulfonamide hydrochloride |
| 953 | + | 4-chloro-N-[3-(methylsulfanyl)phenyl]-N-{2-[3-(1-piperidinyl)propoxy]benzyl}benzene-sulfonamide hydrochloride |
| 954 | + | N-[(2S)-bicyclo[2.2.1]hept-2-yl]-4-chloro-N-{2-[3-(1-piperidinyl)propoxy]benzyl}benzene-sulfonamide hydrochloride |
| 955 | + | 4-chloro-N-(2-methyl-2-propenyl)-N-{2-[3-(1-piperidinyl)propoxy]benzyl}benzene-sulfonamide hydrochloride |
| 956 | + | 4-chloro-N-phenyl-N-(2-{3-[3-(1-piperidinyl)-propoxy]phenyl}ethyl)benzeneslfonamide hydrochloride |
| 957 | + | 4-chloro-N-(2,5-difluorophenyl)-N-{5-methyl-2-[3-(1-piperidinyl)propoxy]benzyl}benzene-sulfonamide hydrochloride |
| 958 | + | N-{3-[2-({[(4-chlorophenyl)sulfonyl]-2,5-difluoroanilino}methyl)phenoxy]propyl}-N-methyl-3,5-dinitrobenzamide |
| 959 | + | N-{4-[2-(1-{[(4-chlorophenyl)sulfonyl]-2,5-difluoroanilino}ethyl)phenoxy]butyl}-N-ethylcyclopropanecarboxamide |
| 960 | + | N-{3-[2-({[(4-chlorophenyl)sulfonyl]-2,5-difluoroanilino}methyl)phenoxy]propyl}-3,4-dimethoxy-N-methylbenzamide |
| 961 | + | 2-((1R)-1-{[(4-chlorophenyl)sulfonyl]-2,5-difluoroanilino}ethyl)benzyl 3,4-difluoro- |

-continued

| NUMBER | ACTIVITY | COMPOUND |
|---|---|---|
| 962 | + | 4-chloro-N-{2-[2-(1-methyl-2-pyrrolidinyl)-ethoxy]benzyl}-N-phenylbenzenesulfonamide hydrochloride |
| 963 | + | 4-chloro-N-phenyl-N-{2-[2-(2-pyrrolidinyl)-ethoxy]benzyl}benzenesulfonamide hydrochloride |
| 964 | + | 4-chloro-N-{5-chloro-2-[3-(1-piperidinyl)-propoxy]benzyl}-N-phenylbenzenesulfonamide hydrochloride |
| 965 | + | 4-chloro-N-{2-[3-(4-hydroxy-4-methyl-1-piperidinyl)propoxy]benzyl}-N-phenylbenzenesulfonamide hydrochloride |
| 966 | + | N-{3-[2-(1-{[(4-chlorophenyl)sulfonyl]-2,5-difluoroanilino}ethyl)phenoxy]propyl}-N-methyl-1-naphthamide |
| 967 | + | 4-chloro-N-{2-[3-(1-piperidinyl)propoxy]-benzyl}-N-(4-pyridinylmethyl)benzenesulfonamide hydrochloride |
| 968 | + | 4-chloro-N-{2-[3-(4-oxo-1-piperidinyl)-propoxy]benzyl}-N-phenylbenzenesulfonamide hydrochloride |
| 969 | + | N-{(2S)-bicyclo[2.2.1]hept-2-yl}-4-chloro-N-{2-[3-(1-piperidinyl)propoxy]benzyl}benzenesulfonamide hydrochloride |
| 970 | + | 4-chloro-N-{3-[2-({[(4-chlorophenyl)-sulfonyl]-2,5-difluoroanilino}methyl)phenoxy]-propyl}-N-methylbenzamide |
| 971 | + | ethyl (2E)-3-[2-({[(4-chlorophenyl)sulfonyl]-anilino}methyl)phenyl]-2-propenoate |
| 972 | + | 4-chloro-N-phenyl-N-(2-{2-[3-(1-piperidinyl)-propoxy]phenyl}ethyl)benzenesulfonamide hydrochloride |
| 973 | + | 4-chloro-N-phenyl-N-{2-[4-(1-piperidinyl)-1-butynyl]benzyl}benzenesulfonamide |
| 974 | + | 4-chloro-N-(2,3,4,5,6-pentafluorobenzyl)-N-{2-[3-(1-piperidinyl)propoxy]benzyl}benzenesulfonamide hydrochloride |
| 975 | + | 4-chloro-N-(5-chloro-2-hydroxybenzyl)-N-phenylbenzenesulfonamide |
| 976 | + | 4-chloro-N-phenyl-N-(2-{[5-(1-piperidinyl)-pentyl]oxy}benzyl)benzenesulfonamide hydrochloride |
| 977 | + | 4-chloro-N-phenyl-N-{2-[4-(1-piperidinyl)-butoxy]benzyl}benzenesulfonamide hydrochloride |
| 978 | + | 4-chloro-N-phenyl-N-{2-[5-(1-piperidinyl)-pentyl]benzyl}benzenesulfonamide hydrochloride |
| 979 | + | 4-chloro-N-{2-[3-(cyclopropylamino)propoxy]-benzyl}-N-phenylbenzenesulfonamide hydrochloride |
| 980 | + | 4-chloro-N-[(1R)-1-methylbutyl]-N-{2-[3-(1-piperidinyl)propoxy]benzyl}benzenesulfonamide hydrochloride |
| 981 | + | 4-chloro-N-phenyl-N-{2-[4-(1-piperdinyl)-butyl]benzyl}benzenesulfonamide hydrochloride |
| 982 | + | 4-chloro-N-(2,5-difluorophenyl)-N-{2-[3-(phenylsulfanyl)propoxy]benzyl}benzenesulfonamide |
| 983 | + | S-methyl 2-[2-(1-{[(4-chlorophenyl)sulfonyl]-2,5-difluoroanilino}ethyl)phenoxy]ethyl-(methyl)thiocarbamate |
| 984 | + | 4-chloro-N-(cyclopropylmethyl-N-{2-[3-(1-piperidinyl)propoxy]benzyl}benzenesulfonamide hydrochloride |
| 985 | + | N-allyl-4-chloro-N-{2-[3-(1-piperidinyl)-propoxy]benzyl}benzenesulfonamide hydrochloride |
| 986 | + | 4-chloro-N-{2-[3-(1-piperidinyl)propoxy]-benzyl}-N-tetrahydro-2H-pyran-4-ylbenzenesulfonamide hydrochloride |
| 987 | + | methyl (2S)-1-{[(4-chlorophenyl)sulfonyl]-2,5-difluoroanilino}(phenyl)ethanoate |
| 988 | + | N-(4-bromophenyl)-4-chloro-N-{2-[3-(1-piperidinyl)propoxy]benzyl}benzenesulfonamide hydrochloride |
| 989 | + | N-{3-[2-({[(4-chlorophenyl)sulfonyl]-2,5-difluoroanilino}methyl)phenoxy]propyl}-3,4,5-trimethoxy-N-methylbenzamide |
| 990 | + | 4-chloro-N-{5-chloro-2-[4-(1-piperidinyl)-1-butynyl]benzyl}-N-phenylbenzenesulfonamide hydrochloride |
| 991 | + | 4-chloro-N-(2-ethynylbenzyl)-N-phenyl-benzenesulfonamide |
| 992 | + | N-(2,5-dichlorophenyl)(phenyl)-N-{2-[3-(1-piperidinyl)propoxy]benzyl}methanesulfonamide hydrochloride |
| 993 | + | 3-(2-{[(phenylsulfonyl)anilino]methyl}-phenyl)propanoic acid |
| 994 | + | (E)-N-(2,5-dichlorophenyl)-2-phenyl-N-{2-[3-(1-piperidinyl)propoxy]benzyl}ethanesulfonamide hydrochloride |
| 995 | + | ethyl 3-(2-{[(phenylsulfonyl)anilino]methyl}-phenyl)propanoate |
| 996 | + | 4-chloro-N-{2-[3-(cyclohexylamino)propoxy]-benzyl}-N-phenylbenzenesulfonamide hydrochloride |
| 997 | + | 4-chloro-N-(2,5-difluorophenyl)-N-(2-{3-[(4-nitrophenyl)sulfanyl]propoxy}benzyl)benzenesulfonamide |
| 998 | + | 4-chloro-N-(4-nitrobenzyl)-N-{2-[3-(1-piperidinyl)propoxy]benzyl}benzenesulfonamide hydrochloride |
| 999 | + | 4-chloro-N-{2-[3-(3,4-dihydro-2(1H)-isoquinolinyl)propoxy]benzyl}-N-phenyl-benzenesulfonamide |
| 1000 | + | N-{3-[2-({[(4-chlorophenyl)sulfonyl]-2,5-difluoroanilino}methyl)phenoxy]propyl}-3,5-difluoro-N-methylbenzamide |
| 1001 | + | N-[2-(allyloxy)benzyl]-4-chloro-N-phenyl-benzenesulfonamide |
| 1002 | + | 3,5-dichloro-N-{3-[2-({[(4-chlorophenyl)-sulfonyl]-2,5-difluoroanilino}methyl)phenoxy]-propyl}-N-methylbenzamide |
| 1003 | + | 4-chloro-N-cyclopropyl-N-{2-[3-(1-piperidinyl)propoxy]benzyl}benzenesulfonamide hydrochloride |
| 1004 | + | 2-({[(4-chlorophenyl)sulfonyl]anilino}-methyl)phenyl trifluoromethanesulfonate |
| 1005 | + | N-phenyl-N-{2-[4-(1-piperidinyl)butyl]-benzyl}benzenesulfonamide |
| 1006 | + | (2S)-2-({[(4-chlorophenyl)sulfonyl]-2,5-difluoroanilino}-2-phenylethyl nicotinate |
| 1007 | + | 3-((4R)-4-{[(4-chlorophenyl)sulfonyl]-2,5-difluoroanilino}-7-fluoro-1,2,3,4-tetrahydro-1-naphthalenyl)propanoic acid |
| 1008 | + | 4-chloro-N-(2,5-difluorophenyl)-N-((1R)-1-{4-fluoro-2-[3-(1,4,5,6-tetrahydro-2-pyrimidinyl)-propyl]phenyl}ethyl)benzenesulfonamide hydrochloride |
| 1009 | + | [2-((1R)-1-{[(4-chlorophenyl)sulfonyl]-2,5-difluoroanilino}ethyl)-5-fluorophenyl]methanesulfonic acid |
| 1010 | + | N-{3-[2-({[(4-chlorophenyl)sulfonyl]-2,5-difluoroanilino}methyl)phenoxy]propyl}-4-ethoxy-N-methylbenzamide |
| 1011 | + | 4-chloro-N-{5-chloro-2-[3-(4-hydroxy-1-piperidinyl)propoxy]benzyl}-N-phenylbenzenesulfonamide hydrochloride |
| 1012 | + | 4-chloro-N-(2,3-dihydro-1H-inden-1-yl)-N-{2-[3-(1-piperidinyl)propoxy]benzyl}benzenesulfonamide hydrochloride |
| 1013 | + | (2R)-2-{[(4-chlorophenyl)sulfonyl]-2,5-difluoroanilino}propanoic acid |
| 1014 | + | S-{3-[2-({[(4-chlorophenyl)sulfonyl]-2,5-difluoroanilino}methyl)phenoxy]propyl} ethanethioate |
| 1015 | + | 4-chloro-N-[2-(2-hydroxyphenyl)ethyl]-N-phenylbenzenesulfonamide |
| 1016 | + | 4-chloro-N-[2-(4-hydroxybutyl)benzyl]-N-phenylbenzenesulfonamide |
| 1017 | + | 4-chloro-N-[2-(4-hydroxybutyl)benzyl]-N- |

| NUMBER | ACTIVITY | COMPOUND |
|---|---|---|
| 1018 | + | 4-chloro-N-phenyl-N-[2-(3-sulfanylpropoxy)-benzyl]benzenesulfonamide |
| 1019 | + | 4-chloro-N-[4-(methylsulfanyl)phenyl]-N-{2-[3-(1-piperidinyl)propoxy]benzyl}benzene-sulfonamide hydrochloride |
| 1020 | + | 4-chloro-N-(2,3-dihydro-1H-inden-2-yl)-N-{2-[3-(1-piperidinyl)propoxy]benzyl}benzene-sulfonamide hydrochloride |
| 1021 | + | tert-butyl 2-{2-[3-(1-piperidinyl)propoxy]-phenyl}-1H-indole-1-carboxylate trifluoro-acetate |
| 1022 | + | N-{5-[(2,5-dichloro{2-[3-(1-piperidinyl)-propoxy]benzyl}anilino)sulfonyl]-4-methyl-1,3-thiazol-2-yl}acetamide hydrochloride |
| 1023 | + | N-{5-[(2,5-dichloro{2-[3-(1-piperidinyl)-propoxy]benzyl}anilino)sulfonyl]-4-methyl-1,3-thiazol-2-yl}acetamide hydrochloride |
| 1024 | + | 2-{2-[3-(1-piperidinyl)propoxy]benzyl}-2H-naphtho[1,8-cd]isothiazol 1,1-dioxide hydro-chloride |
| 1025 | + | 4-chloro-N-(2,5-difluorophenyl)-N-(2-{2-[3-(1-piperidinyl)propoxy]-1-naphthyl}methyl)-benzenesulfonamide hydrochloride |
| 1026 | + | 4-chloro-N-{2-[(5-chloropentyl)oxy]benzyl}-N-phenylbenzenesulfonamide |
| 1027 | + | 4-chloro-N-[2-(methylsulfonyl)phenyl]-N-{2-[3-(1-piperidinyl)propoxy]benzyl}benzene-sulfonamide hydrochloride |
| 1028 | + | tert-butyl 4-{3-[2-({[(4-chlorophenyl)sulfonyl]-anilino}methyl)phenoxy]propyl}-1-piperazine-carboxylate hydrochloride |
| 1029 | + | 4-chloro-N-(2,5-difluorophenyl)-N-(2-{3-[(4-methoxyphenyl)sulfanyl]propoxy}benzyl)-benzenesulfonamide |
| 1030 | + | 4-chloro-N-phenyl-N-[2-(4-pyrdinylmethoxy)-benzyl]benzenesulfonamide hydrochloride |
| 1031 | + | N-phenyl-N-{2-[3-(1-piperidinyl)propyl]-benzyl}benzenesulfonamide |
| 1032 | + | 2-{1-[(4-flurophenyl)sulfonyl]-1H-indol-2-yl}-phenyl 3-(1-piperidinyl)propyl ether trifluoro-acetate |
| 1033 | + | 4-chloro-N-(2,5-difluorophenyl)-N-[2-(2-{1-[4-(trifluoromethoxy)benzoyl]-2-piperidinyl}-ethoxy)benzyl]benzenesulfonamide |
| 1034 | + | (2E)-3-[2-({[(4-chlorophenyl)sulfonyl]anilino}-methyl)phenyl]-N-methoxy-N-methyl-2-propenamide |
| 1035 | + | (2E)-3-[2-({[(4-chlorophenyl)sulfonyl]anilino}-methyl)phenyl]-2-propenoic acid |
| 1036 | + | 4-chloro-N-[3-(methylsulfonyl)phenyl]-N-{2-[3-(1-piperidinyl)propoxy]benzyl}benzene-sulfonamide hydrochloride |
| 1037 | + | 1-{3-[2-({[(4-chlorophenyl)sulfonyl]-2,5-difluoroanilino}methyl)phenoxy]propyl}-1-methylpiperidinium iodide |
| 1038 | + | 1-{3-[2-((2,5-dichloro[(4-chlorophenyl)-sulfonyl]anilino}methyl)phenoxy]propyl}-1-methylpiperidinium iodide |
| 1039 | + | N-[2-(3-bromopropoxy)benzyl]-4-chloro-N-phenylbenzenesulfonamide |
| 1040 | + | 4-chloro-N-[2-(4-hydroxy-1-butynyl)benzyl]-N-phenylbenzenesulfonamide |
| 1041 | + | N-{2-[3-oxo-3-(1-piperidinyl)propyl]benzyl}-N-phenylbenzenesulfonamide |
| 1042 | + | N-hydroxy-3-(2-{[(phenylsulfonyl)anilino]-methyl}phenyl)propanamide |
| 1043 | + | 3-chloro-1-[(4-chlorophenyl)sulfonyl]-2-{2-[3-(1-piperidinyl)propoxy]phenyl}-1H-indole trifluoroacetate |
| 1044 | + | 4-chloro-N-(2,5-difluorophenyl)-N-{2-[3-(1-piperidinyl)propyl]benzyl}-N-phenylbenzenesulfonamide |
| 1045 | + | N-{(1R)-1-[2-(3-bromopropoxy)phenyl]ethyl}-4-chloro-N-(2,5-difluorophenyl)benzene-sulfonamide |
| 1046 | + | 4-chloro-N-(2,5-difluorophenyl)-N-(1-{2-[3-(1H-imidazol-1-yl)propoxy]phenyl}ethyl)-benzenesulfonamide hydrochloride |
| 1047 | + | 4-chloro-N-(2,5-difluorophenyl)-N-(1-{2-[3-(1H-imidazol-1-yl)propoxy]phenyl}ethyl)-benzenesulfonamide |
| 1048 | + | 4-chloro-N-(2,5-difluorophenyl)-N-((1S)-1-{2-[3-(1H-imidazol-1-yl)propoxy]phenyl}ethyl)-benzenesulfonamide hydrochloride |
| 1049 | + | (2R, 3R)-2,4-bis[(4-methylbenzoyl)oxy]-butanedioic acid compound with 4-chloro-N-(2,5-difluorophenyl)-N-((1R)-1-{2-[3-(1H-imidazol-1- |
| 1050 | + | 4-chloro-N-{2-[2-(cyclohexylsulfinyl)ethoxy]-benzy}-N-(2,5-difluorophenyl)benzene-sulfonamide |
| 1051 | + | 4-chloro-N-(2,5-difluorophenyl)-N-{2-[3-(1H-imidazol-1-yl)-1-propynyl]benzyl}benzene-sulfonamide hydrochloride |
| 1052 | + | 4-chloro-N-(2,5-difluorophenyl)-N-[1-(2-hydroxyphenyl)ethyl]benzenesulfonamide |
| 1053 | + | 4-benzoyl-N-((1S)-1-{{(3-[2-({[(4-chloro-phenyl)sulfonyl]-2,5-difluoroanilino}methyl)-phenoxy]propyl}(methyl)amino]carbonyl}-5-{[5-(2-oxohexahydro- |
| 1054 | + | 4-chloro-N-(2,5-difluorophenyl)-N-(2-hydroxy-benzyl)benzenesulfonamide |
| 1055 | + | 4-chloro-N-(2,5-difluorophenyl)-N-{(1R)-1-[2-(2-hydroxyethyl)phenyl]ethyl}benzene-sulfonamide |
| 1056 | + | 4-chloro-N-(2,5-difluorophenyl)-N-((1R)-1-{2-[3-(1H-imidazol-1-yl)propoxy]phenyl}ethyl)-benzenesulfonamide hydrochloride |
| 1057 | + | (2R)-2-{[(4-chlorophenyl)sulfonyl]-2,5-difluoroanilino}propyl isonicotinate |
| 1058 | + | (2R)-2-{[(4-chlorophenyl)sulfonyl]-2,5-difluoroanilino}propyl nicotinate |
| 1059 | + | N-{3-[2-((1R)-1-{[(4-chlorophenyl)sulfonyl]-2,5-difluoroanilino}ethyl)phenoxy]propyl}-N,2,2-trimethylpropanamide |
| 1060 | + | ethyl (2R)-2-{[(4-chlorophenyl)sulfonyl]-2,5-difluoroanilino}propanoate |
| 1061 | + | 4-chloro-N-(2,5-difluorophenyl)-N-((1R)-1-{2-[3-(1-piperidinyl)propoxy]phenyl}ethyl)-benzenesulfonamide hydrochloride |
| 1062 | + | 4-chloro-N-[5-chloro-2-(hydroxymethyl)-phenyl]-N-((1R)-1-{2-[3-(1-piperidinyl)-propoxy]phenyl}ethyl)benzenesulfonamide hydrochloride |
| 1063 | + | 4-chloro-N-(2,5-difluorophenyl)-N-((1R)-1-[4-fluoro-2-(3-hydroxypropyl)phenyl]ethyl}-benzenesulfonamide |
| 1064 | + | 2-[2-(1-{[(4-chlorophenyl)sulfonyl]-2,5-difluoroanilino}ethyl)phenoxy]-N-methyl-acetamide |
| 1065 | + | methyl 3-[2-((1R)-1-{[(4-chlorophenyl)-sulfonyl]-2,5-difluoroanilino}ethyl)-5-fluoro-phenyl]propanoate |
| 1066 | + | 4-chloro-N-(2,5-difluorophenyl)-N-((1R)-1-{2-[3-(1H-1,2,4-triazol-1-yl)propyl]phenyl}-ethyl)benzenesulfonamide |
| 1067 | + | 4-[2-((1R)-1-{[(4-chlorophenyl)sulfonyl]-2,5-difluoroanilino}ethyl)-5-fluorophenyl]butanoic acid |
| 1068 | + | 4-[2-((1R)-1-{[(4-chlorophenyl)sulfonyl]-2,5-difluoroanilino}ethyl)-5-fluorophenyl]butanoic acid |
| 1069 | + | 4-[2-((1R)-1-{[(4-chlorophenyl)sulfonyl]-2,5-difluoroanilino}ethyl)-5-fluorophenyl]butanoic acid |
| 1070 | + | 5-[2-((1R)-1-{[(4-chlorophenyl)sulfonyl]-2,5-difluoroanilino}ethyl)-5-fluorophenyl]butanoic acid |
| 1071 | + | 4-chloro-N-(2,5-difluorophenyl)-N-[(1R)-1-(2-{4-(1,1-dioxido-4-thiomorpholinyl)sulfonyl]-butyl}-4-fluorophenyl)ethyl]benzene-sulfonamide |
| 1072 | + | 4-[2-((1R)-1-{[(4-chlorophenyl)sulfonyl]-2,5- |

-continued

| NUMBER | ACTIVITY | COMPOUND |
|---|---|---|
| | | difluoroanilino}ethyl)-5-fluorophenyl]butanoic acid |
| 1073 | + | 4-[2-((1R)-1-{[(4-chlorophenyl)sulfonyl]-2,5-difluoroanilino}ethyl)-5-fluorophenyl]butanoic acid |
| 1074 | + | 4-chloro-N-(2,5-difluorophenyl)-N-[(1R)-1-(4-[(methylsulfonyl)amino]butyl}phenyl)ethyl]-benzenesulfonamide |
| 1075 | + | 4-chloro-N-(2,5-difluorophenyl)-N-[(1R)-1-(4-[(ethylsulfonyl)amino]butyl}-4-fluorophenyl)-ethyl]benzenesulfonamide |
| 1076 | + | 4-[2-((1S)-1-{[(4-chlorophenyl)sulfonyl]-2,5-difluoroanilino}ethyl)-5-fluorophenyl]butanoic acid |
| 1077 | + | [({4-[2-((1R)-1-{[(4-chlorophenyl)sulfonyl]-2,5-difluoroanilino}ethyl)-5-fluorophenyl]-butanoyl}amino)oxy]acetic acid |
| 1078 | + | 4-chloro-N-(2,5-difluorophenyl)-N-((1R)-1-{2-[4-(2,2-dimethylhydrazino)-4-oxobutyl]-4-fluorophenyl}ethyl)benzenesulfonamide |
| 1079 | + | 4-[2-((1R)-1-{[(4-chlorophenyl)sulfonyl]-2,5-difluoroanilino}ethyl)-5-fluorophenyl]-N-(cyanomethoxy)butanamide |
| 1080 | + | 4-[2-((1R)-1-{[(4-chlorophenyl)sulfonyl]-2,5-difluoroanilino}ethyl)-5-fluorophenyl]butanoic acid |
| 1081 | − | 4-chloro-N-(2-hydroxybenzyl)-N-phenyl-benzenesulfonamide |
| 1082 | − | N-{2-[3-(dimethylamino)propoxy]benzyl}-N-phenylmethanesulfonamide |
| 1083 | − | N-{2-[3-(dimethylamino)propoxy]benzyl}-4-nitro-N-phenylbenzenesulfonamide |
| 1084 | − | N-{2-[3-(dimethylamino)propoxy]benzyl}-2-nitro-N-phenylbenzenesulfonamide |
| 1085 | − | 5-(dimethylamino)-N-{2-[3-(dimethylamino)-propoxy]benzyl}-N-phenyl-1-naphthalene-sulfonamide |
| 1086 | − | 4-chloro-N-[2-(3-hydroxy-3-methyl-1-butynyl)-benzyl]-N-phenylbenzenesulfonamide |
| 1087 | − | 4-chloro-N-phenyl-N-{2-[(trimethylsilyl)-ethynyl]benzyl}benzenesulfonamide |
| 1088 | − | N-[2-(3-hydroxypropyl)benzyl]-N-phenyl-benzenesulfonamide |
| 1089 | − | 4-chloro-N-[5-chloro-2-(4-hydroxy-1-butynyl)-benzyl]-N-phenylbenzenesulfonamide |
| 1090 | − | 4-chloro-2-({[(4-chlorophenyl)sulfonyl]-anilino}methyl)phenyl trifluoromethane-sulfonate |
| 1091 | − | 4-chloro-N-phenyl-N-[2-(3-pyridinylmethoxy)-benzyl]benzenesulfonamide hydrochloride |
| 1092 | − | 4-chloro-N-phenyl-N-[2-(2-pyridinylmethoxy)-benzyl]benzenesulfonamide hydrochloride |
| 1093 | − | (2E)-1-N-(benzyloxy)-3-[2-({[(4-chloro-phenyl)sulfonyl]anilino}methyl)phenyl]-2-propenamide hydrochloride |
| 1094 | − | 4-chloro-N-[4-(methylsulfonyl)phenyl]-N-{2-[3-(1-piperidinyl)propoxy]benzyl}benzene-sulfonamide hydrochloride |
| 1095 | − | N-(2,5-difluorophenyl)-4-(phenylsulfanyl)-N-{2-[3-(phenylsulfanyl)propoxy]benzyl}-benzenesulfonamide |
| 1096 | − | ethyl 4-[2-({[(2-ntrophenyl)sulfonyl]anilino}-methyl)phenyl]butanoate |
| 1097 | − | 4-[2-({[(2-nitrophenyl)sulfonyl]anilino}-methyl)phenyl]butanoic acid |
| 1098 | − | N-{2-[2-(1-{[4-chlorophenyl)sulfonyl]-2,5-difluoroanilino}ethyl)phenoxy]ethyl}-N-methyloctadecanamide |
| 1099 | +++++ | 4-chloro-N-(2,5-dichlorophenyl)-N-[4-nitro-1(R)-methylbutyl]benzenesulfonamide |
| 1100 | +++++ | 4-chloro-N-(5-chloro-2-fluorophenyl)-N-[(methylsulfonyl)amino]-1(R)-methylbutyl]-benzenesulfonamide |
| 1101 | +++++ | 4-chloro-N-(5-chloro-2-fluorophenyl)-N-[(methylsulfonyl)methylamino]-1(R)-methyl-butyl]benzenesulfonamide |
| 1102 | +++++ | 4-chloro-N-(2,5-dichlorophenyl)-N-[3-[2-[(methylsulfonyl)methyl]-1-piperidinyl]-1(R)-methylpropyl]benzenesulfonamide |
| 1103 | +++++ | 4-chloro-N-(2,5-dichlorophenyl)-N-[4-(2-carboxy-3-thiazolidinyl)-1(R)-methylbutyl]-benzenesulfonamide |
| 1104 | +++++ | 4-chloro-N-(2,5-dichlorophenyl)-N-[5-(1,1-dioxido-4-thiomorpholinyl)-1(R)-methyl-propyl]benzenesulfonamide |
| 1105 | +++++ | 4-chloro-N-(2,5-dichlorophenyl)-N-[4-(2-methoxycarbonyl-3-thiazolidinyl)-1(R)-methyl-butyl]benzenesulfonamide |
| 1106 | +++++ | 4-chloro-N-(2,5-dichlorophenyl)-N-[4-(2-carboxy-3-thiazolidinyl)-1(R)-methylpentyl]-benzenesulfonamide |
| 1107 | +++++ | 4-chloro-N-(5-chloro-2-fluorophenyl)-N-[4-nitro-1(R)-methylbutyl]benzenesulfonamide |
| 1108 | +++++ | 4-chloro-N-(2,5-dichlorophenyl)-N-[4-[(3-methylsulfonyl)-1-piperidinyl]-1(R)-methyl-butyl]benzenesulfonamide |
| 1109 | +++++ | 4-chloro-N-(2,5-dichlorophenyl)-N-[4-[(3-methylsulfonyl)-1-piperidinyl]-1(R)-methyl-butyl]benzenesulfonamide |
| 1110 | +++++ | 4-chloro-N-(2,5-dichlorophenyl)-N-[4-nitro-1(R)-methylbutyl]benzenesulfonamide |
| 1111 | ++++ | 4-chloro-N-(2,5-dichlorophenyl)-N-[3-(2-carboxy-3-thiazolidinyl)-1(R)-methylpropyl]-benzenesulfonamide |
| 1112 | ++++ | 4-chloro-N-(2,5-dichlorophenyl)-N-[5-[(3-methylsulfonyl)-1-pyrrolidinyl]-1(R)-methyl-pentyl]benzenesulfonamide |
| 1113 | ++++ | 4-chloro-N-(2,5-dichlorophenyl)-N-[4-(acetyl-amino)-1(R)-methylbutyl]benzenesulfonamide |
| 1114 | ++++ | 4-chloro-N-(5-chloro-2-fluorophenyl)-N-[4-(4-morpholinyl)-1-methylbutyl]benzene-sulfonamide |
| 1115 | ++++ | 4-chloro-N-(2,5-dichlorophenyl)-N-[5-[(3-methylsulfonyl)-1-piperidinyl]-1(R)-methyl-pentyl]benzenesulfonamide |
| 1116 | ++++ | 4-chloro-N-(2,5-dichlorophenyl)-N-[5-[[2-[(methylsulfonyl)-1-piperidinyl]-1(R)-methyl-pentyl]benzenesulfonamide |
| 1117 | ++++ | 4-chloro-N-(2,5-dichlorophenyl)-N-[5-(2-methoxycarbonyl-3-thiazolidinyl)-1(R)-methyl-pentyl]benzenesulfonamide |
| 1118 | ++++ | 4-chloro-N-(2,5-dichlorophenyl)-N-[3-[(3-methylsulfonyl)-1-piperidinyl]-1(R)-methyl-propyl]benzenesulfonamide |
| 1119 | ++++ | 4-chloro-N-(2,5-dichlorophenyl)-N-[3-(2-methoxycarbonyl-3-thiazolidinyl)-1(R)-methyl-propyl]benzenesulfonamide |
| 1120 | ++++ | 4-chloro-N-(2,5-difluorophenyl)-N-[4-(2-isopropoxy-3,4-dioxo-1-cyclobutenyl)amine-1(R)-methylbutyl]benzenesulfonamide |
| 1121 | +++ | 4-chloro-N-(2,5-dichlorophenyl)-N-[4-[2-[(methylsulfonyl)methyl]-1-piperidinyl]-1(R)-methylbutyl]benzenesulfonamide |
| 1122 | +++ | 4-chloro-N-(5-chloro-2-fluorophenyl)-N-[4-(2-isopropoxy-3,4-dioxo-1-cyclobutenyl)amine-1(R)-methylbutyl]benzenesulfonamide |
| 1123 | +++ | 4-chloro-N-(2,5-dichlorophenyl)-N-[5-[(4-methylsulfonyl)-1-piperidinyl]-1(R)-methyl-pentyl]benzenesulfonamide |
| 1124 | +++ | 4-chloro-N-(2,5-dichlorophenyl)-N-[4-[[[(S)hydroxy]phenylmethyl]carbonyl]-amino]-1(R)-methylbutyl]benzenesulfonamide |
| 1125 | +++ | 4-chloro-N-(2,5-difluorophenyl)-N-[3-(2-isopropoxy-3,4-dioxo-1-cyclobutenyl)amine-1(R)-methylpropyl]benzenesulfonamide |
| 1126 | +++ | 4-chloro-N-(2,5-dichlorophenyl)-N-[4-(4-methylsulfonyl)-1-piperidinyl]-1(R)-methyl-butyl]benzenesulfonamide |
| 1127 | +++ | 4-chloro-N-(5-chloro-2-fluorophenyl)-N-[3-(2-isopropoxy-3,4-dioxo-1-cyclobutenyl)amine-1(R)-methylpropyl]benzenesulfonamide |
| 1128 | +++ | 4-chloro-N-(2,5-dichlorophenyl)-N-[4-(2-isopropoxy-3,4-dioxo-1-cyclobutenyl)amine-1(R)-methylbutyl]benzenesulfonamide |

-continued

| NUMBER | ACTIVITY | COMPOUND |
|---|---|---|
| 1129 | +++ | 4-chloro-N-(2,5-dichlorophenyl)-N-[4-[[[(R)hydroxy]phenylmethyl]carbonyl]amino]-1(R)-methylbutyl]benzenesulfonamide |
| 1130 | +++ | 4-chloro-N-(5-chloro-2-fluorophenyl)-N-[3-[2-[4-chloro-N-(5-chloro-2-fluorophenyl)-N-[(3-amino)-1(R)-methylpropyl]benzene-sulfonamide]-3,4-dioxo-1-cyclobutenyl)amine-1(R)- |
| 1131 | +++ | 4-chloro-N-(2,5-dichlorophenyl)-N-[4-[[(methoxy)carbonyl]amino]-1-methylbutyl]-benzenesulfonamide |
| 1132 | +++ | 4-chloro-N-(2,5-dichlorophenyl)-N-[3-[(3-methylsulfonyl)-1-piperidinyl]-1(R)-methyl-propyl]benzenesulfonamide |
| 1133 | +++ | 4-chloro-N-(2,5-dichlorophenyl)-N-[3-(2-methoxycarbonyl-3-thiazolidinyl)-1(R)-methyl-propyl]benzenesulfonamide |
| 1134 | ++ | 4-chloro-N-(2,5-dichlorophenyl)-N-[4-[(3-methylthio)-1-pyrrolidinyl]-1(R)-methylbutyl]-benzenesulfonamide |
| 1135 | ++ | 4-chloro-N-(2,5-dichlorophenyl)-N-[4-[[N-(cyclopropylmethyl)-N-[3-(1H-imidazol-1-yl)-propyl]amino]-1(R)-methylbutyl]benzene-sulfonamide |
| 1136 | ++ | 4-chloro-N-(2,5-dichlorophenyl)-N-[4-[3-[(methylsulfonyl)-1-piperidinyl]-1(R)-methyl-butyl]benzenesulfonamide |
| 1137 | ++ | 4-chloro-N-(2,5-dichlorophenyl)-N-[4-[[(1,1-dimethylethyl)carbonyl]amino]-1-methylbutyl]-benzenesulfonamide |
| 1138 | ++ | 4-chloro-N-(2,5-dichlorophenyl)-N-[4-(azido)-1-methylbutyl]benzenesulfonamide |
| 1139 | ++ | 4-chloro-N-(2,5-difluorophenyl)-N-[3-[2-[4-chloro-N-(2,5-difluorophenyl)-N-[(3-amino)-1(R)-methylpropyl]benzenesulfonamide]-3,4-dioxo-1-cyclobutenyl)amine-1(R)- |
| 1140 | ++ | 4-chloro-N-(2,5-dichlorophenyl)-N-[4-[3-[(methylsulfonyl)-1-piperidinyl]-1(R)-methyl-pentyl]benzenesulfonamide |
| 1141 | ++ | 4-chloro-N-(2,5-difluorophenyl)-N-[3-(2-isopropoxy-3,4-dioxo-1-cyclobutenyl)amine-1(R)-methylpropyl]benzenesulfonamide |
| 1142 | ++ | 4-chloro-N-(2,5-dichlorophenyl)-N-[3-[(3-methylthio)-1-piperidinyl]-1(R)-methyl-propyl]benzenesulfonamide |
| 1143 | ++ | 4-chloro-N-(2,5-dichlorophenyl)-N-[3-[2-[4-chloro-N-(2,5-dichlorophenyl)-N-[(3-amino)-1(R)-methylpropyl]benzenesulfonamide]-3,4-dioxo-1-cyclobutenyl)amine-1(R)- |
| 1144 | ++ | 4-chloro-N-(2,5-dichlorophenyl)-N-[4-[(4-methylthio)-1-pyrrolidinyl]-1(R)-methylbutyl]-benzenesulfonamide |
| 1145 | ++ | 4-chloro-N-(2,5-dichlorophenyl)-N-[4-[[(1,1-dimethylethoxy)carbonyl]amino]-1-methyl-butyl]benzenesulfonamide |
| 1146 | ++ | 4-chloro-N-(2,5-dichlorophenyl)-N-[3-[(4-methylsulfonyl)-1-piperidinyl]-1(R)-methyl-propyl]benzenesulfonamide |
| 1147 | ++ | 4-chloro-N-(2,5-dichlorophenyl)-N-[3-[(3-methylthio)-1-pyrrolidinyl]-1(R)-methyl-propyl]benzenesulfonamide |
| 1148 | ++ | 4-chloro-N-(2,5-dichlorophenyl)-N-[4-[3-[(methylthio)-1-pyrrolidinyl]-1(R)-methyl-butyl]benzenesulfonamide |
| 1149 | ++ | 4-chloro-N-(2,5-dichlorophenyl)-N-[4-[[(phenyl)carbonyl]amino]-1-methylbutyl]-benzenesulfonamide |
| 1150 | ++ | 4-chloro-N-(2,5-dichlorophenyl)-N-[5-[[4-(methylsulfonyl)methyl]-1-piperidinyl]-1(R)-methylpentyl]benzenesulfonamide |
| 1151 | ++ | 4-chloro-N-(2,5-dichlorophenyl)-N-[3-[(3-(methylsulfonyl)methyl]-1-piperidinyl]-1(R)-methylpropyl]benzenesulfonamide |
| 1152 | ++ | 4-chloro-N-(2,5-dichlorophenyl)-N-(4-amino)-1-methylbutyl]benzenesulfonamide |
| 1153 | ++ | 4-chloro-N-(2,5-dichlorophenyl)-N-[4-[(3-methylthio)-1-piperidinyl]-1(R)-methylbutyl]-benzenesulfonamide |
| 1154 | ++ | 4-chloro-N-(2,5-dichlorophenyl)-N-[4-[[(phenoxy)carbonyl]amino]-1-methylbutyl]-benzenesulfonamide |
| 1155 | ++ | 4-chloro-N-(2,5-dichlorophenyl)-N-[4-[[(benzoxy)carbonyl]amino]-1-methylbutyl]-benzenesulfonamide |
| 1156 | ++ | 4-chloro-N-(2,5-dichlorophenyl)-N-[3-[(4-methylthio)-1-piperidinyl]-1(R)-methylpropyl]-benzenesulfonamide |
| 1157 | ++ | 4-chloro-N-(2,5-dichlorophenyl)-N-[4-[[4-(methylsulfonyl)methyl]-1-piperidinyl]-1(R)-methylbutyl)benzenesulfonamide |
| 1158 | + | 4-chloro-N-(2,5-dichlorophenyl)-N-[4-[N-(2,5-dichlorophenyl)-N-[(4-chlorophenyl)sulfonyl]-amino]-1(R)-methylbutyl]benzenesulfonamide |
| 1159 | + | 4-chloro-N-(2,5-dichlorophenyl)-N-[3-[[3-(methylthio)-1-piperidinyl]-1(R)-methyl-propyl]benzenesulfonamide |
| 1160 | +++++ | 4-chloro-N-(5-chloro-2-fluorophenyl)-N-[1(R)-methyl-(4-ethylsulfinyl)butyl]benzene-sulfonamide |
| 1161 | +++++ | 4-chloro-N-[2,5-dichlorophenyl]-N-[1(R)-methyl-(4-[(1-methylethyl)sulfonyl]butyl]-benzenesulfonamide |
| 1162 | +++++ | 4-chloro-N-[2,5-dichlorophenyl]-N-[1(R)-methyl-(4-methylsulfonyl)butyl]benzene-sulfonamide |
| 1163 | +++++ | 4-chloro-N-[5-chloro-2-fluorophenyl]-N-[1(R)-methyl-(4-ethylsulfonyl)butyl]benzene-sulfonamide |
| 1164 | +++++ | 4-chloro-N-[2,5-dichlorophenyl]-N-[1(R)-methyl-(4-ethylsulfonyl)butyl]benzene-sulfonamide |
| 1165 | +++++ | 4-chloro-N-[5-chloro-2-fluorophenyl]-N-[1(R)-methyl-(4-methylsulfonyl)butyl]benzene-sulfonamide |
| 1166 | +++++ | 4-chloro-N-[2,5-difluorophenyl]-N-[1(R)-methyl-(4-methylsulfonyl)butyl]benzene-sulfonamide |
| 1167 | +++++ | 4-chloro-N-[5-chloro-2-fluorophenyl]-N-[1(R)-methyl-(4-methylsulfinyl)butyl]benzene-sulfonamide |
| 1168 | +++++ | 4-chloro-N-[2,5-dichlorophenyl]-N-[1(R)-methyl-(5-ethylsulfonyl)butyl]benzene-sulfonamide |
| 1169 | +++++ | 4-chloro-N-[2,5-dichlorophenyl]-N-[1(R)-methyl-(4-[(1-methylethyl)sulfinyl]butyl]-benzenesulfonamide |
| 1170 | +++++ | 4-chloro-N-[2,5-difluorophenyl]-N-[1(R)-methyl-(4-methylsulfonyl)butyl]benzene-sulfonamide |
| 1171 | +++++ | 4-chloro-N-[2,5-dichlorophenyl]-N-[1(R)-methyl-(4-methylsulfinyl)butyl]benzene-sulfonamide |
| 1172 | +++++ | 4-chloro-N-[2,5-dichlorophenyl]-N-[1(R)-methyl-(4-ethylsulfinyl)butyl]benzene-sulfonamide |
| 1173 | +++++ | 4-chloro-N-[2,5-dichlorophenyl]-N-[1(R)-methyl-(5-ethylsulfinyl)pentyl]benzene-sulfonamide |
| 1174 | +++++ | 4-chloro-N-[2,5-difluorophenyl]-N-[1(R)-methyl-(4-ethylsulfinyl)butyl]benzene-sulfonamide |
| 1175 | +++++ | 4-chloro-N-[2,5-difluorophenyl]-N-[1(R)-methyl-(4-methylsulfinyl)butyl]benzene-sulfonamide |
| 1176 | +++++ | 4-chloro-N-[2,5-dichlorophenyl]-N-[1(R)-methyl-(4-methylthio)butyl]benzene-sulfonamide |
| 1177 | +++++ | 4-chloro-N-[2,5-difluorophenyl]-N-[1(R)-methyl-(4-ethylthio)butyl]benzenesulfonamide |
| 1178 | +++++ | 4-chloro-N-[5-chloro-2-fluorophenyl]-N-[1(R)-methyl-(4-methylthio)butyl]benzene-sulfonamide |
| 1179 | +++++ | 4-chloro-N-[2,5-difluorophenyl]-N-[1(R)-methyl-(4-[(1-methylethyl)sulfinyl]butyl]- |

| NUMBER | ACTIVITY | COMPOUND |
|---|---|---|
| | | benzenesulfonamide |
| 1180 | +++++ | 4-chloro-N-[2,5-dichlorophenyl]-N-[1(R)-methyl-(3-ethylsulfonyl)propyl]benzene-sulfonamide |
| 1181 | +++++ | (6R)-6-[(2,5-dichlorophenyl)-[(4-chlorophenyl)sulfonyl]-amino]-3-thioheptanoic acid |
| 1182 | +++++ | 4-chloro-N-[2,5-dichlorophenyl]-N-[1(R)-methyl-(4-[(2-methylpropyl)sulfinyl]butyl]-benzenesulfonamide |
| 1183 | +++++ | 4-chloro-N-[2,5-dichlorophenyl]-N-[1(R)-methyl-(4-ethylthio)butyl]benzenesulfonamide |
| 1184 | ++++ | 4-chloro-N-[2,5-dichlorophenyl]-N-[1(R)-methyl-(4-[(2-methylpropyl)sulfonyl]butyl]-benzenesulfonamide |
| 1185 | ++++ | methyl(6R)-6-[(2,5-dichlorophenyl)-[(4-chlorophenyl)sulfonyl]-amino]-3-thioheptanoic |
| 1186 | ++++ | (5R)-5-[(2,5-dichlorophenyl)-[(4-chlorophenyl)sulfonyl]-amino]-3-thioheptanoic acid |
| 1187 | +++ | methyl(6R)-6-[(2,5-dichlorophenyl)-[(4-chlorophenyl)sulfonyl]-amino]-3-thioheptanoic acid, 3-oxide |
| 1188 | ++ | 4-chloro-N-[2,5-dichlorophenyl]-N-[1(R)-methyl-(4-[(2-methylpropyl)thio)sulfonyl]-butyl]benzenesulfonamide |
| 1189 | ++ | 4-chloro-N-[2,5-dichlorophenyl]-N-[1(R)-methyl-(3-ethylthio)propyl]benzenesulfonamide |
| 1190 | ++ | 4-chloro-N-[2,5-dichlorophenyl]-N-[1(R)-methyl-(4[(1-methylethyl)thio]butyl]benzene-sulfonamide |
| 1191 | ++ | methyl(6R)-6-[(2,5-dichlorophenyl)-[(4-chlorophenyl)sulfonyl]-amino]-3-thioheptanoic acid, 3,3-dioxide |
| 1192 | ++ | (4R)-4-[N-[5-chloro-2-fluorophenyl][(4-chlorophenyl)sulfonyl]amino]pentylsulfonic acid |
| 1193 | ++ | methyl(6R)-6-[(2,5-dichlorophenyl)-[(4-chlorophenyl)sulfonyl]-amino]-3-thioheptanoic acid, 3-oxide |
| 1194 | ++ | (4R)-4-[N-[2,5-dichlorophenyl][(4-chlorophenyl)sulfonyl]amino]pentylsulfonic acid |
| 1195 | + | methyl(4R)-4-[N-[2,5-dichlorophenyl][(4-chlorophenyl)sulfonyl]amino]pentylsulfonate |
| 1196 | + | (6R)-6-[(2,5-dichlorophenyl)-[(4-chlorophenyl)sulfonyl]-amino]-3-thioheptanoic acid, 3-oxide |
| 1197 | + | (6R)-6-[(2,5-dichlorophenyl)-[(4-chlorophenyl)sulfonyl]-amino]-3-thioheptanoic acid, 3,3-dioxide |
| 1198 | +++++ | 4-chloro-N-[2,5-dichlorophenyl]-N-[4-[(1-azetidinyl)sulfonyl]-1(R)-methylbutyl]-benzenesulfonamide |
| 1199 | +++++ | 4-chloro-N-[2,5-dichlorophenyl]-N-[4-[(methylamino)sulfonyl]-1(R)-methylbutyl]-benzenesulfonamide |
| 1200 | +++++ | 4-chloro-N-[2,5-difluorophenyl]-N-[4-[(1-azetidinyl)sulfonyl]-1(R)-methylbutyl]-benzenesulfonamide |
| 1201 | +++++ | 4-chloro-N-[2,5-dichlorophenyl]-N-[4-[(dimethylamino)sulfonyl]-1(R)-methylbutyl]-benzenesulfonamide |
| 1202 | +++++ | 4-chloro-N-(5-chloro-2-fluorophenyl)-N-[4-[(dimethylamino)sulfonyl]-1(R)-methylbutyl]-benzenesulfonamide |
| 1203 | +++++ | 4-chloro-N-(5-chloro-2-fluorophenyl)-N-[4-[(methylamino)sulfonyl]-1(R)-methylbutyl]-benzenesulfonamide |
| 1204 | +++++ | 4-chloro-N-[2,5-dichlorophenyl]-N-[4-[(1-pyrrolidinyl)sulfonyl]-1(R)-methylbutyl]-benzenesulfonamide |
| 1205 | +++++ | 4-chloro-N-(5-chloro-2-fluorophenyl)-N-[4-[(1-pyrrolidinyl)sulfonyl]-1(R)-methylbutyl]-benzenesulfonamide |
| 1206 | +++++ | 4-chloro-N-[2,5-difluorophenyl]-N-[4-[(dimethylamino)sulfonyl]-1(R)-methylbutyl]-benzenesulfonamide |
| 1207 | +++++ | 4-chloro-N-[2,5-difluorophenyl]-N-[4-[(methylamino)sulfonyl]-1(R)-methylbutyl]-benzenesulfonamide |
| 1208 | +++++ | 4-chloro-N-[2,5-dichlorophenyl]-N-[4-[(ethylamino)sulfonyl]-1(R)-methylbutyl]-benzenesulfonamide |
| 1209 | +++++ | 4-chloro-N-[2,5-dichlorophenyl]-N-[4-[(4-morpholinyl)sulfonyl]-1(R)-methylbutyl]-benzenesulfonamide |
| 1210 | +++++ | N-[4-(aminosulfonyl)-1(R)-methylbutyl]-4-chloro-N-(2,5-dichlorophenyl)benzene-sulfonamide |
| 1211 | +++++ | 4-chloro-N-[2,5-dichlorophenyl]-N-[4-[(4-thiomorpholinyl)sulfonyl]-1(R)-methyl-butyl]benzenesulfonamide |
| 1212 | +++++ | 4-chloro-N-[2,5-dichlorophenyl]-N-[4-[[N-(1-methylethyl)methylamino]sulfonyl]-1(R)-methylbutyl]benzenesulfonamide |
| 1213 | +++++ | 4-chloro-N-[2,5-dichlorophenyl]-N-[4-[(diethylamino)sulfonyl]-1(R)-methylbutyl]-benzenesulfonamide |
| 1214 | +++++ | 4-chloro-N-[2,5-dichlorophenyl]-N-[4-[[(tetrahydro-1,1-dioxido-3-thienyl)amino]-sulfonyl]-1(R)-methylbutyl]benzene-sulfonamide |
| 1215 | ++++ | 4-chloro-N-[2,5-dichlorophenyl]-N-[4-[[(N-cyclopentyl)methylamino]sulfonyl]-1(R)-methylbutyl]benzenesulfonamide |
| 1216 | +++ | 4-chloro-N-[2,5-dichlorophenyl]-N-[4-[(2-methylpropylamino)sulfonyl]-1(R)-methylbutyl]benzenesulfonamide |
| 1217 | +++++ | 4-chloro-N-[5-chloro-2-(hydroxymethyl)-phenyl]-N-[1(R)-methyl-(4-ethylsulfonyl)-butyl]benzenesulfonamide |
| 1218 | +++++ | 4-chloro-N-[5-chloro-2-(hydroxymethyl)-phenyl]-N-[1(R)-methyl-(4-[(1,1-dimethyl-ethyl)sulfonyl]butyl]benzenesulfonamide |
| 1219 | +++++ | 4-chloro-N-[5-chloro-2-(hydroxymethyl)-phenyl]-N-[1(R)-methyl-(4-[(1-methyl-ethyl)sulfinyl]butyl]benzenesulfonamide |
| 1220 | +++++ | 4-chloro-N-[5-chloro-2-(hydroxymethyl)-phenyl]-N-[1(R)-methyl-(4-[(1-methyl-ethyl)sulfonyl]butyl]benzenesulfonamide |
| 1221 | +++++ | 4-chloro-N-[5-chloro-2-(hydroxymethyl)-phenyl]-N-[1(R)-methyl-(4-[(1,1-dimethyl-ethyl)sulfinyl]butyl]benzenesulfonamide |
| 1222 | +++++ | 4-chloro-N-[5-chloro-2-(hydroxymethyl)-phenyl]-N-[1(R)-methyl-(4-ethylsulfinyl)-butyl]benzenesulfonamide |
| 1223 | +++++ | 4-chloro-N-[5-chloro-2-(hydroxymethyl)-phenyl]-N-[1(R)-methyl-(4-[(1-methyl-ethyl)thio]butyl]benzenesulfonamide |
| 1224 | +++++ | 4-chloro-N-[5-chloro-2-(hydroxymethyl)-phenyl]-N-[1(R)-methyl-(4-methylsulfinyl)-butyl]benzenesulfonamide |
| 1225 | +++++ | 4-chloro-N-[5-chloro-2-(hydroxymethyl)-phenyl]-N-[1(R)-methyl-(4-methylsulfonyl)-butyl]benzenesulfonamide |
| 1226 | +++++ | 4-chloro-N-[5-chloro-2-(hydroxymethyl)-phenyl]-N-[1(R)-methyl-(4-phenylthio)-butyl]benzenesulfonamide |
| 1227 | +++++ | 4-chloro-N-[5-chloro-2-(hydroxymethyl)-phenyl]-N-[1(R)-methyl-(4-ethylthio)-butyl]benzenesulfonamide |
| 1228 | +++++ | 4-chloro-N-[5-chloro-2-(hydroxymethyl)-phenyl]-N-[1(R)-methyl-(4-methylthio)-butyl]benzenesulfonamide |
| 1229 | +++++ | 4-chloro-N-[5-chloro-2-(hydroxymethyl)-phenyl]-N-[1(R)-methyl-(4-[(1,1-dimethyl-ethyl)thio]butyl]benzenesulfonamide |
| 1230 | ++++ | 4-methylsulfonyl-N-[5-chloro-2-(hydroxy-methyl)phenyl]-N-1(R)-methyl-(4-methyl-sulfonyl)butyl]benzenesulfonamide |
| 1231 | ++ | (4R)-4-[N-[5-chloro-2-(hydroxymethyl)-phenyl][(4-chlorophenyl)sulfonyl]amino]pentyl-sulfonic acid |
| 1232 | + | 4-ethylthio-N-[5-chloro-2-(hydroxymethyl)-phenyl]-N-[1(R)-methyl-(4-ethylthio)butyl]-benzenesulfonamide |

| NUMBER | ACTIVITY | COMPOUND |
|---|---|---|
| 1233 | +++++ | 4-chloro-N-[5-chloro-2-(hydroxymethyl)-phenyl]-N-[4-[(methylamino)sulfonyl]-1(R)-methylbutyl]benzenesulfonamide |
| 1234 | +++++ | 4-chloro-N-[5-chloro-2-(hydroxymethyl)-phenyl]-N-[4-[(dimethylamino)sulfonyl]-1(R)-methylbutyl]benzenesulfonamide |
| 1235 | +++++ | 4-chloro-N-[5-chloro-2-(hydroxymethyl)-phenyl]-N-[4-(aminosulfonyl)-1(R)-methyl-butyl]benzenesulfonamide |
| 1236 | ++ | 4-chloro-N-[5-chloro-2-(hydroxymethyl)-phenyl]-N-[4-[N-(cyclopropylmethyl)-N-[3-(1H-imidazol-1-yl)-propyl]aminosulfonyl]-1(R)-methylbutyl]benzenesulfonamide |
| 1237 | +++++ | 4-Chloro-N-(2,5-dichlorophenyl)-N-[2-[[[pyrrolidin-1-yl]carbonyl]oxy]-R-1-methyl-ethyl]benzenesulfonamide |
| 1238 | +++++ | 4-Chloro-N-(2,5-difluorophenyl)-N-[2-[[[pyrrolidin-1-yl]carbonyl]oxy]-R-1-methyl-ethyl]benzenesulfonamide |
| 1239 | +++++ | 4-Chloro-N-(2,5-difluorophenyl)-N-[2-[[N'-[3-(1H-imidazol-1-yl)propylamino]-carbonyl]oxy]-(R)-1-methylethyl]benzene-sulfonamide |
| 1240 | +++++ | 4-Chloro-N-(2,5-dichlorophenyl)-N-[2-[[N'-[3-(1H-imidazol-1-yl)propylamino]-carbonyl]oxy]-(R)-1-methylethyl]benzene-sulfonamide |
| 1241 | +++++ | 4-Chloro-N-(2,5-dichlorophenyl)-N-[2-[[[(S)-2-(hydroxymethyl)pyrrolidin-1-yl]]-carbonyl]oxy]-(R)-1-methylethyl]benzene-sulfonamide |
| 1242 | +++++ | 4-Chloro-N-(2,5-dichlorophenyl)-N-[2-[[N'-2-(piperidin-1-yl)ethylamino]carbonyl]-oxy]-(R)-1-methylethyl]benzenesulfonamide |
| 1243 | +++++ | 4-Chloro-N-(2-fluoro-5-chlorophenyl)-N-[2-[[[pyrrolidin-1-yl]carbonyl]oxy]-(R)-1-methylethyl]benzenesulfonamide |
| 1244 | +++++ | 4-Chloro-N-(2-fluoro-5-chlorophenyl)-N-[2-[[N'-[3-(1H-imidazol-1-yl)propylamino]-carbonyl]oxy]-(R)-1-methylethyl]benzene-sulfonamide |
| 1245 | +++++ | 4-Chloro-N-(2-fluoro-5-chlorophenyl)-N-[2-[[N'-[2-(1H-imidazol-4-yl)ethylamino]-carbonyl]oxy]-(R)-1-methylethyl]benzene-sulfonamide |
| 1246 | +++++ | 4-Chloro-N-[5-chloro-2-(hydroxymethyl)-phenyl]-N-[2-[[N'-[3-(1H-imidazol-1-yl)-propylamino]carbonyl]oxy]-(1R)-(2R)-dimethylethyl]benzenesulfonamide |
| 1247 | +++++ | 4-Chloro-N-(2,5-dichlorophenyl)-N-[2-[[[N'-[3-(1H-imidazol-1-yl)propyl]-N'-ethylamino]carbonyl]oxy]-(R)-1-methylethyl]-benzenesulfonamide |
| 1248 | +++++ | 4-Chloro-N-(2,5-dichlorophenyl)-N-[2-[[N'-[3-(1H-tetrazol-1-yl)propylamino]-carbonyl]oxy]-(R)-1-methylethyl]benzene-sulfonamide |
| 1249 | +++++ | 4-Chloro-N-(2,5-dichlorophenyl)-N-[2-[[N'-[2-(hydroxyethyl)-N'-methylamino]-carbonyl]oxy]-(R)-1-methylethyl]benzene-sulfonamide |
| 1250 | +++++ | 4-Chloro-N-(2,5-dichlorophenyl)-N-[2-[[[N'-[3-(1H-imidazol-1-yl)propyl]-N'-methyl-amino]carbonyl]oxy]-(R)-1-methylethyl]-benzenesulfonamide |
| 1251 | +++++ | 4-Chloro-N-[5-chloro-2-(hydroxymethyl)-phenyl]-N-[2-[[[N'-[3-(1H-imidazol-1-yl)-propyl]-N'-cyclopropylmethylamino]carbonyl]-oxy]-(R)-1-methylethyl]benzenesulfonamide |
| 1252 | +++++ | 4-Chloro-N-[5-chloro-2-(hydroxymethyl)-phenyl]-N-[2-[[[N'-[3-(1H-imidazol-1-yl)-propyl]-N'-(2-methylethyl)amino]carbonyl]-oxy]-(R)-1-methylethyl]benzenesulfonamide |
| 1253 | ++ | 4-chloro-N-(2,5-dichlorophenyl)-N-[1-(S)-[2-(methylsulfonyl)ethyl]pyrrolidin-2-yl]ethyl]-benzenesulfonamide |
| 1254 | + | 4-chloro-N-(2,5-dichlorophenyl)-N-[1-(S)-pyrrolidin-2-yl]ethyl]benzenesulfonamide |
| 1255 | + | 4-chloro-N-(2,5-dichlorophenyl)-N-[1-(S)-[1-[(1,1-dimethylethoxy)carbonyl]pyrrolidin-2-yl]-ethyl]benzenesulfonamide |
| 1256 | ++ | (R)-4-Chloro-N-(5-chloro-2-fluorophenyl)-N-[4-[N-(S)-[1-(methoxycarbonyl)-3-methyl-butyl]amino]-1-methyl-4-oxobutyl]benzene-sulfonamide |
| 1257 | +++ | (R)-4-Chloro-N-(5-chloro-2-fluorophenyl)-N-[4-[N-(S)-[1-(methoxycarbonyl)-2-methyl-propyl]amino]-1-methyl-4-oxobutyl]benzene-sulfonamide |
| 1258 | +++++ | (R)-4-Chloro-N-(5-chloro-2-fluorophenyl)-N-[6-[N-(S)-[1-(methoxycarbonyl)-3-methyl-butyl]amino]-1-methyl-6-oxohexyl]benzene-sulfonamide |
| 1259 | +++++ | (R)-4-Chloro-N-(5-chloro-2-fluorophenyl)-N-[6-[N-(S)-[1-(carboxy)-3-methylbutyl]-amino]-1-methyl-6-oxohexyl]benzene-sulfonamide |
| 1260 | +++++ | (R)-4-Chloro-N-(5-chloro-2-fluorophenyl)-N-[6-[N-(S)-[1-(methoxycarbonyl)-3-methyl-butyl]amino]-1-methyl-6-oxohexyl]benzene-sulfonamide |
| 1261 | +++++ | (R)-4-Chloro-N-(5-chloro-2-fluorophenyl)-N-[6-[N-(S)-[1-(methoxycarbonyl)-2-methyl-propyl]amino]-1-methyl-6-oxohexyl]benzene-sulfonamide |
| 1262 | +++++ | (R)-4-Chloro-N-(5-chloro-2-fluorophenyl)-N-[6-[N-(S)-[1-(carboxy)-2-methylpropyl]-amino]-1-methyl-6-oxohexyl]benzene-sulfonamide |
| 1263 | ++++ | (R)-4-Chloro-N-(5-chloro-2-fluorophenyl)-N-[6-[N-(S)-[1-(carboxy)-3-methylbutyl]-amino]-1-methyl-6-oxohexyl]benzene-sulfonamide |
| 1264 | ++ | (R)-4-Chloro-N-(5-chloro-2-fluorophenyl)-N-[5-[N-(S)-[1-(methoxycarbonyl)-2-methyl-propyl]amino]-1-methyl-6-oxopentyl]benzene-sulfonamide |
| 1265 | +++ | (R)-4-Chloro-N-(5-chloro-2-fluorophenyl)-N-[6-[N-(S)-[1-(methoxycarbonyl)-3-methyl-butyl]amino]-1-methyl-5-oxopentyl]benzene-sulfonamide |
| 1266 | +++++ | (R)-4-Chloro-N-(5-chloro-2-fluorophenyl)-N-[5-[N-(R)-[1-(methoxycarbonyl)-2-methyl-propyl]amino]-1-methyl-5-oxopentyl]benzene-sulfonamide |
| 1267 | ++++ | (R)-4-Chloro-N-(5-chloro-2-fluorophenyl)-N-[5-[N-(R)-[1-(methoxycarbonyl)-3-methyl-butyl]amino]-1-methyl-5-oxopentyl]benzene-sulfonamide |
| 1268 | ++ | (R)-4-Chloro-N-(5-chloro-2-fluorophenyl)-N-[5-[N-(S)-[1-(carboxy)-2-methylpropyl]-amino]-1-methyl-5-oxopentyl]benzene-sulfonamide |
| 1269 | ++ | (R)-4-Chloro-N-(5-chloro-2-fluorophenyl)-N-[5-[N-(S)-[1-(carboxy)-3-methylbutyl]-amino]-1-methyl-5-oxopentyl]benzene-sulfonamide |
| 1270 | ++++ | (R)-4-Chloro-N-(5-chloro-2-fluorophenyl)-N-[5-[N-(R)-[1-(carboxy)-2-methylpropyl]-amino]-1-methyl-5-oxopentyl]benzene-sulfonamide |
| 1271 | +++ | (R)-4-Chloro-N-(5-chloro-2-fluorophenyl)-N-[5-[N-(R)-[1-(carboxy)-3-methylbutyl]-amino]-1-methyl-5-oxopentyl]benzene-sulfonamide |
| 1272 | +++++ | (R)-4-Chloro-N-(5-chloro-2-fluorophenyl)-N-[1-(methyl-6-(1,1-dioxo-2-methyl-4-thio-morpholinyl)-6-oxohexyl]benzenesulfonamide |
| 1273 | +++++ | (R)-4-Chloro-N-(5-chloro-2-fluorophenyl)-N-[1-(methyl-6-(1,1-dioxo-3-methyl-4-thio-morpholinyl)-6-oxohexyl]benzenesulfonamide |

| NUMBER | ACTIVITY | COMPOUND |
|---|---|---|
| 1274 | +++++ | (R)-4-Chloro-N-(5-chloro-2-fluorophenyl)-N-[1-(methyl-6-(1,1-dioxo-2-methyl-4-thiomorpholinyl)hexyl]benzenesulfonamide |
| 1275 | +++++ | (R)-4-Chloro-N-(5-chloro-2-fluorophenyl)-N-[1-(methyl-6-(1,1-dioxo-3-methyl-4-thiomorpholinyl)hexyl]benzenesulfonamide |
| 1276 | +++++ | (R)-4-Chloro-N-(2,5-difluorophenyl)-N-[1-[4-fluoro-2-[1-(2-methyl-4-thiomorpholinyl)-butanoyl]phenyl]ethyl]benzenesulfonamide |
| 1277 | +++++ | (R)-4-Chloro-N-(2,5-difluorophenyl)-N-[1-[4-fluoro-2-[1-(1,1-dioxo-2-methyl-4-thiomorpholinyl)butanoyl]phenyl]ethyl]-benzenesulfonamide |
| 1278 | +++++ | (R)-4-Chloro-N-(2,5-difluorophenyl)-N-[1-[4-fluoro-2-[1-(1,1-dioxo-2-methyl-4-thiomorpholinyl)butyl]phenyl]ethyl]benzenesulfonamide |

| NUMBER | COMPOUND | ACTIVITY |
|---|---|---|
| 1279 | 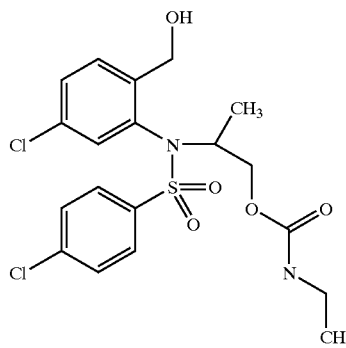 | +++++ |
| 1280 | 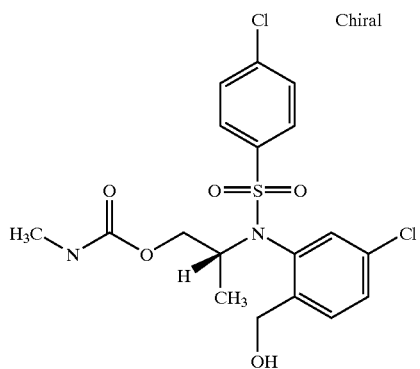 | +++++ |
| 1281 | 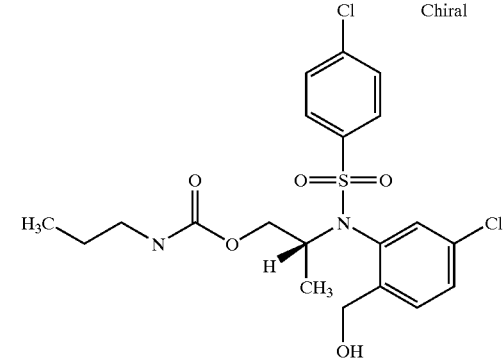 | +++++ |

-continued
| NUMBER | COMPOUND | ACTIVITY |
|---|---|---|
| 1282 | 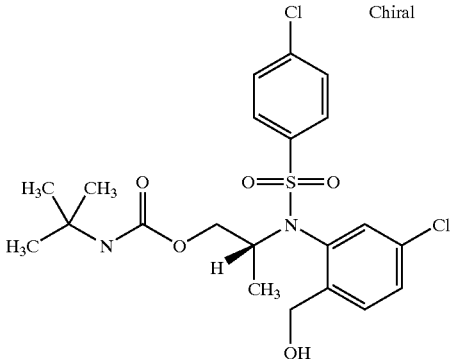 Chiral | +++++ |
| 1283 | 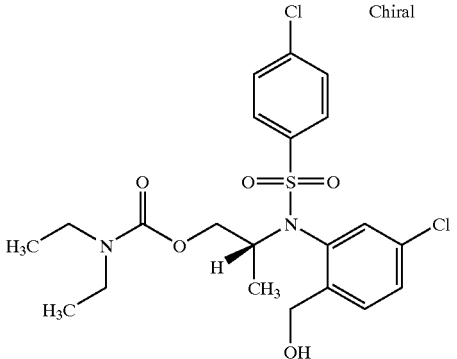 Chiral | +++++ |
| 1284 | 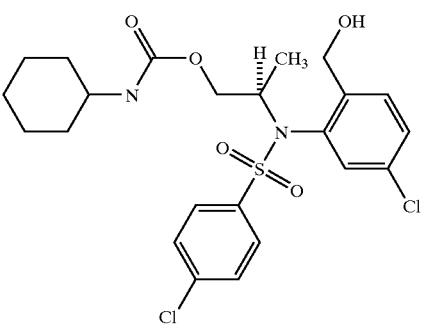 Chiral | +++++ |
| 1285 | 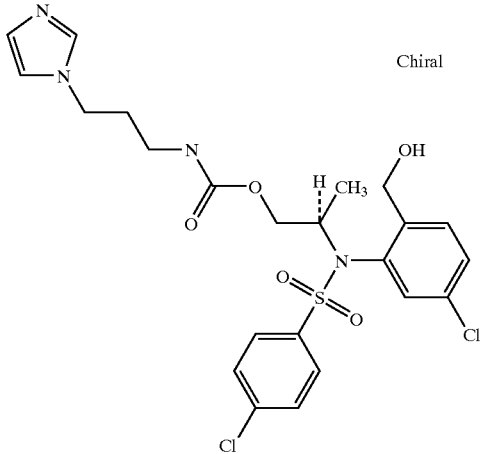 Chiral | +++++ |

| NUMBER | COMPOUND | ACTIVITY |
|---|---|---|
| 1286 | 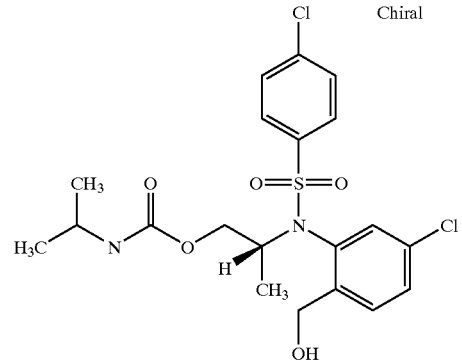 | +++++ |
| 1287 | 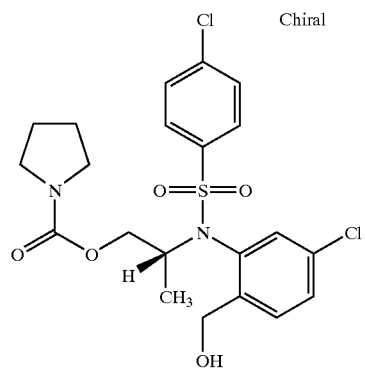 | +++++ |
| 1288 | 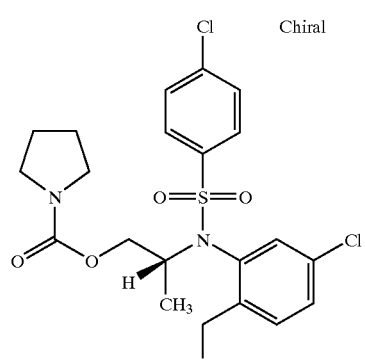 | +++++ |
| 1289 | 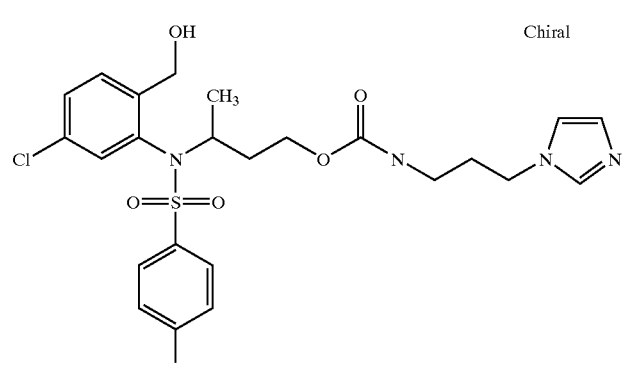 | +++++ |

-continued

| NUMBER | COMPOUND | ACTIVITY |
|--------|----------|----------|
| 1290 | | + |
| 1291 | | +++++ |
| 1292 | | − |

-continued
| NUMBER | COMPOUND | | ACTIVITY |
|---|---|---|---|
| 1293 | 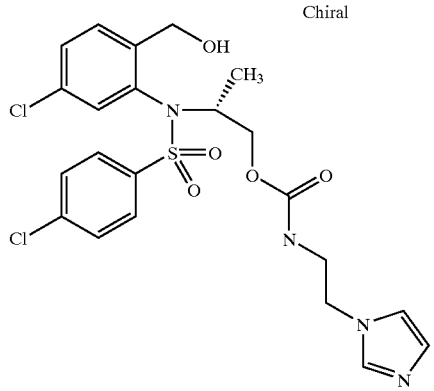 | Chiral | – |
| 1294 | 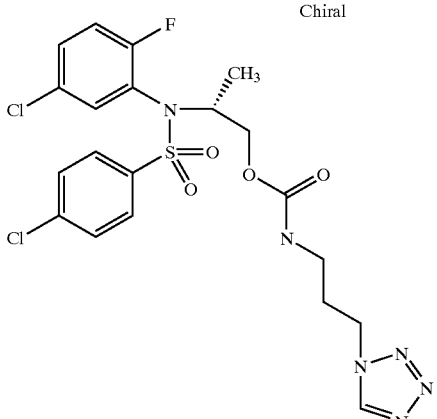 | Chiral | +++++ |
| 1295 | 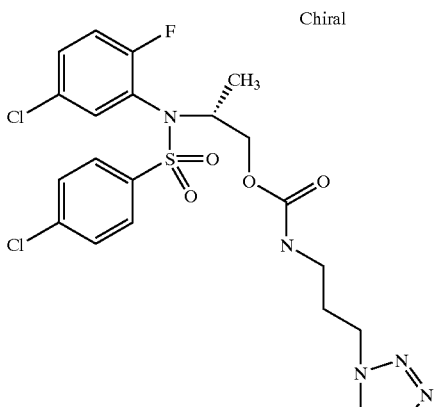 | Chiral | +++++ |

-continued
| NUMBER | COMPOUND | ACTIVITY |
|---|---|---|
| 1296 | 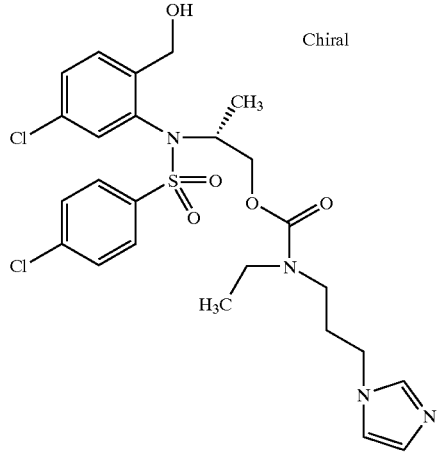 | − |
| 1297 | 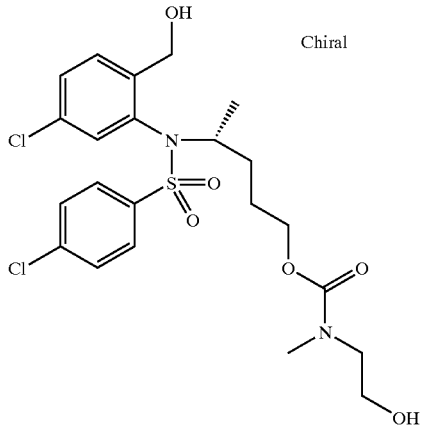 | +++++ |
| 1298 | 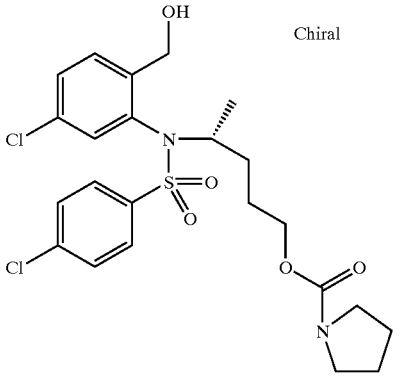 | +++++ |
| 1299 | 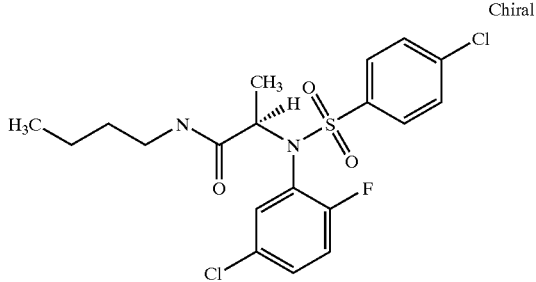 | ++ |

-continued
| NUMBER | COMPOUND | ACTIVITY |
|---|---|---|
| 1300 | 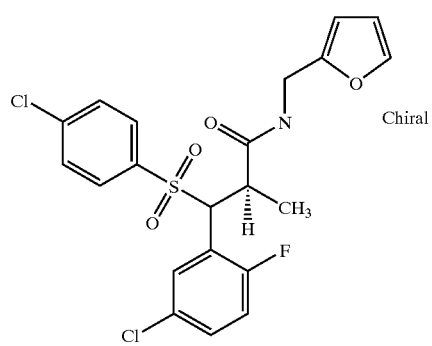 | ++ |
| 1301 | 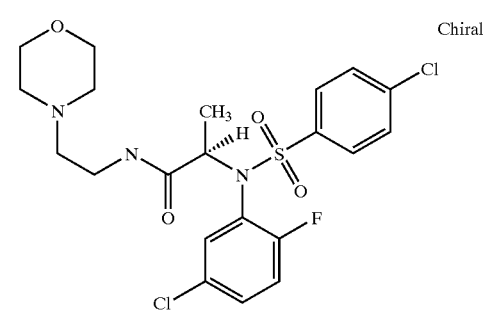 | + |
| 1302 | 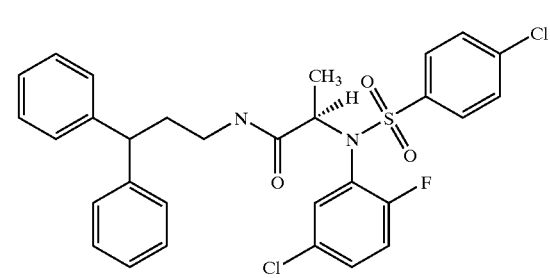 | + |
| 1303 | 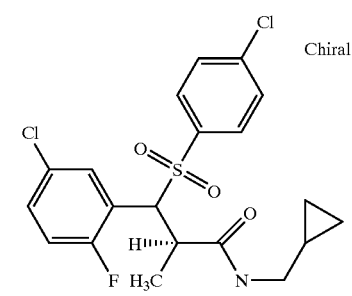 | ++ |
| 1304 | 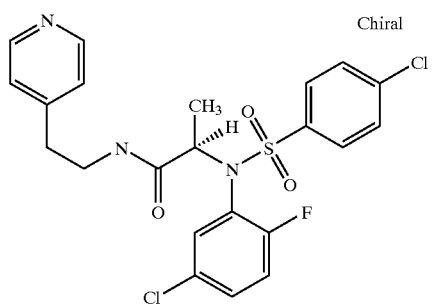 | ++ |

-continued
| NUMBER | COMPOUND | ACTIVITY |
|---|---|---|
| 1305 | 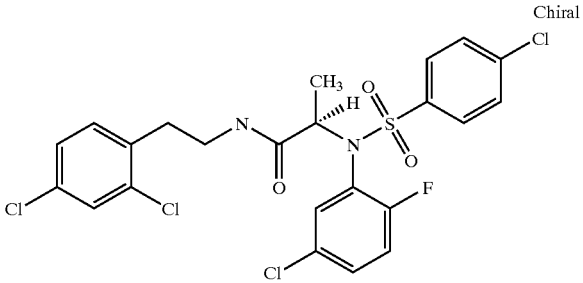 | + |
| 1306 | 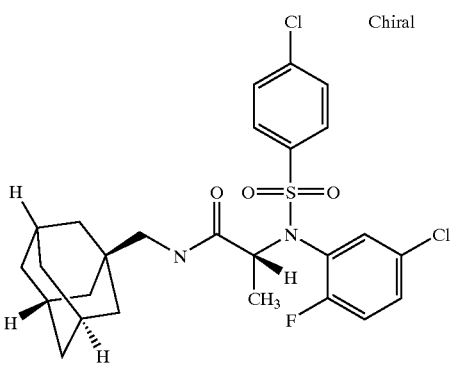 | + |
| 1307 | 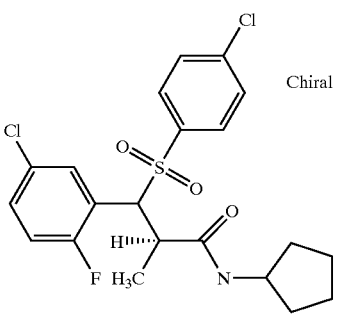 | ++ |
| 1308 | 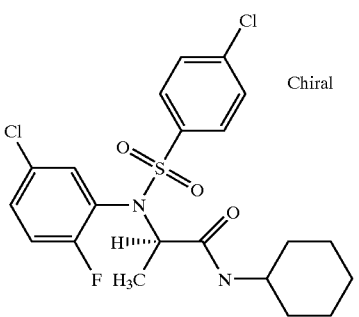 | ++ |

| NUMBER | COMPOUND | ACTIVITY |
|---|---|---|
| 1309 | 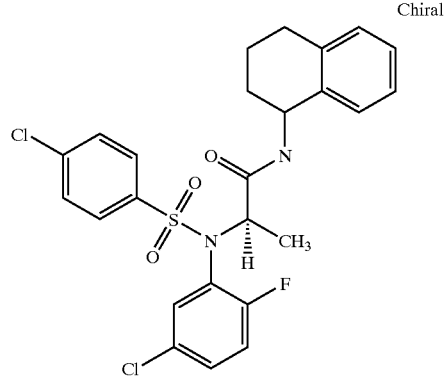 | + |
| 1310 | 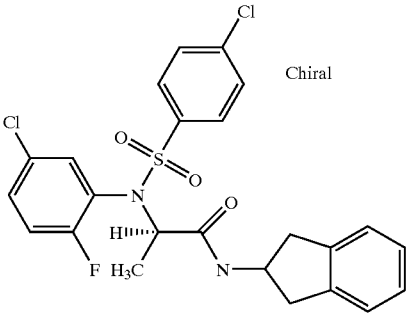 | + |
| 1311 | 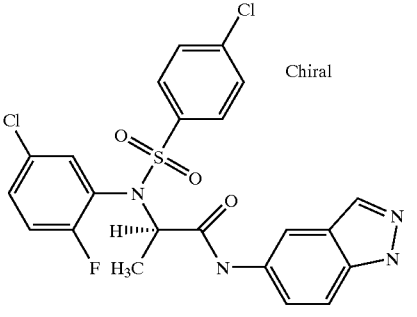 | + |
| 1312 | 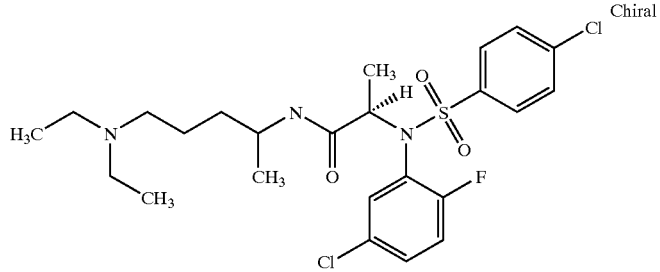 | + |

-continued
| NUMBER | COMPOUND | ACTIVITY |
|---|---|---|
| 1313 | 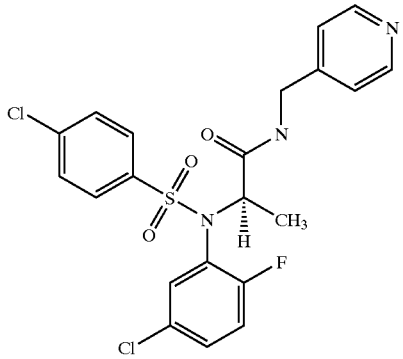 Chiral | ++ |
| 1314 | 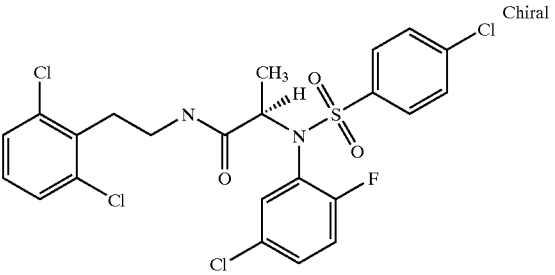 Chiral | ++ |
| 1315 | 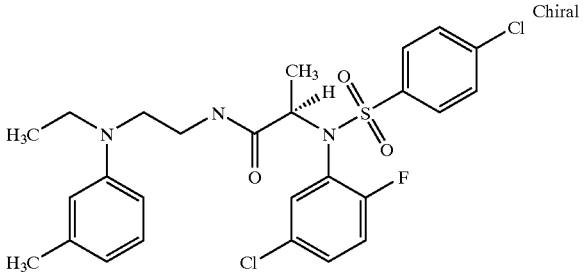 Chiral | + |
| 1316 | 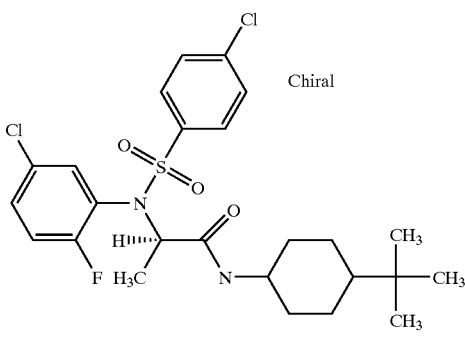 Chiral | + |
| 1317 | 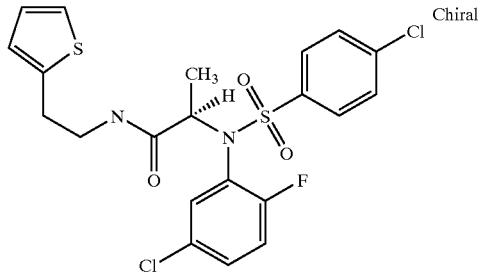 Chiral | + |

-continued

| NUMBER | COMPOUND | ACTIVITY |
|--------|----------|----------|
| 1318 | Chiral | + |
| 1319 | Chiral | + |
| 1320 | Chiral | ++ |
| 1321 | Chiral | ++ |

-continued

| NUMBER | COMPOUND | ACTIVITY |
|---|---|---|
| 1322 | | + |
| 1323 | | + |
| 1324 | | + |
| 1325 | | + |
| 1326 | | + |

-continued
| NUMBER | COMPOUND | ACTIVITY |
|---|---|---|
| 1327 | 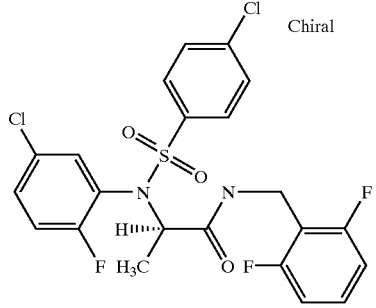 | + |
| 1328 | 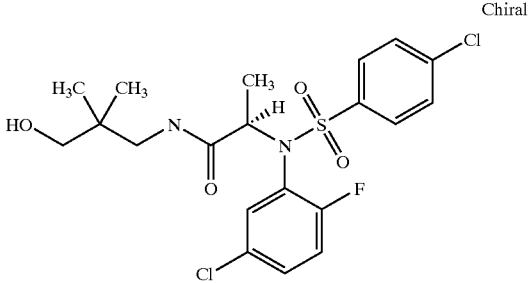 | ++ |
| 1329 | 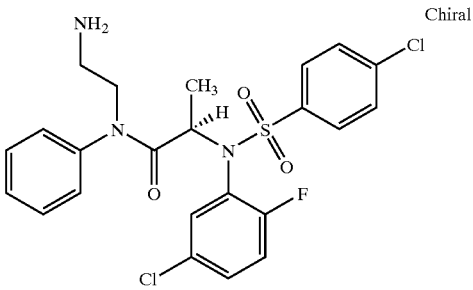 | + |
| 1330 | 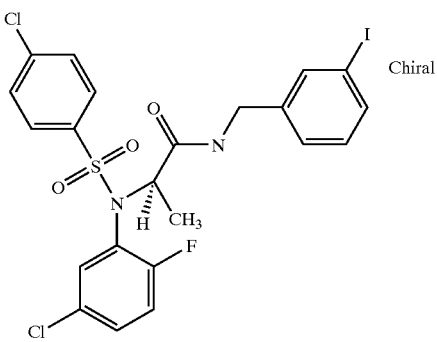 | + |

-continued

| NUMBER | COMPOUND | ACTIVITY |
|---|---|---|
| 1331 | | + |
| 1332 | | ++ |
| 1333 | | + |
| 1334 | | + |

-continued

| NUMBER | COMPOUND | ACTIVITY |
|---|---|---|
| 1335 | | + |
| 1336 | | + |
| 1337 | | + |
| 1338 | | ++ |
| 1339 | | ++ |

-continued
| NUMBER | COMPOUND | ACTIVITY |
|--------|----------|----------|
| 1340 | 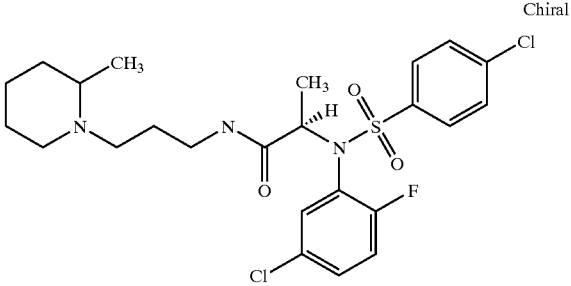 Chiral | + |
| 1341 | 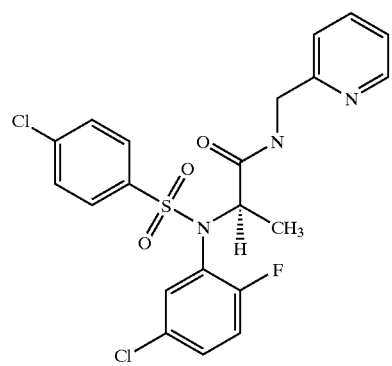 Chiral | ++ |
| 1342 | 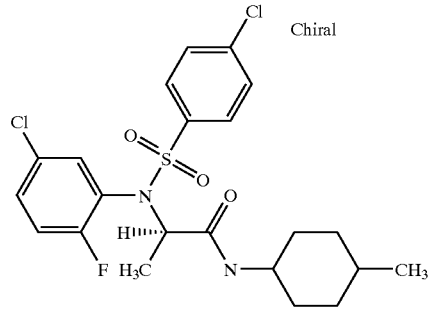 Chiral | ++ |
| 1343 | 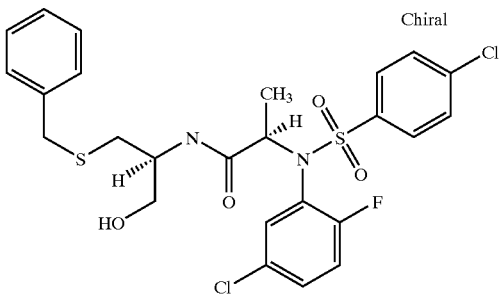 Chiral | + |

-continued
| NUMBER | COMPOUND | ACTIVITY |
|---|---|---|
| 1344 | 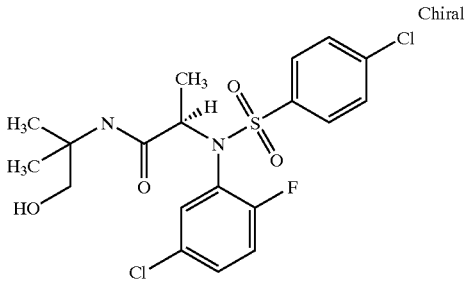 | ++ |
| 1345 | 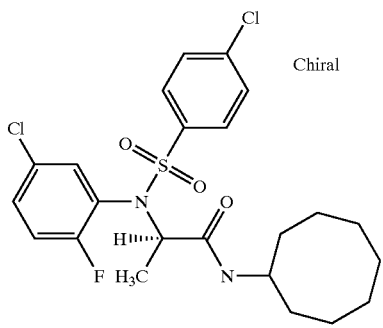 | ++ |
| 1346 | 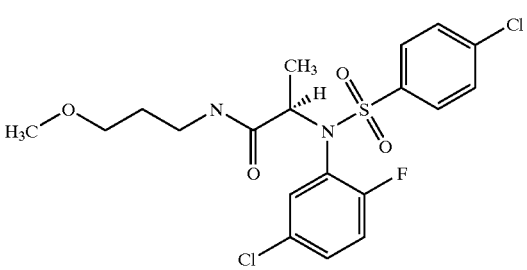 | ++ |
| 1347 | 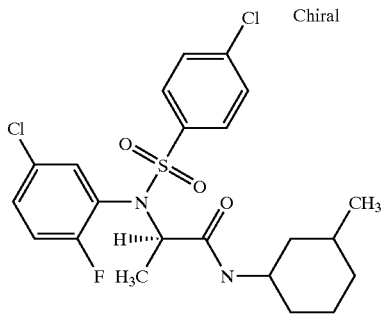 | ++ |
| 1348 | 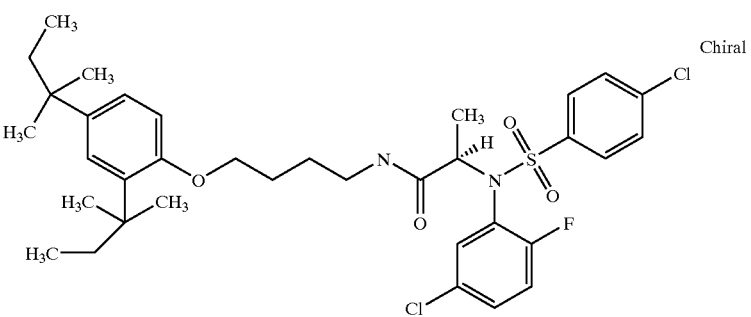 | + |

-continued
| NUMBER | COMPOUND | ACTIVITY |
|---|---|---|
| 1349 | 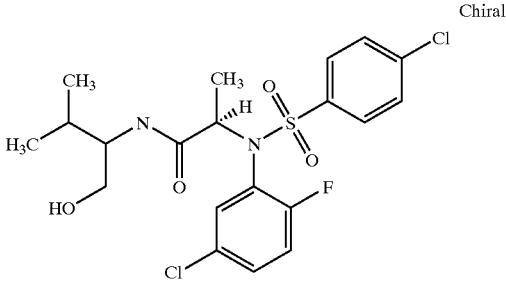 Chiral | ++ |
| 1350 | 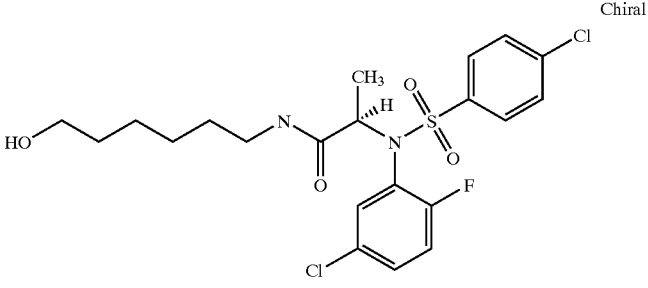 Chiral | ++ |
| 1351 | 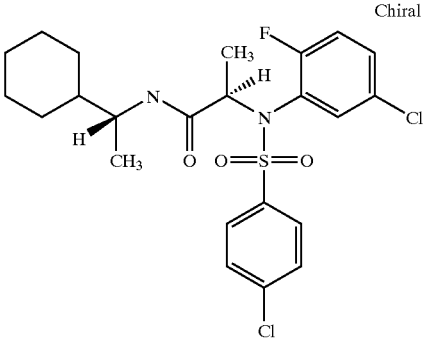 Chiral | + |
| 1352 | 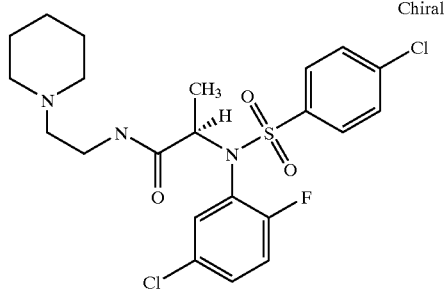 Chiral | + |

-continued
| NUMBER | COMPOUND | ACTIVITY |
|---|---|---|
| 1353 | 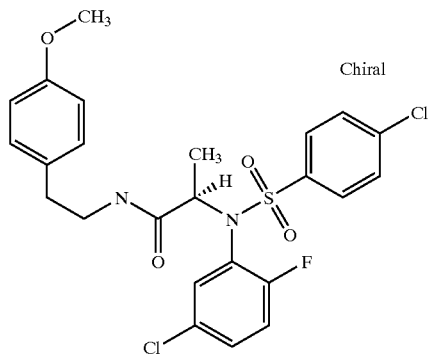 | + |
| 1354 | 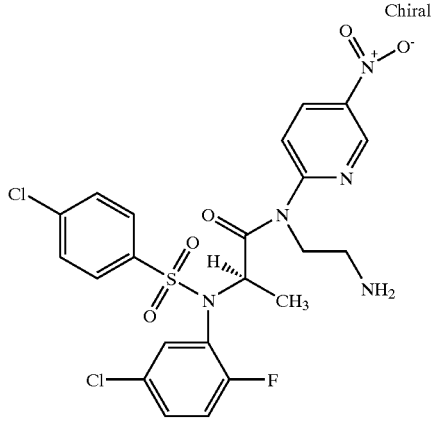 | + |
| 1355 | 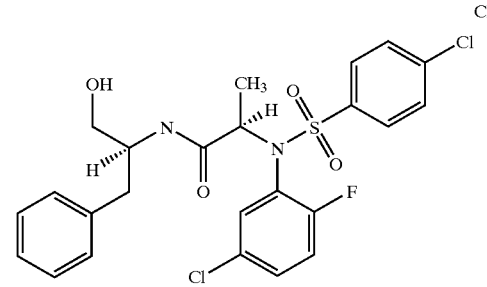 | + |
| 1356 | 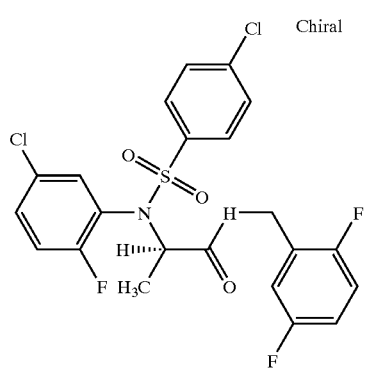 | + |

-continued
| NUMBER | COMPOUND | ACTIVITY |
|---|---|---|
| 1357 | 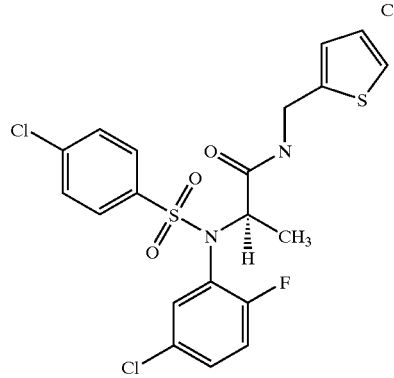 | ++ |
| 1358 | 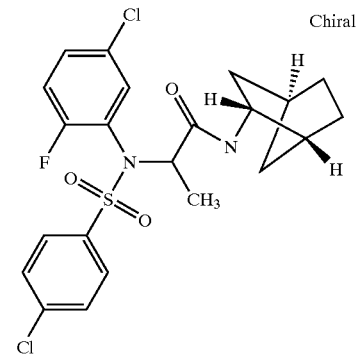 | ++ |
| 1359 | 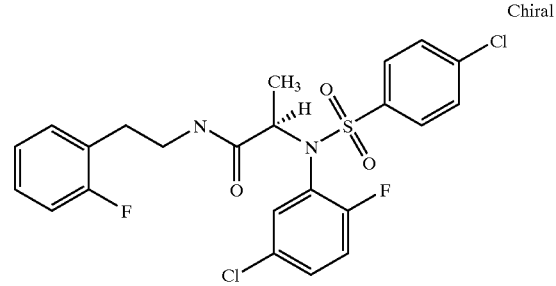 | + |
| 1360 | 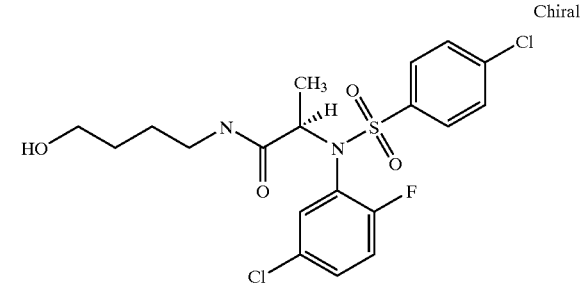 | ++ |

-continued
| NUMBER | COMPOUND | ACTIVITY |
|---|---|---|
| 1361 | 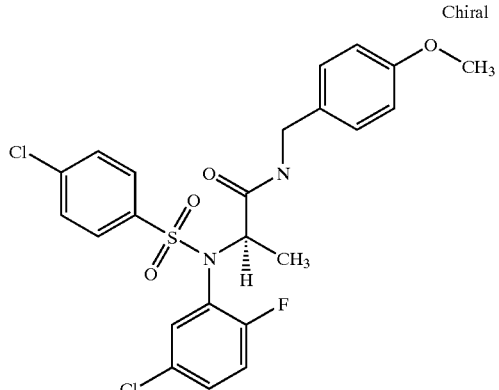 | + |
| 1362 | 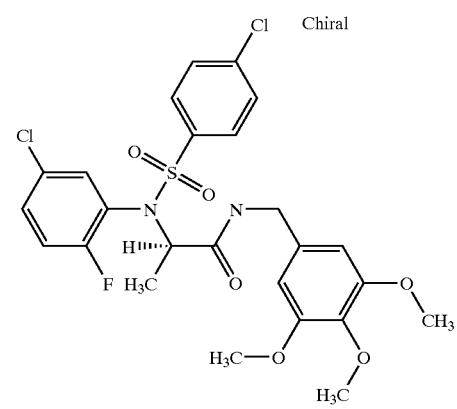 | + |
| 1363 | 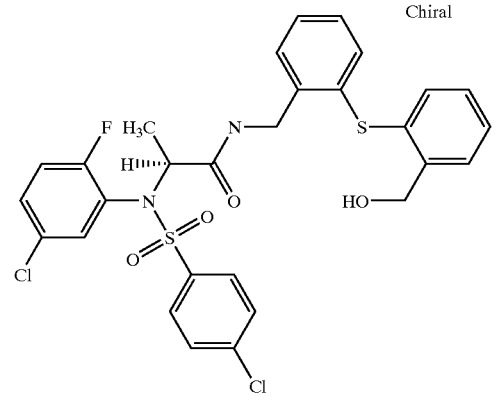 | + |
| 1364 | 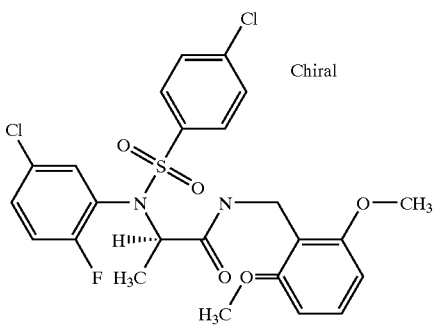 | + |

-continued

| NUMBER | COMPOUND | ACTIVITY |
|---|---|---|
| 1365 | 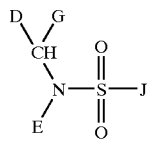 Chiral | + |
| 1366 | Chiral | + |

Inspection of the extensive dates presented in the preceding Table reveals that a wide variety of compounds of the generic formula provided herein display activity in an in vitro cell-based assay.

While the invention has been described in detail with reference to certain preferred embodiments thereof, it will be understood that modifications and variations are within the spirit and scope of that which is described and claimed.

What is claimed is:

1. A compound having the structure:

and pharmaceutically acceptable salts thereof, wherein:
D is hydrogen or lower alkyl;
E is substituted or unsubstituted phenyl;
G is substituted or unsubstituted phenyl; and
J is substituted phenyl, comprising one or more substituents selected from the group consisting of methyl, alkyl substituted by one or more substituents selected from cycloalkyl, cycloalkenyl, aryl, heterocycle, cyano, cyanomethyl, nitro, amino, amide, amidine, hydroxyl, carboxyl, carbamate, ether, ester, sulfonyl, sulfonamide and mercapto, halogen, ether, —S-alkyl, or —S-aryl.

2. The compound of claim 1, wherein:

substituent(s) on E is(are) independently substituted or unsubstituted alkyl, halogen, hydroxy, ester, —S-alkyl, $NO_2$ or $SO_2$;

substituent(s) on G is(are) independently substituted or unsubstituted alkyl, alkenyl, alkynyl, cycloalkyl, halogen, amide, amine, hydroxy, sulfonyl, sulfonamide, —$(CH_2)_n$—O—$(CH_2)_m$-amine, —$(CH_2)_n$—O—$(CH_2)_m$-heterocycle, or —$(CH_2)_n$—O—$(CH_2)_m$-amide, wherein n and m are independently 0, 1, 2, 3, 4 or 5; and substituent(s) on J is(are) independently methyl, halogen, ether, —S-alkyl, or —S-aryl.

3. The compound of claim 2, wherein:

substituent(s) on B and J is(are) halogen; and substituent(s) on G is(are) halogen and/or substituted alkyl.

4. A composition comprising a compound according to claim 1 in a pharmaceutically acceptable carrier therefor.

* * * * *

UNITED STATES PATENT AND TRADEMARK OFFICE
CERTIFICATE OF CORRECTION

| | |
|---|---|
| PATENT NO. | : 6,967,196 B1 |
| APPLICATION NO. | : 09/890927 |
| DATED | : November 22, 2005 |
| INVENTOR(S) | : Smith et al. |

It is certified that error appears in the above-identified patent and that said Letters Patent is hereby corrected as shown below:

At column 6, lines 13-14, the printed patent should read "...substituted or unsubstituted...".

At column 6, line 65, the printed patent should read "...another embodiment of the invention, J...".

At column 10, line 65, the printed patent should read "...to 100 mg/kg/day; with...".

At column 16, line 4, the printed patent should read "...for 1 h at 0° C. followed...".

At column 38, line 27, the printed patent should read "...0° C. for 1 h and subsequently...".

At column 66, line 29, the printed patent should read "Silica gel chromatography...".

At column 126, line 24, the printed patent should read "The filtrate was concentrated...".

At column 156, line 18, the printed patent should read "...was allowed to stir at room temperature...".

At column 174, line 33, the printed patent should read "...under reduced pressure...".

At column 174, line 53, the printed patent should read "...organic layers were washed...".

At column 183, line 60, the printed patent should read "...to afford the desired product...".

At column 184, line 23, the printed patent should read "...mixture was allowed to stir at...".

At column 199, line 65, the printed patent should read "...product that was purified by...".

At column 261, line 18, the printed patent should read "The Scheme 514A process begins...".

At column 261, line 20, the printed patent should read "..an $R^3$-substituted...".

UNITED STATES PATENT AND TRADEMARK OFFICE
CERTIFICATE OF CORRECTION

PATENT NO. : 6,967,196 B1
APPLICATION NO. : 09/890927
DATED : November 22, 2005
INVENTOR(S) : Smith et al.

It is certified that error appears in the above-identified patent and that said Letters Patent is hereby corrected as shown below:

At column 273, line 35, the printed patent should read "...was allowed to warm to...".

Signed and Sealed this

First Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,967,196 B1 Page 1 of 1
APPLICATION NO. : 09/890927
DATED : November 22, 2005
INVENTOR(S) : D. Smith et al.

It is certified that error appears in the above-identified patent and that said Letters Patent is hereby corrected as shown below:

At column 414, line 57, the printed patent should read --...substituent(s) on E and J is(are) halogen;...--.

Signed and Sealed this

Fourth Day of March, 2008

JON W. DUDAS
*Director of the United States Patent and Trademark Office*